US008180457B2

(12) United States Patent
Matos

(10) Patent No.: US 8,180,457 B2
(45) Date of Patent: May 15, 2012

(54) SYSTEM FOR CARDIAC RESUSCITATION

(76) Inventor: Jeffrey A. Matos, New Rochelle, NY (US)

( * ) Notice: Subject to any disclaimer, the term of this patent is extended or adjusted under 35 U.S.C. 154(b) by 45 days.

(21) Appl. No.: 12/848,461

(22) Filed: Aug. 2, 2010

(65) Prior Publication Data

US 2010/0324612 A1 Dec. 23, 2010

Related U.S. Application Data

(62) Division of application No. 11/893,897, filed on Aug. 18, 2007, now Pat. No. 7,769,465, which is a division of application No. 10/460,458, filed on Jun. 11, 2003, now Pat. No. 7,277,752.

(51) Int. Cl.
*A61N 1/18* (2006.01)
*A61N 1/37* (2006.01)

(52) U.S. Cl. ........... 607/60; 607/2; 607/4; 607/5; 607/7; 607/9; 607/10; 607/11; 607/30; 607/31; 607/32; 607/59

(58) Field of Classification Search .................. 607/2, 4, 607/5, 7, 10, 27, 30, 31, 32, 59, 60
See application file for complete search history.

(56) References Cited

U.S. PATENT DOCUMENTS

| 4,102,332 | A  |     | 7/1978  | Gessman |       |
|-----------|----|-----|---------|---------------|-------|
| 5,184,620 | A  |     | 2/1993  | Cudahy et al. |       |
| 5,544,661 | A  |     | 8/1996  | Davis et al.  |       |
| 5,564,429 | A  |     | 10/1996 | Bornn et al.  |       |
| 5,593,426 | A  |     | 1/1997  | Morgan et al. |       |
| 5,782,878 | A  |     | 7/1998  | Morgan et al. |       |
| 6,141,584 | A  |     | 10/2000 | Rockwell et al. |     |
| 6,148,233 | A  |     | 11/2000 | Owen et al.   |       |
| 6,480,745 | B2 | *   | 11/2002 | Nelson et al. ................ 607/60 |
| 7,065,409 | B2 | *   | 6/2006  | Mazar ........................ 607/60 |
| 7,174,216 | B1 | *   | 2/2007  | Dalal ......................... 607/60 |
| 7,383,088 | B2 | *   | 6/2008  | Spinelli et al. .............. 607/30 |
| 7,567,180 | B2 | *   | 7/2009  | Blevins et al. ............ 340/573.1 |
| 7,627,372 | B2 | *   | 12/2009 | Vaisnys et al. ............... 607/5 |
| 2001/0044588 | A1 | * | 11/2001 | Mault ....................... 600/549 |
| 2002/0082665 | A1 | * | 6/2002  | Haller et al. ................ 607/60 |
| 2002/0111542 | A1 | * | 8/2002  | Warkentin et al. ........... 600/300 |

OTHER PUBLICATIONS

New England Journal of Medicine 2000; vol. 343: pp. 1259-1260.
New England Journal of Medicine 2000; vol. 343: pp. 600-606.
Circulation 1999; vol. 100: Abstract 1645, pp. 1-314.
New England Journal of Medicine 2001; vol. 344: pp. 1304-1313.
Annals of Emergency Medicine 1998; vol. 31: pp. 234-240.
New England Journal of Medicine 2000; vol. 343: pp. 1206-1209.
New England Journal of Medicine 2000; vol. 343: pp. 1210-1216.
Circulation 1998; vol. 97: pp. 1321-1324.
Circulation 1999; vol. 100: Abstract 1641, p. 1-313.
New England Journal of Medicine 2000; vol. 342: pp. 1599-1601.

* cited by examiner

*Primary Examiner* — Carl H Layno
*Assistant Examiner* — Allen Porter, Jr.
(74) *Attorney, Agent, or Firm* — Eckert Seamans Cherin & Mellott, LLC

(57) ABSTRACT

System and method for monitoring and controlling, defibrillation and pacing which allows a victim of a cardiac rhythm abnormality immediate access to a medical professional at a central station, who will remotely monitor, diagnose and treat the victim at one of a plurality of remote sites in accordance with the following steps:

(1) providing a plurality of contact electrodes for a victim at a remote site for the receipt of ECG signals and for the application of electrical pulses to the victim;
(2) transmitting the signals from the remote site to a central station and displaying them for review by the medical professional;
(3) the medical professional selecting from a menu of defibrillation and pacing pulses, if the application thereof is appropriate;
(4) transmitting the selection results to the remote site; and
(5) receiving the selection results at the remote site and applying the selected pulses to the victim.

15 Claims, 112 Drawing Sheets

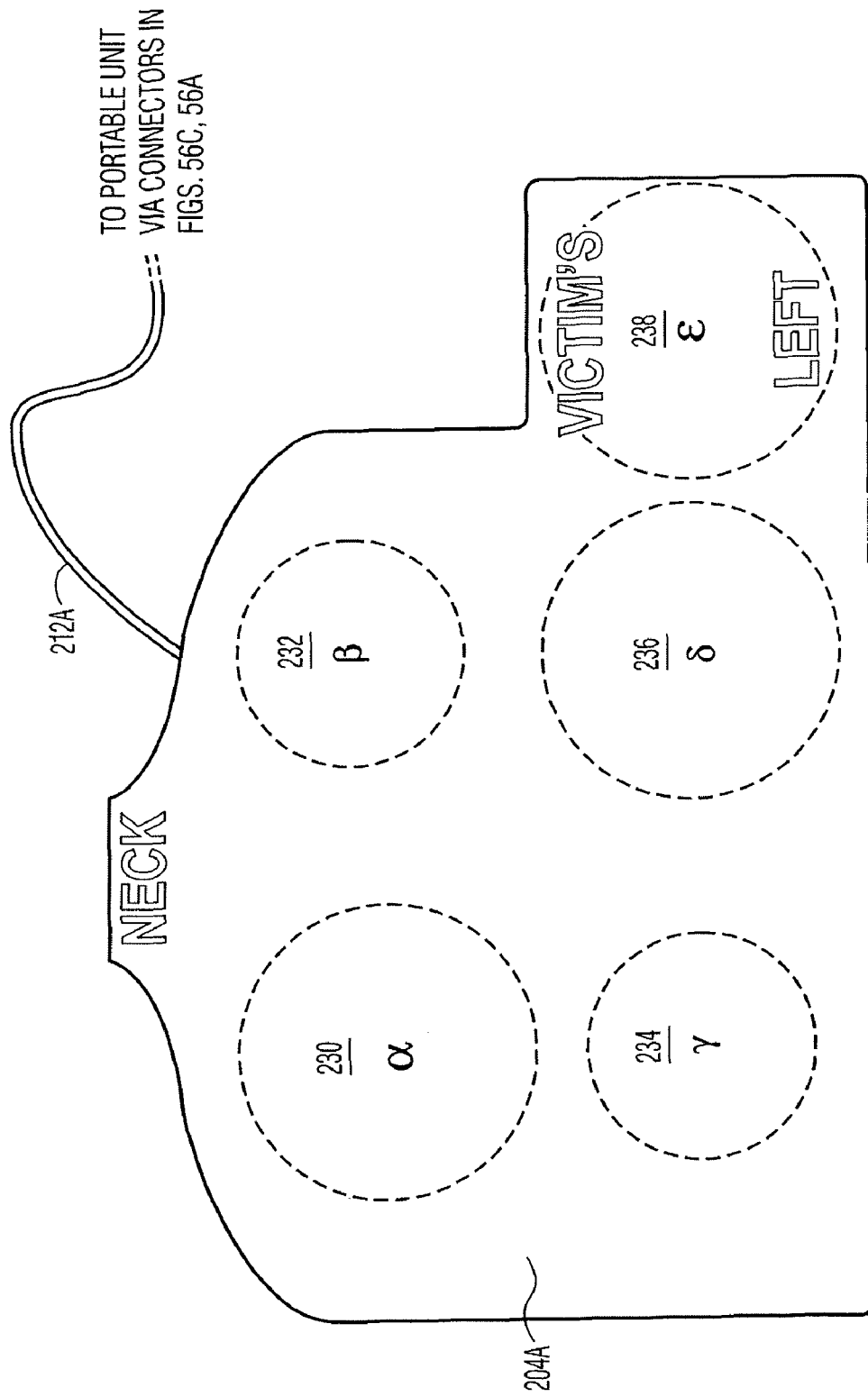

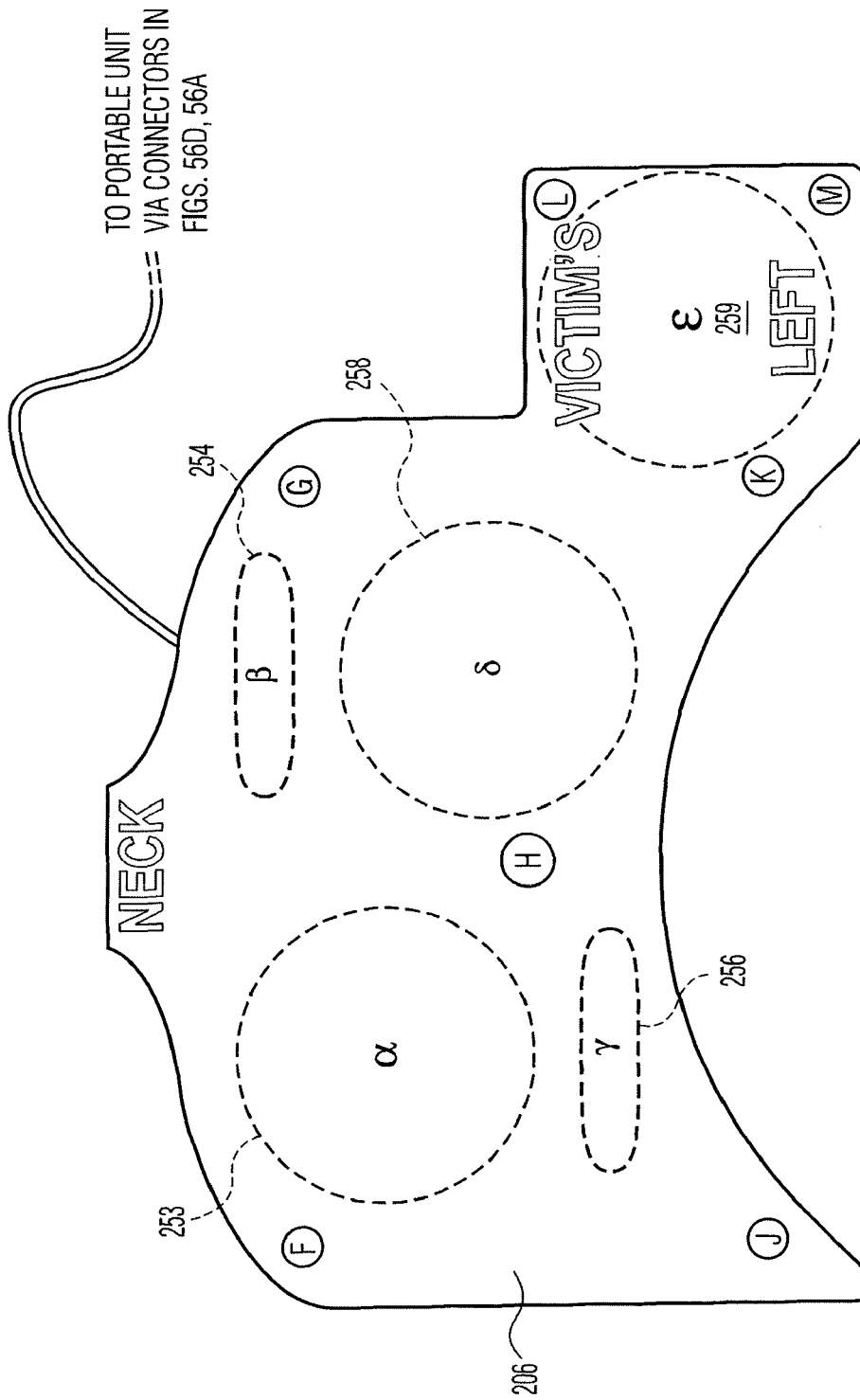

PORTABLE UNIT SCREENS: INSTRUCTIONAL MODE

PORTABLE UNIT SCREENS: TOUCH SENSITIVE MODE

FIGURE 12 LEGEND

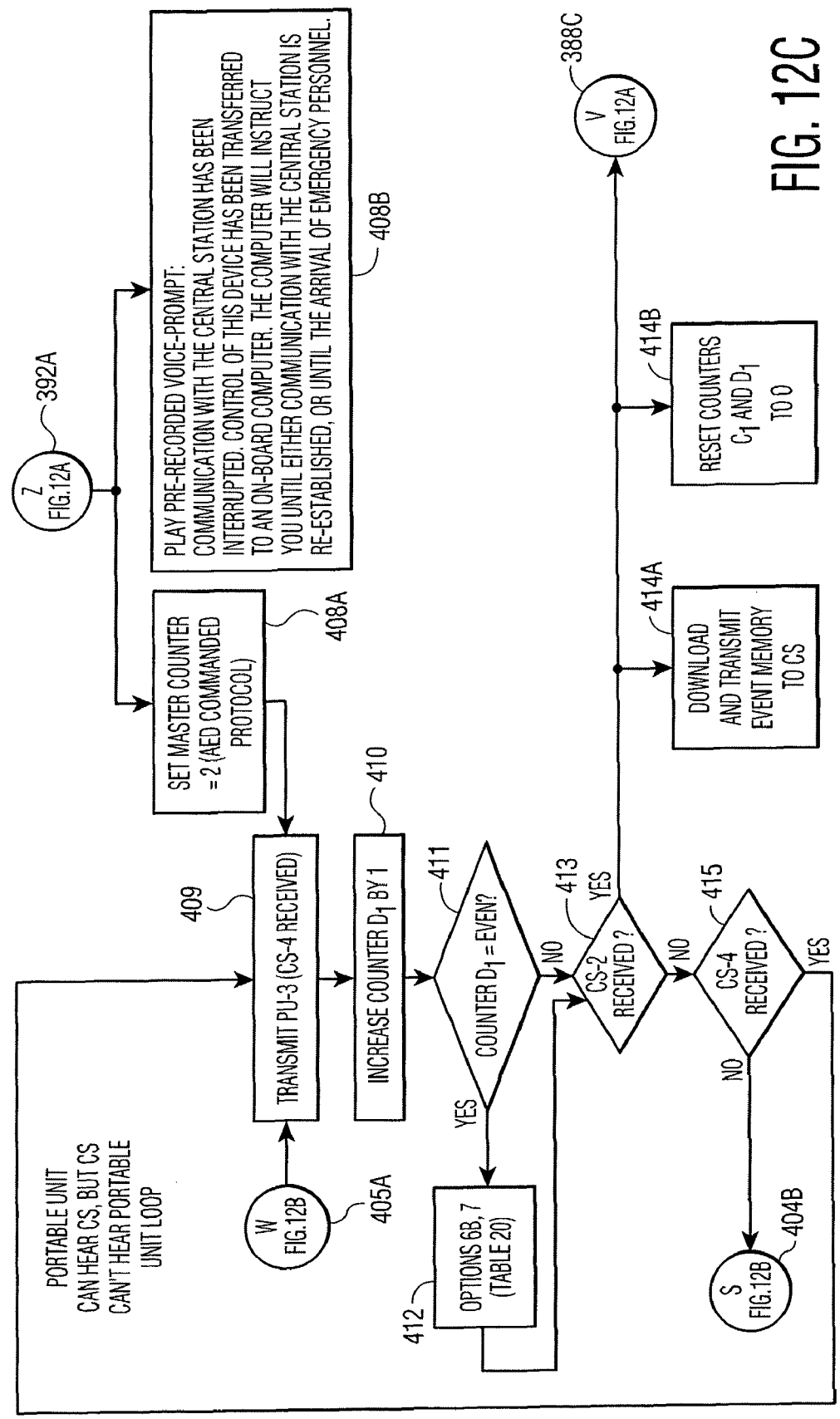

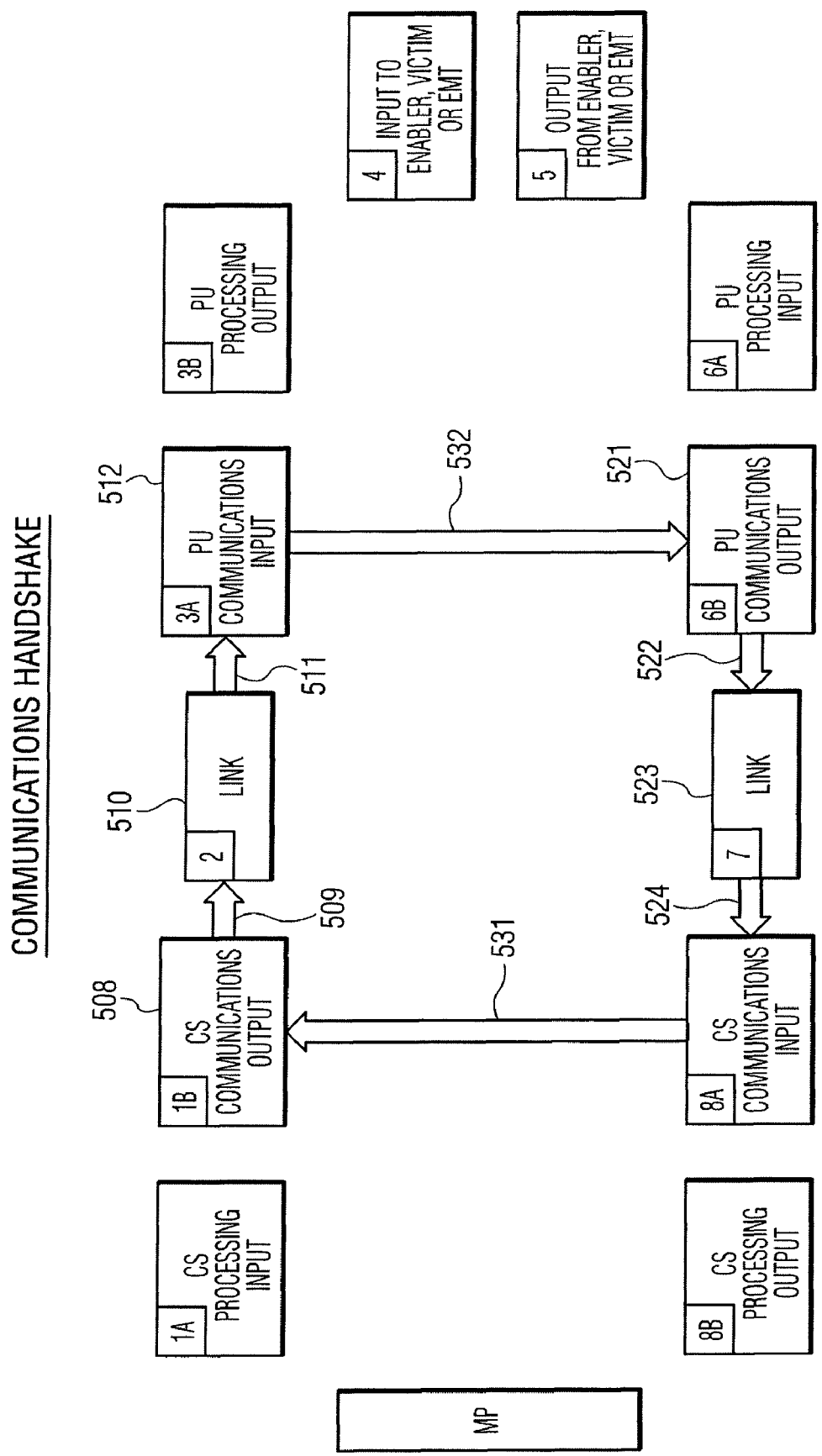

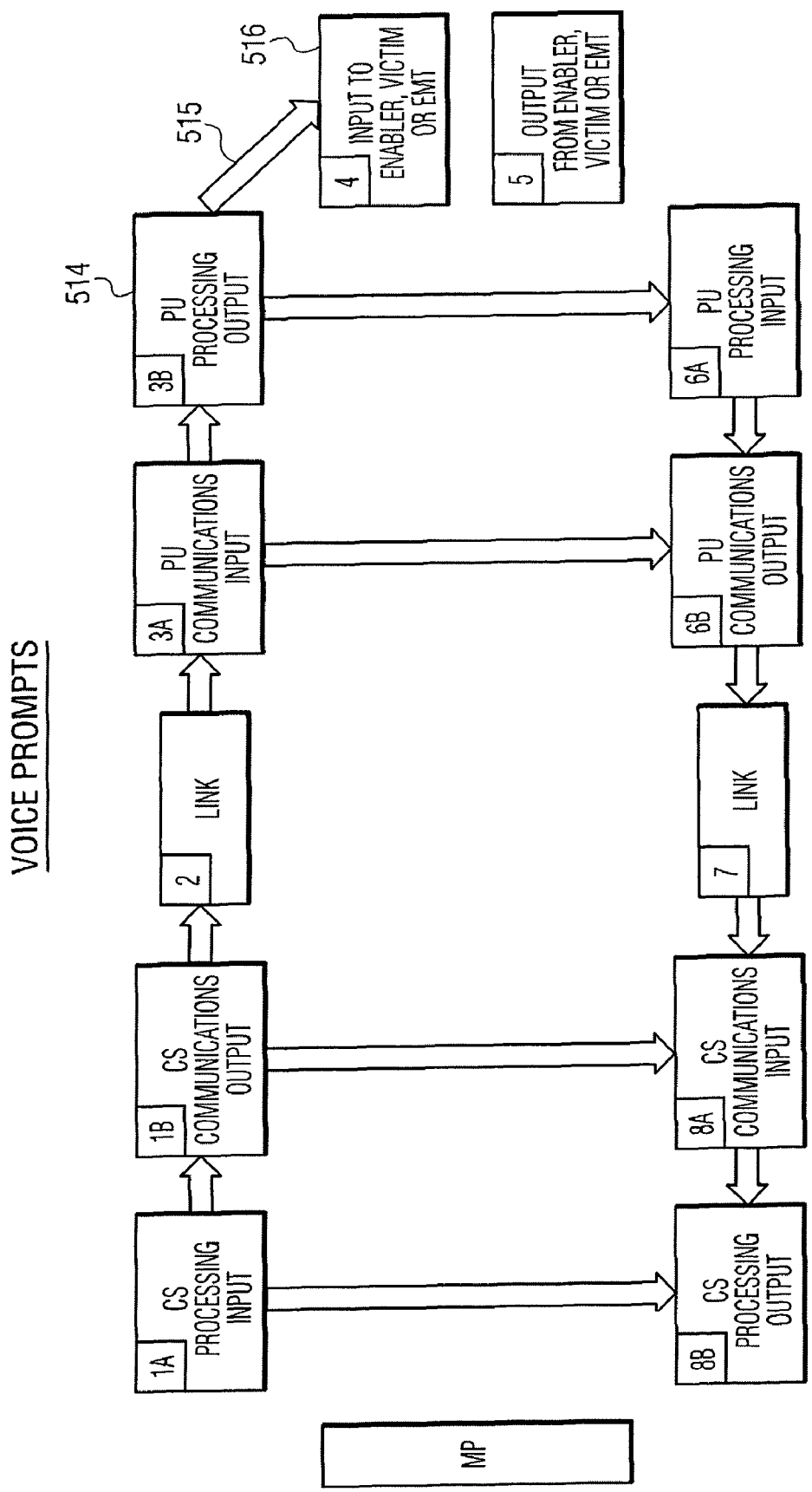

DATA/COMMANDS HANDSHAKE DURING DIAGNOSTIC CHECK
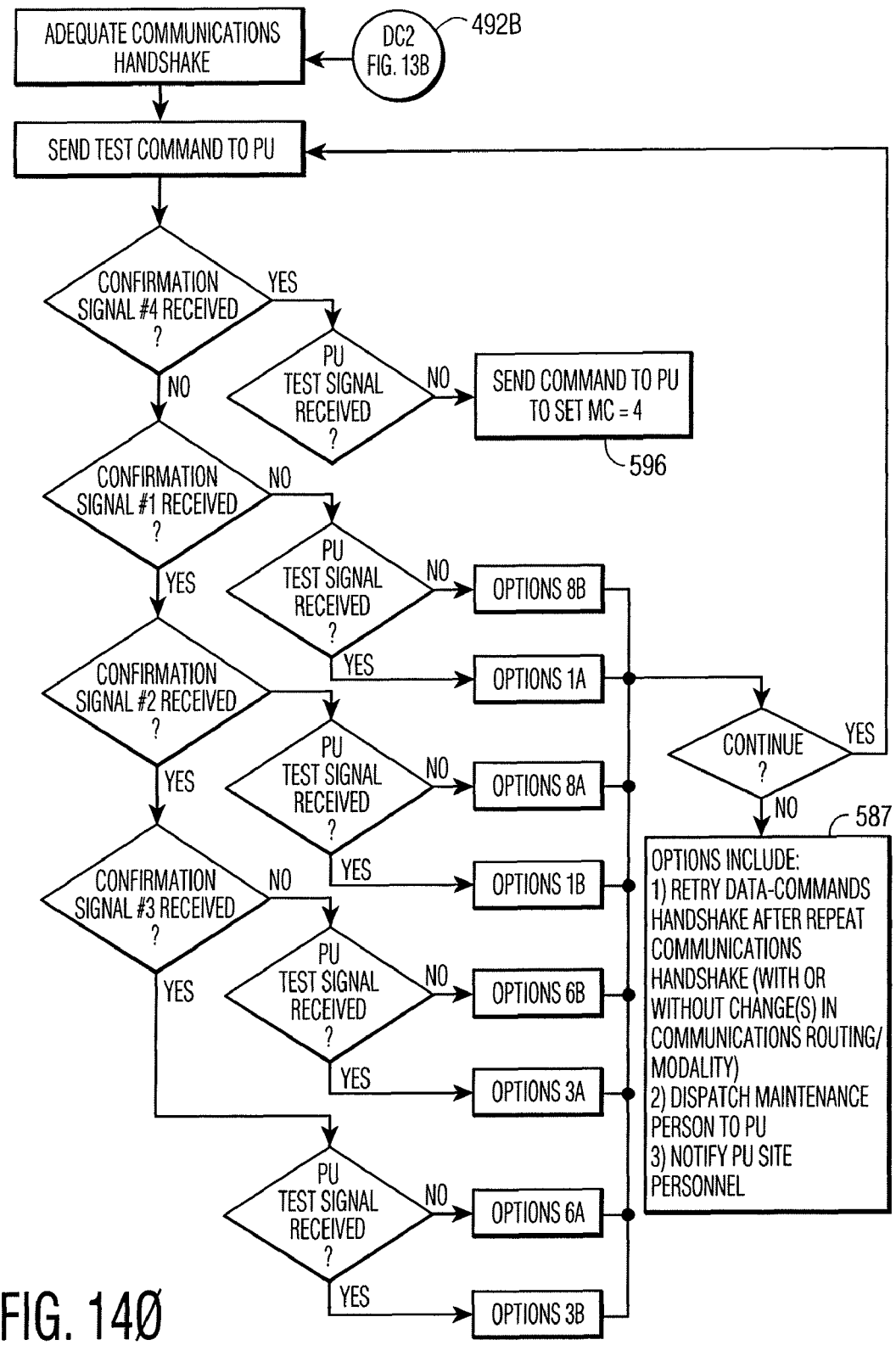
FIG. 14Ø

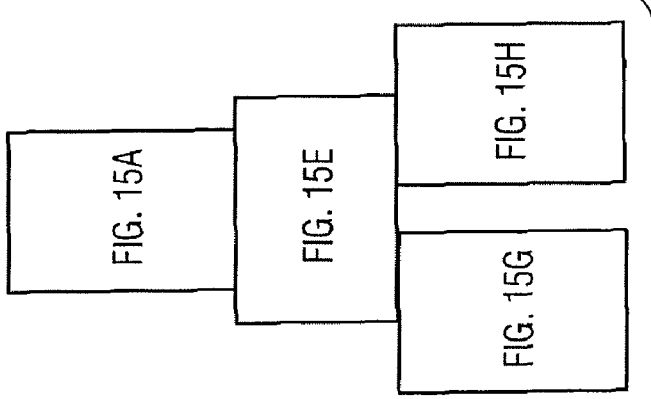
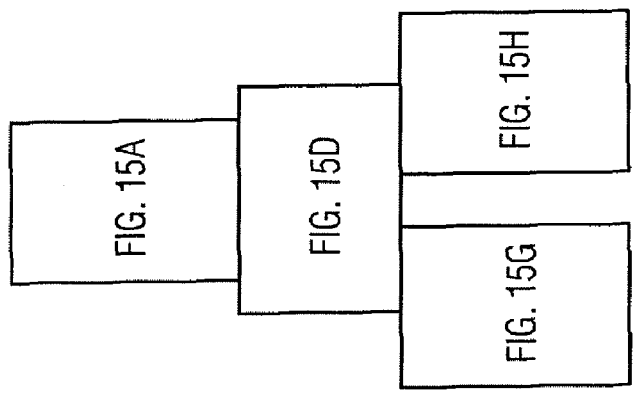
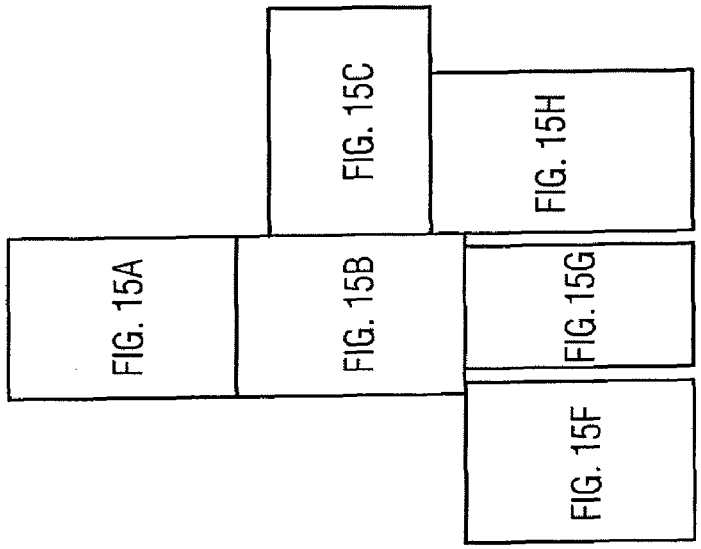
FIG. 15

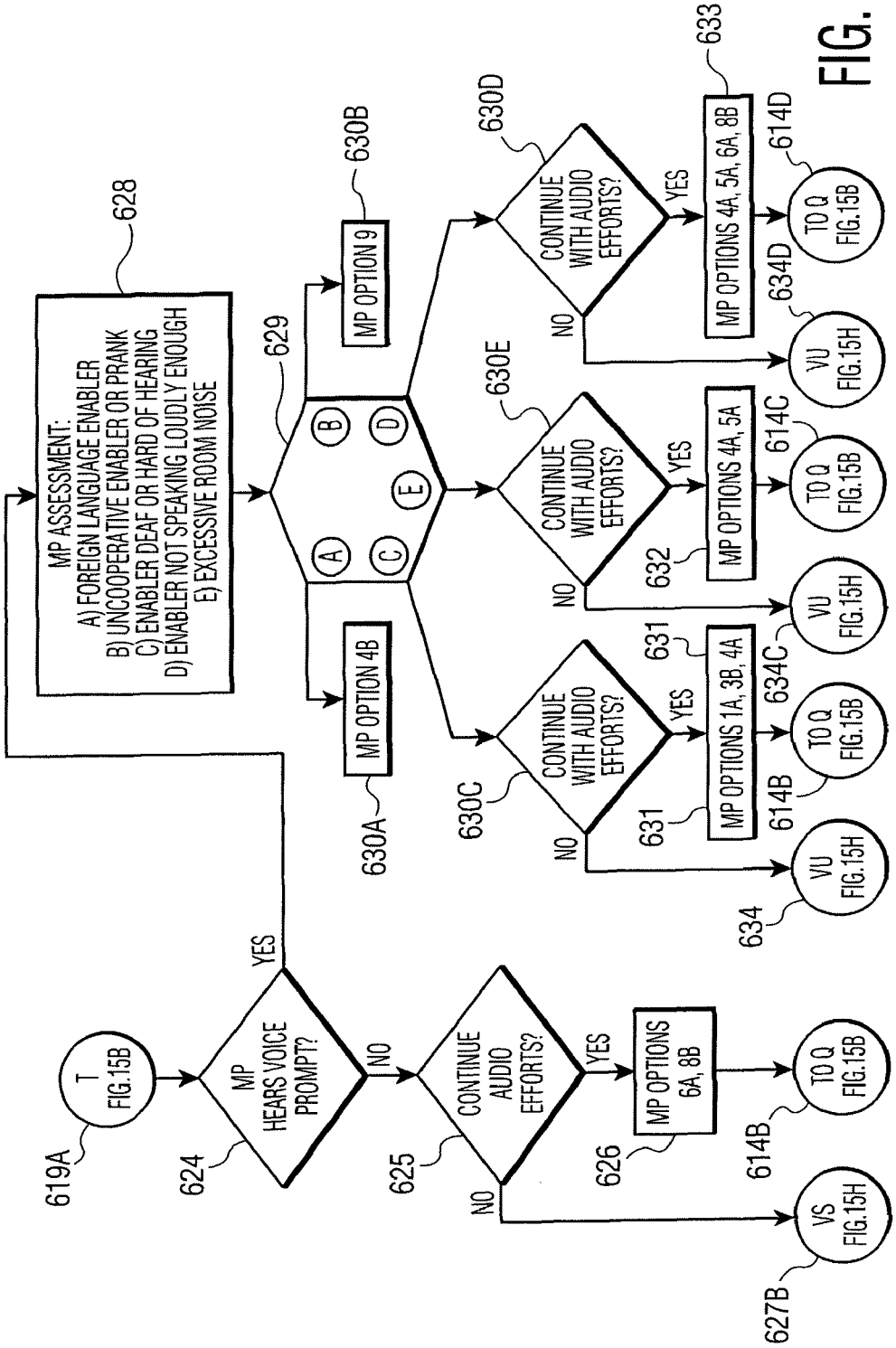

FIGURE 16 LEGEND

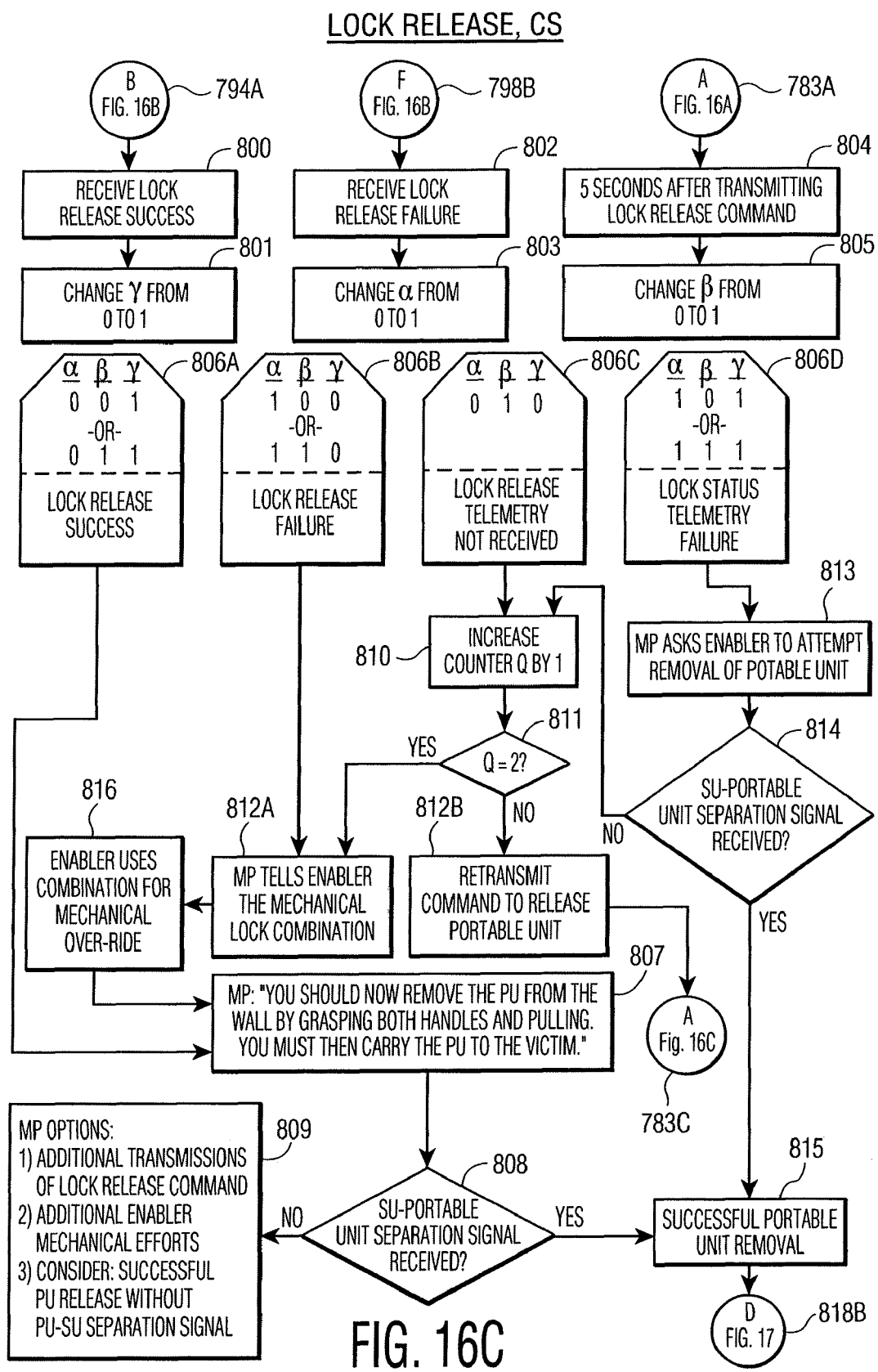

FIGURE 18 LEGEND

SECOND TIER ARRHYTHMIA TRIAGE PROTOCOL

| CONSCIOUSNESS | RESPIRATION | SYSTOLIC B.P. | THERAPY |
|---|---|---|---|
| 0 | 0 | 0 | Hi SHOCK |
| 0 | 0 | 1 | Hi SHOCK |
| 0 | 0 | 2 | Hi SHOCK |
| 0 | 1 | 0 | Hi SHOCK |
| 0 | 1 | 1 | Hi SHOCK |
| 0 | 1 | 2 | Lo SHOCK/ Hi SHOCK |
| 0 | 2 | 0 | Hi SHOCK |
| 0 | 2 | 1 | Lo SHOCK/ Hi SHOCK |
| 0 | 2 | 2 | ATP/ Lo SHOCK |
| 1 | 0 | 0 | Hi SHOCK |
| 1 | 0 | 1 | ATP/ Lo SHOCK |
| 1 | 0 | 2 | ATP/ Lo SHOCK |
| 1 | 1 | 0 | ATP/ Lo SHOCK |
| 1 | 1 | 1 | ATP/ Lo SHOCK |
| 1 | 1 | 2 | ATP |
| 1 | 2 | 0 | ATP/Lo SHOCK |
| 1 | 2 | 1 | ATP |
| 1 | 2 | 2 | ATP |
| 2 | 0 | 0 | ATP/Lo SHOCK |
| 2 | 0 | 1 | ATP/Lo SHOCK |
| 2 | 0 | 2 | ATP/Lo SHOCK |
| 2 | 1 | 0 | ATP/Lo SHOCK |
| 2 | 1 | 1 | ATP |
| 2 | 1 | 2 | ATP |
| 2 | 2 | 0 | ATP/Lo SHOCK |
| 2 | 2 | 1 | ATP |
| 2 | 2 | 2 | ATP |

MP SELECTS THERAPY BASED ON BOX 950

ATP SELECTED? NO → TO M FIG. 20
YES → TO MM FIG. 22

| DEFINITIONS: | 0 | 1 | 2 |
|---|---|---|---|
| CONSCIOUSNESS | SEMICONSCIOUS | RESPONSIVE BUT < ALERT | ALERT |
| RESPIRATION | SAT <60 OR RATE <7 | ALL STATES ≠ 0 OR 2 (SAT 61-79) | SAT >80 & RATE >9 |
| SYSTOLIC B.P. | <70 | 70-89 | >89 |

COMMAND CONFIRMATION AND EVENT LOG

| Time | Event |
|---|---|
| 16:20:00 | BUTTON PRESS |
| 16:20:02 | COMMUNICATIONS HANDSHAKE OK |
| 16:20:03 | TEST COMMAND TO PU |
| 16:20:04 | MC = 1 COMMAND TO PU |
| 16:20:24 | PU LOCK RELEASE COMMAND |
| 16:20:25 | PU LOCK RELEASE |
| 16:20:27 | PU-SU SEPARATION |
| 16:20:31 | PU TOUCHDOWN |
| 16:20:38 | VIDEO DEPLOYMENT |
| 16:20:48 | DEFIB PAD COVER REMOVED |
| 16:20:53 | ECG SIGNALS |
| 16:20:56 | CHARGE PU CAPACITORS |
| 16:20:59 | CHARGE COMPLETION SIGNAL |
| 16:22:01 | DELIVER SHOCK |

FIGURE 51 LEGEND

| FIG. 51A |
|---|
| FIG. 51B |

FIG. 51

FIGURE 55 LEGEND

| FIG. 55A | FIG. 55B |

FIG. 55

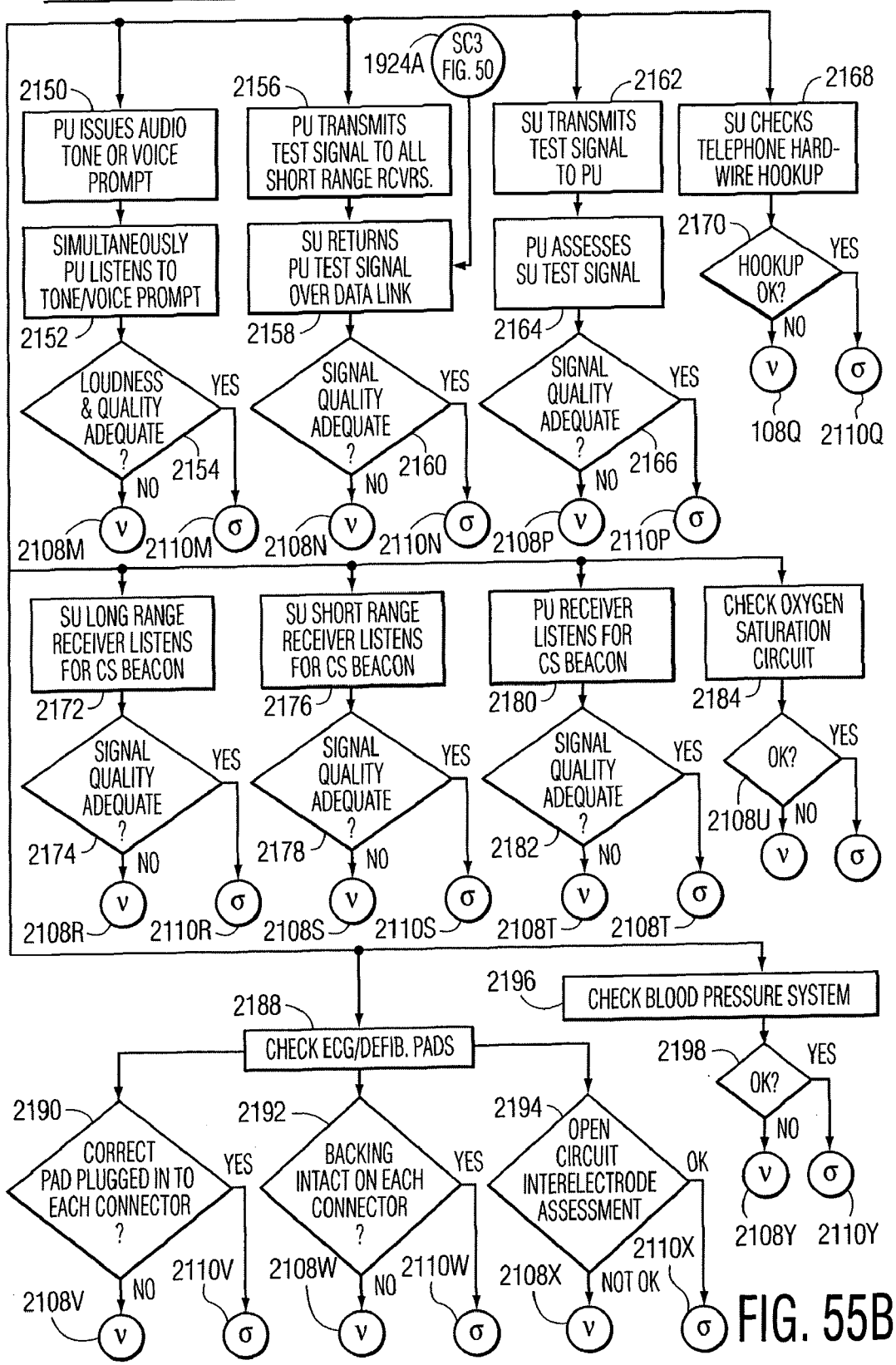

SYSTEM FOR CARDIAC RESUSCITATION

CROSS-REFERENCE TO RELATED APPLICATION

This application is a divisional application of U.S. patent application Ser. No. 11/893,897, filed Aug. 18, 2007, now U.S. Pat. No. 7,769,465, which, in turn, was a divisional of U.S. patent application Ser. No. 10/460,458 filed Jun. 11, 2003, now U.S. Pat. No. 7,277,752.

BACKGROUND OF THE INVENTION

Sudden death from cardiac causes, often due to heart rhythm abnormalities such as ventricular fibrillation (VF) and ventricular tachycardia (VT), claims approximately 225,000 persons annually in the United States (1999 Heart and Stroke Statistical Update—Dallas: American Heart Association, 1998 or approximately one per 1,000 population per year.

Nationwide, only two to five percent of those who suffer an out-of-hospital cardiac arrest are saved (New England Journal of Medicine 2000; Vol. 343: Pgs. 1259-1260). In gridlocked cities like New York City, analysis of the Emergency Medical Service/Fire Department data has shown that less than 1% survive the ordeal. Because of the abysmal survival rate, the first arrest is almost always the last.

Cardiac arrest is the abrupt cessation of the heart's mechanical function leading to loss of consciousness and the rapidly progressing sequence of heart and brain deterioration, irreversible heart and brain damage, and death. This cessation of mechanical function during an arrest is often caused by a sudden chaotic deterioration in the heart rhythm referred to as ventricular fibrillation (VF) or by the sudden onset of a very rapid and mechanically ineffectual rhythm called ventricular tachycardia (VT). In either case, the heart's normal function can usually be restored by a prompt and properly administered electrical shock to the chest, generally referred to as defibrillation, or by application of synchronized electrical pacing signals.

It has been estimated that once an arrest has occurred the mortality rate increases by 10% per minute until definitive therapy commences. If treatment has not yet commenced ten minutes into a cardiac arrest, there is little likelihood of recovery. The evidence that the response time has a profound influence on the rate of successful resuscitation comes from two types of analysis: a) comparisons among studies in which the response times were different; and b) comparisons within studies, where the results of a short response time are compared to a longer response time, within the same population. The discussion of comparisons among studies follows.

Data from New York City and Chicago illustrate the poor results associated with a long response time. There are an estimated 7,000 incidents of cardiac arrest each year in New York City alone. Emergency Medical Service figures during a five year period—1994-1999—revealed that a total of only 168 patients were successfully resuscitated. The average EMS response time, from the time the service was summoned, was reported to be seven minutes. Based on the 10% per minute mortality estimate, one would expect a 70% mortality for a 7 minute response time. The EMS survival figures are much worse than would be expected based on the ten percent per minute mortality estimate. The reason may be that the time from the event onset until actual defibrillation is substantially longer than the 7 minute EMS dispatch and transit interval. This prolongation includes delays: a) from the moment of onset of arrest until EMS is called (referred to below as the "pre-call" interval); and b) from the time of EMS arrival until life-saving therapy is begun (referred to below as the "pre-shock" interval). Even if the sum of these delays is only three minutes, the expected resuscitation rate plunges to a negligible value, and is consistent with the observed very low survival rate. In Chicago (population over 3 million [linear interpolation of 1980 and 1990 census data]; area 228 square miles) the reported results, though slightly better than in New York City, are poor nevertheless. Becker et al. report that 91.4% of patients were dead on arrival at the hospital; 6.8% died in the hospital and 1.8% were discharged alive (New England Journal of Medicine 1993; Vol. 329: Pgs. 600-606). The response time, defined as the interval from the 911 call to the arrival of the ambulance (referred to below as the "call-to-arrival" interval) ranged from 1 to 22 minutes; the median was 6 minutes.

Improved response times are obtained by so called "code teams" in a hospital setting. An analysis of data from Kaye et al. showed that 9.5% of 210 hospitalized patients who suffered a cardiac arrest survived to leave the hospital (Circulation 1999; Vol. 100: Abstract 1645, page I-314). Eisenberg indicates that survival rates for inpatient cardiac arrests have been reported to range from 0 to 29% (New England Journal of Medicine 2001; Vol. 344: Pgs. 1304-1313). The higher survival rates are attributable to faster reaction times in the hospital environment.

Still better results are reported from King County, Wash., where the emergency response system is unusually sophisticated. Sweeny describes a 30% survival to discharge figure (Annals of Emergency Medicine 1998; Vol. 31: Pgs. 234-240) for this group. Similar results are reported from Rochester, Minn. (1993 population 76,865; area 32.6 square miles); White et al. report the results of 158 cardiac arrests between 1990 and 1995. An analysis of their data, in which the survival to hospital discharge is calculated for all arrest victims shows the value to be 26%. They make a more meticulous effort than some prior investigators to define and measure their response time, and they used the "call-to-shock" interval. Analysis of their data shows the value to be 6.0 minutes. (The aforementioned Chicago data was based on a 6 minute "call-to-arrival" interval. The call-to-shock interval is the sum of the call-to-arrival interval plus the pre-shock interval.)

Gambling casinos are an ideal locale for the analysis of the relationship between response time and outcome for two reasons: a) because of the ultra-high level of scrutiny, the time of onset of arrest can be known accurately; and b) because of the high level of stress for some patrons, the arrest rate is enhanced. Valenzuela et al. report on a program in which casino security officers where trained and equipped to rapidly defibrillate arrest victims (New England Journal of Medicine 2000; Vol. 343: Pgs. 1206-1209). There were 148 patients who suffered a casino cardiac arrest in 10 casinos in Nevada and Mississippi during the years 1997-1999. Fifty six victims (38%) were resuscitated and survived to hospital discharge. The interval from "collapse-to-shock" was 4.4 minutes. It represents a very short response time since it is the sum of: (a) the call-to-arrival interval (used in the Chicago study), plus (b) the pre-shock interval, plus (c) the pre-call interval. (The 6 minute Minnesota result was based on call-to-shock, i.e. (a) plus (b).) The interval from collapse to paramedic arrival was 9.8 minutes, which (without early defibrillation by the security officers) would be expected to result in a negligible survival rate.

The two keys to high arrest survival rates are a short interval from onset of arrest until provision of defibrillator shock, and the presence or rapid arrival of expert medical personnel at the arrest site. The compelling nature of the relationship between response time and success rate is further demonstrated by comparisons within studies.

The Rochester study divided victims with ventricular fibrillation (84 of the 158 arrests) into two groups: one group resuscitated by the police, whose call-to-shock time was a mean of 5.6 minutes, and one resuscitated by paramedics, whose call-to-shock time was 6.3 minutes. The fraction of a minute difference in arrival time impacted the survival rate. In the police group, 58% survived to hospital discharge; in the paramedic group with the slightly delayed arrival time, 43% survived to hospital discharge. (These survival values are larger than the previously mentioned 26% because that value included other arrest victims [i.e., victims with asystole and pulseless electrical activity] who are far less likely to be resuscitated than victims with VF.)

The casino data also gives firm support to the relationship between quick shock and hospital survival. Again, looking only at the VF victims, of those who received their first shock in less than three minutes, 74% (26 of 35) survived to hospital discharge, whereas only 49% (27 of 55) who were shocked after three minutes survived to hospital discharge.

The best results, in terms of resuscitation rate, occur in the hospital cardiac electrophysiology testing laboratory. Here, during the conduct of arrhythmia evaluations (referred to as electrophysiologic studies) in high risk patients, life-threatening VT and VF are frequently encountered. However, because of the presence of trained highly experienced arrhythmia physicians and nurses at the procedure, and because of the very short response time (time from onset of VF until time of shock is usually less than 15 seconds), the resuscitation rate is significantly greater than 99%.

The near 100% resuscitation rate in the electrophysiology laboratory represents an ideal that is not likely to be reproduced outside of the laboratory because:

a) the arrests in such a laboratory are all due to VT and VF, not asystole or pulseless electrical activity;

b) these arrests are artificially induced; hence, they are primary electrical disturbances, not electrical disturbances secondary to some other process, such as the sudden blockage of a coronary artery;

c) the response time is extremely short; and d) doctors and nurses specializing in heart rhythm treatment are present at the procedure.

Nevertheless, the electrophysiology laboratory data does show there is nothing about VF per se that implies its irreversibility. As long as the response time is very short and the VF is not secondary to a sudden catastrophic structural problem (such as the abrupt blockage of an artery within the heart), we can expect a very high success rate. This concept is supported by the resuscitation results in patients with implantable cardioverter-defibrillators, which automatically detect and terminate VT or VF. Their response times and success rates, for spontaneously occurring VT and VF are comparable to those of the electrophysiology laboratory. The high success rate for very prompt termination of VF was confirmed in an entirely different setting. Page et al. report initial termination of VF in 13 of 15 (87%) patients who were treated as part of an effort to provide commercial airliners with defibrillators (*New England Journal of Medicine* 2000; Vol. 343: Pgs. 1210-1216).

As the time until shock increases, two types of events seem to occur which markedly reduce the chance of success. First, there is evidence that the longer the response time, the smaller is the fraction of patients actually found to have ventricular fibrillation. In other words, it may well be that in the moments immediately after an out-of-hospital arrest, the fraction of patients with VT or VF among all arrest victims is high; and that as the minutes go by, that fraction decreases. In the casino study, with its very short response time, 71% of victims had VF. In the Rochester study, with its intermediate response time, 53% had VF. In the Chicago study, with its long response time (since the 6 minute reported response time included only the call-to-arrival component), 22% had VF (calculated from their data). The fraction of victims with VF is important because among arrest causes, VF is far more likely to be treatable than either asystole or pulseless electrical activity. (In the Minnesota study there were 74 non-VF victims; and in the casino study there were 43; none of these non-VF victims were resuscitated.)

The second deleterious event which occurs very quickly during VF is the onset of irreversible mechanical damage to the heart muscle. Once such damage occurs, the chance of survival to hospital discharge plummets. The Minnesota study analyzed this by looking at a predictor of survival that they called "ROSC," restoration of spontaneous circulation. ROSC was defined as present when either no cardiopulmonary resuscitation (CPR), or less than one minute of CPR was required. Victims with ROSC also did not require any medication to support their blood pressure. ROSC was a powerful predictor of survival to hospital discharge. Twenty seven of 28 victims (96%) with ROSC survived to hospital discharge; 14 of 56 without ROSC survived to discharge. The police with their 0.7 minute earlier arrival time had a much higher ROSC rate (42%) than did the paramedics (28%).

Automatic external defibrillators or AEDs were used by the police in the Minnesota study. They were used in the airline study and by the casino security officers. These AEDs are intended for use by minimally trained personnel. AED electrodes, which must be properly placed in contact with a cardiac victim's chest wall, allow the device to analyze the electrocardiogram (ECG) signals of a cardiac victim. Based on the ECG signal information which it receives, the AED automatically applies a high defibrillation voltage to these electrodes when its algorithm detects VT or VF. The decision to shock or not to shock, and the magnitude of the voltage application, are determined by circuitry within the device.

A number of systems are known which provide automatic external defibrillation. Equipment of this type is currently distributed by Medtronic Physio-Control, Philips and Cardiac Science, and may be purchased at a cost of about $2,500-$3,000 per unit. This equipment is now intended to be made available at places such as government buildings, casinos, airports, office buildings and sports arenas, and to be carried upon public modes of transportation such as commercial airliners. There is an increasing effort to have them carried aboard police cruisers.

The advantage of AEDs is that they allow a decreased response time by empowering non-medical people who can arrive sooner than paramedics to treat a cardiac arrest. In the Minnesota study, most police cars carried AEDs; they arrived sooner than the paramedics; and they had better results. In the casino study, cited above, security officers defibrillated with AEDs at a mean of 4.4 minutes after victim collapse; the paramedics arrived at a mean of 9.8 minutes after collapse.

On an airliner, the chance of arrest survival without on-board treatment is nil. The cardiac arrest survival rate in Boston increased from 16% to 24% when the number of AEDs was increased from 85 to 185 and all 1650 firefighters were trained to use AEDs and to perform cardiopulmonary resuscitation (*Circulation* 1998; Vol. 97: Pgs. 1321-1324).

Although AEDs have improved survival by decreasing response time they cannot be considered to be the ultimate solution because they lack certain important advantages that a highly trained medical professional possesses. The transfer of a responsibility, which traditionally lies within the domain of the medical profession, to the AED and its operator results in or fails to completely address seven classes of potential problems:

a) the limitation of proper AED performance to conditions addressed by its algorithm;

b) the necessity of assuring the proper electrical interface between the AED and the victim;

c) the persistence of delays not entirely circumvented by the AED;

d) the problem of CPR administration;

e) the problem of potential AED malfunction;

f) the aggravation of problems (b) through (e) in the event that the user of the AED is untrained or inadequately trained; and g) the potential aggravation of any of problems (b) through (f) by the absence of a highly experienced professional taking charge of the emergency scene.

The seven classes of problems (a) through (g) will now be addressed and discussed in detail.

First, an AED relies on its internal artificial intelligence to make a decision about whether to provide a proper high voltage response for termination of a life threatening heart rhythm. The device must be programmed to anticipate as many situations as possible, and it must be programmed to function appropriately during each of those situations, in order for the automated response to have the intended effect of resuscitating the cardiac victim. The use of the device thus decouples the victim's treatment from the intelligence and judgment of a medical professional who normally administers external defibrillation. This usurpation of the medical professional's role by a machine and its minimally trained or untrained operator may, at times, result in incorrect or delayed responses in just those critical moments which can make the difference between life and death.

AEDs, no matter how complex their algorithms are or will become, are not able to perform properly under conditions which are not explicitly addressed by their algorithms. For example, Kanz et al. (*Circulation* 1999; Vol. 100: Abstract 1641, Page I-313) showed that AED-based rhythm diagnosis was often incorrect in the setting of substantial external electromagnetic interference. When 12 units were evaluated in railway stations, sensitivity ranged from 80 to 100%, and specificity ranged from 38 to 100%. In power stations, the performance was even worse, with both sensitivity and specificity ranging from 0 to 100%.

Other important issues which may not be addressed by an algorithm include the management of the victim who is fully or partially conscious with a tachycardia, and the management of a victim with an implantable cardioverter-defibrillator or ICD. Still other issues beyond the scope of current algorithms involve advanced management considerations such as post-defibrillation treatment.

Sophisticated EMTs will not benefit by carrying AEDs since they would be likely to know far more than the information on which an AED algorithm is based. However, a defibrillator device which provides the EMT with an immediately available medical expert consultant could improve arrest outcome.

The second limitation of AEDs relates to electrode positioning. It is known that correct defibrillator pad positioning and application is very important for successful defibrillation. Errors in positioning and poor electrical contact are not uncommon among inexperienced operators. AEDs do not actively guide the user in appropriate pad placement and application (other than by the provision of a diagram). Nor can they detect or correct for inappropriate positioning and application, once it has occurred. A defibrillator device which could provide such guidance would be highly desirable. Although highly sophisticated electronic means could provide such guidance, a human observer with means for observing pad placement could easily accomplish this.

Third, even partially trained AED users can not be expected to match the skills of a highly trained medical professional. For example, the casino study showed that 0.9 minutes elapsed from the time of defibrillator attachment until the time of first shock. A medical professional could accomplish this action in a fraction of this time. A defibrillator device which lets a remote ultra-sophisticated medical professional deliver the shock would therefore save time, when compared with the casino scenario.

Fourth, an AED does not coach an untrained bystander in the performance of CPR. Although CPR is not required in arrests of short duration, the need for it increases as the arrest duration increases. CPR was administered to some patients in the Minnesota study and in the casino study. The improved results in Boston were concomitant with not only an increase in available AEDs but with firefighter CPR training as well. Ewy, in discussing successes with a limited form of CPR which involves chest compression without ventilation, points out that rapid defibrillation and bystander initiated CPR are the major determinants of survival of a VF arrest (*New England Journal of Medicine* 2000; Vol. 342: Pgs. 1599-1560). A defibrillator device which could provide CPR instruction and guidance would be very advantageous. Although instruction prior to CPR could be automated, the processes of guidance during CPR and of suggesting corrective maneuvers during CPR, are far more easily accomplished by a human coach than by an algorithmic one.

Fifth, occasional malfunction of any electrical device is inevitable. Sweeny (cited above) noted seven instances of apparent AED malfunction out of 260 uses. It is far more likely that a medical professional who (i) has expert knowledge of a sophisticated defibrillator device and its backup systems, and (ii) constantly monitors the functioning of the defibrillator device during its operation, would be able to work around a device malfunction. (In the Sweeney study, use of AEDs in a Charlotte, N.C. EMS program did not result in outcome improvement.)

Sixth, in each of the reports cited herein, in which AEDs were used, their use was by a trained operator. It is inevitable that an untrained user will perform less accurately and take more time to do so. However, given that: (i) the ideal response time after an arrest would be even less than that during the casino study (in which victims were essentially under constant observation), and that (ii) the police or fire department response time is unlikely to ever be shorter than the casino response time; then the only likelihood of achieving the requisite ultra-short response time is by having a device that can be used by an entirely untrained bystander. Such a device would have to be more user-friendly than an AED. Such a device would have to be capable of both: (i) defibrillation, and (ii) closely linking an untrained bystander with an expert medical professional who could guide him through every aspect of the resuscitation process. AEDs do not meet this requirement. Indeed, the AEDs which have been installed to date typically display a warning to the potential user that the device is intended for use by trained personnel only.

Finally, since the aforementioned ideal external defibrillator device will require some level of participation by a human enabler (that is, a non-medically trained person who is available to use the device to defibrillate a victim of cardiac arrest), the creation of an environment in which the enabler functions optimally is critical. AEDs cannot address the anxiety or reluctance of an individual operator and may, in fact contribute to these. The cumulative effect of such feelings among a group of bystanders, may contribute to the chaos and pandemonium which not infrequently accompany a cardiac arrest. On the other hand, the voice of an experienced medical professional, taking charge, providing instructions, and making decisions, is often a great source of reassurance and stability, giving the assurance of proper conduct. AEDs cannot provide this human element.

Clearly, once a patient has suffered and survived an initial, lifethreatening cardiac event, that patient must be monitored closely so that the proper treatment may be brought to bear on an emergency basis. The U.S. Pat. No. 5,544,661 to Davis et al. discloses a patient monitoring system which includes a portable device, attached to a patient, and a central station. The portable device includes an ECG and a photo-plethysmograph connected to the patient, and an arrhythmia analysis circuit which includes an expert system for determining whether pre-established critical parameters have been exceeded. The portable device also includes a wireless wide area communication circuit for automatically contacting the central station via a public cellular telephone network when the expert system determines that assistance is needed. When the central station is contacted, the patient's ECG waveforms, measurements and trends are sent to the central monitoring station and a two-way voice channel between the patient and the central station is automatically opened. The central station includes a computerized facility from which a clinician can observe both the real time data being sent from the patient and the patient's historical records. The clinician can talk to the patient through the two-way voice channel and can also activate therapeutic devices attached to the patient such as an external defibrillator, a pacer or an automatic drug infusion device.

Similarly, the U.S. Pat. No. 5,564,429 to Born et al. discloses a cardiorespiratory alert system which comprises a patient unit, a base station and a remote unit. In a hospital configuration, several patient units can communicate with the base station, which is located centrally, for example at a nurse's station. In a home configuration, the base station can reside near the patient's bedside. In both cases, the communication between the patient unit and the base station is by way of radio telemetry. The base stations are designed to communicate with a remote unit, either by radio telemetry or by use of commercial telephone lines.

The system provides alerts to the remote unit when life-threatening conditions are detected in a patient, yet it is tolerant to the presence of artifact so that false positive alerts are reduced.

Upon sensing a life-threatening condition, a "caregiver", who staffs the remote unit or "dispatcher station", may remotely activate various devices, including an external defibrillator, pacer and drug infusion device, and/or may contact an EMS unit in the patient's immediate locale, in an attempt to save the patient's life.

The subject matter of both the U.S. Pat. Nos. 5,544,661 and 5,564,429 is incorporated herein by reference.

The systems disclosed in these two patents require that the portable patient unit be worn at all times so that ECG and other patient critical information can be continuously monitored. These systems cannot be used in a normal emergency situation where a patient has no advance warning of a cardiac event and is therefore neither prepared nor monitored by a lifesaving system. The U.S. Pat. No. 5,184,620 discloses a method of monitoring a patient's cardiac activity using a so-called "electrode pad" having a plurality of electrode sites which, upon placement against the patient's chest wall, provide ECG signals for determining if cardiac pacing and/or defibrillation is required. Certain combinations of electrodes provide the path for pacing signals whereas other combinations provide a path for defibrillation current.

The U.S. Pat. Nos. 5,593,426 and 5,782,878 (which have a similar disclosure) disclose a "communicator" for connecting each of a plurality of automatic external defibrillators ("AEDs") to a central communication station. The central station receives information from an AED, such as patient ECG data and defibrillator operation data, and transmits information, such as use instructions for a bystander, to this AED.

The U.S. Pat. No. 4,102,332 describes a portable defibrillator, with a preprogrammed dialer, that telephones a physician when activated by a patient. While the physician and patient communicate with each other via the defibrillator's communication system, the physician can control the operation of the defibrillator from his or her remote location. During use, the defibrillator sends operation and status data to the physician.

The U.S. Pat. No. 6,141,584 discloses an automatic external defibrillator (AED) which is capable of storing ECG data and defibrillator data and "handing off" this data, via an infrared link, to equipment of emergency medical personnel when they arrive on the scene of a cardiac arrest.

The U.S. Pat. No. 6,148,233 discloses a wearable automatic external defibrillator; that is, a defibrillator which is worn by a patient having one or more contact electrodes attached to the chest wall of the patient for transmitting defibrillation energy to the patient and for receiving ECG information from the patient. This patent is directed specifically to the contact electrode(s) which can be worn by a patient for a relatively long time without skin irritation or damage. This system is designed for patients who have previously experienced cardiac arrhythmias but are, perhaps, not ready for an implanted defibrillator/pacer.

Finally, there are numerous patents which relate to ICDs. Such devices, which are also a form of automatic defibrillator, are in constant electrical communication with the human heart. When implanted, such ICDs operate independently, without external controls, to treat ventricular fibrillation (VF), ventricular tachycardia (VT) and supraventricular arrhythmias by applying one or more voltage pulses to the heart.

In their formal definitions, cardioversion refers to the delivery of a shock which is synchronized to the heart's electrical activity and defibrillation refers to an asynchronous shock. For simplification, unless otherwise noted, either one of the terms cardioversion and defibrillation shall hereinafter be referred to as simply defibrillation, and either one of the terms cardiovertor and defibrillator shall hereinafter be referred to as simply defibrillator. Such simplification is not intended to narrow the scope of the invention described herein, but is merely for the purpose of avoiding repeated use of the respective lengthy and rather awkward medical terminology.

SUMMARY OF THE INVENTION

It is a principal object of the present invention to provide the services and superior ability of a highly-skilled medical professional (as compared to a fully automated apparatus) for diagnosing and treating cardiac arrest or any other cardiac rhythm abnormality. As used hereinafter, the term cardiac arrest is intended to include, and shall include, all types of cardiac rhythm abnormality.

It is a further object of the present invention to provide a system which can markedly decrease the response time of a medical professional to a cardiac arrest by facilitating lifesaving electrical therapy to the heart before the arrival of an emergency medical service or any other trained personnel.

It is a further object of the present invention to provide a system for resuscitation after the onset of cardiac arrest which affords: a) a degree of communication redundancy; b) a network of backup systems; and c) a certainty of execution of operator commands which are required for practical operation of the system by a remote medical professional.

It is a further object of the present invention to provide a system for resuscitation after the onset of cardiac arrest which can operate completely automatically in the event of a telecommunication breakdown or other fault which prevents a medical professional from using his or her judgment to control the operation of a defibrillator and/or pacing unit.

It is a further object of the present invention to allow a skilled medical professional to remotely monitor and manage a cardiac arrest which may occur at one of a plurality of remote sites, thus alleviating the anxiety and avoiding the pandemonium which often accompany the typical cardiac event. This skilled medical professional would be able to maintain a standard of care that an untrained or minimally trained AED user could not.

It is a further object of the present invention to provide a Universal Pad which may be used to apply multiple cardiac monitoring, pacing and defibrillation electrodes to the chest wall of a cardiac victim.

These objects, as well as further objects which will become apparent from the discussion that follows, are achieved, in accordance with the present invention, by providing a cardiac monitoring and external defibrillation system which comprises a central station and a plurality of remote, emergency site portable units, and a means for the central station to communicate with and control the remote site portable units. Once a remote site portable unit is attached to a victim of a cardiac arrest, the central station is capable of displaying selected items of real-time cardiac information for a human operator, in particular a medical professional, and issuing control signals, at the command of the medical professional, for controlling the application of defibrillation pulses to the victim. Prior to and after defibrillation pulses are applied, cardiac and possibly respiratory information is received from the cardiac victim at the remote site for evaluation by the medical professional. This information and information documenting all actions taken by the medical professional is automatically stored for subsequent download to an emergency medical team (EMT), a hospital, or other medical facility which eventually becomes responsible for care and treatment of the victim. Throughout the process of emergency care, the medical professional can communicate by voice and/or video and/or displayed text to instruct the emergency site enabler and to receive information from the enabler about the victim.

In particular, each of the plurality of remote sites is provided with an emergency cardiac monitoring and external defibrillation apparatus in the form of a portable unit. This apparatus includes a variety of means to apply contact electrodes to the chest wall of the cardiac victim. One such means is a Universal Pad; that is, a semi-rigid, flexible pad, adapted to be placed on the chest wall of a cardiac victim, which incorporates a plurality of cardiac contact electrodes at suitable positions for monitoring ECG signals and applying defibrillation and/or pacing pulses to the victim.

The portable unit at the remote site also includes a transmitting/receiving device for sending cardiac and respiratory information to, and receiving control signals from, the central station and for sending and receiving voice, text and video.

The remote site portable unit also includes a defibrillator circuit, connected to the contact electrodes for applying high voltage defibrillation pulses to these electrodes in response to defibrillation control signals received from the central station. The remote site apparatus may include a cardiac pacing circuit, connected to the contact electrodes for applying lower voltage cardiac pacing pulses to these electrodes in response to pacing control signals received from the central station.

The cardiac monitoring and external defibrillator system, according to the invention, provides and incorporates a number of advantageous features. These include:

Enabling the medical professional at the central station to decide whether the situation merits use of the emergency apparatus at the remote site;

Enabling the medical professional to summon the local emergency medical service (i.e. by contacting the "911" emergency service in the locale of the remote site);

Enabling the medical professional to direct the initial application of the Universal Pad and/or other contact electrodes on the victim's body;

Enabling the medical professional to direct a subsequent application of the Universal Pad and/or other contact electrodes when the initial therapy did not succeed for any reason; for example, due to incorrect placement of the electrodes or due to anatomic or other considerations.

Enabling the medical professional to compensate for less than perfect orientation of the electrodes applied to the victim's chest wall without reapplying the Universal Pad;

Enabling the medical professional to view the victim's ECG and make a rhythm diagnosis whose accuracy can exceed the best algorithm of fully automated defibrillation equipment;

Enabling the medical professional to make a determination as to whether any one or more of the contact electrodes are making poor contact with the victim's chest wall, and to compensate for such poor contact;

Enabling the medical professional to defibrillate along different spatial axes, and/or different points on the victim's body, thereby increasing the chance of a successful outcome during a cardiac arrest;

Enabling the medical professional to deliver alternate therapies including pacing;

Enabling the medical professional to decide whether high energy shock, low energy shock, pacing and/or CPR, or perhaps no therapy at all, is appropriate;

Enabling the medical professional to control multiple parameters of electrical therapy including voltage, pulse width, pulse shape, pulse energy and timing;

Enabling the medical professional to instruct the enabler in the proper CPR technique;

Enabling the medical professional to monitor and, if necessary, correct the enabler in the proper performance of cardiopulmonary resuscitation (CPR);

Enabling the medical professional to assess the victim's respiratory and blood pressure status;

Enabling a single medical professional to supervise a plurality of enablers at different cardiac arrest scenes;

Enabling a medical professional to triage the supervision of simultaneously occurring cardiac arrests to other medical professionals;

Enabling the medical professional to avoid chaos, panic, inaction, delayed action or inappropriate action by allowing this medical professional to supervise emergency scene enablers;

Enabling the medical professional to release a lock holding the portable unit to a wall or to another stationary object, or to a wall-mounted stationary unit at the remote site of the cardiac arrest;

Enabling the medical professional to see a victim of cardiac arrest, an enabler at the scene, the placement of cardiac electrodes on the victim's chest as well as the administration of CPR;

Enabling the medical professional at the central station, and/or the system itself, to diagnose a failing component or group of components of the system and to bypass or provide a substitute for these components;

Enabling the medical professional at the central station, or the system itself, to assess the existence and/or maintenance of proper communication between the central station and the remote site of the cardiac arrest and to remediate any problem by switching a communication channel, route or modality in any segment of the communication links;

Enabling the medical professional to utilize communication modalities other than voice, such as text and/or video;

Enabling the medical professional to receive a confirmation signal that a command, such as a command to defibrillate with a specific shock energy and with specific cardiac electrodes, was duly executed;

Enabling the medical professional to receive error signals indicating that a command was not properly executed or that either the remote equipment or the central station has malfunctioned;

Enabling the medical professional, and/or the system itself, to switch to an AED backup if necessary;

Enabling the medical professional, and/or the system itself, to transfer control of the portable unit to an emergency medical team, if necessary and if appropriate;

Enabling the medical professional to properly identify emergency medical personnel, before transferring control of the portable unit to such personnel;

Enabling the medical professional to properly brief emergency medical personnel on events which transpired before their arrival at the scene of the emergency;

Enabling the medical professional to assist emergency medical personnel during and after a cardiac arrest by accessing databases which may contain information about the victim and/or his medications and/or his implanted pacemaker or defibrillator (if any);

Enabling the medical professional to assist emergency medical personnel during and after a cardiac arrest by monitoring the victim's cardiac and respiratory status;

Enabling the medical professional to assist emergency medical personnel during and after a cardiac arrest by providing advice and guidance concerning the medical management of the victim;

Enabling the medical professional to assist emergency medical personnel during and after a cardiac arrest by providing advice and guidance concerning the operation of the portable unit;

Enabling the medical professional or other trained personnel to supervise the reattachment of the portable unit to the wall or to the stationary unit or its return to the position in which it was located prior to the cardiac arrest;

Enabling the medical professional or other trained personnel to supervise the restocking of the portable unit;

Enabling the medical professional or other trained personnel to visually inspect the portable and stationary units;

Enabling the medical professional or other trained personnel to assess the electrical and mechanical functioning of the portable and stationary units;

Enabling the medical professional to maintain a complete, secure, encrypted record of the events and data related to a cardiac arrest;

Enabling the medical professional to transmit information concerning the arrest in a secure, encrypted manner, in accordance with local and federal statutes and regulations;

Enabling the medical professional to control the function of an implanted medical device;

Enabling the medical professional to work with a foreign language speaking enabler via an interpreter, or a computer program which performs such function; and Enabling the medical professional to deal with a potential prankster or vandal by visually identifying such individual.

According to a particular feature of the invention, the emergency cardiac monitoring and external defibrillation apparatus, which is disposed at each of a plurality of remote sites, is divided into two separate units:

(1) a stationary unit, adapted for permanent installation at the remote site, which is capable of communicating with the central station and has a transmitting/receiving device for electronic communication with a portable unit; and (2) a portable unit, releasably attached to the stationary unit, which has a transmitting/receiving device for electronic communication with the stationary unit.

The portable unit and the stationary unit are joined together by a releasable lock which is controlled from the central station by a portable unit release signal. When the medical professional determines that an enabler should take the portable unit to the side of a cardiac victim, he may generate and transmit the portable unit release signal.

Advantageously, the portable unit is provided with a sensor for sensing when it has been released from attachment to the stationary unit. The portable unit is preferably also provided with a sensor to sense when the portable unit has been placed on the floor next to a victim with a proper orientation of the unit (i.e., with the proper side up).

According to a particular feature of the present invention, the stationary unit comprises a battery charger and the portable unit comprises a battery for powering the electronic circuits therein. When the portable unit is attached to the stationary unit, the battery charger maintains the battery in a charged condition. The stationary unit may also be provided with a battery backup to safeguard against a power failure.

To initiate the operation and to alert the medical professional, the portable unit is preferably provided with a button, to be pressed by someone (e.g., a bystander) in the vicinity of the victim, in the case of a medical emergency. This button may, for example, have a large red cross and/or the words "MEDICAL EMERGENCY" imprinted thereon. The person who presses this button, and then becomes an "enabler", facilitates or "enables" the resuscitation of the victim under the direction of the medical professional. Pressing the button initiates the communication process between the enabler and the medical professional.

Although the preferred communication modality is from portable unit to and from stationary unit by radio frequency, and from central station to and from the stationary unit via public access telephone company land line, the medical professional or the system can, if desirable, select an alternate route. Examples of such selections would include using a radio frequency link between the central station and the stationary unit, or bypassing the stationary unit, with a link from the portable unit to the central station. Furthermore, although the public telephone network may be used, a private network or the Internet could also be used.

In a preferred embodiment the system initially establishes proper function of the communication components, which link the central station and the portable unit during the first step or layer of a handshake routine. A series of such handshakes occurs, each incorporating the previous one and each encompassing a larger circle of sub-systems, until there is complete informational exchange between the medical professional and the enabler. Such handshakes are utilized throughout the duration of the cardiac arrest to ensure robust and reliable communication between the medical professional and each of the enabler, the victim (in which case the communication consists of an electrical link) and the emergency medical team. Each handshake is rendered least likely to fail by the availability of multiple levels of backup systems Once the basic communication handshake has been effected, the proper functioning of the next layer of components is quickly confirmed. This layer includes the ability of the system to send and receive voice and data in each direction, the ability of the medical professional to properly transmit commands, and the proper receipt of the commands by the portable unit. Diagnostic features within the system allow for the identification of and substitution for a failing sub-system or sub-unit within either the central station, the stationary unit or the portable unit. Such identification and substitution may be performed with or without the active participation of the medical professional.

Thereafter, according to a particular feature of the present invention, the handshaking is extended to include actual communication between the medical professional and the enabler. In particular, the medical professional will attempt to verbally communicate with the enabler in the local language.

According to a preferred feature of the invention, at least voice communication is made available between the portable unit and the central station. Advantageously, the words spoken by the medical professional are displayed as text on the portable unit so that the enabler may see as well as hear the instructions given. A video link is also desirable and, in accordance with a preferred feature of the invention, the medical professional at the central station is provided with a device for remotely controlling the orientation of a video camera on the portable unit, so that the medical professional may best see the enabler, the victim and even the portable unit itself. To facilitate hands-free voice communication with the enabler at the remote site, the portable unit is preferably provided with a microphone and loudspeaker, and with a headset which contains earphone and microphone.

In the event that proper communication between the medical professional and the enabler can not be established and/or maintained, backup AED function is available. The portable unit will select the AED function if either the initial handshake fails, or if there are either substantial interruptions to, or degradation of a previously established communications link. AED control can also be selected by the medical professional if he deems the quality of the communications link to be inadequate.

The medical professional may continue to monitor an event even though control may have been handed over to the AED. If the medical professional later finds that robust communication has been re-established, he may resume and take control back from the AED. In such a case, the medical professional would be able to securely download the encrypted information pertaining to any gap in the data/event sequence, from the data storage unit within the portable unit.

A master control unit within the portable unit selects which person, or which circuitry controls the executive functioning of the portable unit. When communication with the central station is established, the master control unit lets the medical professional control executive functioning. A communications failure results in the AED having control. When one or more members of an emergency medical team is/are present, the master control unit is designed to give this team the opportunity to control the portable unit. Yet another function of the master control unit is to allow a remote person to perform diagnostic testing and information exchange with the portable unit.

Following the initial establishment of communication between the medical professional and the enabler, the medical professional may ask the enabler for a description of the event and may thereby decide whether release of the portable unit from the stationary unit is appropriate. Thereafter, if and when the portable unit is released, the enabler may be directed to carry the unit to the victim's side.

At this point the medical professional may instruct the enabler as to the proper selection, positioning and application of the contact electrodes and/or the Universal Pad.

Once the electrodes have been applied, the medical professional will begin to receive and review ECG data from the victim. Based on this information the medical professional will use his judgment to decide upon the proper initial therapy. For example, the medical professional may decide to apply a defibrillation pulse of a particular energy and waveform through a particular combination of electrodes. Alternatively, the medical professional may decide that pacing is a more appropriate therapy or that no electrical therapy is needed.

After the administration of the initial electrical therapy the medical professional will reassess the condition of the victim, by using the transmitted ECG and other transmitted data, and decide upon the next step.

In particular, if the first therapy was either unsuccessful, partially successful or transiently successful, the medical professional may elect to either repeat the identical therapy or to modify it, either qualitatively or quantitatively. For example, if a 100 joule shock applied between one particular pair of electrodes (e.g., specific ones of the electrodes on the Universal Pad) was unsuccessful, the medical professional might then elect to apply a 150 joule shock between a different combination of two or more electrodes on the Universal Pad.

In order for a medical professional to properly and safely administer remote therapy during an emergency situation, he needs to receive reliable confirmation that each command: a) was properly sent from the central station; b) was properly received at the remote site; and c) was properly executed. With a confirmation system in place, if a command for a particular therapy is not followed by the restoration of a normal rhythm, the medical professional can conclude that the therapy itself failed; rather than having to consider the possibility that treatment failure may have resulted from a failure of the system to actually render the medical professional-directed treatment.

Cardiopulmonary resuscitation (CPR) can substantially improve the outcome of certain cardiac arrests, especially if electrical therapy does not rapidly restore normal cardiopulmonary function. If and when the medical professional feels that CPR is a desirable adjunct to electrical therapy, he may instruct or coach the enabler in proper CPR technique. The instruction may be via video and/or audio transmission from the central station to the portable unit during the arrest.

At the time that the portable unit is released, the cardiac monitoring system according to the invention may automatically contact the local emergency unit. When such emergency personnel arrive, the medical professional can hand off some or all responsibility to the on-scene emergency medical team (EMT), after the EMT has been properly identified.

For this to occur, the medical professional would issue a command to the master control circuit. This would convert the portable unit into a manually controlled device. The medical professional could then continue to observe and advise in such a situation.

In addition to monitoring ECG signals from the victim, the portable unit may be provided with a blood pressure measuring device (e.g., an automatic cuff for measuring systolic and diastolic pressure of the victim); and/or a pulse oximetry monitoring device for measuring the blood oxygen content of the victim.

As used herein, the term "pulse oximetry" is intended to include the measurement of any blood gases (oxygen, carbon dioxide and the like), blood pH, blood sugar or any other blood component.

According to a further aspect of the invention, the Universal Pad is a multi-electrode pad which includes five defibrillator electrodes arranged in two separate rows with two electrodes in a first, upper row and three electrodes in a separate, lower row. These electrodes may be used in combinations of two or more for defibrillation, pacing and/or ECG recording. Advantageously, a plurality of ECG electrodes, which are smaller than the defibrillator electrodes, are distributed adjacent to the five defibrillator electrodes; These electrodes may be used in combinations of two or more for ECG recording. Alternatively, ECG recording may be accomplished using a mixture of defibrillator electrodes and ECG electrodes.

In another embodiment of the Universal Pad, the electrodes are arranged in a matrix of many separated electrodes. This gives the medical professional additional flexibility in selecting combinations of two or more electrodes to which defibrillation and/or pacing pulses are to be applied and from which ECG signals are to be received.

Other arrangements of contact electrodes, adapted for application to the victim's body, may also be used. For example, the portable unit may be operated with two or more standard individual contact electrodes for receiving ECG signals and applying defibrillation and/or pacing pulses.

According to a particular feature of the present invention, the Universal Pad, or any of the contact pads, may be provided with a protective and insulating backing that is peeled off prior to use. Means are provided to signal to the medical professional at the central station when the backing is peeled off. When the backing is peeled off, the medical professional is informed as to which electrode pad, from among a variety of pads with different electrode configurations, is actually being used by the enabler.

According to a particular feature of the invention, the male and female versions of the cable connectors which link the electrode pads with the portable unit, hereinafter referred to as Universal Connectors, allow a number of advantageous features. These include: a) the ability to attach any of a variety of electrode pads which terminate in a female Universal Connector, to any male Universal Connector of the portable unit; b) the ability of the medical professional to know which (if any) particular variety of pad is attached to each of the portable unit Universal Connectors; and c) the ability of the medical professional to know when the backing material has been removed from an electrode pad.

According to a particular feature of the invention, a video system is provided which serves the following functions:

a) If one way video is provided from the portable unit to the central station:
 (i) It lets the medical professional view an incorrect pad orientation and advise the enabler to correct it.
 (ii) It lets the medical professional directly visualize the victim for diagnostic and management purposes: state of consciousness, presence of seizure activity, head positioning.
 (iii) It allows the medical professional to give advice concerning CPR technique.
 (iv) It is useful for ruling out a prankster, in the event that initial button press is followed by absent, inadequate or inappropriate verbal response from a potential enabler.
 (v) During a system diagnostic check, the video camera may be oriented to inspect the physical integrity of the portable and stationary units.

b) If two way video is provided between the portable unit and the central station:
 (i) It allows the medical professional to illustrate proper defibrillator pad positioning and orientation. The correct position and orientation could be shown as a cartoon or virtual image superimposed on the actual image of the victim.
 (ii) It allows detailed illustration of CPR technique. This too could be superimposed or overlaid onto the actual image of the victim.
 (iii) It can help the medical professional to identify various components of the system to the enabler by displaying them.
 (iv) It can help the medical professional to instruct the enabler as to the application of blood pressure measuring, pulse oximetry and ancillary paraphernalia included in the tool-kit of the portable unit.
 (v) An image of the medical professional may have a reassuring effect upon the enabler and upon other bystanders.

In another preferred embodiment of the present invention, the medical professional may guide a person who is returning the previously used portable unit to the location in which it is intended to remain when not in use. Such guidance may include: a) information about replacing and restocking components of the portable unit tool-kit; b) information about the location to which the portable unit must be returned; and c) positioning and orienting information to allow the portable unit to be properly attached to a stationary unit or stationary lock.

In another preferred embodiment of the invention a global positioning system within the portable unit may allow the medical professional to know the location of any such portable unit. This would facilitate the medical professional's ability to keep track of the location of each portable unit, especially if it has been transported to a substantially different location during or after its use. It would also let the medical professional ascertain the location of an en-route EMT, if the EMT was transporting a portable unit which was equipped with a global positioning system.

In another preferred embodiment of the present invention, the central station and/or the emergency defibrillation apparatus disposed at the remote sites include a storage device which stores the ECG signals and possibly other data received from the victim and the control and other signals transmitted from the central station. In addition, the voice, text and video communications may be stored for later review. In this way, a cardiac arrest "event" can be analyzed and reviewed for later instructional, medical and legal purposes. Such storage, review and analysis would be in compliance with pertinent local and federal statutes and regulations.

A still further advantageous feature of the present invention includes providing means at the portable unit (such as a keyboard, real or virtual) to permit communication with the central station by text, in the event of breakdown in voice communication. As already mentioned above, the instructions of the medical professional at the central station, which are normally transmitted by voice, can be displayed in text at the portable unit. Another alternative communications interface with the enabler would include portable unit or central station initiated voice prompts and/or speech recognition.

According to a particular, advantageous feature of the present invention, means are provided at the portable unit to transmit control signals to and receive data signals from an ICD or a pacemaker, which has been previously implanted in the victim's chest. In this way, a medical professional may attend to the emergency medical needs of this type of victim as well. In this case, the contact electrodes which receive ECG signals and which transmit defibrillator and/or pacing pulses to the heart have already been implanted, thus eliminating the need for an enabler to place any contact electrodes on the victim's chest.

According to a particular feature of the invention, communication between the portable unit and the central station may traverse a route in which there may be more than one stationary unit and/or one or more additional portable units, with each of said stationary units and said additional portable units functioning as a repeater, i.e. as a communications relay.

Finally, it is contemplated that in a large, extensive system with many portable units at various remote sites more than one cardiac arrest may occur simultaneously. Accordingly, the invention provides means for: a) a single medical professional supervising multiple simultaneous arrests; b) one central station with multiple attendant medical professionals and a means for triaging the supervision of cardiac arrests among them; and c) a network of central stations, each with one or more attendant medical professionals, and a means for triaging the supervision of cardiac arrests among them.

For a full understanding of the present invention, reference should now be made to the following detailed description of the preferred embodiments of the invention as illustrated in the accompanying drawings.

BRIEF DESCRIPTION OF THE DRAWINGS

FIG. 5A is a front elevational view of a preferred embodiment of a "Universal Pad" which may be used with the cardiac monitoring and external defibrillation system according to the present invention to apply contact electrodes to the chest wall of a victim.

FIG. 5C is a front elevational view of a second alternative embodiment of a Universal Pad according to the present invention.

FIGS. 16B and 16C, taken together, are a flow chart illustrating the process by which the medical professional releases the locking mechanism which attaches the portable unit to the stationary unit.

FIG. 21 is a table and flow chart illustrating the various possible treatments when a victim's condition, based on information the medical professional receives, is less severe than cardiac arrest.

FIG. 44 illustrates a touch-sensitive display screen at the central station for assessing confirmation and error signals.

FIGS. 55A and 55B are flow charts showing the diagnostic checking routine for the portable unit.

DETAILED DESCRIPTION OF THE PREFERRED EMBODIMENTS

Contents

Figure 1:
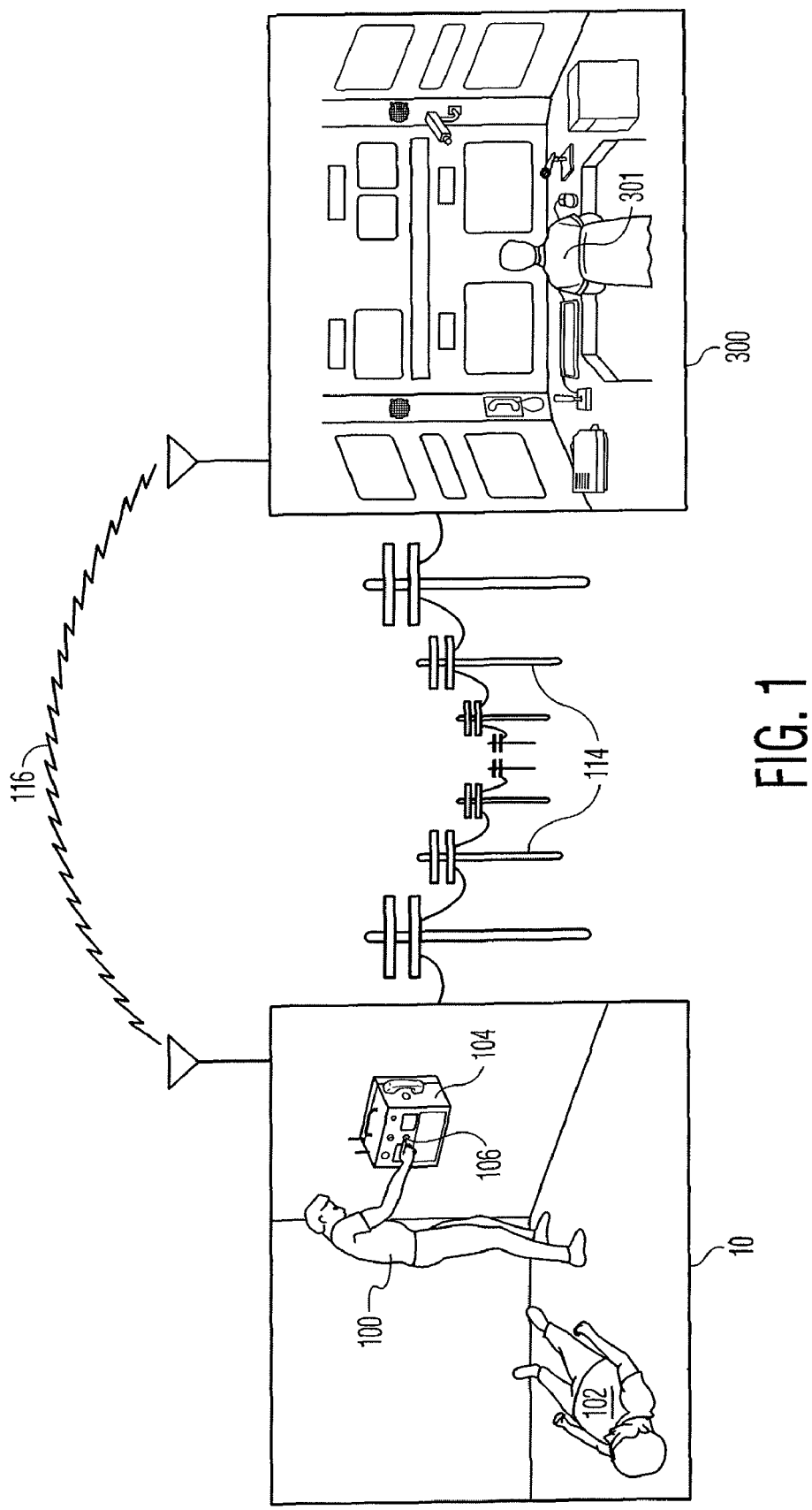
FIG. 1 is a representational diagram of the scene of a medical emergency and of a central station, each equipped with the resuscitation system according to the present invention.

1. System Overview
    1.1 Description of the Emergency Scene
    1.2 Description of the Central Station
    1.3 Block Diagram of the System
        1.3.1 Two Unit System: Portable Unit and Central Station
            1.3.1.1 System Operation when PU-CS Link is Intact
            1.3.1.2 AED Backup in the Event of Communication Failure; Role of the Master Control Unit
        1.3.2 Three Unit System: Portable Unit, Stationary Unit and Central Station
    1.4 Figure Assignments 2. Portable Unit and Stationary Unit: Exterior Elements
   2.1 Portable Unit: Front and Right Side Panels
   2.2 Portable Unit: Tool-kit
   2.3 Portable Unit: Rear and Left Side Panel
   2.4 Stationary Unit: Front and Side Panels
   2.5 Portable Unit: Screens
3. Electrode Pads
   3.1 Physiology of Defibrillation
   3.2 Torso-Shaped Multi-electrode Pads
   3.3 Matrix Electrode Pad
   3.4 Single Electrode Pads
4. Sample Cardiac Arrest and System Operation
   4.1 Overview of Sample Arrest
      4.1.1 Phase One: Initial Enabler Action
      4.1.2 Phase Two: Handshakes Linking Enabler and MP
         4.1.2.1 Role Played By Handshakes; Relationship Between Handshakes and Backups; Relationship Between Handshakes and Links
         4.1.2.2 Backup Systems for a Failed Handshake
         4.1.2.3 Four Handshakes which Link the Enabler and the MP
            4.1.2.3.1 The Communication Handshake
            4.1.2.3.2 The Data/Commands Handshake
            4.1.2.3.3 The Audio Handshake
            4.1.2.3.4 The Informational Handshake
         4.1.2.4 Role of the Stationary Unit in the Handshake Protocol
            4.1.2.4.1 Single Direct Link Between PU and CS as the Default Routing Approach; Stationary Unit Functions as a Backup
               4.1.2.4.1.1 Direct PU-CS Link Can Not Be Established; Failure of One But Not Both Possible PU-SU Connections; Successful SU-CS Connection
               4.1.2.4.1.2 Direct PU-CS Link Can Not Be Established; Failure of Both Possible PU-SU Connections and/or Failure of SU-CS Connection
            4.1.2.4.2 Two Connections: One from PU to SU and One from SU to CS as the Default Routing Approach
               4.1.2.4.2.1 Two-Segment Default; Initial PU-CS Link Successful
               4.1.2.4.2.2 Two-Segment Default; Initial PU-CS Link Unsuccessful
            4.1.2.4.3 Redundant Links, in which There is Both a Direct PU-CS Link and an Indirect PU-SU-CS Link
            4.1.2.4.4 More Elaborate Routes for the PU-CS Link
            4.1.2.4.5 Depth of Handshake Layers
      4.1.3 Phase Three: Transport of PU to Victim; Victim-MP Handshake; PU Setup at Victim's Side
         4.1.3.1 PU Release and Transport
         4.1.3.2 Handshakes Linking Victim and MP
            4.1.3.2.1 The Four Layer Victim-MP Link
            4.1.3.2.2 Backup Systems for Failure in the Victim-MP Link
         4.1.3.3 MP Commands, Confirmation Signals and Error Signals
         4.1.3.4 Telemetry Signals
      4.1.4 Emergency Medical Management of the Cardiac Arrest by the Medical Professional
         4.1.4.1 Defibrillation and Pacing by the MP
         4.1.4.2 Other Actions Directed by the MP to Support Blood Pressure
      4.1.5 Phase Five: Management Immediately Post Electrical Resuscitation
      4.1.6 Phase Six: EMT Arrival, Transfer of Control of the PU from MP to EMT
         4.1.6.1 EMT Choices Other Than Assuming Control of the PU Currently Attached to the Victim
         4.1.6.2 Handshakes Linking EMT and MP
            4.1.6.2.1 First and Second Layers of EMT-MP HS: Password which Gives Control of PU to EMT, Rather Than Giving Control of PU to AED/P
            4.1.6.2.2 Third and Fourth Layers of EMT-MP HS
      4.1.7 Management by the EMT, after Transfer of PU Control to the EMT, by the MP
         4.1.7.1 Transfer of PU Control
         4.1.7.2 Briefing of EMT by MP
         4.1.7.3 Method of PU Operation by the EMT
         4.1.7.4 MP Role During EMT Use of the PU
            4.1.7.4.1 Medical and Technical Support by the MP
            4.1.7.4.2 Pharmacologic Support by the MP
      4.1.8 MP Role After Victim Arrives at the Hospital
   4.2 Sample Cardiac Arrest: Correspondence Between Events During the Arrest, Flow Diagrams, Screens, Handshakes and Confirmation Signals
   4.3 Role of the Medical Professional
      4.3.1 Expert Decisions Made by the MP During the Cardiac Arrest
         4.3.1.1 MP Decision to Change the Defibrillation Vector for the Second Shock
         4.3.1.2 MP Distinction Between Asystole and Ventricular Fibrillation
         4.3.1.3 MP Action to Improve Victim's Blood Pressure
         4.3.1.4 Other MP Decisions Requiring Medical Expertise
      4.3.2 Enabler Guidance by the MP
         4.3.2.1 Enabler Guidance in Proper Application of the Electrode Pad
         4.3.2.2 Enabler Guidance in Cardiopulmonary Resuscitation
         4.3.2.3 Enabler Guidance in Other Activities
      4.3.3 EMT and Physician Guidance by the MP
   4.4 Time Allocation During the Sample Cardiac Arrest
      4.4.1 General Considerations Regarding Prediction of Duration
      4.4.2 Enabler Travel Time
      4.4.3 Duration of Other Enabler Tasks
      4.4.4 Time Allocation for MP Tasks During Phase Four
      4.4.5 Time Allocation Involving EMT Events
      4.4.6 Correction for Simultaneous or Nearly Simultaneous Tasks or Events
   4.5 Further Details Concerning Specific Issues During the Sample Cardiac Arrest
      4.5.1 Phase One: Amount of Time for Enabler to Reach PU
      4.5.2 Specific Issues During Phase Two
         4.5.2.1 Initial and Subsequent MP Screens
         4.5.2.2 Facilitated Lock Release in the Event of Failure of Handshake #1 or #2
      4.5.3 Specific Issues During Phase Three
         4.5.3.1 The MP Interface with Emergency Medical Services
         4.5.3.2 Enabler Action During Transport of PU to Victim
         4.5.3.3 MP Assessments and Actions, Upon Arrival of the PU at the Victim's Side
         4.5.3.4 Enabler Headset Handshake
      4.5.4 Specific Issues During Phase Four
         4.5.4.1 Wide Variety of MP Choices for Defibrillation and Pacing Parameters; Central Station Screens which Correspond to these Choices
         4.5.4.2 MP Instructs Enabler in the Application of Blood Pressure and Blood Oxygen Saturation Devices
      4.5.5 Specific Issues During Phase Five
         4.5.5.1 Possible Performance of CPR During Phase Five 4.5.5.2 Multiple Possible Types and Sources of Victim Related Information
4.5.5.3 Multiple Possible Means of Tracking Local Emergency Services
4.5.6 Specific Issues During Phase Six
4.5.6.1 Analogous Aspects of the Enabler-MP Link During Phase Two, and the EMT-MP Link During Phase Six
4.5.6.2 Timing of EMT Arrival
4.5.6.2.1 Time Saved by Using the Invention: Estimation of the Earliest Possible Defibrillation by EMT, Without the Invention
4.5.6.2.2 More Realistic Estimates for EMT Defibrillation
4.5.7 Specific Issues During Phase Seven
4.5.7.1 Overview of Phase Seven: Two Sequences of Events
4.5.7.1.1 Analogous Aspects of Phase Seven and Phase Three
4.5.7.1.2 Two vs. One Portable Unit at the Arrest Scene
4.5.7.2 Two Portable Units Available: New Versus Old PU as the Replacement Unit
4.5.7.2.1 Option One: Old PU Remains Attached to the Victim; New PU to be Attached to the Stationary Unit; Transportation of the New PU to the SU
4.5.7.2.2 Option Two: New PU is Attached to the Victim; Old PU to be Reattached to the Stationary Unit
4.5.7.3 Housekeeping Activities Before Returning the Old PU to the SU; Transportation of the Old PU to the SU
4.5.7.3.1 MP Role During Housekeeping
4.5.7.3.2 Choice of Individual to Perform the Housekeeping Activities
4.5.7.3.3 Electrode Pad Replacement; Oximetry Sensor Replacement
4.5.7.3.4 Replacement of Non-Disposable Items
4.5.7.3.5 Video Boom and Antenna Retraction Prior to Moving the PU
4.5.7.3.6 Transportation of the Old PU to the SU
4.5.7.4 Attachment of the PU to the SU
4.5.7.4.1 Who Performs the Attachment?
4.5.7.4.2 Mechanical Issues in the Attachment Process
4.5.7.4.3 Endpoint for PU-SU Attachment
4.5.7.4.4 Checking the PU Post-Attachment
4.5.7.5 Choices in the Event of Communications Failure During Phase Seven
4.5.7.5.1 EMT Communications Choices Using Only One Portable Unit
4.5.7.5.2 EMT Communications Choices Using a Second Portable Unit
4.5.7.5.2.1 Choice in which PU-2 is the Only PU which Communicates with the Central Station
4.5.7.5.2.2 Choices in which Both PU-1 and PU-2 are Used in Tandem; Even More Elaborate Links
4.5.7.6. Possible Need for Two Nearly Simultaneous MP Conversations During Phase Seven
4.5.7.7 The Circumstance in which EMT Does Not Bring a Replacement PU
4.5.7.7.1 Option Three: Sole PU Remains at the Arrest Scene
4.5.7.7.2 Option Four: Sole PU is to be Transported with the Victim
4.5.7.8 Protocol Endpoints During Phase Seven
4.5.7.8.1 Definition of Victim Detachment from PU
4.5.7.8.2 Circumstances in which a PU Would Not Be Promptly Replaced
4.5.7.8.2.1 PU Non-Replacement at the Arrest Site
4.5.7.8.2.2 Non-Replacement of the EMT PU
4.6 Post-Arrest Issues
4.6.1 On-Site Equipment Inspection and Assessment
4.6.1.1 Timing of the On-Site Visit
4.6.1.2 Items Assessed During the On-Site Evaluation Process
4.6.2 Remote Equipment Inspection and Assessment
4.6.2.1 Timing of the Remote Evaluation Process
4.6.2.2 Items Assessed During the Remote Evaluation Process
4.6.3 PU and SU Hardware and Software Updates
5. Flow Diagrams
5.1 Communications Handshake
5.1.1 Overview
5.1.2 Communications Handshake, PU Component
5.1.3 Communications Handshake, CS Component
5.1.4 Handshakes During Diagnostic Checking
5.2 The Data/Commands Handshake
5.3 Audio and Informational Handshakes
5.3.1 Part I, Audio Handshake
5.3.2 Audio Handshake, Part II
5.3.2.1 Using Voice Prompts
5.3.2.2 Without Voice Prompts, Version 1
5.3.2.3 Without Voice Prompts, Version 2
5.3.3 Audio Handshake, Part III
5.3.4 Informational Handshake
5.4 PU Transport and Setup at the Victim's Side
5.4.1 PU Transport
5.4.2 PU Arrival at Victim; PU Setup
5.4.2.1 PU Touchdown and Video Setup
5.4.2.2 Audio Communications Adjustment, If Necessary
5.4.2.2.1 Audio Communications Overview
5.4.2.2.2 Audio Communications Flow Diagram Following PU Touchdown
5.4.2.3 Non-Audio Communication Backups
5.4.2.4 Initial Victim Assessment
5.4.2.5 Electrode Pad Application
5.4.2.6 Electrode Pad Assessment
5.5 Flow Diagrams: Arrhythmia Management
5.5.1 First Tier Arrhythmia Triage Protocol
5.5.1.1 Overview
5.5.1.2 Details of Arrhythmia Triage
5.5.1.2.1 Bradycardia/Paced Rhythm Decision
5.5.1.2.2 Tachycardia/No Tachycardia Decision
5.5.1.2.3 Options in the Event that the Rhythm Diagnosis is Uncertain
5.5.1.3 Other Approaches to First Tier Arrhythmia Triage
5.5.2 Shock Administration Protocol
5.5.3 Second Tier Arrhythmia Triage Protocol
5.5.3.1 Overview
5.5.3.2 Alternative Tachycardia Termination Techniques
5.5.3.3 The MP's Assessment of the Appropriateness of the Use of Alternative Tachycardia Termination Techniques
5.5.3.4 Algorithm for Considering Alternative Tachycardia Termination Techniques Based on State of Consciousness, Respiratory Status and Blood Pressure
5.5.4 Anti-Tachycardia Pacing
5.5.4.1 Background
5.5.4.2 Anti-Tachycardia Pacing Protocol
5.5.4.3 Other Possible Anti-Tachycardia Pacing Protocols
5.5.5 Bradycardia/Pacing Protocol
5.5.5.1 Overview 5.5.5.2 External Pacing Not in Progress; MP Decision Whether to Start Pacing
5.5.5.3 External Pacing Is in Progress; MP Decision Whether to Check Underlying Rhythm
5.5.5.4 MP Considerations Concerning Termination of Pacing
5.6 Command Confirmation
6. Central Station Screens
  6.1 Basic Communications Screens
    6.1.1 Communication Status and Master Control Screen
    6.1.2 Voice Prompt Screen
  6.2 Portable Unit Setup Screens
    6.2.1 Portable Unit Deployment Screen
    6.2.2 The Video Control and Instruction Screen
    6.2.3 Initial ECG Screen
  6.3 Arrhythmia Management Screens
    6.3.1 Defibrillation Management Screens
    6.3.1.1 Paths to Main Defibrillation Screen
    6.3.1.2 Method of Operation: Defibrillation Screens
    6.3.1.2.1 Default Values: Main Defibrillation Screen
    6.3.1.2.2 Non-default Values
    6.3.1.2.2.1 Defibrillation Energy Screen
    6.3.1.2.2.2 Synchronization Screen
    6.3.1.2.2.3 Pulse Shape Screen
    6.3.1.2.2.4 Electrode Setup Screens
    6.3.1.2.2.4.1 Five Electrode Pad Setup Screen
    6.3.1.2.2.4.2 Matrix Electrode Pad Setup Screen
    6.3.1.2.2.4.3 Single Electrode Pad Setup Screen
    6.3.1.3 Unconventional Defibrillation Methods
    6.3.1.4 Paths From Main Defibrillation Screen
    6.3.2 Anti-Tachycardia Pacing Screen
    6.3.2.1 General Considerations
    6.3.2.2 Default Values
    6.3.2.3 Non-Default Values
    6.3.2.4 Paths from Anti-Tachycardia Pacing Screen
    6.3.3 Bradycardia Pacing Screens
    6.3.3.1 Paths to Main Pacing Screen
    6.3.3.2 Method of Operation: Bradycardia Pacing Screens
    6.3.3.2.1 Default Values
    6.3.3.2.1.1 Common versus Different Parameters for Bradycardia Pacing and for Anti-Tachycardia Pacing
    6.3.3.2.2 Non-Default Values
    6.3.3.2.2.1 Pacer Amplitude Screen
    6.3.3.2.2.2 Bradycardia Pacing Rate Screen
    6.3.3.2.2.3 Pulse Shape Screen/Pacing
    6.3.3.2.2.4 Electrode Setup Screens/Pacing
    6.3.3.2.2.5 Pacemaker Sensing
    6.3.3.2.2.5.1 Sensing from the Electrode Arrangement with the Largest R-Wave
    6.3.3.2.2.5.2 Sensing from the Electrode Arrangement used for Pacing
    6.3.3.2.2.5.3 Sensing from an Electrode Arrangement Selected by the MP
    6.3.3.2.3 Termination of Pacing
    6.3.3.3 Paths from Main Pacing Screen
  6.4 MP-Directed PU Diagnostic Check and Maintenance Screen
  6.5 Master Triage Screen
  6.6 Main Screen Menu
  6.7 Command Confirmation and Event Log
7. Block Diagrams: Units and Major Components of the System
  7.1 The Portable Unit
  7.2 The Stationary Unit
  7.3 The Master Control Unit
  7.4 The Central Station
  7.5 The Stationary Unit Decoder
  7.6 The Portable Unit Decoder
  7.7 The Portable Unit Encoder
  7.8 The Central Station Decoder
  7.9 The Central Station Encoder
8. Miscellaneous
  8.1 Diagnostic Check
  8.2 Universal Connectors
  8.3 Network of Central Stations
  8.4 Multiple Communication Modalities and Routes
  8.5 Multiple Possible Routes and Relays Between PU and CS
  8.6 Control of an Implantable Cardioverter-Defibrillator by the MP
  8.7 Defibrillation Using Two or More Different Shocks in One Victim
  8.8 Monitoring Adequacy of Ventilation During Resuscitation Using Pressure and/or Flow Monitoring
  8.9 Monitoring Adequacy of Ventilation During Resuscitation Using Transthoracic Impedance

TABLES

| | |
|---|---|
| 1) Master Control States | 1.3.1.2 |
| 2) Summary of Figures | 1.4 |
| 3) ECG Recording Configuration on Five Electrode Pad | 3.2 |
| 4) ECG Recording Configuration on Five Electrode Pad with Seven Sensing Electrodes | 3.2 |
| 5) ECG Recording Configuration on Thirty Two Electrode Pad | 3.3 |
| 6) Seven Phases of Activity During A Cardiac Arrest | 4.1 |
| 7) Four Layers of Handshake Linking Enabler and MP | 4.1.2.1 |
| 8) PU-CS Routing Analysis and Backup When SU is Available | 4.1.2.4.1 |
| 9) Four Layers of Handshake Linking Victim and MP | 4.1.3.2.1 |
| 10) Four Layers of Handshake Linking EMT and MP | 4.1.6.2 |
| 11) Events During an Hypothetical Cardiac Arrest | 4.2 |
| 12) Deployment of the Old PU after EMT Arrival | 4.5.7.1.2 |
| 13) Communication Choices Using the Second PU as a Relay | 4.5.7.5.2.2 |
| 14) Flow Diagrams of Events During a Cardiac Arrest | |
| 15) Central Station Screen Summary | |
| 16) Signals During Communication (Layer #1) Handshake | |
| 17) Testing During Data/Commands (Layer #2) Handshake | |
| 18) Testing During Audio (Layer #3) Handshake | |
| 19) Testing During Enabler-MP Handshake: Which Tests are Abnormal for Each Component Failure | |
| 20) Options for Communications Enhancement During the Four Handshakes of the Enabler-MP Link | |

Appendices

1) Voice Prompts
2) Abbreviations
1. System Overview

In the text hereinabove and hereinbelow, both of the terms "medical emergency" and "cardiac arrest" are used to describe the event for which the invention may be used. A cardiac arrest is one type of medical emergency in which collapse occurs because the heart's electrical or mechanical function is severely abnormal. The initial heart rhythm during a cardiac arrest is usually either ventricular fibrillation (VF), ventricular tachycardia (VT), bradycardia or asystole; Occasionally, the rhythm is normal (pulseless electrical activity). A cardiac arrest can be diagnosed when the electrocardiogram of the victim of a medical emergency shows VF, VT, asystole or profound bradycardia. Certain types of bradycardia, VT and other tachycardias may constitute medical emergencies, although they may not be associated with complete collapse, and thus may not be considered to be cardiac arrests. Certain types of collapse, such as pulseless electrical activity, may constitute a medical emergency even though they may be associated with a normal heart rhythm; The absence of a palpable pulse and/or measurable blood pressure is required for this diagnosis.

1.1 Description of the Emergency Scene

FIG. 1 shows an overview of the scene of a medical emergency scene 10 during the moments after the victim is first observed. In this preferred embodiment of the invention, an enabler 100, i.e. a person who observes a victim of a medical emergency 102 and wishes to participate in the resuscitation of said victim, begins the process by pressing emergency button 106 (hereinafter referred to as "button press") on portable unit 104. Victim 102 may be conscious or unconscious. Enabler 100 is a person with no prior medical or emergency training.

By pressing the button, the enabler 100 causes the portable unit to establish a communications link with a central station 300 in which highly skilled personnel are situated. A medical professional 301 then guides enabler 100 through a series of steps, each of which requires no medical expertise on the part of enabler, that will allow the medical professional to diagnose and, if necessary, directly control resuscitative maneuvers on victim 102 via portable unit 104. Such maneuvers include defibrillating or pacing the heart. Communication between the scene of the medical emergency and the central station may be via a telephone system 114 (either copper-based, optical fiber based, radio frequency based, or hybrid), or via radio frequency link 116 (either direct, with repeaters, with satellite linkages or a hybrid system). The presence of backup and/or redundant communication modalities, results in a highly robust link between the scene of the emergency and the central station. However, in the event that all communication systems fail, a backup automatic defibrillation system allows continued operation of the system.

Figure 2A:
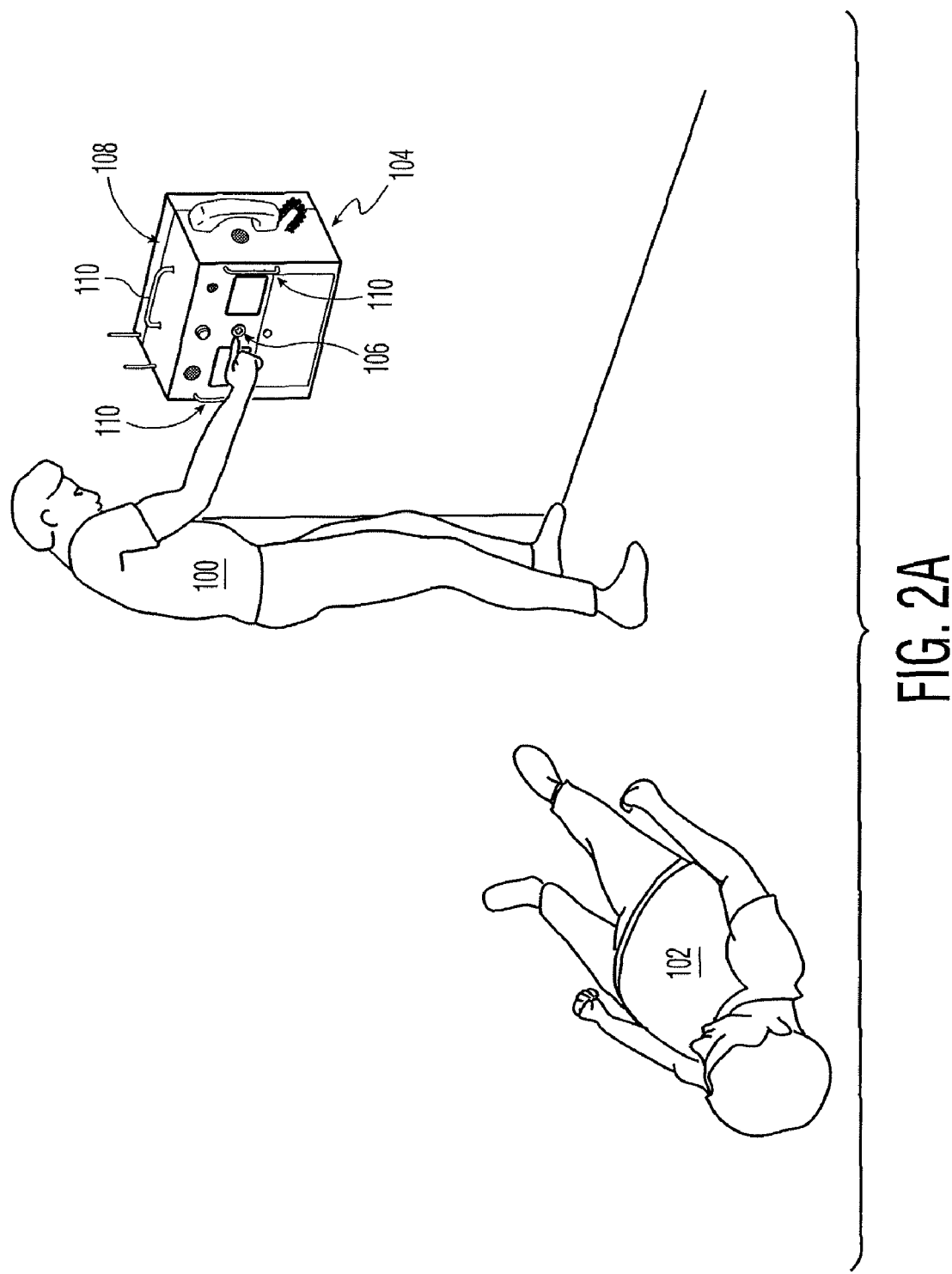
FIG. 2A is a perspective view showing a typical medical emergency situation in which a victim lies on the floor and a bystander becomes an enabler by activating the cardiac monitoring and defibrillation system according to the present invention.

Referring to FIG. 2A, in the preferred embodiment, portable unit 104 is attached to stationary unit 108, which is anchored to a wall. Emergency button 106 is labeled in a manner which allows enabler 100 to easily and rapidly discern that it is to be pressed in the event of a medical emergency. It may, for instance, have a large red cross on its surface. It may have the words "Medical Emergency" or "Press Button for Medical Emergency" or other similar wording on its surface or immediately adjacent. The words would be plainly visible from a distance.

Portable unit 104 and stationary unit 108 may be situated in any public place such as an airport, a shopping mall, a gambling casino, a restaurant, etc. Alternatively these units may be situated in non-public places such as a person's home or an office. Another alternative would involve the placement of such units within a medical facility, e.g. a hospital, nursing home or rehabilitation facility.

Pressing emergency button 106 causes communication between the portable unit and the central station to be quickly established. Immediately following an initial electronic handshaking process, the central station is automatically informed of the exact location of the portable unit. The medical professional then identifies himself to the enabler 100, and confirms that both the medical professional and enabler 100 can hear and understand each other. The medical professional then inquires as to the nature of the situation that enabler 100 has observed. If the medical professional decides that the resuscitative equipment contained in portable unit 104 will be useful for the resuscitation of victim 102, the medical professional will cause a lock to release the portable unit 104, from the stationary unit, 108. The medical professional will tell enabler 100 to detach portable unit 104 from stationary unit 108 by grasping handles 110, and to quickly carry the portable unit 104 to the victim's side.

Figure 2B:
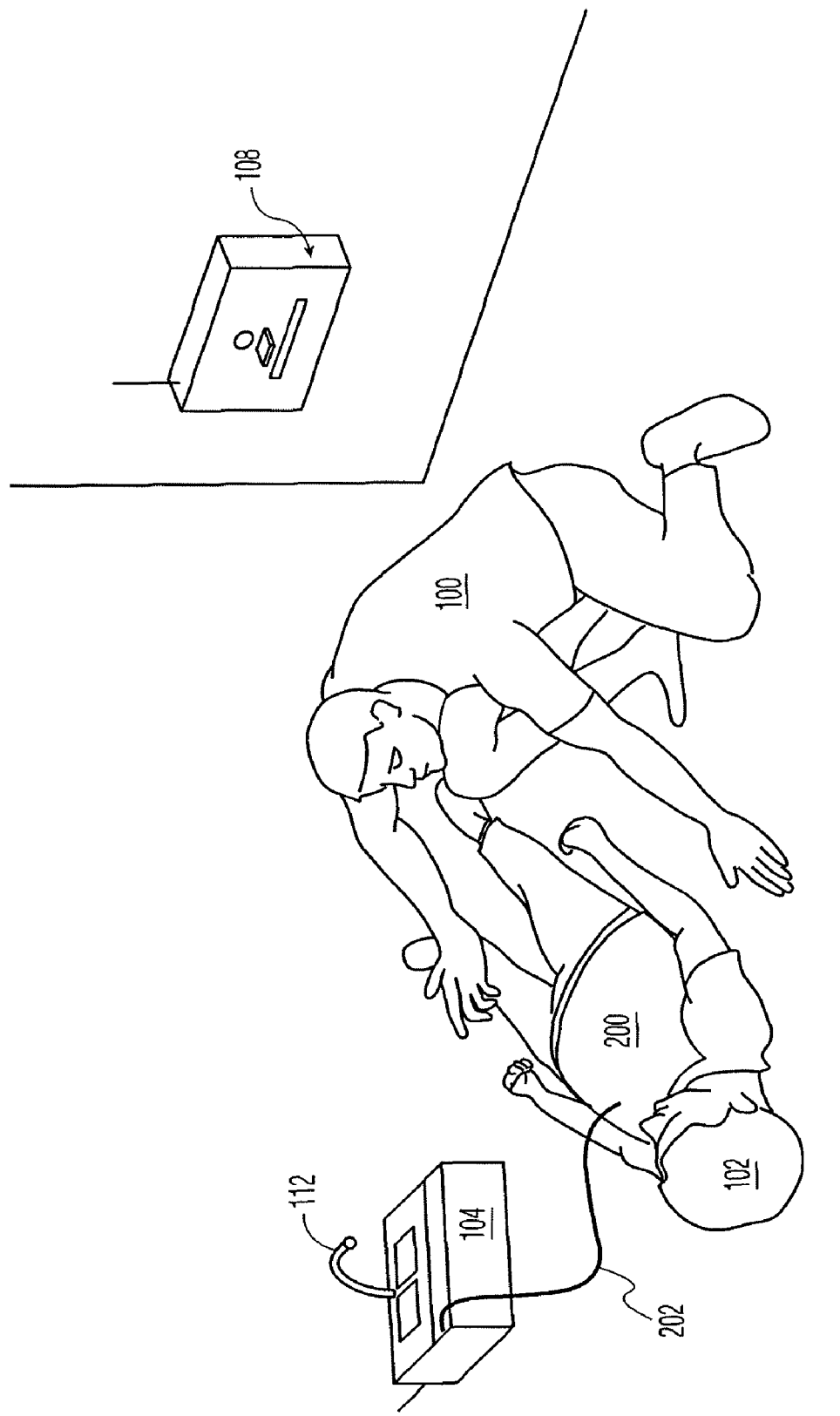
FIG. 2B is a perspective view showing a typical medical emergency situation in which a victim lies on the floor and an "enabler" utilizes the cardiac monitoring and external defibrillation system according to the present invention.

FIG. 2B is another overview of the system, showing the scene of the medical emergency after the medical professional has released the portable unit and instructed the enabler to transport it to the victim's side. The portable unit 104 is situated immediately adjacent to the victim 102. Electrode pad 200 has been attached to the chest of victim 102. The electrode pad 200 allows a medical professional to observe the victim's electrocardiogram, and to control the application of electrical energy to the victim, for either pacing, cardioverting or defibrillating the heart. The electrode pad 200 is initially situated within a storage compartment of portable unit 104. Detailed instructions describing removal of the electrode pad 200 from the portable unit 104 and describing the process of application of the electrode pad 200 to the chest of victim 102 will be provided to enabler 100 by the medical professional. Electrical energy is conveyed between electrode pad 200 and the portable unit 104 by a cable 202 which consists of multiple insulated wires.

The medical professional's ability to instruct the enabler 100 in the proper application of the electrode pad 200 to the victim 102 is enhanced by medical professional's being able to see the victim 102 and to observe the enabler's application of the electrode pad 200. The medical professional observes the scene via a television camera which may be built into the portable unit 104. Video apparatus is contained within a video boom 112, which may be extended from the portable unit 104, and pointed in any direction. The video apparatus may include one or more lenses and means for remote focusing. It may further include means for collecting light and amplifying it. The projection 112 may be moved in three dimensions by either enabler 100 or the medical professional, via telemetry signals between the central station and the portable unit 104.

Enabler 100 may be instructed in additional maneuvers by the medical professional. These include various forms of circulatory and/or respiratory assist for victim 102 including cardiopulmonary resuscitation.

Portable unit 104 communicates with central station either directly, or indirectly via stationary unit 108. FIG. 2b shows a radio frequency link between portable unit 104 and stationary unit 108, but other types of link are possible including infrared light based or hard-wiring.

1.2 Description of the Central Station

Figure 3:
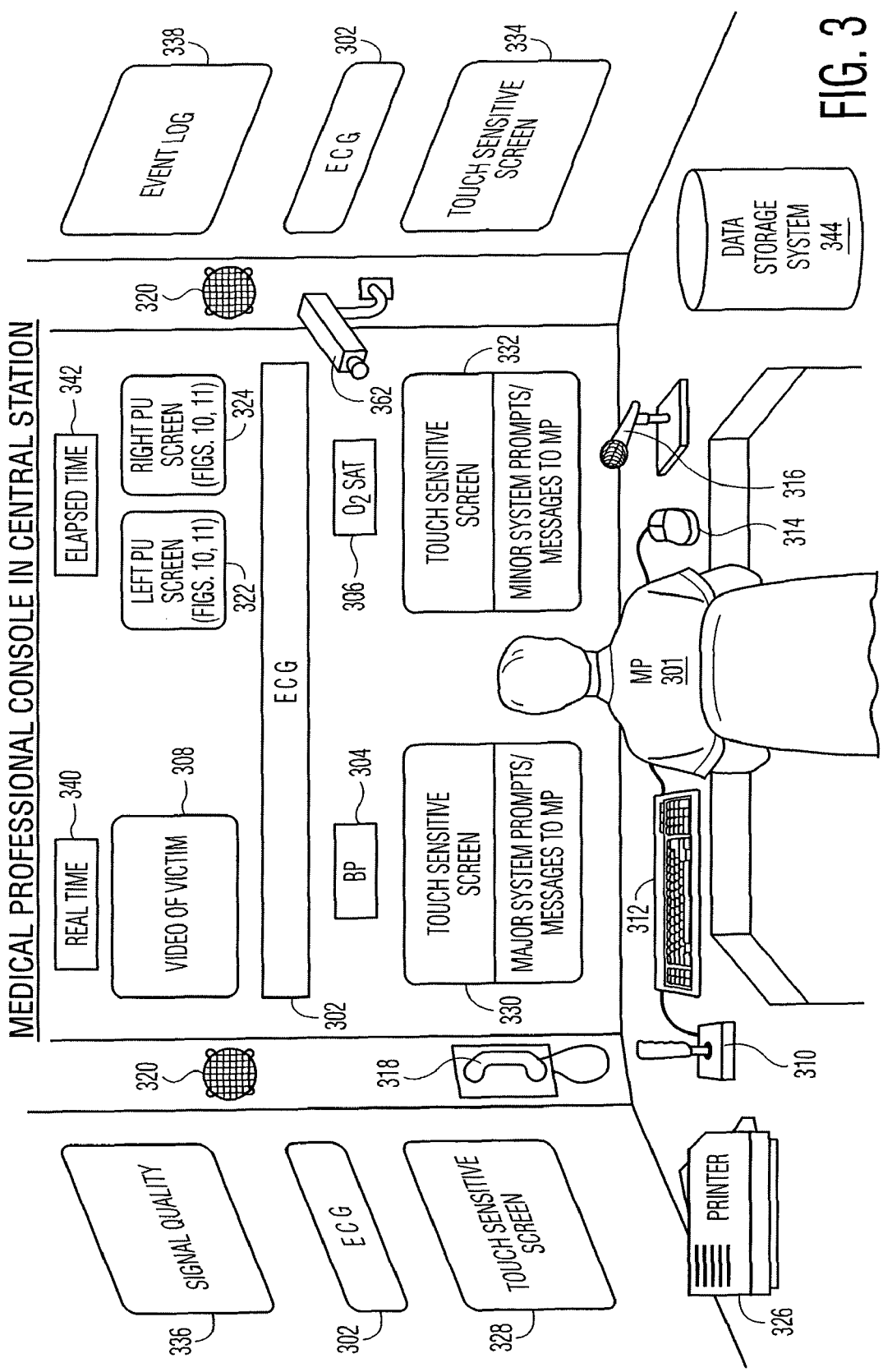
FIG. 3 is a representational diagram of the various display screens and control devices at the central station in the cardiac monitoring and external defibrillation system according to the present invention.

FIG. 3 shows a view of the medical professional's console or control panel. The medical professional 301 sits with easy access to multiple video displays, inputting devices and communication systems. These allow the medical professional to evaluate the victim, treat the victim, and communicate with the enabler, who is instructed by the medical professional. The video displays allow the medical professional to observe the physiologic status of the victim of a medical emergency, to have access to other data relating to the current medical event and prior medical events for this victim, to have access to signal quality and communication options, access to triage status and triage options and access to higher echelons of advice, either from a computer-based expert system, or from a super-expert medical professional. The inputting devices allow the medical professional 301 to directly control various aspects of the management of the medical emergency such as defibrillation and pacing of the heart. They also allow him to control the communications link with the portable unit and enabler. They also allow the medical professional 301 to provide audio and video instructional information for the enabler.

The victim's electrocardiogram is displayed on screens 302. Many different display formats are possible including one, two or multiple simultaneous electrocardiogram leads, as well as the ability to freeze and hold a tracing on one screen (for reference or for further analysis), while continuing to view "live" electrocardiograms on another screen. The victim's blood pressure data is displayed on screen 304, and oxygen saturation data is displayed on screen 306. Other parameters of respiratory status, blood sugar, body temperature and other physiologic parameters may also be displayed.

The medical professional 301 may observe the victim and the performance of the enabler at the emergency site on screen 308. The medical professional 301 controls the field to which he has video access by manipulating the video boom 112 of the portable unit 104. The length and orientation of the video boom may be controlled by the medical professional using joystick 310. The medical professional 301 may also control the video boom via the keyboard 312, the mouse, 314, or via a touch sensitive screen.

In a preferred embodiment of the system, the medical professional's carries on an audio dialog with the enabler, and possibly other medical professionals including emergency services local to the victim and including higher level medical experts. The medical professional's voice is picked up by microphone 316, mounted near said medical professional. Alternatively the medical professional may wear a lapel-type microphone, may wear a headset containing a microphone, or may use telephone handset 318. The medical professional hears the voice of the person with whom he is communicating via either speakers 320, earphones, a headset containing earphones plus microphone, or telephone handset 318.

If audio communication is not effective for any reason, the medical professional has the option of transmitting and receiving text messages to and from the enabler. Keyboard 312 may be used to input text messages. The message, as displayed to the enabler can be seen by the medical professional on screen 322. Text messages from the enabler are viewed by the medical professional on screen 324, and may be printed by printer 326. Printer 326 may also be used to print other data including electrocardiograms, other physiologic data, archived information about the victim's medical history, communications information and/or a complete log of the current medical event. In the event of complete failure of communications, the portable unit's automatic external defibrillation circuits (see below) would allow resuscitative efforts to proceed.

In a preferred embodiment, the medical professional inputs commands which control electrical therapy to the victim including defibrillation and pacing. Each of the parameters which control these processes (e.g. pulse energy, pulse width, synchronization) may be selected by the medical professional. One means of selection is via touch sensitive screens 328, 330, 332, and 334. A menu of possible choices is displayed on the touch sensitive screen. The medical professional selects his choice by touching the appropriate spot on the screen with either his finger or a wand. Alternatively, such choices can be made by moving the mouse which moves a pointer on the screen(s), and by clicking over the appropriate choice. The medical professional may also input commands via keyboard 312, using either the arrow keys to navigate among choices displayed on the screen, or by directly inputting commands that are alphabetic (e.g. "control S" for shock) or numeric (e.g. "100" for shock energy), or by using the "f keys." The medical professional my also input commands by voice, using a voice recognition system.

Since the number of possible menus and displays may exceed the number of video screens, the medical professional may select the content of each screen by accessing a screen menu. The screen menu lists all possible (touch-sensitive) sub menus and (non-touch-sensitive) displays. The medical professional uses the screen menu to assign a sub-menu or a display to each screen. FIG. 3 shows one such assignment.

Passive screens 336 and 338 are not touch sensitive and are used to display information. Examples of such screens would include the event log, communications information and the victim's medical history.

Screens 322 and 324 are identical in display content to the corresponding two screens on the portable unit 104, This allows the medical professional to view exactly what the enabler 100 is viewing. Besides text messages, these screens may be used, at the direction of the medical professional, to display instructional videos for the enabler, or, a live video of the medical professional, for purposes of reassurance or instruction.

In the event that the enabler is himself a medical professional, electrocardiograms or other physiologic data, and defibrillator and pacing control screens may be enabled, and displayed on screens 322 and 324.

The medical professional 301 may receive advisory prompts, shown in FIG. 3 on the lower portion of screens 330 and 332. Such prompts may include expert system based suggestions for medical management, changes in a physiologic parameter noteworthy enough to bring to the immediate attention of the medical professional, changes in communications status, changes in triage status, or changes in the operating integrity of any part of the system.

The current time is displayed on screen 340; the elapsed time, from the start of the emergency call is displayed on screen 342. Other time intervals, including time since definitive therapy begins, or elapsed time starting with the estimated moment of the victim's collapse, may also be displayed.

Many other display arrangements are possible, including those with different numbers of screens, different geometric arrangements of screens and different inputting devices.

An on site data storage system 344 allows the medical professional to have access to patient databases, pacemaker and implantable defibrillator information, drug information, expert system programs for management of medical emergencies and information about local emergency response teams around the world. It also allows for storage of data pertaining to the current medical emergency.

Figure 4A:
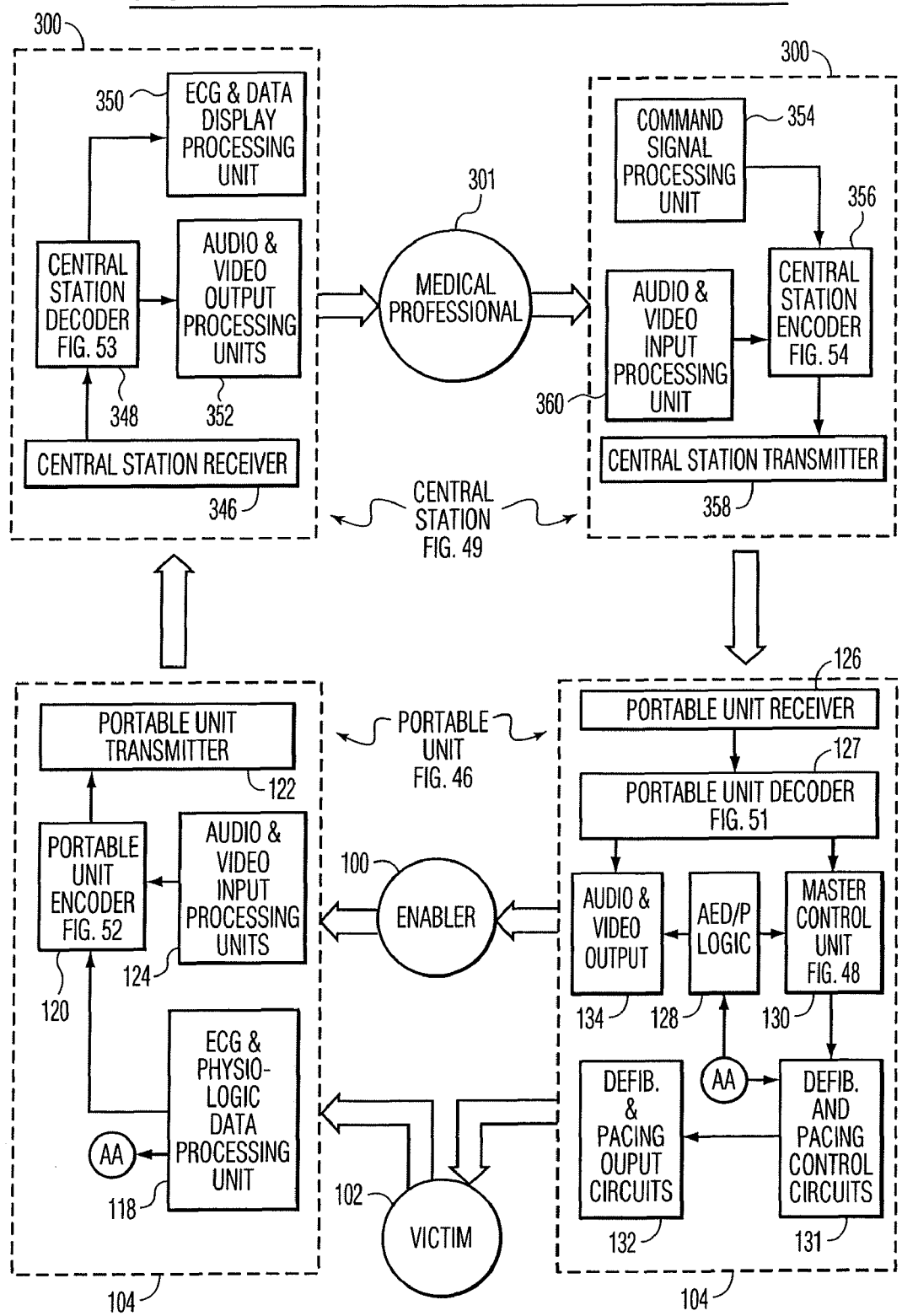
FIG. 4A is a block diagram of the cardiac resuscitation system, without a stationary unit, in overview.
Figure 4B:
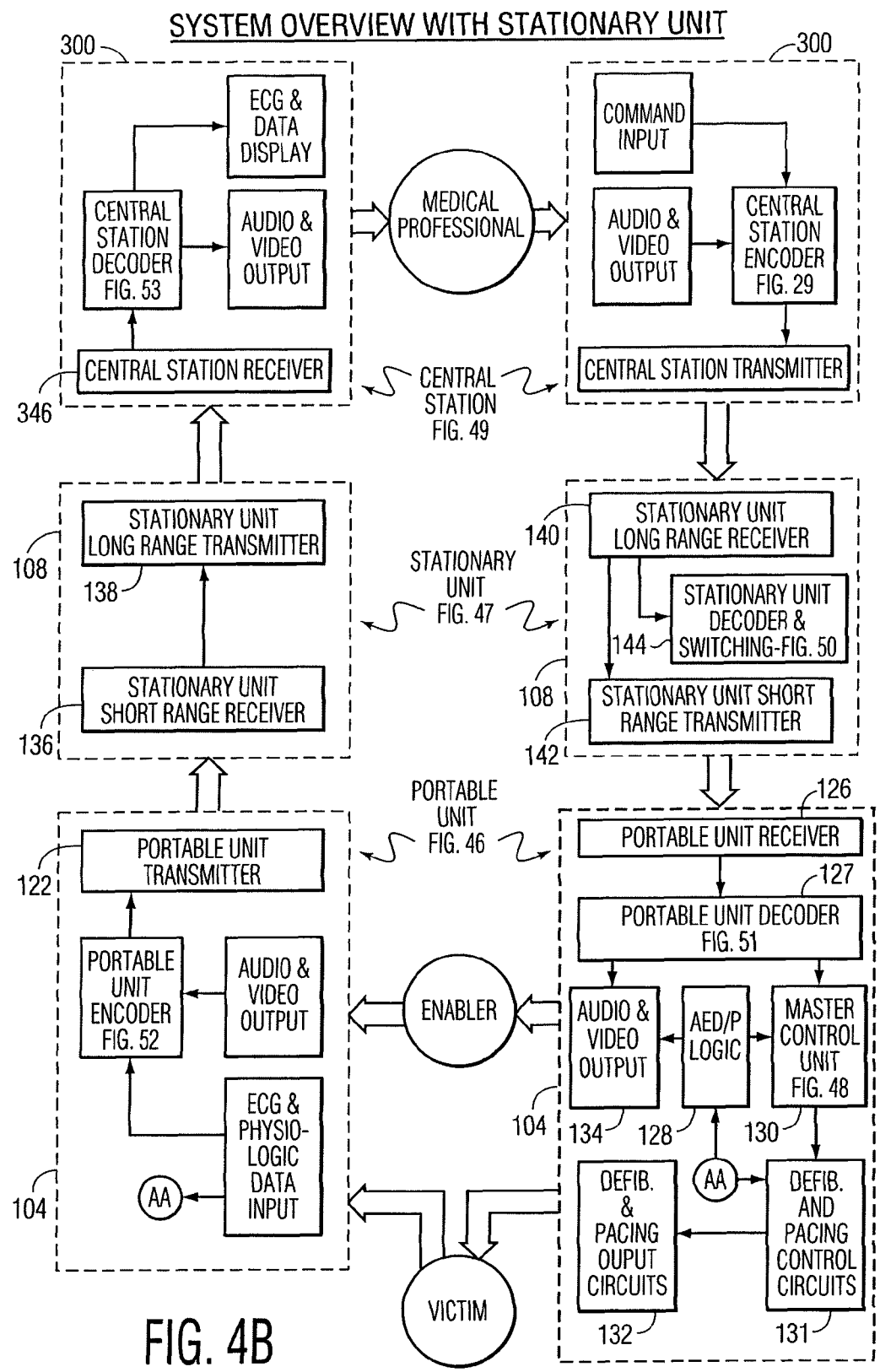
FIG. 4B is a block diagram of the cardiac resuscitation system, with a stationary unit, in overview.

1.3 Block Diagram of the System
1.3.1 Two Unit System: PU and Central Station
1.3.1.1 System Operation When PU-CS Communication Is Intact FIG. 4A is a diagrammatic overview of the system, showing greater detail than FIG. 1. It shows the flow of information (including the medical professional's control of defibrillation and pacing) within the system, after it has been attached to the victim 102. To simplify the presentation, FIG. 4A shows an embodiment of the system in which the portable unit 104 communicates directly with the central station 300, without a stationary unit 108 interposed between. FIG. 4B is analogous to FIG. 4A, but it includes the stationary unit.

Referring to FIG. 4A, portable unit 104 obtains the ECG and other physiologic data from the victim 102. These signals are amplified, filtered, digitized and processed by ECG and physiologic data processing unit 118.

Processing unit 118 has three outputs: a) to the PU encoder 120; b) via <AA> to "AED/P," the automatic external defibrillator/pacer analysis, logic and control unit 128; and c) via <AA> to defibrillator and pacing control circuits 131. The signals from data processing unit 118 to the PU encoder 120 (described in detail below) are encoded and transmitted to the central station 300 by portable unit transmitter 122. The portable unit transmitter may output into either a public telephone network, the Internet via public telephone network, or a private communication system, either hard-wired, radio frequency, or hybrid. The signals from data processing unit 118, via <AA>, are used by the AED/P analysis, logic and control unit 128 which automatically controls defibrillation and pacing, in the event of communications failure between the PU and the CS. The signals from data processing unit 118, via <AA> to the defibrillator pacing and control circuits 131: a) may be used to provide a synchronization (timing) signal for defibrillation and b) is used to provide inhibitory signals if pacing is performed for bradycardia.

Referring again to inputs to the PU, audio input signals including the voice of enabler 100 and video input signals showing the victim and the scene of the emergency are amplified, filtered, digitized and processed by the portable unit audio and video input processing units 124. The audio and video data is then encoded by portable unit encoder 120, and then transmitted by portable unit transmitter 122.

Central station 300 receives information sent by the portable unit via central station receiver 346. The receiver can receive either radio frequency or hard-wired signals. The signals are decoded by central station decoder 348 (described in detail as FIG. 53). The decoder supplies ECG and physiologic data signals which are processed by the ECG and physiologic data processing unit 350 and displayed on the appropriate screens (302, 304 and 306, in FIG. 3) for viewing by the medical professional 301. The decoder output also supplies audio and video information which is processed by the central station audio and video output processing units 352, and thus heard and seen by the medical professional 301.

Using the ECG data, the medical professional can diagnose an abnormal heart rhythm in a victim. In the event that the victim has suffered a cardiac arrest, the medical professional can cause the portable unit to supply a defibrillating shock to the victim. Lesser degrees of abnormality can also be diagnosed and treated by the medical professional. The medical professional would defibrillate a patient by selecting each of a number of parameters including shock energy, pulse configuration, the particular electrodes of the defibrillator pad through which energy is to pass (see ahead), and timing of shock. The value or choice for each of these parameters would be inputted by the medical professional through any of a variety of input devices (shown in FIG. 3) including touch sensitive screens 328, 330, 332 and 334; keyboard 312, or mouse 314. The command signals are processed by command signal processing unit 354. These signals are then encoded by the central station encoder (described separately in FIG. 54) and then transmitted by the central station transmitter 358. The central station transmitter may interface with a variety of communication systems, as is the case with the portable unit transmitter 122, described previously.

The medical professional accomplishes a number of desirable goals by speaking with the enabler. These include:

a) carrying on an initial dialogue with the enabler to assess whether these is an emergency and whether use of the portable unit 104 is appropriate;

b) supplying instructions for properly transporting the unit and setting it up at the side of the victim;

c) supplying instruction for properly placing a defibrillation pad on the chest of the victim;

d) informing the enabler and other bystanders to avoid contact with the victim at the moment of a defibrillation shock;

e) instructing the enabler in cardiopulmonary resuscitation;

f) instructing the enabler to obtain, if possible, identifying information about the victim (to facilitate patient database access);

g) prompting the enabler to supply neurologic information, specifically, the enabler's assessment of the state of consciousness or responsiveness of the victim; and h) reassuring the enabler and other bystanders, since a cardiac arrest situation is often attended by a certain degree of pandemonium and chaos.

The medical professional's audio and video inputs are processed by the central station audio and video processing unit 360. After amplification, filtering, digitization, formatting and other signal processing, these signals are passed to the central station encoder 356, and then transmitted by the central station transmitter 358 along with command signals. Central station video inputs include instructional materials related to pad placement and the correct performance of cardiopulmonary resuscitation. Allowing the enabler to see the medical professional, though not medically necessary may, in some cases, provide a measure of reassurance for an anxious enabler, and/or during a difficult resuscitation effort.

Audio and video information transmitted by the central station is received by the portable unit receiver 126, decoded by decoder 127, and amplified and processed by the portable unit audio and video output processing unit 134. This unit drives speakers and/or headphones, and a video display for enabler.

The medical professional's commands for: a) the master control unit 130; and b) the portable unit defibrillator and pacing control circuits 131, are received by portable unit receiver 126 and decoded by portable unit decoder 127. As long as communication between the central station and the portable unit is intact, commands from the central station, outputting from decoder 127 are passed through master control unit 130 to defibrillator and pacing control circuits 131. Control circuits 131 control defibrillator and pacing output circuits 132, the medium voltage (used for pacing) and high voltage (used for defibrillation) generating apparatus within the portable unit. Specifically, defibrillator and pacing control circuits 131 control all aspects of defibrillation pulse production including onset of capacitor charging, timing of discharge, pulse amplitude, shape and energy. If pacing (a medium voltage repetitive electrical stimulation) is necessary, circuits 131 control the pacing rate and mode, as well as pulse amplitude, shape and energy. The defibrillator and pacing output of the unit is coupled to the victim via cable 202 and electrode pad 200.

1.3.1.2 AED Backup in the Event of Communication Failure; Role of Master Control Unit In the event of a failure of communication between the portable unit 104 and the central station 300, the portable unit may utilize automatic external defibrillator/pacer analysis, logic and control circuits 128, instead of commands from the medical professional, for control of PU electrical therapy. Automatic external defibrillators, AED's, as they are known in the art, contain circuits which analyze electrocardiogram signals, and, if ventricular fibrillation is detected, apply a high voltage shock to the victim of a cardiac arrest. They can provide pre-programmed voice prompts, for user instruction.

There are two situations which would result in transfer of control of defibrillation from the medical professional to the AED/P within the PU. The first such situation is in the event of failure of communications in either direction (or both directions) between the portable unit and the central station. In a preferred embodiment of the invention, a complex system of handshakes between the PU and the CS, described below, is used to constantly monitor the integrity of communications. The second such situation is in the event that the MP decides that the quality of the communication link is inadequate. At such time, he may send a control signal which transfers control of the PU to the AED/P.

Control of pacing and defibrillation is via the master control unit 130. The master control unit is, at all times, in one of five possible states. The particular state that it is in, determines who or what will control the major functions of the portable unit. Under normal operating conditions, the PU is controlled by the medical professional. But under certain circumstances, it becomes desirable to allow control by either the AED/P in the PU, or by an on-scene emergency medical team, or "EMT." (Hereinafter EMT will be used to refer to both the entire emergency medical team and an individual member of the team who may communicate with the MP and who may be given access to PU control. EMT may also refer to a physician or other highly qualified person at the scene of the cardiac arrest.) Functions controlled by the master control unit 130 include high voltage charging and delivery and release of the PU locking mechanism. The matrix which shows the relationships between: a) master control unit state; b) who or what is in control; and c) which functions are subject to this control is shown in table 1, and described below.

TABLE 1

Master Control States

| Master Control State | PU Control By | Charge High Voltage Enable | Deliver High Voltage Enable | AED/P Enable | Control Of PU by TSS Enable | Lock Release Enable |
|---|---|---|---|---|---|---|
| 0 | MP | No | No | No | No | No |
| 1 | MP | Yes | Yes | No | No | Yes |
| 2 | AED/P | Yes | Yes | Yes | No | Yes |
| 3 | EMT | Yes | Yes | No | Yes | Yes |
| 4 | MP | Yes | No | No | No | No |

The state of the master control unit determines whether defibrillation and pacing are controlled by the MP, by the AED/P circuits, or by an on-scene emergency medical team. State 0 is the quiescent state, in which the PU remains, until activated when an enabler presses the emergency button 106. If, after enabler describes the emergency to the MP, the MP decides to release the PU, MP sends a command to the PU which causes master control unit 130 to enter state 1. In state 1, high voltage charging and delivery is enabled, and lock release is enabled. In the event that proper communication between the MP and the enabler can not be established or maintained, the master control unit enters state 2. In state 2, lock release no longer requires MP approval, and the PU functions as an AED/P. If a qualified Emergency Medical Team arrives, the MP may transfer control of the PU to the EMT by sending a command to the PU which causes the master control unit to enter state 3. In state 3, the EMT controls the PU by selecting commands on the PU touch sensitive screen, "TSS," in much the same way that the MP would. Master control state 4 (see Sections 4.5.7.4.4 and 4.6.2), is entered when a diagnostic check of the PU is performed. In state 4, although the high voltage circuits may be charged, high voltage may not be delivered.

The AED/P analysis, logic and control unit 128 receives ECG information from ECG and physiologic data input processing unit 118 (described above) via <AA>. If VF is detected and if the master control unit has enabled control of defibrillation and pacing by the AED/P, the AED/P control unit 128 would have access to defibrillator and pacing control circuits 131. In this situation, a defibrillation control signal from the AED/P unit 128 would be relayed through master control unit 130 and cause defibrillator and pacing control circuits 131 to cause defibrillator and pacing output circuits 132 to provide a shock to the victim. The AED/P unit 128 also provides pre-programmed audio instructional information, which is amplified and processed by audio and video output unit 134.

1.3.2 Three Unit System: Portable Unit, Stationary Unit and Central Station

In the aforementioned embodiment, the portable unit and the central station communicate directly. In a preferred embodiment of the invention, the portable unit and the central station communicate via a stationary unit, 108, as shown in FIG. 4B. This three-unit arrangement allows for a portable unit with a less sophisticated receiver, and a less powerful transmitter. It will enhance the ability of the portable unit to remain in communication with the central station, even when operating deep inside of a building or other structure where electromagnetic wave propagation from the outside may be significantly attenuated.

As shown in FIG. 4B, the stationary unit functions as a repeater, consisting of two receivers and two transmitters. Stationary unit short-range receiver 136 receives signals from the portable unit transmitter 122. The information contained in these signals is transmitted by stationary unit long-range transmitter 138 to central station receiver 346. As was the case with the two unit system described in FIG. 4A (in which the portable unit communicated with the central station without an intermediary stationary unit), in the three-unit system described in FIG. 4B, the stationary unit long range transmitter 138 may output into either a public telephone network, the Internet via public telephone network, or a private communication system, either hard-wired, radio frequency, or hybrid.

Signals sent by the central station transmitter 358 are received by the stationary unit long-range receiver 140. Communication modalities for CS transmitter 358 and SU long-range receiver are similar to those previously mentioned for the SU long-range transmitter 138 and CS receiver 346. The information contained in these signal is transmitted by the SU short range transmitter 142 to the PU receiver 126 using a communication modality similar to the link between the PU transmitter 122 and the SU short range receiver 136.

The medical professional can control routing of signals between the stationary unit and the central station. In particular, he can control which of a multiplicity of communication options are used for these links. This process includes the transmission of routing control signals from the CS transmitter 358 to the SU long range receiver, from whence they are decoded by SU decoder 144 (described below).

Other communication options under the control of the MP include:

a) the option to switch from a three unit system (i.e. a system which includes the SU) to a two unit system (PU and CS, without SU) while the system is in use;

b) the option to switch from a two unit to a three unit system while the system is in use;

c) the control of the communications link (e.g. public telephone network, private network, radio frequency, Internet, etc.) between the SU and the PU (This process includes the transmission of routing control signals from the CS transmitter 358 to the PU long range receiver, from whence they are decoded by PU decoder 127 [described below].); and d) the option to allow communication control (viz. the aforementioned choices involving routing and selection of communications modality) to be: (i) automatic (i.e. performed by the system), (ii) manual (i.e. performed by the MP), or (iii) a hybrid involving automatic control with the option of manual override.

1.4 Figure Assignments

The figure assignments for the overviews of the system, as well as all other figures is shown below, in Table 2.

TABLE 2

| FIG. | Subject |
|---|---|
| | Summary of Figures |
| | Overviews |
| 1 | System Overview |
| 2A, 2B | Emergency Scene Overviews |
| 3 | View of Central Station |
| 4A, 4B | Block Diagrams of Flow of Information among PU, SU, CS; Enabler, Victim and Medical Professional |
| | Electrode Pads |
| 5A-G | Views of Defibrillating/Pacing Pads Portable and Stationary Unit Hardware |
| 6-11 | Views of Portable Unit and of Stationary Unit |
| | Flow Diagrams: Four Handshakes Comprising Enabler-MP Link |
| 12 | Communication Handshake - PU component |
| 13 | Communication Handshake - CS component |
| 14 | Data/Commands Handshake |
| 15 | Audio Handshake |
| 16 | Informational Handshake and PU Lock Release |
| | Flow Diagrams: Portable Unit Deployment |
| 17 | Transport of PU to victim |
| 18 | PU Setup at victim's side |
| | Flow Diagrams: Arrhythmia Management |
| 19 | Arrhythmia Diagnosis |
| 20 | VF Treatment |
| 21 | Second Tier Arrhythmia Treatment |
| 22 | Anti-Tachycardia Pacing |
| 23 | Bradycardia Treatment |
| | Flow Diagram: Confirmation Signals |
| 24 | MP Command Execution and Confirmation, and PU Telemetry |
| | CS Screens |
| 25-44 | Control Screens for Medical Professional |
| | Block Diagrams: Units and Major Components of the System |
| 45-49 | Portable Unit, Stationary Unit and Central Station: Block Diagrams |
| 50-54 | Decoders and Encoders: Block Diagrams |
| | Miscellaneous |
| 55A-B | Diagnostic Check: Block Diagram |
| 56A-F | Universal Connectors (Pads to Portable Unit) |
| 57 | Network of Central Stations: Block Diagram |
| 58 | Communication Options |
| 59 | Signal Routing: Block Diagram |

TABLE 2-continued

| FIG. | Subject |
|---|---|
| | Summary of Figures |
| 60 | Control of ICD via CS |
| 61 | Resuscitation with Two Defibrillators |
| 62 | Resuscitation with Pressure and Flow Monitoring |
| 63 | Transthoracic Impedance Monitoring |

Figure 6A:
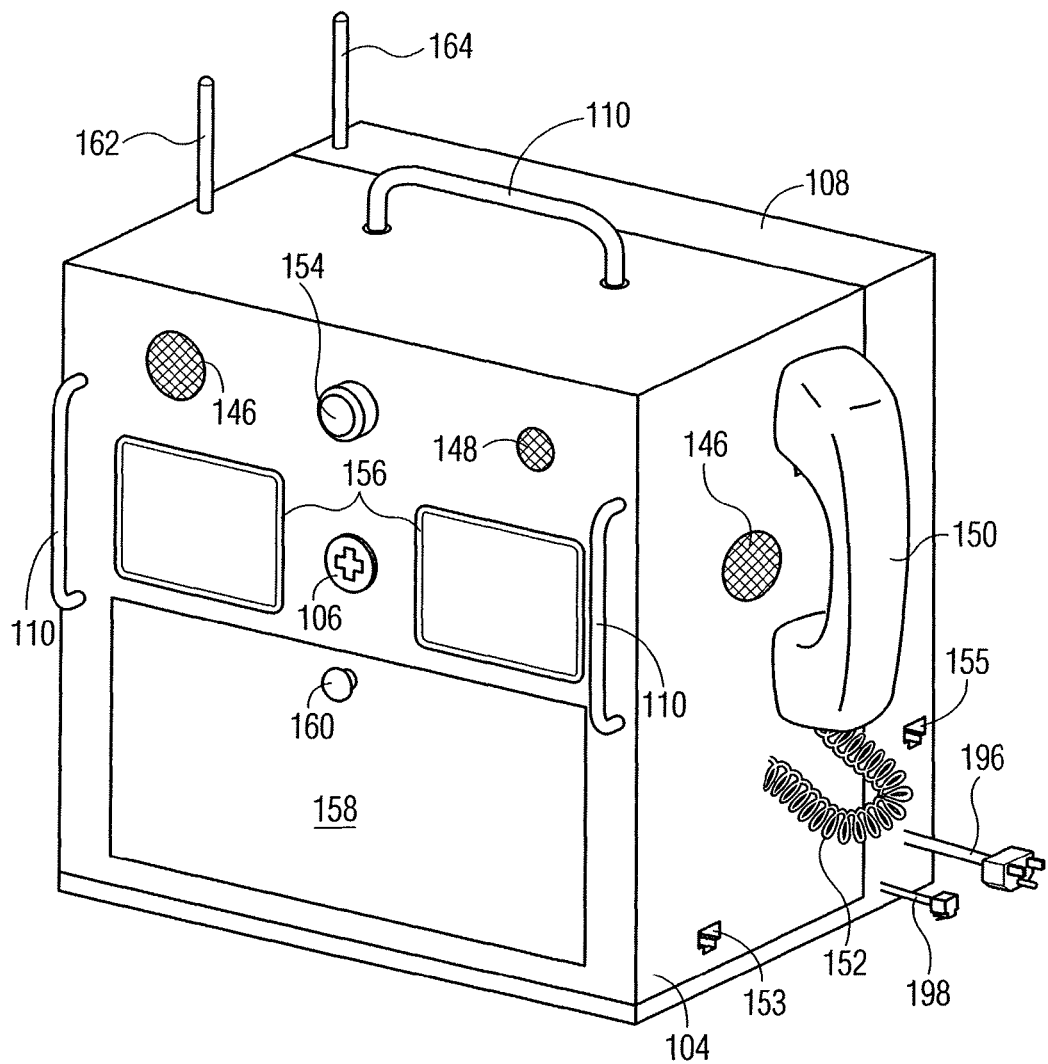
FIG. 6A is a perspective view of the external configuration of a wall-mounted device at a remote station of the cardiac monitoring and external defibrillation system according to the present invention.

2. Portable Unit and Stationary Unit: Exterior Elements 2.1 Portable Unit: Front and Right Side Panels FIG. 6A shows the portable unit 104 attached to the stationary unit 108, as would be the case prior to removal of the portable unit by an enabler. Emergency button 106 is conspicuous, plainly visible from a distance. Handles 110 facilitate enabler's detachment of the PU from the SU, and enabler's carrying the PU to the victim's side.

Speakers 146 allow the enabler to hear the MP's voice. They may be situated in any one of a number of different geometrical arrangements, and their number may vary from a single speaker, to one or more on one or more faces of the PU. In general, their location would optimize enabler hearing, regardless of how the PU is put down and oriented at the victim's side. One or more microphones 148 are similarly placed to allow the MP to hear enabler, regardless of PU orientation. Telephone handset 150 may be optionally used by enabler in a noisy environment or if he is hard of hearing. The decision to use it may be made by the enabler himself, or at the suggestion of the medical professional in the central station. The handset is in electrical communication with the PU communication system via multi-wire cable 152. {Alternatively, the handset may have a wireless link to the PU.}

A female telephone jack 153 on the PU allows it to receive information from another PU (see Section 4.5.7.5.2.2). A female telephone jack 155 on the SU allows it to receive information from another PU (see FIG. 9 and Sections 4.5.7.5.1 and 4.5.7.5.2.2).

Video camera 154 allows the medical professional to view the environment of the portable unit. Before the unit is activated by the enabler, the outer optical surface of the camera is flush with the surface of the PU. However, the viewing apparatus is deployed on an extensible boom (112 in FIG. 2B; also well seen in FIG. 6B. The boom can be extended from the unit, and aimed in any direction, under the control of the medical professional. Video input from the portable unit allows the MP a number of advantages including:

a) the ability to observe anyone who presses emergency button 106; this will (i) act as a deterrent to inappropriate or prank activation of the unit, and (ii) allow the MP to more easily determine when such a prank activation is occurring;

b) the ability to instruct the enabler in the placement of electrode pad(s), by either (i) verbally instructing the enabler as he applies the electrode pad(s), or (ii) visually instructing the enabler by showing him a live video of the victim's torso, upon which MP has superimposed visual prompts such as arrows, an outline of the pad, or a cartoon version of the pad;

c) the ability to observe whether enabler has correctly placed electrode pad(s) 202 (FIG. 2B);

d) the ability to instruct the enabler in other resuscitation related acts, including cardiopulmonary resuscitation by either (i) verbally instructing the enabler as her performs these maneuvers, or (ii) visually instructing the enabler by showing him a live video of the victim, upon which MP has superimposed visual prompts appropriate for the maneuver;

e) the ability to observe the victim; and f) the ability to observe the portable unit itself; this would be accomplished by extending the boom outside of the unit, and causing the boom to angulate at one or more points along its shaft, so that the net effect is a 180 degree reversal in the angle at which the camera is oriented; this would allow intermittent inspection of the unit by the MP.

Portable unit video screens 156 allow the user of the portable unit to view video information. As mentioned previously such information includes: a) text messages from the MP, in the event that the enabler can not hear the MP's voice; b) instructional video regarding (i) correct electrode pad placement and orientation, and (ii) proper execution of various maneuvers including cardiopulmonary resuscitation; and c) the medical professional.

In one embodiment of the invention, one or more of the screens would be touch sensitive. In the event that the MP can not properly hear the enabler, the MP may instruct the enabler to respond by touching virtual buttons on the screen with labels such as "yes" and "no". Alternatively, other potential answers to MP questions may be displayed as virtual buttons. Alternatively, a virtual keyboard may be displayed, to allow enabler to make a more detailed textual response.

Finally, in the event that the enabler is replaced at some point during the emergency by an EMT, it will be possible to allow the EMT to: a) view the victim's electrocardiogram; and b) have access to control of defibrillation and pacing by making one or both of screens 156 touch sensitive. In this situation, the medical professional in the central station, upon receiving evidence that the EMT is properly identified and or qualified, would send a command to the PU (See discussion of master control, ahead; Also see Table 1.) which would enable control of the PU via the touch sensitive screens and display the victim's electrocardiogram on these screens. The two screens on the PU would then function in a manner analogous to the control panel in the central station.

There are many possible ways in which the screens may be arranged geometrically. There may be one or more screens, or none. Finally "screen-in-screen" and split screen displays are possible.

Figure 7A:
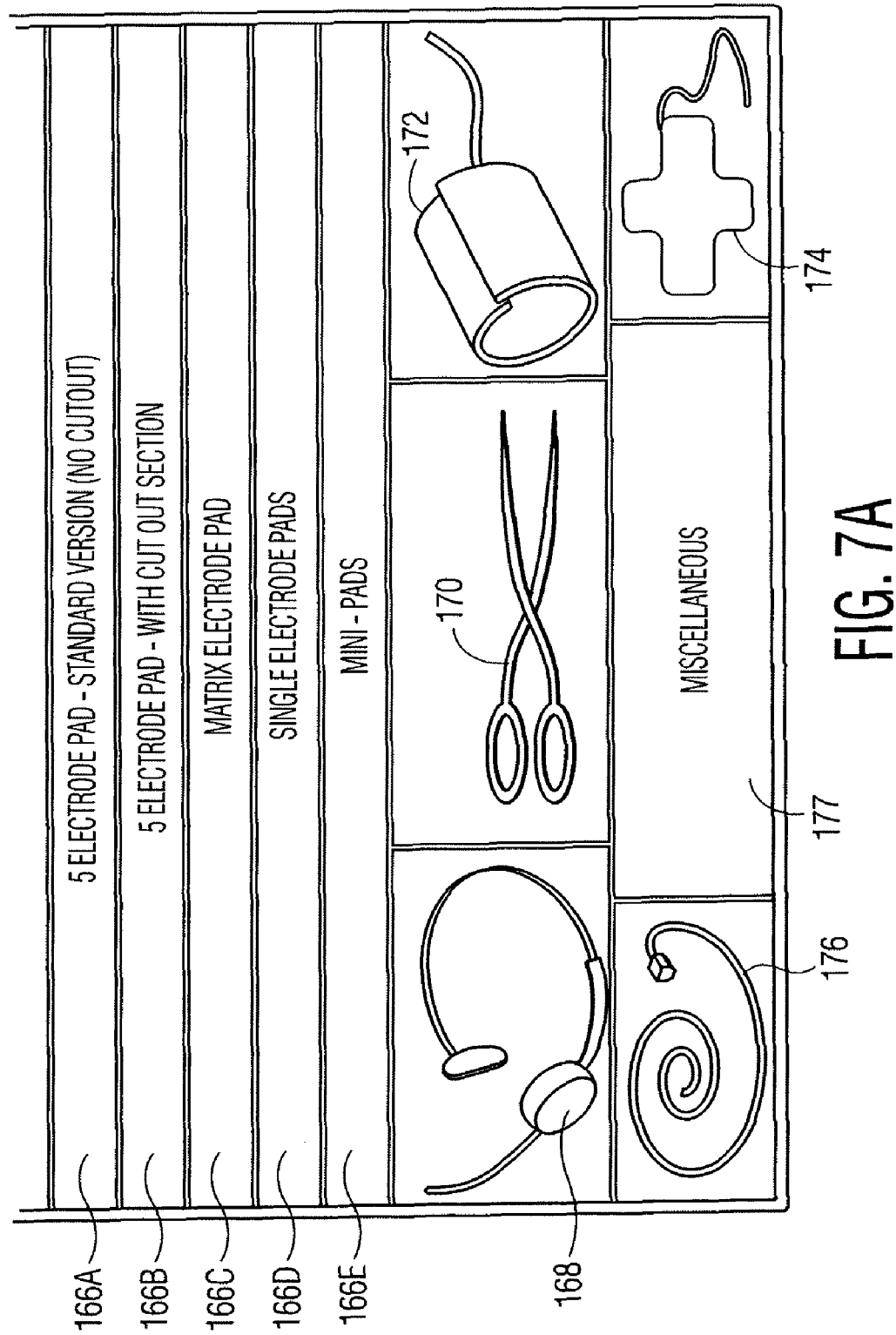
FIG. 7A is a front elevational view of the equipment cabinet in the portable unit of FIG. 6B.
Figure 7B:
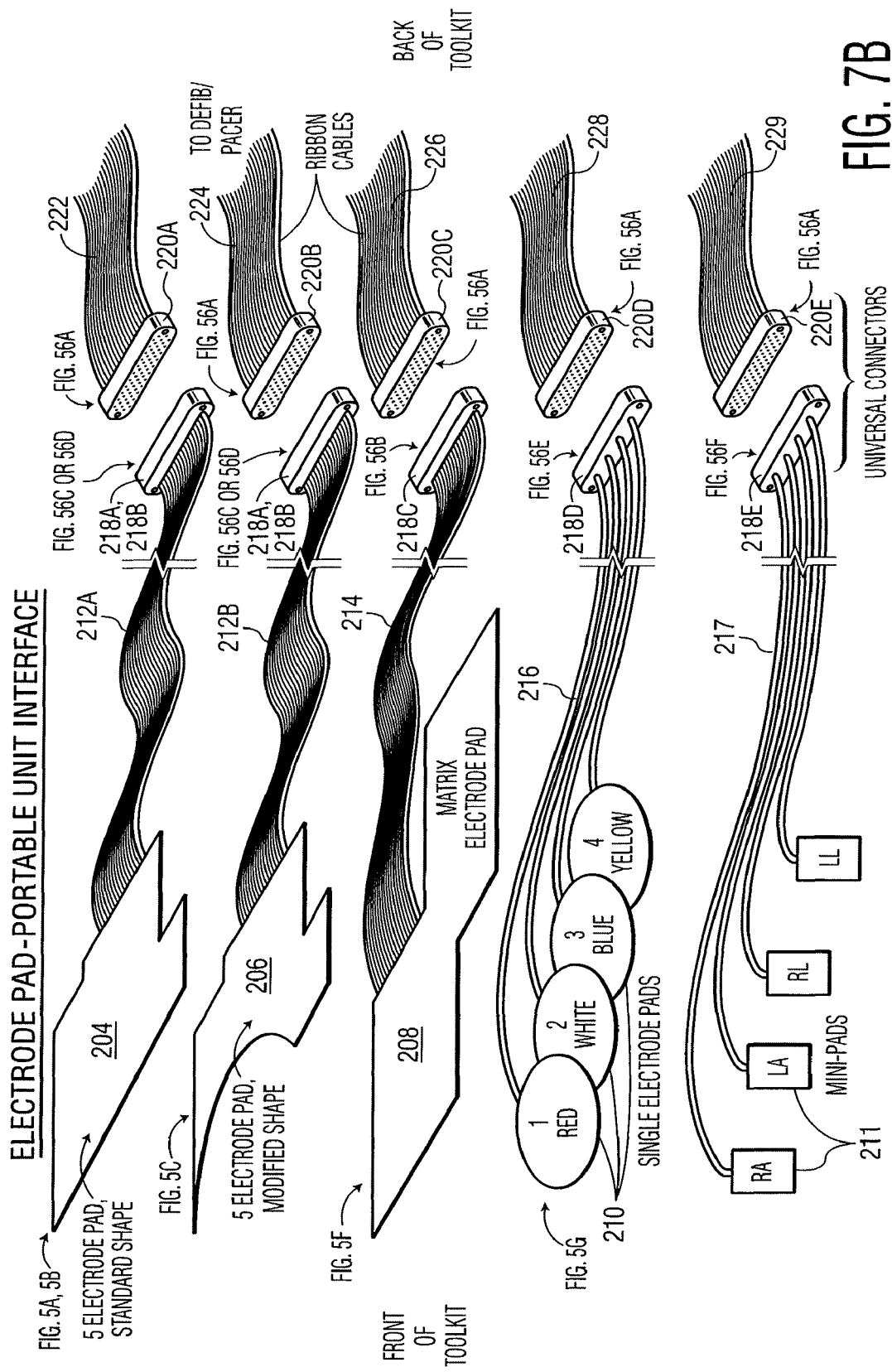
FIG. 7B is a representational diagram showing how the Universal Pads and/or contact electrodes, disposed in the portable unit, may be connected.

Door 158 covers a tool-kit, the contents of which are visible in FIGS. 7A and 7B. The door is locked until either: a) the MP releases it; or b) the PU is detached from the SU and placed down on the ground or other firm surface. Knob 160 facilitates enabler's opening of the door, once it has been released.

Antenna 162 allows the PU to be in radio communication with the SU. The antenna may be fixed in length, extendible (and retractable) manually, or extendible (and retractable) in response to a command by the MP. It may be contained entirely within the PU housing at all times; or it may lie partially or fully outside of the PU housing at all times; or it may, prior to the emergency, be situated entirely within the PU and be extended outside of the housing during the emergency, at the discretion of the MP. The antenna may also allow communication directly with the central station, i.e. without doing so via the SU. More than one antenna may be used to optimize communications over a wide range of frequencies.

Antenna 164 allows the SU 108 to be in radio communication with the PU 104. The antenna may be fixed in length, extendible (and retractable) manually, or extendible (and retractable) in response to a command by the MP. It may be contained entirely within the SU housing at all times; or it may lie partially or fully outside of the SU housing at all times; or it may, prior to the emergency, be situated entirely within the SU and be extended outside of the housing during the emergency, at the discretion of the MP. Either the same antenna or another one (with or without the same external control options as antenna 164) may be used to allow the SU to communicate via radio frequency with the CS. There may be additional SU antennas to optimize communications a) between PU and SU, and b) between SU and CS over a wide range of frequencies.

Figure 6B:
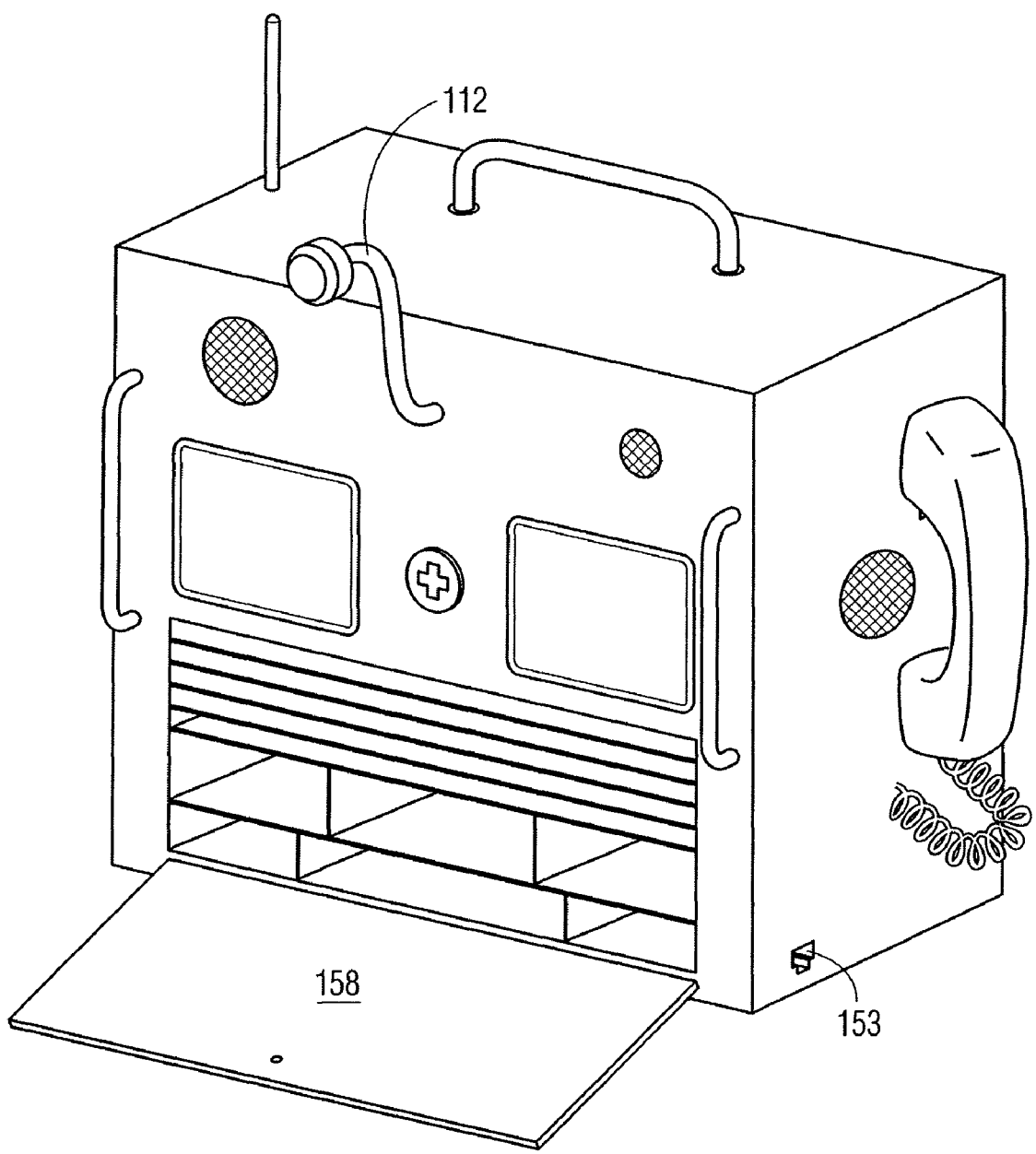
FIG. 6B is a perspective view of the detachable portion (so-called "portable unit") of the wall-mounted device of FIG. 6A.

FIG. 6B shows portable unit 104 without stationary unit 108. It shows partial extension of the video boom 112. It also shows door 158 in the open position, revealing multiple shelves and compartments within the tool-kit.

2.2 Portable Unit: Tool-kit

FIG. 7A shows the contents of the tool-kit. Five compartments 166A-166E contain electrode pads of various shapes and configurations. Each one is already wired into the portable unit, and ready to be applied to the victim. The choice of which of the pads is to be used, is made by the medical professional. Element 168 is a headset with microphone, which may make it easier for either the enabler or the medical professional to hear, in a noisy environment. The headset-microphone unit may be wireless, or hard-wired into the portable unit. Element 170 is a pair of scissors, to be used by the enabler, if necessary, to cut the shirt or blouse of a victim, in order to allow rapid placement of the electrode pad against the skin of the victim. Element 172 is a blood pressure cuff. It is of the automatically inflating and recording variety, as is known in the art. Upon instruction by the medical professional, enabler places it around the arm of a victim, allowing the MP in the central station to have intermittent blood pressure readings. Element 174 is a pulse oximetry transducer and holder. Upon instruction by the MP, enabler places it around the finger of a victim, allowing the MP in the central station to determine the victim's arterial oxygen saturation. Element 176 is a telephone wire and jack. One end of the wire is connected directly to the PU, allowing it to have a hard-wired interface with the public telephone network. The free end of the wire, terminating in a male jack, may be used by the enabler or EMT to connect the unit to the public telephone network, in the event that wireless communication to or from the portable unit is inadequate. Compartment 177 contains one or more spare pads which terminate in Universal Connectors (see ahead) but which are not, while stored in compartment 177, wired into the system. Compartment 177 also contains any one or more of a variety of items, including spare items for any of the aforementioned tool-kit supplies, an oral airway, gloves, telephone cable extensions, an apparatus for measuring the victim's cardiac output, the data from which may be transmitted to the MP (along with other victim data), and apparatus to assist in providing respiratory support for the victim. It may also contain a variety of items to be used by a physician, nurse, emergency medical technician including medications, intravenous administration fluids and apparatus and a stethoscope.

FIG. 7B shows a side view of the upper five compartments 166A-166E of the tool-kit. Item 204 is a defibrillating pad which contains five large electrodes, and which may additionally contain seven small electrodes for recording the electrocardiogram. Cable 212A electrically connects the pad to the female version of the universal connector 218A (for the pad without ECG electrodes) or 218B (for the pad with ECG electrodes). This mates with the male version of the universal connector 220A, which is electrically connected to the portable unit via cable 222.

Electrode pad 206 is similar to pad 204, in terms of electrode content and configuration, but its shape has been modified to allow greater conformity to the female torso. It is connected by cable 212B to female universal connector 218B, which mates with male universal connector 220B, which is connected to the portable unit by cable 224.

Electrode pad 208 contains a matrix of 32 electrodes. It is connected by cable 214 to female universal connector 218C, which mates with male universal connector 220C, which is connected to the portable unit by cable 226.

Electrode pads 210 each consist of a single defibrillating/pacing electrode. They are connected by wires 216 to female universal connector 218D, which mates with male universal connector 220D, which is connected to the portable unit by cable 228. Pads 210 are easily distinguished from each other, by either color, numeric markings, alphabetic markings, or any combination of these. They would be selected at the discretion of the medical professional, and two or more would be positioned under the direction of the MP.

Mini-pads 211 are intended for placement on the extremities for recording the ECG, and are not used as defibrillating/pacing electrodes. They are to be used when the MP decides that there is no need for defibrillation or pacing. They could be used when a conscious victim either doesn't need or refuses to allow the placement of defibrillating/pacing electrodes on the torso. They are connected by cable 217 to female universal connector 218E, which mates with male universal connector 220E, which is connected to the portable unit by cable 229. Labels RA, LA, RL and LL on the mini-pads refer to right arm, left arm, right leg and left leg, the intended placement locations. The mini-pads could also be color or number coded.

Individual defibrillating electrodes 210 and ECG electrodes 211 are well known in the art, and hence no further description of these elements is necessary. Different shapes and numbers of these single pads are possible.

Cables 212A, 212B, 214, 216 and 217 are of sufficient length to extend from the portable unit to the victim. Universal connectors 218A-218E and 220A-220E would ordinarily remain inside of the portable unit tool-kit compartment during use. However, cables 222, 224, 226, 228 and 229 are of sufficient length so that pulling on cables 212A, 212B, 214, 216 and 217 exposes the universal connector pair, allowing an already used electrode pad to be easily replaced.

2.3 Portable Unit: Rear and Left Side Panel

Figure 8:
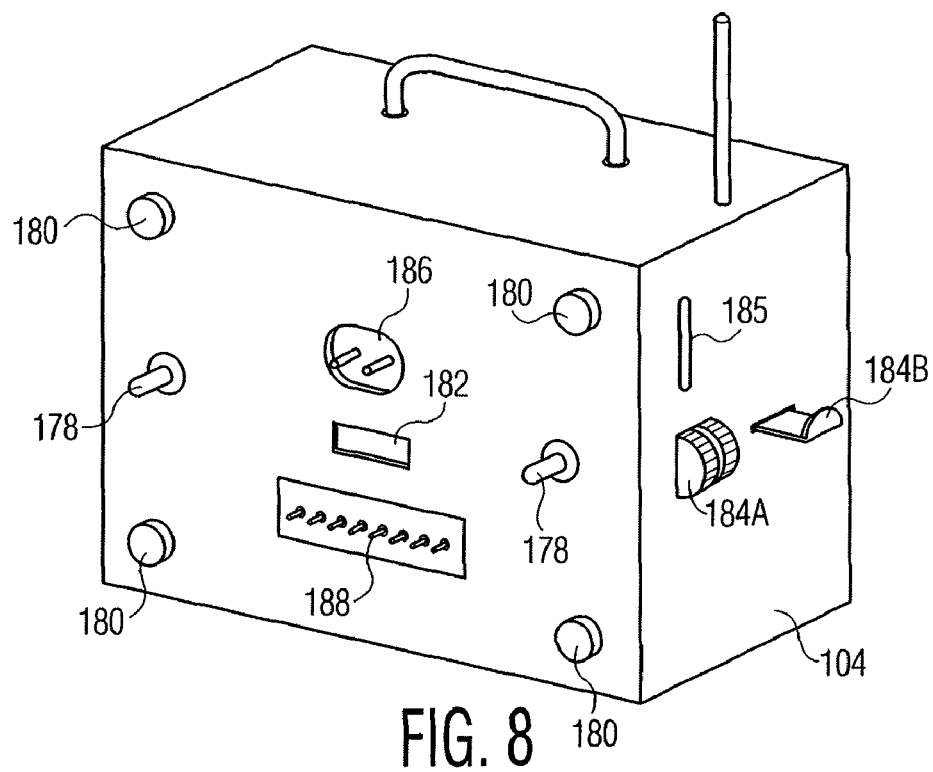
FIG. 8 is a perspective view of the rear panel of the portable unit of FIG. 6B.

FIG. 8 shows a view of the portable unit from the back, also showing the left side of the unit, i.e. the side opposite that which contains telephone handset 150. The back contains two or more sensor switches 178. These are push-button type switches, with a spring to keep the center dowel normally extended outwards. In the preferred embodiment, when the PU is not in use, the back of the PU is in close proximity to the outer surface of the stationary unit 108 (see FIGS. 6A and 9). This proximity results in the dowel of sensor switches 178 being pushed in. When the PU is removed from the SU, the spring-loaded dowel pops out, the sensor switch changes state, allowing the MP to know that the PU was removed from the SU. When the PU is placed on a surface such that its back faces down, the MP is once again notified, since sensor switches 178 will again change state as the dowel is pushed back in. And when the PU is later reconnected to the SU, the MP can gauge the adequacy of the reconnection procedure by the response of sensor switches 178.

The sensor switches may have more than two positions, allowing the MP to ascertain with greater accuracy whether the PU has been properly positioned during replacement. When three or more sensors are present, they may be distributed both horizontally and vertically, allowing the MP to have three dimensional information about the position of the PU as it is replaced, and thereby allowing the MP to more fully guide the person performing the PU replacement (see Section 4.5.7.4.3).

Four feet 180 allow the PU, once separated from the SU, to rest on a flat surface, with back side facing down, but without the back being flush against the flat surface.

Figure 9:
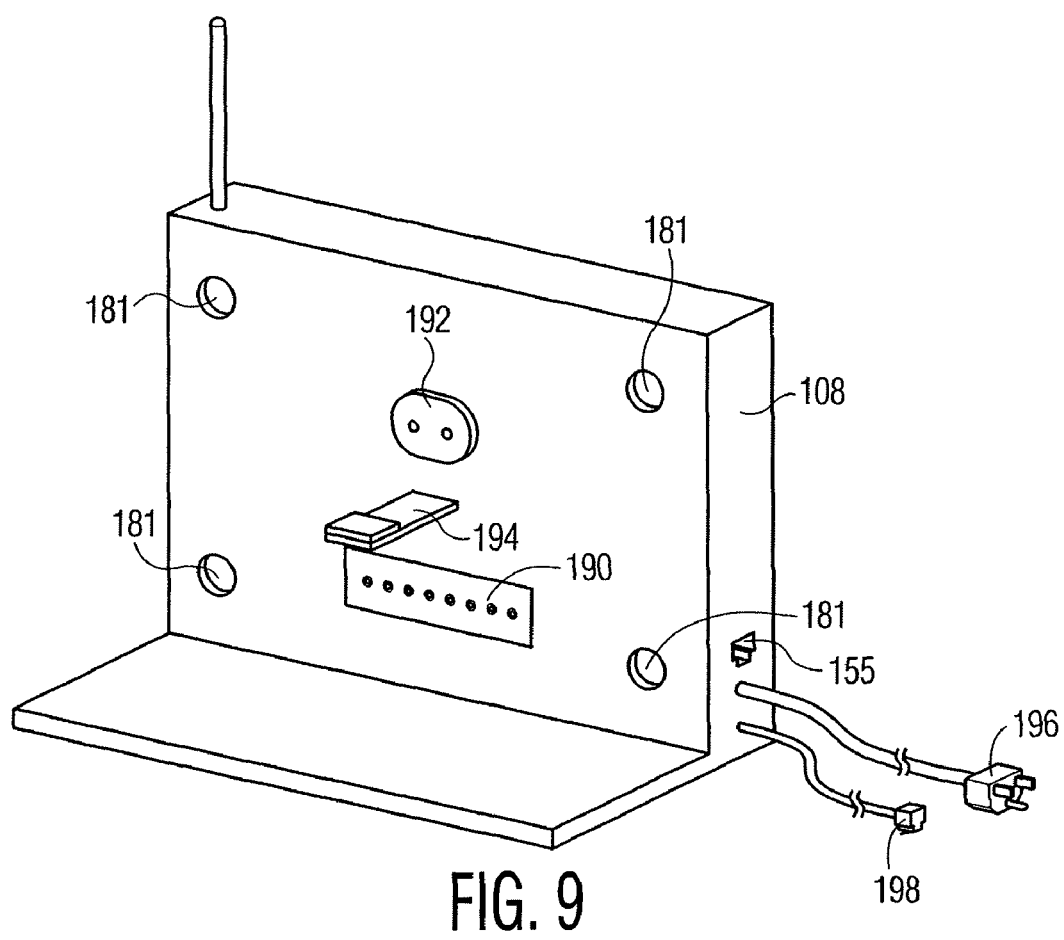
FIG. 9 is a perspective view of the base portion (so-called "stationary unit") of the wall-mounted device at the remote station with the portable unit removed.

In a preferred embodiment of the invention the PU, in its quiescent state, is locked to the SU. The SU is shown in FIG. 9. Receptacle and electromagnetic lock 182, FIG. 8, admits projection 194, FIG. 9 from the SU, to which it locks. This prevents removal of the PU from the SU by unauthorized persons. After the medical professional determines that a particular situation warrants the use of the PU, he sends a signal from the central station which causes the electromagnetic lock 182 to release its hold on projection 194.

In the event that either the lock release signal is not properly received or processed, or in the event of mechanical failure in the electromagnetic release mechanism, a backup, purely mechanical release mechanism is present. Combination lock and release mechanism 184 consists of a combination type lock, 184A as is known in the art. When enabler correctly turns its one or more wheels to the correct combination, he can push lever 184B which causes the release of projection 194. The combination would be made available to enabler by voice or text message, when appropriate. The combination lock and release mechanism are seen on the side of the PU opposite the side which contains telephone handset 150.

Embodiments of the invention without an SU are possible. Embodiments of the invention in which the locking projection 194 comes form a stationary object other than a stationary unit are possible; for example, the locking projection may be attached directly to a wall. Embodiments of the invention without a lock are also possible.

Embodiments of the invention with other backup lock release mechanisms are possible including: a) an electrical mechanism which actively releases the lock in the event of communications failure (locking mechanism normally closed); b) an electrical mechanism which passively releases the lock in the event of communications failure (locking mechanism normally open); and c) lock releases which include both mechanical mechanisms (the aforementioned) and electrical mechanisms (either (a) or (b)).

Element 186 is a power connector, which feeds electrical power into the portable unit. This source of power is used to operate the PU 104 and to charge its batteries, while it is in contact with the stationary unit 108. The PU power connector connects to the SU power connector 192, FIG. 9. Embodiments of the invention in which the PU receives electrical power directly from an alternating current source are possible. Embodiments of the invention in which the PU has long shelf-life batteries and does not have an alternating current supply are also possible.

Element 188, FIG. 8 is the PU telemetry connector which mates with the SU telemetry connector 190, FIG. 9. These telemetry connectors carry information between PU 104 and SU 108 before they have been separated. Such information includes audio and video signals, text messages and telemetry signals between the MP and the enabler. In a preferred embodiment of the invention, the SU serves as an intermediate communications link between the PU and the central station. Embodiments in which the PU may or must communicate directly with the central station are also possible. Such an embodiment may have an external male telephone jack (such as element 176 within the tool-kit) for attachment to the public telephone network.

The left side also contains a magnetic card reading device 185. This allows the MP to have access to the information on a card which may contain victim medical history. It also allows the MP to have access to information on a card which properly identifies EMT personnel, before control of the PU is transferred.

2.4 Stationary Unit: Front and Side Panels

The stationary unit 108 is L-shaped, allowing its lower portion to support the PU. Line cord and plug 196 allow for supply of outside power. Telephone cable and male jack 198 allow for connection of the SU to the public telephone network. Female telephone jack 155 allows the SU to receive a direct telephone connection from a PU. The SU may have four depressions in its surface, positioned where the PU feet 180 come in contact with it. These depressions are wide enough to admit the PU feet, and are of a depth that is less than the height of the PU feet. This allows the PU feet to partially penetrate the SU surface. This geometry, along with sensor switches 178 having more than two positions, allows the MP to distinguish:

a) when the PU has been detached from the SU by the enabler (all center dowels of switches 178 in the fully extended position); from b) when the PU is placed properly on the ground or another level surface (all center dowels of switches 178 in the partially extended position); from c) when the PU has been properly returned to its correct position on the SU shelf (all center dowels of switches 178 in the fully retracted position); from d) when the PU is improperly positioned on the SU shelf (not all center dowels of switches 178 fully retracted).

2.5 Portable Unit: Screens

Figure 10:
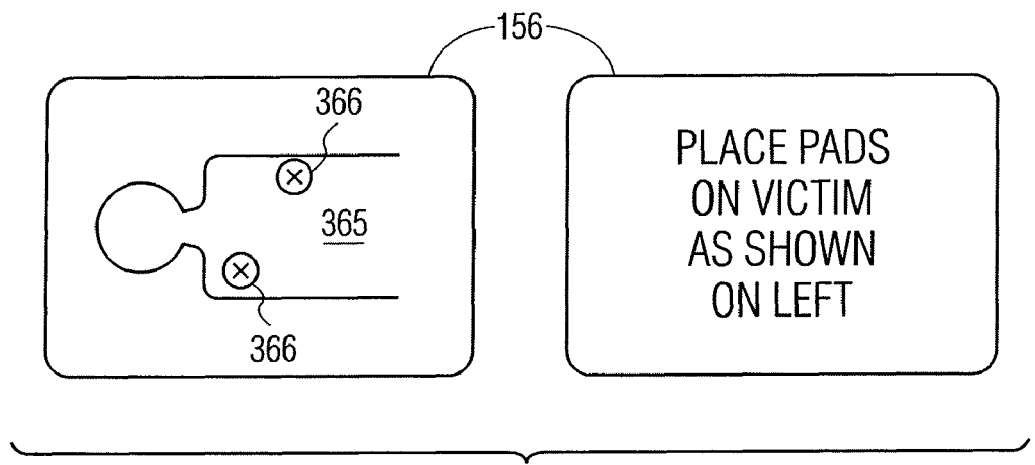
FIG. 10 illustrates preferred images which may appear on the two display screens of the portable unit.
Figure 11:
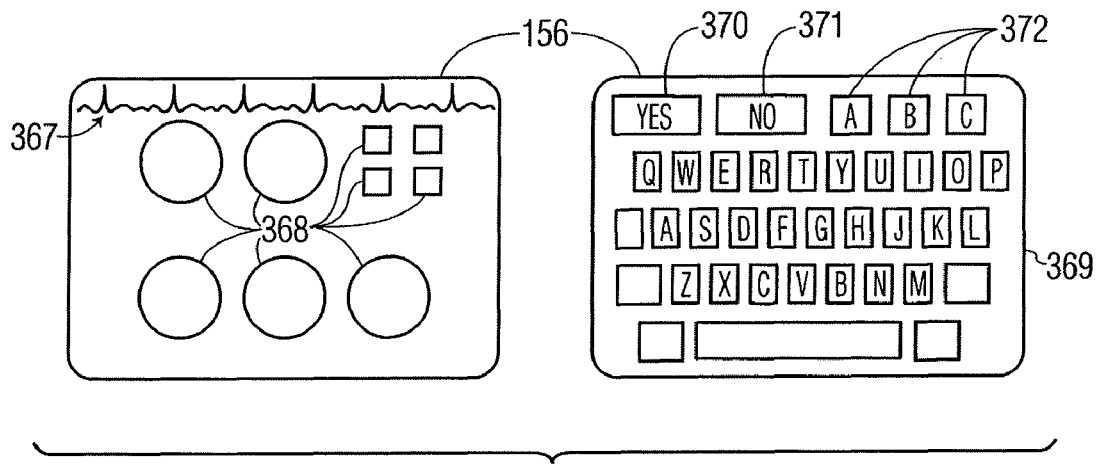
FIG. 11 illustrates alternative preferred images which may appear on the two display screens of the portable unit.

FIGS. 10 and 11 show various configurations for PU screens 156. (See FIG. 6A for frontal PU view.)

The left screen in FIG. 10 shows an instructional video. In the example shown, a cartoon 365 of the victim is seen along with cartoon designations of ideal electrode pad locations 366. Alternatively, the screen may show the actual victim 102, visualized by PU video camera 154; with superimposed markings or overlays, manipulated by the MP, indicating desired electrode pad placement. Alternatively, other instructional videos including techniques of cardiopulmonary resuscitation may be displayed. Alternatively, a video display of the medical professional in the central station may be displayed.

The right screen in FIG. 10 shows a text message from the medical professional 301 in the central station 300. Such messages may be utilized in the event of poor quality reception of CS signals at the PU, a noisy emergency scene, or a heard-of-hearing enabler.

FIG. 11 shows the use of the PU screens in a touch sensitive mode. The left PU screen shows a control panel similar to that utilized by the medical professional in the central station. This screen is displayed only under special circumstances. The MP can enable local (i.e. victim-side) control of the portable unit, in the event of arrival of trained medical personnel at the emergency scene, or if the enabler himself is a qualified medical professional. The MP enables EMT control of the PU by sending a command to set the master control unit 130 to state 3 (see Table 1, above). When EMT control is enabled by the MP, the victim's electrocardiogram tracing 367 is displayed. Virtual control buttons 368 on a touch sensitive control screen allow control of defibrillation, pacing, monitoring and other functions. The on-site professional would be able to access any of the portable unit control screens available to the central station medical professional.

The right screen in FIG. 11 shows a virtual keyboard 369, with a "YES" key 370, a "NO" key 371 and "hot-keys" 372. This screen allows the enabler 100 to send text messages to the medical professional in the event of poor quality audio reception of PU signals at the CS, or in the event of a noisy emergency scene.

The screen functions shown in FIGS. 10 and 11 need not occupy a full screen. Screen-in-screen and split screen displays are also possible.

3.0 Electrode Pads

3.1 Physiology of Defibrillation

The termination of ventricular fibrillation during a cardiac arrest is accomplished by passing a brief, high voltage pulse between two electrically conducting pads on a victim's chest. Since the success of the defibrillating pulse is dependent on the achievement of sufficient voltage gradient, over sufficient volume of heart tissue, proper positioning of the defibrillating electrodes is critical. If the electrodes are too close to each other, regions of cardiac muscle not near the electrodes will have insufficient voltage gradient, and the defibrillation attempt will be unsuccessful. Similarly, if the electrodes are not sufficiently near the heart, an unsuccessful defibrillation attempt may ensue.

Standard operating procedure for defibrillation calls for the passage of an electric current between two pads on the victim's chest, one placed high on the chest to the right of the midline, and one placed on the far left side of the chest, beneath the nipple. Alternate approaches involve a single electrode on the chest surface (generally referred to as anterior) and another electrode on the back (generally referred to as posterior.

In the preferred embodiment of the invention, the medical professional has access to more than two defibrillation electrodes. This allows the MP to select what he believes to be the optimum vector or pathway for defibrillation energy applications. If the first defibrillating shock is unsuccessful, the MP, when more than two defibrillation electrodes are present, would be able to change the pathway of defibrillation energy for a subsequent shock, by changing the choice of electrodes. The ability to change the choice of electrodes also allows the MP to compensate for inaccuracies in positioning and/or orienting the electrode pad. It also allows the MP to make adjustments for different victim sizes and different heart sizes.

3.2 Torso-Shaped Multi-Electrode Pads

FIG. 5A shows the non-victim side of a five electrode "pad" 204A It is torso shaped, with an extended portion, labeled "VICTIM'S LEFT" which is intended to wrap around the victims left side, that is, the victim's left axillary region, slightly below the level of the breast. Individual electrodes, as are known in the art, are located at 230, 232, 234, 236 and 238, each of which contains electrically conductive material on the patient side of the pad. A wire extends from each electrode; the five wires, though insulated from each other, coalesce to form cable 212A. Easily seen labels reading "NECK" and "VICTIM'S LEFT" are intended to help the enabler properly position the pad on the victim's torso.

The selection of defibrillating electrode location generally calls for having as much of the heart's mass lying on a direct path between the defibrillating electrodes. Therefore, the typical defibrillation effort would entail the application of energy between electrode 230, labeled $\alpha$, located over the right upper torso; and electrode 236, labeled $\delta$, located beneath the left breast. If such a shock did not result in the restoration of a normal rhythm, a second effort involving electrodes 230 ($\alpha$) and 238 ($\epsilon$) would be a reasonable choice. The $\alpha$-$\epsilon$ pair might be a good first choice for a very large patient. This choice, and all other choices of electrodes would be made by the medical professional's selecting these electrodes from among a menu of options. With a five electrode pad, the MP may choose any of ten possible pairs of electrodes. (The value of ten ignores polarity considerations.) The MP may elect to apply energy when two or more electrodes are made electrically common. An example of this would be to make electrodes 236 ($\delta$) and 238 ($\epsilon$) electrically common, and to apply energy between electrode 230 ($\alpha$) and the composite $\delta/\epsilon$ electrode. In principle, the use of 3, 4 and 5 electrode combinations increases the number of possible electrode combinations 90. (The value of 90 ignores polarity considerations.). Although in practice, many of these 90 combinations would not be clinically sensible, some would be.

In the event that the electrode pad is improperly positioned or oriented on the torso of the victim, the presence of a multiplicity of electrodes gives the MP some latitude in correcting the error, without having to ask the enabler to remove and reposition the pad. For example, if the pad were rotated 90 degrees, such that electrode 230 ($\alpha$) was positioned at the left (instead of right) upper torso, and electrode 234 ($\gamma$) was positioned at the right upper torso; the MP could apply energy between electrodes 234 ($\gamma$) and 232 ($\beta$), accomplishing what a standard $\alpha$-$\delta$ application would, had the pad been properly oriented.

In the event that one or more electrodes is making poor contact with the patient, the MP can identify the poorly contacting electrode(s) and can either work around it or ask the enabler to correct the condition. Circuitry within the PU performs impedance measurements between certain electrode combinations to identify poorly contacting electrode(s). For each measurement, one electrode is electrically isolated, and the other four electrodes are electrically common. For example, the MP would know that the $\delta$ electrode is making poor contact if the impedance measurement of $\delta$ vs. electrically common $\alpha/\beta/\gamma/\epsilon$ is high, while the impedance value of each other combination of one electrode against the other four, e.g. $\alpha$ vs. $\beta/\gamma/\delta/\epsilon$ is low. Using such an approach, a low impedance measurement implies that the electrically isolated electrode (and at least one other electrode) is making good contact. A high impedance reading implies that either the electrically isolated electrode (and/or all of the electrically common electrodes) is making poor contact. Other impedance measuring algorithms can also identify poorly contacting electrodes. The only distinction that cannot be made by such an approach is the correct identification of a single electrode making good contact, when all of the remaining electrodes are making poor contact.

The medical professional may work around a poorly contacting electrode if he feels that a properly contacting adjacent electrode will make a reasonable substitute. For example, if the $\delta$ electrode is found to be making poor contact, the MP may elect to defibrillate using the $\alpha$-$\epsilon$ pair, instead of the standard $\alpha$-$\delta$ pair. Alternatively, the MP may ask the enabler to apply pressure over the surface of the $\delta$ electrode, perhaps using a circular motion, in order to achieve better $\delta$ electrode contact.

Combinations of two or more electrodes may also be used to apply a lower voltage energy to the victim's torso for pacing the heart. The medical professional would select the choice of electrodes in the same way that he selects the defibrillating electrodes. The choice of pacing electrodes need not be the same as the choice of defibrillating electrodes.

Table 3 shows how combinations of two or more electrodes may be used to record seven of the twelve standard electrocardiogram leads.

TABLE 3

ECG Recording Configuration on Five Electrode Pad

| Lead | Electrode #1 | Electrode #2 |
|---|---|---|
| I | $\alpha$ | $\beta$ |
| II | $\alpha$ | $\delta$ |
| III | $\beta$ | $\gamma$ |
| aVR | $\alpha$ | $\beta + \gamma$ |
| aVL | $\beta$ | $\alpha + \gamma$ |
| aVF | $\gamma$ | $\alpha + \beta$ |
| V3/V4 | $\delta$ | $\alpha + \beta + \gamma$ |
| V6 | $\epsilon$ | $\alpha + \beta + \gamma$ |

An eighth configuration, listed in the table as V3/V4 records a composite of the standard lead V3 and lead V4, because of the large size of the $\delta$ electrode. Furthermore, the medical professional may elect to record between any combination of electrodes, giving him, in principle, a total of 90 recording options.

Different numbers, shapes and locations of large electrodes could accomplish the tasks of defibrillation, pacing, ECG monitoring and monitoring of appropriate pad contact.

Figure 5B:
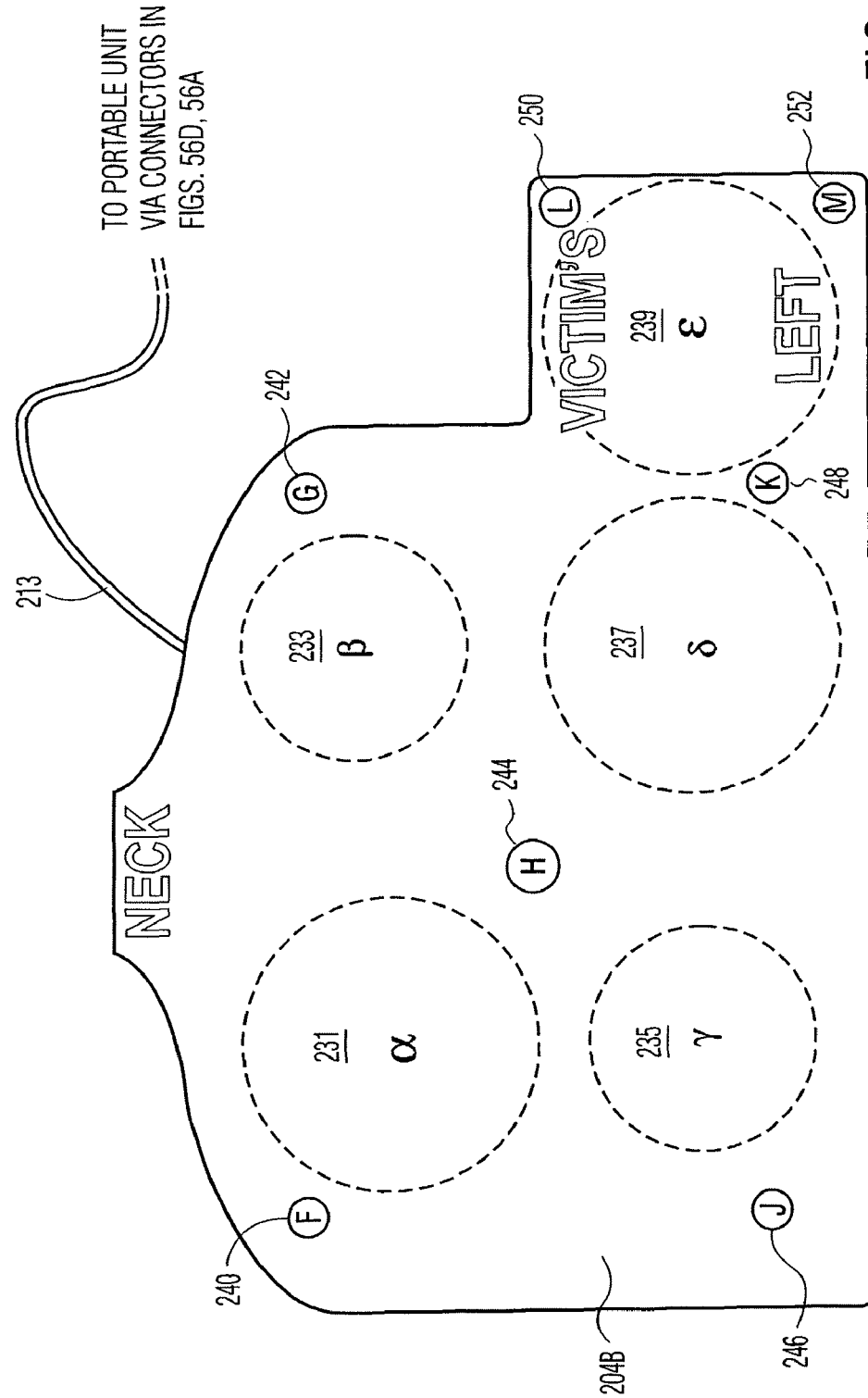
FIG. 5B is a front elevational view of an alternative embodiment of a Universal Pad according to the present invention.

Element 204B in FIG. 5B is a modified version of the standard electrode pad 204A. In addition to the five defibrillating electrodes, it contains multiple smaller electrodes 240 (F), 242 (G), 244 (H), 246 (J), 248 (K), 250 (L) and 252 (M). Table 4 shows how combinations of these electrodes could be used to record 10 of the 12 leads of a standard electrocardiogram.

TABLE 4

ECG Recording Configuration on Five Electrode Pad with Seven Sensing Electrodes

| Lead | Electrode #1 | Electrode #2 |
|---|---|---|
| I | F | G |
| II | F | K |
| III | G | J |
| aVR | F | G + J |
| aVL | G | F + J |
| aVF | J | F + G |
| V1 | H | F + G + J |
| V3/V4 | $\delta$ | F + G + J |
| V5 | K | F + G + J |
| V6 | $\epsilon$ | F + G + J |

Electrode 250 (L), though not situated at one of the standard electrocardiogram lead locations, may nevertheless be of value to the medical professional. The non-victim side of the pad is shown in FIG. 5B. The conductive surface of each of the ECG electrodes faces the opposite or victim side of the pad. A wire extends from each of electrodes 240-252. These wires coalesce to form cable 213, which also contains the five wires extending from the five defibrillating electrodes.

Impedance measurements involving combinations of the seven small electrodes may be utilized to identify poorly contacting electrodes, using an algorithm similar to that described for the large electrodes. Alternatively, an algorithm involving impedance measurements between combinations of large and small electrodes could be utilized. The only advantage of this latter algorithm is that in cases where only one large and only one small electrode are making proper contact, it could identify which are the properly contacting ones. The algorithm which uses only the five large electrodes, and the algorithm which uses only the seven small ones would fail to identify the properly contacting ones, in circumstances in which only one large and one small electrode are making proper contact.

An improperly contacting small electrode may indicate that part of an adjacent large electrode is making poor contact. This would be useful information, since partial non-contact of a large electrode would be more difficult to diagnose from impedance measurements and since partial non-contact could reduce the chance of defibrillation success. If, for example, all impedance measurements are low except that between electrode L and the composite of F/G/H/J/K/M, it would imply that the area of poor pad contact might extend beyond small electrode L to large electrode ϵ. If electrode ϵ was going to be used for defibrillation, the MP would then ask the enabler to apply pressure over electrodes L and ϵ, in order to establish better contact between these electrodes and the skin surface.

Different numbers, shapes and locations of small and/or large electrodes could accomplish the tasks of defibrillation, pacing, ECG monitoring and monitoring of appropriate pad contact.

Element 206 in FIG. 5C is a modified version of the electrode pad 204B. The lower perimeter, i.e. the perimeter adjacent to electrodes J, γ, H, δ and K has been modified to curve upwards to exclude a region overlying the breasts of a female victim. The purpose of the modification is to assure better electrode contact for female victims. The pad is shaped so that at least some breast tissue would lie caudal to the pad, i.e. between the pad and the victim's feet. The breast tissue would thereby not prevent the γ and the δ pads from making proper contact. Pad 206 contains an elliptically shaped β electrode 254, which allows for rostral displacement of the δ electrode, i.e. towards the victim's head, to accommodate breast tissue. The γ electrode 256 is also elliptical in shape, to allow some of the tissue of a female victim's right breast to lie outside of the perimeter of the pad. The ϵ electrode 259 is similar in shape and position to its counterpart, element 239 in the unmodified version of this pad shown in FIG. 5B.

In all other aspects the properties and operation of pad 206 are similar to pad 204B.

Modifications of pad 206 are possible including modification in the shape of any electrode, modifications in which the β and γ electrodes are omitted, modifications in which the long axis of either of the β or γ electrodes is not horizontally oriented, and modifications in which the center of the δ electrode is displaced in either the rostral, caudal, right or left directions. Modifications are also possible in which the size of the α electrode 253 and the δ electrode 258 are smaller than their counterparts in non-concave electrode pad. Modifications are also possible in which the shape of the caudal surface, though concave, differs from that shown in FIG. 5C.

Other modifications of pad 206 are possible in which different numbers and locations of small and/or large electrodes could accomplish the tasks of defibrillation, pacing, ECG monitoring and monitoring of appropriate pad contact.

Modifications of pad 206 are possible which do not contain the seven small ECG electrodes In this case, its operation would be similar to pad 204A.

Figure 5D:
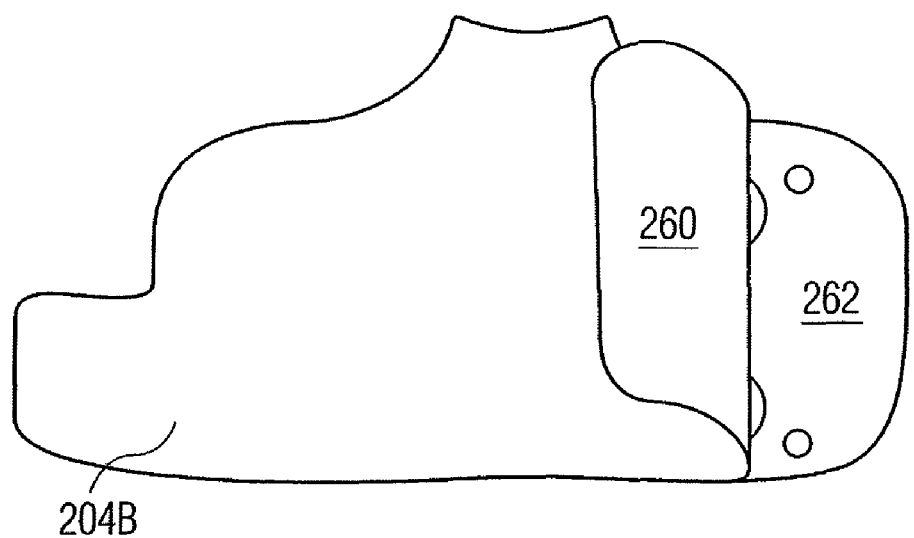
FIG. 5D is a rear elevational view of the Universal Pad according to the present invention showing a peel-off backing covering the contact electrodes.

FIG. 5D shows a view of pad 204B from the side opposite that shown in FIG. 5B. A portion of the protective backing 260 has been peeled off and partially folded. Removing the backing, a procedure performed by the enabler under the direction of the medical professional, exposes the conductive surface of the electrodes as well as an adhesive surface 262. The adhesive surface holds the pad and its electrodes onto the victim's chest, after the pad has been initially placed there by the enabler.

Figure 5E:
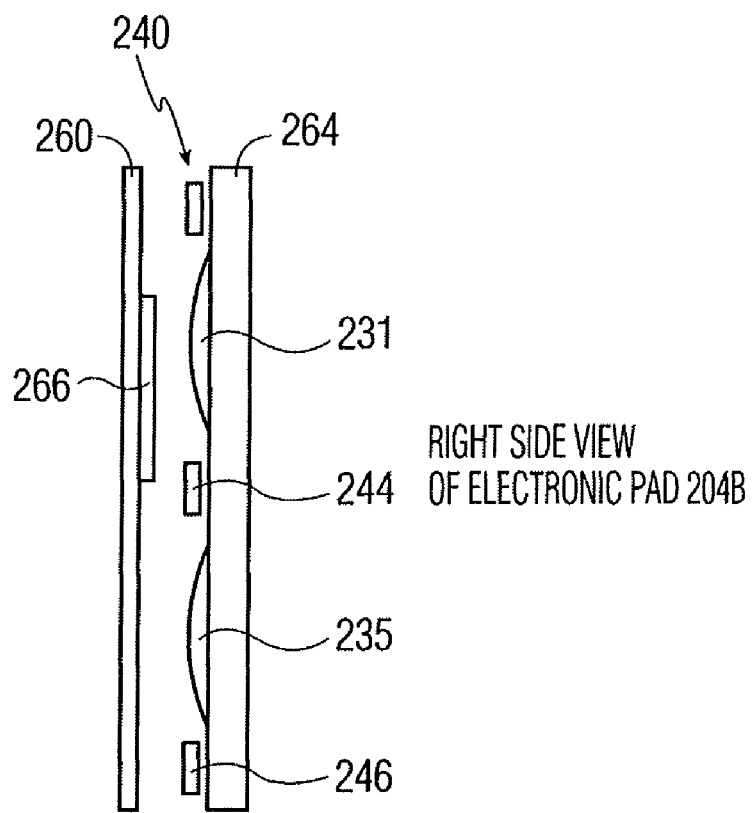
FIG. 5E is a side elevational view of the Universal Pad showing the pad substrate, the contact electrodes and the peel-off backing.

FIG. 5E shows an edge view of pad 204B, with a view toward the edge which is to be applied to the victim's right. Electrodes 240, 231, 244, 235 and 246, are seen in profile. The electrodes protrude from a non-conductive semi-rigid supporting material 264. A conductive strip 266 is attached to backing 260, and extends from electrode 231 to 244. Conductive strip 266 maintains a low resistance path between electrodes 231 and 244 while the backing is in place. The MP can determine when the enabler has removed the backing, by observing a sudden rise in the resistance of this path. Strip 266 can extend between any two adjacent electrodes.

In an alternative embodiment, the strip would touch each of two small conductive areas adhering to supporting material 264, which are not ECG electrodes, but which are conductive surfaces dedicated exclusively to allowing the assessment of contact between the backing and the pad. This approach avoids the placement of conductive additional conductive material in contact with the ECG electrode gel. One wire would extend from each of these conductive surfaces to join cable 213, FIG. 5B.

In another alternative embodiment, a conductive strip is attached to one point on the surface of supporting material 264, runs along the surface of backing material 266, and, at its other end, is attached to another point on the surface of supporting material 264. Each of the two attachment points on 264 is electrically in contact with a wire which goes on to form part of cable 213. When the enabler pulls off the backing material, the conductive strip is broken, terminating electrical continuity between the wires at the two ends of the strip.

Edge and back views of pads 204A and 206 show features analogous to those seen in FIG. 5E, showing the side view of pad 204B.

3.3 Matrix Electrode Pad

Figure 5F:
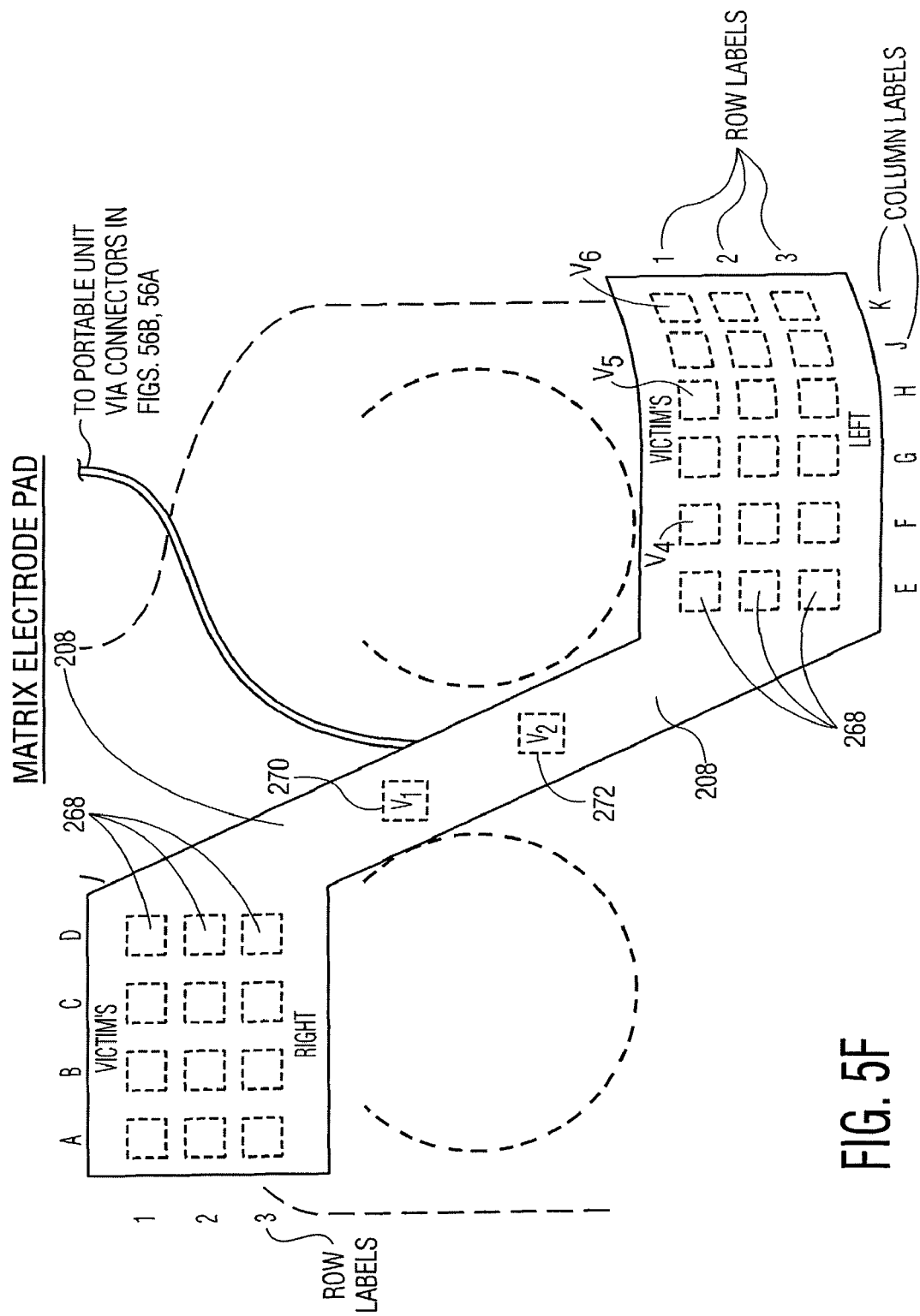
FIG. 5F is a front elevational view of still another alternative embodiment of a Universal Pad having a large number of contact electrodes.

FIG. 5F shows another type of multi-electrode pad 208, hereinafter referred to as a matrix electrode pad. One group of electrodes is situated to contact the upper right side of the victim's chest. Another group of electrodes is situated to contact the left side of the victim's chest, beneath the breast. Additional electrodes lie on a strip which extends diagonally between the two aforementioned groups of electrodes.

The large number of closely spaced electrodes in the upper right and lower left groups allows the MP to "construct" composite defibrillating and pacing electrodes of desired shape and location by rendering each of a number of adjacent small electrodes electrically common. The electrodes are made electrically common within the portable unit, following the commands of the medical professional.

In the embodiment shown in FIG. 5F, thirty electrodes, 268 are each designated by a unique column label (using letters A through K) and row label (using numerals 1 through 3). Thus, the electrode which, on the victim, is most rightward and most rostral is designated as A1, while the electrode which is most leftward and caudal is designated as K3. Actual row and column labels may be printed on the non-victim side of the pad. Two additional electrodes, 270 and 272 are situated on the diagonal strip which connects the right and left sections of the pad. They are designated $V_1$ and $V_2$, labels which are consistent with 12 lead ECG designations.

When using the pad to defibrillate or pace a victim, the medical professional 301 would construct a composite electrode by commanding the portable unit 104 to make a group of electrodes electrically common. For example, the nine electrodes A1-A3, B1-B3 and C1-C3 form a three by three array which could serve as the right chest electrode, analogous to the a electrode 230 on the five electrode pad 204A, FIG. 5A.

If instead of selecting the electrodes in columns A, B and C, the MP selects the nine electrodes in columns B, C and D, he has effectively "moved" or shifted the location of the right chest electrode toward the midline of the chest. If he wishes to use a larger right chest electrode, he could select all twelve of the electrodes in columns A, B, C and D. If he wishes to use a smaller right chest electrode he could select a two by two array, e.g. A1, A2, B1 and B2; a two by three array, e.g. A1, A2, A3, B1, B2 and B3; or an irregularly shaped array, e.g. A1, A2, A3, B1 and B2. He could select a single electrode, or he could select a non-contiguous group of electrodes. Thus any combination of the twelve right sided electrodes could form the right chest electrode.

The left chest electrode is selected in a manner similar to that for the right chest electrode. For example, the nine electrodes in columns G, H and J would be a typical choice. If the MP wished to "move" or shift the left chest electrode further leftwards, he could select the nine electrodes in columns H, J and K. If the MP desired a more rightwards location, the electrodes in columns F, G and H could be selected. As is the case with the right chest electrode combination, any combination of left sided electrode(s) could constitute the composite left electrode.

Electrocardiogram recording is accomplished by utilizing two or more of the thirty two electrodes, as described in Table 5.

TABLE 5

ECG Recording Configuration on Thirty Two Electrode Pad

| Lead | Electrode #1 | Electrode #2 |
| --- | --- | --- |
| I-like | A3 | K1 |
| II | D1 | E3 |
| V1 | V1 | A1 + A3 + C1 + E3 + G3 + J3 |
| V2 | V2 | A1 + A3 + C1 + E3 + G3 + J3 |
| V3 | E1 | A1 + A3 + C1 + E3 + G3 + J3 |
| V4 | F1 | A1 + A3 + C1 + E3 + G3 + J3 |
| V5 | H1 | A1 + A3 + C1 + E3 + G3 + J3 |
| V6 | K1 | A1 + A3 + C1 + E3 + G3 + J3 |

Because of this pad's diagonal orientation, certain modifications in recording technique are required. The absence of electrodes in the vicinity of the left arm results in inability to display lead III and the three augmented leads. Lead I is recorded from the pair of electrodes which are closest to horizontal on the pad. However, the geometry of the pad may result in inability to achieve a perfectly horizontal orientation; hence Table 4 refers to this lead as "I-like." Similarly, the ordinarily horizontal relationship of leads $V_1$ and $V_2$ might be modified to accommodate the diagonal region of the pad. The electric potential at the six V leads, ordinarily subtracted from that of a composite of right arm, left arm and leg, is in this case subtracted from a modified composite consisting of electrodes A1, A3, C1, E3, G3 and J3. Other electrode combinations than those listed in Table 5 could be used, if, at the MP's discretion, the medical situation called for such an analysis.

The electrode combination used to defibrillate a victim may be different than the electrode combination used for pacing, which in turn may be different from the combinations used for ECG recording.

As described above in connection with the pads containing five defibrillating/pacing electrodes (FIGS. 5A and 5B), in the event that one or more electrodes in the matrix pad 208 is making poor contact with the patient, the MP can identify the poorly contacting electrode(s) and can either work around it or ask the enabler to correct the condition. Circuitry within the PU performs impedance measurements between electrode combinations to identify poorly contacting electrode(s). For each measurement, one electrode is electrically isolated, and the other thirty one electrodes are electrically common, in a manner similar to that described for the aforementioned pads. For example, the MP would know that electrode D3 is making poor contact if the impedance measurement of D3 vs. an electrically common composite of the other 31 electrodes, is high, while the impedance value of other combinations of electrodes is low The medical professional may work around a poorly contacting electrode if he feels that a properly contacting adjacent electrode will make a reasonable substitute. Alternatively, the MP may ask the enabler to apply pressure over the surface of the poorly contacting electrode, in order to achieve better electrode contact.

Different numbers, shapes, sizes and locations of electrodes could accomplish the tasks of defibrillation, pacing, ECG monitoring and monitoring of appropriate pad contact. The shape of the pad and the length of the diagonal region is preferably designed to fit the average size person. The electrodes themselves need not be of uniform size or shape, and the inter-electrode distance need not be uniform.

The back of the pad is constructed in a manner similar to that shown in FIG. 5E. The conductive strip allowing the monitoring of backing removal extends between any two adjacent electrodes.

3.4 Single Electrode Pads

Another approach to electrode pads is the placement of two or more single electrode defibrillator/pacing pads, as are known in the art, upon the torso. In the embodiment shown in FIG. 5G, three single electrode pads, 210, are in place on the torso. A greater or lesser number of these single electrode pads may be used. (Four pads shown in FIG. 7B.) These single electrode defibrillator/pacing pads are available in the tool-kit section of the Portable Unit, as described above in connection with FIG. 7B. The pads are distinguished from each other by the presence of a numeral on the non-victim surface of the pad, by color, by shape or by more than one such feature. The medical professional instructs the enabler in the proper location of each electrode as described previously A wire, 216, extends from each pad leading to universal connector, type D, 218D.

Figure 5G:
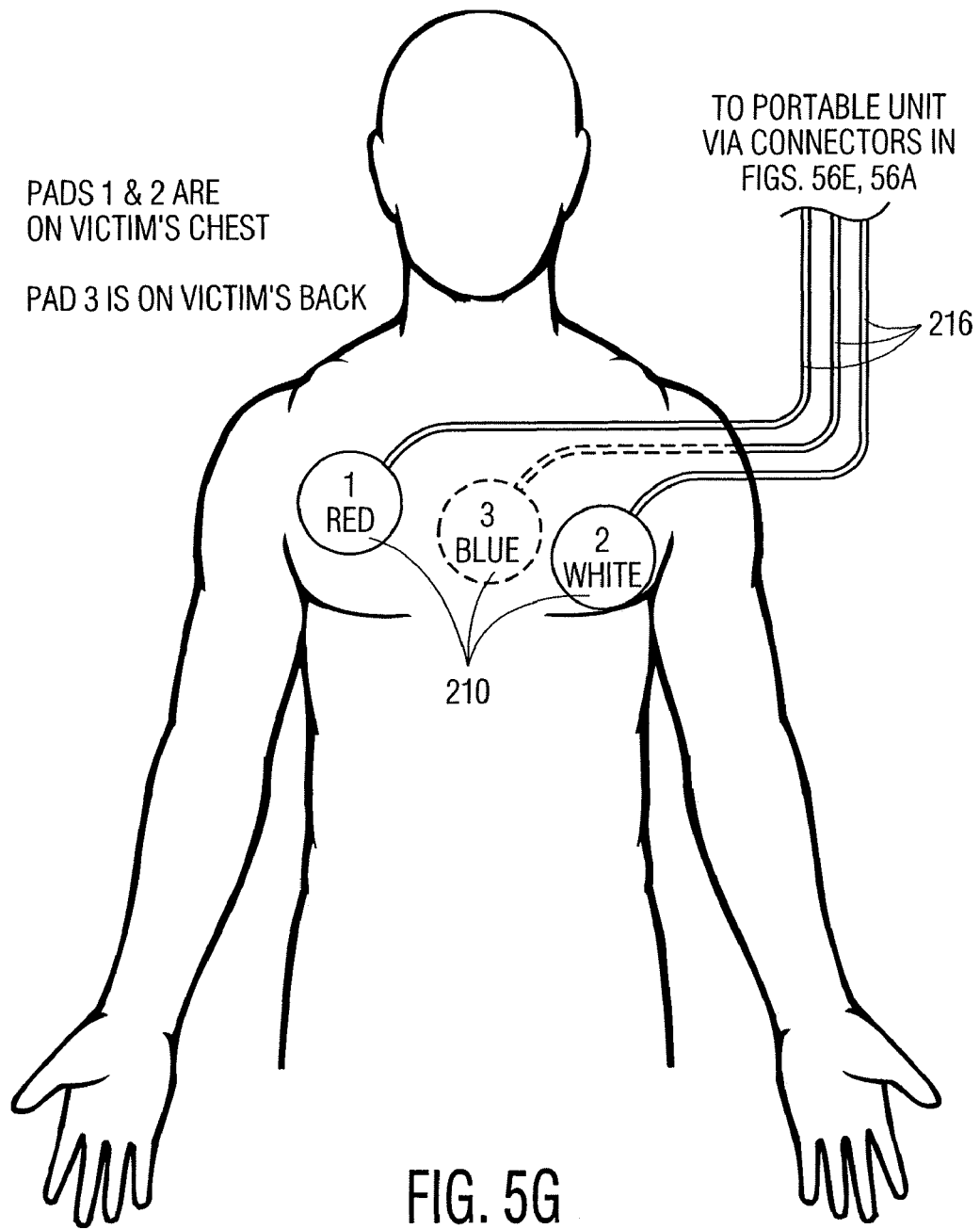
FIG. 5G is a front elevational view of three single electrode pads, two on a victim's chest, and one on his back.

Standard operating procedure for defibrillation calls for the passage of an electric current between two pads on the victim's chest, one placed high on the chest to the right of the midline, and one placed on the far left side of the chest, beneath the nipple. Alternate approaches involve a single electrode on the chest surface (generally referred to as anterior) and another electrode on the back (generally referred to as posterior), indicated by dashed lines. FIG. 5G shows the placement of two anterior electrodes (labeled "1" and "2" on the pads) and one posterior electrode (labeled "3" on the pad). The posterior placement is indicated in the figure by dashed lines. By placing more than two electrode pads on the torso, the medical professional has options beyond those available for the two electrode approach. These include: a) the ability to repeat defibrillation using a different combination of electrodes if a first attempt fails; b) the ability to apply defibrillating energy simultaneously between more than two electrodes (For example, in FIG. 5G, energy could be applied between pad 1 and pad 2, and between pad 1 and pad 3, simultaneously. Furthermore, this simultaneous application need not involve the same voltage or waveform between the different pairs of electrodes.); and c) the ability to apply energy to different pairs non-simultaneously.

The single electrode pads may be used for defibrillation, for pacing and/or for recording the electrocardiogram. Any number, shape and size of electrode pads may be utilized; and they need not be of uniform shape or size. Their location may be anywhere on the body, in accordance with proper medical practice.

4. Sample Cardiac Arrest and System Operation
4.1 Overview of Sample Arrest For illustrative purposes, an hypothetical cardiac arrest is discussed. The seven major phases of the events during the hypothetical cardiac arrest are described in Table 6:

TABLE 6

Seven Phases of Activity During a Cardiac Arrest

| Phase | Time (m:ss) | Activity |
| --- | --- | --- |
| 1 | 0:00-0:31 | Initial enabler action from the time he first sees victim until button press (activation of the PU by the enabler) |
| 2 | 0:31-0:50 | A series of four "handshakes" between the MP and the enabler: a) communication, b) telemetry c) audio, and d) informational |
| 3 | 0:50-2:19 | Transport of PU from pre-arrest location to victim's side; setup of PU at victim's side; four layer handshake between victim MP, including diagnosis of ventricular fibrillation |
| 4 | 2:19-3:18 | MP treats victim: a) first shock b) second shock c) first pacing d) second pacing; Treatment causes normalization Of heart rhythm |
| 5 | 3:18-7:25 | CPR, if necessary; victim identification; victim data retrieval; tracking and waiting for the emergency medical team (EMT) |
| 6 | 7:25-7:43 | A series of four handshakes between the MP and the EMT |
| 7 | 7:43-variable | MP transfers control of PU to EMT; MP advises EMT; MP guides enabler in replacement of PU |

4.1.1 Phase One: Initial Enabler Action

The start time, the moment when the enabler 100 first observes the Victim 102, a person who has suffered a cardiac arrest due to ventricular fibrillation, is arbitrarily designated with a time of 0:00. This marks the start of phase one. Nearly all of phase one, which ends when enabler presses the emergency button 106, is the time for the enabler to move from the victim to the portable unit 104.

4.1.2 Phase Two: Handshakes Linking Enabler and MP

Phase two involves a consecutive series of four handshakes, each one confirming a progressively broader link between the enabler and the medical professional.

4.1.2.1 Role Played By Handshakes; Relationship Between Handshakes and Backups; Relationship Between Handshakes and Links The handshakes play an important role in the operation of the system. Since decision making, when performed by the MP, occurs in a location separated from the emergency scene, it is essential that the MP know at all times if his link with the PU is robust. And it is vital that if the MP believes that his link with the PU is not robust, he can take corrective action by: a) directing the PU, the SU or CS to remedy or restore the link; and/or b) directing the PU to switch its guidance from MP-based, to an onboard guidance system, the AED/P (by directing the PU to enter Master Control State 2). It is equally vital that the PU can, at all times evaluate the ongoing link with the MP; and that the PU can, if it recognizes that the link with the MP is not robust, take corrective action by: a) attempting PU-based or SU-based maneuvers to remedy or restore the link; and/or b) switch its guidance from MP-based, to an onboard guidance system, the AED/P (by itself entering Master Control State 2, without the necessity of the MP for this transition). Accordingly, preferred embodiments of this invention provide means for implementing one or more layers of "handshake" (HS). And preferred embodiments of this invention provide means for implementing the aforementioned corrective actions, with one or more levels of backup, in the event of handshake failure.

In a preferred embodiment of the invention, each handshake after the first one builds on the previous handshake, by either expanding the route over which information exchange is confirmed, or by adding a more complex form of information exchange. The four handshakes of this embodiment may therefore be conceptualized as being layered, each on top of the previous one. The execution of all four handshakes confirms the integrity of a link (see Appendix 2). The four handshakes linking the EN and the MP are summarized in table 7, below.

TABLE 7

Four Layers of Handshake Linking Enabler and MP

| Layer # | Handshake Type | Between | Backup #1 | Backup #2 | Backup #3 |
| --- | --- | --- | --- | --- | --- |
| 1 | Communication | PU & CS | Δ route | Δ mode | MC = 2 |
| 2 | Data/Commands | PU & CS | Δ coding | Δ HS | MC = 2 |
| 3 | Audio | | | | |
| 3A | MP to EN | EN & MP | Headset | Voice Pr | Text Pr |
| 3B | EN to MP | EN & MP | Headset | Keyboard | SpeechRec |
| 4 | Informational | EN & MP | Interp'r | FoLanRec | Video CAM |

Embodiments of the invention with a greater or lesser number of handshakes are possible. Embodiments of the invention in which two or more of the aforementioned handshakes are merged are also possible. Embodiments of the invention in which one of the aforementioned layers is subdivided into multiple layers are possible. Embodiments of the invention in which some or all of the handshakes are not layered, each on top of the previous one, are possible. Embodiments of the invention in which other links (e.g. the Victim-MP link, or the EMT-MP link) have a different number of handshakes or a different handshake format are also possible.

4.1.2.2 Backup Systems for a Failed Handshake

For each HS, three levels of backup are listed. Embodiments of the invention with a larger or smaller number of backups are possible. Embodiments of the invention are possible which use the same backups listed in Table 7, but utilize them in a different order. Embodiments of the invention with different backup systems are possible.

Referring to Table 7, for the first two layers of HS, backup #1 and backup #2 are maneuvers which attempt to remedy or restore a less than adequate or interrupted handshake. The third level of backup for the layer #1 and layer #2 handshakes, PU self-programming to Master Control State 2, transfers control of the PU to the AED/P 128, the automatic circuitry which lets the PU function without a link to the central station. Another group of backup options for these two layers, not listed in the table, includes the substitution of a redundant hardware unit for a failed one (by electronic means), once the failure has been located. Yet another option is the manipulation of antenna size, orientation, location, number or shape. Hardware substitution and antenna manipulation may involve the PU, the SU and/or the central station. Backup systems for failed handshakes are discussed in detail, below.

The AED/P is not likely to be necessary for backing up the third and fourth layers of HS (see below). There are a variety of communications enhancing features (see Table 7 and the text below) which perform the backup functions for layers #3 and #4 of the enabler-MP link.

Figure 12:
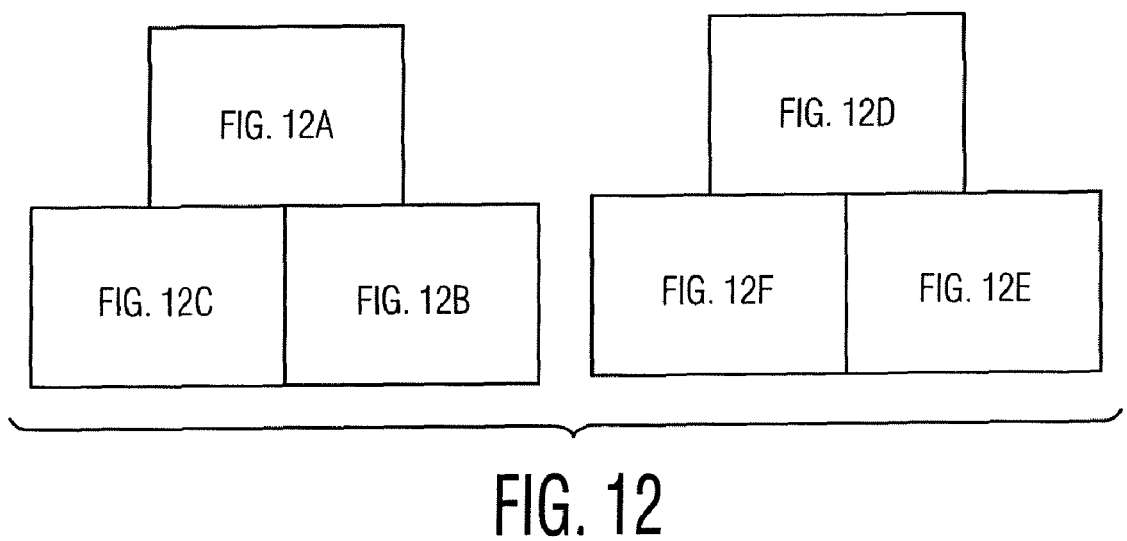
FIG. 12 are a flow chart showing the communication handshake protocol at the PU.

4.1.2.3 Four Handshakes which Link the Enabler and the MP
4.1.2.3.1 The Communication Handshake When the enabler presses the emergency button, the first of the handshakes, a communication handshake, is established between the portable unit and the central station. This handshake is described in detail below in connection with FIG. 12. It continuously lets the PU know that the CS is receiving PU signals and responding properly, while simultaneously letting the CS know that the PU is receiving CS signals and responding properly.

The handshake involves the transmission of signals over a route that may include, in succession:
 a) the PU microprocessor (which first receives the "button press" signal);
 b) the PU encoder;
 c) the PU transmitter;
 d) the CS receiver;
 e) the CS decoder;
 f) the CS microprocessor
 g) the CS encoder;
 h) the CS transmitter;
 i) the PU receiver; and
 j) the PU decoder.

The PU decoder then sends a signal to the PU microprocessor, completes the first cycle around this loop. Activation of the PU microprocessor also may thus be considered to mark the first step of the second cycle of what is a continuous set of cycles for the entire duration of the handshake. Any time a microprocessor fails to receive the appropriate signal, it initiates the transmission of alternate signals to reflect its altered input (see below and Table 16). If the PU microprocessor receives signals indicating a handshake failure, it may initiate actions which activate one the backup systems listed in Table 7. If the handshake is unsuccessful, despite multiple attempts using multiple communication routes and modalities, the microprocessor will cause the PU to switch to Master Control State 2, and thereby: a) hand control of defibrillation and pacing over to the automatic external defibrillator/pacer (AED/P) control logic; and b) enable lock release of the PU from the SU (such that MP "approval" of the release is no longer necessary).

Embodiments of the invention are possible in which the communications handshake involves either a greater or a smaller number of components than the ten listed above as (a) through (j). Embodiments of the invention are possible in which there is only a one-way handshake, e.g. by having the PU receive a continuously transmitted CS signal, and by having the PU microprocessor react to the absence of such a signal by causing backup measures to be instituted.

When the SU is part of an attempted PU-CS link, the ten item list ((a) through (j) above) is modified to allow for a PU-SU communication handshake and a SU-CS communication handshake (see Sections 4.1.2.4.1, 4.1.2.4.5 and Table 16) Such handshakes would test the SU transmitters and receivers and the SU microprocessor.

4.1.2.3.2 The Data/Commands Handshake

Once the communication handshake is established, a data and command handshake follows. The data/commands handshake cannot occur unless the communication handshake is running continuously in the background. This second layer handshake lets the MP know: a) that data from the PU can be transmitted from the PU and received by the CS; and b) that commands can be transmitted from the CS, and can be received and executed by the PU.

The handshake involves the transmission of signals over a route that includes, in succession:
 a) the CS processing input;
 b) the CS encoder;
 c) the CS communications output;
 d) the PU communications input;
 e) the PU decoder
 f) the PU processing output
 g) the PU processing input;
 h) the PU encoder;
 i) the PU communications output;
 j) the CS communications input;
 k) the CS decoder;
 l) the CS processing output;

The CS and the PU microprocessors may be involved at multiple points along this sequence (see ahead). This handshake may be initiated by an audio signal or sound at the CS. Alternatively it may be initiated by a non-audio command at the CS such as a signal to the PU to send a test ECG. The aforementioned involve two-way handshakes. Alternative methods of handshaking could involve one-way handshakes which may include continuously or intermittently emitted test signals from either the PU or the CS end.

This data/commands handshake traverses a wider loop than does the communication handshake. A completed data/commands handshake confirms the proper functioning of: a) all of the components included in the communication handshake; b) the CS processing (which includes audio and non audio) input and output components, and the PU processing input and output components; and c) other components which may be involved in test commands and test signals.

The data/commands handshake may be repeated to confirm the proper execution of each of multiple test commands, or the proper transmission of each of multiple test signals. Alternatively these commands and signals may traverse the system simultaneously. The data/commands handshake may be repeated continuously, intermittently or performed just once during a particular medical emergency (see Section 5.).

Embodiments of the invention are possible in which the data/commands handshake involves either a greater or a smaller number of components than those referred to above. Embodiments of the invention are possible in which there are one or more different one-way and/or one or more different two-way data/commands handshakes.

When the SU is part of an attempted PU-CS link, the routine is modified to allow for a PU-SU data/commands handshake and a SU-CS data/commands handshake (see Sections 4.1.2.4.1, 4.1.2.4.5 and Table 16). Such handshakes would further evaluate the SU transmitters and receivers and the SU microprocessor.

If the layer two handshake is unsuccessful, despite the first two backup approaches (listed in Table 7 and discussed below), then PU entry into Master Control State 2, with resultant enabling of AED/P logic and lock release, is the third level backup approach, as was the case with an unsuccessful communication handshake. After the layer two handshake is complete, the successful transmission and execution of commands is documented by a series of confirmation signals described below; Unsuccessful transmission or execution of individual commands is documented by a series of error signals described below.

Both the communication and the data handshakes may be established very quickly, i.e. within a time interval on the order of one second or less.

4.1.2.3.3 The Audio Handshake

After establishment of the data and command handshake, the ability to exchange audio is established during the third layer of handshake. The MP must determine that he can hear the enabler clearly and that the enabler can hear him clearly. Most of the time, any difficulty in this area will be easily remedied (by the MP or by the system) by adjusting an amplifier gain control, or by adjusting another signal conditioning parameter at either the PU or the CS end.

The audio handshake traverses a wider loop than does the data/commands handshake. This handshake involves the proper passage of information among: a) the twelve data/commands items listed as (a) through (1) in Section 4.1.2.3.2, above; and b) the enabler and the medical professional. Their ability to hear each other involves: a) the proper functioning of the aforementioned twelve items; b) the enabler's ability to adequately hear the audio output of either the PU speakers 146, or the PU handset 150; and c) the MP's ability to properly hear the voice of the enabler, picked up by either PU microphone 148 or PU handset 150. (It is assumed that the speakers, microphones, handsets and/or headsets at the central station can be reliably used and optimized by the MP.)

When the SU is part of the PU-CS link, a suboptimal audio response may be remedied (by the MP or by the system) by the adjustment of a SU amplifier gain control, or by the adjustment of another signal conditioning parameter among the SU receivers and transmitters, in addition to such adjustments at either the PU or the CS end.

The backups for this third layer are devices or techniques intended to support a marginally functioning audio system. They include:

a) EN using PU handset 150 or headset 168;
b) MP triggering of voice prompts (Voice Pr) which have been pre-recorded and stored in the PU;
c) MP sending text messages (Text Pr) which appear on one of the PU screens 156;
d) EN using a virtual keyboard displayed on one of the touch sensitive screens, 156, of the PU; and
e) MP using a speech recognition program (SpeechRec) within the PU.

In the event of the enabler not hearing the MP properly, techniques (a), (b) and (c), above, would be used. In the event of MP not hearing the enabler properly, techniques (a), (d) and (e), above, would be used. The detailed algorithm for this is discussed below.

There is little or no need for AED/P backup for the third layer of handshake. The reason is as follows. With a successful second layer of HS, it has been established that data can flow from PU to CS, and commands may be transmitted to and executed by the PU. If EN can not hear MP directly, then either a) voice or text prompts are recognized by the EN, in which case the MP can proceed to deal with the emergency, in full control of the PU, and able to communicate indirectly with the enabler, or b) voice or text prompts are not recognized by the enabler, in which case an AED would not be likely to function either.

4.1.2.3.4 The Informational Handshake

The fourth layer of handshake is an informational one. Nine seconds are slotted, starting at 0:41 for the MP to request and receive a description of the medical emergency. During and immediately following the description, the MP decides if the event being described is one in which the PU can be used to help the victim. Backup systems include an interpreter (Interp'r) or a foreign language recognition program (FoLanRec) to deal with a foreign language speaking enabler, and a video camera (Video CAM) to help distinguish a bona fide enabler from a potential prankster. Since this fourth layer of handshake establishes the appropriateness of the medical emergency and of the enabler, AED/P backup is not appropriate for this layer.

This handshake involves a more complex form of information exchange than that of the audio handshake. Since the informational handshake deals with cognitive issues (viz. the victim diagnosis) it does not involve any additional communication or audio equipment.

4.1.2.4 Role of the Stationary Unit in the Handshake Protocol

The discussion up to now has not addressed the distinction between a "direct PU-CS link" (i.e. a link between the PU and the CS in which information does not pass through the SU), and an "indirect PU-CS link" (in which the PU-CS link is the composite of a PU-SU segment [wherein information passes between the PU and the SU] and a SU-CS segment [wherein information passes between the SU and the CS]). Either a direct PU-CS link or an indirect PU-CS link must be established. This distinction in routing will now be addressed.

4.1.2.4.1 Single Direct Link Between PU and CS as the Default Routing Approach; Stationary Unit Functions as a Backup Conceptually, the simplest approach to a PU-CS link is one in which button press results in the attempted establishment of a direct PU-CS communication link. With such a link, information is sent from the PU to the CS without passing through the SU, and information and commands are sent from the CS to the PU without passing through the SU; The communication in this approach is "wireless."

"Wireless," hereinabove and hereinbelow, refers to communications without a material connection between the two communicating units; such as communication methods employing radio frequency or infrared signal carriers. "Wire," hereinabove and hereinbelow, refers to communications with a material connection between the two communicating units; such as copper, other metal or optical fiber connections. A wireless connection may include multiple segments, some of which use wire.

Table 8 and the discussion which follows in this Section and in Section 4.1.2.4.2 address the backup approaches available in the event of a failure in any segment of the PU-CS link, when there is a SU available or involved. "Segment" is hereinabove and hereinbelow defined as a spatially distinct portion of a link, such that the composite effect of all of the segments constitutes the effect of the entire link. Thus the PU-SU segment plus the SU-CS segment constitute the PU-CS (or PU-SU-CS) link. The second through fifth columns of the table refer to each possible segment or link between the PU and the CS. Within Section 4.1.2.4, the term "connection" refers to the physical aspect of a segment, and is used nearly synonymously with "segment." In the table, "PU-SU wire" refers to the connection between the PU and the SU via connectors 188 and 190; "PU-SU Wireless" refers to a wireless connection between the PU and the SU. In the analysis which follows in Sections 4.1.2.4.1 through 4.1.2.4.4, a link or segment is assumed to be established when the first two layers of handshake, i.e. communications (see Section 4.1.2.3.1) and data/commands (see Section 4.1.2.3.2) are established. This is further discussed in Section 4.1.2.4.5, below.

TABLE 8

PU-CS Routing Analysis and Backup When SU is Available

| State # | PU-SU Wire | PU-SU Wireless | SU-CS | PU-CS | Backup #1 | Backup #2 | Backup #3 |
|---|---|---|---|---|---|---|---|
| 1 | Any | Any | Any | + | Communication | Communication | Intact |
| 2 | Any | + | + | − | Communication | Communication | Intact |
| 3 | + | − | + | − | PU-176 to SU | PU-176 to CS | MC = 2 |
| 4 | − | − | + | − | MC = 2 | PU-176 to CS | |
| 5 | Any | Any | − | − | MC = 2 | PU-176 to CS | |

Key
+ = communication intact between indicated units
− = communication not intact between indicated units
Any = + or −, i.e. communication may or may not be intact between indicated units
PU-176 to CS = enabler uses PU wire/jack 176 to connect PU to Telco, i.e. the public telephone network
PU-176 to SU = enabler uses PU wire/jack 176 to connect PU to SU
MC = 2 = Master Control State 2

In this format (i.e. primary attempt is a direct PU-CS link), only if a wireless link between the PU and the CS could not be established (States #2-#5 in Table 8), would the stationary unit become a unit of the communication chain. In such a situation the backup would involve trying to establish an indirect PU-CS link (i.e. via the SU) The sequence of events could be:

a) button press;
b) attempt to establish a direct PU-CS link fails;
c) the PU, over its connection to the SU via connectors 188 and 190, causes the SU to attempt to establish a connection with the CS;
d) the SU establishes a connection with the CS; the PU-CS link is then complete since PU is already connected to SU via connectors 188 and 190; the enabler and the MP can now communicate; and
e) the PU then attempts to establish a wireless connection with the SU.

Once step (d) is completed, the exchange of vital information between the enabler and the MP can begin (via the wire connection between the PU and the SU), while the system attempts to establish a wireless connection between the PU and the SU. If the attempt (step (e), above) is successful, a proper wireless PU-CS link will have been established, and the PU is ready for detachment from the SU, if the MP decides that the detachment is necessary (based on the enabler's description of the medical emergency).

The attempted two-segment link between PU and CS can only succeed if both segments, the PU-SU segment, and the SU-CS segment can be established. Section 4.1.2.4.1.1 refers to the situation when: a) both segments can be established; but b) one (but not both) of the PU-SU forms of connection (wire and wireless) can not be established. Section 4.1.2.4.1.2 refers to the situation when one or both of the PU-SU segment and the SU-CS segment can not be established.

4.1.2.4.1.1 Direct PU-CS Link Can Not Be Established; Failure of One But Not Both Possible PU-SU Connections; Successful SU-CS Connection The PU-SU segment can be initially established with either a wire or wireless PU-SU connection.

If the direct connection between the PU and the SU via connectors 188 and 190 is not intact, the PU may attempt to contact the SU via a wireless route. If the PU-SU wireless route is established, and if it is followed by the establishment of a SU-CS connection (State #2, Table 8), a proper PU-CS link will have been established. State #5 (see Table 8), in which the PU-SU wireless route is established but the SU-CS connection can not be established is discussed below in Section 4.1.2.4.1.2

If a wireless PU-SU connection can not be established, but the wire connection via connectors 188 and 190 is intact, and a SU-CS connection has been established, (State #3, Table 8), the enabler and the MP can communicate only if the PU remains attached to the SU. In this situation, the enabler is advised by the MP of a number of options including:

a) the option to plug the telephone wire/male jack 176 (from the PU tool-kit) into the female telephone jack 155 of the SU, and thereby to operate the PU with a wire connection to the SU;
b) the option to use both the wire/jack 176 and an extension wire (located within the PU tool-kit) in tandem, if the wire/jack 176 is not likely to be of sufficient length to reach from the SU to the location where the PU must be placed in proximity to the victim;
c) the option to transport the PU to the victim (if certain victim-related criteria have been met):
  (i) Prior to removal of the PU form the SU (and thereby terminating enabler-MP audio contact), the MP instructs the enabler about upcoming procedures and about how the enabler may interact with the AED/P; He also instructs the enabler that they may be able to resume their communication once the PU has been moved to a location near the victim, either by wireless means, or by having the enabler then plug wire/jack 176 (with or without extension) into a female jack of the public telephone network.
  (ii) After properly instructing the enabler, the MP may then give a command to the PU to enter Master Control State 2.
  (iii) Enabler then detaches the PU from the SU and transports it to the victim;
  (iv) During transport the PU and the CS will attempt to contact each other; if contact is successful, the enabler-MP interaction proceeds as described hereinabove and hereinbelow;
  (v) if contact is unsuccessful through the time that enabler arrives at the victim's side, the enabler has the options of either plugging the telephone wire/jack 176 directly (or via the extension) into the public telephone network, or of continuing to use the PU in its AED/P backup mode. The enabler is reminded of these options and of associated details via voice prompts.

There a multiple possible variations in the timing of the setup of the wireless version of the PU-SU connection: a) the PU-SU connection could be wireless from the beginning, i.e. from the time of button press; b) the PU-SU connection could initially be via connectors 188 and 190, but attempts to establish a wireless PU-SU connection could proceed before, or at the same time as the attempt to establish the SU-CS connection (rather than first establishing the SU-CS connection, as is the scenario described in Section 4.1.2.4.1). If, using one of these variations, the PU-CS link fails to be established, the backups include: a) attempting to use a wire connection for the PU-CS link; b) attempting to use a wire connection for the PU-SU segment; c) AED/P backup (described below in Section 4.1.2.4.1.2).

4.1.2.4.1.2 Direct PU-CS Link Can Not Be Established; Failure of Both Possible PU-SU Connections and/or Failure of SU-CS Connection If the direct PU-CS link has failed, then communication between the enabler and the MP can not occur unless an indirect PU-CS link can be established. The indirect link can not be established if: a) neither a wire nor a wireless connection between the PU and the SU can be established (State #4, Table 8); or b) a SU-CS connection can not be established (State #5, Table 8). In either of these two situations, the system must switch to the AED/P backup. The scenario could be:

a) The PU switches to Master Control State 2.

b) The PU then issues voice prompts directing the enabler to remove the PU and transport it to the victim's side, if certain victim-related criteria are met (see below).

c) The enabler then detaches the PU from the SU and transports it to the victim.

d) From this point in time onwards, the PU will make periodic attempts to communicate directly with the CS. If such an attempt is successful, then the enabler-MP interaction may take place as is described hereinabove and hereinbelow.

e) If the PU does not make contact with the CS by the time the PU is placed next to the victim (sensor switches 178 signaling placement of the PU), a voice prompt then tells the enabler that he has two options. The enabler may select option (i), and then go to option (ii) if option (i) is unsuccessful, or may select option (ii) initially:

(i) to extend telephone wire/male jack 176 (with or without the extension) from the PU tool-kit to connect to a female jack of the public telephone network; and after sensing such connection the PU will attempt to establish a link with the CS; if the attempt is successful, then the enabler-MP interaction takes place as described hereinabove and hereinbelow; if the attempt is unsuccessful, the enabler proceeds with option (ii) (which follows hereinbelow);

(ii) to use the PU as an automatic external defibrillator; the PU will then further instruct the enabler via voice prompts.

It is highly unlikely that a SU-CS connection would not be able to be established, since: a) there are many possible routes including the public telephone network, the internet, private communications networks, or combinations of these; and b) the ability to establish the SU-CS connection would be examined and assured at the time that the SU is initially set up, and at other times when diagnostic checking is performed (see below). It is also highly unlikely that neither form of PU-SU connection would be able to be established, for the same two aforementioned reasons regarding the likelihood of being able to establish a proper SU-CS connection.

4.1.2.4.2 Two Connections: One from PU to SU and One SU to CS as the Default Routing Approach In a preferred embodiment of the invention, a portable unit would be wired directly to the SU via connectors 188 of the PU (FIG. 8) and 190 of the SU, and a stationary unit (FIG. 9) would be connected via its telephone wire and male jack 198 directly to the public telephone network. Therefore a PU-SU-CS link, free of any wireless segments, could be initially established. The advantage of this approach (as opposed to the direct PU-CS link) is that the absence of any wireless segment within the system will render the link robust. The disadvantage of this approach is that in order for the system to be usable in conjunction with a victim, another connection must be established when the PU is transported to the side of a victim; Either a wireless PU connection (to either the SU or the CS) must be established; or a wire must be extended from the PU (to either the SU or a female jack of the public telephone system).

In this PU-SU-CS format, the sequence of events could be:

a) button press;

b) the PU, over its connection to the SU via connectors 188 and 190, causes the SU to attempt to establish a connection with the CS;

c) the SU establishes a connection with the CS; the PU-CS link is then complete since PU is already connected to SU via connectors 188 and 190; the enabler and the MP can now communicate; and d) the PU then attempts to establish a wireless connection with the SU.

The analysis of the backup approaches for the two-segment PU-SU-CS link can be dichotomized by considering: a) the situation in which the two-segment approach is initially successful (Section 4.1.2.4.2.1, below); and b) the situation in which the two-segment approach initially fails (Section 4.1.2.4.2.2, below). The backups ultimately consist of the same approaches as those discussed in Sections 4.1.2.4.1.1 and 4.1.2.4.1.2 above, except that: a) the backups also include an attempt to establish a direct PU-CS link (This link assumed to have failed in the backup approaches discussed in Sections 4.1.2.4.1.1 and 4.1.2.4.1.2.); and b) the order in which the backups are selected may differ from that in the Sections hereinabove.

4.1.2.4.2.1 Two-Segment Default; Initial PU-CS Link Successful

Once step (c) is successfully completed, the exchange of vital information between the enabler and the MP can begin (via the wire connection between the PU and the SU), while the system attempts to establish a wireless connection between the PU and the SU. If the attempt (step (d), above) is successful, a proper wireless PU-CS link will have been established, and the PU is ready for detachment from the SU, if the MP decides that the detachment is necessary (based on the enabler's description of the medical emergency).

If the attempt (step (d) above) is unsuccessful, the PU may then attempt to establish a wireless connection directly with the CS. If the latter attempt is successful, a proper wireless PU-CS link will have been established. If the latter attempt is unsuccessful, the situation is the one described by State #3, Table 8; three backup options are listed in the table and described in paragraphs (a), (b) and (c) in Section 4.1.2.4.1.1. These options include extending the PU-SU wire connection (paragraphs (a) and (b), Section 4.1.2.4.1.1), moving the PU to the victim and then attempting either a wire or wireless PU-CS connection (paragraph (c), Section 4.1.2.4.1.1) or using the AED/P function of the PU (paragraph (c), Section 4.1.2.4.1.1).

An alternate sequence is possible as the follow-up to step (c) (of this Section). Instead of next performing step (d), in which the PU attempts to establish a wireless link with the SU, the PU could instead attempt to establish a wireless link with the CS. If this failed, it could then attempt to establish a wireless link with the SU; and if the latter attempt failed, the three backup options of paragraphs (a), (b) and (c) of Section 4.1.2.4.1.1 would be employed.

There a multiple possible variations in the timing of the setup of the wireless version of the PU-SU connection: a) the PU-SU connection could be wireless from the beginning, i.e. from the time of button press; b) the PU-SU connection could initially be via connectors 188 and 190, but attempts to establish a wireless PU-SU connection could proceed before, or at the same time as the attempt to establish the SU-CS connection (rather than first establishing the SU-CS connection, as is the scenario described earlier in this Section). If, using one of these variations (in the timing of the setup of the PU-SU wireless connection), the PU-CS link fails to be established, the backups are among those already described including: a) attempting to use a wire connection for the PU-SU segment; b) attempting a direct PU-CS link; and c) using AED/P backup.

4.1.2.4.2.2 Two-Segment Default; Initial PU-CS Link Unsuccessful

According to the four step scenario described in Section 4.1.2.4.2, button press does not result in the establishment of a two segment PU-CS link, then: a) the PU-SU wire connection (step (b)) will have failed; and/or b) the SU-CS connection (step (c)) will have failed.

A logical backup option would then be to try to establish a direct PU-CS link. If this failed, an attempt to establish a wireless PU-SU connection would follow. If both of these attempts failed, the backup would be the AED/P function of the PU (paragraph (c), Section 4.1.2.4.1.1).

Alternatively the order of the aforementioned wireless attempts could be reversed, such that the wireless PU-SU connection is first attempted, and if it fails, the wireless PU-CS connection is attempted. Again, the AED/P function is the backup if both of these fail.

Failure to establish either a PU-SU connection or a SU-CS connection is highly unlikely for the reasons stated above at the conclusion of Section 4.1.2.4.1.2

4.1.2.4.3 Redundant Links, in which There is Both a Direct PU-CS Link and an Indirect PU-SU-CS Link Another approach to the establishment of the PU-CS link is to attempt to simultaneously establish both a direct PU-CS link and an indirect (two segment) PU-SU-CS link. There could be up to three simultaneous initial attempts including: a) a direct PU-CS (wireless) link; b) an indirect PU-SU-CS link, in which the PU-SU segment is a wireless connection; and c) an indirect PU-SU-CS link in which the PU-SU segment is a wire connection.

As soon as any one of these was established communications between the enabler and the MP could begin. There would then be multiple options:

a) If the first established link is a direct PU-CS link, a second link might or might not be attempted involving the PU-SU-CS route, with a wireless PU-SU connection. If established, the second link could then be available as an immediate backup, if the PU-CS link is interrupted.

b) If the first established link is an indirect PU-SU-CS link, in which the PU-SU connection is wireless, a second link might or might not be attempted involving a direct PU-CS link. If established, the second, direct PU-CS link could then be available as an immediate backup, if the indirect PU-SU-CS link is interrupted.

c) If the first established link is an indirect PU-SU-CS link in which the PU-SU segment is a wire connection, a second route must be established (to allow detachment of the PU from the SU). Approaches in which only one second route is established (i.e. either a wireless PU-SU connection or a wireless PU-CS connection) have been described above in Section 4.1.2.4.2.1. Another alternative is to attempt to establish both wireless connections; one could then serve as the primary route and the other as a backup If none of these three routes were viable, the backup would be via the AED/P function of the PU, described above in Section 4.1.2.4.1.2.

The advantage of establishing multiple simultaneous communication routes is that it renders the system more robust. The disadvantage is a potential cost increase.

Embodiments of the invention with a larger number of simultaneous routes between the PU and the CS are possible.

4.1.2.4.4 More Elaborate Routes for the PU-CS Link

Embodiments of the invention in which the routing for the PU-CS link is other than as described above (the direct link and the indirect PU-SU-CS link) are possible. These include:

a) PU-SU-CS links which use a SU different than the SU to which the PU was attached;

b) links in which two or more SUs operate in tandem (one of which may or may not be the SU to which the PU was initially attached;

c) links in which there are two or more PUs operating in tandem (see Section 4.5.7.5.2.2, below);

d) links in which there are two or more central stations operating in tandem; and e) combinations of (a) through (d), above.

4.1.2.4.5 Depth of Handshake Layers

Since the audio handshake (layer 3, Section 4.1.2.3.3) and the informational handshake (layer 4, Section 4.1.2.3.4) between the enabler and the MP involve actual conversation, neither one can take place until both the PU-SU segment and the SU-CS segment have been established. Therefore, in the discussion in Sections 4.1.2.4.1 through 4.1.2.4.4, it has been assumed that either a PU-SU segment or a SU-CS segment is complete as soon as the first two layers of handshake occur. The third (and then the fourth) layer handshakes (between the enabler and the MP) are attempted after: a) both the PU-SU and the SU-CS segments are established (with completed first and second layer handshakes); and/or b) the PU-CS link is established (with completed first and second layer handshakes).

4.1.3 Phase Three: Transport of PU to Victim; Victim-MP Handshake; PU Setup at Victim's Side 4.1.3.1 PU Release and Transport Referring again to Table 6, phase three begins when the MP decides that the PU should be used for a resuscitation effort, and, having so decided, issues a command to release the lock which secures the PU to the SU. Preferred embodiments of the invention have backup lock release mechanisms which may be either mechanical, electrical or both (see Section 2., description of FIGS. 8 and 9).

During the time that the enabler is transporting the PU to the victim's side, there is frequent reassessment of the quality of the enabler-MP link. If the link either deteriorates in quality or is lost as the PU is being moved, the MP, the system, and/or the enabler may utilize any of the backups listed in Table 7 or Table 8 and discussed in conjunction with these tables. If the MP notes that the quality of the enabler-MP link is deteriorating as the PU is being moved, he may so inform the enabler and may provide specific corrective instructions to the enabler (see tables 7 and 8 and the associated discussion).

Phase three, like phase one, also includes an interval of variable duration, encompassing the transit time for the enabler carrying the PU to the victim's side. The enabler's speed, while carrying the PU, is assumed to be 1 mile per hour slower than it was when he was walking without the PU, and hence a travel time that is 11 seconds longer than the phase one travel interval is allotted.

4.1.3.2 Handshakes Linking Victim and MP

After the electrode pad is applied during phase three, an electrical link between the victim and the MP, consisting of a layered sequence of handshakes, establishes: a) that the electrode pad is making appropriate contact with the victim; and b) that the diagnosis is ventricular fibrillation.

4.1.3.2.1 The Four Layer Victim-MP Link

The victim-MP link is conceptually similar to the link between the enabler and the MP described above. Table 9, below, summarizes the main features of this series of handshakes.

TABLE 9

Four Layers of Handshake Linking Victim and MP

| Layer # | Handshake Type | Between | Backup #1 | Backup #2 | Backup #3 |
|---|---|---|---|---|---|
| 1 | Communication | PU & CS | Δ route | Δ mode | MC = 2 |
| 2 | Data/Commands | PU & CS | Δ coding | Δ HS | MC = 2 |
| 3 | Electrical | | | | |
| 3A | MP to Vi | VI & MP | pressure | Δ electrode | Δ pad |
| 3B | Vi to MP | VI & MP | p/Δ gain | Δ electrode | Δ pad |
| 4 | Informational | VI & MP | Δ gain | Δ ECG lead | Δ pad |

The handshakes which constitute layers 1 and 2 will have already been established during the enabler-MP link, before phase three begins. In addition, the ongoing functionality of these two layers is continuously re-evaluated. In layer 3 of the victim-MP link, the handshake is based on: a) the determination that impedance measurements in the circuits that include the pad electrodes and the victim are within the proper range (referred to in the table as "MP to victim"); and b) adequate quality of the electrical signals, if any, recorded from the victim (referred to in the table as "victim to MP"). Layer 4, the informational handshake, consists of the MP reading the electrocardiogram signals and thereby diagnosing the victim's heart rhythm.

As was the case with the link between enabler and MP: Within the link between the victim and the MP, layer 2 is based on an intact layer 1, layer 3 is based on an intact layer 2, and layer 4 is based on an intact layer 3.

4.1.3.2.2 Backup Systems for Failure in the Victim-MP Link

The backups for problems within the first two layers of the Victim-MP link are similar to those for the enabler-MP link. The electrical (third layer) handshake, analogous to the audio handshake of the enabler-MP link, has backups intended to address a poor electrode-victim interface.

If impedance readings are high (third layer handshake; MP to victim), the MP may ask the enabler to temporarily press down over the section of the pad or pads which show a high impedance, hoping to thereby improve electrode-victim contact. If this fails, the MP may be able to work around the problem by using other better functioning electrodes, if they are present in adequate number and location. If neither of these is successful, the MP may ask the enabler to remove the electrode pad, and to reapply it or another pad.

If the ECG signal is of poor quality (third layer handshake; victim to MP), the MP has all of the options previously mentioned for improving the impedance. The notation of p/Δ gain refers to dual first level MP options of either: a) asking the enabler to apply pressure over the pad, as described above; or b) changing the amplifier gain on the channel(s) corresponding to a low amplitude ECG signal.

During the informational phase, when the MP must diagnose the rhythm abnormality, the first level of backup involves switching the ECG lead. This is a non-mechanical process which involves looking at different pairs of recording electrodes, hoping to identify a pair with a signal that can lead to the rhythm diagnosis. Besides the backup options of changing gain and changing electrode pad, there are a variety of signal enhancing options that are discussed below in Section 4.3.1.2.

4.1.3.3 MP Commands, Confirmation Signals and Error Signals

Confirmation signals are first utilized in phase three, and extensively in phase four. Like the handshakes, they are an important feature of an emergency management system in which the expert who is making and enacting decisions (the MP) is physically separated from the device that he is controlling. In a preferred embodiment, confirmation signals tell the MP that the command that he initiated has reached a certain checkpoint along its intended route. Error signals tell the MP that a command failed to reach a certain checkpoint. Other types of error signals inform the MP of faults within the system, or faults at the periphery of the system. System is defined as the hardware and software which comprise the PU or PUs, the CS, and the SU (if any). The periphery of the system is defined as any device or individual (other than the victim) which interfaces with the system. Such devices would include blood pressure and oxygen saturation sensors, and the electrode pads. Faults involving individuals interfacing with the system include improper EMT or MP identification.

A simplified version of the sequence of events following an MP command, including confirmation signals, is a) MP issues command;
b) CS transmits the command;
c) PU receives the command;
d) PU executes the command;
e) PU transmits a confirmation signal that indicates that the command was executed;
f) CS receives the transmitted confirmation signal;
g) CS displays the confirmation signal; and
h) MP sees the confirmation signal.

In the aforementioned format, there is a single confirmation signal for each command which indicates its successful execution. In a preferred embodiment of the invention, a more complex system of confirmation signals is used which utilizes multiple confirmation signals for each command. For a given command, each successive confirmation signal confirms the proper progress of the command as it passes each of a number of checkpoints in its traversal of the route from MP to point of execution. Command confirmation may occur:

a) after the command is encoded, indicating that it was properly formulated and encoded;
b) after the command is transmitted, indicating that transmission was proper;
c) after it is received by the PU; and
d) after it is executed by the PU.

Error signals are made available to the MP to indicate failure of the command to traverse a given point in the system.

Identification of the location of a fault in the system is based on which particular confirmation signal(s) and which particular error signal(s) are received by the MP. Embodiments in which a greater or a lesser number of confirmation and error signals occur are possible.

In the event of failure of execution of a command, the MP can exercise various backup options including:

a) repeating the command;
b) reassessing the robustness of communication and performing necessary remedial measures (see below);
c) handing control over to the built in backup system, the AED/P; or
d) the substitution of a redundant hardware unit for a failed one (by electronic means), once the failure has been located.

This confirmation system will be described in detail below.

4.1.3.4 Telemetry Signals

Telemetry signals may be considered to be analogous to confirmation signals. Telemetry signals are sent from PU to CS, indicating a PU-based event that was not initiated directly by the MP. Examples include detachment of the PU from the SU by the enabler, and touchdown of the PU after proper orientation by the enabler. Other telemetry signals may indicate faults within the system, or be part of a periodic system diagnostic evaluation.

4.1.4 Phase Four: Emergency Medical Management of the Cardiac Arrest by the Medical Professional The fourth of six phases of the hypothetical cardiac arrest encompasses the treatment, by the MP, of the victim's heart rhythm abnormalities. For illustrative purposes, four treatment steps are shown. In its most simplified form, a cardiac arrest could consist only of one step: a single corrective shock, followed by the emergence of a normal rhythm. In order to more fully illustrate some of the capabilities of a preferred embodiment of the invention, the arrest described herein (in connection with Tables 6 and 10) is a more complex one.

4.1.4.1 Defibrillation and Pacing by the MP

In the arrest described in Tables 6 and 10, the first shock fails to terminate VF. The MP then alters the shock vector by changing one of the pair of electrode pads through which the defibrillating pulse is applied. The MP then causes the PU to deliver a second shock. The MP notes that the second shock was successful in terminating VF, but that asystole (the absence of any cardiac electrical activity), has ensued post-shock. He treats this by causing the PU to deliver pacing stimuli to the victim's chest, at a rate of 60 beats per minute.

4.1.4.2 Other Actions Directed by the MP to Support Blood Pressure

Two minutes and forty three seconds into this hypothetical arrest, an acceptable heart rhythm has been restored. The MP must now determine if the restoration of reasonable electrical function to the victim's heart is accompanied by a parallel restoration of mechanical function. The MP must therefore determine if the victim has adequate blood pressure and respiratory function. In order to make this determination, the enabler is brought into play again, briefly. The MP asks the enabler to assist in the application of a non-invasive blood pressure device and a transducer for measuring the victim's blood oxygen status. The MP observes a borderline low blood pressure. He then reduces the pacing rate and observes the emergence of a normal rhythm, and a rise in blood pressure. This completes phase four.

4.1.5 Phase Five: Management Immediately Post Electrical Resuscitation

During phase five, cardiopulmonary resuscitation is performed, if deemed necessary by the medical professional. The MP obtains victim identification and prior medical information. The MP also communicates with the en-route emergency medical team, and reports their estimated time of arrival to the enabler.

4.1.6 Phase Six: EMT Arrival, Transfer of Control of the PU from MP to EMT

The onset of phase six is marked by the arrival of the EMT. The MP may, if the EMT is appropriately qualified and identified, hand over control of the PU to the emergency medical team. In the scenario described by the sample arrest in Section 4.2, below, we assume that the EMT is desirous of such transfer.

4.1.6.1 EMT Choices Other Than Assuming Control of the PU Currently Attached to the Victim Other EMT choices include:

a) EMT wishes to assume control over rhythm management using another portable unit (hereinafter referred to as "new PU") which is an embodiment of the invention, but not the same unit which up until that moment was used on the victim (hereinafter referred to as "old PU") (The new PU and the old PU may or may not be identical embodiments of the invention.).

b) EMT wishes to have the MP continue to manage heart rhythm abnormalities, using the old PU, with EMT function then restricted to (i) starting an intravenous line for the victim, (ii) giving intravenous medication if necessary, (iii) performing CPR (cardiopulmonary resuscitation) if necessary and (iv) transporting the victim to the hospital;

c) the same scenario as (b), except that EMT wishes to do this with the new PU;

d) EMT wishes to assume control over rhythm management using a defibrillator apparatus which is different than the invention;

4.1.6.2 Handshakes Linking EMT and MP

The transfer of control of the PU from MP to EMT is based on a series of four handshakes, which are conceptually similar to the four handshakes which establish the enabler-MP link at the start of the emergency. Layers 1 and 2 of the EMT-MP link may be identical to those of the EN-MP link: communication and data/command handshakes, running continuously in the background. Layer 3 is an audio handshake between the MP and the EMT. They both confirm that they can adequately hear each other, with the MP making any appropriate adjustments to facilitate this, as was the case with the enabler-MP handshake. The fourth handshake involves the exchange of information between the MP and the EMT. After the audio link is secure, the MP asks the EMT for either a password ("PWD") (which may be numeric or one or more words), or seeks other evidence that EMT is represented by an appropriate, competent individual (which may be determined by fingerprint, voice, facial and/or iris recognition, or by direct conversation). EMT identification thus constitutes the informational, fourth layer of the EMT-MP link.

The four layers which constitute the link between the EMT and the MP, and the backups for these four layers are summarized below, in Table 10:

TABLE 10

Four Layers of Handshake Linking EMT and MP

| Layer # | Handshake Type | Between | Backup #1 | Backup #2 | Backup #3 |
|---|---|---|---|---|---|
| 1 | Communication | PU & CS | Δ route | Δ mode | PWD: MC = 3 |
| 2 | Data/Commands | PU & CS | Δ coding | Δ HS | PWD: MC = 3 |
| 3 | Audio | | | | |
| 3A | MP to EMT | MP & EMT | Headset | Voice Pr | Text Pr |
| 3B | EMT to MP | EMT & MP | Headset | Keyboard | SpeechRec |
| 4 | Informational | EMT & MP | Interp'r | Voice Re | Video CAM |

4.1.6.2.1 First and Second Layers of EMT-MP HS: Password Which Gives Control of PU to EMT, Rather Than to Giving Control of PU to AED/P As discussed in Section 4.1.3.2.1, the handshakes which constitute layers 1 and 2 will have already been established during the enabler-MP link, and the ongoing functionality of these two layers is continuously re-evaluated. As is indicated in Table 10, the first two levels of backup for an EMT-MP handshake failure in layer #1 or #2 are identical to those for the enabler-MP link.

The third level of backup for an EMT-MP handshake failure in layer #1 or #2 differs from that of the enabler-MP handshake. It involves the use of a password by the EMT. The password, when appropriately supplied, causes the PU to enter Master Control State 3, which enables control of the unit by the EMT. This approach differs from that used in the enabler-MP link, in which the third level of backup for handshake failure in layers #1 and #2 is entry of the PU into Master Control State 2, enabling control of the unit by the AED/P. The rationale for this difference in approach is that if communication (or data/commands exchange) between the PU and the CS fails when the EMT is present, it makes more sense to give control of the PU over to the EMT, rather than giving it over to the AED/P. Accordingly, the EMT is provided with a password which, in the event of failure of PU-CS handshakes at layers #1 or #2, will allow the EMT to cause PU to enter Master Control State 3, giving EMT control of the PU. The password may be supplied to the EMT when the EMT is summoned, or at an earlier time. Alternatively, password acceptance may require matching pre-programmed EMT anatomic features (fingerprint, iris, etc.).

In a preferred embodiment, as long the handshakes in layers #1 and #2 are intact, password acceptance requires the participation of the MP, and occurs in level four. Only in the event of handshake failure in layers #1 or #2, would the EMT password cause the transfer of control of the PU to the EMT, without the MP causing such transfer. This approach makes the system least likely to have its control usurped by an inappropriate person.

4.1.6.2.2 Third and Fourth Layers of EMT-MP HS

The third layer of this handshake, is entirely analogous to the third layer of the enabler-MP handshake. The goal is the establishment and confirmation of adequate quality audio in both directions. The backups for the third layer are the same in both cases.

As indicated above, the informational handshake of level four is the password. Backup systems are intended to enhance EMT identification, in the event that a putative password does not match. The backups include an interpreter, and techniques for recognizing individual characteristics including voice (Voice Re), facial and other anatomic features (via video camera).

4.1.7 Management by the EMT, after Transfer of PU Control to the EMT, by the MP

The traditional role of the emergency medical team includes all aspects of the management of the victim from the time they arrive at the scene of the emergency, until they arrive in hospital.

4.1.7.1 Transfer of PU Control

Once the EMT is deemed by the MP to be appropriate, and desirous of assuming control over the PU, the MP may transfer control of the PU to the EMT. Phase seven begins when the MP decides that control of the PU should be transferred to the EMT, and, having so decided, issues a command to effect such transfer. Phase seven ends when both: a) the victim is no longer attached to the PU; and b) when the PU has been returned to the SU (see Section 4.5.7.8).

4.1.7.2 Briefing of EMT by MP

Following the transfer of control, the MP provides the EMT with information which summarizes the events which occurred prior to the arrival of the EMT, and other data deemed to be important by either the MP or the EMT. Such information would include:

a) the victim's current status including (i) his rhythm status over the last few minutes (Meanwhile, the victim's real time rhythm status, i.e. the current ECG, would be displayed on one of the PU screens.) and (ii) his current vital signs;
b) the victim's initial heart rhythm;
c) the major events that took place during the resuscitation, i.e. defibrillation and pacing, and the results of each therapeutic intervention by the MP;
d) the victim's blood pressure recordings during the event;
e) the victim's respiratory status during the event;
f) the elapsed time since MP involvement with the emergency began;
g) the elapsed time since the emergency began (if known);
h) the victim's latest and prior states of responsiveness;
i) information obtained from enabler's initial description of the victim, i.e. that obtained immediately before MP release of the PU to the enabler;
j) information about the victim's medical history; including (i) events immediately preceding the current emergency and (ii) events and medical conditions which predate the current situation; and
k) information about the victim's medications, if any;
l) information about the victim's medication allergies, if any;
m) information about victim's next of kin, if known. Items (a) through (f) are stored within the PU memory for the duration of the event. They are also stored within the CS memory, as are items (j) through (m), if known. Items (g), (h) and (i) may be related to the EMT by the MP. All victim and event data, audio and video recordings become a part of the permanent CS record.

Storage and transmission of victim-related and event-related information is performed in compliance with all local and federal statutes regarding privacy, encryption and restriction of access.

The duration of the information presentation and the level of detail will depend on: a) the severity of victim's condition at the moment of EMT take-over; and b) the number of EMT personnel. (A larger team means that someone is more likely to be free to obtain the information.)

The information may be presented in any of the following formats:

a) enabler narrative by voice communication;
b) text summary, on one of the PU screens;
c) ECG summary (the important recordings made during the resuscitation procedure), on one of the PU screens;
d) text printout (A small printer may be included in the PU.);
e) ECG printout; and
f) combinations of (a) through (e).

In addition to supplying the EMT with patient related information, the MP may, if necessary, provide the EMT with information about the use and operation of the PU.

4.1.7.3 Method of PU Operation by the EMT

Figure 28:
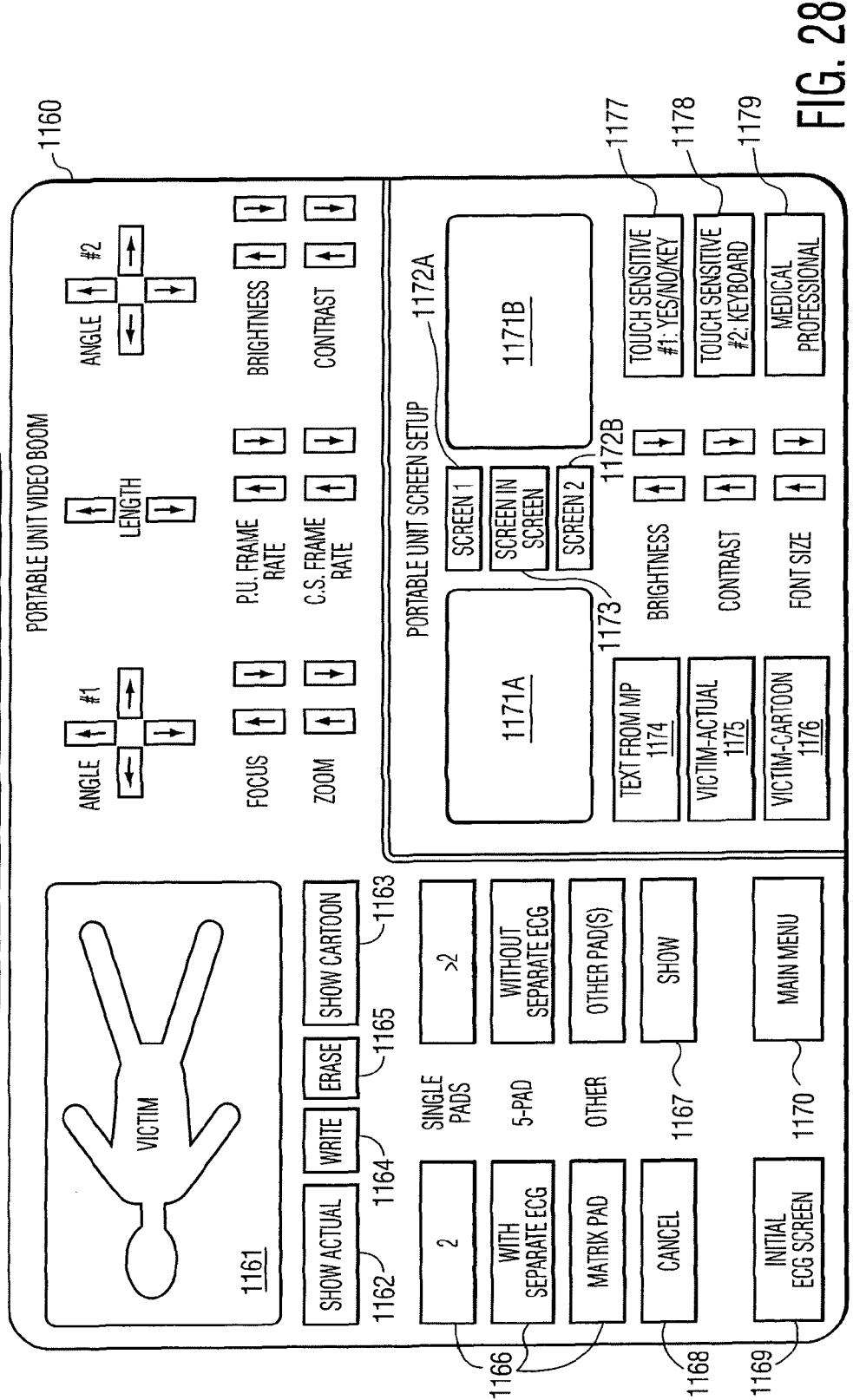
FIG. 28 illustrates a touch-sensitive display screen at the central station for controlling the video camera and video displays at the portable unit.

The EMT uses the PU in a similar fashion to the way that the medical professional uses his console at the central station. That is, the PU screens 156: a) display vital information such as the victim's ECG, blood pressure and respiratory status; b) serve as touch sensitive screens with the same screens for defibrillator and pacer control, and for ECG viewing and electrode pad setup as those used by the MP (FIGS. 29 through 40); and c) can display an appropriately truncated version of the Screen Menu (FIG. 43) used in the central station (The truncated Screen Menu does not give the EMT access to screens which would be inappropriate and unnecessary for the EMT, such as the Video Control Screen (FIG. 28). Additional screen capacity may be achieved with screenin-screen and split screen methodology, as was discussed in Section 2. In a preferred embodiment of the system, the PU may generate instructional prompts, either voice or text, to help guide the EMT regarding PU operation.

4.1.7.4 MP Role During EMT Use of the PU
4.1.7.4.1 Medical and Technical Support by the MP In a preferred embodiment of the invention, the MP link with the PU remains intact, even after handoff of PU control to the EMT. Therefore the MP may continue to:

a) view victim data (ECG and other);
b) view EMT commands;
c) speak with the EMT; and
d) observe the arrest scene.

Therefore, there are a number of possible formats for the relationship of MP to EMT, during EMT use of the PU. These include:

a) active involvement by the MP, in an advisory capacity, in medical decision making (i.e. MP makes suggestions about victim management whenever MP feels it is appropriate);
b) involvement in a medical advisory capacity, only when consulted by the EMT;
c) active involvement by the MP, in an advisory capacity, in a technical support role (i.e. advising the EMT about PU operation whenever MP feels it is appropriate);
d) involvement in a technical support role, only when consulted by the MP; and
e) no MP involvement whatsoever.

"Active" may refer to any frequency of giving advice, from frequent to infrequent. Which of (a) through (e) is selected may be based on both EMT and MP preference, and may be based on local statutes or protocol. The choice of (a) through (e) may vary during the course of a particular emergency. For example: Although the EMT might be fully capable of medical management of the victim and proper use of the PU, he might fail to notice a sudden change in the victim's heart rhythm. This could occur while the EMT is starting an intravenous line for the victim. The MP, in such a situation, could immediately inform the EMT.

Medical advice which the MP could provide includes:
a) helping the EMT make a correct rhythm diagnosis;
b) helping the EMT select the correct treatment modality (e.g. shock versus giving intravenous medication);
c) helping the EMT select the correct treatment parameters (e.g. high energy shock versus low energy shock);
d) advising the EMT as to the adequacy of CPR performance (e.g. by monitoring oxygen saturation);
e) advising the EMT of a sudden change in the victim's status which the EMT may not have noticed (see example above); and
f) pharmacologic advice (see below).

At any time, the EMT may request that the MP resume control of the PU. This may occur if:
a) additional electrical therapy is necessary (defibrillation or pacing) and the EMT feels that the MP's medical expertise is superior to EMT's
b) the EMT feels that the MP's technical expertise (regarding operation of the portable unit) is superior to EMT's;
c) one or more members of the emergency medical team is involved in medical activities such as CPR or intravenous line placement, which do not allow them to pay adequate attention to heart rhythm issues;
d) one or more members of the emergency medical team is involved in transport activities, which do not allow them to pay adequate attention to heart rhythm issues;
e) combinations of (a) through (d).

4.1.7.4.2 Pharmacologic Support by the MP

Once one of the members of the emergency medical team has started an intravenous line for the victim, there is the opportunity to administer a variety of intravenous medications including:

a) drugs to help regulate the heart rhythm (antiarrhythmic drugs);
b) drugs to increase the intensity of the heart's mechanical action (inotropic drugs);
c) drugs which increase the heart rate (chronotropic drugs);
d) drugs which alter the metabolic status; and
e) drugs which prevent blood clotting (antithrombotic agents) or promote clot dissolution (thrombolytic agents).

The EMT opportunity to administer intravenous medication adds another item to the potential MP advisory role. The MP advice may be based on: a) the MP's own expertise; b) rapid access to other experts in pharmacologic matters; and c) rapid access to databases which contain pharmacologic information. The MP pharmacologic advice to the EMT may include:

a) suggestions or information about choice of drug (if any), and dosage;
b) suggestions about rate and route of drug administration;
c) advice about expected drug effect;
d) advice about potential drug-drug interactions;
e) reminders about current victim medications (if known) drug allergies (if known).

4.1.8 MP Role After Victim Arrives at the Hospital

The MP may continue to function in an advisory capacity after the victim reaches a hospital. That is, treating physicians at the hospital which receives the victim may wish to utilize the MP, because of a number of potential of advantages to such an approach including:

a) the MP's high degree of expertise and experience in the management of heart rhythm abnormalities may exceed that of any of the physicians in the hospital;
b) the MP's rapid access to other experts;
c) the MP's rapid access to pharmacologic databases;
d) the MP's rapid access to the victim's past medical history; and
e) the fact that the MP has become familiar with the victim and his response to therapy over the course of the current medical event.

It is furthermore possible that hospital physicians may request that the MP resume control of electrical therapy, for each of the reasons (listed above) that EMT may make such a request.

4.2 Sample Cardiac Arrest: Correspondence Between Events During the Arrest, Flow Diagrams, Screens, Handshakes and Confirmation Signals Table 11 shows the sequence of events that constitute the hypothetical cardiac arrest. This table also shows the correspondence between:

a) events during the arrest;
b) flow diagrams, FIGS. 12 through 23, showing the functional interaction among the system, the enabler and the medical professional;
c) some of the actual screens that the MP views during an arrest (The complete set of screens consists of FIGS. 24-44. Ten of the 19 screens are mentioned in Table 11.);

d) the handshakes, discussed above and summarized in Tables 7, 8 and 9; and e) the confirmation signals which let the MP know that his commands were properly executed.

Explanatory comments in the table are indented.

TABLE 11

Events During an Hypothetical Cardiac Arrest

| Time m:ss | Event | Flow Diagram FIG. # | CS Console FIG. # |
|---|---|---|---|
| | Phase One | | |
| 0:00 | Enabler (EN) sees emergency victim (VI) and decides to help | | |
| 0:01 | EN heads for nearest Portable Unit (PU) | | |
| 0:31 | Button press by EN | 12 | |
| | Phase Two | | |
| 0:31 | PU transmits handshake (HS) signals to Central Station (CS) | 12 | 25 |
| 0:32 | Completion of Communication HS between PU and CS (Table 7, VI-MP Link, HS #1) | 12 13 | 25 |
| 0:32 | Completion of Data/Command HS between PU and CS (Table 7, HS #2) | 14 | 25 |
| 0:32 | CS identifies PU as Unit #643025, located in Columbus, Ohio | | |
| 0:33 | MP identifies himself | 15 | |
| 0:37 | EN confirms that he can hear the MP; MP confirms that he can hear the EN; These constitute completion of Audio HS between EN and MP (Table 7, HS #3A and #3B) | 15 | 25 |
| 0:41 | MP asks EN to describe the emergency | 16A | |
| 0:44 | Begin EN's description of the emergency | 16A | |
| 0:50 | End EN description; MP decides that this emergency warrants intervention by MP and PU This constitutes completion of Informational HS between EN and MP (Table 7, HS #4) | 16A | |
| | Phase Three | | |
| 0:50 | MP issues commands to a) release PU lock b) call 9-1-1 nearest to EN | 16A | 27 |
| 0:50 | CS transmits and PU receives Lock Release Command | 16A 24 | 44 |
| 0:51 | Electromagnetic Lock releases PU from Stationary Unit (SU) | 16B | |
| 0:51 | PU transmits and CS receives lock release confirmation | 16B 24 | 44 |
| 0:52 | MP sees lock release confirmation | | 27 |
| 0:53 | MP tells EN to detach PU from SU, and to transport PU to VI | 16C | 27 |
| 0:55 | EN detaches PU from SU; | | |
| 0:55 | PU transmits and CS receives and displays PU removal telemetry signal | 24 | 44 |
| 0:56 | MP sees removal telemetry signal | 16C | 27 |
| 0:56 | EN transports PU to VI; During transport, MP provides EN with additional instructions | 17 | |
| 0:56 | During transport, there is continuous updating of the link between EN and MP | | 25 |
| 1:37 | EN tells MP that he has arrived at VI's side | 18A | |
| 1:39 | MP tells EN how and where to put PU down | 18A | |
| 1:41 | EN puts down PU; This automatically releases tool-kit door and transmits PU touchdown telemetry signal; CS receives and displays telemetry | 18A 24 | 44 |
| 1:42 | MP sees PU touchdown telemetry signal; On PU Deployment Screen, MP presses GO TO VIDEO CONTROL SCREEN; This Brings up Video Control Screen | 18A | 27 28 |
| 1:42 | MP optimizes audio to and from EN | 18B | 44 |
| 1:46 | MP asks EN if VI is unconscious; VI answers affirmatively | 18D | |
| 1:48 | MP, working from Video Control Screen, extends video boom, so its end protrudes from PU | 18A | 28 |
| 1:50 | MP instructs EN in exposing VI's chest | 18E | 28 |
| 2:00 | MP determines that pad 204B is optimal (5 large/7 small electrodes) and tells EN to get it from top shelf of tool-kit | 18E | 28 |
| 2:05 | EN pulls pad 204B, and the cable and Universal Connector which attach pad to the PU, from the tool-kit shelf | 18E | 28 |
| 2:07 | MP instructs EN in proper pad location, orientation, and application method | 18E | 28 |
| 2:09 | EN peels off pad cover; Cover removal telemetry signal is transmitted by PU and is received and displayed by CS | 24 | 44 |
| 2:11 | EN applies pad to VI's chest | | |
| 2:14 | MP sees that pad is properly placed; On Video Control Screen, MP presses INITIAL ECG SCREEN; This brings up Initial ECG Screen | 18F | 28 29 |
| 2:15 | MP observes adequate impedance value for each pad electrode This constitutes Part A of the Electrical HS between VI and MP (Table 9, VI-MP Link, HS #3A) | 18F | 29 |
| 2:17 | MP notes that ECG is of good quality on Initial ECG Screen This constitutes part B of the Electrical HS between VI and MP (Table 9, HS #3B) | 18F | 29 |
| 2:17 | MP diagnoses ventricular fibrillation This constitutes the informational HS between VI and MP (Table 9, HS #4) | 19 | 29 |
| | Phase Four | | |
| 2:18 | MP selects MAIN DEFIB SCREEN on Initial ECG Screen; This brings up Main Defib Screen | | 29 33 |
| 2:18 | MP tells EN to avoid contact with VI due to impending defibrillator shock | 20 | |
| 2:19 | MP decides to use default defibrillation parameters (i.e. α and δ pads) | | |
| 2:20 | MP selects ALL DEFAULT VALUES, then selects ACCEPT on Main Defib Screen | 20 | 33 |
| 2:20 | CS transmits and PU receives command to begin charging PU defibrillator capacitors; charging begins | 24 | 44 |
| 2:23 | Capacitor charging complete; PU sends and CS receives and displays charge completion confirmation | 24 | 44 |
| 2:25 | MP notes charge completion signal, confirms persistence of VF, and issues command to deliver shock by selecting DELIVER on Main Defib Screen | 20 | 24 ECG 33 |
| 2:25 | CS transmits shock command to PU; PU receives command and delivers default shock to VI | 24 | 44 |
| 2:25 | PU sends, and CS receives and displays shock confirmation data | 24 | 44 |
| 2:26 | MP notes confirmation and notes persistence of VF, post-shock | 19 | 24 ECG |

TABLE 11-continued

Events During an Hypothetical Cardiac Arrest

| Time m:ss | Event | Flow Diagram FIG. # | CS Console FIG. # |
|---|---|---|---|
| 2:27 | MP decides to deliver another defibrillating shock | 20 | |
| 2:28 | MP tells EN to avoid contact with VI due to impending defibrillator shock | 20 | |
| 2:29 | MP decides to alter defibrillation vector (by using the α and ε pads) to enhance chance of success of next shock) | 20 | |
| 2:30 | MP selects OTHER under ELECTRODES on Main Defib Screen; This brings up Five Electrode Setup Screen | 20 | 33 31 |
| 2:31 | MP selects α, ε electrode pair on Five Electrode Pad Setup Screen by touching the following sequence: 1) α 2) ε 3) ACCEPT This brings up Main Defib Screen | 20 | 31 33 |
| 2:33 | On Main Defib Screen, MP selects additional parameters of upcoming second defibrillator shock by touching the following sequence: 1) MAX under ENERGY 2) NO under SYNCH 3) DEFAULT under WAVEFORM 4) ACCEPT | 20 | 33 |
| 2:35 | CS transmits and PU receives commands to switch to α, ε pair of defibrillator electrodes and to begin charging PU defibrillator capacitors; charging begins | 24 | 44 |
| 2:38 | Capacitor charging complete; PU sends and CS receives and displays charge completion confirmation | 24 | 44 |
| 2:40 | MP notes charge completion signal, confirms persistence of VF, and issues command to deliver shock by selecting DELIVER on Main Defib Screen | 20 | 24 ECG 33 |
| 2:40 | CS transmits shock command to PU; PU receives command and delivers second shock to VI, via α and ε pads | 24 | 44 |
| 2:40 | PU sends, and CS receives and displays shock confirmation data | 24 | 44 |
| 2:43 | MP observes termination of VF and notes presence of asystole (flat line); MP decides to begin pacing the heart, to accelerate the heart rate | 19 | ECG |
| 2:44 | MP selects MAIN PACING SCREEN on Main Defib Screen; This brings up Main Pacing Screen | 23 | 33 38 |
| 2:46 | MP selects ALL DEFAULT VALUES; then selects DELIVER on Main Pacing Screen | 23 | 38 |
| 2:46 | CS transmits command to PU to begin pacing at 60 BPM (pacing mode, pulse width, amplitude and pad choice are also specified in the command) | 24 | 44 |
| 2:46 | PU receives commands and begins pacing at 60 BPM | 24 | 44 |
| 2:46 | PU sends, and CS receives and displays pacing confirmation data | 24 | 44 |
| 2:48 | MP notes pacing at 60 BPM | | ECG |
| 2:48 | MP instructs EN to remove blood pressure cuff and oximetry sensor from tool-kit and apply them to VI | 22 | |
| 2:49 | From Screen Menu, MP selects VIDEO CONTROL SCREEN; This brings up Video Control Screen from which MP Displays instructional video for EN | | 44 28 |
| 2:56 | MP observes that victim's blood pressure is 80/50 (low) and that the oxygen saturation value is 96% (adequate) | | BP SAT |
| 2:57 | MP decides to reduce pacing rate in order to: a) observe victim's underlying rhythm; and b) in attempt to increase victim's blood pressure by restoring atrioventricular synchrony | | |
| 2:57 | MP selects OTHER next to RATE on Main Pacing Screen; This brings up Bradycardia Pacing Rate Screen | 23 | 38 40 |
| 2:58 | MP touches 55, followed by ACCEPT on Bradycardia Pacing Rate Screen; This returns Main Pacing Screen | 23 | 40 38 |
| 2:59 | MP sets default values for other pacing parameters by touching: 1) DEFAULT under AMPLTIUDE 2) DEFAULT under WAVEFORM 3) DEFAULT under PACING ELECTRODES 4) DEFAULT under SENSING 5) DELIVER | 23 | 38 |
| 3:01 | CS sends command to PU to change pacing rate from 60 to 55 BPM | 24 | 44 |
| 3:01 | PU receives command and changes pacing rate to 55 BPM | 24 | 44 |
| 3:01 | PU sends, and CS receives and displays pacing confirmation data | 24 | 44 |
| 3:04 | MP observes emergence of victim's own normal sinus rhythm at 58 BPM | 19 | ECG |
| 3:05 | MP decides that pacing is no longer necessary and touches STOP PACING on Main Pacing Screen | | 38 |
| 3:05 | CS sends command to PU to stop pacing | 24 | 44 |
| 3:05 | PU receives command and stops pacing | 24 | 44 |
| 3:05 | PU sends, and CS receives and displays stop pacing confirmation | 24 | 44 |
| 3:07 | MP observes that pacing has ceased | | ECG |
| 3:18 | MP observes that victim's blood pressure has risen to 100/60 The victim's heart rate, rhythm blood pressure are now considered to be adequate. | | BP |

Phase Five

| | | | |
|---|---|---|---|
| 3:18 | MP asks EN to obtain VI's name and other identifying data, from persons accompanying the VI, from the VI himself, or from VI's wallet | | |
| 3:24 | EN provides MP with VI identification | | |
| 3:27 | MP enters VI identification into Archival Database | | |
| 3:31 | MP views display of VI past medical history, obtained from databases | | |
| 3:36 | MP informs EN that estimated time of arrival of local Emergency Medical Team (EMT) is in four minutes | | 27 |

Phase Six

| | | | |
|---|---|---|---|
| 7:25 | Arrival of EMT | | |
| 7:27 | MP identifies himself to EMT | | |
| 7:31 | EMT says that they can hear the MP; MP confirms that he can hear the EMT; These constitute completion of Audio HS between EMT and MP (Table 10, HS #3A and #3B) | | |
| 7:35 | MP asks EMT for password; EMT's knowledge of password proves they are qualified to take over management of the case from the MP | | |
| 7:39 | EMT provides password | | |

TABLE 11-continued

Events During an Hypothetical Cardiac Arrest

| Time m:ss | Event | Flow Diagram FIG. # | CS Console FIG. # |
|---|---|---|---|
| 7:43 | MP confirms that password is correct, i.e. it indicates a qualified EMT; MP decides to transfer control of PU To EMT This constitutes completion of Informational HS between EMT and MP (Table 10, HS #4) | | |
| | Phase Seven | | |
| 7:43 | MP informs EMT that password has been confirmed and that control of the PU will now be transferred to the EMT | | |
| 7:47 | On the Communications Status and Triage Screen, MP selects GO TO EMT | | 25 |
| 7:47 | CS transmits command to change the Master Control Unit state from its present value of 1 (MP control of the PU) to 3 (allowing EMT control of the PU); PU receives command (Table 1) | 24 | 44 |
| 7:47 | Master Control Unit 130 changes state, allowing EMT control of PU; PU sends, and CS receives and displays change of state confirmation The transfer of control of the PU from MP to EMT is now complete; EMT can now control PU, using the same screens that MP was using | 24 | 44 |
| 7:48 | MP briefs EMT about current victim status, about events that have transpired during the past eight minutes, and about victim's medical history and identification, if known | | |

Beyond this point, the MP role and time allocations are highly variable and are discussed in Sections 4.17, 4.18, 4.45, and 4.57. Phase seven ends when both: a) the PU is disconnected from the victim; and b) the PU is returned to the SU.

4.3 Role of the Medical Professional 4.3.1 Expert Decisions Made by the MP During the Cardiac Arrest One very important role of the MP is the making of expert management decisions. The expertise and judgment of the MP and the flexibility and capability of the system allow the resuscitation procedure to be performed as if a medical doctor specializing in heart rhythm disorders, or a highly trained emergency medical technician was actually present at the emergency scene. Three examples of major MP decisions, which occur during the sample arrest, are: a) the MP decision to change the defibrillation vector for the second shock, and the capability of the system and the electrode pad to accommodate the decision; b) the MP ability to reliably distinguish asystole from VF post second shock and his decision to begin bradycardia pacing at that time; and c) the MP decision to slow the pacing rate from 60 to 55, in an attempt to improve the blood pressure by restoring AV synchrony. These three examples will now be discussed, to be followed by a discussion of other significant MP management decisions.

4.3.1.1 The MP Decision to Change the Defibrillation Vector for the Second Shock Our present understanding of the physiology of defibrillation is that the high voltage discharge depolarizes a significant fraction of the cardiac tissue. The shock thus momentarily prevents the propagation of the multiple fibrillatory wavefronts that are the basis of VF, and thereby causes the termination of VF. Since VF is a metastable heart rhythm, momentarily interrupting it allows for the emergence of a generally more stable rhythm, the heart's normal (or sinus) rhythm.

However, if the electrode pads are located in positions that do not allow the shock to depolarize enough of the fibrillating heart muscle, the shock is ineffective and VF persists despite the shock. It is therefore common procedure, during the conduct of an actual VF resuscitation, for the physician or other properly trained person to select alternate electrode pad positioning, if one or more shocks fail. Such repositioning is most likely to be necessary in the case of either a large victim, or in certain medical disease states where the heart itself has enlarged considerably. In the preferred embodiments which utilize multi-electrode pads, the MP can accomplish electrode repositioning electronically. In the case of the five electrode pad, shown in FIGS. 5A-E, the MP accomplishes the desired repositioning by simply selecting the more laterally located $\epsilon$ electrode, in place of the previously ineffective $\delta$ electrode. The fact that the $\alpha,\epsilon$ pair of electrodes encompasses a greater amount of cardiac tissue than the standard $\alpha,\delta$ pair makes it more likely to be effective.

The MP has a variety of options to choose from in the event of an ineffective shock for VF. They include:

a) simply repeating the shock without changing any parameters;

b) changing the shock vector, i.e. changing the anatomic relationship between electric current flow and the heart's position, as was done for the second shock in the example discussed;

c) increasing the energy of the shock;

d) changing the waveform of the shock, and e) instructing the enabler in the performance of CPR, and then shocking the victim.

State of the Art AED systems do not have the flexibility to accomplish the five options listed above. Furthermore, if they did have one or more of these options, they would not be endowed with the superior ability of a highly trained professional to choose which among the options would be ideal. However, utilizing a preferred embodiment of this invention, a medical professional would have all of these options and be in a position to choose intelligently from among them. Based on his judgment, the MP might be more inclined to choose the second option, i.e. a shift in electrode location, if he:

a) noted that a previous shock using standard electrode positioning was ineffective;

b) knew from video observation (or enabler description) that the victim was large;

c) knew from video observation that the multi-electrode pad had not been positioned perfectly at the time that the enabler placed it on the victim's chest; and/or d) knew, from either accessing the database or from a person accompanying the victim, that the victim's medical history included an enlarged heart or a medical condition or diagnosis associated with an enlarged heart. (In the scenario in Table 11, the database is not accessed until after the resuscitation is complete, but it could have been accessed earlier.)

4.3.1.2 MP Distinction Between Asystole and Ventricular Fibrillation

The second example of the combination of MP expertise and judgment and the invention's flexibility and capability resulting in a successful outcome, relates to the MP diagnosis of asystole following the second shock. Asystole, the absence of any cardiac electrical activity can occur after a successful defibrillation shock. It is more likely to occur after a long duration of VF, than after a brief episode. At times, the electrocardiographic distinction between VF and asystole is subtle. Although the "textbook" electrocardiogram (ECG) of VF consists of a continuously varying high frequency, low amplitude oscillation, and the "textbook" ECG of asystole is a perfectly flat, featureless line, at times one sees ECG tracings which might be described as falling in-between the aforementioned textbook descriptions. For example, during the phenomenon known as "fine VF," the ECG undulations are so low in amplitude that the tracing may be misread as asystole. And during some episodes that actually are asystole, the baseline may wander enough (either due to jostling of the victim, the pad or the cable, by the resuscitation team) so that even an expert cardiologist is uncertain about whether to read the ECG as asystole or fine VF.

The diagnostic problem is compounded by the fact that the treatment for VF is entirely different than the treatment for asystole. Fine VF is treated by administering a defibrillator shock. Asystole is treated by pacing the heart. A defibrillator shock is useless for asystole and pacing the heart is impossible during VF. Thus the distinction between the two rhythms is of much more than academic interest.

In principle, an algorithm could be created which could distinguish between these two rhythms as well as an expert professional. The reality is, that as of the current time, no algorithm with the discriminating power of the most expert professional exists.

If the distinction between these two rhythms is especially difficult, the options available to the MP using a preferred embodiment of the current invention include one or more of the following:

a) recording for a longer period of time, in order to have a larger information sample;

b) asking enabler to make sure that no individual is, for the moment in contact with the victim or the cable between the victim and the PU;

c) causing the PU to sample the ECG more frequently than it does with nominal settings, resulting in more accurate ECG reproduction (In a preferred embodiment the system, according to the invention, all information is transmitted between the central station and the portable unit in digital form.);

d) digitizing the ECG signal with a greater number of bits per sample, resulting in more accurate ECG reproduction;

e) increasing the bandwidth allocated for transmission of ECG information, either (i) on the already established communication channel between the PU and the CS, or (ii) by establishing an additional channel;

f) switching ECG transmission temporarily to a non-real time format in which: (i) the amount of ECG information recorded per unit time is increased (by increasing either the sampling rate or the number of bits per sample), (ii) the information is temporarily stored in a buffer, and (iii) the information is transmitted over the nominal bandwidth allocation;

g) encoding the ECG information differently, using a real time format;

h) setting up another communication channel between PU and CS and transmitting an analog version of the ECG signal i) in the event of a degraded ECG signal due to distortion due to communication problems, comparing the MP rhythm analysis with that of the on-site AED/P logic unit, 128;

j) making the decision to empirically shock the victim, i.e. making the assumption that the rhythm is fine VF; and k) making the decision to empirically pace the victim, i.e. making the assumption that the rhythm is asystole.

Options (c), and (d) involve recording a reproduction of the ECG signal. Option (a) also provides more (but not more accurate) information for the MP. Options (f), (g) and (h) involve changes in the format for ECG encoding. Option (i) would be useful if the MP still had diagnostic uncertainty, despite any of the options (a) through (h) directed at providing the MP with more or higher quality ECG information.

In the scenario described in Table 11, the MP was able to make the distinction, correctly diagnosing asystole at 2:43 and instituting cardiac pacing as of 2:46.

4.3.1.3 MP Effort to Improve Blood Pressure

The third example of MP expertise and judgment combining favorably with the invention special features involves the MP commands at 2:57 to reduce the pacing rate. Proper management by the MP, in this scenario, involved giving consideration to the possibility that the low blood pressure (80/50) during pacing may have been caused or accentuated by the pacing itself. This phenomenon is not uncommon and is sometimes referred to as pacemaker syndrome. This syndrome may occur when pacing the heart results in an unnatural sequence of electrical activation of the four heart chambers, resulting in suboptimal mechanical performance. It may result during external pacing because such pacing cannot sequentially stimulate the atria followed by the ventricles.

In normal individuals, the atria contract first and the ventricles contract 0.12 to 0.20 seconds later. Optimal cardiac function is often associated with the proper sequence and timing of electrical activation of the heart. When atrial contraction precedes ventricular contraction, referred to as atrioventricular or AV synchrony, a number of mechanical advantages obtain including: a) an increase in the pre-contraction volume of the ventricles, meaning more blood is available to be pumped; and b) an increase in the pre-contraction ventricular wall tension, which optimizes ventricular mechanical contraction. The decrease in cardiac mechanical performance resulting from the loss of AV synchrony is quite variable from person to person; in some persons the decrease is trivial, in others it is profound.

In the arrest described in Table 11, pacing was necessary because of asystole following the second defibrillation shock. It would not be unusual for a heart, which just suffered through some minutes of the oxygen and nutrient deprivation of a cardiac arrest, to exhibit depression of electrical and mechanical function. Although external pacing can stimulate the ventricles and thereby remedy the asystole, it can not stimulate the atria and ventricles in proper sequence. The low blood pressure which follows (MP becomes aware of it at 2:56.) may be due to a combination of both of the aforementioned factors: a) pacemaker syndrome due to loss of AV synchrony; and b) depression of mechanical function post arrest. MP options at that juncture would be: a) lower the pacing rate; b) increasing the pacing rate (to try to stimulate the heart to pump more blood, albeit at a lower pressure); or c) leaving the pacing rate as is. This is a clinical decision, often made by cardiologists and cardiac rhythm specialists. The decision is based on many factors including the presence, if any, of ongoing rhythm instability (as evidenced by premature beats, for example), the victim's past medical history, and other clinical parameters.

The logic behind lowering the pacing rate is that after a short period of pacing for asystole, the heart may recover enough to have its own pacemaker cells resume functioning. As such a recovery ensues, the cells may begin to fire slowly at first, and then have their rate gradually normalize. However, if external pacing is occurring at a rate which is greater than the rate at which the heart's pacer cells are firing, ventricular activation will be preempted by the stimulus from the external pacer. By lowering the pacing rate, the MP can determine: a) if such a recovery is occurring, and if it is; b) whether allowing the victim's rate to fall so that the heart's pacemaker cells can "take over" and so that AV synchrony can resume, results in a more favorable blood pressure.

The decision is a complex one because lowering the heart rate may, in some victims, promote the emergence of greater instability, either electrical (i.e. heart rhythm related) or mechanical (blood pressure decline). In a worst-case scenario it could lead to another arrest. This underscores the value of having an expert make such decisions.

4.3.1.4 Other MP Decisions Requiring Medical Expertise

Other decisions made by the MP (and unrelated to his interaction with either the enabler [see Section 4.3.2] or the EMT [see Section 4.3.3]) during the sample arrest which require medical expertise include:

a) the choice of which particular electrode pad to use (occurs at 2:03 during the sample arrest);

b) defibrillation parameters other than the choice of which electrodes to use, such as energy, pulse configuration, synchronization (occurs at 2:19 and 2:33 during the sample arrest);

c) pacing parameters other than the choice of which pacing rate to use, such as pulse width, amplitude, electrode choice (occurs at 2:46 during the sample arrest); and d) the duration of pacing (occurs at 3:05 during the sample arrest).

Other MP decisions which require expertise, might need to be made during another arrest, but which were not needed during the sample arrest include:

a) when to choose antitachycardia pacing (a form of rapid pacing intended to terminate certain tachycardias) instead of administering a shock;

b) the parameters of antitachycardia pacing (see FIG. 37) including the initial rate of pacing, the number of paced beats, the interval between successive paced beats, the interval between last victim beat and first paced beat, the pulse width, and the pulse amplitude;

c) the number of antitachycardia pacing attempts;

d) the change, if any, in antitachycardia pacing parameters from one attempt to the next;

e) the decision, in the case of a victim who is known to have an implantable cardioverter defibrillator or "ICD," about whether to let his ICD treat a rhythm abnormality, or whether MP should perform preemptive therapy;

f) the decision about when to begin CPR (see Section 4.5.5.1);

g) the decision about when to terminate CPR;

h) the decision, if on-site physicians and/or EMT are unavailable, about when to terminate all therapy (see Sections 4.5.3.2 (b), 4.5.5.2 (i) and 4.5.7.8.1 (d)).

4.3.2 Enabler Guidance by the MP

The aforementioned MP decisions illustrate the value of the MP for decision-making capability at the level of an expert cardiac rhythm specialist. There are other MP actions, which guide the performance of the enabler, which are also important. These include: a) proper application of the electrode pad; b) cardiopulmonary resuscitation; and c) a number of other enabler actions.

4.3.2.1 Enabler Guidance in Proper Application of the Electrode Pad(s)

Proper electrode pad positioning is critical for reasons previously mentioned. In brief, the shock must be delivered between two electrodes that are situated, approximately, on opposite sides of the heart. The greater the deviation from such positioning, the less the chance that a shock will be successful. Although multi-electrode pads like the five electrode pad and the matrix pad allow the MP to compensate for minor or moderate errors in pad application or orientation, the MP is less likely to be able to correct for gross errors.

The MP has multiple options for instructing the enabler in the placement of electrode pad(s). The MP may verbally instruct the enabler as he applies the electrode pad(s). The MP may visually instruct the enabler by showing him a live video of the victim's torso, upon which MP has superimposed visual prompts such as arrows, an outline of the pad, or a cartoon version of the pad. If the PU and video boom are situated such that superimposition of visual prompts is impractical, the MP may show still or moving images, kept on file, which illustrate proper pad application.

During the sample arrest presented in Table 11, the MP guides the enabler in electrode pad application at 2:07. The adequacy of the application is assessed at 2:15 and 2:17 (see Table 11 and Section 4.5.3.3).

4.3.2.2 Enabler Guidance in Cardiopulmonary Resuscitation

Cardiopulmonary resuscitation is another procedure for which the MP can provide instruction and guidance. Although not included in the scenario in Table 11, CPR is a common procedure during cardiac arrests attended by emergency medical teams. CPR consists of a rhythmic series of properly timed chest compressions intended to propel blood through the circulatory system. In addition, as its name implies, CPR may include means to move air in and out of the victim's lungs, a process referred to as ventilation. The person or persons who perform CPR (hereinafter referred to as "resuscitating person(s)") may be: a) the enabler; b) anyone else at the scene of the cardiac event; or c) a combination of the enabler and another resuscitating person.

The chest compressions are performed by rhythmically pressing down over the victim's sternum, or breastbone. There are also experimental devices intended to accomplish a similar result.

Ventilation may be accomplished by properly placing a mask over the victim's mouth and nose, and squeezing an attached bag which pumps air into the lungs; the weight of the chest wall and the elasticity of the lungs result in the expulsion of the air without the need for active external intervention. Another ventilation option is so called "mouth to mouth" resuscitation, during which a resuscitating person places his mouth over the victim's mouth (or upon a device interposed between his mouth and the victim's mouth), and blows air into the victim's lungs. At times, chest compression is performed without such ventilation.

The need for CPR will depend on both the cause of the cardiac arrest and the amount of time between the onset of the rhythm abnormality and its remedy. The success rate for defibrillation without CPR, when the defibrillation takes place very quickly after the onset of VF, is very high. The longer the elapsed time until defibrillation, the greater the likelihood that CPR will be necessary. The need for CPR may be determined in each of the following ways:

a) CPR will need to be administered if, at the time of the initial recording, the victim's electrocardiogram shows that the rhythm is normal, but the blood pressure or oxygen saturation readings are, in the opinion of the MP, unacceptably low.

b) CPR will need to be administered if, post-shock or post-pacing, after an initially abnormal rhythm has been normalized, the blood pressure or oxygen saturation readings are, in the opinion of the MP, unacceptably low.

c) CPR will need to be administered if ventricular fibrillation or tachycardia is present which is not responding to electrical shocks.

d) In addition there is more recent evidence to suggest that CPR may even have a beneficial effect immediately before the administration of a first defibrillating shock.

The MP can assist the enabler and/or other resuscitating person in the performance of CPR in each of the following ways:

a) Using means similar to those for illustrating proper electrode pad application, the MP may use one of the PU screens 156 to illustrate where on the chest the resuscitating person must apply pressure. Screen use may entail images superimposed on that of the victim, or previously prepared instructional video materials.

b) The MP may use PU screens 156 to illustrate other aspects of chest compression including the proper relation between the resuscitating person's right and left hands, and the proper body position for the resuscitating person.

c) The MP may coach the resuscitating person during the performance of chest compression. Such coaching may address the rate of compression and the vigor with which it is performed.

d) Because the mechanical disruption caused by chest compression often interferes with the ability to record a high quality electrocardiogram, the MP may, from time to time, ask the resuscitating person to suspend chest compression for a few seconds. During such time, the ECG signal is clearer; such interruptions give the MP a better view of the rhythm status during chest compression.

e) The MP may also, from time to time, request a pause in chest compression to recheck the victim's blood pressure. This check must occur in the absence of chest compression, since chest compression would mask the victim's cardiac performance.

f) Using means similar to those for illustrating proper electrode pad application, the MP may use one of the PU screens to illustrate proper ventilation technique.

g) During ventilation, the MP may coach the resuscitating person as to the proper rate of ventilation. Such coaching would also address the way that chest compression and ventilation should be coordinated. (The manner of coordination is different when there are two resuscitating persons, as opposed to a single resuscitating person.)

h) Using oxygen saturation data from a sensor which has been applied to the victim by the enabler, the MP will be able to have some indication as to the adequacy of ventilation. The MP may use this information to give further guidance to the resuscitating person(s).

i) The presence of airway pressure and flow monitoring sensors within either a mask (part of the bag and mask ventilating apparatus) or within a device interposed between the resuscitating person's mouth and the victim's mouth would give the MP another way of determining the adequacy of ventilation (see Section 8.8). The MP may use this information to guide the resuscitating person in his use of the ventilating apparatus.

j) Ventilation adequacy could also be monitored by measuring the impedance between chest electrodes. Since air has a lower conductivity than body fluids, as the chest inflates with air, impedance across the chest increases. Certain implanted pacemakers, as are known in the art, perform such measurements within the body, in order to determine ventilation status. The MP may use such impedance information to guide the enabler or other resuscitating person in his use of the ventilating apparatus (see Section 8.9).

k) Finally, during the performance of CPR, there is enough uncertainty and hesitancy on the part of all but highly experienced emergency personnel, that any reassurance that can be provided during CPR is an asset.

It should be noted that: a) CPR is not required during all resuscitations; and b) even in a situation where enabler and anyone else at the scene is either unwilling or unable to do CPR (or is unable or unwilling to perform chest ventilation), the ability of the invention to provide MP expertise in performing the electrical part of the resuscitation and other functions is expected to be of substantial value.

4.3.2.3 Enabler Guidance in Other Activities

Other ways in which the MP can guide the enabler, facilitating the performance of enabler tasks include:

a) guiding the enabler in properly positioning the PU near the victim (occurs at 1:39 during the sample arrest);

b) guiding the enabler in removing victim clothing which may prevent access to the chest (occurs at 1:56 during sample arrest), discussed below in section 4.5.3.3;

c) guiding the enabler in properly applying the blood pressure and oxygen saturation monitoring devices (occurs at 2:48 during sample arrest), discussed below in section 4.5.4.2;

d) guiding the enabler, post EMT arrival, during certain activities aimed at making the PU ready for its next use, hereinafter referred to as "housekeeping" (see Section 4.5.7.3, below);

e) guiding the enabler, post EMT arrival, in reattaching a PU to the SU (see Section 4.5.7.4, below); and f) reassuring the enabler during the commotion and pandemonium that may accompany a cardiac arrest (occurs intermittently throughout the MP-enabler interaction).

4.3.3 EMT and Physician Guidance by the MP

The role of the MP expands, once the EMT arrives. MP responsibilities then include:

a) properly identifying the EMT;

b) briefing the EMT about the victim's current condition and the events that transpired during the previous minutes (see Section 4.1.7.2);

c) instructing the EMT in PU operation, if necessary (see Section 4.1.7.4.1);

d) providing heart rhythm related diagnostic and management advice, if necessary (see Section 4.1.7.4.1);

e) providing pharmacologic advice (see Section 4.1.7.4.2); and f) providing guidance about cessation of therapy.

As indicated above (see Section 4.1.8), the MP guidance role may also include providing historical, diagnostic and management advice for the physician(s) to whom the EMT transfers to victim.

4.4 Time Allocation During the Sample Cardiac Arrest 4.4.1 General Considerations Regarding Prediction of Duration Time allocations during the sample arrest are estimates, based on the experience of the inventor. For some events, such as the time it takes the MP to correctly read an electrocardiogram, the actual duration is expected to deviate little from the estimated duration, under most circumstances. (Hereinafter, the extent of deviation of actual durations from estimated values is referred to as "the variance.") For other events, such as transporting the PU, substantially greater variance is expected. Finally, there are certain events such as the duration of phase seven, where the variance is so great, that no attempt has been made to predict event duration.

4.4.2 Enabler Travel Time

Nearly all of phase one in the hypothetical arrest represents the time it takes the enabler to reach the portable unit. The amount of time will be a function of both: a) the distance between the victim and the PU; b) the walking/running speed of the enabler; and c) the enabler's ability to determine where the nearest PU is located. Thirty seconds is assumed; The enabler (assuming a speed of 3.5 miles per hour) is expected to be able to walk approximately 50 yards in this time. It is therefore possible that phase one could be substantially shorter or longer than the allotted 31 seconds.

The return trip, i.e. enabler's transport of the PU from its attachment to the stationary unit (which may be wall mounted) is also of variable duration. The duration will be determined by: a) the distance between the PU and the victim; and b) the enabler's speed while carrying the PU. If we assume that the enabler transports the unit moving slightly slower than he did without having to carry the PU (2.5 miles per hour is assumed), and if we again assume an approximately 50 yard distance, the time required will be 41 seconds. The total transport time for the PU is thus assumed to be approximately 71 seconds.

4.4.3 Duration of Other Enabler Tasks

Though virtually every event which requires enabler action will vary in duration, depending on the particular enabler and event, some event durations are less predictable than others. Enabler events whose variances may be substantial include:
  a) enabler's description of the emergency for the MP;
  b) enabler's baring the chest of the victim;
  c) enabler's application of the electrode pad to the victim;
  d) enabler's application of blood pressure and oxygen saturation measuring equipment to the victim; and
  e) enabler's identifying the victim.

Enabler events with a lesser degree of variance include:
  a) enabler's initial decision to help the victim;
  b) the audio handshake between the enabler and the MP;
  c) removing the PU from the SU; and
  d) orienting the PU video boom.

4.4.4 Time Allocation for MP Tasks During Phase Four

Although the duration of individual MP actions is far more predictable than the duration of either enabler or EMT actions, the number of therapeutic MP actions required to resuscitate a victim is highly uncertain. Four MP interventions (two shocks, and two different bradycardia pacing efforts) were included in the hypothetical arrest scenario presented here. If only a single defibrillating shock had been required to restore a normal rhythm, that restoration would have occurred at 2:26 into the arrest. The second shock added another 17 seconds; and the need for pacing added another 19 seconds.

The second shock and the pacing thus add another 36 seconds to the time until normal rhythm is restored. These 36 seconds, when added to the aforementioned 71 seconds of variable transport time, total up to one minute and 47 seconds. Thus more than half of the time until normal rhythm is restored in the current scenario, must be considered to be substantially variable.

4.4.5 Time Allocation Involving EMT Events

Two EMT related time estimates are also highly variable. The first concerns the time that it takes the EMT to arrive. Arrival at 7:25 (which is six minutes and thirty five seconds after being called by the MP) is a realistic value for some areas of the United States. The time of EMT arrival is one of much reduced importance, because the definitive treatment for the arrest occurs substantially before such arrival. The second highly variable EMT event is the duration of phase seven, and the individual events which comprise it. Since both the duration and the number of phase seven events is highly variable (in part related to regional aspects of EMT policy and procedure), no attempt has been made to predict the duration of phase seven.

4.4.6 Correction for Simultaneous or Nearly Simultaneous Tasks or Events

Another time-related issue is that certain MP tasks may appear to have a surprisingly short time earmarked for their performance. This is because some of these tasks, though listed in the table as sequential, are expected to be performed simultaneously. For example: during phase three, the MP could adjust the video boom (allocation in Table 11 is 1:54 to 1:56) and instruct the EN (allocated for 1:56 to 2:03) simultaneously. Therefore, the time to do the video adjustments is really from 1:54 to 2:03, not from 1:54 to 1:56. There are many other examples of this overlap phenomenon. There are also instances of events which overlap, and of events and tasks which overlap; in each instances, appropriate adjustment of estimate duration has been made.

4.5 Further Details Concerning Specific Issues During the Sample Cardiac Arrest

What follows is a discussion of specific events and issues during the aforementioned hypothetical arrest.

4.5.1 Phase One: Amount of Time for Enabler to Reach PU

This is dependent on a number of factors and is discussed in 4.4, above.

4.5.2 Specific Issues During Phase Two 4.5.2.1 Initial and Subsequent MP Screens At 0:31, as the initial handshake is occurring between the enabler and the MP, the MP console in the central station immediately changes to reflect the new event. In the scenario described in Table 11, three MP screens are activated without the MP needing to select them: a) the Communications Status and Triage Screen, FIG. 25 (first noted in Table 11 at 0:31); b) the Portable Unit Deployment Screen, FIG. 27 (first noted at 0:51); and c) the Confirmations Screen, FIG. 24 (first noted at 0:51). These screens allow the MP to perform the initial operations during the early period of his interaction with the enabler.

Figure 31:
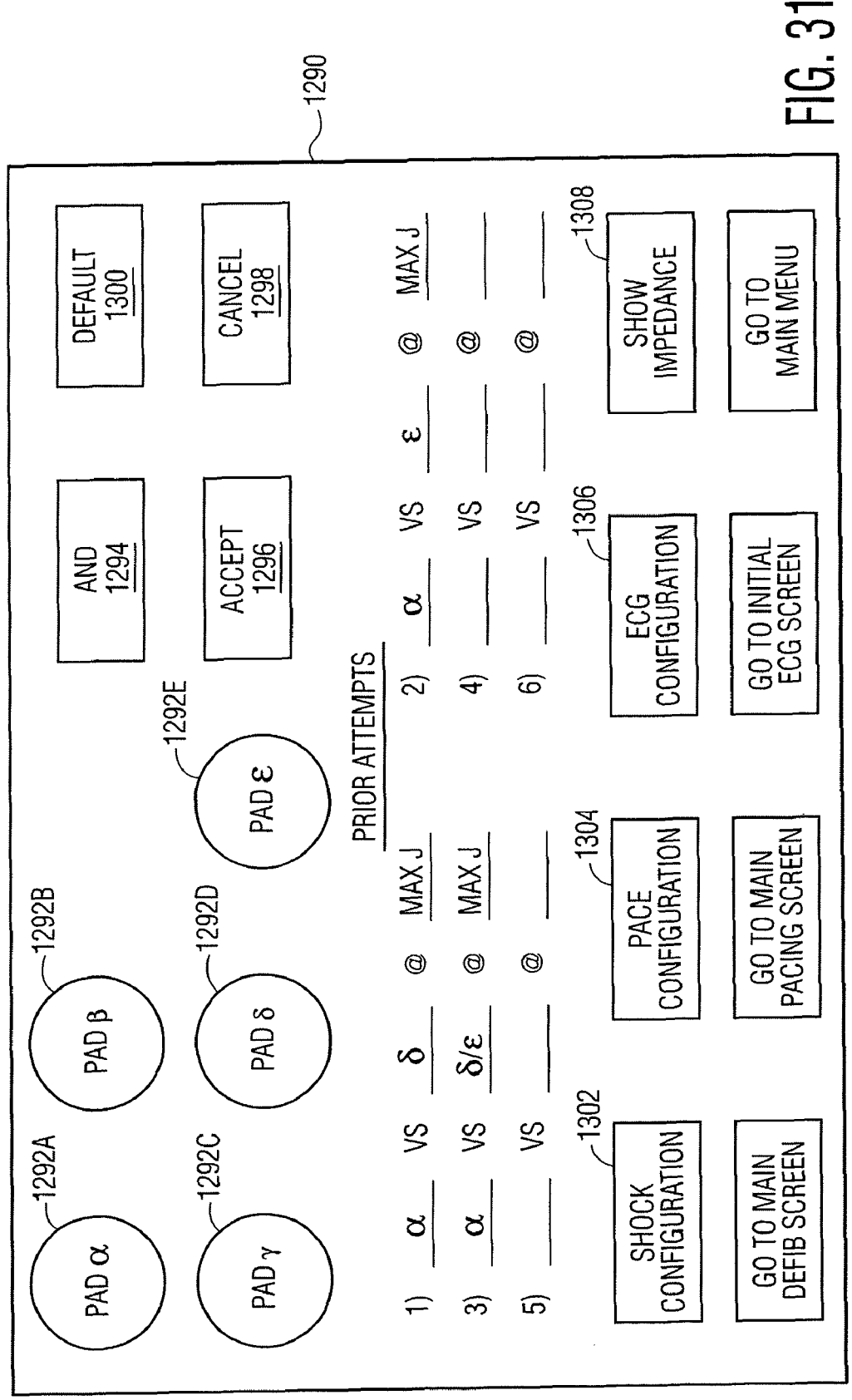
FIG. 31 illustrates a touch-sensitive display screen at the central station for selection of electrodes on the five electrode pad.

The MP selection of new screens can occur in one of five ways:

a) Most screens generally have touch-selected choices for each other screen that may be needed next. Thus the PU Deployment Screen, FIG. 27, has a GO TO VIDEO CONTROL SCREEN button, since the Video Control Screen is the screen likely to be the one from which the MP works, after finishing with the PU Deployment Screen Similarly, the Video Control Screen, FIG. 28, has an INITIAL ECG SCREEN button, since the latter screen is likely to follow the Video Control Screen. The Initial ECG Screen, FIG. 29, lets the MP navigate to any one of the three screens likely to be needed next; the Main Pacing Screen, FIG. 38; the Main Defibrillation Screen, FIG. 33; and the Antitachycardia Pacing Screen, FIG. 37. The Antitachycardia Pacing Screen allows one-touch navigation to the Main Pacing and Main Defibrillation Screens. The Main Pacing and Main Defibrillation Screens each allow one-touch navigation to multiple other screens, each of which deals with one particular parameter of pacing (e.g. rate) and defibrillation (e.g. energy).

b) Each of the screens which deal with individual pacing and defibrillation parameters allows rapid transit back to Main Pacing or Defibrillation Screens, by pressing ACCEPT.

c) The Screen Menu, FIG. 44, can be accessed at any time by pressing a "hot key" or keys (e.g. Control, S) on the MP keyboard. When this is done, the Screen Menu appears on one of the MP touch sensitive screens. This menu provides access to every possible MP screen.

d) The Screen Menu can also be accessed directly from a number of other screens, e.g. the Five Electrode Pad Setup Screen, FIG. 31, by a touch sensitive box.

e) The MP may prefer to configure his array of touch sensitive screens so that the Screen Menu is on display at all times.

There are various ways that newly called up screens can displace previous ones. These include:

a) having the previously used screen "move" one screen up, rightwards, or leftwards. At a point when live screen capacity is exceed, the overflow screen is no longer displayed (until and unless it is selected again);

b) always displaying certain fundamentally important screens such as Confirmations (FIG. 24), Main Defibrillation (FIG. 33) and Screen Menu (FIG. 43); leaving the remaining touch sensitive screens to be used as needed;

c) having successively used screens overlay each other. For example, selecting OTHER under Electrodes on the Main Defibrillation Screen (as was done during the sample cardiac arrest in Table 11), brings up the appropriate electrode setup screen (FIG. 31, for the five-electrode pad). This screen would be superimposed upon the Main Defibrillation Screen until the appropriate selections are made (the α and ε pads) after which the Five Electrode Pad Setup Screen would disappear and the Main Defibrillation Screen would reappear;

d) combinations of the approaches described in (a), (b) and (c).

Note that the number of screens available for viewing may be increased by: a) simply designing the MP console (FIG. 3) so that it contains more screens; or b) using screen-in-screen or split screen technology, allowing each physical screen to simultaneously show more than one menu or display.

4.5.2.2 Facilitated Lock Release in the Event of Failure of Handshake #1 or #2

As mentioned in Section 4.1.2.3.1, the third level of backup for a failed communication handshake or a failed data/commands handshake is during the enabler-MP link is for the PU to automatically enter Master Control State 2. This transfers control of defibrillation and pacing to the AED/P 128. Master Control State 2 also enables release of the mechanism which locks the PU to the SU. The actual release may be: a) fully automatic, whereby entry into Master Control State 2 directly causes lock release; b) enabler facilitated, in which a voice prompt tells the enabler a combination which is entered on a keyboard; or c) enabler facilitated, in which a voice prompt tells the enabler a combination which is used to open a mechanical combination lock.

Figure 27:
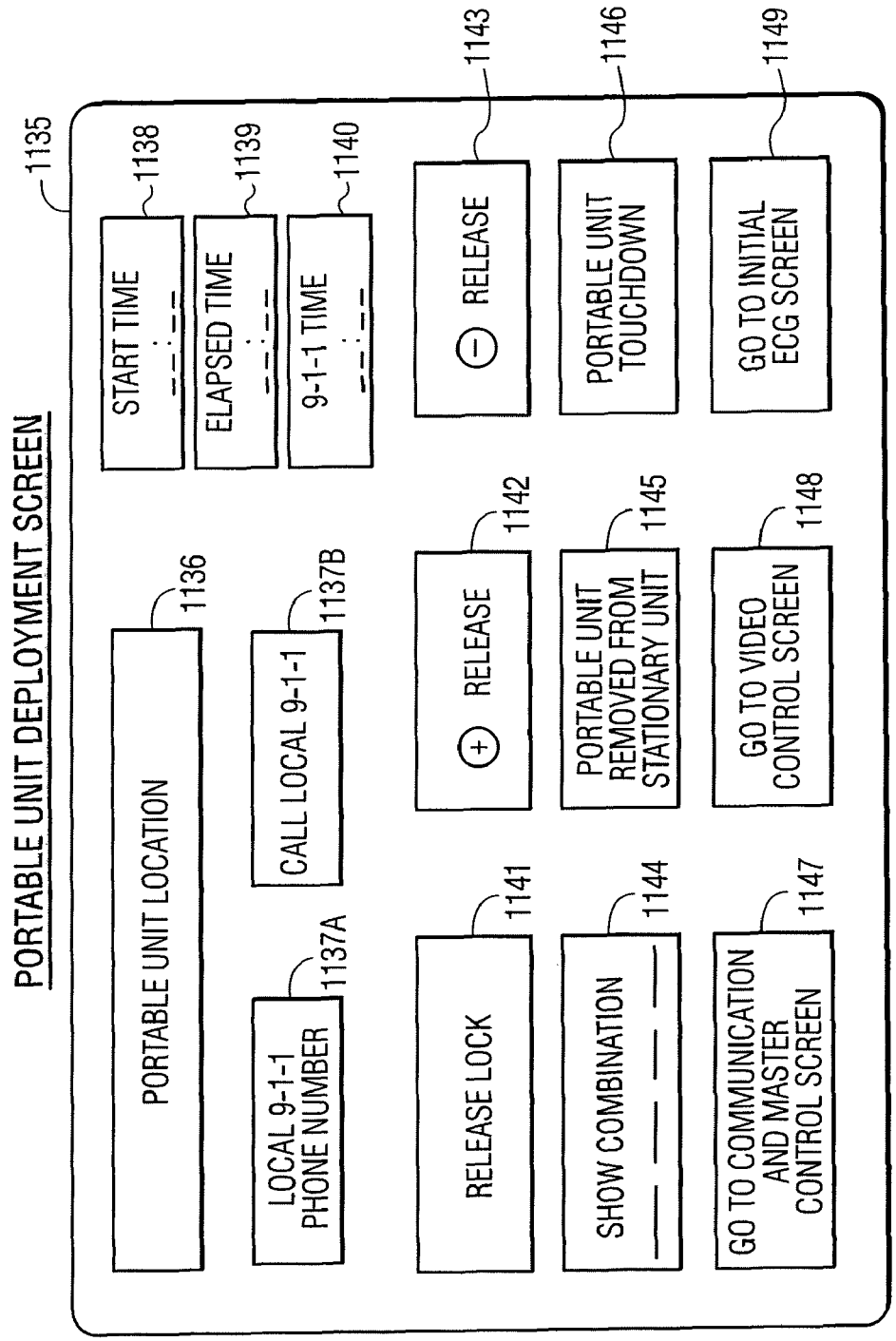
FIG. 27 illustrates a touch-sensitive display screen at the central station for controlling deployment of the portable unit.

4.5.3 Specific Issues During Phase Three 4.5.3.1 The MP Interface with Emergency Medical Services At 0:50 during the sample arrest outlined in Table 11, the emergency medical team local to the victim is called by the central station. They may be called: a) directly by the MP; b) by a CS administrator, or other person working with the MP (so that MP's attention need not be diverted from dealing with the EN); or c) by computer. As shown in FIG. 27, the PU Deployment Screen, the MP may be provided with access to information about:

a) the hospital nearest the victim;

b) the emergency service (fire department, police or hospital based) nearest the victim;

c) estimated arrival times for the nearest emergency service; and d) telephone numbers for contacting these emergency services.

4.5.3.2 MP Actions During Transport of PU to Victim

At 0:56, the enabler begins moving the PU to the victim's side. (For additional discussion and illustration of this event, see Section 5.4.1 and FIG. 17.) During this time, if it is established that EN and MP can hear each other well while EN is transporting the PU, MP may further discuss the situation with EN. During such discussion, MP would:

a) ask for and obtain additional description of the emergency;

b) ask for the victim's identification, if known (This would allow the MP to begin searching one or more databases for further information about the victim's past medical history, about a health care proxy (if any) and about advance directives (if any). In Table 11, the identification information is obtained later, i.e. during phase five);

c) tell EN exactly how the PU should be situated (i.e. with handles and screens facing upwards), when placed on the ground or on a stable, flat surface, very near to the VI;

d) give EN a preview, if time allows, of other tasks to be performed, upon arrival at the VI; and e) reassure the EN—i.e. that MP is highly experienced, that MP will do all of the decision making, that MP will guide EN through a series of simple steps that require no prior medical training, and that an emergency medical team has been summoned.

At 1:42, immediately after EN puts down the PU near the VI, MP will reassess the quality of the audio link between himself and the EN, and make any adjustments necessary to optimize audibility at both ends. (For additional discussion and illustration of this event, see Section 5.4.2.2 and FIG. 18B.) If necessary, MP may ask EN to use a headset, containing both microphone and earphone, contained in the tool-kit section of the PU. This would be especially useful in either a noisy environment, or if EN is hard of hearing. The headset could be wired directly into the PU or could have a wireless link to the PU.

4.5.3.3 MP Assessments and Actions, Upon Arrival of the PU at the Victim's Side

At 1:46, shortly after arrival of the MP at the VI, MP asks EN for an update on the VI. If the victim had regained consciousness during the time that EN had been in transit, then the next step would be for the MP to further assess the VI, either by direct observation (checking for victim motion or speech) or via the EN (who might, upon prompting by the MP, ask questions of the VI). Based on this further assessment, MP would decide whether there is a need to expose the victim's chest for application of one of the larger electrode pads. If it is anticipated that the likelihood of needing pacing or a defibrillation shock is substantial, then application of one of the electrode pads with this capability would be the next step. If, however, such therapy is not likely to be needed, the Mini-Pads 211, located on the fifth shelf from the top of the PU (see FIG. 7B) could be used as standard ECG leads, and be applied by the EN (under direction of the MP) to the arms and legs of the victim. This would provide the MP with an electrocardiographic tracing from which he could determine the victim's heart rate and rhythm. In the scenario of Table 11, in which the victim has had a cardiac arrest due to ventricular fibrillation, the victim did not (and could not have) regained consciousness; the EN thus informs the MP that the victim is unconscious.

At 1:54, after adjustment of the PU video camera, if the MP determines that the PU location is sub-optimal, e.g. too far from the victim, MP will inform EN of the need to reposition the PU.

At 1:56, the instruction in exposing the victim's chest includes telling the EN: a) the reason for exposing the chest; b) that there is a scissors in the tool-kit, which can be used, if necessary; and c) the extent of the area which needs to be bare, to accommodate the electrode pad(s). The MP may display instructional video materials on the PU screen 156 which illustrate the location of the scissors within the tool-kit (FIG. 7A) and the proper approach to clothing removal. When displaying instructional video materials, the MP would work from Video Control and Instruction Screen, FIG. 28 (discussed below).

Based on MP observations of the victim while EN is exposing the chest, MP decides which of the electrode pads contained in the tool-kit best suits the victim. In the current scenario electrode pad 204B is selected (at 2:03) which could be used on a male, or a female who did not have large breasts.

This pad has five large defibrillating electrodes and seven small ECG electrodes. The choice of pad is based on MP judgment and experience.

At 2:15 and at 2:17 during the sample arrest, the MP assesses how well the pad has been applied to the victim's skin by observing (at 2:15) the display of impedance measurements for each electrode, and by observing (at 2:17) the multi-lead ECG signal. These are displayed in the central station on the Initial ECG Screen (FIG. 29, discussed below) and on the dedicated ECG screen 302 (FIG. 3). According to techniques known in the art the system would optimize the ECG signal; the MP would have the option of changing the system-selected parameters (e.g. the gain) or otherwise adjusting the signal. The MP might tell the enabler to press down over one or more sections of the pad if the MP observes high impedance readings or low amplitude ECG recordings corresponding to such an area.

4.5.3.4 Enabler Headset Handshake

The enabler may need to use a headset-microphone combination 168, contained in the tool-kit, if either he or the MP are not hearing each other well. If the headset-microphone is wireless, then its proper linkage to the PU may be confirmed by: a) a formal handshake routine analogous to the first three layers of the enabler-MP handshake (see Sections 4.1.2.3.1 through 4.1.2.3.3 and Table 7); or b) a much simpler audio handshake, analogous to layer three only, primarily intended to allow for the adjustment of gain controls on each end. The simpler handshake described in (b) would be the approach if the headset-microphone had a wire connection to the PU.

4.5.4 Specific Issues During Phase Four:

4.5.4.1 Wide Variety of MP Choices for Defibrillation and Pacing Parameters; Central Station Screens which Correspond to these Choices The MP has access to a wide variety of treatment choices concerning the details of defibrillation and pacing; The choices selected during the sample arrest represent only a small fraction of the available options.

Figure 36:
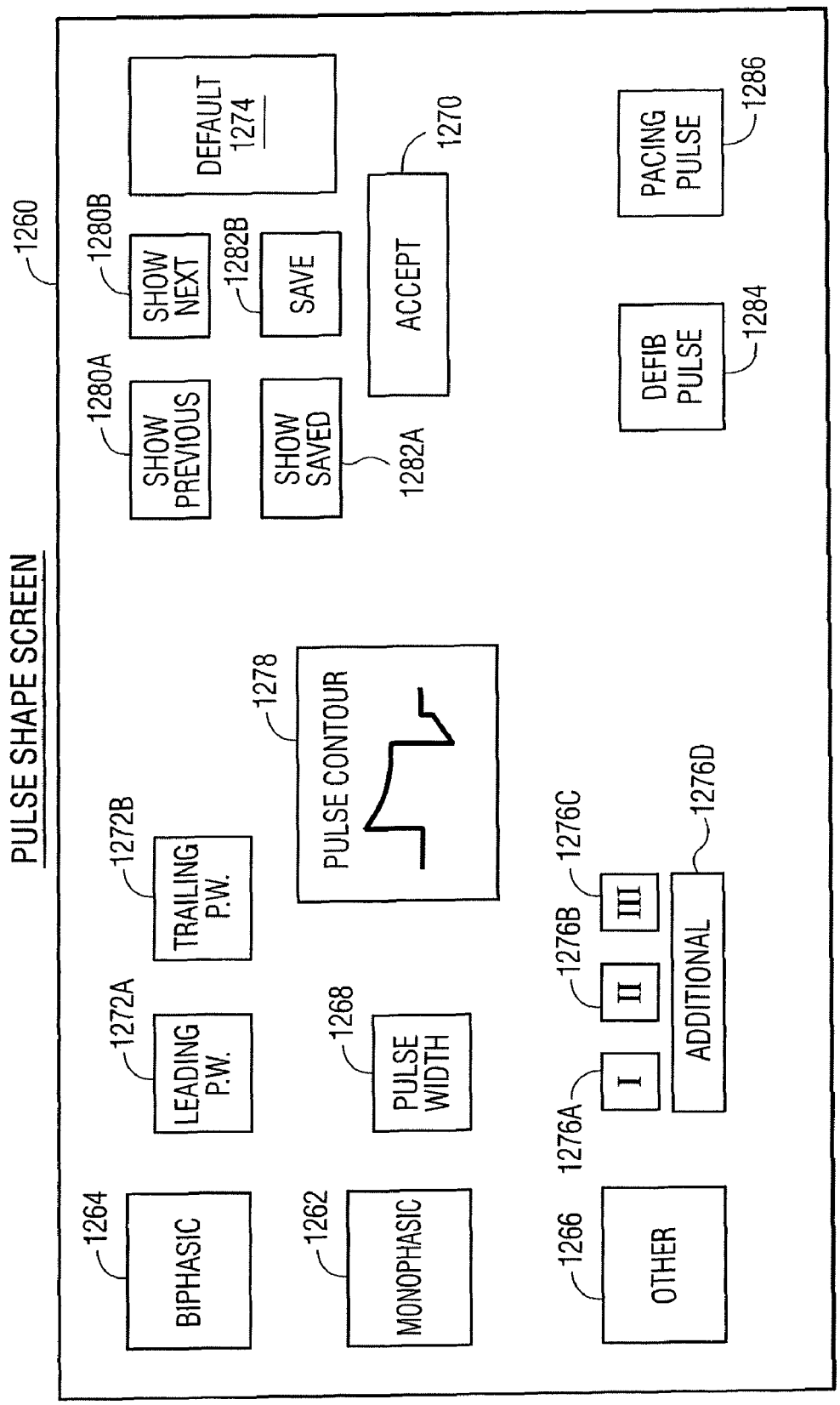
FIG. 36 is illustrates a touch-sensitive display screen at the central station for control of defibrillation and pacing pulse shape.

During the sample arrest, when defibrillation was necessary, the MP initially chose default values of shock parameters; When a second shock was necessary, the MP chose to alter the electrode pair through which the defibrillation energy was directed. Other MP options concerning defibrillation parameters include: a) changing defibrillation energy (FIG. 34, Defibrillation Energy Screen); b) changing shock synchronization (FIG. 35, Synchronization Screen), i.e. the precise timing of energy application; and c) changing the shape of the defibrillation pulse contour (FIG. 36, Pulse Contour Screen).

During the sample arrest, when pacing was necessary to treat a slow heart rhythm post-shock, the MP initially chose default values of pacing parameters; He later decreased the pacing rate. Other MP options concerning pacing parameters include: a) changing the pacer amplitude (FIG. 39, Pacer Output Screen); and b) changing the pacer pulse contour (FIG. 36, Pulse Contour Screen).

These central station screens, and others are discussed below in section 6.

4.5.4.2 MP Instructs Enabler in the Application of Blood Pressure and Blood Oxygen Saturation Devices At 2:48 during the sample attest, once bradycardia pacing has commenced, the MP must determine the victim's blood pressure and blood oxygen saturation. The MP thus gives audio instructions to the enabler. The MP may also display instructional video materials on the PU screen 156 which illustrate the location of these two devices within the PU tool-kit (FIG. 7A) and the proper technique of their application to the victim. When displaying instructional video materials, the MP would work from Video Control and Instruction Screen, FIG. 28 (discussed below). The results of blood pressure and oxygen saturation determinations are displayed on screens 304 and 306 respectively, on the MP console in the central station (FIG. 3).

4.5.5 Specific Issues During Phase Five 4.5.5.1 Possible Performance of CPR During Phase Five Once the blood pressure and blood oxygen saturation information is available, the MP will be able to make a determination as to the need, if any, for cardiopulmonary resuscitation. As was discussed above in section 4.3.2.2, CPR will need to be administered if, after the rhythm has been optimized, the blood pressure or oxygen saturation is, in the judgment of the MP, unacceptably low.

It is also possible that CPR would be needed during phase four. As was discussed above in section 4.3.2.2, this would be the case if either: a) ventricular fibrillation or tachycardia was present which was not responding to electrical shocks; or b) the MP determined that the administration of CPR before giving a shock was desirable.

4.5.5.2 Multiple Possible Types and Sources of Victim Related Information

Once the victim has been identified, the MP may obtain information about:

a) the victim's past medical history;
b) the victim's last or baseline electrocardiogram;
c) the victim's current medication names and doses;
d) the victim's allergies, drug and non-drug;
e) about an implanted pacemaker or defibrillator, including the manufacturer, model and programmed settings;
f) the names and telephone numbers of one or more of the victim's physicians;
g) the names and telephone numbers of hospitals or clinics where the victim may have been treated;
h) information about victim's next-of-kin; and
i) information about health care proxy and advance directive, if any, i.e. legal documents which may specify who and how health care decisions are to be made for this victim, if victim cannot participate in such decisions.

Such information may come from a number of databases or sources including:

a) a database maintained by the central station (which may be located (i) at the central station, (ii) at one or more off-site locations, or (iii) both);
b) the victim's physician(s);
c) hospitals or clinics where the victim had been treated;
d) private corporations or other business entities which may maintain such databases; and
e) government based data archives including Medicare, Medicaid, and other state and foreign sources.
f) a card or other item carried by the victim onto which medical information has been encoded, which may be decoded by apparatus within the PU.

The encoding, transmission, retrieval, display and storage of the aforementioned information would be carried out in accordance with all government regulations regarding privacy.

Although victim identification during the sample arrest occurs during phase five, it could occur as early as phase three or as late as phase six; or not at all.

4.5.5.3 Multiple Possible Means of Tracking Local Emergency Services

At 3:36 during the sample arrest, the MP informs the enabler of the estimated time of arrival of the local Emergency Medical Team. In a preferred embodiment of the invention, the Portable Unit Deployment Screen (FIG. 27) displays this estimate. Such information may be obtained:

a) from an EMT estimate which is inputted directly to the central station;

b) from a verbal estimate supplied by the EMT;

c) from (i) global positioning (GPS) equipment within an EMT vehicle, (ii) a computer program which estimates travel time (such as Microsoft® Expedia™ Trip Planner 98), and (iii) a computer on which this program runs; whereby GPS-derived data regarding EMT location is inputted into the computer which is running the travel time program, and the computer supplies the central station console with estimated arrival time information, which is displayed on the Portable Unit Deployment Screen (FIG. 27); or d) from a non-automated version of (c), in which the location of the EMT is manually entered into the aforementioned travel time program.

Using any of these methods, the MP may track the location of more than one EMT and thereby facilitate the deployment of such teams by:

a) informing an emergency medical team of the location of another team or team(s);

b) directing the team with the shortest estimated arrival time to proceed to the scene of the emergency;

c) directing the most well equipped team to the scene of the medical emergency;

d) using information about the location of a team and how well equipped it is to select the most appropriate team or team(s).

4.5.6 Phase Six: Specific Issues During Phase Six 4.5.6.1 Analogous Aspects of the Enabler-MP Link During Phase Two, and the EMT-MP Link During Phase Six As was discussed in 4.1.6.2, the four handshakes which constitute the EMT-MP link are analogous to the four handshakes which constitute the enabler-MP link (see also Tables 7 and 9, above).

Another analogous feature resides in the third level of backup, in the event of failure of a handshake in layer #1 or #2. In each of the two links, the system is designed to allow a "probably appropriate" user to have access to the PU; i.e. it gives the "benefit of the doubt" to the person desiring access. In each of the two links, the primary mode of operation is for the MP to approve the release of the unit, either: a) physically, with the PU to be removed from the SU, following the enabler-MP link; or b) electrically, to be controlled by the EMT, following the EMT-MP link. The secondary mode is to allow release of the unit without MP approval, as described above and below, in the event of handshake failure.

In the event of a failure of either of the first two handshakes between enabler and MP, the enabler can gain access to the PU without the MP having to release the unit. In this case, the PU (functioning in Master Control State 2, independent from the CS) informs the enabler of the combination to a lock, mechanical or electrical, which releases the PU from the SU; In an alternative embodiment, the PU could be automatically released in the event of handshake failure in the first two layers of the enabler-MP link.

Similarly, in the case of the EMT-MP link, as was discussed above in Section 4.1.6.2.1, a failure of either of the first two handshakes lets the EMT bypass the usual MP-based password approval; The PU itself will accept a pre-programmed EMT password, without MP approval, in the event of an unsuccessful communication or data/command handshake.

4.5.6.2 Timing of EMT Arrival

During the sample arrest, the EMT is called at 0:50 and arrives at 7:25. This constitutes an elapsed time of six minutes and thirty five seconds, which is a reasonable estimate by large city standards One way to view the effectiveness of the invention is to consider how much time was saved by instituting life-saving therapy (i.e. defibrillation) before the EMT arrived. It is possible to estimate a lower boundary for this parameter.

4.5.6.2.1 Time Saved by Using the Invention: Estimation of the Earliest Possible Defibrillation by EMT, Without the Invention A number of assumptions must be made to perform this estimation:

a) Assume that EMT had been called at the moment of button press, i.e. 0:31 (see Table 11). This assumes that the amount of time required to press the button is the amount of time required to call 9-1-1.

b) Assume that six seconds are needed to describe the event to the EMT dispatcher. This is the same estimate used for the sample arrest. This puts their dispatch at 0:37.

c) Assume (as was assumed during the sample arrest, above) that six minutes and thirty five seconds is the time from EMT dispatch until EMT arrival. This puts their arrival time at 7:12 after enabler noticed the victim d) Assume that from the moment of EMT arrival until they assess the victim, remove or cut the victim's upper garment, hook up their defibrillator, diagnose VF, charge their defibrillator and finally shock the VF, is 30 seconds, i.e. an extremely rapid performance. This puts the time of first shock at 7:42 after enabler noticed the victim.

e) Assume that the first shock was effective. The only reason to make such an assumption (aside from trying to come up with the lowest possible estimate of the time to EMT termination of VF) would be if the EMT did a substantially better job of attaching and orienting the electrode pad than did the MP/enabler. In reality, it is likely that MP/enabler shocks will be more successful than EMT shocks, because the MP/enabler shocks will be administered much sooner than the EMT shock. The time of the shock when the invention is not used is 7:42; the time (of the [definitive] second shock) when the invention is used is 2:40 (Table 11).

Working with the aforementioned five assumptions, definitive therapy comes nearly five minutes sooner (2:40 vs. 7:42), using the invention. It is estimated that cardiac arrest mortality increases by roughly ten percent per elapsed minute without therapy. Therefore, using these extremely optimistic estimates for EMT performance, the invention would be expected to cause an approximately 50% reduction in the mortality from a cardiac arrest.

4.5.6.2.2 More Realistic Estimates for EMT Defibrillation

Two issues make the aforementioned estimate of EMT performance (without the invention) especially optimistic:

a) Assumption (e). Because ventricular fibrillation is assumed to have been going on for more than seven minutes before EMT arrival (without the invention), there is a good chance that the first shock will not be successful. Multiple shocks might be required. A period of CPR might need to precede one or more of the shocks. And, it is possible that a successful shock at this late time might not occur until after intravenous medication has been administered. If this is the case, even more time is lost.

b) In the current analysis, it has been assumed that the endpoint for resuscitation is the time of termination of VF. If, instead, the endpoint of the resuscitation process is assumed to be the moment when a survivable blood pressure is restored, then there may be an even greater disparity between the resuscitation time without the invention, compared to that with the invention. The prolonged time of abnormal heart rhythm (without the invention) is again the reason. During the minutes when the heart is in VF, unless CPR is performed, the blood pH falls, the level of potassium in the blood rises, and the heart muscle cells suffer from oxygen deprivation and accumulation of toxic metabolites. The result is that even when VF is terminated, the heart's mechanical performance is initially poor. The longer the period of VF without any therapy, the greater the time until good mechanical performance can be restored, if ever. Thus, the five minute delay until the definitive shock is administered (when the invention is not used), causes additional delay in the restoration of proper cardiac mechanical performance.

4.5.7 Specific Issues During Phase Seven 4.5.7.1 Overview of Phase Seven: Two Sequences of Events Two sequences of events occur during phase seven of the sample cardiac arrest. The first involves transfer of control to the EMT. The second involves replacement of the PU.

4.5.7.1.1 Analogous Aspects of Phase Seven and Phase Three

The first and most important sequence of events during phase seven, parallels events during phase three (in which the enabler obtains the PU, and is guided by the MP in its setup), and involves EMT obtaining control of the PU, with MP guidance of the EMT. This sequence of events includes:

a) release of the PU to the EMT (see Section 4.1.7.1);

b) presenting the details of the event with the EMT (see Section 4.1.7.2);

c) instructing the EMT in the operation of the PU, when such instruction is needed (see Sections 4.1.7.2 and 4.1.7.4.1); and d) attaching a new PU to the victim, (occurs only when EMT brings a new PU and it is to be attached to the victim; see Section 4.5.7.2.2).

The second sequence of events during phase seven is analogous to a time-reversed version of phase three events, and involves attaching a PU to the SU. Such phase seven events include:

a) replacing the non-disposables in the PU tool-kit, when necessary (see Section 4.5.7.3.4);

b) retracting the video boom and the PU antenna, when necessary (see Section 4.5.7.3.5);

c) transporting a PU back to the SU (see Sections 4.5.7.2.1 and 4.5.7.3.6); and d) attaching this PU to the SU (see Section 4.5.7.4.3).

"When necessary," above, pertains only to scenarios in which the old PU is returned to the SU.

The phase three events which are paralleled by the aforementioned phase seven events are discussed above in Sections 4.1.3.1 and 4.5.3.2; and are listed in the phase three portion of Table 11.

4.5.7.1.2 Two vs. One Portable Unit at the Arrest Scene

There is complexity in describing PU deployment because: a) the EMT may or may not bring along another PU; and b) in each of these two situations, the old PU may or may not be returned to the SU. This results in two independent choices, each with two possible outcomes; the result is four possible options, described below and in Table 12.

TABLE 12

Deployment of the Old PU After EMT Arrival

| Option | Section | Old PU To: | New PU To: | Housekeeping |
|---|---|---|---|---|
| 1 | 4.5.7.2.1 | Victim | SU | Not Required |
| 2 | 4.5.7.2.2 | SU | Victim | Required |
| 3 | 4.5.7.7.1 | SU | No New PU | Required |
| 4 | 4.5.7.7.2 | Victim | No New PU | Not Required |

If the EMT brings a replacement PU, there are two ways of deploying the old and the new portable units, hereinafter referred to as "option one" (old PU remains attached to victim; described in Section 4.5.7.2.1) and "option two" (old PU returned to SU; described in Section 4.5.7.2.2). These two options are further discussed below in Sections 4.5.7.3 through 4.5.7.6, and 4.5.7.8.2.

If the EMT does not bring a replacement PU there are two ways of deploying the old PU, hereinafter referred to as "option three" (old PU is returned to SU; described in Section 4.5.7.7.1) and "option four" (old PU remains attached to victim and is transported to hospital; described in Section 4.5.7.7.2). These latter two options are further discussed below in Sections 4.5.7.3, 4.5.7.4, 4.5.7.5.1 and 4.5.7.8.2.

4.5.7.2 Two Portable Units Available: New Versus Old PU as the Replacement Unit

In a preferred embodiment of the invention, the PU, in between events, is detachably mounted on a stationary unit which is permanently mounted on a wall at approximately eye level as shown in FIG. 2A. Before the enabler and EMT leave the scene of the arrest, it is therefore desirable that one of them attaches one of the portable units to the SU. The other PU is transported to the hospital, attached to the victim.

4.5.7.2.1 Option One: Old PU Remains Attached to the Victim; New PU to be Attached to the Stationary Unit; Transportation of the New PU to the SU This is the scenario which is assumed to occur during the sample cardiac arrest, referred to in Section 4.1.6. (The scenario in 4.1.6.1, choice (b), also entails leaving the old PU attached to the victim.) It is the procedurally simpler than the scenario described immediately below (Section 4.5.7.2.2) in which the old PU is left behind, and the new PU is attached to the victim.

Unless otherwise specified, the present remarks refer to embodiments of the invention which have a stationary unit.

The current scenario (new PU left at the emergency scene) requires:

a) that the EMT brings another PU to the emergency scene;

b) that during a future emergency, the MP can match the new PU serial or identification number, with the PU location (This matching process is hereinafter referred to as "PU localization.");

c) that the new PU is transported to the SU; and d) that the new PU becomes physically attached to the SU (discussed in Section 4.5.7.4, below).

There are a variety of ways that PU localization may be accomplished:

a) The EMT may simply read the serial number of the new PU to the MP, who would enter it into the central station computer.

b) The EMT may press the emergency button on the new PU. The new PU would then transmit its serial number to the MP who could enter it into the central station computer. Various means are available to let the MP know that the button press on the new PU is intended to indicate localization at the same site as the old PU, and does not constitute a different emergency.

c) The new PU may be programmed to transmit its identification information when it gets attached to the SU (see below), with the SU supplying the location identifier.

d) In a preferred embodiment of the invention, a global positioning system within the new PU would notify the CS of its location. This notification may be automatic or initiated by button press, and would optimally occur shortly after EMT arrival.

As indicated above, the new PU must be transported to the SU, to prepare the site for a future emergency. If enabler is the person transporting the new unit, he should know the SU location. If someone other than enabler is transporting the unit, either the MP or the enabler may inform him of the SU location.

4.5.7.2.2 Option Two: New PU is Attached to the Victim; Old PU to be Reattached to the Stationary Unit This is the scenario which is referred to in Section 4.1.6.1, choices (a) and (c).

This scenario (old PU left behind) requires:

a) that the EMT brings another PU (the "new PU") to the emergency scene;

b) that the EMT presses the emergency button on the new PU and goes through an abbreviated handshake routine to link the new PU with the CS;

c) that the old PU be detached from the victim;

d) that the new PU be attached to the victim;

e) that there be an abbreviated handshake routine to confirm the link between the new PU and the victim;

f) that certain "housekeeping" functions be performed to make the old PU ready for future re-use (discussed in Section 4.5.7.3, below);

g) that the old PU is transported to the SU; and h) that the old PU becomes physically reattached to the SU (discussed in Section 4.5.7.4, below).

The handshake which follows the button press to link the new PU to the CS is conceptually similar to the enabler-MP link described in Section 4.1.2, but simpler. The reasons for the simplification are: a) AED/P backup is not needed; b) other backups are simpler as well, since the EMT and the MP are already in communication via the old PU; and c) the fourth layer of handshake, the informational handshake, is markedly simplified, compared to its counterpart during the enabler-MP handshake (when the enabler described the emergency to the MP); the only information that the EMT needs to give is the serial or identification number of the new PU, if it was not transmitted automatically at the time of new PU button press.

The universal connectors, discussed below, allow quick and easy detachment of an electrode pad from the PU, and reattachment of another electrode pad to the PU. In the current scenario, electrode pad 204B (five large defibrillating electrodes, seven small ECG electrodes; FIG. 5B) was used. This pad utilizes female universal connector "UC" 218A which connects to male UC 220A of the PU (FIG. 7B). To switch portable units, the EMT would:

a) disconnect the female and male universal connectors 218A and 220A on the new PU;

b) disconnect the female and male universal connectors 218A and 220A on the old PU (thereby briefly detaching the victim from the PU and leaving him briefly unmonitored);

c) attach the female UC 218A which terminates the cable extending from the electrode pad attached to the victim, to the male UC 220A which terminates the cable extending from the tool-kit (FIG. 7B) of the new PU, thereby re-establishing victim monitoring; and d) attach the female UC 218A which terminates the cable extending from the unused electrode pad, to the male UC 220A which terminates the cable extending from the tool-kit of the old PU, thereby making the old PU ready for re-use.

The EMT and/or MP confirm that the victim's electrode pad is properly attached to the new PU with a handshake which is analogous to but simpler than the third layer of the victim-MP link (see Section 4.1.3.2.1 above). Simplification results from the fact that the electrode pad was already shown to be functional and properly placed during its earlier use. The handshake is performed by: a) observing the electrocardiogram tracing on the new PU; and b) going to the Initial ECG Screen (FIG. 29) and confirming that the impedance values (which assess the quality of the pad-victim interface) are in proper range. Troubleshooting for this activity involves the backups presented above in Table 9 (Section 4.1.3.2.1).

The brief period of absence of victim monitoring is a disadvantage of this approach, compared with the approach described in Section 4.5.7.2.1, in which the old PU is never detached from the victim. However, a 'Y' connector arrangement, in which the some or all of the electrodes in the pad are in electrical continuity with a second cable which terminates in a second female connector, could prevent this problem. This second cable would be attached to the new PU before the first cable would be detached from the old PU; Accordingly, there would never be a time when the victim was not attached to at least one of the portable units.

The process of preparing the old PU for reuse and of reattaching it to the SU is described below (see Sections 4.5.7.3 and 4.5.7.4).

4.5.7.3 Housekeeping Activities Before Returning the Old PU to the SU; Transportation of the Old PU to the SU If the old PU is to be left at the scene of the emergency (as occurs in options two and three), the ideal approach would be to do as many things as possible to restore it to a ready-to-use condition. Such restoration activities are herein referred to as housekeeping activities. The electrode pad is generally not reusable; the same may be true of the oximetry sensor. In a preferred embodiment of the invention, extra pads and oximetry sensors (if disposable) are stored in the miscellaneous section 177 of the tool-kit of the PU (FIG. 7A) and can be used to replace these disposable items (see Section 4.5.7.3.3). Used, non-disposable items must be returned to the tool-kit (see Section 4.5.7.3.4).

4.5.7.3.1 MP Role During Housekeeping

The MP role in housekeeping activities involves:

a) confirming proper electrode pad replacement;

b) guiding on-site person(s) in the performance of certain activities;

c) inspecting the PU during or after these activities, to confirm their proper performance; and d) retracting the video boom, once inspection is complete (see Section 4.5.7.3.5).

e) making sure that after the event is over, a replacement PU is properly positioned, functioning and supplied.

4.5.7.3.2 Choice of Individual to Perform the Housekeeping Activities

The choices for who performs the on-site housekeeping activities include:

a) the EMT;

b) the enabler;

c) another bystander at the scene of the emergency, other than the person who has functioned as the enabler; and d) a person (arriving after the medical emergency) from, or related to the same organization that includes the central station and/or the medical professional (see section 4.6).

e) combinations of the above.

We shall assume, in the sections that follow, that the enabler performs this function. The MP would make sure that at least one of these persons is selected, and that the person or persons responsible for these activities: a) is aware of their responsibilities; and b) carries them out.

4.5.7.3.3 Electrode Pad Replacement; Oximetry Sensor Replacement

In the case of option two, when a new PU is substituted for the old one, electrode pad replacement should have already been performed (see four step process in Section 4.5.7.2.2), using a replacement pad from the tool-kit of the new PU. If an EMT who is under time pressure does not perform the fourth step listed in Section 4.5.7.2.2 (i.e. replacing the pad on the old PU), the enabler (or person performing the housekeeping functions) would do it at this point. (The same replacement process would occur in the case of option three [EMT does not bring a PU and leaves the PU at the arrest scene], see Section 4.5.7.7.1.)

In order to accomplish this task, the enabler must: a) disconnect the used pad; b) remove a new pad from the tool-kit; and c) connect the new pad.

The old pad is removed by disconnecting the female universal connector 218A (to which the pad is attached) from the male UC 220A. A new pad, labeled to indicate that it is the same one which has been used, is removed from the tool-kit and connected to universal connector 220A.

The MP has two ways of knowing that this procedure was performed properly: First, the female UC (the UC which comes from the electrode pad) has certain pairs of pins which are electrically common (see below and see FIGS. 56B-56F). The UC for each of the different types of pad has a different pair of electrically common pins. Therefore, by observing the impedance readings for the circuits involving the previously used pad, it is possible for the MP to know: a) that the old pad was disconnected; b) that the new pad was connected; and c) that the correct pad was connected. Furthermore, in a preferred embodiment of the invention, the MP can know that the enabler did not simply reconnect the old pad, as follows: The electrical continuity created by the conductive strip 266 within the pad backing 260 (see Section 3.2 and FIG. 5E) distinguishes an unused pad (with intact backing and conductive strip) from one with the backing removed.

Second, the MP can use the video camera of the old PU to observe enabler's performance. This may be useful if enabler is unsure about which pad to select, or how physically to connect or disconnect the UCs. The MP can also use the video camera to make sure: a) that the enabler gently pushes the pair of UCs 218A and 220A and ribbon cables 212A and 222 onto the appropriate shelf (166A) in the upper portion of the tool-kit; and b) that the enabler then places the newly attached pad on the appropriate shelf in front of the UCs and cables. However, although visual confirmation is valuable, the ultimate verification of a properly completed pad replacement is electrical, as described above.

The oximetry sensor 174 would also be replaced at this time, if it is the disposable type, by simply disconnecting the old one (if not already done by the EMT) and replacing it with a spare from the tool-kit.

4.5.7.3.4 Replacement of Non-Disposable Items

The MP would make sure that the enabler places the blood pressure cuff 172 and scissors 170 in the appropriate compartments of the PU tool-kit (FIG. 7A). If the oximetry sensor 174 is the non-disposable type, it too would be returned to the tool-kit at this time.

If either the wireless headset 168 or the telephone cable 176 has been used, they now need to be replaced. The MP can re-attempt communication by means which do not require the headset (e.g. via PU speakers 146 and PU microphone 148, or via PU handset 150) or the telephone cable; But the MP must first tell enabler the remainder of the replacement plan, in case communication is immediately lost or later interrupted, once these items 168 and 176 are returned to the tool-kit. The remainder of the plan involves: a) closing the tool-kit door; b) transporting the PU back to the SU; and c) attaching the PU to the SU (as described below in 4.5.7.4)

MP confirmation that these steps have taken place is either based on enabler's statement to this effect, or by observation via video camera. If communication is terminated (because it was based on the headset and/or the telephone cable) before all enabler tasks are confirmed, they can be confirmed once communication is re-established, after the PU is returned to the SU.

4.5.7.3.5 Video Boom and Antenna Retraction Prior to Moving the PU

Prior to moving the PU, the MP must retract the video boom 112 so that the video camera 154, if it has been deployed, is returned to a position inside of the PU. This protects it from damage during the move. This can be performed once the inspection process is complete.

Prior to enabler's moving the PU, the MP may instruct the enabler to lower the PU antenna 162, if it has been raised. MP may inform the enabler that if communication disruption occurs once the antenna is lowered, then enabler's choices are to: a) raise the antenna and press the emergency button; or, b) return the old PU to the vicinity of the SU, and then attempt to re-establish communication, by button press, with or without antenna extension. In a preferred embodiment of the invention, antenna movement is directly controlled by the MP, by mechanical means as are known in the art. If MP wishes to avoid the potential disruption in communication that might occur as a result of antenna lowering, he may allow the PU to be transported without retracting the antenna.

4.5.7.3.6 Transportation of the Old PU to the SU

If the old PU is being returned to the SU, the MP, as soon as the video boom is retracted, informs the enabler that he may return the PU. If enabler is the person returning the unit, he should know where it came from. If someone other than enabler is returning the unit, either the MP or the enabler may inform him of the SU location.

4.5.7.4 Attachment of the PU to the SU

Such attachment occurs during option one (Section 4.5.7.2.1), option two (Section 4.5.7.2.2) and option three (Section 4.5.7.7.1).

4.5.7.4.1 Who Performs the Attachment?

The choices for who attaches the new or old PU to the SU are identical to those for the performance of the housekeeping functions, discussed above in Section 4.5.7.3.1. Again, we shall assume that the enabler performs this function.

4.5.7.4.2 Mechanical Issues in the Attachment Process

FIG. 9 shows that the SU has a shelf in its lower portion, which supports the PU. Replacing the PU requires sliding it across the shelf, from the front of the shelf to back of the shelf; so that the power connector 186 on the PU (FIG. 8) engages its counterpart, power connector 192 on the SU. In similar fashion, telemetry connector 188 on the PU engages its counterpart 190 on the SU. Meanwhile, the locking projection 194, extending from the SU will engage the PU receptacle and electromagnetic lock within the SU.

A variety of mechanical mechanisms (not shown in FIG. 8 or 9) may facilitate the attachment procedure:

a) The SU shelf may include small wheels or cylindrical rollers on its surface, to facilitate sliding the PU back toward the vertical part of the SU.

b) Alternatively (or, in addition), the PU may also include such small wheels or rollers on its under-surface. (The under-surface of the PU is defined as the surface opposite the that which contains the handle shown in FIG. 8.)

c) Locator pins may project from the SU and enter receptacles in the PU to help guide the PU as the enabler pushes it into place.

d) A narrow "wall" at each edge of the SU shelf would help guide the PU.

e) Grooves in the SU shelf with matching projections on the under-surface of the PU, or the inverse arrangement with grooves in the PU under-surface and matching projections on the SU shelf, would help guide the PU.

The MP may facilitate the attachment procedure by informing the enabler of the mechanical guides which help align and position the PU as it returned to the SU.

4.5.7.4.3 Endpoint for PU-SU Attachment

The goal for this step is to have the enabler return the PU to the position in which it is attached to the SU, and in which it is designed to remain, in between deployments: hereinafter referred to as the "home position." In the home position:

a) each of the sensor switches 178 has its central dowel depressed by an appropriate amount;

b) each of the PU feet 180 is resting in its proper position with respect to the SU shelf;

c) the PU telemetry connector 188 properly engages its counterpart, the SU telemetry connector 190;

d) the PU power connector 186 properly engages its counterpart, the SU power connector 192; and e) the SU locking projection 194 properly enters and engages PU receptacle and electromagnetic lock 182.

The MP may gauge the progress and adequacy of the PU-SU attachment process by monitoring a number indicators available to him: These indicators include the following:

a) The PU sensors switches 178 (FIG. 8, Section 2.3) will provide position and orientation information as the PU nears its home position. As the PU nears the home position, the central dowel within the sensor switch is depressed, providing position information. Proper orientation of the PU is deduced when multiple sensor switches show identical degrees of depression (to within the limits of measurement) simultaneously. The greater the number of sensor switch positions, and the greater the number of sensor switches, the more detailed is the position and alignment information available to the MP. Furthermore, when three or more sensor switches are present, their placement in any non-linear pattern will give the MP information about misalignment of "pitch" or "yaw."

b) The MP will know when the PU telemetry connector 188 (FIG. 8) properly engages the SU telemetry connector 190 (FIG. 9) as the home position is approached.

c) In the home position, the SU locking projection 194 (FIG. 9) engages the electromagnetic locking mechanism 182 within PU. Sensors within the locking mechanism can inform the MP of proper engagement.

d) Other sensors (not shown): (i) mechanical, (ii) photoelectric, (iii) laser or (iv) continuity, may be positioned in the SU shelf 108, the PU bottom and the PU back. They would give the MP additional PU position information, as the PU slides toward the home position.

e) A grid, cross, dot, mark, pattern, picture, or mirror could be placed on a wall opposite the PU (i.e. the wall which the screen side of the PU faces). Sighting through the video camera would allow for the detection of misalignment, though this could only occur once the enabler has moved out of the way. The MP could also use a combination of these indicators.

The MP would inform the enabler, if MP has evidence of either misalignment or insufficient advancement of the PU, and would tell enabler of suggested corrective action.

It would also be possible to guide the enabler automatically (e.g. with voice prompts) without MP involvement. This approach would be useful: a) in the event of communications failure (see Section 4.5.7.5, below); or b) if (i) a new PU was being mounted and (ii) the PU localization process (see Section 4.5.7.2.1) had not yet been performed.

There are a variety of approaches to informing the enabler as to when the PU has been properly and adequately advanced, and is correctly situated in the home position:

a) The MP may tell the enabler that the PU is properly positioned.

b) An audible mechanical click may be heard when the lock engages.

c) The PU may emit a tone or a voice prompt indicating proper attachment.

d) One or both of the screens 156 may flash and/or provide a text message indicating proper attachment.

e) Resistance to further PU motion (either towards or away from the back wall of the SU) could serve as an indicator.

4.5.7.4.4 Checking the PU Post-Attachment

Attaching the PU to the SU initiates a diagnostic checking routine that is described below (see Section 4.6.2). When this occurs, the PU enters Master Control State 4 (see table 1 and Section 1.3.1.2) The check is performed whether the attached PU is an old or a new one. Electrical functioning within the PU and the SU, as well as the integrity of the PU-SU connections are assessed.

Using the video camera 154, the MP may also perform a visual check which includes: a) an inspection of the PU and SU; and b) an assessment of the functioning of the PU screens 156 (see Section 4.6.2)

4.5.7.5 Choices in the Event of Communications Failure During Phase Seven;

Once the EMT has arrived and assumed control of the PU, a communications failure with the central station would not be nearly as momentous as one prior to EMT arrival.

If a break in communications occurs, the MP, immediately aware of it, makes efforts to restore the link using techniques referred to above, in Section 4.1.2, and below. The PU would: a) notify the EMT (by voice prompt, screen message or text printout), who would have multiple communication possibilities (see Section 4.5.7.5.1, below); b) present EMT with an audio, video or printed summary of the arrest (containing the information stored in the PU, i.e. the first six of the thirteen items listed above in Section 4.1.7.2), if MP had not completed this task before communications interruption; and c) present EMT with an audio, video or printed version of PU operating instructions, if the MP had not completed this task before communications interruption.

4.5.7.5.1 EMT Communications Choices Using Only One Portable Unit

If he becomes aware of a communications failure between the PU and the CS, the EMT has the following choices:

a) The EMT may make no active effort to restore communication, allowing MP to perform this function.

b) The EMT may access a simplified version of the Communications and Triage Screen (FIG. 25) from the truncated Screen Menu, via PU screen 156. This would allow the EMT to chose "GO TO AED/P". Such a choice could be useful if the EMT is busy doing other activities and not able to attend to the ECG monitor. The EMT could, alternatively select a monitoring function, which (i) sounds an audible alarm if a heart rate or rhythm abnormality is detected by the PU, but (ii) does not render treatment, allowing EMT performance of the latter. Yet another EMT alternative via the modified Communications and Triage Screen is a hybrid of the two previously mentioned approaches. That is, the AED/P could be set up to (i) sound an audible alarm if a heart rate or rhythm abnormality is detected by the PU, and (ii) delay treatment for a programmable number of seconds, such that the AED/P gives the EMT a certain amount of time to render treatment, before the AED/P does.

c) The EMT may attempt to restore communications by plugging telephone cable 176 (see Section 2.2 and FIG. 7A), extending from the PU attached to the victim, into a nearby telephone jack of the public telephone network, if available, at the arrest scene. The EMT would then attempt to re-establish communication with the MP via the public telephone network. This attempt would be initiated by simply pressing emergency button 106 on the portable unit (FIG. 6A).

d) The EMT may attempt to restore communications by plugging telephone cable 176, extending from the PU attached to the victim, into the female telephone jack 155 of the stationary unit, if he is within reach of it. The EMT would then attempt to re-establish communications with the MP via the SU by pressing emergency button 106 on the PU.

e) The EMT may manipulate PU antenna 162 by either (i) extending or retracting it and/or (ii) changing its orientation; followed in either case by pressing emergency button 106 on the PU.

4.5.7.5.2 EMT Communications Choices Using a Second Portable Unit

The EMT, if he has brought a PU to the arrest scene, may attempt to contact the MP via the PU not currently attached to the victim, hereinafter referred to as "PU-2" (whether it be the new or the old one). Certain actions by the EMT may render the second PU more likely to communicate with the MP, than is the PU which is attached to the victim, hereinafter referred to as "PU-1." These actions include:

a) moving PU-2 outside or nearer to the outside of a building;

b) moving PU-2 so that it is within reach of a telephone jack which allows connection to the public telephone network;

c) moving PU-2 so that it is located in between the stationary unit and PU-1; and d) moving PU-2 to any other location.

There are two possible approaches to using PU-2: a) using PU-2 as the only PU; and b) using both PU-1 and PU-2 in tandem.

4.5.7.5.2.1 Choice in which PU-2 is the Only PU which Communicates with the Central Station The rationale for using PU-2 as the only PU, instead of PU-1 is because PU-2 might be capable of communication with the CS even though PU-1 is not. Possible reasons for non-equivalent performance of the PUs are: a) PU-2 being a different model portable unit (though nevertheless an embodiment of the invention) with a more robust communications system; b) PU-2 being in a different position, allowing for greater signal strength (in either or both directions) than PU-1; or c) a malfunction in PU-1.

If PU-2 is successful in communicating with the central station, methods of using it include: a) simply using it as a communication device between MP and EMT, without PU-2 having a direct link to the victim; b) connecting PU-2 to the victim's electrode pad by switching the universal connectors (analogous to the procedure described in Section 4.5.7.2.2); or c) connecting PU-2 to PU-1 by extending the telephone cable 176 coming from PU-1, to PU-2, resulting in tandem operation of the PUs. (There are also other possible means of linking PU-2 to PU-1, see below.)

4.5.7.5.2.2 Choices in which Both PU-1 and PU-2 are Used in Tandem; Even More Elaborate Links There are multiple possible configurations using both PUs in tandem operation. The features of the link that may be varied include:

a) The first segment of the link, i.e. that from PU-1 to PU-2, may be wireless or wire. The terms "wireless" and "wire" have been defined above, in Section 4.1.2.4. In a preferred embodiment of the invention, the wire may be cable 176 coming from PU-1 which may be plugged into female jack 153 of PU-2.

b) The second segment of the link, i.e. that from PU 2 towards the central station, may connect PU-2 with either (i) the stationary unit or (ii) the central station.

c) If the second segment of the link is between PU-2 and the SU, it may be wireless or wire. If it is a wire link, it may be achieved by plugging telephone cable 176, extending from the PU-2, into the female telephone jack 155 of the stationary unit.

d) If the second segment of the link is between PU-2 and the central station, it may be wireless or wire. If it is a wire link, it may be achieved by plugging telephone cable 176, extending from PU-2, into a female telephone jack of the public telephone network.

Table 13, below, lists different possible combinations of the aforementioned first segment and second segment choices.

TABLE 13

Communication Choices Using the Second PU as a Relay

| | Segment #1 | Segment #2 | |
|---|---|---|---|
| Choice | PU-1 to PU-2 | PU-2 to SU | PU-2 to CS |
| 1A | Wireless | | Wireless |
| 1B | Wireless | Wireless | |
| 2A | Wireless | | Wire to TELCO |
| 2B | Wireless | Wire to SU | |
| 3A | Wire | | Wireless |
| 3B | Wire | Wireless | |
| 4A | Wire | | Wire to TELCO |
| 4B | Wire | Wire to SU | |

Even more elaborate links involving larger numbers of PUs in tandem are possible.

Replacement of a PU at the SU is more complex when the link between the MP and the EMT or victim consists of two PUs. If a third PU is available, it may be attached to the SU. If not there may be a period without communication between the MP and the EMT or victim, during which time one of the PUs is moved to the SU and attached to it (as described in Section 4.5.7.4, above).

4.5.7.6. Possible Need for Two Nearly Simultaneous MP Conversations During Phase Seven During the first four phases of the sample arrest, there are a number of times when the MP may be called upon to perform multiple tasks simultaneously (see Section 4.4.6). During these phases, however, there is virtually no instance when the MP must speak to two individuals simultaneously. (Even when MP calls the emergency medical team local to the victim, MP need not interrupt his conversation with the enabler [see Section 4.5.3.1].)

Figure 42:
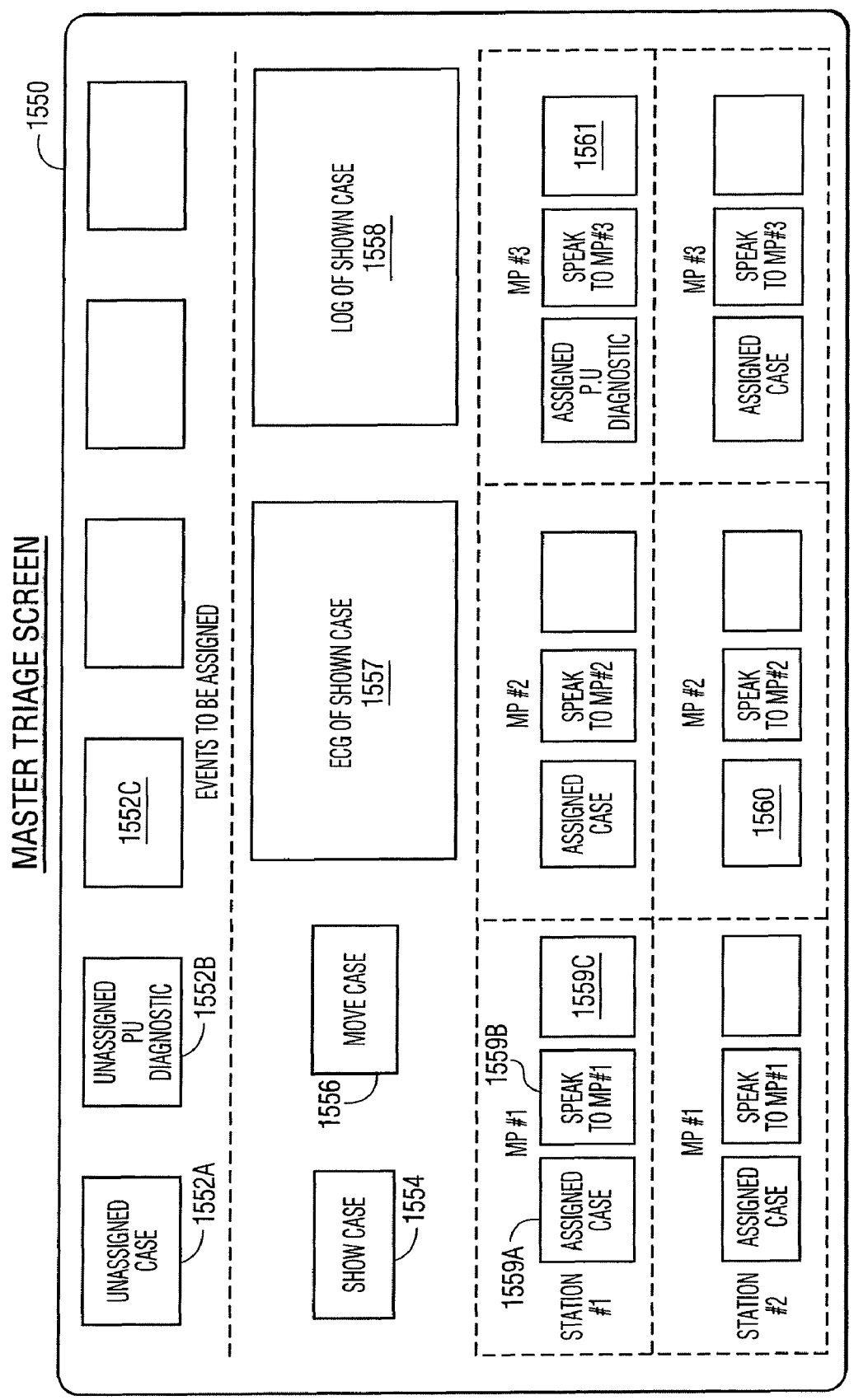
FIG. 42 illustrates a touch-sensitive display screen at the central station for controlling the triage of multiple medical emergencies among multiple medical professionals at multiple central stations.
Figure 43:
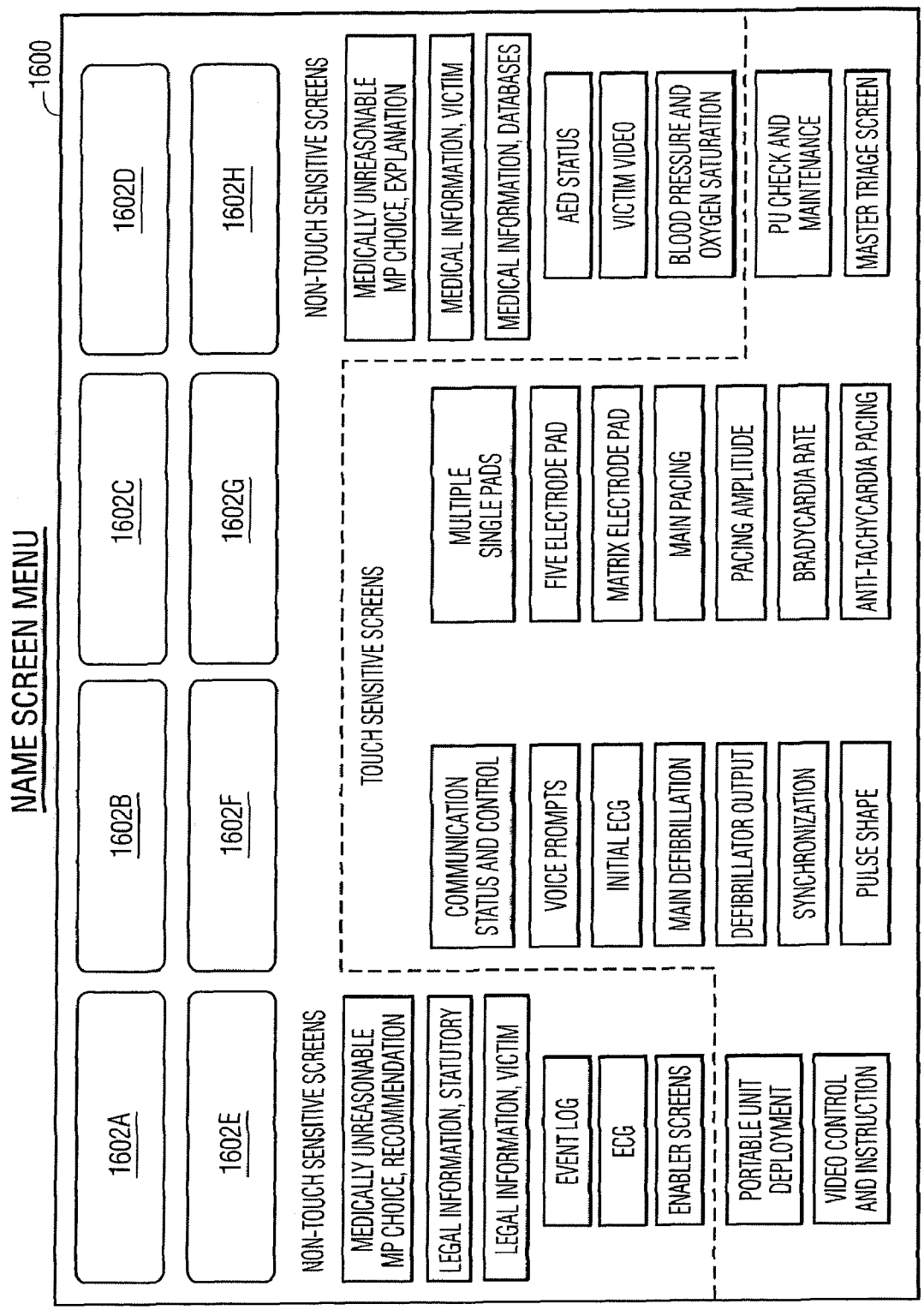
FIG. 43 illustrates a touch-sensitive display screen at the central station for selection of screens to displayed on the central station console.

Since phase seven involves both MP guidance of the EMT and MP guidance of the person replacing the PU, it is possible that, under circumstances when two PUs are present at the arrest scene, the MP would be called upon to conduct separate but simultaneous conversations with each of the EMT and the enabler. However, this need for coincidental action is expected to be easily remediable since:

a) It is always possible to delay PU housekeeping and replacement;

b) PU housekeeping and replacement consists of multiple sub-tasks; therefore, the MP could interweave his supervision of one or more of these sub-tasks with his supervision of the EMT;

c) The EMT is expected to be capable of a certain substantial level of expertise and competence so that MP should be able to break away from conversation with the EMT for brief periods of time; and d) The MP has the ability to assign excess workload immediately by accessing the Master Triage Screen (FIG. 42) from the Screen Menu (FIG. 43). The Master Triage Screen (discussed below) allows the MP to observe the activity of other MPs and hand off work to one or more of them, as needed.

4.5.7.7 The Circumstance in which EMT Does Not Bring a Replacement PU

If the EMT does not bring a second PU, then either: a) at some point prior to leaving the scene of the arrest, he must detach the PU from the victim (option three); or b) the PU remains attached to the victim and both are transported to the hospital (option four).

4.5.7.7.1 Option Three: Sole PU Remains at the Arrest Scene

If EMT is to leave the PU at the arrest scene, the MP requests that either the enabler or the EMT perform the housekeeping functions discussed in Section 4.5.7.3, and then return the PU to the SU (as per Section 4.5.7.4). In this circumstance, the EMT would maximally benefit from the expertise of the MP by delaying PU detachment as long as is practical.

4.5.7.7.2 Option Four: Sole PU is to be Transported with the Victim

If the PU is to be transported with the victim to the hospital, a replacement PU must be supplied to the arrest scene. This circumstance is referred to and discussed below in Sections 4.5.7.8.2 and 4.6.1.

4.5.7.8 Protocol Endpoints During Phase Seven

Phase seven ends when both: a) the victim is no longer attached to the PU; and b) a PU has been attached to the SU.

4.5.7.8.1 Definition of Victim Detachment from PU

The victim is no longer attached to the PU if:

a) the victim is disconnected from PU after arriving in the hospital;

b) the victim regains consciousness during the arrest, and insists on being disconnected from the PU, and leaving under his own power;

c) the EMT brings a non-PU defibrillator to the arrest, disconnects the PU from the victim, and leaves the PU at the arrest scene; or d) the victim, after all appropriate medical and statutory consideration, is no longer considered to be a candidate for further therapeutic efforts, and is disconnected from the PU (see Sections 4.3.1.4 (h), 4.5.3.2 (b), and 4.5.5.2 (i)).

Furthermore, if, after assuming control of the PU, EMT (or physicians) wish no MP involvement, then the victim-related interaction with the system according to the invention may effectively end.

4.5.7.8.2 Circumstances in which a PU Would Not Be Promptly Replaced 4.5.7.8.2.1 PU Non-Replacement at the Arrest Site Ordinarily, a PU is reattached to the SU. This will occur if: a) the EMT brings a new PU and the new PU is attached to the SU (option one; described in Section 4.5.7.2.1); b) the EMT brings a new PU, the new PU is attached to the victim, and the old PU is attached to the SU (option two; described in Section 4.5.7.2.2); or c) the EMT does not bring a new PU, the old PU is left at the arrest scene, and is reattached to the SU (option three; described in Section 4.5.7.7.1).

The circumstances under which reattachment of a PU to the SU would not occur are: a) although the EMT brings a new PU, no one attaches it to the SU; or b) the EMT does not bring a new PU and takes the old PU (attached to the victim) to the hospital (option four; 4.5.7.7.2). In either of these two circumstances, a person responsible for maintaining the portable units (see Section 4.6.1) will have to be dispatched to the scene, to ensure PU replacement.

4.5.7.8.2.2 Non-Replacement of the EMT PU

The PU which EMT brought to the hospital may be left there (see Section 4.1.8). If so, either EMT must later retrieve and restock it, or a person responsible for maintaining the portable units (see Section 4.6.1) will have to be dispatched to the hospital to retrieve it.

4.6 Post-Arrest Issues

Two types of PU and SU maintenance procedures assure that the equipment is ready and optimized for future use. These procedures: a) confirm that the PU is properly stocked and prepared for subsequent events; and b) confirm the proper functioning and integrity (both physical and operational) of the PU and SU; and c) replace or update PU hardware or software as needed.

4.6.1 On-Site Equipment Inspection and Assessment

The first type of maintenance procedure involves periodic on-site visits to each PU or PU/SU combination by a person whose duty it is to inspect, assess, repair, update and/or replace portable and stationary units. This person may be: a) from, or related to the same organization that includes the central station and/or the medical professional; or b) from another organization whose function is to maintain portable and stationary units.

4.6.1.1 Timing of the On-Site Visit

An on-site visit must occur:

a) if neither enabler, EMT or any other person reattached a PU to the SU, at the arrest scene, at the time of previous PU use;

b) if EMT is no longer has a PU, having previously had one (see Section 4.5.7.8.2.2, above);

c) if a PU has been damaged as a result of vandalization, or has been stolen;

d) if the amount of any disposable items in a PU (spare versions of which are kept in the PU tool-kit) has fallen below an acceptable number;

e) if any non-disposable item (e.g. wireless headset) ordinarily kept in a PU tool-kit is found to be missing;

f) if, during a remote equipment assessment and inspection (see Section 4.6.2, below), a PU and/or SU malfunction is detected which can not be remedied from a remote location; or g) if a hardware update or replacement is required.

An on-site visit may occur:

a) after any use of a portable unit;

b) if there is a question of attempted vandalization of, or tampering with a PU, even though it functions properly during a remote inspection and assessment;

c) in order to replace or update software; or d) on a periodic basis, even if a PU and SU show no definitive signs of needing direct attention.

4.6.1.2 Items Assessed During the On-Site Evaluation Process

The duties of this person performing this inspection and assessment include (but are not limited to):

a) performing any post-arrest housekeeping functions which were not done, were not completed, or were not done properly, at the time when enabler (or other designated person) was requested to perform them;

b) restocking any necessary disposable items (such as electrode pad(s)) which may have been used during the last event(s);

c) restocking any non-disposable items (such as scissors 170, headset 168) which may not have been properly replaced at the time of the last use;

d) replacing one or more rechargeable PU and or SU batteries (see below), if necessary;

e) inspecting and assessing areas and parts of the system which are not easily assessed by the video camera including but not limited to:

(i) cables 212A, 212B, 214, 216, 217, 222, 224, 226, 228 and 229 which link already hooked up electrode pads within the PU tool-kit (FIG. 7B);

(ii) universal connectors 218A-E and 220A-E, checking for damage or pin misalignment;

(iii) telephone cable 176 within the PU tool-kit (FIG. 7A);

(iv) oximetry sensor 174 and the cable which links it to the PU (FIG. 7A);
(v) blood pressure apparatus 172 and its link to the PU;
(vi) headset 168;
(vii) connectors 186, 188 on the rear surface of the PU and the front surface of the SU 190, 192;
(viii) PU antenna 162 and SU antenna 164, making sure neither is bent or broken, and that the motorized deployment mechanism, if any, is sound;
(ix) video camera 154 (FIG. 6A) and its extensible boom 112 (FIG. 6*b*); and
(x) SU locking projection 194 (FIG. 9) and the PU-SU lock and its associated sensors;
f) inspecting and assessing the SU connection with the public telephone network;
g) inspecting and assessing the SU power connection;
h) cleaning and/or disinfecting any part of the system which may require such procedure; and
i) replacing a PU, SU, or both, if (i) it cannot be properly made ready for future use, or (ii) a newer, improved version of it has become available (see Section 4.6.3, below). The replacement may involve an entire unit or one or more parts, circuit boards or components of the unit(s).

4.6.2 Remote Equipment Inspection and Assessment

Figure 41:
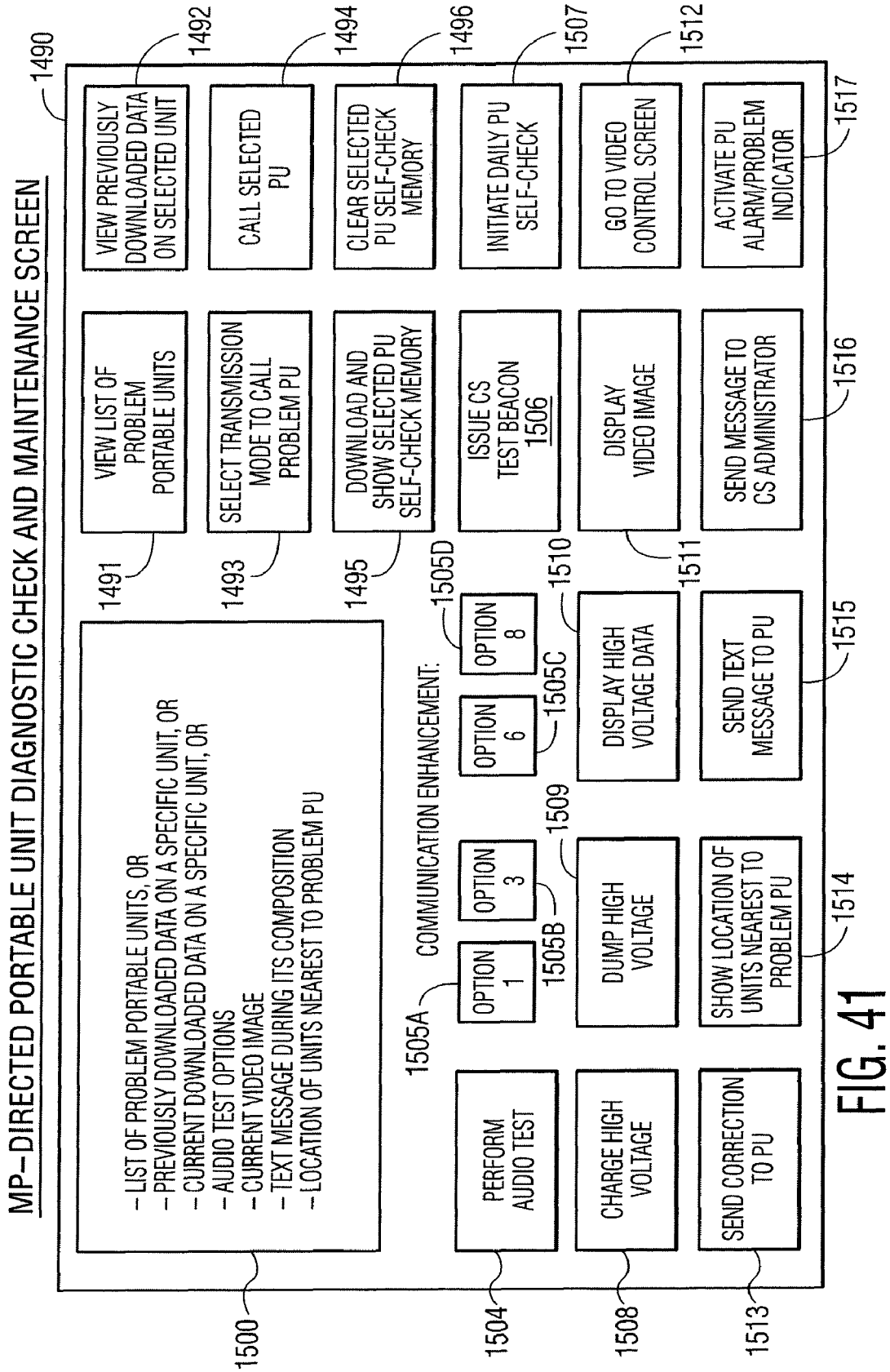
FIG. 41 illustrates a touch-sensitive display screen at the central station for the performance of diagnostic testing upon a portable and/or stationary unit at a remote location.
Figure 55A:
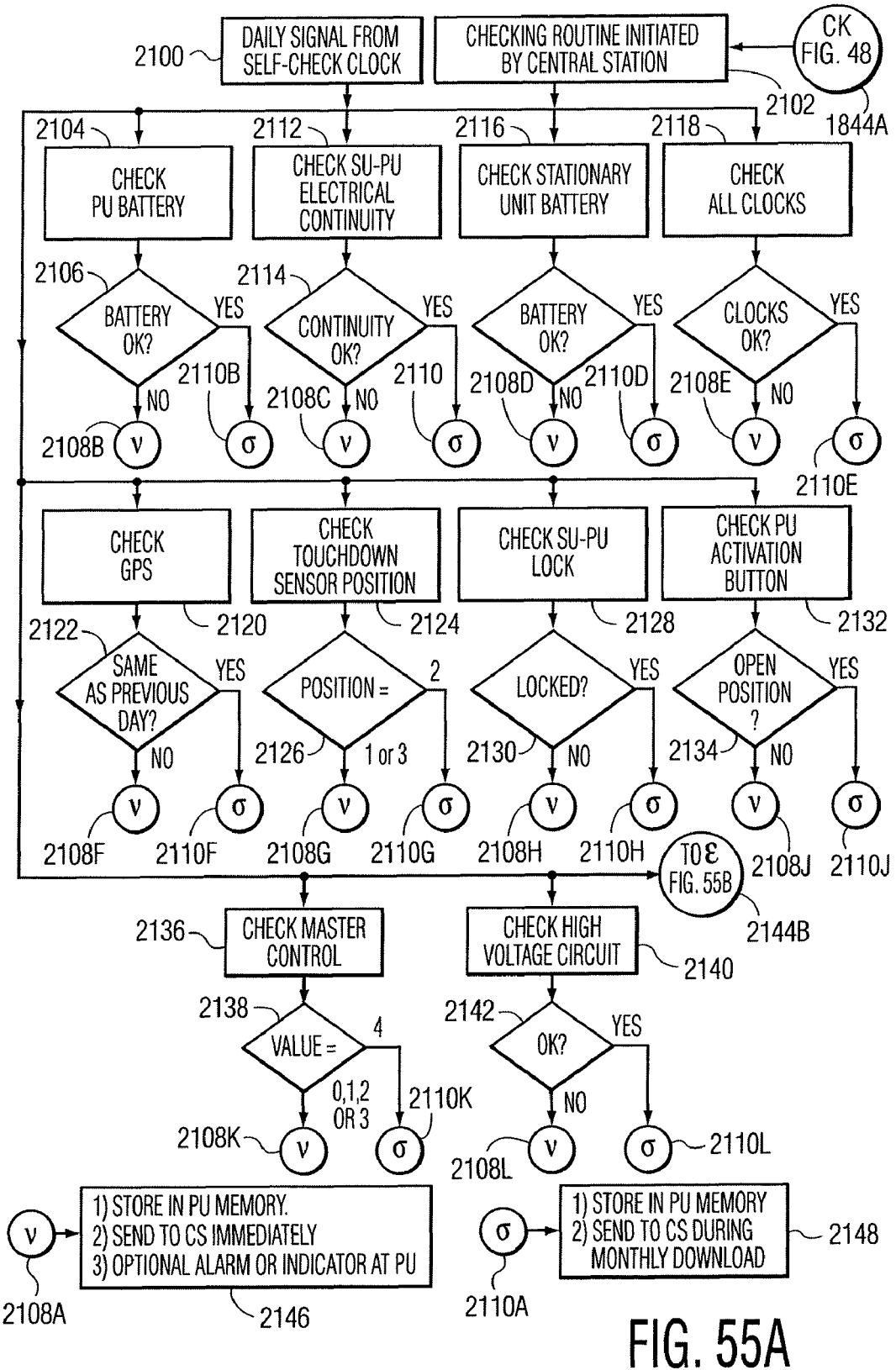

The second type of maintenance procedure involves the confirmation of proper PU and SU functioning by performing periodic remote diagnostic evaluation of both the PU and the SU. The evaluation may occur over any or all of the communications modalities which link: a) the PU/SU; and b) the CS or another diagnostic facility (see Section 4.6.2.1). The person performing the inspection and assessment may be the MP or another technically qualified person. In order to perform this process, a command is sent to the PU which causes the master control unit 130 to enter master control state 4 (see Table 1 and Section 1.3.1.2 and below). FIGS. 55A and 55B (discussed below) show the flow diagrams related to such diagnostic checking. FIG. 41 (discussed below) shows the screen menu which allows the person performing the inspection to do so.

4.6.2.1 Timing of the Remote Evaluation Process

A remote inspection and assessment:
a) occurs after the PU has been used, as soon as a replacement PU is attached to the SU (see Section 4.5.7.4.4);
b) may be periodically initiated from the outside by (i) the central station or (ii) another diagnostic facility with equipment similar to that of the central station but not necessarily staffed by medical professionals;
c) may be periodically initiated by the PU (see below), on a routine basis; and
d) may be initiated by the PU at non-routine times, if it detects a fault (e.g. low voltage).

4.6.2.2 Items Assessed During the Remote Evaluation Process

This inspection and assessment includes but is not limited to:
a) the PU battery;
b) the SU battery;
c) the position of all PU sensor switches;
d) all connectors;
e) high voltage circuitry within the PU;
f) the electrode pads;
g) blood pressure and oxygen saturation sensors;
h) the connection with the public telephone network;
i) the PU transmitters and receivers;
j) the SU transmitters and receivers;
k) the PU external audio and video elements;
l) the wireless headset;
m) the PU global positioning system; and
n) clocks within the PU/SU.

In addition, the PU can be used to inspect itself by using the video camera 154. This can be done by (i) extending the video boom 112, and (ii) having it turn back on itself, thus causing it to become U-shaped, and thereby allow the camera to look back at the PU. This same technique can be used to determine if the PU screens 156 are performing properly. An alternative technique for visualizing the PU and its screens would involve a mirror placed on a wall opposite the PU. The video camera could be pointed at the mirror to allow PU/SU inspection and assessment.

4.6.3 PU and SU Hardware and Software Updates

From time to time, improved versions of the PU hardware or software may become available.

Hardware may be replaced at the time of an on-site visit. Hardware replacement may include: a) individual PU or SU parts, circuit boards, or components; or b) the entire PU or SU. Hardware may be replaced because of: a) a malfunctioning part, circuit board, component or unit; or b) the desire to replace a part, circuit board, component or unit with one which is newer or has improved features.

Software may be replaced or updated (i) during a PU on-site visit, or (ii) remotely, by downloading it from the central station via any of the communication modalities available between the CS and the PU/SU (see below).

TABLE 14

Flow Diagrams of Events During a Cardiac Arrest

| | Event | FIG. |
|---|---|---|
| 1) | Communications handshake, PU component | 12 |
| 2) | Communications handshake, CS component | 13 |
| 3) | Data/Commands handshake between portable unit and central station | 14 |
| 4) | Audio handshake between enabler and medical professional | 15 |
| 4) | Informational handshake between enabler and medical professional | 16A |
| 5) | PU-SU Lock Release | 16B-C |
| 6) | Enabler transports portable unit to victim | 17 |
| 7) | Medical professional directs enabler in portable unit setup | 18 |
| 8) | Medical professional assesses rhythm | 19 |
| 9) | Medical professional administers defibrillation and pacing, as needed | 20-23 |
| 10) | Confirmation and Error Signals | 24 |

TABLE 15

Central Station Screen Summary

| FIG. | Screen Content |
|---|---|
| 25 | Communication Status and Triage |
| 26 | Voice Prompts |
| 27 | Portable Unit Deployment |
| 28 | Video Control and Instruction |
| 29 | Initial ECG |
| 30 | Electrode Matrix Pad Setup |
| 31 | Five Electrode Pad Setup |
| 32 | Multiple Single Electrode Pad Setup |
| 33 | Main Defibrillation |
| 34 | Defibrillation Energy |
| 35 | Synchronization |
| 36 | Pulse Contour |
| 37 | Antitachycardia Pacing Parameters |
| 38 | Main Pacing |
| 39 | Pacing Amplitude |
| 40 | Bradycardia Pacing Rate |
| 41 | MP-Directed Portable Unit Check and Maintenance |
| 42 | Master Triage |
| 43 | Main Screen Menu |
| 44 | Command Confirmation and Event Log |

TABLE 16

Signals During Communication (Layer #1) Handshake

| Sent by Portable Unit: | | Sent by Central Station: | |
|---|---|---|---|
| PU-1 | Button Press | CS-1 | Button Press Received |
| PU-2 | Intact Handshake | CS-2 | Intact Handshake |
| PU-3 | CS-4 Received | CS-3 | PU-4 Received |
| PU-4 | No CS Signal Received | CS-4 | No PU Signal Received |
| PU-5A | Pseudo-Button Press: Fault Detected During PU-initiated Daily Self-Diagnostic Check | CS-5 | Pseudo Button Press Received |
| PU-5B | Pseudo-Button Press: PU Call to CS for Routine Monthly Self-Diagnostic Check | | |
| PU-6 | Pseudo-Button Press: CS-6 Received | CS-6 | Diagnostic Check Initiated by CS |

Note:
The format in this table applies to direct PU-CS handshakes. An analogous format may be used for a PU-SU handshake, for a SU-CS handshake, or for a handshake between any two units in which a communication handshake is attempted.

TABLE 17

Testing During Data/Commands (Layer #2) Handshake

| COMPONENT: | 1A | 1B | 2 | 3A | 3B | 4 | 5 | 4B | 6A | 6B | 7 | 8A | 8B |
|---|---|---|---|---|---|---|---|---|---|---|---|---|---|
| Confirmation #1 | X | | | | | | | | | | | | X |
| Confirmation #2 | X | X | | | | | | | | | | X | X |
| Confirmation #3 | X | X | X | X | | | | | | X | X | X | X |
| Confirmation #4 | X | X | X | X | X | | | | X | X | X | X | X |
| Test Signal | | | | | | | | | X | X | X | X | X |
| MP Receiving Voice Prompt = MP (VP) | | | | X | | | | | X | X | X | X | X |

Key
1A = CS Audio Input
1B = CS Transmitter
2 = CS to PU Routing
3A = PU Receiver
3B = PU Audio Output
4A = Enabler Hearing
4 = Enabler Cooperation
4B = Enabler Speaking
6A = PU Audio Input
6B = PU Transmitter
7 = PU to CS Routing
8A = CS Receiver
8B = CS Audio Output
X = Explicit Testing of Component

TABLE 18

Testing During Audio (Layer #3) Handshake

| COMPONENT: | 1A | 1B | 2 | 3A | 3B | 4A | 4 | 4B | 6A | 6B | 7 | 8A | 8B |
|---|---|---|---|---|---|---|---|---|---|---|---|---|---|
| MP Hearing EN = MP (EN) | | | | | | | X | X | X | X | X | X | X |
| EN Hearing Voice Prompt = EN (VP) | | | | X | X | i | i | i | i | i | i | i | I |
| EN Hearing MP = EN (MP) | X | X | X | X | X | X | i | i | i | i | i | i | i |

Key
1A = CS Audio Input
1B = CS Transmitter
2 = CS to PU Routing
3A = PU Receiver
3B = PU Audio Output
4 = Enabler Hearing
5 = Enabler Speaking
6A = PU Audio Input
6B = PU Transmitter
7 = PU to CS Routing
8A = CS Receiver
8B = CS Audio Output
X = Explicit Testing of Component
i = Implicit Testing of Component
Note:
It is also possible to test the stationary unit transmitters and receivers during the audio handshake. Such testing is not explicitly addressed in this table.

TABLE 19

Testing During Enabler-MP Handshake: Which Tests are Abnormal for Each Component Failure

| TEST: | VSE | SE | LE | VLE | MP (AB) | MP (VP) | MP (EN) | EN (VP) | EN (MP) |
|---|---|---|---|---|---|---|---|---|---|
| 1A fails | – | – | – | – | + | + | + | + | – |
| 1B fails | + | – | – | – | + | + | + | + | – |
| 2 fails | + | + | – | – | + | + | + | + | – |
| 3A fails | + | + | – | – | + | + | + | + | – |
| 3B fails | + | + | + | – | + | – | + | – | – |
| 4A fails | + | + | + | + | + | + | +/– | – | – |
| 4 fails | + | + | + | + | + | + | +/– | – | – |
| 4B fails | + | + | + | + | + | + | – | + | + |
| 6A fails | + | + | + | – | – | – | – | +* | +* |
| 6B fails | + | + | – | – | – | – | – | +* | +* |
| 7 fails | + | + | – | – | – | – | – | +* | +* |
| 8A fails | + | – | – | – | – | – | – | +* | +* |
| 8B fails | – | – | – | – | – | – | – | +* | +* |

Key
+ All components evaluated by this test: properly functioning.
– One or more components evaluated by this test: not properly functioning.
+/– Test result may be positive or negative.
+* Enabler hears MP or VP, but MP is not aware of this.
1A = CS Audio Input
1B = CS Transmitter
2 = CS to PU Routing
3A = PU Receiver
3B = PU Audio Output
4 = Enabler Hearing
5 = Enabler Speaking
6A = PU Audio Input
6B = PU Transmitter
7 = PU to CS Routing
8A = CS Receiver
8B = CS Audio Output
X = Explicit Testing of Component
i = Implicit Testing of Component
Note:
It is also possible to test the stationary unit transmitters and recievers during the audio handshake. Such testing is not explicitly addressed in this table.

TABLE 20

Options for Communications Enhancement During the Four Handshakes of the Enabler-MP Link

| Options 1-3: | Modifications in the CS-to-PU Arm |
|---|---|
| Options 1a: | Changes in CS processing input |
| Options 1b: | Changes in CS communications output |
| Options 2: | Changes in CS-to-PU routing at Central Station or at Stationary Unit |
| Options 3a: | Changes in PU communications input |
| Options 3b: | Changes in PU processing output |
| Options 4-5: | Modifications in the PU-to-Enabler and in the Enabler-to-PU Arms |
| Option 4a: | Ask Enabler to use headset |
| Options 4b: | In the event of a non-English speaking Enabler, Medical Professional options include:<br>i) Hand off the conversation to a foreign language speaking medical professional who restarts the protocol, or<br>ii) Use foreign language voice prompts |
| Option 5a: | Ask Enabler to speak louder and/or to more directly face the PU while speaking |
| Option 5b: | Use speech recognition technology |
| Options 6-8: | Modifications in the PU-to-CS Arm |
| Options 6a: | Changes in PU processing input |
| Options 6b: | Changes in PU communications output |
| Options 7: | Changes in PU-to-CS routing at Portable Unit or at Stationary Unit |
| Options 8a: | Changes in CS communications input |
| Options 8b: | Changes in CS processing output |
| Option 9: | Other Central Station Alternative |
| Option 9: | In the event of a suspected mischievous act, Medical Professional calls police or security local to the Portable Unit. (Further assessment may be based on observations made with the video camera within the Portable Unit.) |

Note:
It is also possible to modify the CS-to-PU arm and the PU-to-CS arm by making changes in the stationary unit transmitters and receivers. These possibilities are not addressed in this table.

5. Flow Diagrams 5.1 Communications Handshake 5.1.1 Overview

In order to remotely manage the highly critical situation of a cardiac arrest in a safe manner, a situation must be created that is as close as possible to the remote MP being present at the emergency scene. A highly robust communication system, which reacts quickly and efficiently to failures, potential failures or degradation of "fidelity" is mandatory. A series of backup systems must be available. In order for these backup systems to work with maximal efficiency, the need for their function must be instantly recognized.

Remote resuscitation is made practical by AED backup, as discussed previously, and by a system which reacts instantly to a communications interruption by bringing this backup system on line. To accomplish near instantaneous recognition of communications interruption, a constantly repeating handshaking process between the CS and the PU occurs during system operation. At the first sign of communications interruption, the AED is brought on-line, and it continues to function as the "director" of the resuscitation until satisfactory communication between the CS and the PU is re-established.

The flow diagrams describe a multilayer handshaking process. The communications handshake perpetually reconfirms the existence of an intact communications link between the CS and the PU. The data/commands handshake (FIG. 14) is performed once after the completion of the initial communications handshake; It is repeated if the communications handshake is interrupted and is effectively repeated with the transmission and execution of each command by the MP, as evidenced by the cascade of confirmation signals which follow each command. The audio handshake is performed formally once per event, but is, in principle continuously updated whenever conversation between the MP and the enabler (or EMT) takes place.

Figure 12A:
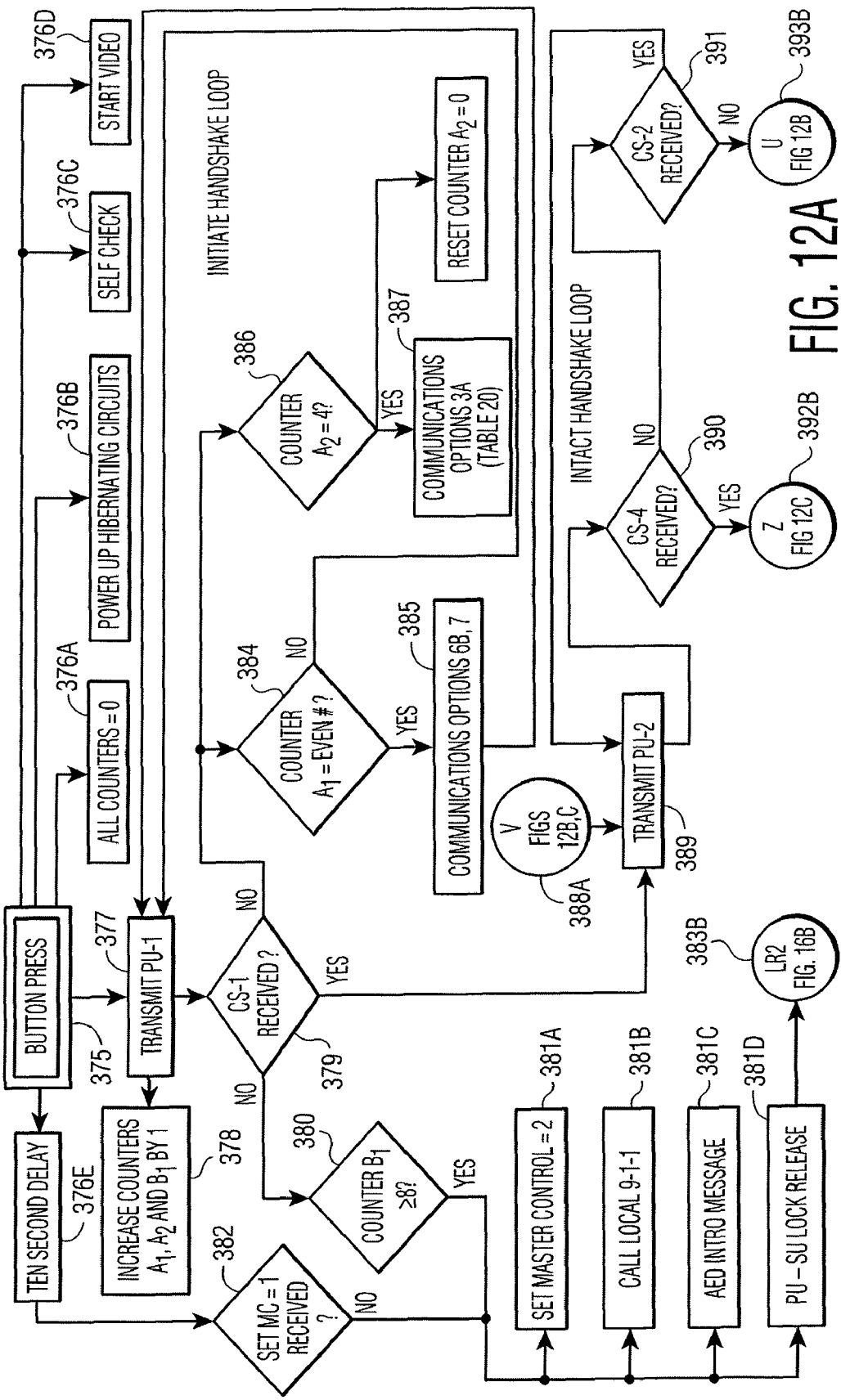
Figure 12B:
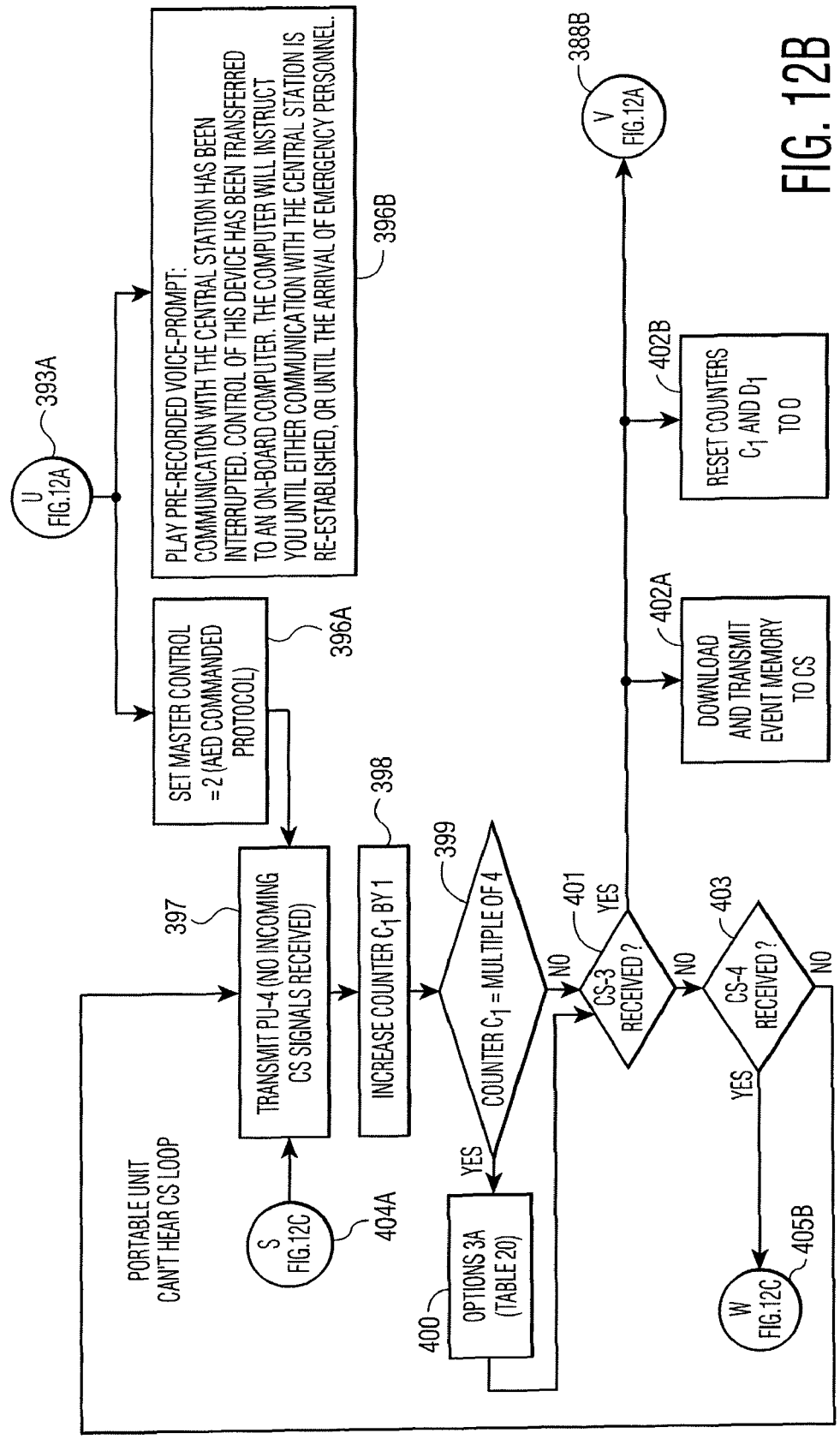
Figure 12D:
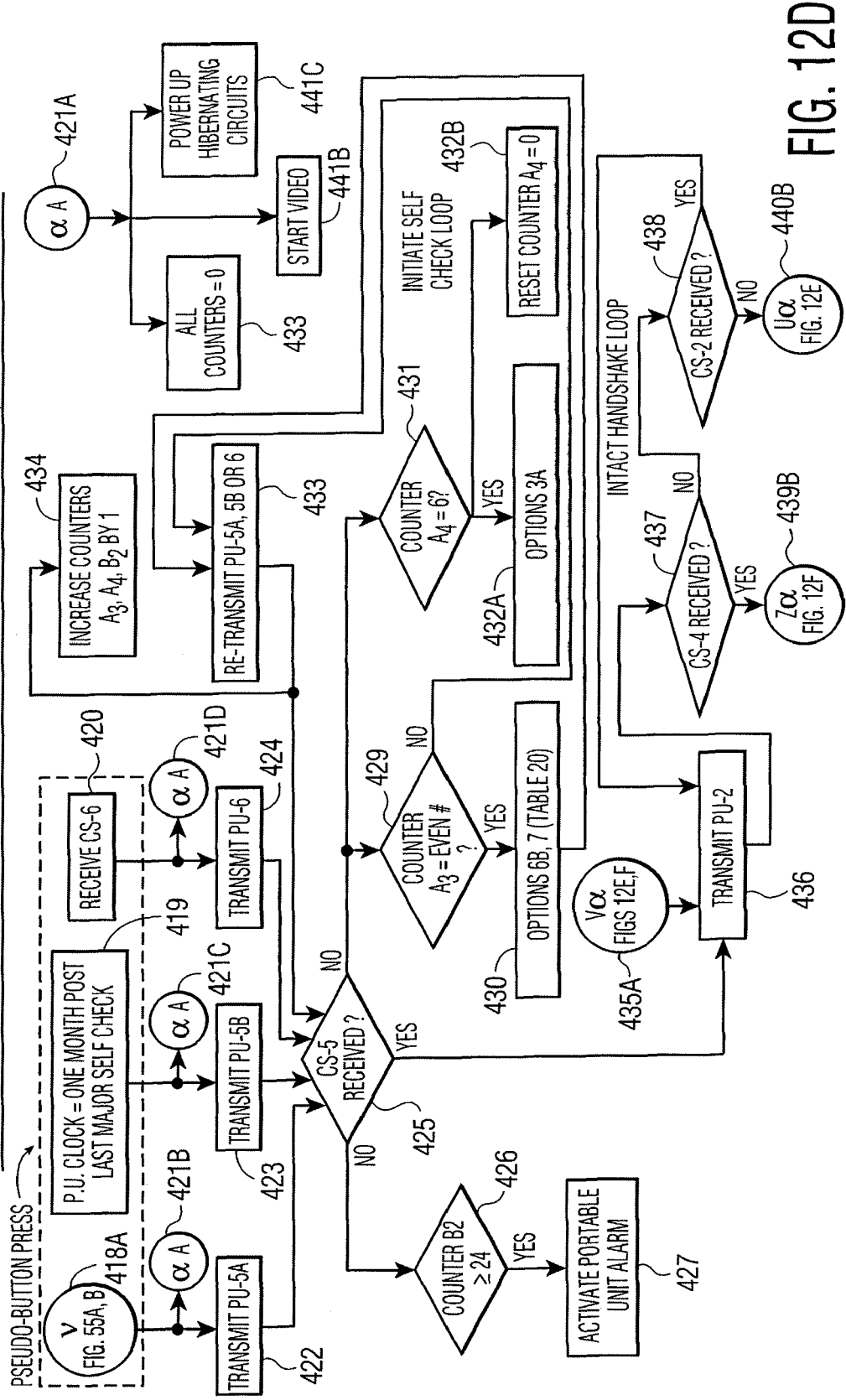
Figure 12E:
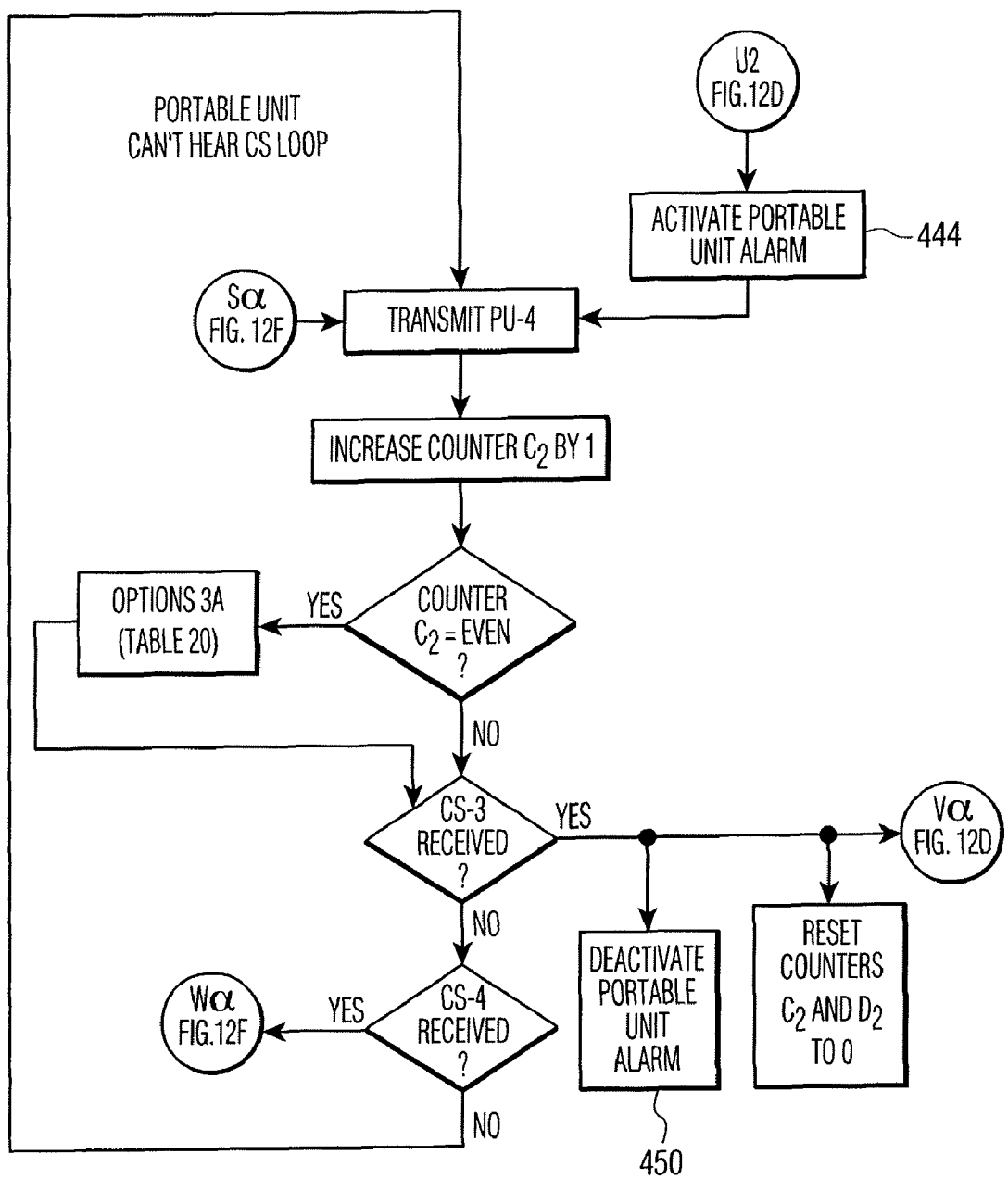
Figure 12F:
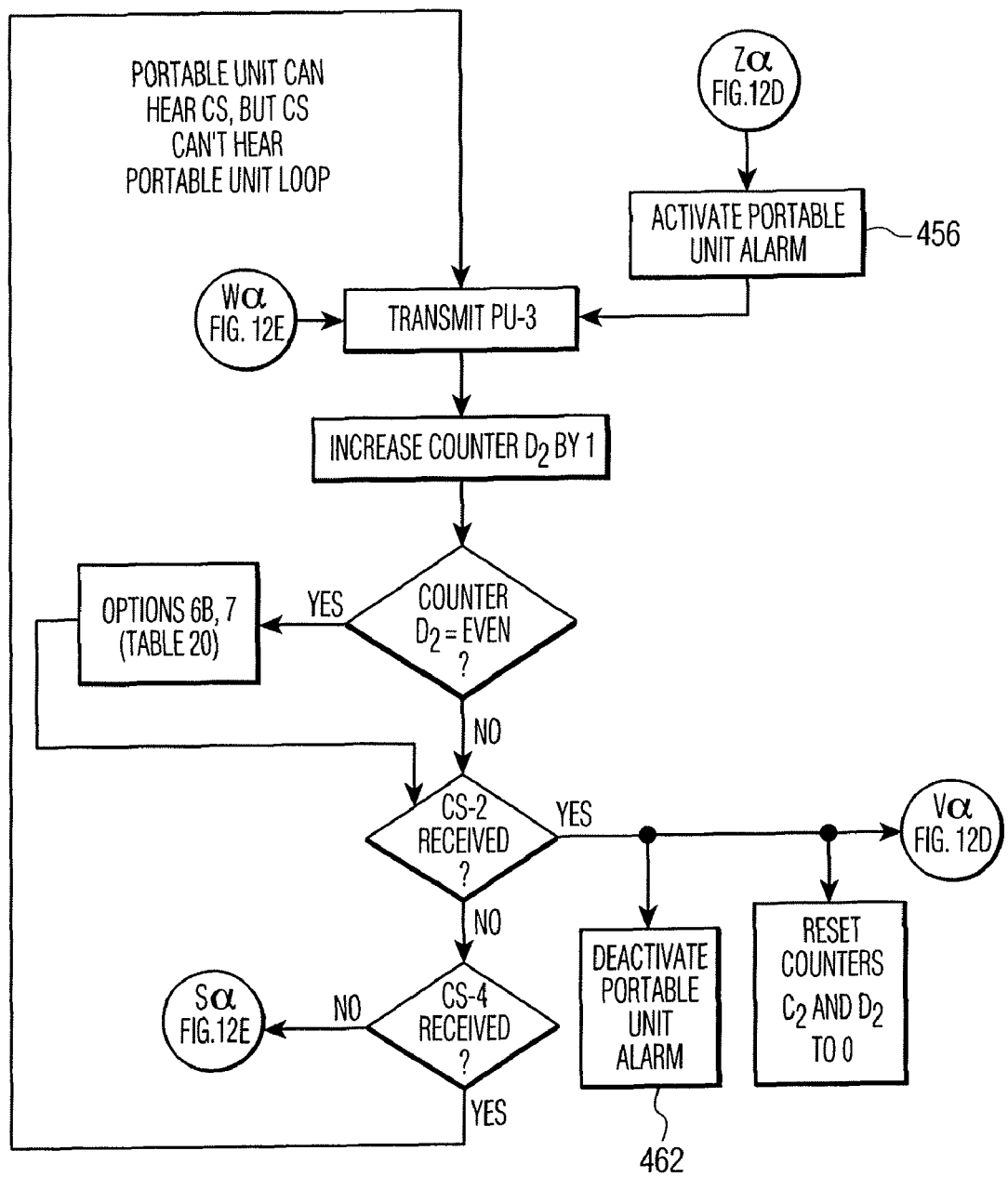
Figure 13A:
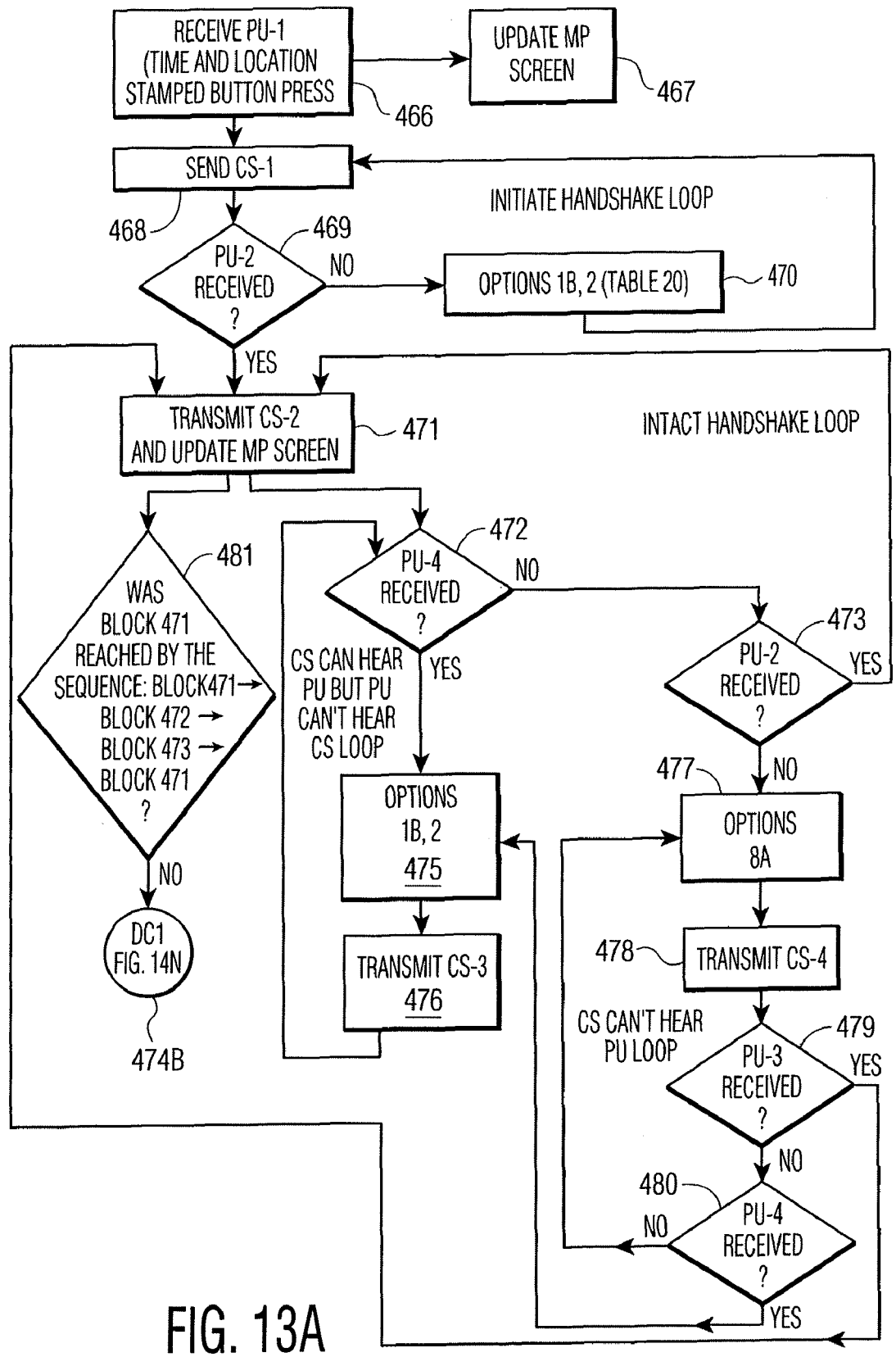
FIG. 13 are a flow chart showing the communication handshake protocol at the CS.
Figure 13B:
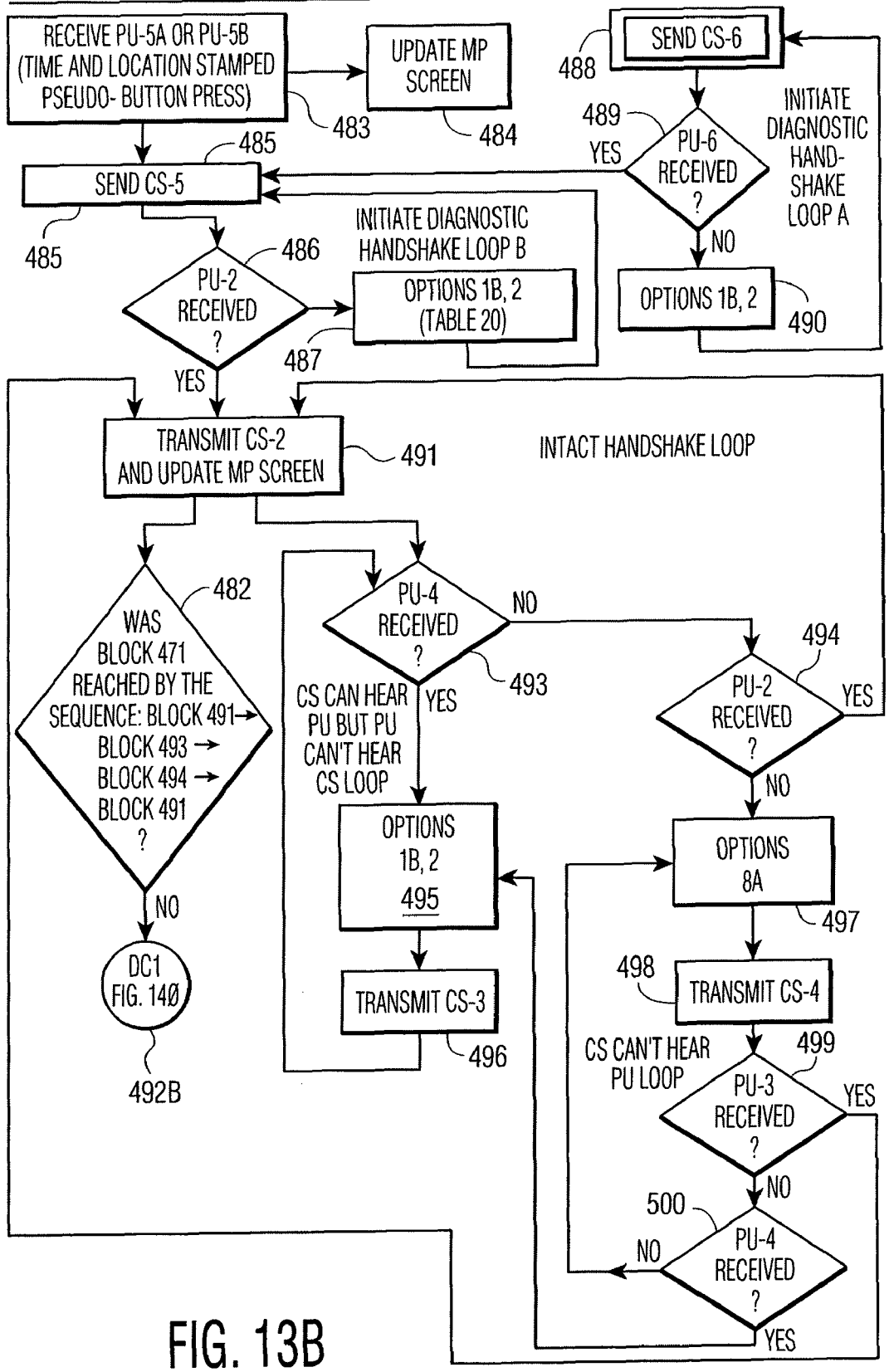

FIGS. 12A, 12B and 12C show the flow diagram for the PU component of the communications handshake during system operation; FIG. 13A shows the CS component. FIGS. 12D, 12E and 12F show the flow diagram for the PU component of the communications handshake during diagnostic evaluation; FIG. 13B shows the CS component. Table 16 shows the definitions of each of the eight communications handshaking signals, and additional signals during diagnostic testing. Table 20 gives additional information about "options" referred to in these figures. Tables 17, 18 and 19 also contain relevant information.

In general, the handshake sections hereinbelow do not address the SU component. Doing so would add much complexity to the discussion, without contributing to the substance of it. The SU is discussed specifically above, and is addressed again in Section 7.

5.1.2 Communications Handshake, PU Component

Following "button press", i.e. depression of the PU activation button 106 by a potential enabler, block 375, (FIG. 12A) leads to the zeroing 376A of all counters, the powering up 376B of hibernating circuits, the initiation 376C of a self checking routine (which may include all or part of the diagnostic check depicted in FIG. 55), the activation 376D of the PU video camera and the initiation, 376E of a ten second delay during which interval the completion of a proper communications handshake and a data/commands handshake must occur or AED function is activated.

Block 375 also leads to block 377, the transmission by the PU of an initiating handshaking signal designated PU-1 and indicating button press (see Table 16). When the CS receives PU-1 it sends CS-1 (Button Press Received). When CS-1 is received by the PU, block 379, the PU transmits PU-2 (Intact Handshake, PU Side), block 389.

The CS will, in response to PU-2, transmit CS-2 (Intact Handshake, CS Side). The PU will, in response to CS-2, transmit PU-2. This continuous exchange of PU-2 and CS-2 signals constitutes an intact communications handshake between the PU and the CS.

If, at block 379, CS-1 is not received, block 384 checks if counter $A_1$ is even. Since at block 377 all counters were increased by 1, it is odd the first time through, resulting in no change in communication parameters, and therefore resulting in a repeat transmission of PU-1 using the same communication parameters as for the first PU-1 transmission.

If CS-1 is not received following a second PU-1 transmission, (which results in an increase in $A_1$ to the value 2) block 379 leads to 384 which leads to 385, communications options 6B, 7 (see Table 20). The system makes an alteration in PU communications output (option 6B) or routing (option 7), returning to block 377 and another transmission of PU-1.

As long as the handshake fails to occur, one of options 6B or 7 will be changed with every other transmission of PU-1. Because it is possible that the CS is responding and the PU is not receiving the response, block 386 will, with every fourth attempt at communication with the CS, exercise one of options 3A, block 387A, changing the PU communications input characteristics.

If the eighth transmission of PU-1 is not followed by a response from the CS, block 380, the backup plan is invoked which includes:

a) block 381A, the setting of MC=2, enabling AED function;

b) block 381B, the calling of local 9-1-1, pre-programmed into the device;

c) block 381C, the issuance of an AED introductory message; and d) the release of the PU-SU lock, with block 381D leading to block 383B.

The same four events occur if, block 382, the data/commands handshake is not completed within 10 seconds.

There are two ways in which an already established loop of continuously repeating transmitted PU-2 and received CS-2 signals may be interrupted. The first is if the CS fails to detect a PU signal and transmits CS-4 (No PU Signal Received by the CS). The second is if the PU does not receive any CS signal. Therefore the "Intact Handshake Loop" consists of a continuously repeating sequence of:

a) block 389 (PU-2 transmission);

b) block 390 with a negative response (i.e. no CS-4 signal received by the PU); and c) block 391 with a positive response (i.e. CS-2 received).

If CS-2 is not received, the protocol leads to block 393B, block U 393A (FIG. 12B). This results in a) the issuance of voice prompt 396B shown in the figure, which informs the enabler of upcoming AED control, and b) setting MC=2, block 396A. The latter leads to a loop of continuously repeating events which will occur as long as the PU does not receive as CS signal of any kind. The loop consists of:

a) the transmission by the PU of PU-4 (No CS Signal Received), block 397;

b) an increase in counter $C_1$ by 1, block 398;

c) a check of the value of this counter, block 399. If the value is a multiple of four, then, block 400, one of options 3A (modify PU communications input) occurs;

d) Whether or not it is a multiple of four, block 401, checks if CS-3 has been received by the PU (which would indicate the last PU transmission, PU-4, was received by the CS). (i) If yes, the fact that the CS has responded to a PU handshake signal (PU-4) and that the PU has received a CS signal (CS-3) indicates the restoration of two-way communication. Accordingly, blocks 402B and 402A, counters are reset and the PU event memory is transmitted to the CS, so that the MP may learn what has transpired during the communications interruption. Then block 388B leads to block V 388A (FIG. 12), returning to the "Intact Handshake Loop". (ii) If CS-3 was not received, block 403 checks if CS-4 was received. If no, block 397 is a retransmission of PU-4 and the beginning of another passage around the "Portable Unit Can't Hear CS Loop." Every fourth time around this loop, counter $C_1$ will be a multiple of four, resulting in a change in options 3A. If, at block 403, CS-4 was received by the PU, indicating that the CS has not received a PU handshake signal, block 405B leads to FIG. 12C, indicating a different set of incomplete handshake conditions: i.e. that the PU is now receiving handshake signals and the CS is not. This condition—CS-4 received by the PU—can also occur during the "Intact Handshake Loop" of FIG. 12A, if block 390 indicates that CS-4 has been received by the PU, leading to block 392B, to block Z 392A, FIG. 12C.

The events that follow parallel but are not identical to those depicted in FIG. 12B. The loop which indicates that the CS is not detecting PU handshake signals, but that the PU is detecting CS signals (implicit in the PU receipt of CS-4) consists of blocks 409 (at which the transmission of PU-3 indicates that the PU has received CS-4), 410, 411, 413 and 415. The AED message 408B and the setting of MC=2, block 408A, occur if the loop is entered from block Z 392A but not from block W 405A, because in the former case, it marks the end of an intact handshake; In the latter case it marks the perpetuation of a condition of inadequate communication. Counter $D_1$ changes every other time through the loop. When its value is even, block 412 results in one of communication options 6B or 7 (discussed above). The loop is exited by one of two events:

a) If CS-2 is received, block 413 leads to blocks 414A (download and transmit memory to CS), 414B (reset counters) and 388C (return to "Intact Handshake Loop").

b) If neither CS-2 nor CS-4 is received, block 415 leads to block 404B, to block S 404A and a return to the aforementioned "PU Can't Hear CS Loop" of FIG. 12B.

At all times, one of the aforementioned three loops will be in progress. It is possible that conditions in which certain signals are at the margin of acceptability, and hence are at times classified as present, and at other times as absent, will result in "hunting", i.e. continuously shifting from one loop to another. An anti-hunting algorithm could easily stabilize the condition; such an algorithm would decrease the frequency of transitions from one loop to another, e.g. by requiring multiple consecutive similar results before making a transition from one loop to another.

Implicit in the handshaking process is that the timing of PU and of CS handshaking signals correspond. This is easily accomplished by means known in the art.

The values for which the counter change receiving or transmission characteristics are, to a certain extent arbitrary, as is the delay until AED function is begun.

5.1.3 Communications Handshake, CS Component

FIG. 13A shows the CS events during the communications handshake. Upon receipt of PU-1, block 466, the MP is notified block 467 and the CS sends handshake signal CS-1 (PU-1 Received), block 468. The CS then waits for PU-2, which would indicate that the PU has received CS-1. This indicates an intact communications handshake in that the CS has detected the PU signals (PU-1 and PU-2) and can infer that the PU has detected the CS signal (since PU-2 implies that CS-1 was received by the PU). This initiates the "Intact Handshake Loop". If, however, PU-2 was not received, block 469 leads to block 470 and options 1B (change in CS communications output) and/or 2 (change in CS routing).

The "Intact Handshake Loop" at the CS consists of blocks 471, followed by
  a) block 471 (CS-2 transmission);
  b) block 472 with a negative response (i.e. no PU-4 signal received by the CS); and
  c) block 473 with a positive response (i.e. PU-2 received).

If PU-2 is not received, the protocol leads to block 477 and a loop which indicates that the CS cannot hear the PU, consisting of blocks 477, 478, 479 and 480. Each time 477 is reached one or more of options 8A (CS communications input) is modified. Each time 478 is reached, a CS-4 signal is sent (indicating that PU signal has not been received). There are two possible exits from the loop:
  a) If PU-3 is received, indicating that the PU has received the CS-4 signal, and, since the CS is receiving the PU-3 signal, therefore indicating that each is capable of detecting the other. This results in a return to the "Intact Handshake Loop".
  b) If PU-4 is received, it indicates a change in status to another unsatisfactory handshaking state. At such a juncture, the CS is now in receipt of PU signals, but the signal, PU-4, indicates that the PU is not in receipt of CS signals. This leads to a loop involving blocks 472, 475 and 476. Each transit through the loop results in a modification of either CS communications output (option 1B) or routing (option 2). Each transit results in the retransmission of CS-3, attempting to let the PU know that the PU-4 signal last sent was received. Exit from the loop occurs when a PU-4 signal is not received, and can lead to either a return to the intact handshake loop (if PU-2 is next received, block 473), or to the "CS Can't Hear PU Loop" (if PU-2 is not next received, block 473).

After the completion of an adequate communications handshake, whether for the first time during an emergency event, or following the sequence of a) intact communications handshake, b) interruption in communications handshake and c) restoration of communications handshake, the data/commands handshake must be established before the audio and informational handshakes. Accordingly, if block 471 was reached after an initial communications handshake or a restored one, block 481 leads to block 474B and initiation (or re-initiation) of the data/commands handshake (see FIG. 14N).

5.1.4 Handshakes During Diagnostic Checking

If, during a periodic self checking routine, the PU discovers a fault (see FIG. 55) it attempts to contact the CS by initiating a "Pseudo-Button Press." This event is initiated when fault detection leads to block ☐ 418A, which leads to the sending of handshake signal PU-5A, (Table 16) analogous in action to PU-1. The routine which follows the Pseudo-Button Press is very closely analogous to an actual button press and, as such, FIG. 12D is analogous to 12A, FIG. 12E is analogous to 12B, FIG. 12F is analogous to 12C and FIG. 13B is analogous to 13A.

The other events which can initiate a Pseudo-Button Press include:
  a) the monthly routine for transmitting the results of daily PU-SU self checks to the CS, wherein block 419 leads to block 423 and the transmission of handshake signal PU-5B; and
  b) the receipt by the PU of signal CS-6, block 420, indicating a diagnostic check initiated by the CS, and resulting in the transmission of PU-6 (indicating that the PU has received CS-6).

The events which follow the initial signal transmission by the PU after the Pseudo-Button Press parallel those after a real Button Press:
  a) Receipt of CS-5 (block 425) is analogous to receipt of CS-1 by the PU;
  b) The "Intact Handshake Loop" (blocks 436, 437 and 438 continuously repeating) during the diagnostic check consists of the identical sequence of events as those during ordinary system operation;
  c) The exit from the "Intact Handshake Loop" in the event that CS-2 is not received leads to block U 440B and the "Portable Unit Can't Hear CS Loop" of FIG. 12E. The only difference between FIG. 12E and 12B is that the enabler voice prompt and the MC=2 setting are herein replaced by the activation of a PU alarm, block 444, upon entering the loop, and its deactivation, block 450, upon leaving the loop.
  d) The exit from the "Intact Handshake Loop" in the event that CS-4 is received leads to block Z 439B and the "Portable Unit Can Hear CS, But CS Can't Hear Portable Unit Loop" of FIG. 12F. The only difference between FIG. 12F and 12C is that the enabler voice prompt and the MC=2 setting are replaced by the activation of the PU alarm, block 456, upon entering the loop, and its deactivation, block 462, upon leaving the loop.

There is no need for backup AED function, since there is no victim, and hence the elements corresponding to AED backup do not have a parallel in FIG. 12D, except for the activation of the PU alarm, block 427, after 24 attempts (block 426) to establish a handshake.

The flow diagram for the CS component of the diagnostic handshake differs from the regular handshake of FIG. 13A only in that the former has two "Initiate Handshake Loops", since both the CS and the PU can initiate this communication.

5.2 The Data/Commands Handshake

Figure 14A:
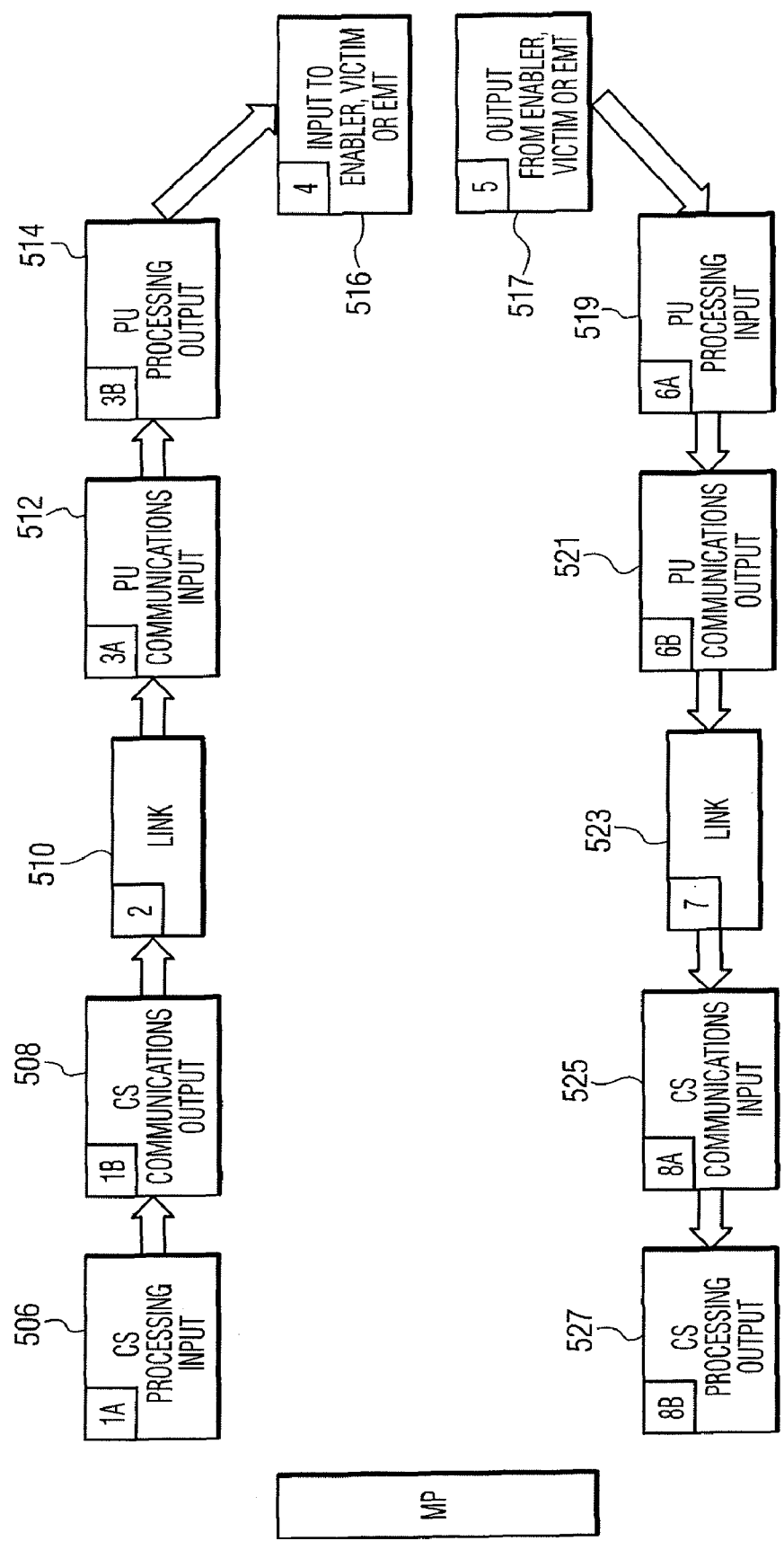
FIG. 14 are a flow chart showing the data/commands handshake protocol at the central station of the system according to the present invention.

FIG. 14A introduces a representation of the invention which facilitates some of the analysis and discussion of its operations. It shows the flow of information such as a command (in a general sense) from the MP through the CS, through a CS-to-PU communications link, through the PU to either the enabler (giving him instructions), the victim (e.g. delivering a shock) or the EMT (e.g. asking him to identify himself). This flow is followed by a return flow of information, toward the MP. In the case of the enabler, it may be his description of the victim. In the case of the victim, it may be his ECG signals. In the case of the MP, it may be his identifying information. The information then enters the PU, passes through a PU-to-CS communications link, then through the CS and on to the MP.

Each of the twelve components of this sequence has been given an alphanumeric designation, listed in the upper left corner of each box, and corresponding to the options listed in Table 20, and also referred to in Tables 17-19.

Thus the full summary of information flow from the MP consists of the following sequence:

1A) the CS Processing Input 506,
1B) the CS Communications Output 508,
2) the CS-to-PU Communications Link 510,
3A) the PU Communications Input 512,
3B) the PU Processing Output 514,
4) the Input to the Enabler, Victim or EMT 516,
5) the Output from the Enabler, Victim or EMT 517,
6A) the PU Processing Input 519,
6B) the PU Communications Output 521,
7) the PU-to-CS Communications Link 523,
8A) the CS Communications Input 525,
8B) the CS Processing Output 527.

FIG. 14B shows the communications handshake, consisting of a continuous wave of signaling involving the core components of the system: elements 508, 510, 512, path 532 (which lies within the PU), 521, 523, 525 and 531 (lying within the CS).

Figure 14C:
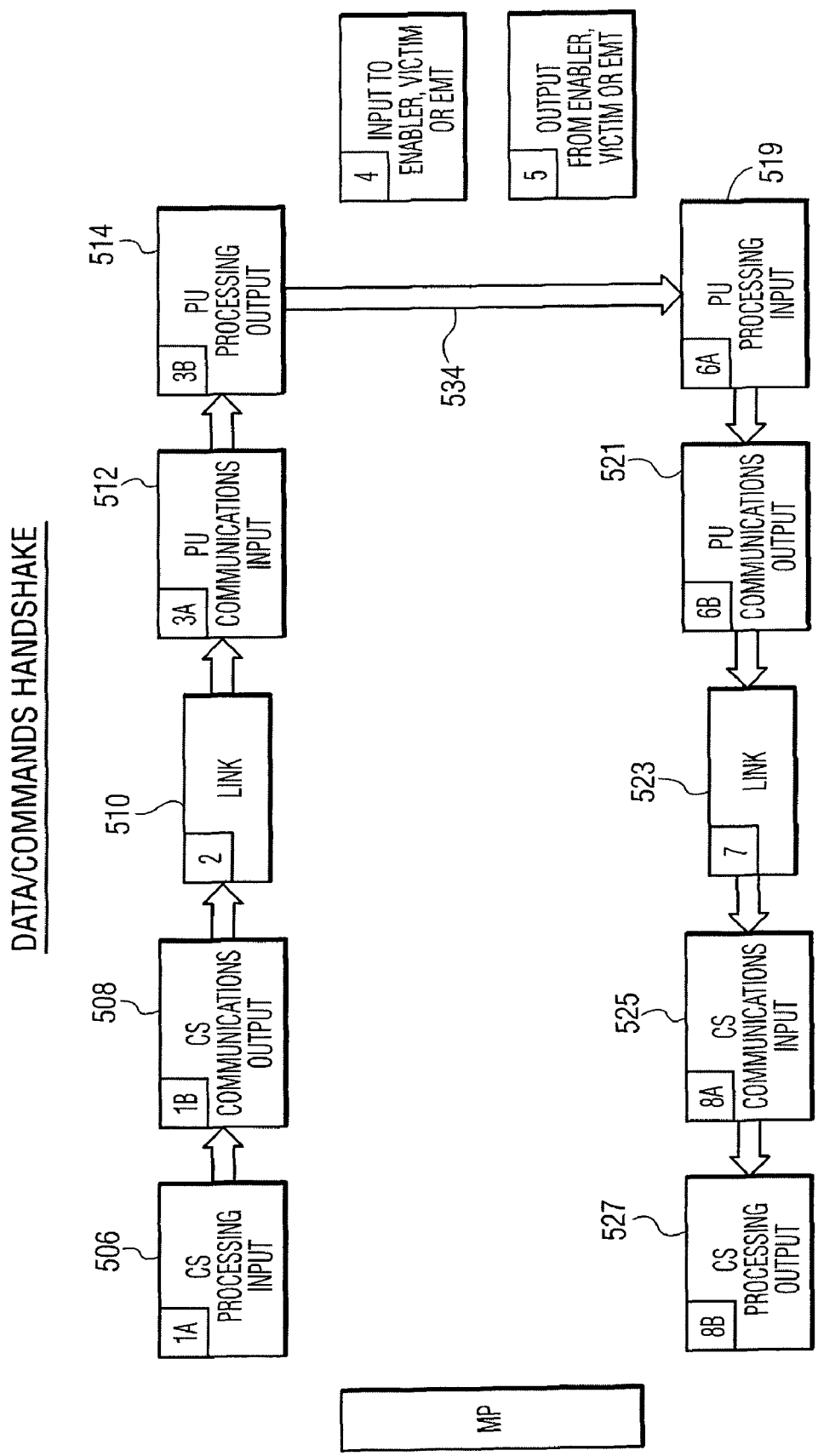

FIG. 14C shows the crux of the data/commands handshake. In order to show that the system is functional beyond the core components evaluated by the communications handshake, a command is sent from the MP to the CS Processing Unit 506, and on to 508, 510, 512, 514, path 534, 519, 521, 523, 525 and 527. Path 523 may lie within the PU or extend outside of it. An example of a command which would serve this purpose and remain inside the system would be a command for the PU Processing Unit 519 to issue a internal test signal for transmission to the CS as a data signal. This is shown schematically in FIG. 14I, where test signal 535 is produced and passed along to the CS Processing Output. An example of a command which would extend outside of the PU would be the production of a sound by the PU speaker, which is then inputted through the PU microphone. The result of such testing is a demonstration that the components outside of the core are intact, and that the system is ready for operation.

Confirmation signals are used to locate a fault if the data/commands handshake fails (see below). In the event that the command depicted in FIG. 14C does not result in a return signal to the MP, the system can assessed in smaller steps, such that a fault is easier to pinpoint.

Figure 14D:
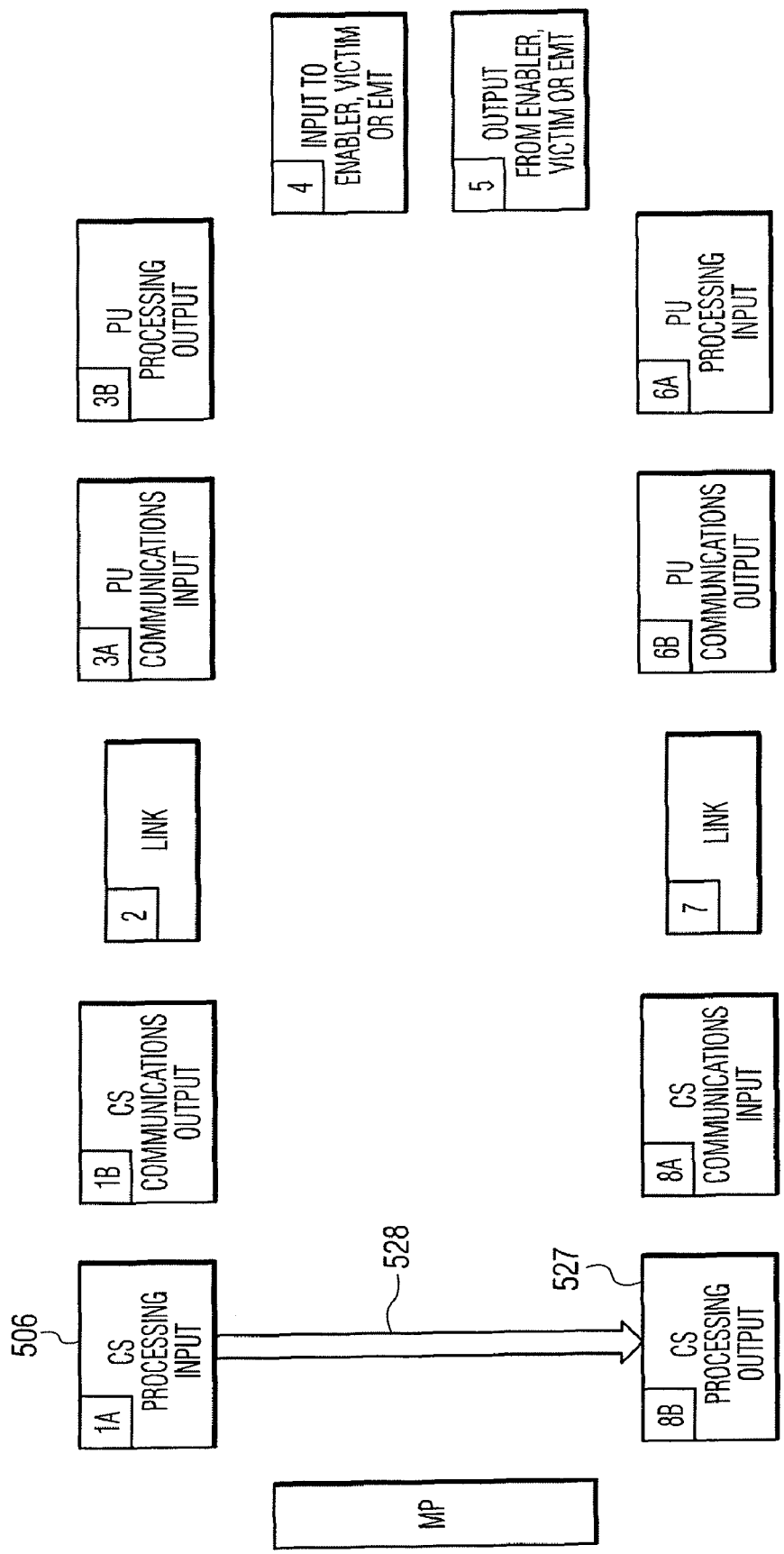

FIG. 14D shows confirmation signal #1, going from 506, along path 528 to 527 and back to the MP. If it is intact, it shows that both unit 1A and 8B are functional. If it is not, it shows that one of the two units is not intact. The use of test signal 535, or a test signal emanating from 8A could allow the distinction between the two possible malfunctions.

Figure 14E:
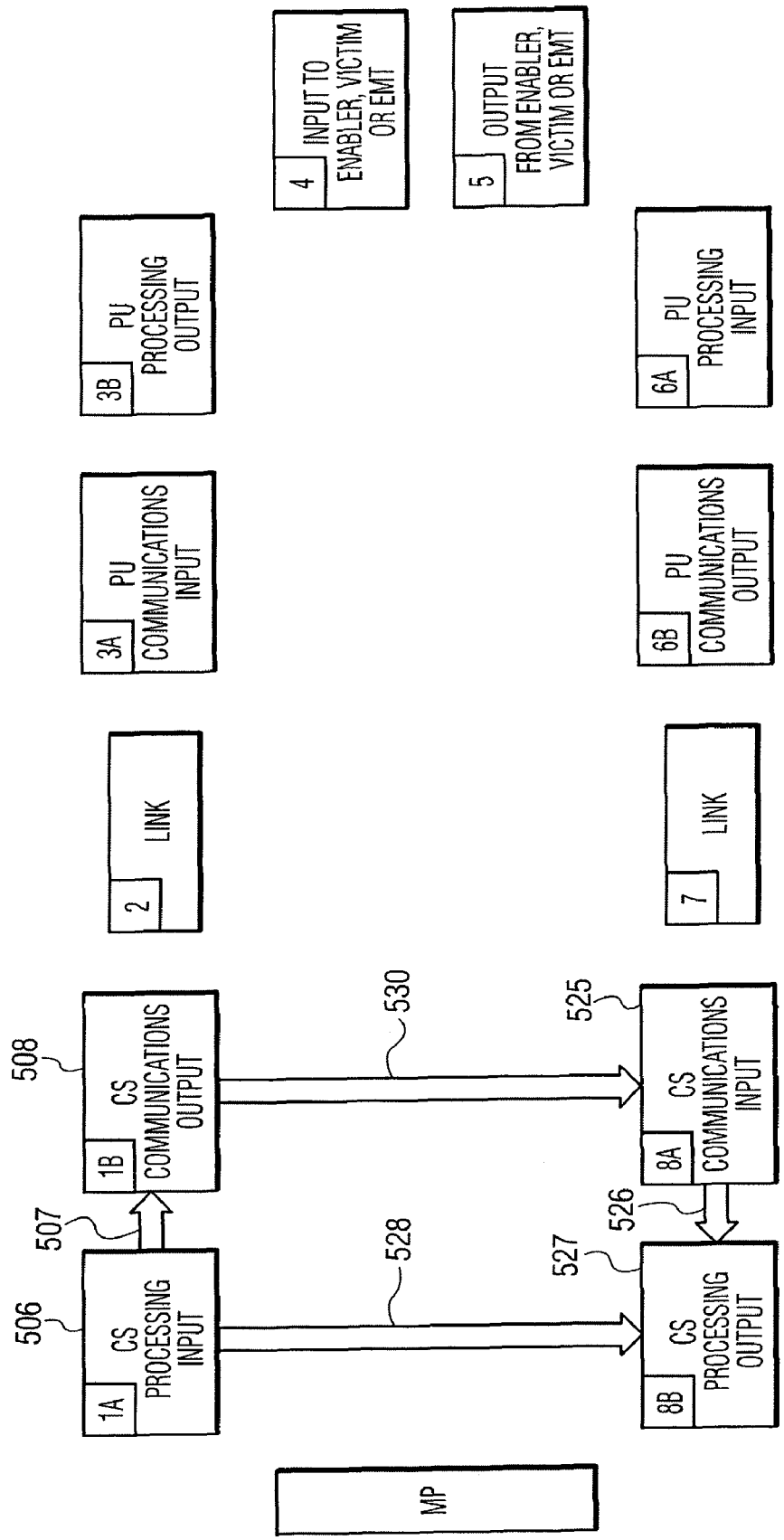

FIG. 14E shows (in addition to confirmation signal #1) confirmation signal #2, going from 506, to 508, along path 530, to 525 and back to 527. If confirmation signal #1 was intact and #2 was not, it would isolate a fault to either unit 1B or 8A. An test signal emanating "upstream" from 525 could distinguish the two possibilities.

Figure 14F:
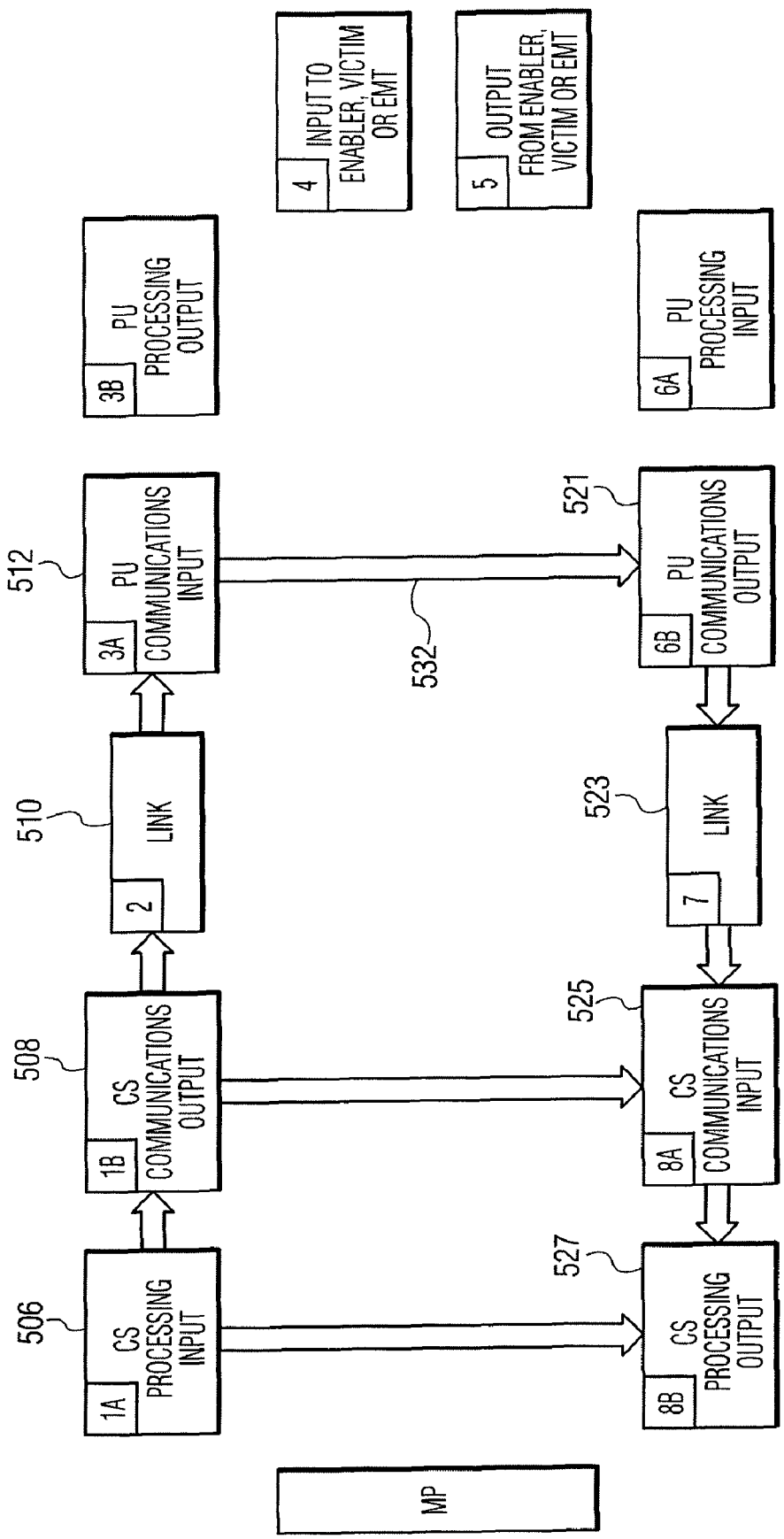

FIG. 14F shows (in addition to confirmation signals #1 and #2) confirmation signal #3. It traverses 506, 508, 510, 512, path 532, 521, 523, 525 and 527. A failure to receive confirmation signal #3 would occur if either 3A or 6B failed. The two possibilities would be distinguished by a test signal upstream from 521.

Figure 14G:
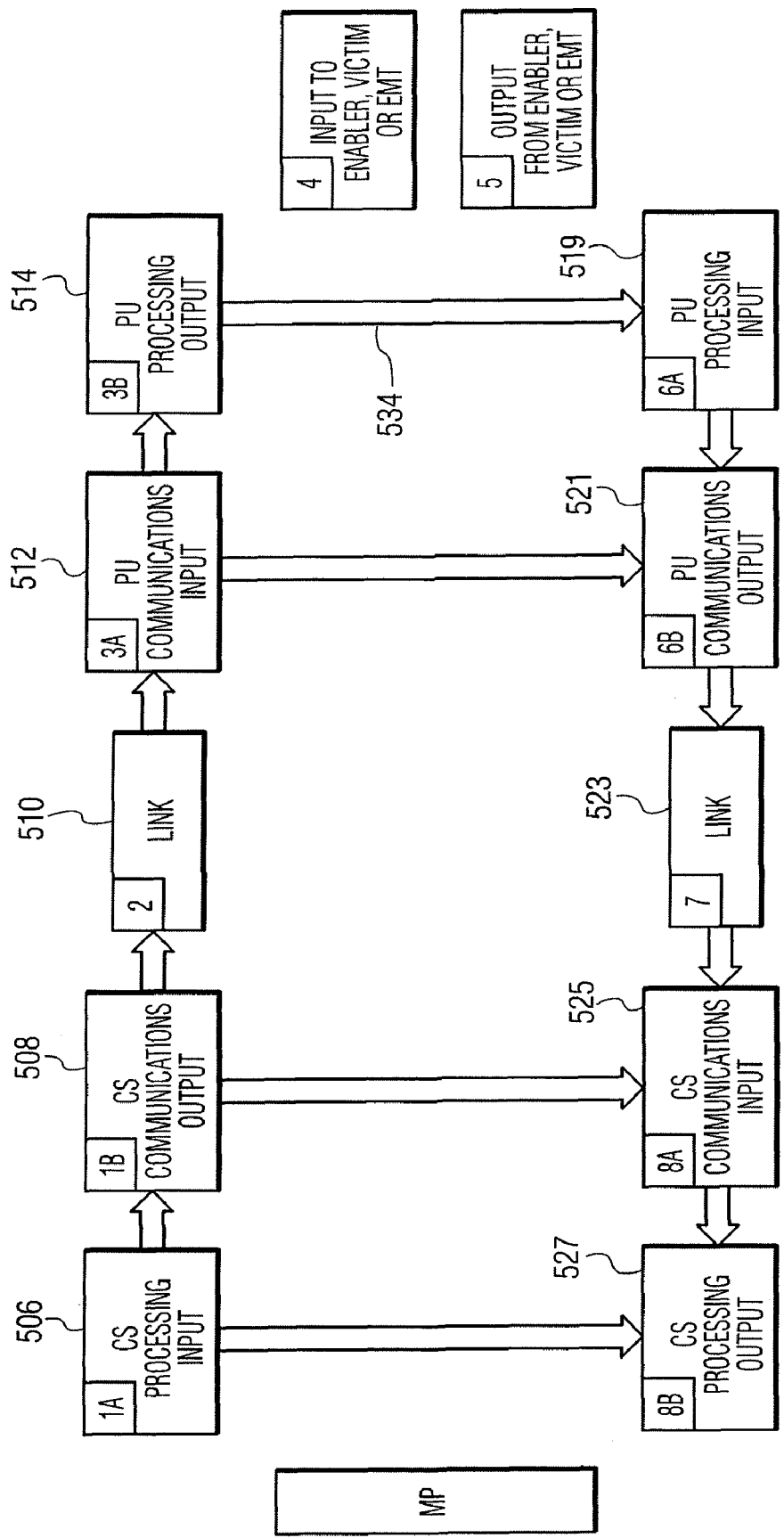

FIG. 14G shows the presence of all four confirmation signals. This is the expected result when a system command (e.g. release PU-SU lock) is issued by the MP.

Figure 14H:
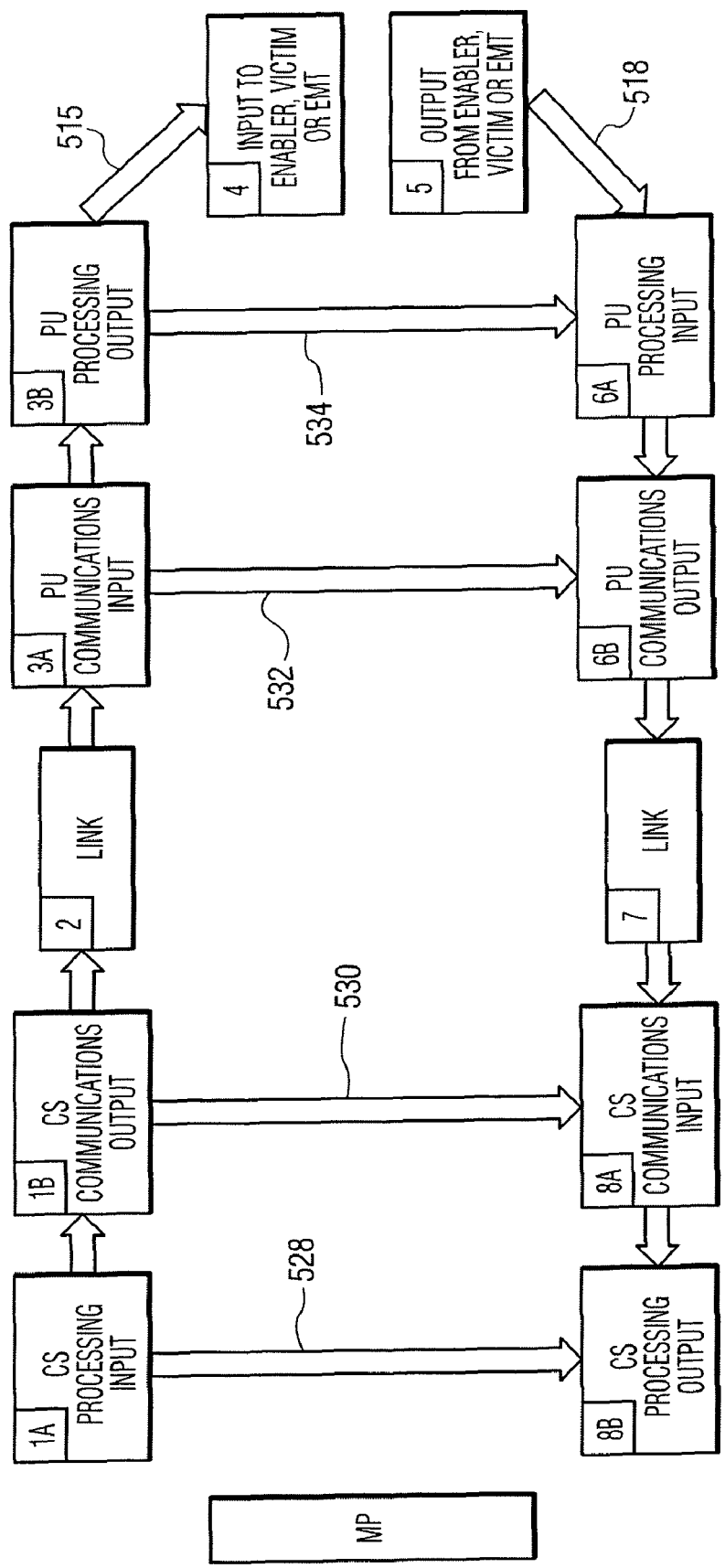
Figure 14I:
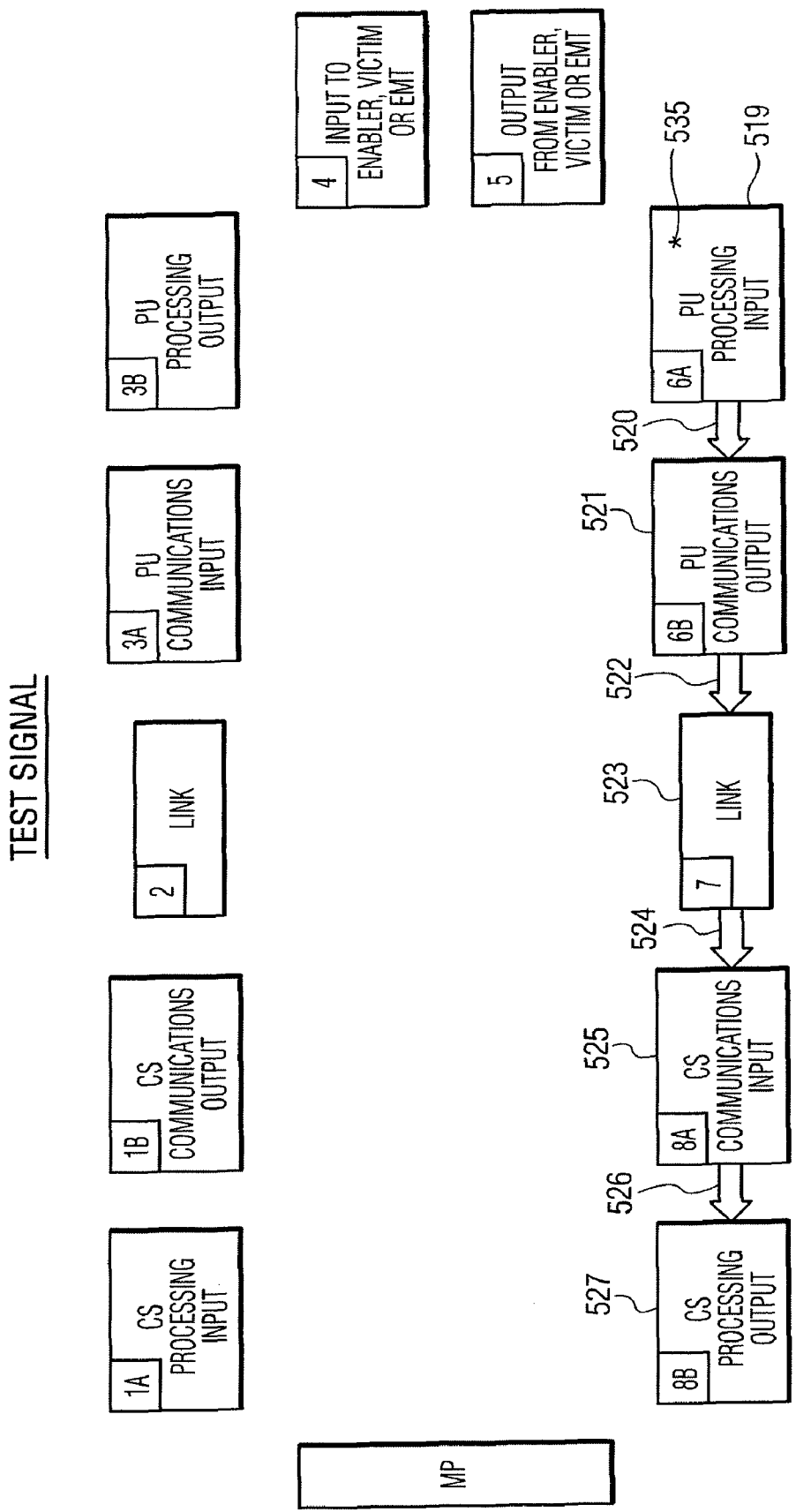

FIG. 14H shows the expected result when a command is issued which affects the victim. For example, the command to defibrillate would result in confirmation signal #1 along path 528, confirmation signal #2 along path 530, confirmation signal #3 along path 532 and confirmation signal #4 along path 534, and the command itself along path 515. The delivery of the shock, resulting in an electrocardiographic change along path 518 would then be transmitted back to the MP as previously described.

FIG. 14J shows voice prompts, a modality for isolating and fixing a problem with audio communication between the MP and the enabler. By using voice prompts, the MP can communicate over a channel that might not be adequate to support voice. These are discussed below.

Figure 14K:
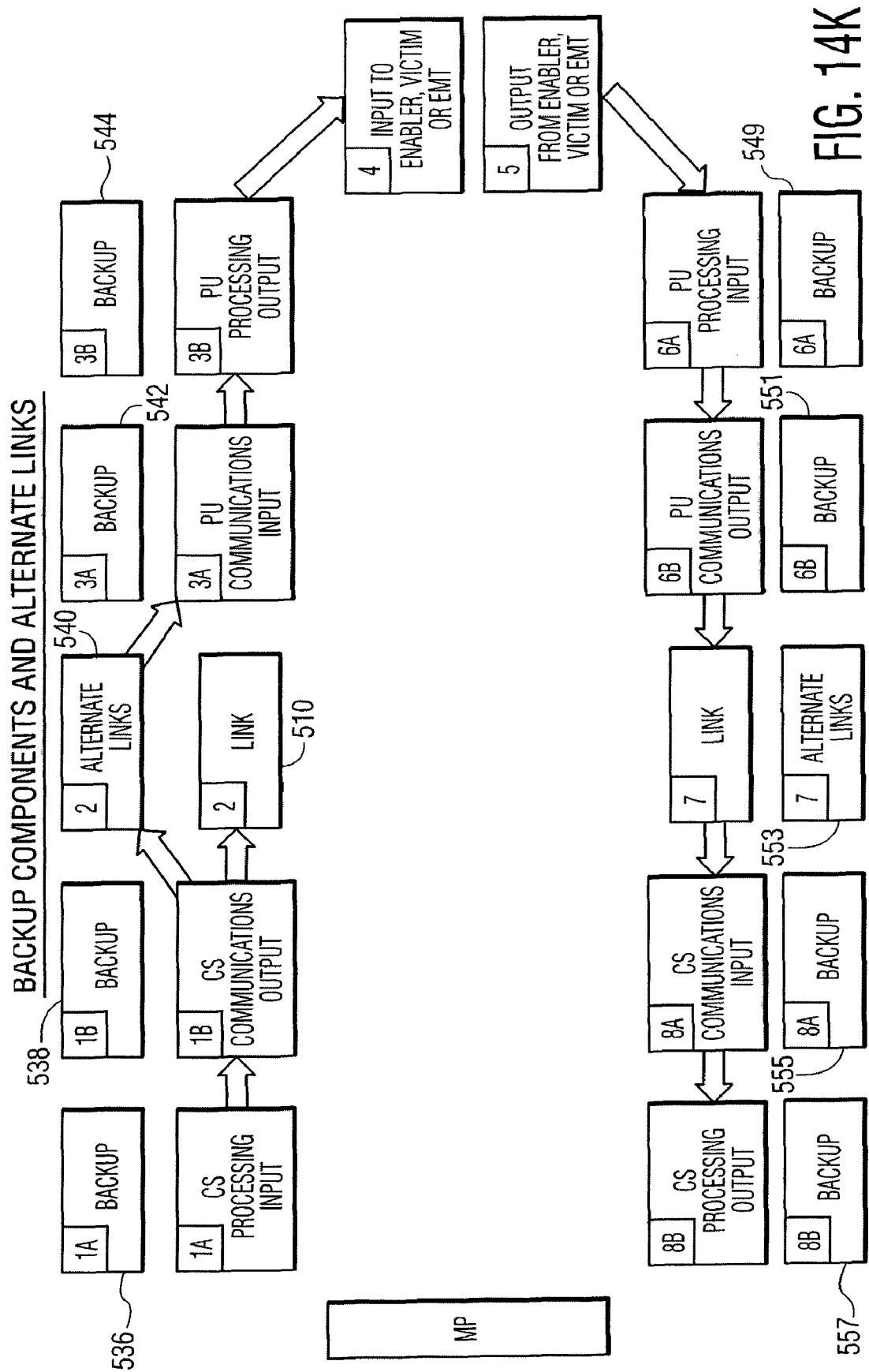

FIG. 14K shows the presence of a backup for each hardware component of the system: elements 536, 538, 542, 544, 549, 551, 555 and 557, and backup communication links 540 and 553. The figure shows a failure of link 510 to support communication between 1B and 3A. It shows the use of alternate link 540, in place of 510.

Figure 14L:
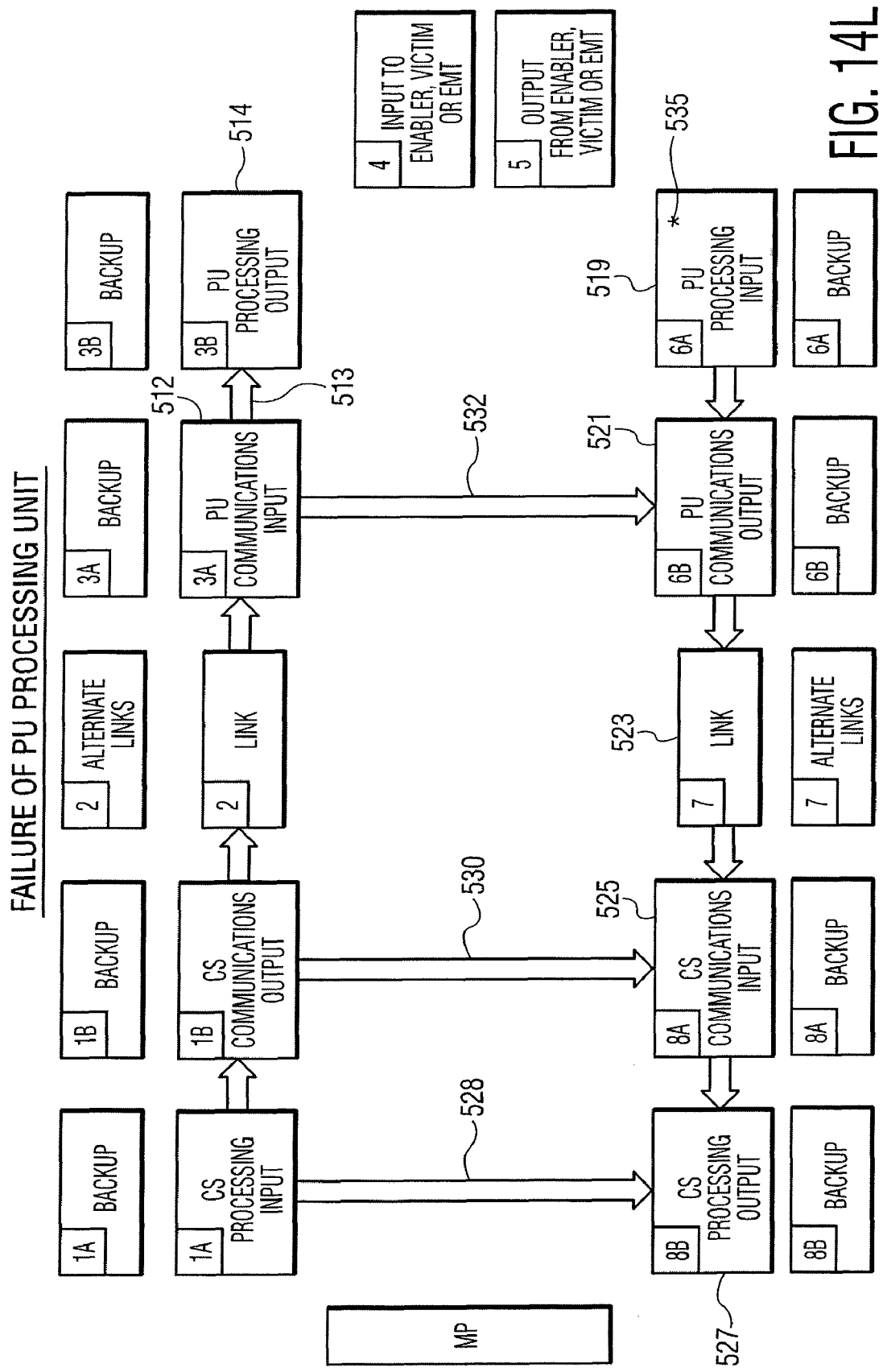
Figure 14M:
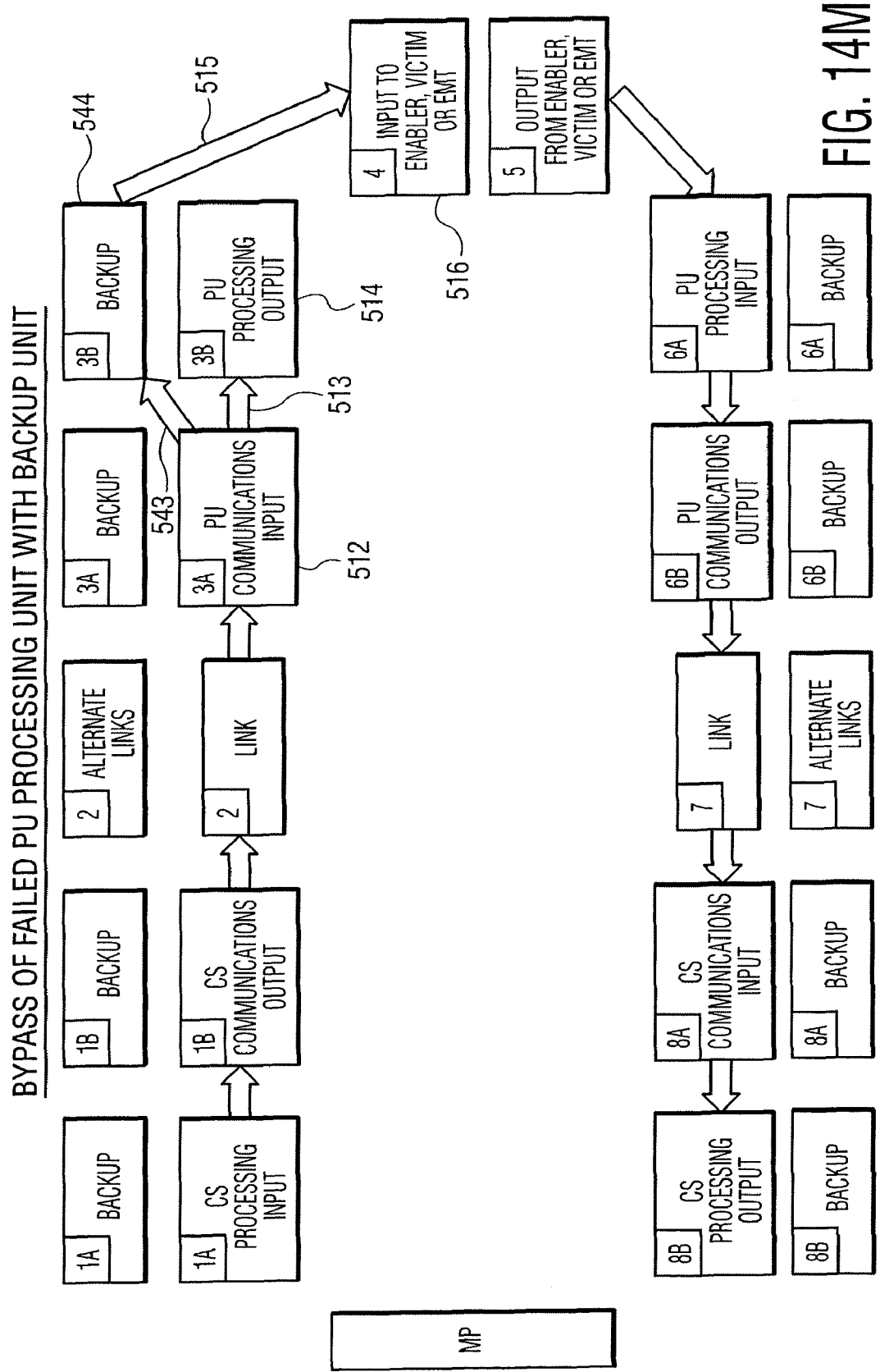

FIG. 14L shows the failure of confirmation signal #4, indicating a failure of either 3B or 6A. The figure also shows the test signal 535 properly transmitted from 6A to 6B, indicating that the failure of confirmation #4 is due to a fault in 3B. FIG. 14M shows the bypassing of 3B by signal 543 to backup 3B unit 544, which interacts with the enabler/victim/EMT as 514 was intended.

Figure 14N:
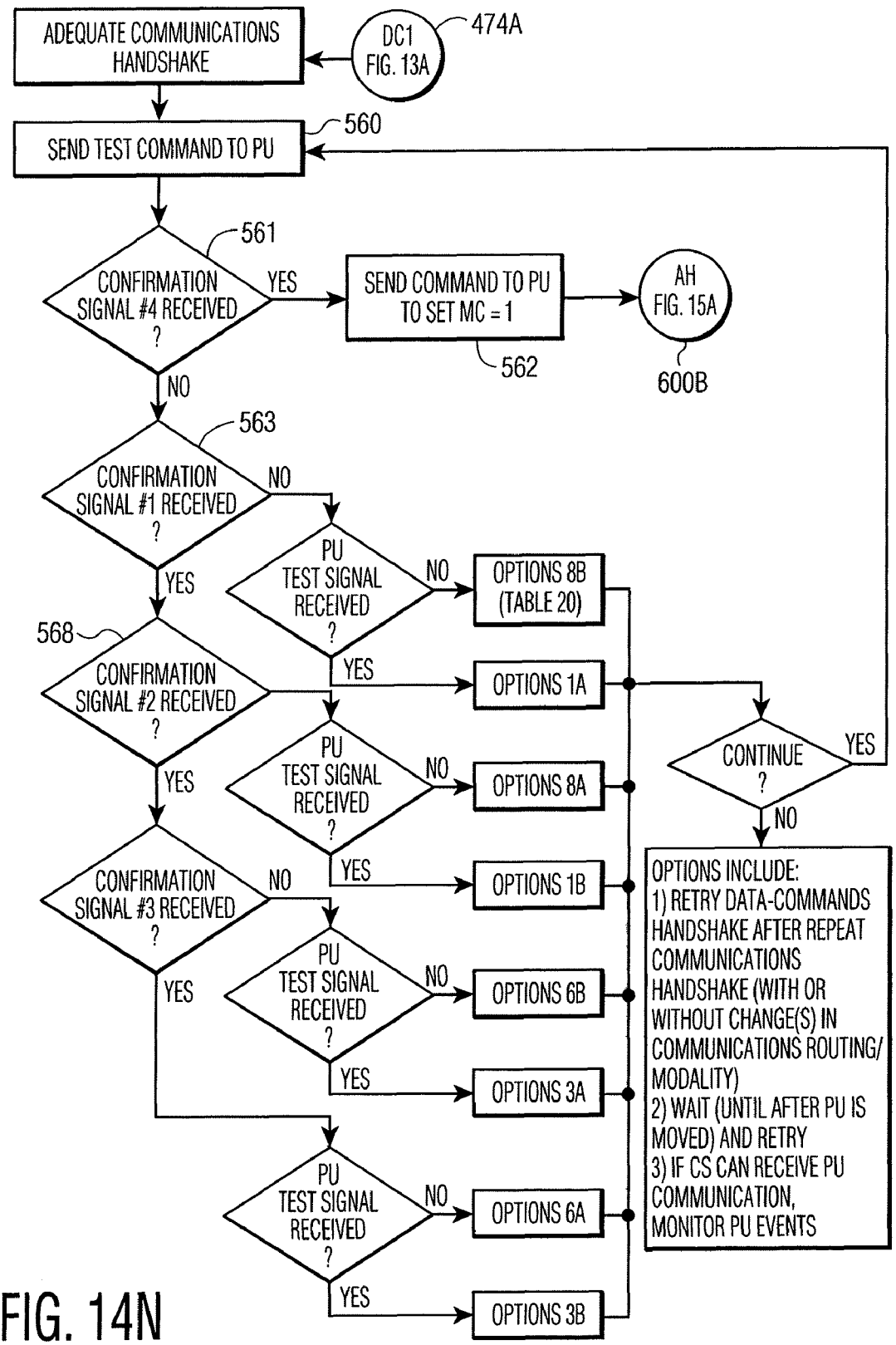

FIG. 14N is a flow diagram showing one possible data/commands handshake. After the completion of the CS end of the communications handshake, block 481 of FIG. 13A, indicating an "Intact Handshake Loop" leads to block 474B, to block DC1 474A of FIG. 14N. A test command, block 560, is sent through the system as shown in FIG. 14C. If, block 561, confirmation signal #4 is received, the handshake is successful and the MP sends a command to the master control unit of the PU to set MC=1, allowing him to control all aspects of the PU. This leads to block 600B and the audio handshake with the enabler.

If confirmation signal #4 is not received, the algorithm asks, block 563, if confirmation signal #1 has been received, as per FIG. 14D. If no, the fault is either with 8B or 1A. Using the PU test signal, as discussed above the distinction between 8B and 1A is made.

If confirmation signal #1 has been received, the algorithm asks, block 568, if confirmation signal #2 has been received, as per FIG. 14E. If no, the fault is either with 8A or 1B. Using the PU test signal, as discussed above the distinction between 8A and 1B is made.

If confirmation signal #2 has been received, the algorithm asks, block 571, if confirmation signal #3 has been received, as per FIG. 14F. If no, the fault is either with 6B or 3A. Using the PU test signal, as discussed above the distinction between 6B and 3A is made.

If confirmation signal #3 has been received, the fault is either with 6A or 3B. Using the PU test signal, as discussed above the distinction between 6A and 3B is made.

Once the faulty component is localized, various compensatory processes can be performed. These may involve changing gain, filtering, noise suppression, modulation, bandwidth or other techniques as are known in the art. They may also involve switching to a backup component, as demonstrated in FIG. 14M.

If the data/commands handshake has not succeeding, the MP decides, block 566, whether to continue his efforts to remedy it. If he decides to do so, another test command is sent, block 560. If he decides not to his options, box 567, include a) a repeat of the communications handshake, with or without changes in communications routing/modality, b) retrying after the PU is in a slightly different location, or c) going to AED control and, if possible, monitoring PU events while trying to establish a better handshake.

The data/commands handshake during diagnostic testing is shown in FIG. 14O. It is functionally similar to the non-testing version in 14N. Its input is from 492B, FIG. 13B. If successful, it results in the transmission of a command to set MC=4. Troubleshooting is identical to FIG. 14N. If the MP chooses not to continue after a failed attempt(s), box 587, the options, besides starting from a new communications handshake, include dispatching a maintenance person to the PU and/or notifying PU site personnel.

Other data/commands handshakes are possible including:

a) those based on using a top-down approach in which, if confirmation signal #4 is not received, confirmation #3 is sought; and if not received #2 is sought etc.;

b) those based on using a bottom-up approach in which, confirmation signal #1 is first checked for. If confirmation signal #1 is not received, confirmation #2 is sought; and if not received #3 is sought etc.;

c) approaches in which a large number of sources of test signals in different places along the communications loop allows the isolation of a fault. Such a format could also use either a top-down approach or a bottom-up approach.

In practice, the signal assessments and the entire handshaking process could be extremely rapid.

5.3 Audio and Informational Handshakes 5.3.1 Part I, Audio Handshake

Figure 15A:
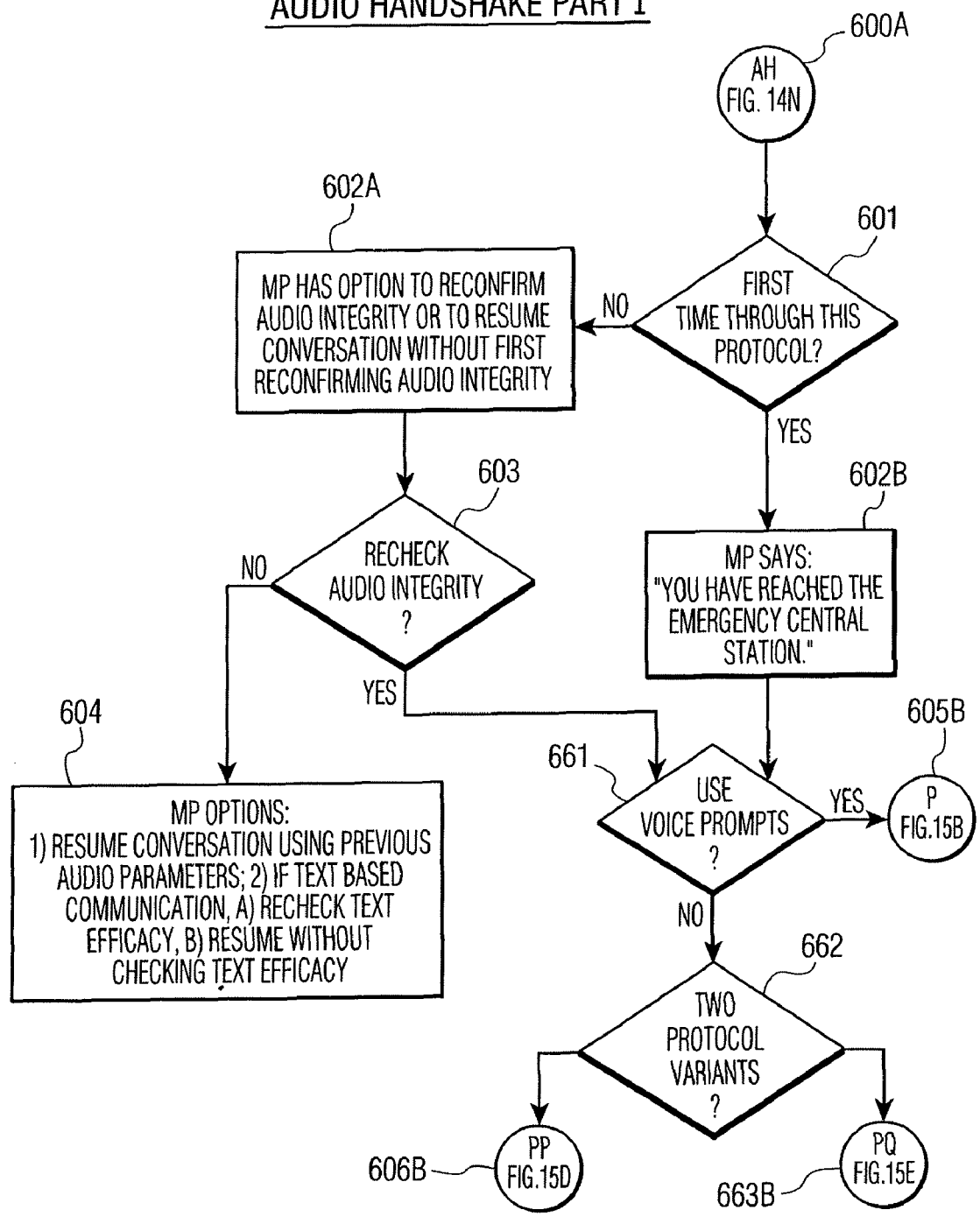
FIG. 15 are a flow chart showing the audio handshake protocol between the enabler and the medical professional located at the central station of the system according to the present invention.
Figure 15B:
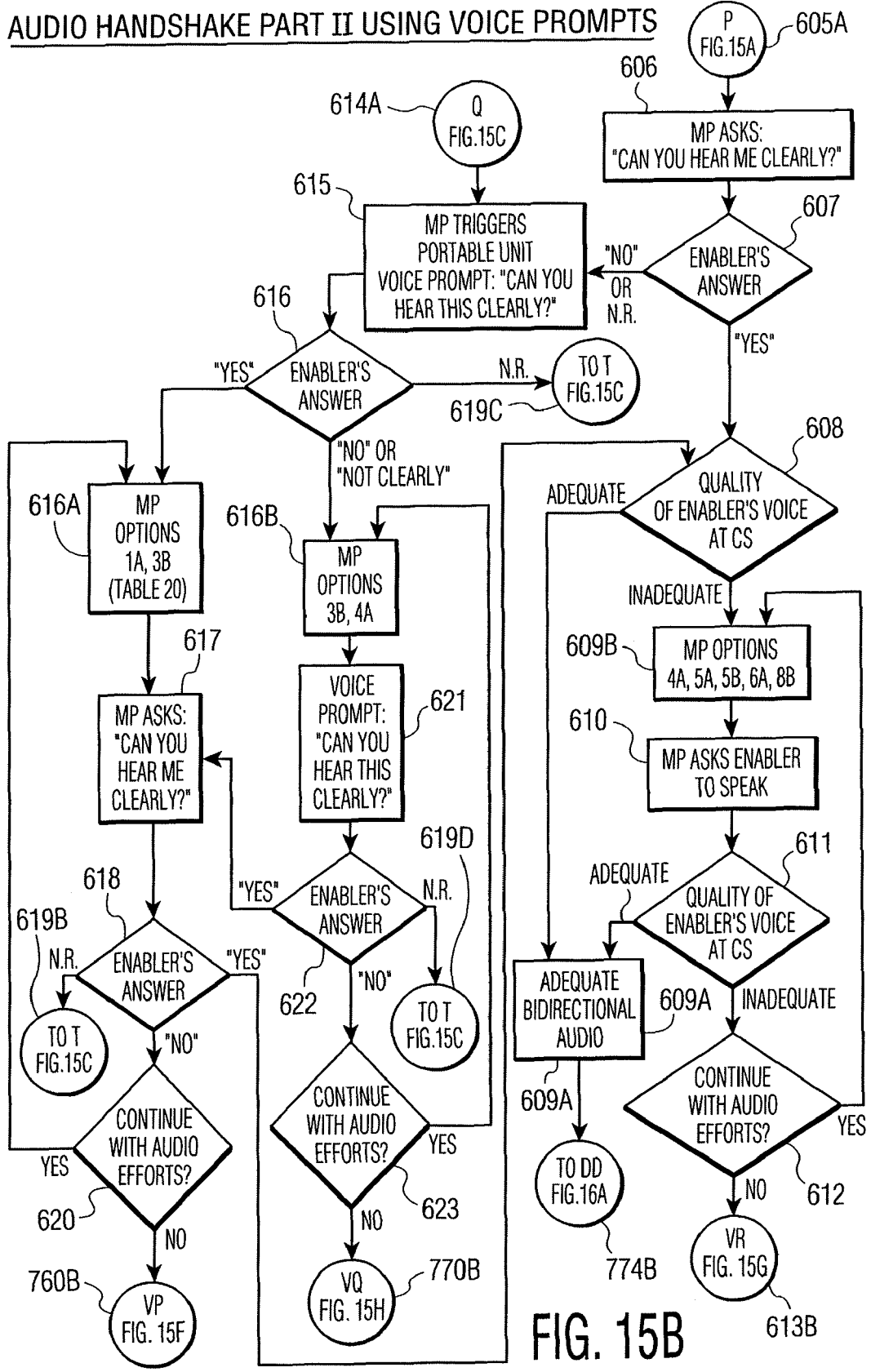
Figure 15D:
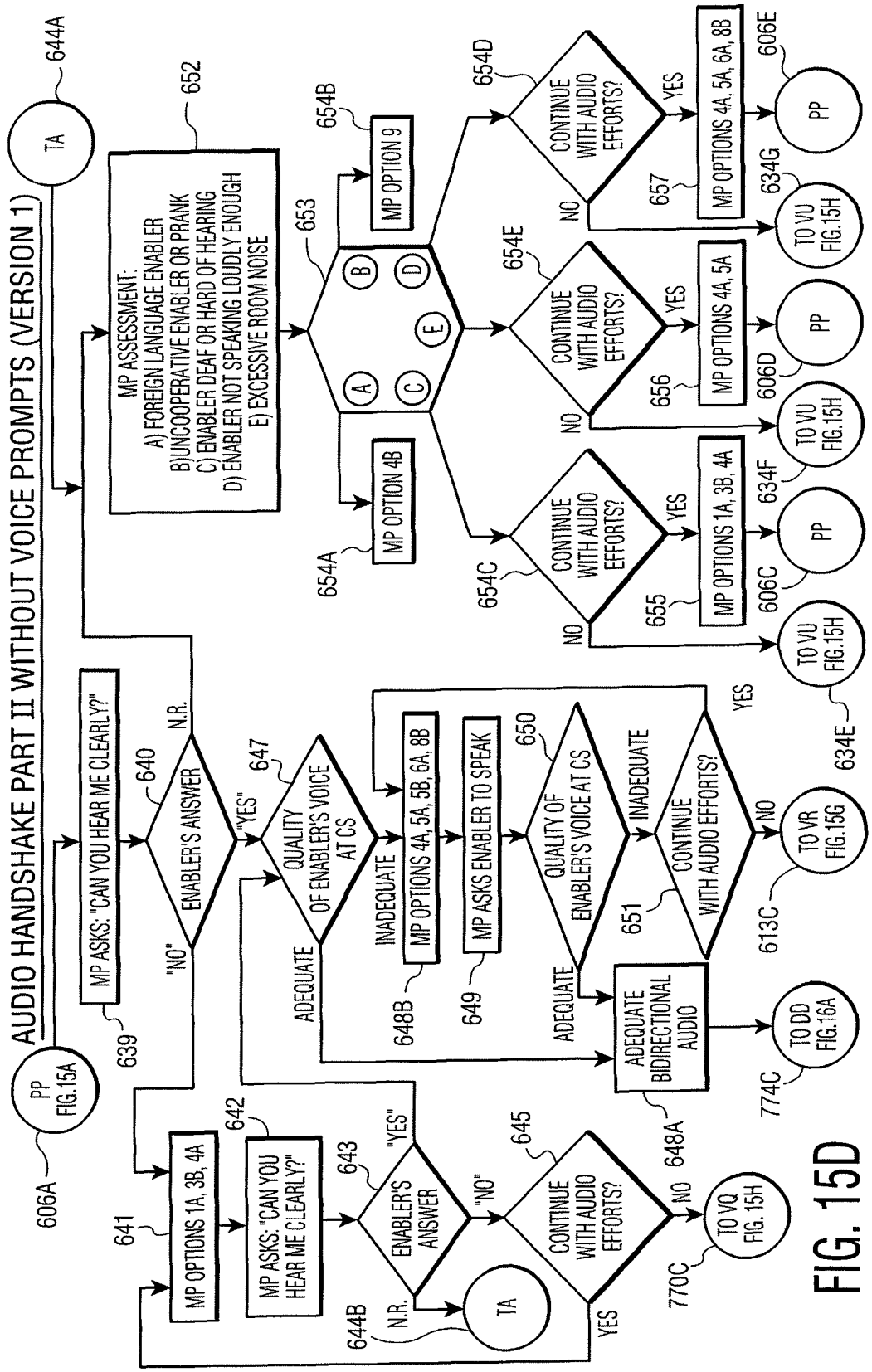
Figure 15E:
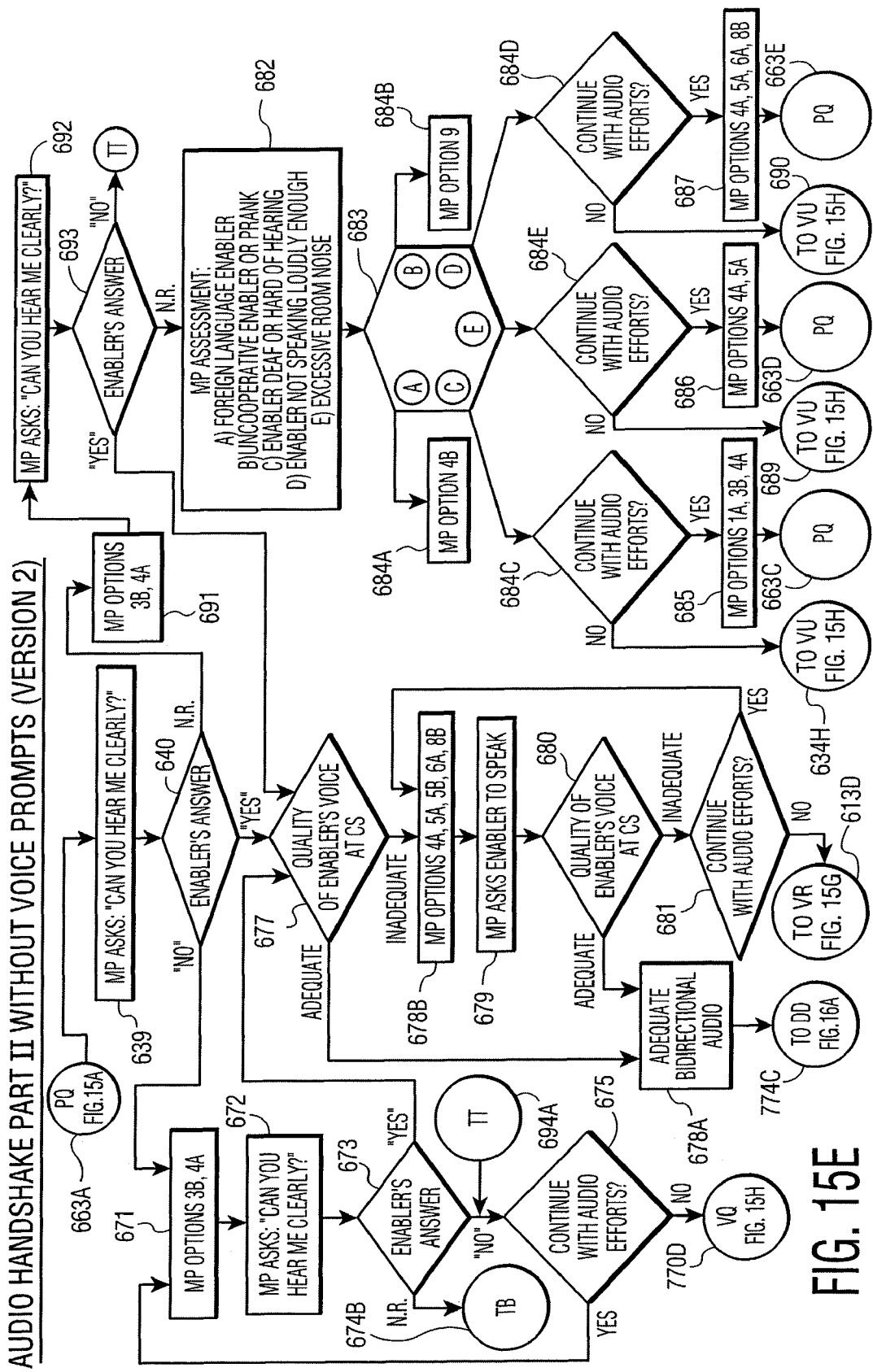

The output of the data/commands handshake leads to the audio handshake, block AH 600A, FIG. 15A. If, block 601, traversing this handshake for the first time, block 602B results in the MP identification announcement. Three methodologies are shown in FIGS. 15B through 15H, corresponding to the three outputs of blocks 661 and 662. With one approach, using voice prompts, block 602B leads to 661 to 605B TO 605A FIG. 15B. For the two approaches without voice prompts, block 602B leads to block 661 to 662 and to either 606B, 606A (FIG. 15D) or 663B, 663A (FIG. 15E. If the MP has already been through the protocol, but has returned to it because of an interruption in communications he has the option 602A to recheck audio integrity or to bypass this step.

5.3.2 Audio Handshake, Part II 5.3.2.1 Using Voice Prompts

The MP starts by asking the EN "Can you hear me clearly?" block 606. If EN answers "YES", block 607 leads to 608 where the MP assesses the quality of the EN voice at the CS. If it is good, then adequate bidirectional audio has been achieved which leads to DD FIG. 16A and the informational handshake.

If at 608 the quality of EN's voice at the CS is inadequate, MP options include, (block 609B) 4A, 5A, 5B, 6A and 8B. The MP then, 610 asks EN to speak, and reassesses the quality of EN's voice at block 611. If still inadequate and, at 612, he wishes to persist with audio efforts, the MP proceeds through another loop of 609 (selecting another communications enhancement), 610, and 611. If he decides to abandon efforts at two-way audio communication, the protocol leads to 613A, FIG. 15G.

If, at 607, the EN answer was either "NO" or there was no response, the MP issues, at 615, a voice prompt, VP, asking if the EN can hear the VP. If, at 616, the answer is yes, the best MP options, block 616A, for improving audio communication are 1A and 3B. The MP himself then asks again, at 617, if the EN can hear him clearly. If, at 618, the answer is YES, he returns to 608. If the answer is "NO" he decides whether to continue with audio efforts, block 620. If yes, he repeats the loop of blocks 616A, 617, 618 and, if necessary, 620. If no, he proceeds to VP 760A, FIG. 15F. If the EN answer at 616 was "NO" or "NOT CLEARLY" the best options are 3B and 4A. He selects at block 616B, and issues another VP at 621. If the EN answer is "YES", the protocol returns to 617. If the answer is "NO" the EN must decide 623 whether to persist with audio. If yes, he repeats the loop 616B, 621, 622 and possibly 623. If no, he proceeds to VQ 770A, FIG. 15H.

If at any of blocks 616, 622 or 618 there is no EN response, the protocol goes to T 619A, FIG. 15C. At 624, if the MP does not hear the VP, he decides at 625 to either continue audio efforts (options 6A or 8B), block 626 leading to Q 615A or does not, leading to VS in FIG. 15H. If the MP does hear the VP then block 628 lists five possible reasons for no EN response. AT 629, the MP decides which of these five is most likely leading to one of 630A-630E. His options then range from continuing to use electronic means of enhancement, to asking the EN to use the wireless headset in the PU tool-kit to calling 9-1-1 in the event of suspected prank. If he wishes to persist with audio efforts, he returns to Q 614A (FIG. 15B) and tries the VP again. If he wishes to use a non-audio format he goes to VU 634A of FIG. 15H.

5.3.2.2 Without Voice Prompts, Version 1

If the MP uses this approach, 662 leads to PP 606A to 639 where the MP asks: "CAN YOU HEAR ME CLEARLY?" If the EN answer is "YES", then the sequence 647, and either 648A or 648B, 649, 650, 651 is identical to the sequence 608, and either 609A or 609B, 610, 611, 612 in the Voice Prompt version of Part II, discussed above in Section 5.3.2.1. The exit points are also identical.

Figure 15F:
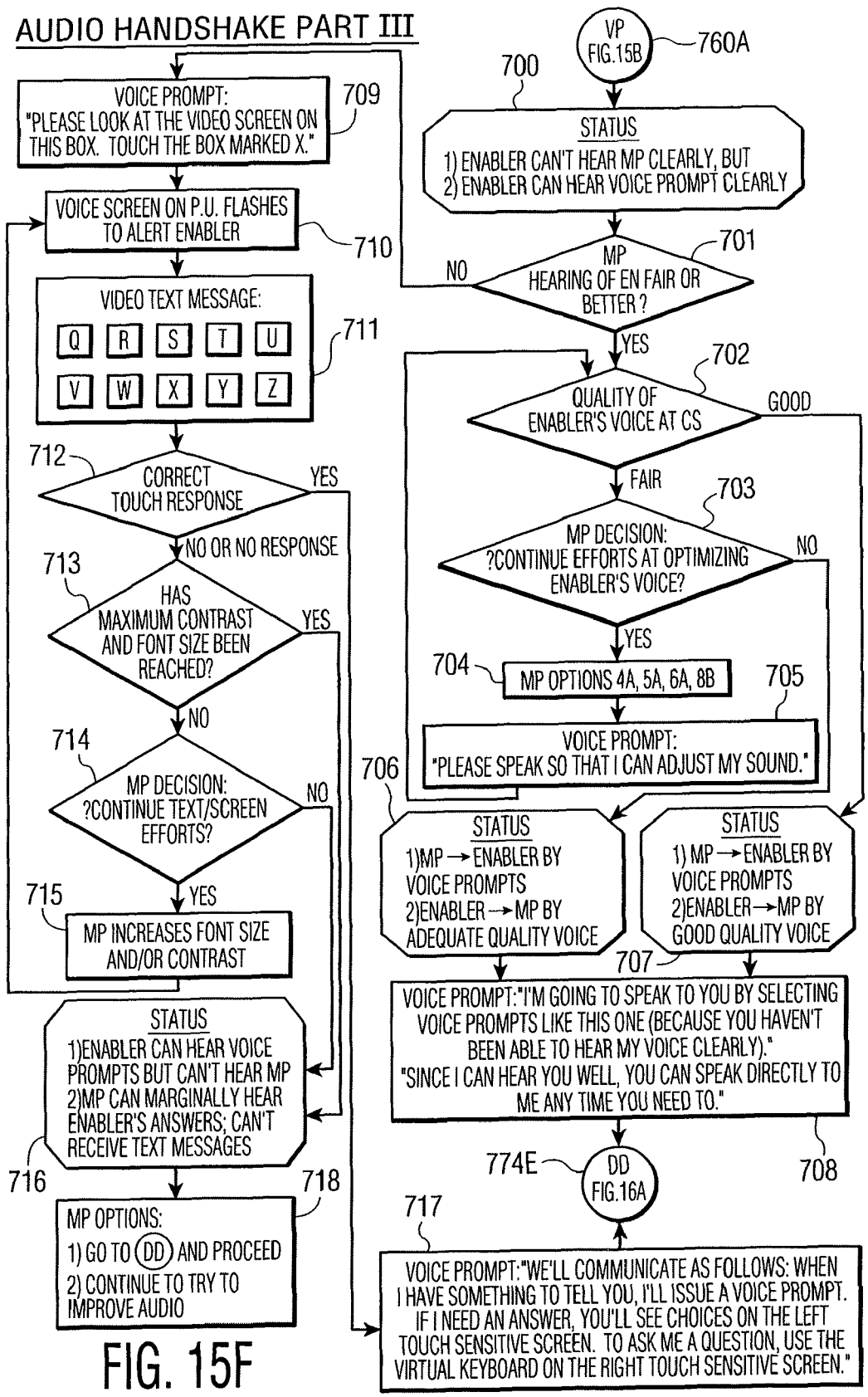
Figure 15G:
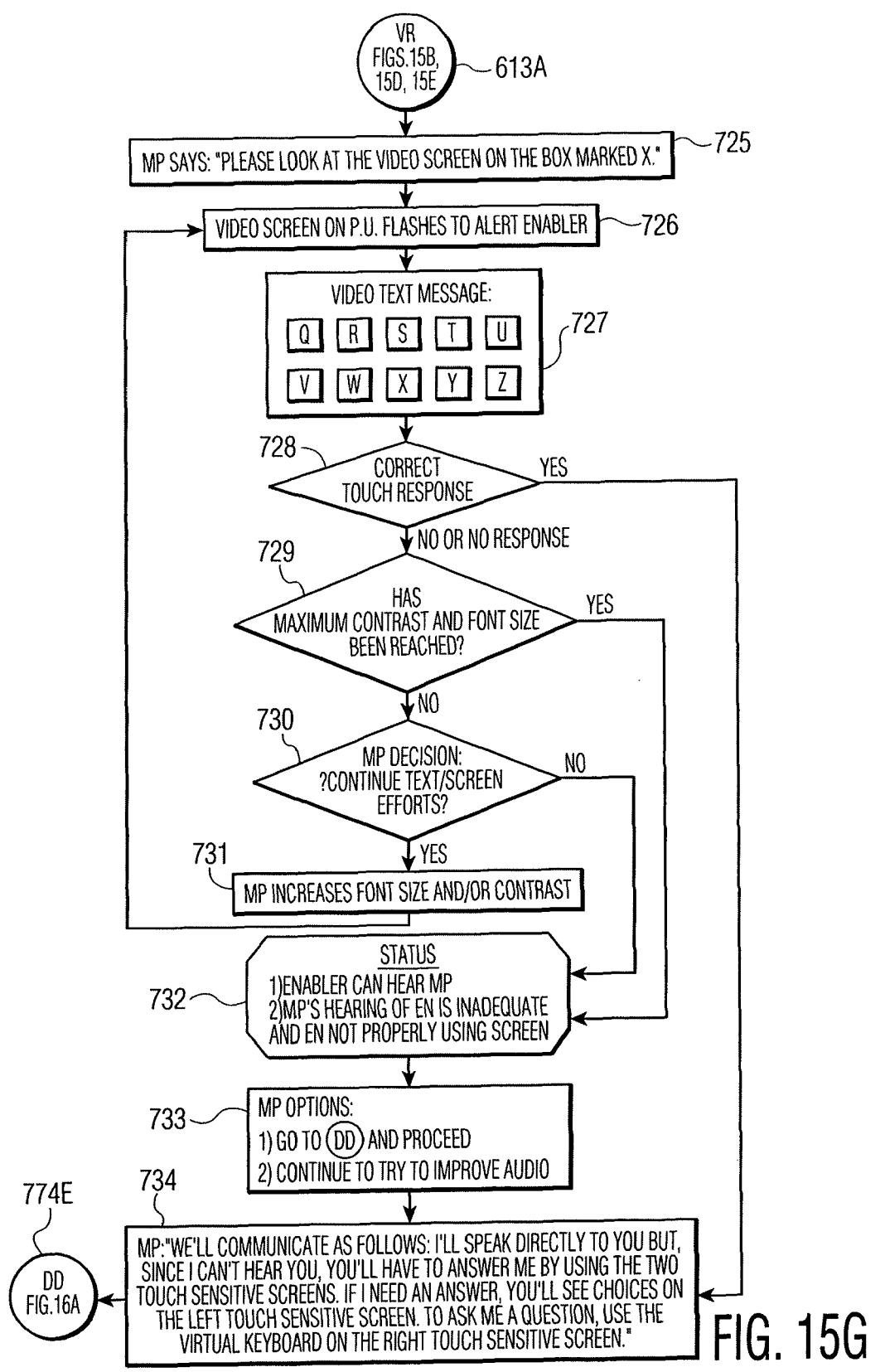
Figure 15H:
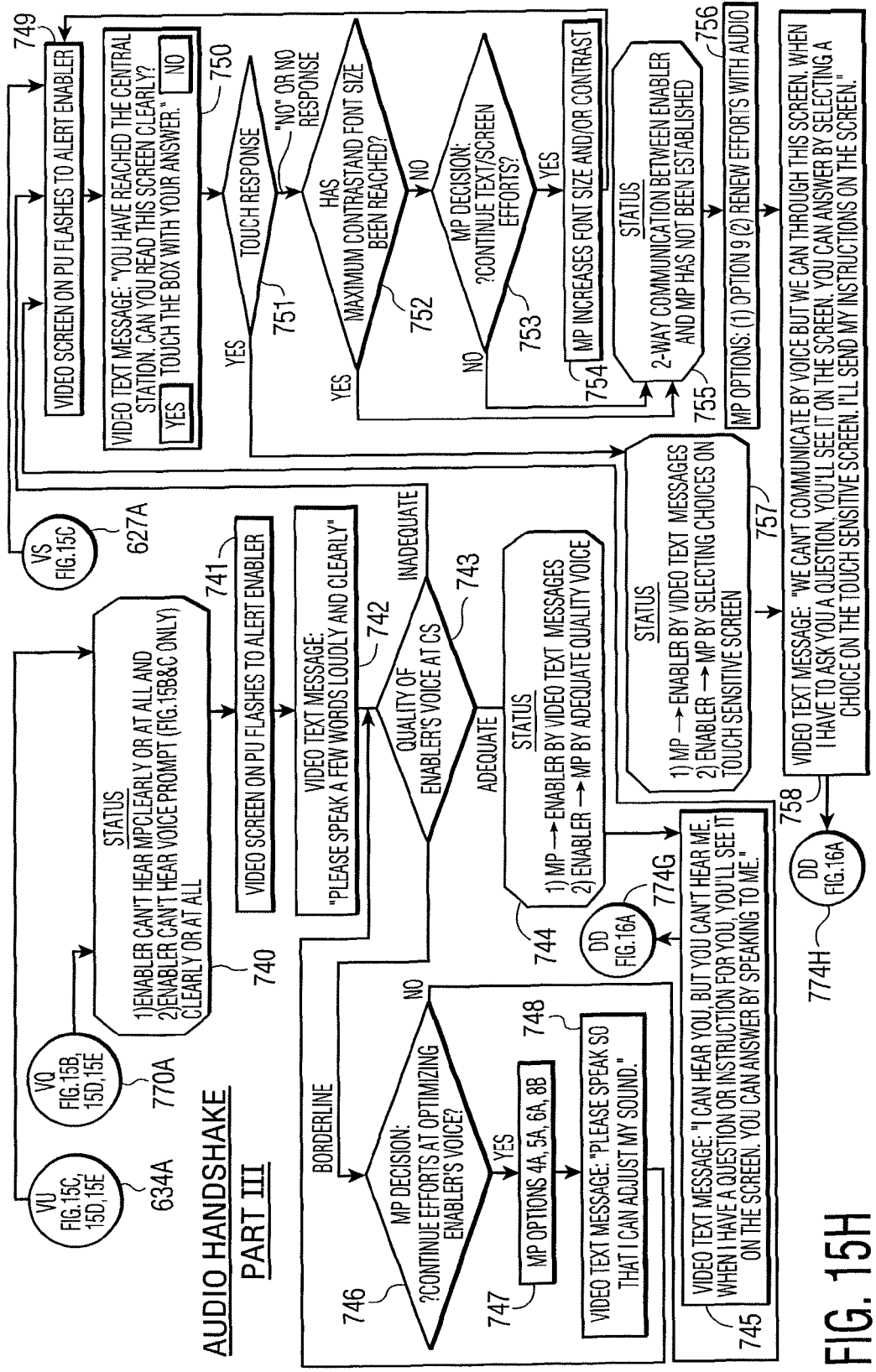

If, at 640, there is no response, the protocol proceeds to 652 with cascade of options 654A to 654E which parallel those in the VP Section 5.3.2.1 above, emanating from 628 and 630A-630E. The endpoints for this branch of the protocol are also VU 634A if the MP decides to seek text communication. If he persists with audio efforts, he returns to block PP 606A. If at 640 the EN response was "NO" the MP options are, block 641, 1A, 3B and 4A. After again asking, at 643, if the EN can hear him, he can go to either:

a) another loop through 641, 642, 643 if the EN answer is "NO" and the MP wishes to persist with audio;

b) 652 if there is no EN answer, and proceed as previously described; or c) go to VQ 770A, FIG. 15H.

5.3.2.3 Without Voice Prompts, Version 2

This approach is very similar to that discussed in 5.3.2.2 except that at block 640, the MP tries either option 3B or 4A, block 691, and again asks "CAN YOU HEAR ME CLEARLY?", block 692.

There are three possible responses:

a) If there is still no response, he proceeds 682 to 683 to a cascade of options which are identical to 652, 653 of version 1 without VP.

b) If the answer is "YES", he returns to the same loop that was encountered in both previously discussed versions of Part II in which the EN can hear the MP, and the MP's ability to hear the EN is under evaluation.

c) If the answer is "NO", this leads to □ 694A and a decision, 675 to either abandon the current audio effort VQ 770A, FIG. 15H, or to loop through 671, 672, 673 and 675 after trying one of options 1A, 3B or 4A again.

5.3.3 Audio Handshake, Part III

In Part III of the Audio Handshake Protocol, the MP acknowledges that either one or both arms of his communication with the EN will require text format, and that it is possible that communication may not at all be possible. The MP uses the video screens on the PU. If he can hear the enabler, but the enabler can not hear him, or hears him marginally (protocol entry points VQ and VU) he can communicate by sending text messages to the EN, and having the EN speak his responses, block 745, FIG. 15H.

In the opposite situation, where he cannot hear the enabler, but the enabler can hear him, block 734, they can communicate by having the MP speak directly to the EN and by having the EN send text messages on one or both of the PU touch sensitive screens. If neither side can hear the other, they can communicate by two-way text messages, as shown in block 757, FIG. 15H.

In the voice prompt variants of the protocol, the enabler may be able to hear the voice prompts better than a garbled or distorted version of the MP's voice, if communication conditions are poor; The MP may be able to hear the EN well enough, blocks 706 and 707, or may ask the EN to use the touch sensitive PU screen, block 717. These are shown in FIG. 15F.

One outcome arm, block 716 results in the EN only being able to hear voice prompts, and the MP hearing the EN only marginally. Although this is a sub-optimal outcome, it is still better than MC=2, i.e. switching to AED function, since in that case, the EN also hears voice prompts but doesn't have the benefit of the MP in charge of the situation. Even though voice communication is marginal, the narrower bandwidth which would support ECG and command transmission, having already been evaluated during the data/commands handshake, would suffice.

5.3.4 Informational Handshake

Figure 16:
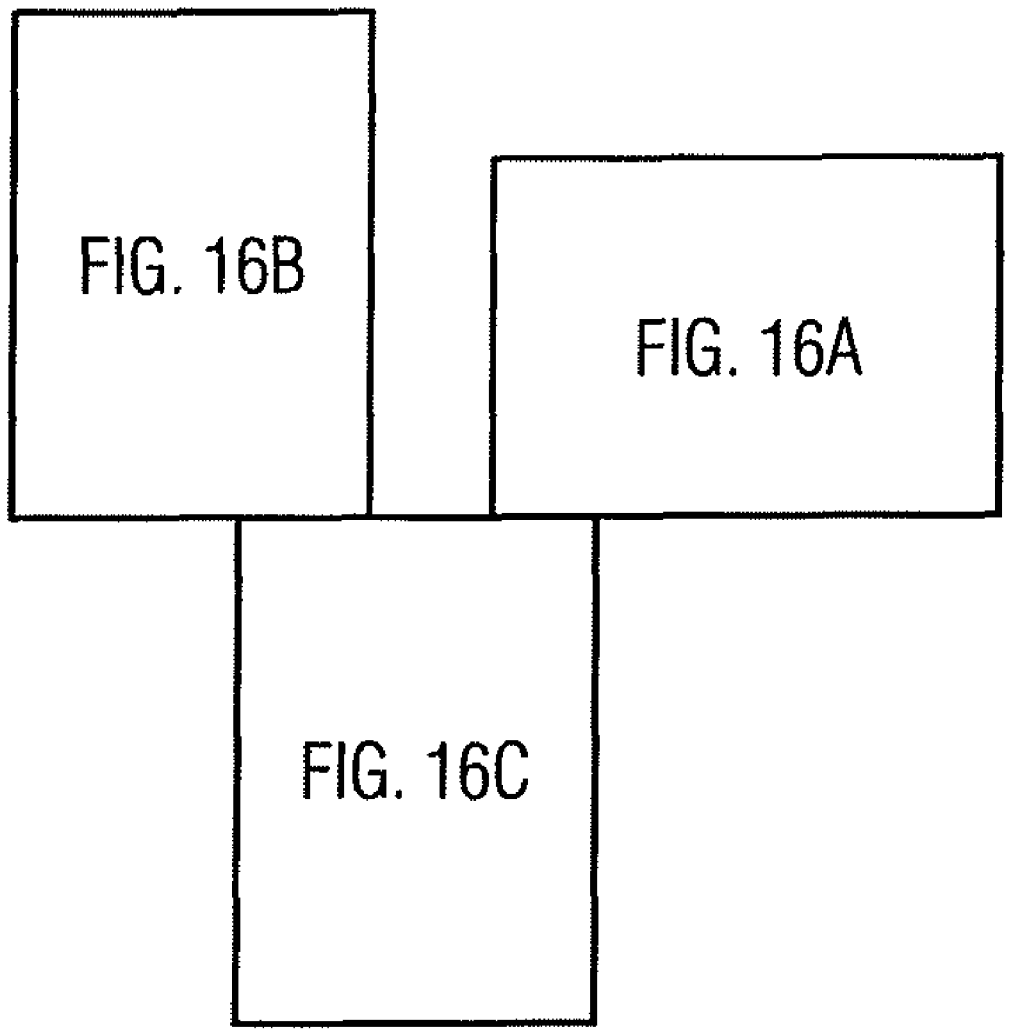
FIG. 16 comprises FIGS. 616A, 16B and 16C.
Figure 16A:
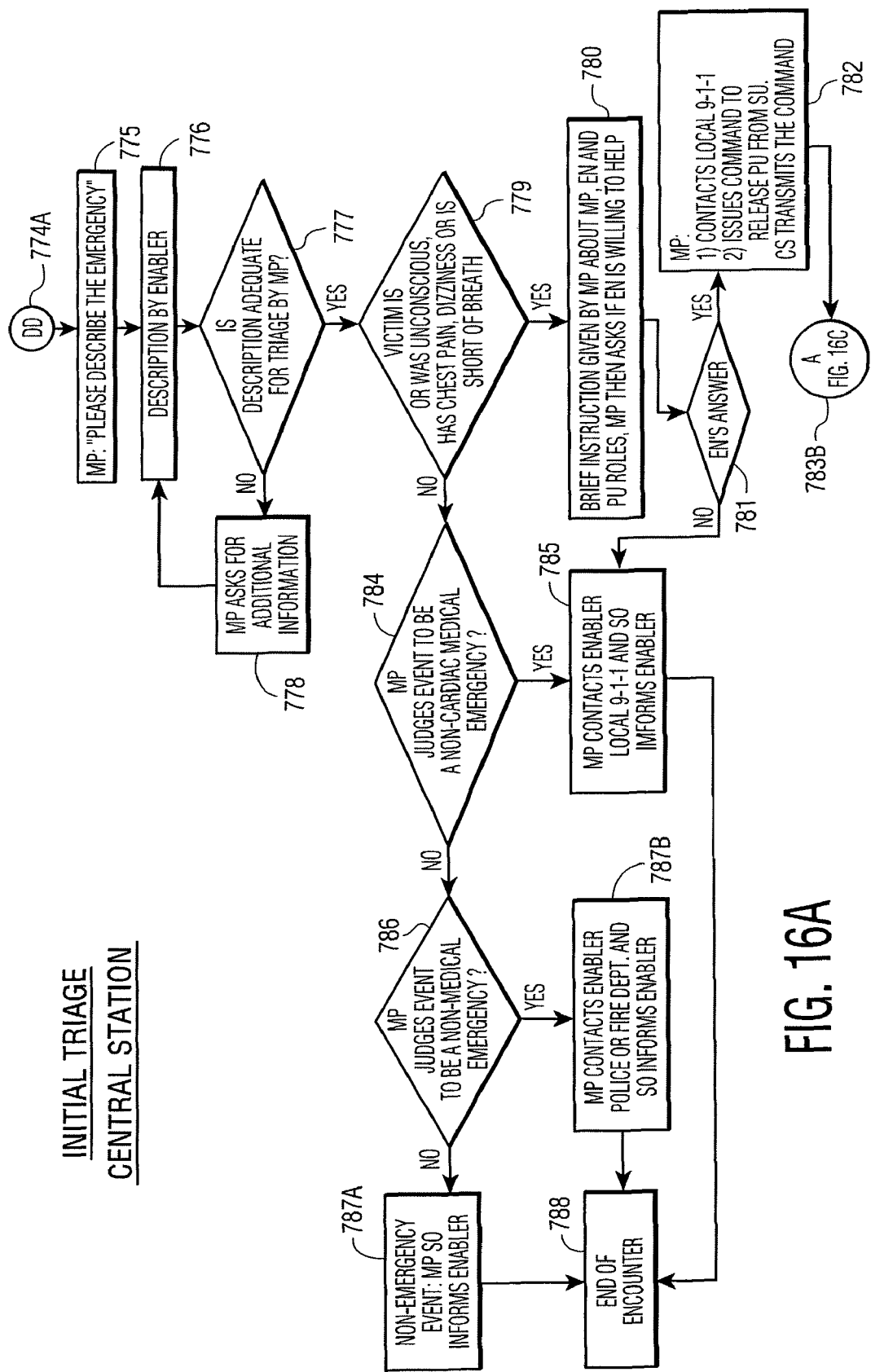
FIG. 16A is a flow chart showing the informational handshake protocol between the enabler and the medical professional located at the central station of the system according to the present invention.

Having established an adequate communication modality leads to DD 774A and the start of the informational handshake, shown in FIG. 16A. The MP must know determine the reason for the Button Press, and whether it is reasonable to release the PU for use in the current situation.

After asking the victim to describe the emergency, listening to his answer, asking for additional information if necessary, blocks 775 to 778, the MP classifies the event in one of four categories using the algorithm in blocks 779, 784 and 786:

a) an actual or possible cardiac emergency, 780;
b) a non-cardiac medical emergency, 785;
c) a non-medical emergency, 787B; or
d) a non emergency, 787AS.

If it is classified as a cardiac emergency, he asks the EN if he is willing to participate 780. If the answer is "YES", he immediately takes the steps in box 782 including releasing the PU lock.

Figure 16B:
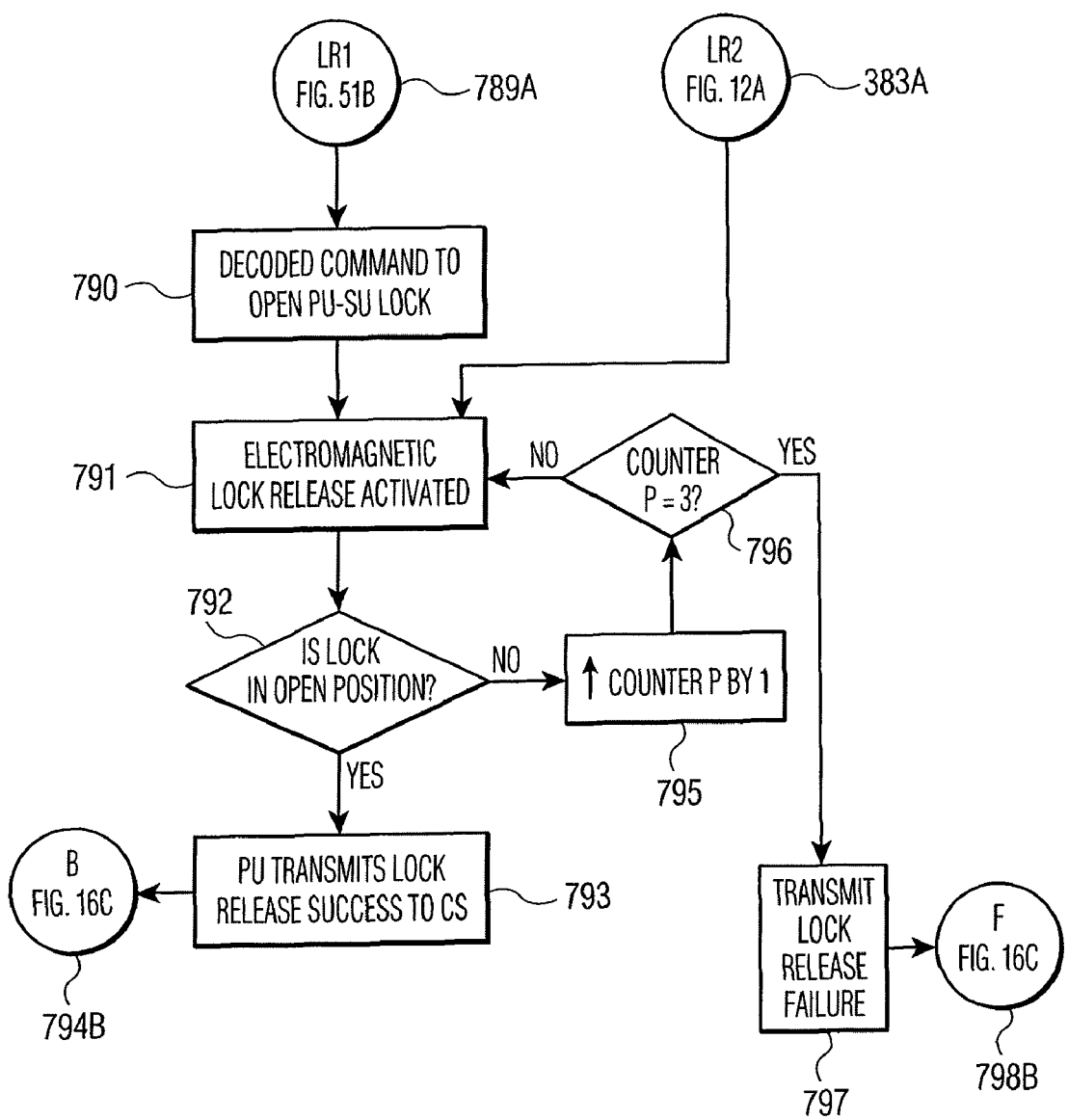

FIGS. 16B and 16C are directed at a backup plan for a lock release failure. In FIG. 16B, 790, the command to release the lock leads to 791, the attempted release and 792, an assessment. If the release is successful, the PU transmits a telemetry signal, block 793, which appears on the CS event log. If unsuccessful, two more tries are made, looping over block 791, 792, 795 and 796. If still unsuccessful, a failure signal is transmitted. In either case (or in the case of uninterpretable telemetry), the protocol proceeds to FIG. 16C If lock release was successful, block 806A leads to 807, and the MP instructs the EN in removing the PU. The MP should then, 808, 815 receive a PU-SU separation signal, leading to start of the cardiac management protocol in Section 5.4 and FIG. 17. A problem with lock release is handled by any one of the following options:

a) having the EN try to remove the PU even though telemetry suggests that it is locked in place, blocks 813, 814 and, if successful, 815;
b) re-transmitting the command to release the PU, blocks 812B, 783C;
c) telling the enabler the mechanical lock combination 816, 807, 808.

5.4 PU Transport and Setup at the Victim's Side
5.4.1 PU Transport

The MP, after a) having decided that the situation described by the enabler represents a bona-fide emergency for which the PU should be utilized, and (b) having released the PU-SU locking apparatus, will want to give additional instructions to the enabler.

Figure 17:
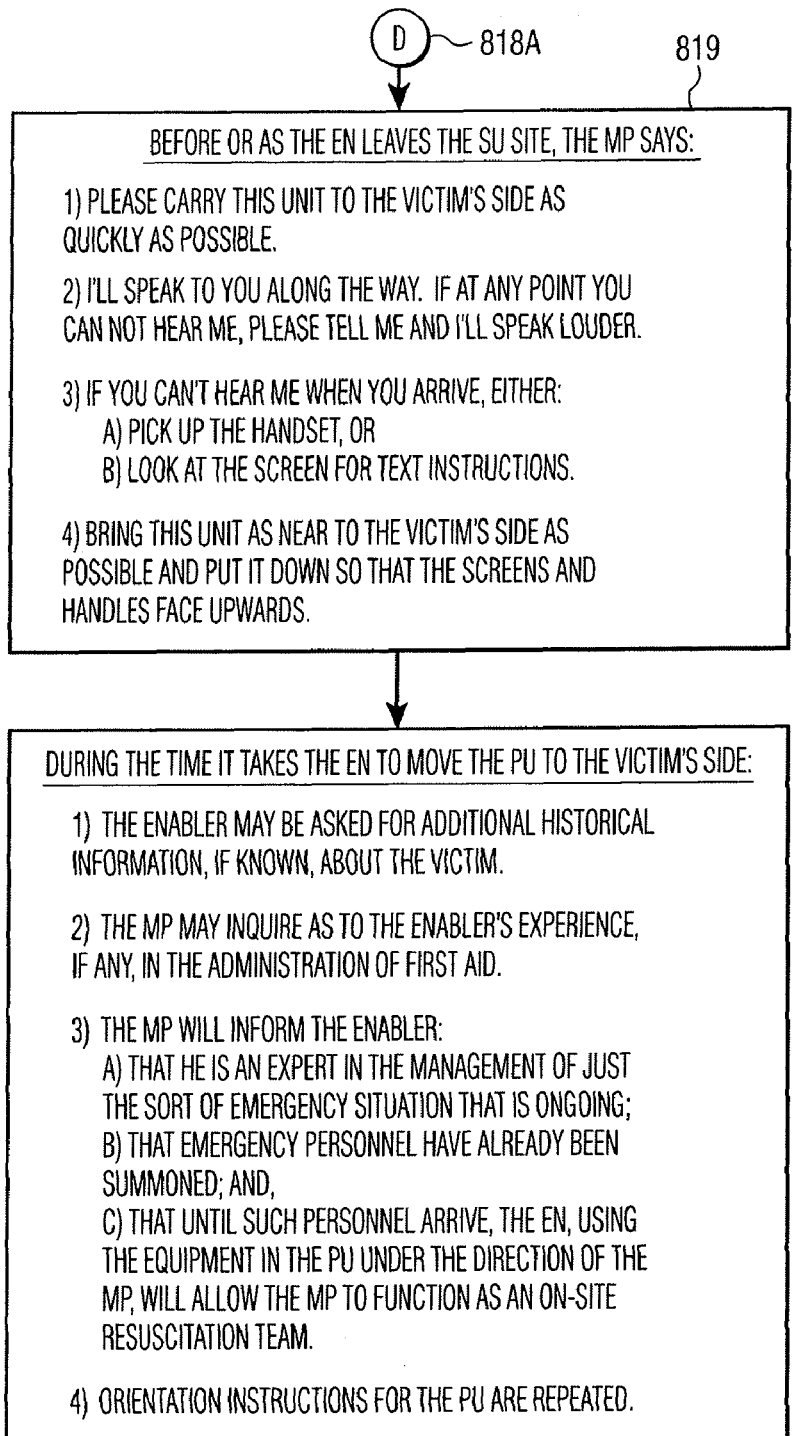
FIG. 17 is a flow diagram showing typical voice instructions of a medical professional offered during the transport of the portable unit from the stationary unit to the victim according to the present invention.

Block D 818A, FIG. 17, (reached from block 818B, FIG. 16C) leads to box 819, which shows the first group of instructions. The MP has three choices as to the timing of his giving these instructions:

a) He could give them while the enabler is transporting the PU to the victim. The advantage of this approach is that it saves time. The approximately thirty seconds that it takes to deliver the instructions in box 819 would be added to the time before victim treatment begins, if PU transport did not begin until after their enunciation to the enabler. The disadvantage of this approach is that the enabler may not hear them as well, during transport of the PU, because the PU is further away from his ear than it would have been when it was attached to the PU. The MP could compensate for this by increasing the audio volume at the PU. He would be guided in this process by intermittently asking the enabler if he, the EN, could adequately hear the MP. In a preferred embodiment of the invention, the presence of multiple PU speakers 146 (FIG. 6A and Section 2.1), each of which projects in a different direction, optimizes the chance of good reception. Another potential disadvantage of this approach is that the quality of the audio communication between the MP and the EN may not be as good as when the PU was attached to the SU. In a preferred embodiment of the invention, the presence of redundancy in the communication, makes this scenario unlikely to occur.

b) The MP could give the instructions in box 819 before he releases the PU. Having already established good communication with the EN, the MP would be assured that the instructions were received. However, the delay implicit in this approach makes it undesirable unless the situation is non-urgent.

c) Hybrid approaches involve giving as much of the instructions as possible in the moments while the PU is being detached from the SU. To facilitate this, a truncated version of the contents of box 819 (e.g. "Carry this unit to the victim's side as quickly as possible.") could first be given as the PU is being detached from the SU.

In Section 4.4.2, the calculation of the time for transportation of the PU to the victim is discussed. In that discussion and during the Sample Cardiac Arrest (Section 4.2, Table 11, Time 0:56 to 1:37), various estimates are made including a 2.5 mile per hour walk rate while carrying the PU and a 50 yard distance. These result in a hypothetical 41 second transport time. In actuality, both shorter and longer transport times will occur.

If the EN arrives at the victim before the completion of the MP's narration of the contents of box 819, the MP can: a) accelerate his delivery of the instructions; and/or b) truncate the contents (since some of the instructions may be repeated after the EN has arrived at the victim's side).

Box 820 contain additional dialog that would be appropriate—time permitting—during the transport of the PU to the victim. None of the dialog is absolutely essential, (orientation instructions for the PU having been given in box 819,) so that if the EN arrives at the victim before any or all of the contents of box 820 is completed, it can be deferred.

The enabler would have already given a very brief version of what he knows of the victim situation during EN's initial dialog with the MP. If there is time during PU transport, the MP may ask the EN for more information (if known) about either the victim's past medical history or the current victim situation. The MP may also ask whether the EN has had any experience in the administration of first aid. The MP gives assurance to the enabler, as indicated in box 820, that the MP can guide an inexperienced person through the steps needed to allow the assessment and treatment of the victim, and that an emergency medical team has been sent for. Orientation instructions for proper placement of the PU may be repeated at this time.

Figure 18:
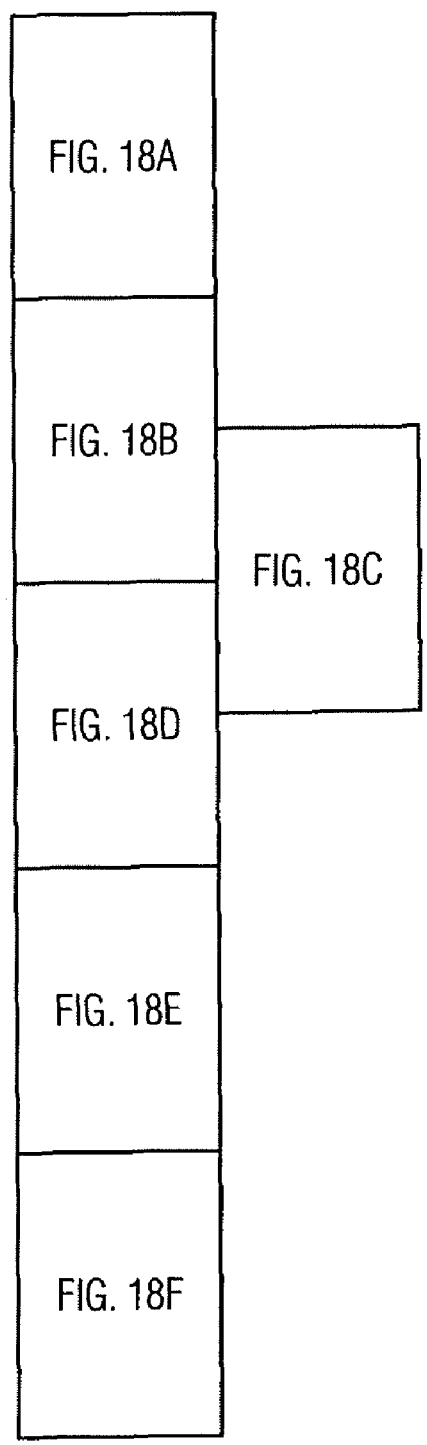
FIGS. 18A, 18B, 18C, 18D, 18E and 18F, taken together, are a flow chart showing voice and video instructions offered by the medical professional, and the medical professional's receipt of information and issuance of video control commands during the setup of the portable unit at the victim's side.

Following box 820, block 823B leads to FIG. 18, the flow diagrams showing PU arrival and setup.

5.4.2 PU Arrival at Victim; PU Setup 5.4.2.1 PU Touchdown and Video Setup

Figure 18A:
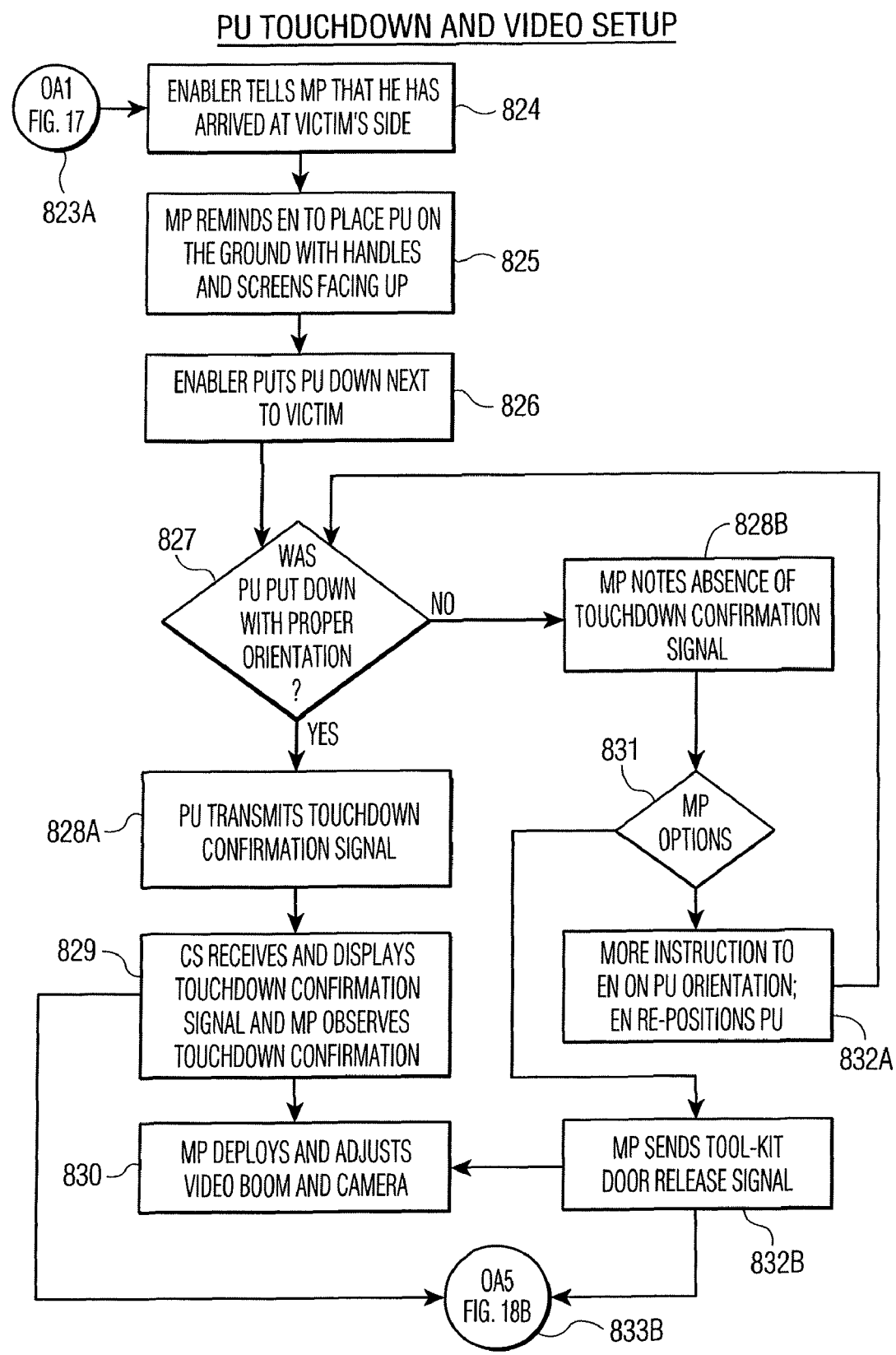

The flow diagram of FIG. 18A corresponds to the events which take place upon the arrival of the enabler with the PU, at the site of the victim.

The events it shows begin with block OA1 823A which follows block 823B (FIG. 17). In blocks 824, 825 and 826:
 a) The EN tells the MP that he has arrived at the victim;
 b) The MP reminds the EN of the proper method of placing the PU; and
 c) The EN puts the PU down next to the victim.

Blocks 824 and 825 are optional. Having previously been instructed in proper PU placement, the EN may perform this task on arrival without the dialog referred to in boxes 824 and 825.

If the PU was properly placed on a surface next to the victim (handles and screens facing upwards), block 827, the PU removal/touchdown sensors 178 (FIG. 8), acting like push-button switches, cause the PU to generate a touchdown confirmation signal (see Section 2.3). The touchdown information:
 a) causes the PU to release the lock which secures the PU tool-kit door 158 (FIGS. 6A and 6B); and
 b) is transmitted by the PU to the central station, block 828A, where it is displayed, on the Portable Unit Deployment Screen (see FIG. 27) and observed by the MP, block 829. These immediately aforementioned events occur from 1:41 to 1:42 during the Sample Cardiac Arrest (Table 11).

If, after the EN has placed the PU, the MP does not receive the touchdown confirmation signal, block 828B, he has two choices, block 831:
 a) He can quickly further instruct the EN in proper PU placement, block 832A, returning to block 827, where once again the issue of correct PU placement is addressed; or
 b) He can send a tool-kit door release signal, block 832B. If PU placement was sub-optimal and if audio communication between MP and EN is sub-optimal (discussed in the following section), preventing easy communication of placement instructions by the MP, the MP will choose to release the tool-kit door. The wireless headset contained in the tool-kit would then be available to the EN which would possibly facilitate communication and PU placement.

Once the MP is satisfied with PU placement, he can set up (block 830) the PU video camera. In a preferred embodiment these steps include:
 a) sending one or more signals to the PU to extend the video boom 112 (FIG. 6B) and to properly orient it (see discussion of FIG. 28) so that the MP can see the victim; and
 b) adjusting parameters of video quality such as brightness, contrast, focus, etc. (upper right hand portion of FIG. 28). Although the process of video camera adjustment is presented before the section on audio communication adjustment hereinbelow, the two adjustments would be performed simultaneously, in order to maximally shorten the resuscitation time.

Following the events described in this section, block 833B leads to block OA5 833A (FIG. 18B) at which time audio communication adjustments, if needed, are performed.

5.4.2.2 Audio Communications Adjustment, If Necessary 5.4.2.2.1 Audio Communications Overview Though MP may make audio adjustments at anytime during his exchange with the enabler or emergency personnel, the most likely times for such adjustments would be:
 a) immediately after the MP and the EN begin speaking;
 b) during the time that the EN is transporting the PU to the victim; and
 c) shortly after the of the EN and the PU arrive at the victim's side.

Adjustments of what the EN hears ("EN audio") may involve one or more of:
 a) increasing the audio volume by increasing the gain at the PU;
 b) various other electronic enhancements of EN audio such as:
  i) changing the emphasis of different audio frequency components at the PU;
  ii) changing the noise suppression at the PU;
  iii) changing the bandwidth allocation for EN audio;
  iv) changing type of modulation, channel or routing of EN audio; and
  v) changing EN audio signal processing at the CS end.
 c) switching from the PU speaker 146 and microphone 148 combination to a wireless headset 168 (FIG. 7A) in the PU tool-kit, and adjusting one or more of the parameters which affect the quality of EN headset audio.

Adjustments of what the MP hears ("MP audio") may involve one or more of:
 a) increasing the audio volume at the CS;
 b) various other electronic enhancements of MP audio such as:
  i) changing the emphasis of different audio frequency components at the CS;
  ii) changing the noise suppression at the CS;
  iii) changing the bandwidth allocation for MP audio;
  iv) changing type of modulation, channel or routing of MP audio; and
  v) changing audio signal processing at the PU end.
 c) switching from the PU speaker 146 and microphone 148 combination to a wireless headset 168 (FIG. 7A) in the PU tool-kit.

Figure 25:
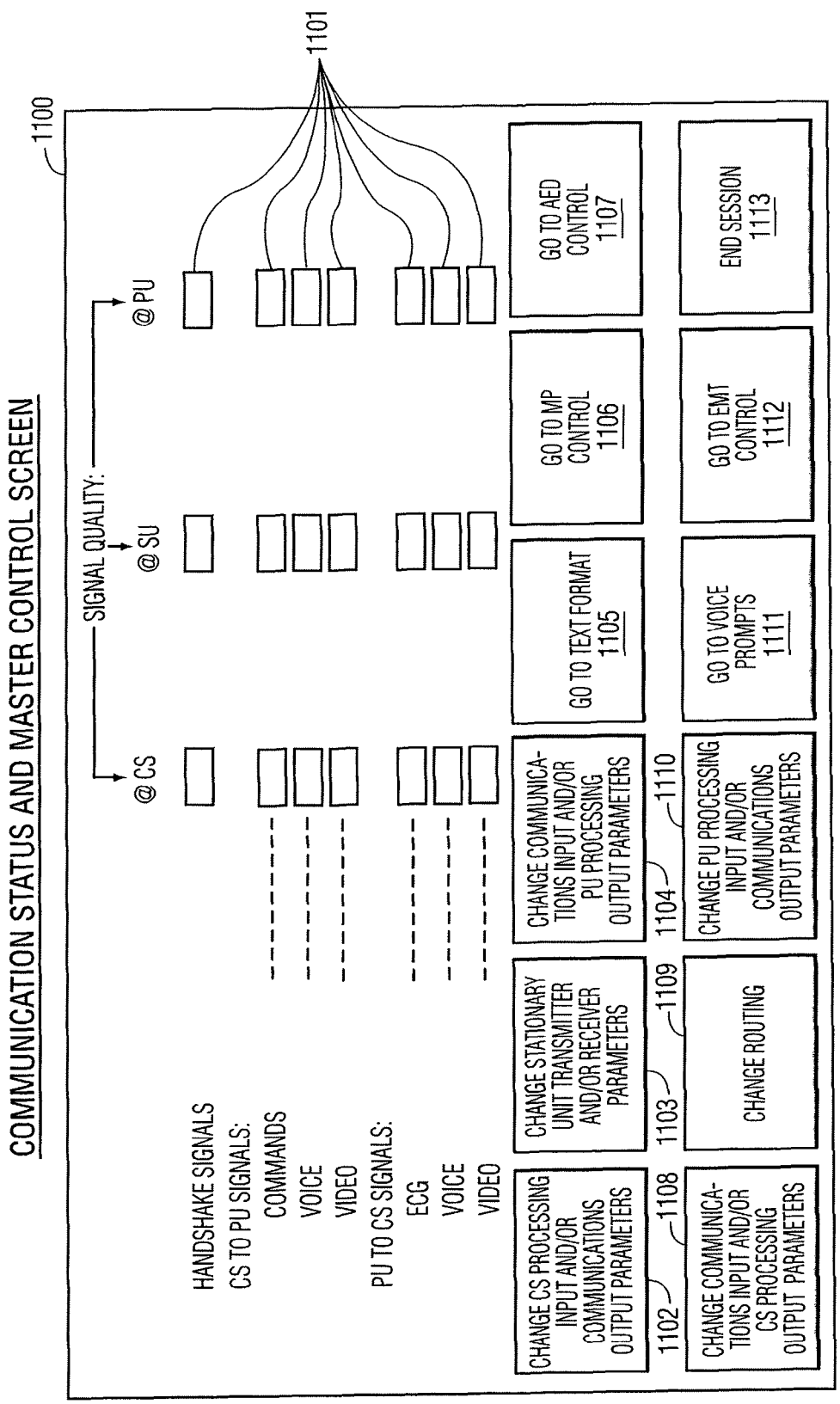
FIG. 25 illustrates a touch-sensitive display screen at the central station for assessing and controlling communication with portable and stationary units at remote sites.

The MP controls the above parameters by using the Communication and Master Control Screen shown in FIG. 25 (via menus such as "CHANGE CENTRAL STATION RECEIVER PARAMETERS" and "CHANGE PORTABLE UNIT RECEIVER PARAMETERS").

5.4.2.2.2 Audio Communications Flow Diagram Following PU Touchdown

Figure 18B:
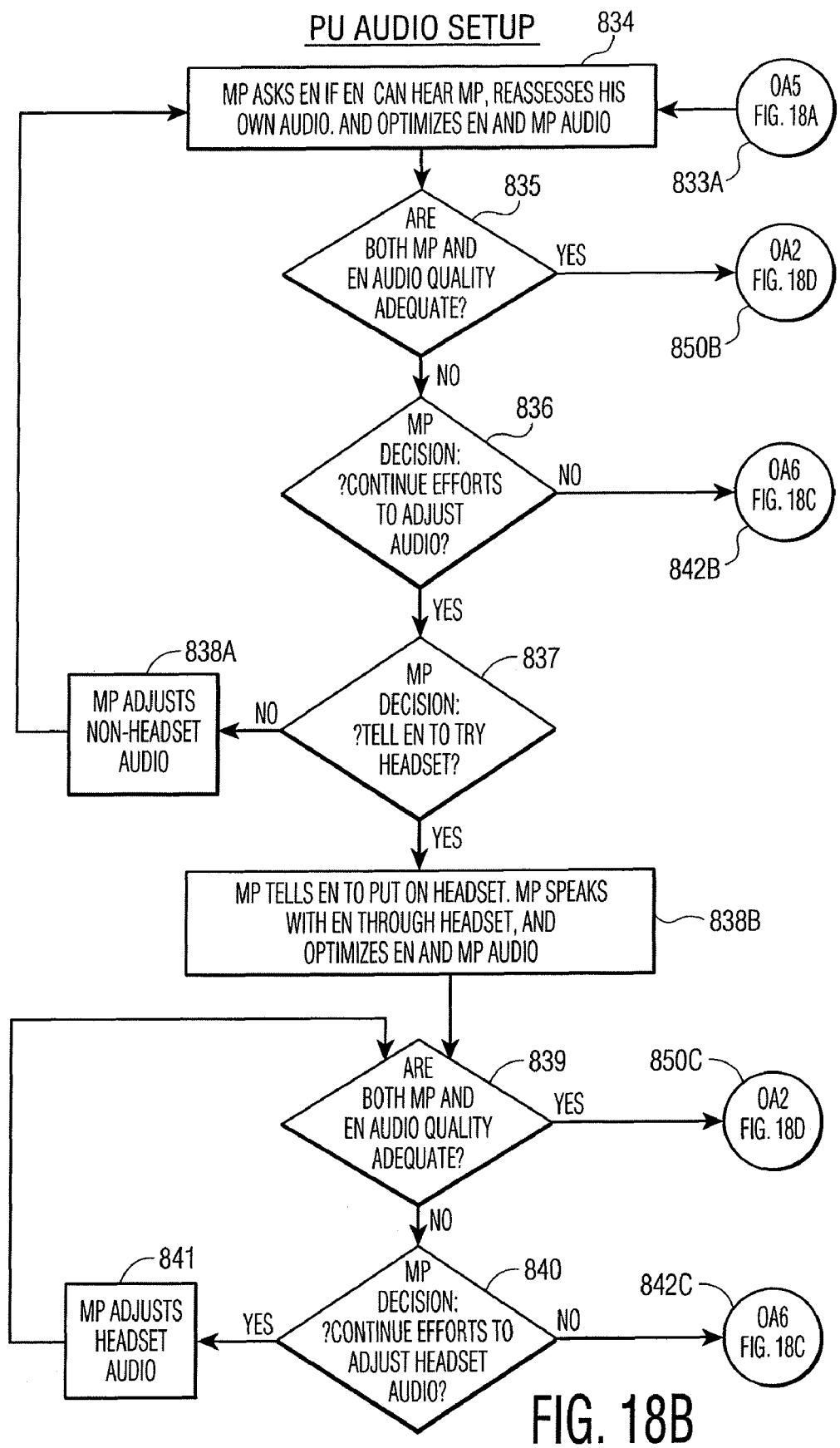

FIGS. 18B and C shows the communications adjustments when the PU is placed at the victim's side. Block OA5 833A (reached from block 833B, FIG. 18A) leads to block 834 where the MP:
 a) asks the enabler if he, the enabler can hear the MP well;
 b) optimizes EN audio;
 c) reassesses his own audio (i.e. MP audio); and
 d) optimizes his own audio.

Figure 18C:
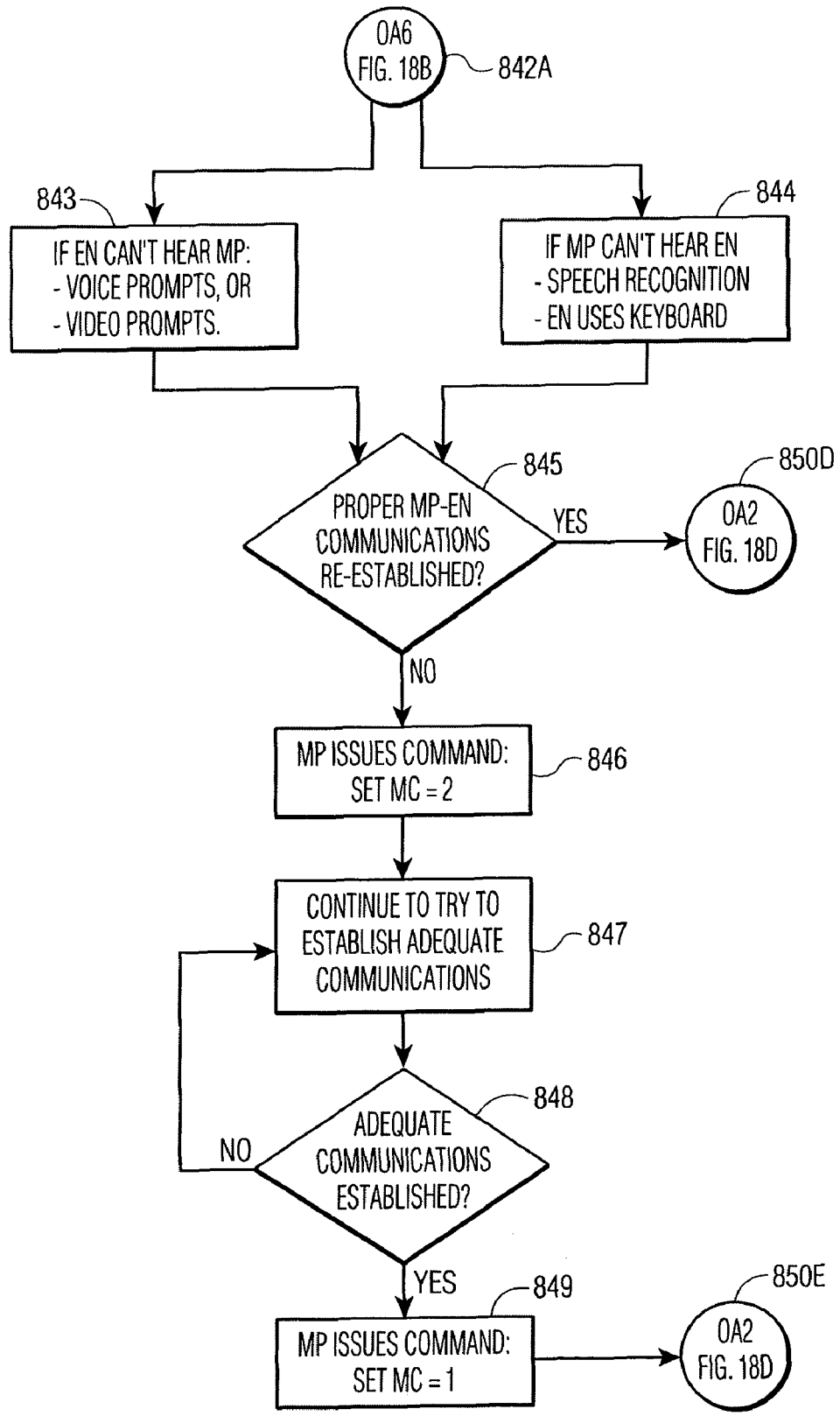
Figure 18D:
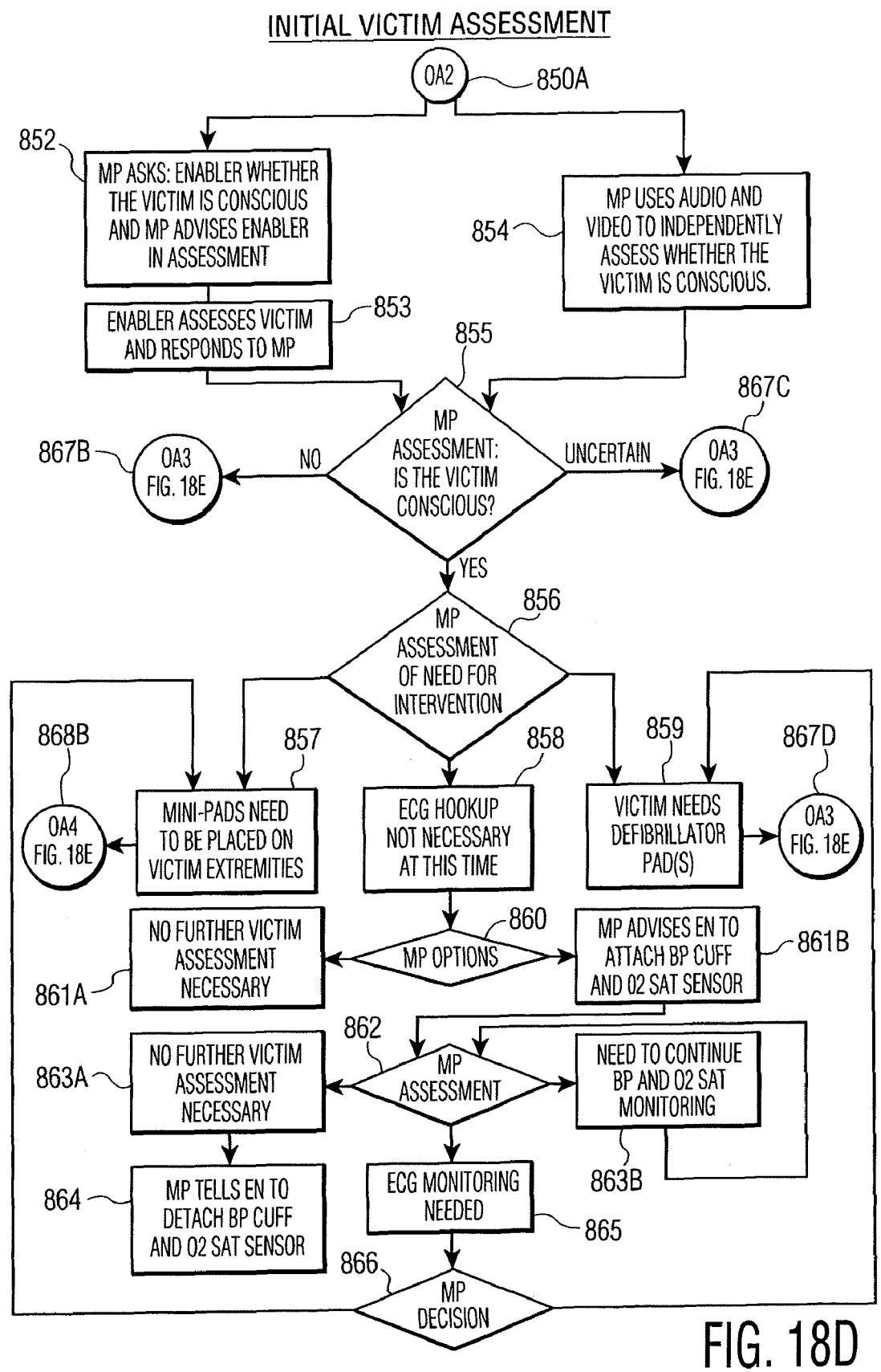

If both enabler and MP audio are adequate, block 835 leads to block 850B which leads to block OA2 850A of FIG. 18D, the beginning of victim assessment by the MP. If either the EN audio or the MP audio is inadequate, the MP, at block 836, decides whether to continue with efforts to adjust the audio. If he decides not to continue, block 836 leads to block 842B, then to block OA6 842A (FIG. 18C), which leads to non-audio communication methods. If he decides to continue with efforts to optimize audio, at block 837 he has the option of asking the EN to use the wireless headset. If the MP decides, instead, to continue to optimize the audio without resorting to the headset, block 837 leads to block 838A—an adjustment of one or more of the aforementioned audio parameters—which then leads back to block 834 and a reassessment of the audio quality.

The wireless headset contains both a microphone and one or two earphones. If, at block 837, the MP decides to have the EN utilize the wireless headset, the MP, at block 838B:

a) asks the EN to remove it from the toolkit and put it on;
 b) speaks with the EN through the headset; and
 c) optimizes both MP and enabler audio.

If both enabler and MP audio quality are then adequate, block 839 leads to block 850C which leads to block OA2 850A of FIG. 18D, the beginning of victim assessment by the MP. If either the EN audio or the MP audio is still inadequate, the MP, at block 840, decides whether to continue with efforts to adjust the headset audio. If he decides not to continue, block 840 leads to block 842C, then to block OA6 842A (FIG. 18C), which leads to non-audio communication methods. If he decides to continue with efforts to optimize audio, block 840 leads to block 841—an adjustment of one or more of the headset audio parameters—which then leads back to block 839 and a reassessment of the audio quality.

5.4.2.3 Non-Audio Communication Backups

If MP attempts to optimize audio communication with the enabler are unsuccessful, there are, in a preferred embodiment of the invention, multiple backup options, as indicated in FIG. 18C. If the MP was not able to optimize enabler audio and/or MP audio, blocks 842B and 842C (FIG. 18B) lead to block 842A (FIG. 18C). Then, if the enabler cannot hear the MP, block 843, the MP may use either voice prompts (prerecorded short messages held within the PU memory) or video prompts (text messages shown on PU screens 156 [FIG. 6A and right hand portion of FIG. 10]). If the MP cannot hear the enabler, block 844:

a) The MP can ask the enabler to respond to MP questions using a touch-sensitive screen based virtual keyboard 156 (see right hand portion of FIG. 11), where the enabler
  (i) provides yes/no responses (e.g. by touching "YES" 370 or "NO" 371 on the PU touch sensitive screen);
  (ii) answers questions in a multiple choice format (e.g. by touching "A", "B" or "C" 372 on the PU touch sensitive screen); or
  (iii) answers questions with text messages (e.g. by using a standard keyboard arrangement 369), if the yes/no or multiple choice formats are inadequate; or
 b) The MP can use speech recognition techniques, as are known in the art, using software which runs on the PU microprocessor (see below), and thereby encode the answers to MP questions, after which the coded response is transmitted to the CS.

If both EN audio and MP audio are inadequate, then the MP may use one of the techniques listed in block 843 and one of the techniques in block 844 to establish non-audio two-way communication.

Blocks 843 (EN non-audio options) and 844 (MP non-audio options) each lead to block 845. If the MP, is satisfied that proper two-way communication with the enabler is established (albeit non-audio communication in one or both directions), block 845 leads to block 850D, and then to block OA2 850A (FIG. 18D), the start of victim assessment.

If the MP is not satisfied with the communications, he sends a command to the PU which sets the master control unit 130 to state 2 (MC=2), block 846, which enables the AED/P i.e. the automatic external defibrillator/pacer. This allows the PU to function without MP guidance (see Section 1.3.1.2), in a manner known in the art. During the time that the PU is functioning in this automatic mode: a) the MP continues to try to establish a better communications link with the enabler, block 847; and b) the MP may monitor PU activity, including ECG and AED activity, if these are transmitted to him with adequate quality.

If adequate two-way communication between the MP and the enabler is later established, block 848, the MP sends a command to the PU which sets the master control unit to state 1 (MC=1), block 849, which disables the AED/P and returns control of the PU to the MP. This leads to block 850E, block OA2 850A and victim assessment. If, however, during the period of communication blackout the AED/P-directed resuscitation effort had proceeded to a point beyond initial victim assessment (e.g. to ECG analysis or defibrillation therapy), then block 849 would lead to the appropriate later point in the flow diagrams (e.g. block G 900A [FIG. 19] or block M 914A [FIG. 20]).

As long as proper two-way communication between the MP and the enabler is not reestablished, the effort to do so goes on, with block 848 leading back to 847, and again to 848, in a continuously repeating "loop".

The aforementioned is not intended to represent the only possible sequence of steps in the establishment of non-audio communication. Other options include but are not limited to:

a) not attempting any of the non-audio communication means delineated in blocks 843 and 844;
 b) attempting some but not all of the non-audio communication means delineated in blocks 843 and 844; and
 c) having block 848 lead back to block 834 (FIG. 18B).

5.4.2.4 Initial Victim Assessment

The medical treatment of a conscious person is far different than that of an unconscious one and therefore, the MP must determine the victim's state of consciousness.

After having established that his communication is adequate block OA2 850A, the MP determines the victim state of consciousness by asking the enabler 852 and using both the enabler response 853 along with his own assessment 854. If the victim is unconscious or if there is uncertainty about his state of consciousness, block 855 leads to 867B or 867C, each of which leads to block OA3 867C and defibrillator pad application.

If the victim is conscious, block 856 leads to three possible MP choices:

a) He can decide 857 that ECG electrodes, "mini-pads" should be placed on the victim's extremities so that an ECG can be recorded to further assess the victim. Block 868B leads to block OA4 868A, FIG. 18E.

b) He can decide 859 that the victim is, despite being conscious, potentially in need of a shock or pacing, either at that time or in the near future, and that therefore application of a standard pacing/defibrillation pad is in order. Block 867D leads to block OA3 867A, FIG. 18E.

c) He can decide 858 that ECG hookup is unnecessary, at which point his options 860 include either the termination of victim assessment 861A or an assessment of the victim's blood pressure and/or oxygen saturation. In case of the latter, he advises and instructs the enabler 861B in the attachment of these devices (located in the PU tool-kit). Once he obtains this additional information he decides 862 either (i) that no further victim assessment is needed 863A, (ii) that a continued period of blood pressure and/or oxygen saturation is needed 863B, returning to 862 (and ongoing reassessment until he decides otherwise or the victims condition changes), or (iii) that ECG monitoring is now needed 865, in which case he must further decide 866 if the electrode pads are to be mini-pads, block 857 leading to blocks 868B and OA4 868A, or standard defibrillator pads, block 859 leading to 867D to OA3 867A.

5.4.2.5 Electrode Pad Application

Figure 18E:
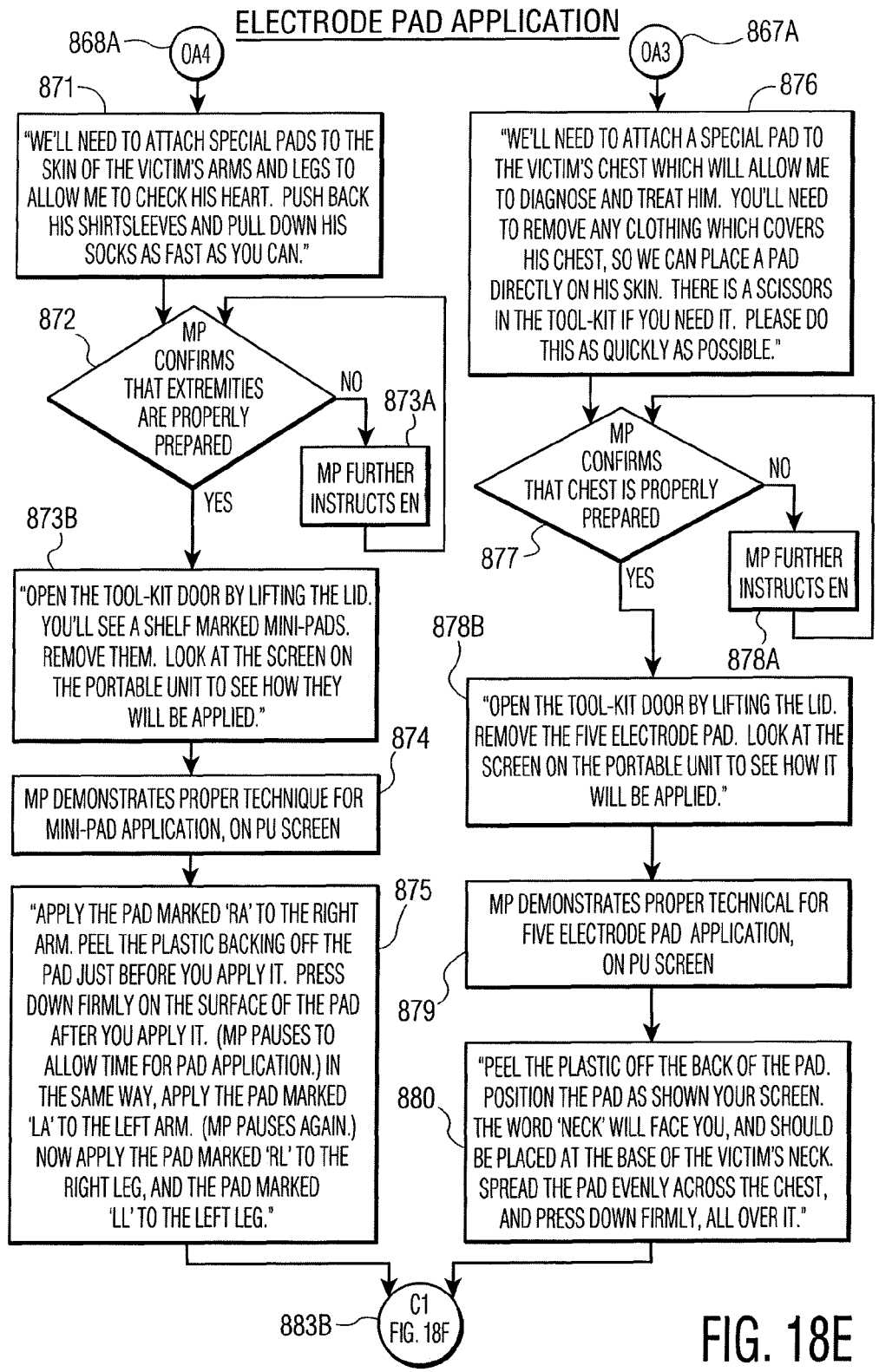
Figure 18F:
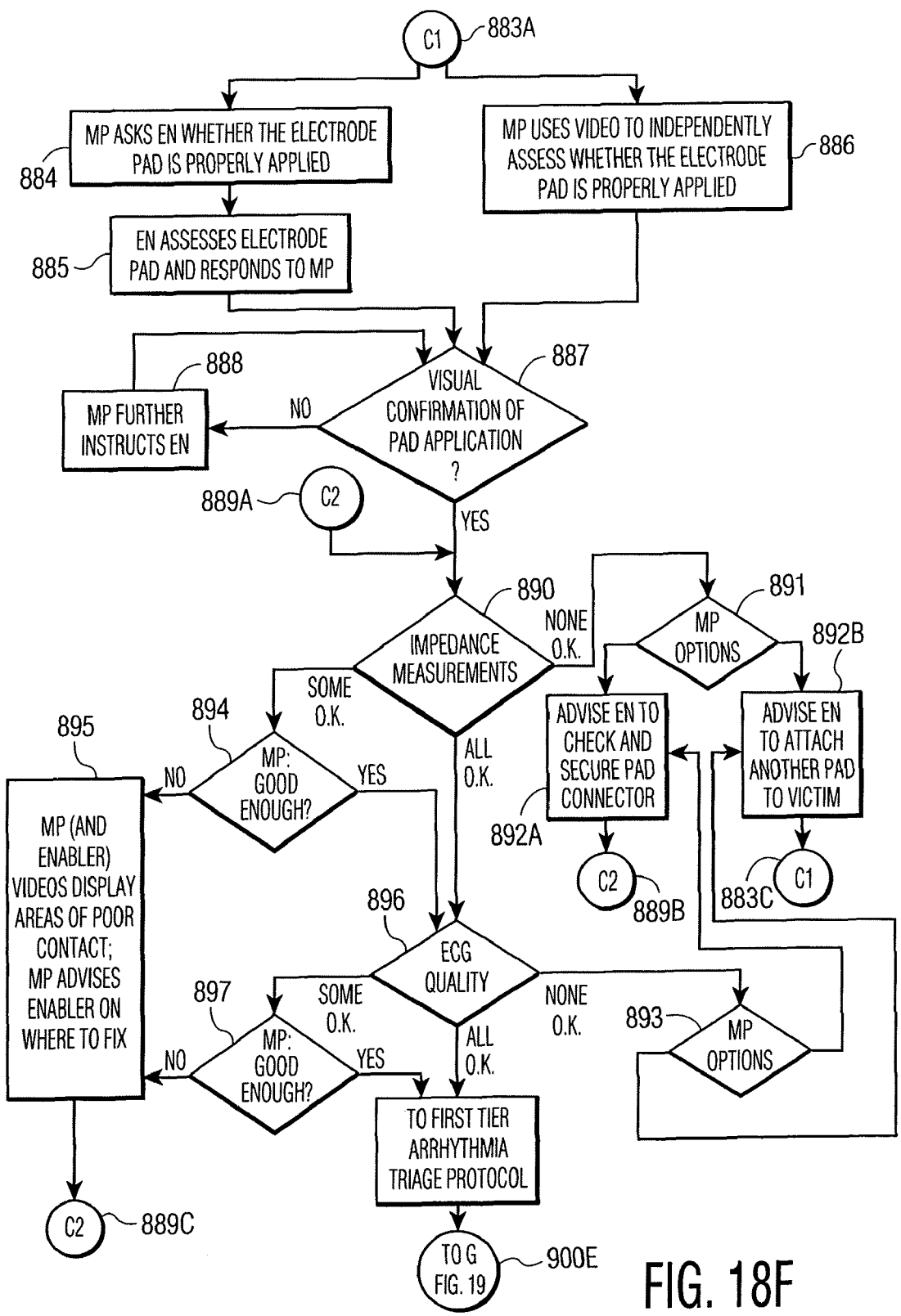

FIG. 18E shows two algorithms for electrode pad application, in a parallel display format. The left side of the figure shows mini-pad application; The right side shows standard defibrillation pad application. The instruction procedure for each is similar.

The MP starts by telling the enabler of the task (baring the extremities [in the case of mini-pads] or the chest [in the case of standard defibrillating/pacing pads) to be performed, blocks 871 (in the case of mini-pads) and 876 (in the case of large pads). The MP then checks, either by asking or by direct visual observation, that the task has been performed, blocks 872 and 877. If performance is unsatisfactory, he provides further instruction, blocks 873A and 878A and continues to repeat the cycle of instruction and evaluation until he is satisfied. The MP then advises the enabler to open the PU toolkit and remove the appropriate pad, blocks 873B and 878B. The MP demonstrates proper pad application for the enabler on the PU screen, blocks 874 and 879 (see below, Section 6.2.2 and FIG. 28). The MP verbal or text instruction for pad application is shown in blocks 875 and 880.

With the pad(s) having been applied, the two paths through the flow diagrams reunite at block 883B and proceed to the electrode pad assessment. If at any point, the heart rhythm or clinical status of a victim with mini-pads deteriorates, the application of defibrillation pad(s) would be a consideration, necessitating a second pass through the electrode pad application routine, this time starting at block OA3 867A.

5.4.2.6 Electrode Pad Assessment

The assessment begins with visual assessment of the adequacy of pad application. The MP proceeds by asking the enabler 884 and using both the enabler response 885 along with his own visual assessment 886. If, block 887, pad application is grossly inadequate, the MP further instructs the enabler 888, then visually reassesses pad application and the cycle repeats until the MP is satisfied. When the MP is satisfied, impedance measurements are made 890 to assess the pad electrically, with three possible outcomes:

a) If the measurements are all satisfactory, the MP assesses ECG quality 896. If satisfactory, he goes ahead to the first tier arrhythmia triage protocol via block 900E. If only some are satisfactory, he decides 897 either (i) that the situation is "good enough", feeling that the extra time expenditure to achieve a better result is not likely to be justified, and proceeds to block 900E, or (ii) that he will ask the enabler to improve pad application. If so, he may use the impedance measurements and/or ECG signal quality to identify one or more areas which are making poor contact, and either let the enabler know the location or, block 895, show him on the PU screens. This leads to block 889C, to block C2 889A and a reassessment of impedance measurements. If none of the measurements is satisfactory, he decides 893 either (i) to advise the enabler to check and secure the pad connector, block 892A to block 889B to block C2 889A and a reassessment of impedance, or (ii) to advise the enabler to attach another electrode pad, block 892B to block 883C to block C1 883A.

b) If only some of the initial impedance measurements were satisfactory, block 894, the MP decides whether they are good enough. If yes, this leads to block 896 and the aforementioned assessment of ECG quality. If no, this leads to block 895 and the aforementioned assessment of specific areas of poor pad contact.

c) If none of the initial impedance measurements were adequate, block 891 leads to either block 892A or block 892B at which time the MP makes the same decision as when none of the ECG tracings were adequate.

In practice, the aforementioned sequence of steps can happen very quickly. If pad application was done well, the chance of a satisfactory quality ECG is high. If ECG quality is high from the start, a streamlined approach could skip the visual assessment and/or the impedance measurements. However, the pad application requirements for optimum defibrillation exceed those required for ECG recording.

5.5 Flow Diagrams: Arrhythmia Management 5.5.1 First Tier Arrhythmia Triage Protocol 5.5.1.1 Overview FIG. 19, the First Tier Arrhythmia Triage Protocol, shows an approach to MP decision making in the moments immediately after the electrocardiogram information becomes available to him. (Other approaches to this tier of triage are possible, see Section 5.5.1.3, below.)

Hereinbelow, a rhythm which is paced by the victim's own pacemaker or implantable defibrillator is classified and referred to as either normal/nearly normal, or bradycardia, based on the resulting rate. "Pacing" or "a paced rhythm", unless otherwise specified, refers to external pacing. Although the traditional electrocardiographic definitions of bradycardia (rate less than 60) and tachycardia (rate greater than 100) are possible set-points, the MP is ultimately guided by his judgment, as to whether to classify a rhythm as a bradycardia or tachycardia. A well tolerated rate of bradycardia or tachycardia would not necessitate treatment.

Figure 19:
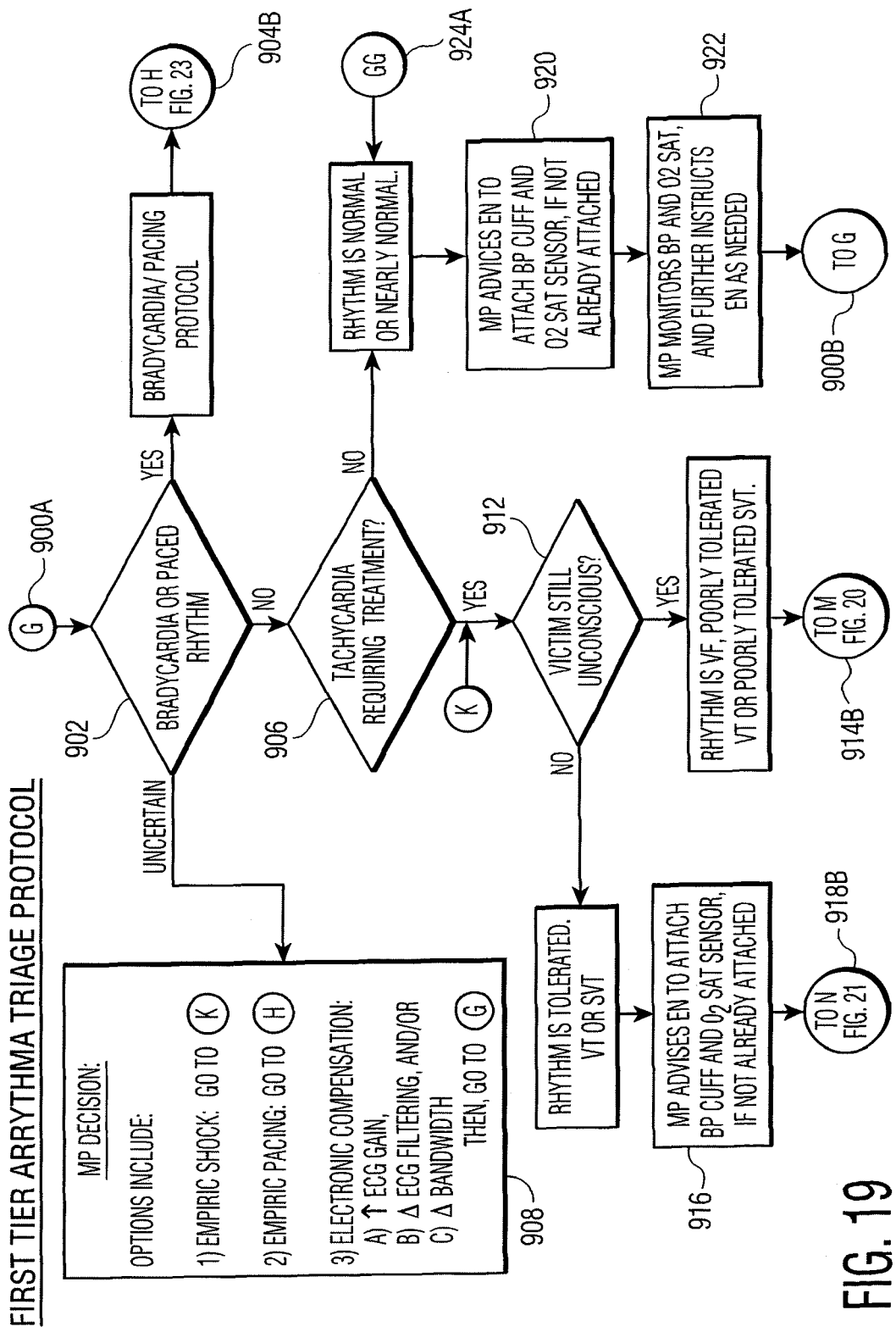
FIG. 19 is a flow diagram illustrating the medical professional's process of heart rhythm analysis based on a victim's ECG during a medical emergency.
Figure 20:
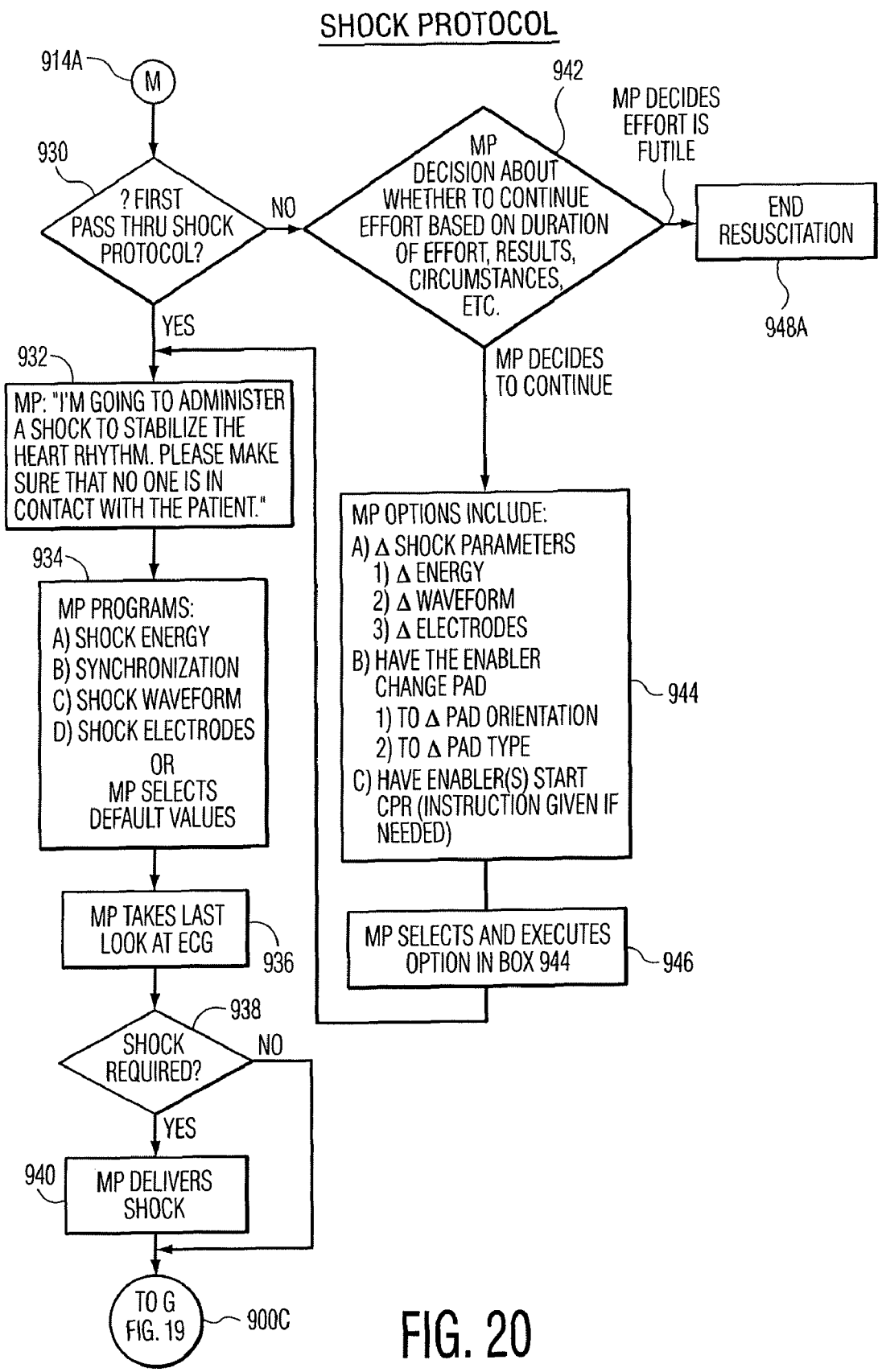
FIG. 20 is a flow chart of the medical professional's protocol for treating ventricular fibrillation and ventricular tachycardia.
Figure 22:
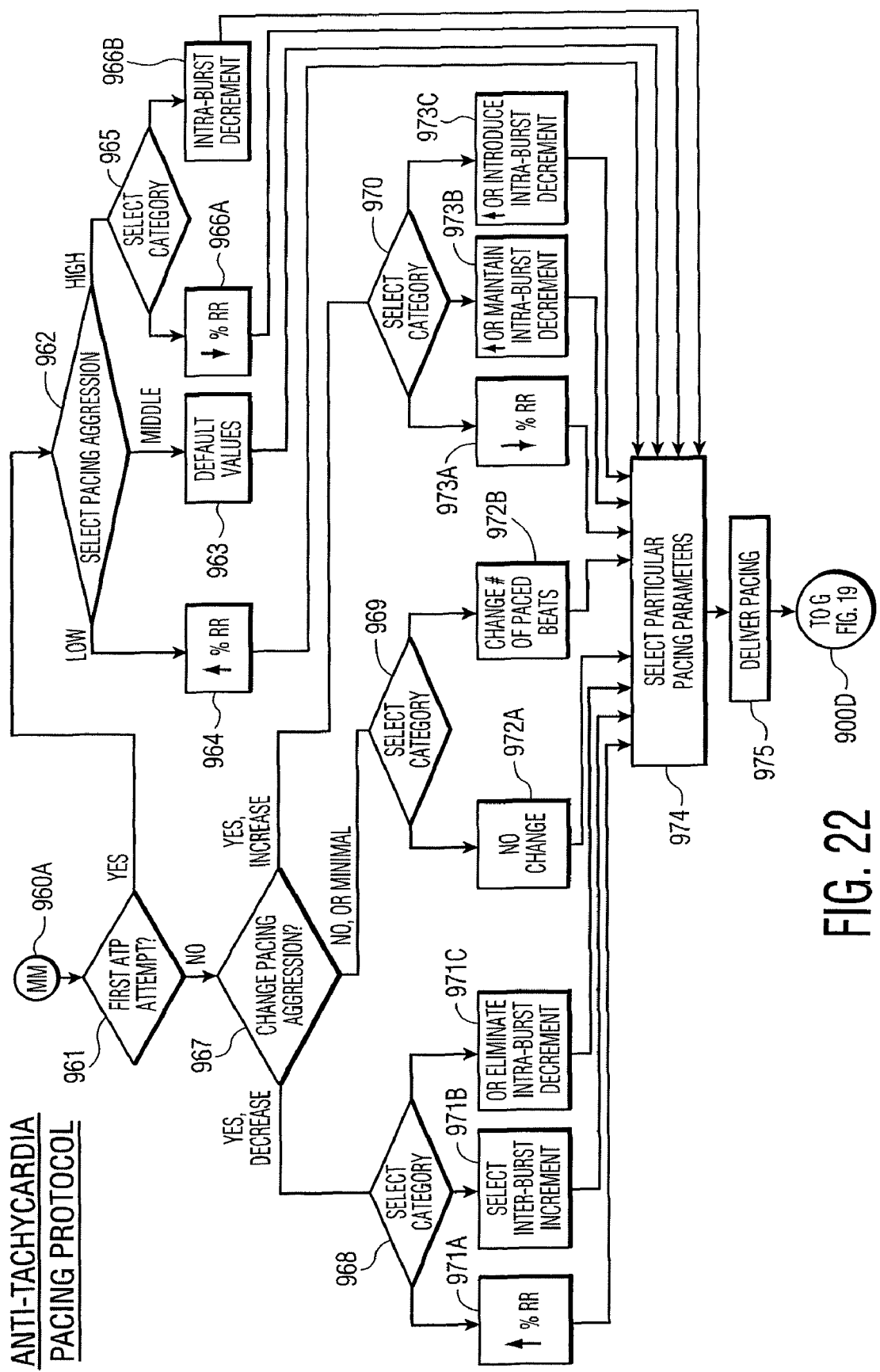
FIG. 22 is a flow chart of the medical professional's protocol for treating tachycardia with anti-tachycardia pacing.

There are two inputs to FIG. 19. The principal input is block G 900A, which is arrived at from FIG. 18C, after a successful electrode pad application to the victim results in a satisfactory quality ECG. The MP then interprets the ECG, leading to five possible outcomes:

a) bradycardia or an externally paced rhythm (leads to FIG. 21);

b) a tachycardia requiring a shock, i.e. ventricular fibrillation (VF), poorly tolerated ventricular tachycardia (VT) or poorly tolerated supraventricular tachycardia (SVT) (leads to FIG. 20);

c) a well tolerated tachycardia not requiring a shock (leads to FIG. 22);

d) a normal or near normal rhythm;

e) a rhythm which can not be interpreted in an unequivocal manner, either because of sub-optimal signal quality, or because even a perfect electronic representation of the rhythm would still result in equivocation.

Each of the first three outcomes leads to a different flow diagram, see below. A normal rhythm results in continued looping through FIG. 19, as the MP continuously monitors the victim's rhythm after the initial assessment of it. If the rhythm is not unequivocally interpretable, the MP has a variety of choices which are discussed below.

The second input to FIG. 19 is block GG 924A. If the victim has a bradycardia which does not require treatment, then the Bradycardia/Pacing Protocol (FIG. 23 [entered from block 904B of FIG. 19]) leads back to FIG. 19 via block GG 924A. Further monitoring of such a "nearly normal" rhythm is discussed below.

5.5.1.2 Details of Arrhythmia Triage 5.5.1.2.1 Bradycardia/Paced Rhythm Decision The availability of an ECG signal leads to block G 900A, which leads to block 902 at which the MP decides if the rhythm is a bradycardia or a paced rhythm. There are three possible outcomes:

a) If it is either a bradycardia or a paced rhythm, the MP goes to the Bradycardia/Pacing Protocol (FIG. 21), as indicated by block 904B.

b) If it is neither a bradycardia nor a paced rhythm, the MP proceeds to block 906 for a tachycardia triage decision, discussed (see Section 5.5.1.2.2, below).

c) If the rhythm is uncertain the MP chooses from three options, shown in box 908 (see Section 5.5.1.2.3, below).

5.5.1.2.2 Tachycardia/No Tachycardia Decision

At block 906, the MP decides if the rhythm is either a tachycardia which requires treatment, or a rhythm which is normal, or nearly normal and which therefore requires no treatment.

If the rhythm is a tachycardia which requires treatment, the MP—at block 912—quickly reassesses whether the victim is conscious or unconscious, since one generally does not wish to administer a shock to a conscious victim. The MP performs this assessment by either speaking with the enabler, by making his own audio and video observations (FIG. 18D), or both. In cases where the rhythm is either VF, poorly tolerated VT, or poorly tolerated SVT, the victim will be unconscious and the MP proceeds to the Shock Administration Protocol, FIG. 20, via block 914B.

If the victim is conscious during a tachycardia (in which case it cannot, for all practical purposes, be VF), the MP—at block 916—instructs the enabler in the attachment of the blood pressure cuff and blood oxygen saturation sensor. (If the enabler has already performed this, i.e. during a previous pass through the protocol, the step in block 916 is skipped. The MP then proceeds to the Second Tier Arrhythmia Triage Protocol, FIG. 22, via block 918B.

If, at block 906, the MP decides that the rhythm requires no treatment at that moment, the rhythm is classified as normal or nearly normal. The MP—at block 920—instructs the enabler in the attachment of the blood pressure cuff and blood oxygen saturation sensor. (The step in block 920 is skipped if these devices have been previously attached.) Next, as shown in block 922, the MP further instructs the enabler, if necessary, (e.g. in the administration of CPR) and continues to monitor the victim's ECG. The protocol for continued monitoring is identical to the aforementioned, and, accordingly the flow diagram indicates a return to block G 900A via block 900B.

5.5.1.2.3 Options in the Event that the Rhythm Diagnosis is Uncertain

If the MP, upon initially analyzing the ECG, is uncertain as to the correct rhythm diagnosis, he may either make an empiric decision to treat based on his best guess as to the rhythm diagnosis, or he may take steps to improve the signal quality and then attempt diagnosis again. In the case of an empiric decision to treat, if the MP thinks that the rhythm is most likely to be either VF, VT or SVT (choice #1 in box 908) he would proceed to block K 910, in preparation for treatment; If the MP thinks that the rhythm is most likely to be a bradycardia (choice #2 in box 908), he would proceed to the Bradycardia/Pacing Protocol, FIG. 21, via block 904B. If the MP wishes to try to electronically improve the signal quality before making his rhythm assessment (choice #3 in box 908), he has a number of options including:

i) increasing the ECG gain at a number of possible points in the system including within the PU, within the SU or within the central station;

ii) changing the ECG signal filtering at any of the aforementioned points within the system; alternatively the MP could use other noise reduction techniques to improve signal quality; and/or, iii) improving signal quality by causing the PU to sample the signal more frequently, or to use a greater number of bits per sample, and, if necessary, to allocate a greater bandwidth for the ECG signal, or to use other techniques as are known in the art to allow for the transmission of a greater amount of ECG information from the PU to the CS.

If the MP decides to improve signal quality, he then returns to block G 900A and reassesses the ECG.

5.5.1.3 Other Approaches to First Tier Arrhythmia Triage

The first tier of arrhythmia triage shown in FIG. 19 and discussed above is subject to a number of variations Possible variations include:

a) having the MP make the tachycardia/no tachycardia decision before the bradycardia/no bradycardia decision;

b) having the MP make one single selection among four choices: bradycardia, tachycardia, normal/nearly normal rhythm, or uncertain rhythm; rather than making the selection—as shown in FIG. 19—in two steps;

c) having the MP make one single selection among five choices: bradycardia, poorly tolerated tachycardia, well tolerated tachycardia, normal/nearly normal rhythm, or uncertain rhythm; rather than making the selection—as shown in FIG. 19—in three steps; and d) merging the first tier and second tier (see below) components of arrhythmia triage.

5.5.2 Shock Administration Protocol

The Shock Administration Protocol is shown in FIG. 20. The MP reaches the entry point to this protocol, block M 914A from block 914B, FIG. 19, the First Tier Arrhythmia Triage Protocol.

If it is the first pass through this protocol (indicated at block 930), the MP warns the enabler that a shock is coming and that neither he nor anyone else should be in direct contact with the victim (indicated at block 932). As indicated in block 934, the MP then programs the parameters that specify the shock (see below, Section 6.3.1.2 and FIG. 33) by selecting either the default choices or by selecting specific choices of energy, synchronization, waveform and electrode pattern. The MP then takes a last look at the ECG (block 936) to make sure that the rhythm has not spontaneously changed to one which does not require a shock. If the rhythm is unchanged (block 938), the MP then administers the shock (block 940). Following shock administration, the MP must reassess the rhythm, indicated by block G 900C (which leads to block G 900A at the top of FIG. 19, the First Tier Arrhythmia Triage Protocol). If, at block 938, the MP did observe a last-moment change in the rhythm, he does not administer the shock, and thus bypasses block 940, and, in the flow diagram, is returned to the start of the First Tier Arrhythmia Treatment Protocol.

If one or more shocks have already been administered, and the shock protocol is re-entered because of VF, poorly tolerated VT or poorly tolerated SVT, then block 930 leads to block 942. At block 942 the MP will need to make a decision about whether continued efforts to resuscitate a victim are to be pursued.

The decision to continue resuscitative efforts leads to box 944, which includes a variety of MP options:

a) changing the shock parameters by
  (i) changing the energy of the shock,
  (ii) changing the shock waveform, or
  (iii) changing the choice of shock electrodes;
b) having the enabler change the electrode pad:
  (i) by removing the currently applied ones and reapplying a new one of the same type, but having the pad positioned or oriented differently from the removed pad, or (ii) by removing the currently applied one, and reapplying a different type of pad or pads; and, c) having the enabler start cardiopulmonary resuscitation (CPR) under the guidance of the MP.

At block 946, the MP selects one of these options and causes its execution by inputting the appropriate commands (see Section 6.3.1.2). This leads back to block 932, in which the MP warns the enabler that he is about to administer a shock.

If, at block 942, the MP had decided not to continue with resuscitative efforts, the rhythm assessment and treatment protocols end at block 948A. The MP would consider making a decision to terminate therapy if he was repeatedly unsuccessful in his efforts to terminate a tachycardia which does not support life, if reasonable treatment options had been exhausted, and if neither medical nor emergency personnel were on-scene nor were expected to arrive on scene. The MP is much better qualified to make this termination decision than an enabler using an AED would be. (See below, Sections 5.5.5.2, 5.5.5.3 and especially 5.5.5.4, for a discussion of protocol endpoint considerations in the event of failure of pacing.)

5.5.3 Second Tier Arrhythmia Triage Protocol
5.5.3.1 Overview

FIG. 21, the Second Tier Arrhythmia Triage Protocol, shows an approach to MP decision making in the event of a well tolerated tachycardia. There are two reasons why the MP might want to consider a therapy other than a high energy shock (referred to in the figure as "Hi Shock" {ok?}) if the victim is tolerating the tachycardia First, a high energy shock is painful, and therefore is something to be avoided, if possible, in the case of a conscious or semi-conscious victim. Second, the presence of a well tolerated tachycardia implies that the urgency for immediate termination of the tachycardia is lessened. In the case of ventricular fibrillation or poorly tolerated ventricular tachycardia, the need for immediate restoration of a normal rhythm is based on the exquisitely time-sensitive consequences of inadequate blood flow to the brain (and is based, to a lesser degree, on other considerations including blood flow to the heart muscle and shifts in pH and potassium). But in the case of a well tolerated tachycardia, the blood flow to the brain and vital organs may be normal or near normal, in which case gentler tachycardia termination measures, though potentially more time consuming, are a reasonable alternative to the hi energy shock.

5.5.3.2 Alternative Tachycardia Termination Techniques

There are four means of tachycardia termination other than a high energy shock:

a) For certain tachycardias, viz. atrial flutter and some forms of monomorphic VT, a low energy shock (referred to in FIG. 21 as "Lo Shock") will effectively terminate the tachycardia. Shock energy values of 25 joules often lead to success, and values as low as ten or fewer joules may be successful; These are to be compared with values such as 200 joules for a high energy shock. Although the victim's discomfort associated with a low energy shock is not necessarily decreased in proportion to the energy reduction (i.e. a 10 joule shock seems to be more than one tenth as painful as a 100 joule shock), the lower energy shock may afford some reduction in discomfort.

b) Anti-tachycardia pacing is a means of tachycardia termination that involves stimulating the heart at a rate which is different (and generally faster) than the tachycardia rate. This is generally performed for a few seconds at a time, and entails energy application that is orders of magnitude less than a defibrillation shock. It may require multiple attempts (see below) and therefore is more time consuming than either a high or low energy shock. (See Section 5.5.4.1, below.)

c) Certain types of supraventricular tachycardia (and atrioventricular reciprocating tachycardia) may terminate if the victim performs or is subjected to so-called "vagal maneuvers," i.e. procedures which momentarily alter the extent of vagal stimulation of the heart. These include coughing, the Valsalva maneuver, ice water application to the face, and other techniques. The MP has the option of suggesting one or more of these if he feels that they are appropriate. The suggestion may be made to the enabler or, if appropriate, directly to the victim. When appropriately trained emergency medical personnel are present, the MP may suggest the performance of carotid sinus massage as another possible means of tachycardia termination.

d) Trained emergency medical personnel, once they have established intravenous access, may administer certain antiarrhythmic drugs (discussed above) which may terminate a variety of different tachycardias. The MP, as discussed above, may suggest such therapy.

5.5.3.3 The MP's Assessment of the Appropriateness of the Use of Alternative Tachycardia Termination Techniques Physicians and other medical professionals dealing with a tachycardia victim will assess the urgency of treatment by evaluating such basic parameters as the victim's state of consciousness, the respiratory status and the blood pressure. Additional considerations are the heart rate, cardiac output, the duration of tachycardia, the victim's cardiac history and recent cardiac status (if known), whether the victim appears to be ashen or cyanotic, whether the victim is diaphoretic and the presence or absence of ischemic findings on the ECG. The better the victim is tolerating the tachycardia—in the opinion of the MP—the more latitude the MP has to continue to pursue alternative, i.e. non-aggressive means of tachycardia termination.

The MP will continually reassess tachycardia toleration for the duration of time that he pursues non-aggressive means; If at any point the victim becomes less tolerant of the tachycardia, the MP would have the option of switching to a more aggressive means of tachycardia termination (such as a high energy shock).

The ideal situation for less aggressive therapy would be:
a) conscious victim;
b) adequate respiratory status;
c) adequate blood pressure;
d) heart rate less than 200 BPM;
e) minimally reduced cardiac output demonstrated by the findings of a cardiac output sensor;
f) short duration of tachycardia;
g) no history of heart attack or heart failure;
h) no pallor, cyanosis or diaphoresis; and,
i) no signs of ischemia on the ECG.

As indicated above in Section 5.5.1.2.2, the MP assesses the victim's state of consciousness either directly or by asking the enabler.

The respiratory status is assessed by oxygen saturation sensor 174 (FIG. 7A)—included in the toolkit of the PU, and put on a finger of the victim, by the enabler, under the direction of the MP. Alternative means for assessing the respiratory status include:

a) a carbon dioxide sensor;
b) assessing the respiratory rate and the presence or absence of pallor or cyanosis by direct visual inspection via the video camera;
c) assessing the respiratory rate by asking the enabler;
d) assessing the respiratory status by measuring transthoracic impedance Pallor, cyanosis and/or diaphoresis may be assessed via the video camera or by questioning the enabler, or both.

The blood pressure is assessed by using an automatically inflating blood pressure cuff 172 (FIG. 7A). The cardiac output may also be assessed by non-invasive means, as are known in the art. The heart rate is assessed by the ECG, which also provides information about ischemia and sets a lower limit to the duration of tachycardia. Information from the enabler or other bystanders may provide additional information about tachycardia duration. These individuals may also provide information about the victim's cardiac history, if any.

In practice, the MP would use as many of the aforementioned types of information as was available, in making a decision about the appropriateness of one of the less aggressive therapies.

Algorithms for selecting the appropriate technique for tachycardia termination, incorporating the aforementioned information, are potentially of extraordinary complexity, since a) there is potentially a large amount of victim related information, and b) the total experience of the MP, as well as information on arrest management and outcomes, which may be accumulating data bases may also influence the MP decisions. One possible algorithm, based on three very important parameters, is illustrated and discussed in the next section.

5.5.3.4 Algorithm for Considering Alternative Tachycardia Termination Techniques Based on State of Consciousness, Respiratory Status and Blood Pressure The MP reaches this algorithm, shown in box 950 (FIG. 21) from the First Tier Arrhythmia Triage Protocol in the event of a tolerated tachycardia, via the sequence of blocks 912, 916 and 918B (all in FIG. 19); leading to block 918A of FIG. 21.

The lower portion of FIG. 21 shows a method of the assignment of a grade of 0, 1 or 2 for each of the aforementioned three victim parameters. Section 5.5.3.3 discusses how the MP obtains the information needed to make these assignments. Once a grade is assigned for each of these three parameters, the algorithm in box 950 indicates the assignment of one or two possible therapies. Where a choice between two types of therapy is possible, e.g. ATP/Lo Shock (where the MP may choose either ATP or a low energy shock), the MP uses his discretion (and/or some or all of the additional information previously discussed) to decide between the two choices.

For example, if the victim was alert (Consciousness Grade=2), had an oxygen saturation of 85% (Respiration Grade=2) and had a systolic blood pressure of 80 (B.P. Grade=1), the MP approach indicated by box 950 would be to attempt ATP, anti-tachycardia pacing.

The MP thereby selects one of three therapeutic aproaches, a high energy shock, a low energy shock or ATP. At block 952, the MP selects the details of the treatment (e.g. the number of joules, in the case of a shock). If ATP has been selected, block 954 leads to block 960B which leads to block MM 960A (FIG. 22), the Anti-tachycardia pacing Protocol. If ATP has not been selected, block 954 leads to block 914C which leads to block M 914A, the Shock Administration Protocol.

If the initial therapy administered per the above protocol does not terminate the tachycardia, but does result in more well tolerated tachycardia, the algorithm again leads to box 950, and a reassessment of the appropriateness of the various alternative therapies. Although box 950 contains a large amount of information, the repeat assignment of the grades for consciousness, respiration and blood pressure can generally be performed very quickly. (The large amount of information in the box thus reflects the complexity entailed in reducing decision making to an algorithm.)

Many different types of algorithms are possible besides the one shown in FIG. 21:

a) The cutoffs for the assignments of each of the three grades is not unique. Algorithms are possible, for example, in which the cutoff between a B.P. grade of 0 and of 1 is a value other than 70.

b) Algorithms are possible in which the number of possible grades for any or all of the parameters is more or less than three.

c) Algorithms are possible which are formatted as flow diagrams rather than the tabular format of FIG. 21.

d) Algorithms are possible in which a greater or lesser number than three parameters contribute to the treatment decision.

5.5.4 Anti-Tachycardia Pacing
5.5.4.1 Background

During ventricular tachycardia, the act of pacing the ventricles at rates above (and rarely, below) the tachycardia rate may result in termination of the tachycardia. This procedure is known as anti-tachycardia pacing or ATP. Although termination of a tachycardia using ATP may take longer than termination by a shock, and although the efficacy rate of ATP is lower than that of a shock, ATP may be the desirable approach in a conscious or semi-conscious victim, since a shock may cause more discomfort than pacing. Anti-tachycardia pacing may also be used to terminate other types of tachycardia including supraventricular tachycardia and atrioventricular reciprocating tachycardia (a tachycardia that involves the atria and the ventricles).

The typical ATP "burst" would consist of eight beats of pacing at a rate of 20 to 60 beats per minute above the tachycardia rate. There are three possible outcomes when a burst of ATP is administered:

a) the victim's tachycardia may terminate; or, b) there may be no effect on the tachycardia; or, c) the tachycardia may accelerate to one that is less well tolerated (including the possibility of fibrillation).

If the tachycardia is terminated by ATP, the result is as good as if a shock had terminated it.

If the ATP attempt did not affect the tachycardia but was, in the judgment of the MP, well tolerated, then one or more additional ATP bursts could be attempted. The MP must therefore quickly decide:

a) if he wants to attempt ATP again;

b) if yes, does he want to make the next attempt more aggressive, less aggressive, or of similar aggressiveness to the prior attempt; and, c) if the answer to a) is "yes", and having decided on the "degree of aggressiveness", the MP must then select from a large number of particular pacing options (see ahead).

A more aggressive burst is less likely to leave the tachycardia unchanged; it is generally more likely to either successfully terminate the tachycardia or accelerate it. One of the primary determinants of pacing aggressiveness is the rate of the pacing.

One simple way of assuring that the pacing rate is appropriately related to the tachycardia rate is to use a measure related to the inverse of rate, the cycle length. The cycle length, also known as the RR interval (i.e. the interval between R-waves on the ECG) is the time between tachycardia beats. Since the RR interval is typically measured in milliseconds (MSEC), and the heart rate in beats per minute (BPM), a conversion factor is necessary:

$$RR \text{ interval [MSEC]} = 60,000 \div \text{heart rate [BPM]}$$

One way of quickly selecting a burst pacing rate is to make the ATP RR interval a percentage of the tachycardia RR interval. With such an approach, a paced RR interval which is:

a) 70% of the tachycardia RR interval would be considered aggressive;

b) 80% of the tachycardia RR interval would be considered moderate; and, c) 90% of the tachycardia RR interval would be considered conservative.

Using such an approach, the MP could quickly select one of the major determinants of the aggressiveness of his burst pacing by specifying the percentage of the tachycardia RR interval that he wishes to use for the ATP RR interval: the "% RR". Typical values of % RR when burst pacing is successful, range from 75 to 88. In a preferred embodiment of the invention, the selection of the ATP rate by the MP is based on the % RR.

5.5.4.2 Anti-Tachycardia Pacing Protocol

FIG. 22 shows one possible approach to anti-tachycardia pacing. The MP arrives at the entry point to the ATP protocol, block MM 960A, from exit point of the Second Tier Arrhythmia Triage Protocol, block 960B (FIG. 21) which corresponds to the decision by the MP to use ATP therapy.

Block 961, at the time of the first ATP attempt, leads to block 962, at which juncture the MP selects from among three classes of approach, based on the aggressiveness of the pacing attempt. The approach which entails a moderate degree of aggressiveness is the selection of the default values of ATP parameters, block 963, which might be 8 paced beats at an RR interval which is 82% of the tachycardia RR interval (see Section 6.3.2.2, below). If the MP wishes to choose a less aggressive approach he could choose a % RR interval which is longer than the default value, as indicated by block 964. The actual choice of % RR is selected, block 974, from a variety of possible values (see Section 6.3.2.3 and FIG. 37 which shows the screen used by the MP for selection), e.g. 84%, 86%, 88% etc. If the MP wishes to select a more aggressive approach than the default values, block 965, he would have two sets of options: a) selecting a % RR which is shorter than the default value, block 966A, or b) selecting an intra-burst decrement (whereby the pacing rate increases during the ATP attempt), block 966B. Each of these more aggressive approaches has its own menu of options (shown in FIG. 37), from which the MP makes a particular selection at block 974. Having specified the details of the upcoming ATP attempt, the MP then delivers the ATP, 975, after which the protocol returns him, block 900D, to the First Tier Arrhythmia Triage Protocol (FIG. 19).

Block 961, at the time of the second and any later ATP attempts, leads to block 967, at which point the MP selects from among three types of approach:

a) increasing the aggressiveness of the next ATP attempt;

b) not changing the aggressiveness of the next ATP attempt; or, c) decreasing the aggressiveness of the nest ATP attempt.

The default approach is to slightly increase the degree of aggressiveness with each successive pacing attempt. This is accomplished by decreasing the paced RR interval by 10 MSEC. With each successive attempt.

For example, treatment of a 200 BPM tachycardia with ATP parameters which would be typical of a default selection (see Section 6.3.2.2) would entail:

a) Since the tachycardia rate is 200 BPM, the tachycardia RR interval is 300 MSEC.

b) Assuming a default % RR of 82, the RR interval of the first ATP burst would be 0.82×300 MSEC=246 MSEC (which corresonds to a pacing rate of 244 BPM).

c) Assuming a default inter-burst decrement of 10 MSEC, the second ATP burst (if needed) would be delivered with an RR interval of 246−10=236 MSEC (which corresponds to a rate of 254 BPM).

d) Assuming another ATP attempt with the default setting, the third ATP burst would be delivered with an RR interval of 236−10=226 MSEC (265 BPM).

Referring again to the ATP protocol shown by FIG. 22, the default 10 MSEC decrease in the burst cycle length with successive pacing attempts is depicted by the sequence of blocks 967, 970, 973B. At block 973B, maintaining the inter-burst decrement (at 10 MSEC) is the default setup. An increase in the inter-burst decrement to a value greater than 10, block 973B, would constitute an even more aggressive approach. Other methods of increasing aggressiveness are by selecting a shorter % RR interval than the last one to be utilized (block 973A) and by introducing or increasing the value of an intra-burst decrement (block 973C). Once the category of increased aggressiveness is selected from among blocks 973A, 973B and 973C, the exact choice is specified (e.g. introducing a 5 msec intra-burst decrement) at block 974 and delivered at block 975.

If the MP wishes to leave the aggressiveness of a second or later ATP attempt unchanged compared to the previous attempt, block 967 would lead to block 969. The option categories would then include a) leaving all ATP parameters unchanged, block 972A, or b) changing the number of paced beats, block 972B.

If the MP wishes to decrease the aggressiveness of a second or later ATP attempt, compared to the previous attempt, block 967 would lead to block 968. The option categories would then include a) increasing the % RR interval, block 971A, b) selecting an inter-burst increment (i.e. making the upcoming paced RR interval longer than the corresponding interval during the immediately previous event), box 971B, or c) decreasing or eliminating the intra-burst decrement (if one is present), box 971C.

Figure 37:
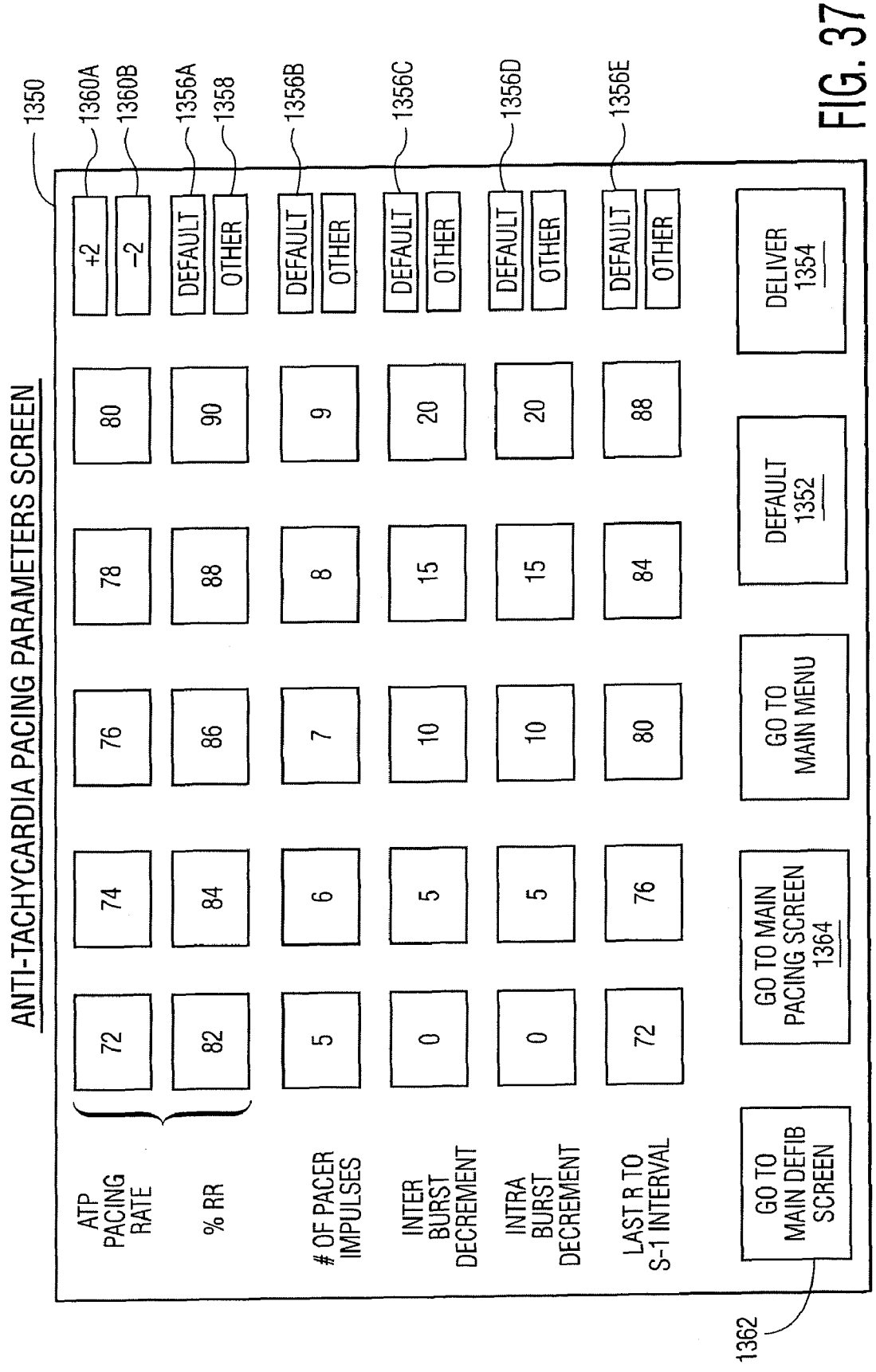
FIG. 37 is a diagram of the central station touch-sensitive display screen for controlling anti-tachycardia pacing.

As was the case with an ATP attempt of increased aggressiveness, with attempts of unchanged or decreased aggressiveness, the MP (working from the Anti-Tachycardia Pacing Parameters Screen 1350 [FIG. 37]) then selects the particular pacing parameters, block 974, and delivers pacing, block 975. Repeat rhythm observation follows, block 900D.

5.5.4.3 Other Possible Anti-Tachycardia Pacing Protocols

The number of possible protocols for selecting ATP parameters is very large. Other possible approaches include Protocols a) which do not refer to aggression but do refer directly to specific pacing parameters;

b) in which there is a programmable minimum paced RR interval;

c) in which the intra-burst decrement is not the same for each beat of the burst; and, d) in which the last R to S-1 interval (FIG. 37) varies.

Approaches to tachycardia management which do not include anti-tachycardia pacing are possible.

5.5.5 Bradycardia/Pacing Protocol 5.5.5.1 Overview

Figure 23:
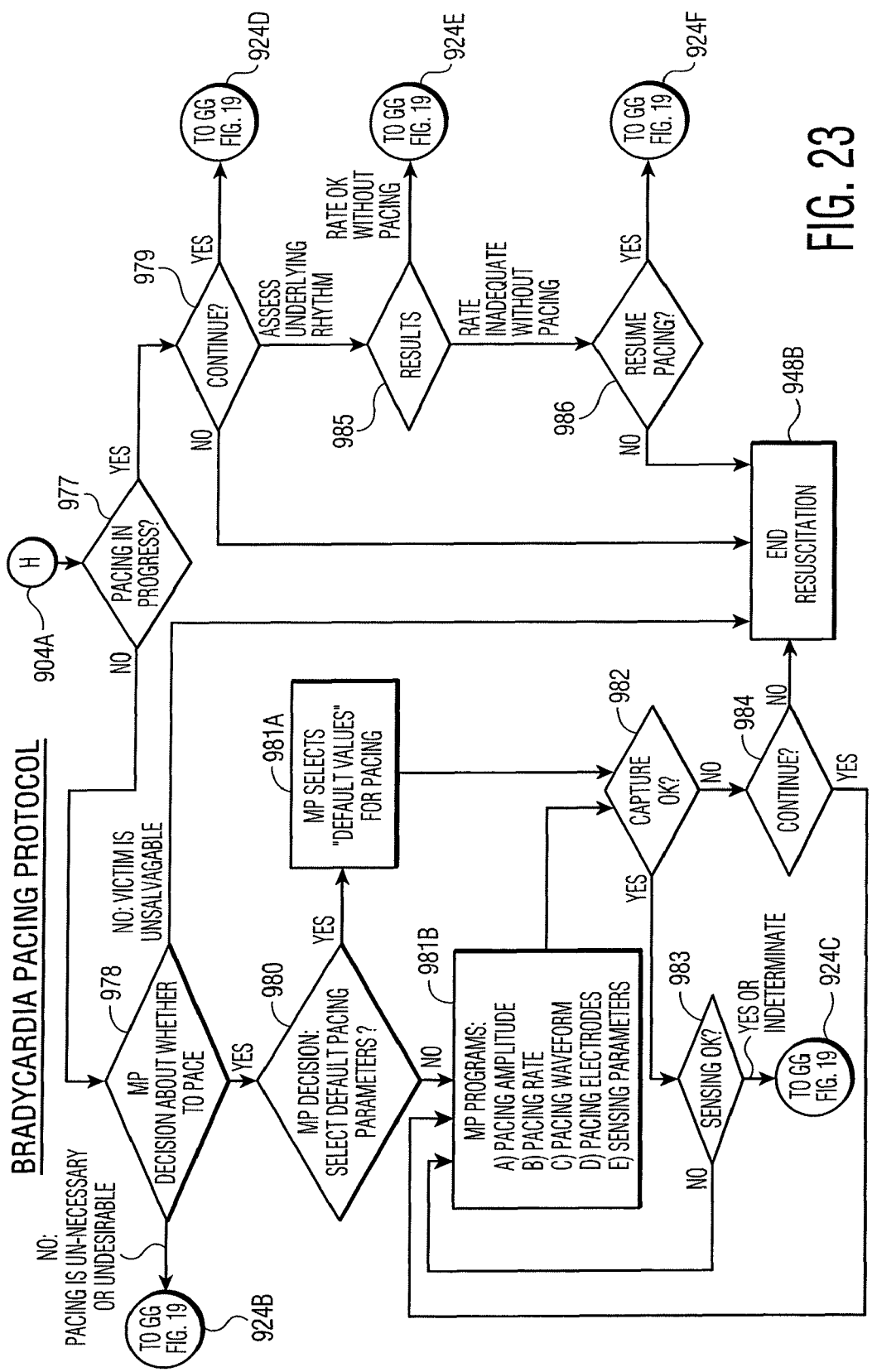
FIG. 23 illustrates the protocol of a medical professional in the case of bradyarrhythmia in a victim.

If bradycardia or a paced rhythm is encountered during the First Tier Arrhythmia Triage Protocol, block 904B (FIG. 19) leads to block H 904A, the entry point to the Bradycardia/Pacing Protocol (FIG. 23). At block 977, the protocol bifurcates, depending on whether external pacing is in progress. If it is not in progress, block 978, the MP decides whether to implement it and, if pacing is to be implemented:

a) the pacing parameters;

b) whether capture of paced impulses is properly occurring; and, c) whether sensing of non-paced impulses is properly occurring.

If pacing is in progress, block 979, the MP has the options of:

a) continuing it;

b) stopping it; and, c) briefly interrupting it to assess the underlying rhythm.

In a preferred embodiment of the invention, the MP may, at times, need to make a decision about ending a resuscitation effort. (This was discussed, above, in Section 5.5.2 for the case of incessant ventricular fibrillation.) The situation in which the victim does not respond to pacing is discussed below, in Sections 5.5.5.2, 5.5.5.3 and 5.5.5.4.

5.5.5.2 External Pacing Not in Progress; MP Decision Whether to Start Pacing

At block 978, the MP makes a selection among three possible approaches:

a) If the bradycardia is mild, he may decide that treatment is unnecessary or undesirable. This leads to block 924B, returning to the First Tier Arrhythmia Treatment Protocol, block GG 924A (leading to block 920, discussed above in Section 5.5.1.2.2).

b) If the bradycardia requires pacing, the MP, at block 980, decides whether to use the default pacing parameters. If he decides to use them, block 981A, he selects this choice on a screen, keyboard, or other inputting device. In a preferred embodiment of the invention, he makes the selection by touching "ALL DEFAULT VALUES" (element 1372) on the touch sensitive Main Pacing Screen (FIG. 38), as was the case during the Sample Cardiac Arrest (Section 4.2, Table 11, Time 2:46). If he wishes to choose non-default parameters, block 981B, he makes his selections (as per, for example, Table 11, Times 2:57, 2:58 and 2:59) for each of the pacing parameters. After the selection of either default or non-default pacing parameters, the MP checks, at block 982, to see if pacemaker capture (electrical activation of the heart following the pacemaker impulse) is occurring. If capture is occurring, the MP may have or want the opportunity to determine if sensing (inhibition of the pacemaker when there is an underlying rhythm of adequate rate) is proper, block 983, using techniques known in the art. There are four possible outcomes following the assessment of capturing and sensing:

(i) Both capturing and sensing are proper, in which case block 983 leads to block 924C and a return to the First Tier Arrhythmia Triage Protocol. The return is consistent with the need for essentially continuous reevaluation of the rhythm during the time that the MP is monitoring the victim. If the MP had selected pacing parameters or a default set of parameters in which external signals do not reset the timing of pacing (i.e. asynchronous pacing, or sensing=off), then sensing at block 983 is defined (for the operation of the flow diagram) as adequate.

(ii) Capturing is intermittent or is not occurring at all, and the MP wishes to continue efforts to pace. In this case, block 982 leads to block 984 and then a return to block 981B at which point the MP would make an alteration in either the pacing amplitude, the pacing waveform or the pacing electrodes. Capture would then be reassessed, block 982.

(iii) Capturing is satisfactory, but sensing is not.

In this case block 982 leads to block 983 which leads to block 981B and a readjustment of sensing parameters: either an increase in sensitivity or a change in the sensing electrodes (see below), followed by a reassessment of pacing at block 982 and sensing at block 983. Alternatively, the MP may choose to ignore an occasional failure to sense, in which case block 983. If there are no events to sense once pacing is initiated, the MP has the options of either proceeding with pacing, or transiently slowing the pacing rate to further assess sensing.

(iv) Capture is not occurring, the MP has exhausted all possible means of achieving capture, and neither medical nor emergency personnel are on-scene nor are they expected to arrive on scene. The MP may, at this juncture, block 984, need to make a decision about whether continued efforts to resuscitate the victim are to be terminated, block 948B. (See below, Section 5.5.5.4 regarding pacing termination and see above, Section 5.5.2 for the analogous situation with treatment-refractory ventricular fibrillation.)

5.5.5.3 External Pacing Is in Progress; MP Decision Whether to Check Underlying Rhythm If external pacing was in progress at the time of entry into the Bradycardia/Pacing Protocol, block 977 leads to block 979, at which point the MP has three options:

a) He can continue external pacing, in which case block 979 leads to block 924D, and a return to the First Tier Arrhythmia Triage Protocol.

b) He may decide to briefly interrupt pacing or slow the pacing rate, in order to assess the underlying rhythm (see, for example, Table 11, Time 2:57). If the result, block 985, is that the victim is found to have a satisfactory underlying rhythm, external pacing is not restarted, and the protocol returns, via block 924E, to the First Tier Arrhythmia Triage Protocol. If the result is that the rate is inadequate to support the victim, the MP decides, block 986, between (i) resumption of pacing, block 924F, and (ii) if resuscitation is deemed futile, cessation of pacing, block 948B.

c) He may find that pacing, though it results in electrical activation of the heart, fails to generate any significant mechanical activity (i.e. cardiac output/blood pressure). If the MP has exhausted all possible means of achieving the restoration of mechanical function, and neither medical nor emergency personnel are on-scene nor are they expected to arrive on scene, the MP may need to make a decision to terminate resuscitation, block 948B.

5.5.5.4 MP Considerations Concerning Termination of Pacing

There are instances when bradycardia pacing may be futile.

a) Attempted pacing of the heart may fail to result in any cardiac electrical activity. This might be the case, for example, in a victim who was discovered too late to be able to be resuscitated.

b) Pacing of the heart may result in cardiac electrical activity but fail to result in significant mechanical activity, so called "electro-mechanical dissociation." This might be the case in a victim who has had a pulmonary embolus (a blood clot which lodges in the lungs), or after a myocardial infarction (heart attack) involving the loss of function of a large segment of the heart muscle.

In order for an MP to consider the termination of pacing, one or more of the following factors would be likely to be addressed:

a) the performance of CPR; It is possible that pacing may become effective after the performance of CPR. In a preferred embodiment of the invention the MP has various means for causing the performance of CPR including instructing the enabler and/or the use of a device which automatically performs CPR;

b) changes related to the electrode pad; These may include:
  (i) removing the pad and re-applying the same one or a similar one, in a different position;
  (ii) removing the pad and re-applying a different one, in the same, or in a different position; or
  (iii) adding one or more additional electrode pads—e.g. to the victim's back or left side (while keeping the original electrode pad in place);
c) the duration of the resuscitation effort (The longer the resuscitation goes on without the restoration of adequate circulatory status, the less likely it is to ever achieve a satisfactory outcome.);
d) the proximity of the nearest emergency medical personnel;
e) the previously documented wishes of the victim, if such wishes are available to the MP; and,
f) local and federal statute.

The MP is much better qualified to address the aforementioned issues than an enabler using an AED would be. These aforementioned six considerations apply to the suspension of resuscitation effort in the event of refractory VF (Section 5.5.2, above).

5.6 Command Confirmation

Command confirmation is a fundamental part of the remote management of a highly critical situation. In order for remote management to be practical, the MP know with certainty whether each of his commands was properly executed. The system of confirmation signals is intended to do this, as well as to identify not only the presence of a system fault but its location.

Command confirmation is illustrated and discussed:
a) in handshake section 5.2, in connection with FIGS. 14D through 14G;
b) in screen section 6.7, in connection with FIG. 44; and
c) in hardware sections 7.6, 7.7, 7.8 and 7.9, in connection with FIGS. 51A through 54.

Figure 24:
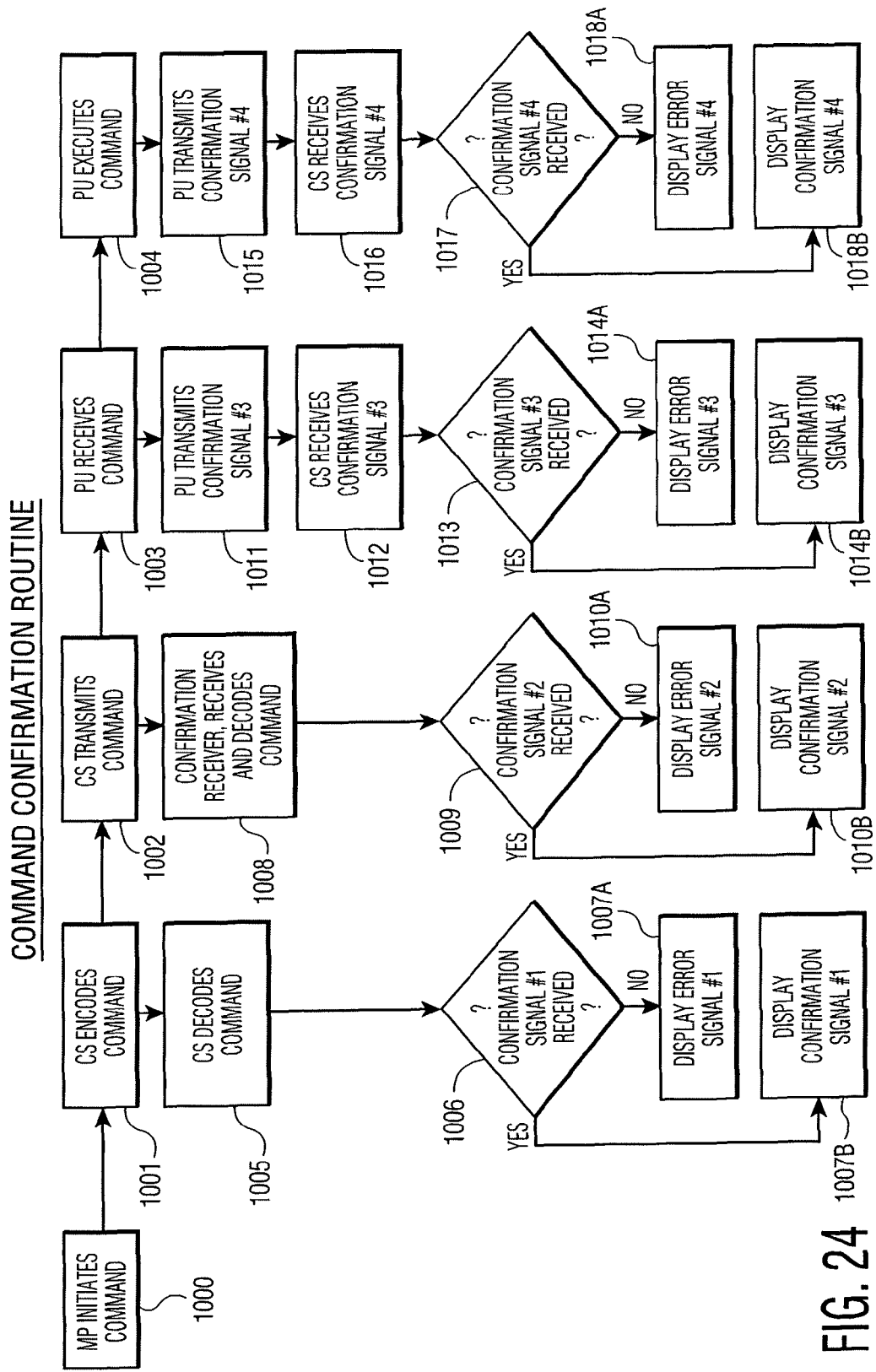
FIG. 24 is a flow diagram illustrating the confirmation protocol for transmission of messages between the central station and a remote station in the cardiac monitoring and external defibrillation system according to the present invention.

FIG. 24 is a flow diagram which illustrates the command confirmation routine. Each command will generate four confirmation signals 1007B, 1010B, 1014B and 1018B if it properly traverses the system and is executed. A failure at some point in the system, either in the transmission of the command to its target in the PU, or in the transmission of information back to the CS, will result in the generation of an error signal, viewed on the CS display console.

A command, block 1000, is encoded 1001 in the CS and then decoded 1005 in the CS. If, block 1006, the decoded command matches the initial one, the receipt of confirmation signal #1 is displayed 1007B; if not, error signal #1 1007A is displayed. This is illustrated in FIG. 14D.

Figure 49:
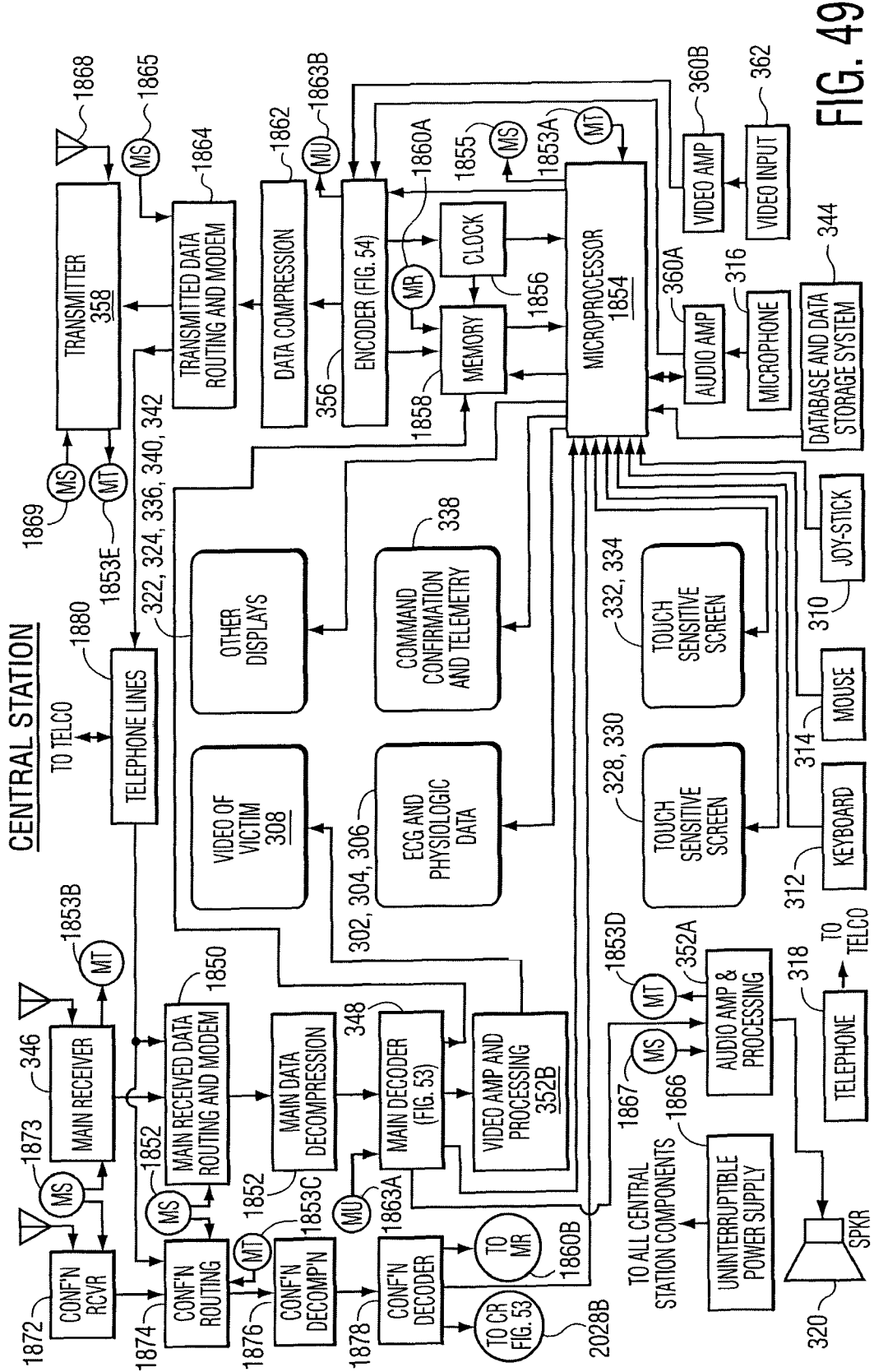
FIG. 49 is a block diagram of the electronic circuits of the central station.

Confirmation signal #2 is generated when there is evidence that the command has been properly transmitted from the CS. FIG. 49 illustrates how this occurs. The transmitted command 1002 is received, block 1008. If, block 1009, the command is properly received, the receipt of confirmation signal #2 is displayed 1010B; if not, error signal #2 1010A is displayed. This is illustrated in FIG. 14E.

When the PU receives a command, block 1003, it retransmits, block 1011 a "copy" of it back to the CS as confirmation signal #3. If, block 1013, the CS receives the copy, the receipt of confirmation signal #3 is displayed 1014B; if not, error signal #3 1014A is displayed. This is illustrated in FIG. 14F.

When the PU executes the command, block 1004, it transmits, block 1015, a confirmation signal indicating the execution. If, block 1017, the confirmation signal is received, the receipt of confirmation signal #4 is displayed 1018B; if not, error signal #4 1018A is displayed. This is illustrated in FIG. 14G.

6. Central Station Screens 6.1 Basic Communication Screens 6.1.1 Communication Status and Master Control Screen FIG. 25 shows the Communication Status and Master Control Screen.

The top portion of the screen is a graphic display of signal quality at the CS, the SU and the PU. Boxes 1101 can be colored green or red to indicate acceptable or unacceptable signal quality. Alternatively, more colors or a numeric format may be used to supply more detailed information. This information may be used in three ways:

a) Although the communication system would ordinarily optimize communication routing and each of the appropriate transmitter and receiver parameters, the MP is given the option to make his own choices in this regard (see below).

b) The MP may be aided in the decision about whether to select an alternate communication modality (i.e. screen text messages rather than speaking to the enabler, or having the enabler make touch sensitive responses rather than having the MP listening to the enabler) by the display of signal quality.

c) The MP may decide that communication is so marginal that he wishes to make use of the backup AED function of the portable unit.

The lower portion of the screen:

a) gives the MP access to selecting or overriding system choices for communication parameters and features;

b) gives the MP access to alternative communication modalities; and c) allows the MP to select the state of the master control unit.

Touch sensitive button 1102 allows the MP to change any aspect of the CS processing input (referred to as options 1A in Table 20 and shown schematically as block 506 in FIG. 14A) and/or any aspect of the CS communications output (referred to as options 1B and represented as block 508 in FIG. 14A). In a preferred embodiment of the invention, touching 1102 brings up a menu of options (not shown) which may overlay screen 1100, split the screen, or appear on another screen.

Touch sensitive button 1104 allows the MP to change any aspect of PU communications input (referred to as options 3A in Table 20 and shown schematically as block 512 in FIG. 14A) and/or any aspect of the PU processing output (options 3B and block 514 in FIG. 14A). Touch sensitive sub-menus (not shown) allow these selections.

Touch sensitive button 1110 allows the MP to change any aspect of PU processing input (options 6A and block 519 in FIG. 14A) and/or any aspect of the PU communications output (options 6B and block 521 in FIG. 14A).

Touch sensitive button 1108 allows the MP to change any aspect of CS communications input (options 8A and block 525 [FIG. 14A]) and/or any aspect of the CS processing output (options 3B and block 527).

In the preferred embodiment of the invention, in which a stationary unit links the PU and the CS, modifications are possible in the input and output characteristics of the SU, a menu for which is accessed by touching 1103. This allows the MP to modify SU input from the CS, SU output to the PU, SU input from the PU and SU output to the CS. The MP may also modify the communication path between the CS and the PU (options 2 and 7 in Table 20 and blocks 510 and 523 in FIG. 14A) by having access to communications routing. If a SU is interposed between the PU and the CS, the number of routing options increases.

If, despite attempts by the system or the active efforts of the MP, it is not possible to maintain satisfactory voice communication, the MP has the option of using text messages in either (or both) sides of his communication with the enabler (see discussion of FIG. 15). By touching 1105, he can change the enabler input to a touch sensitive screen method, his own input to text messages for the enabler, or both. He can select voice prompts (see below) by touching 1111, which takes him to the Voice Prompt Screen shown in FIG. 26.

After a satisfactory data-commands handshake, the MP takes control of the PU by touching 1106 which sends a command to the master control unit in the PU to set MC=1 (see FIGS. 14O, 48, 51A and 54). If communication is interrupted, the PU automatically reverts to MC=2, i.e. AED control. There may also be other circumstances where the MP wishes to voluntarily set MC=2; One example is a communication degradation after setting MC=1, that is not severe enough to automatically set MC=2 but which the MP deems to result in his inability to satisfactorily control the situation. In such a circumstance, the MP touches "GO TO AED CONTROL" 1107. Transmission of this command is similar to that of MC=1, in terms of the hardware involved. If at some later time after sending "GO TO AED CONTROL" communications improve, the MP may again touch "GO TO MP CONTROL" to reset MC=1.

Upon the arrival of qualified emergency medical personnel, the EMT, the MP can hand control over by touching "GO TO EMT CONTROL" 1112. This sends a command to set MC=3, allowing the EMT to use the PU as the MP uses it.

At the conclusion of a procedure the MP sends a command to return the PU to its standby state by touching "END SESSION" 1113. This sends a command to set MC=0.

If the MP wishes to do a diagnostic check of the PU-SU system, he calls up the MP Directed Portable Unit Diagnostic Check and Maintenance Screen (see Section 6.4 and FIG. 41) which allows him to set MC=4 and perform the check. He can access that screen by entering "CONTROL M" on the keyboard, which brings up the Main Screen Menu 1600, on which he selects "PU CHECK AND MAINTENANCE" (see Section 6.6 and FIG. 43).

6.1.2 Voice Prompt Screen

The MP may choose to use voice prompts in the event of communication difficulties. He may also make this choice in the case of a foreign language speaking MP, if an interpreter is not available.

Figure 26:
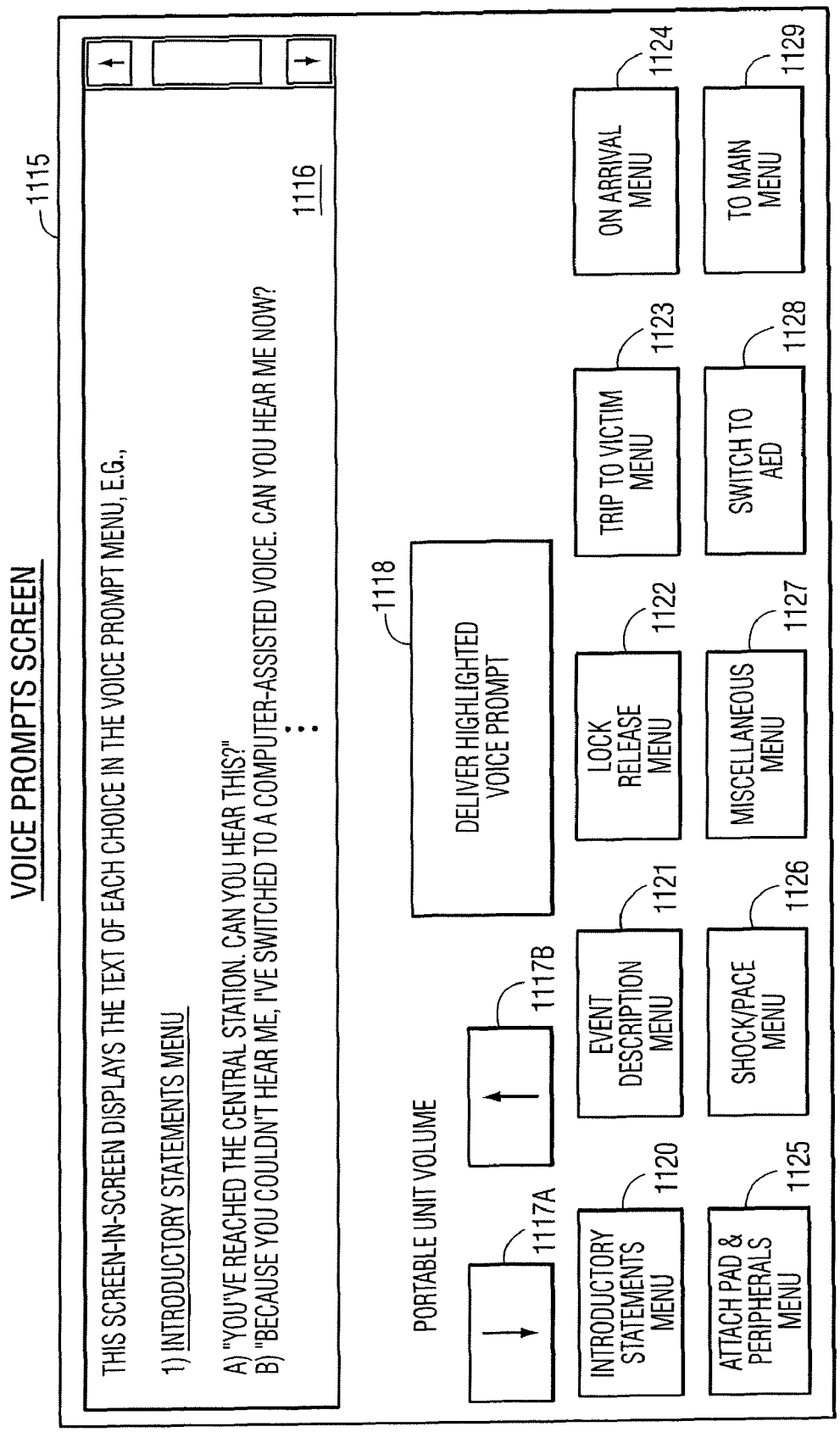
FIG. 26 illustrates a touch-sensitive display screen at the central station for controlling voice prompts at the portable unit.

FIG. 26 shows screen 1115 which provides the MP with access to an extensive menu of voice prompts (see Appendix 1) and methodology for their selection and delivery.

Since there are many situations which may occur during a cardiac arrest or emergency, the list of possible voice prompts is necessarily long. To facilitate the MP's selection among the possible voice prompts, the menu has been divided into nine sub-menus:

a) the "INTRODUCTORY STATEMENTS MENU", block 1120;
b) the "EVENT DESCRIPTION MENU", block 1121;
c) the "LOCK RELEASE MENU", block 1122;
d) the "TRIP TO VICTIM MENU", block 1123;
e) the "ON ARRIVAL MENU", block 1124;
f) the "ATTACH PADS AND PERIPHERALS MENU", block 1125;
g) the "SHOCK/PACE MENU", block 1126;
h) the "MISCELLANEOUS MENU", block 1127 and
i) the "SWITCH TO AED MENU," block 1128.

Some of the sub-menus have only a few choices (e.g. seven for the SHOCK/PACE menu) while others are longer. The ATTACH PADS AND PERIPHERALS MENU has one hundred choices—of necessity a large number because a) these acts involve one of the portions of the resuscitation procedure where enabler participation is mandatory, and b) correct performance by the enabler will increase the chance of a successful resuscitation.

In order to allow the MP to rapidly scan the menu items, they are presented on the screen-in screen 1116, once the MP touches one of 1120-1128 and selects a sub-menu. He can use the scroll bar on the right of the screen, the arrow keys on the keyboard and the mouse to rapidly scan the list. Once he finds an appropriate choice, he can deliver it by touching 1118. Methods for streamlining selection include a) shortening the menu and b) allowing the MP to select a choice by entering the first word or a key word on the keyboard.

If the MP wishes to increase or decrease the volume at the PU at which the prompt is delivered, he can do so using 1117B or 1117A.

6.2 Portable Unit Setup Screens
6.2.1 Portable Unit Deployment Screen

The MP will release the PU from its locked state after:

a) satisfactory communication with the enabler is confirmed (FIG. 15);
b) the MP confirms that he is or is may be dealing with a cardiac emergency (FIG. 16A, block 779); and
c) the MP confirms that the enabler is willing to help (FIG. 16A, block 781).

When these conditions are met (block 782), the MP a) calls the 9-1-1 which corresponds to the PU location and b) releases the PU.

Screen 1135 displays the PU location in block 1136, and the telephone number of the 9-1-1 nearest the victim, in block 1137A, both items of information having been obtained at the time of the data-commands handshake. The MP summons the emergency medical team by touching 1137B. If their estimated arrival time is known, it can be displayed in block 1140.

To release the PU, the MP touches 1141 on the PU Deployment Screen 1135, shown in FIG. 27. When the electromagnetic lock successfully opens, releasing the PU from the SU, the PU transmits a telemetry signal to the CS (block 793, FIG. 16B) which is shown in block 1142, on screen 1135. It is also registered on the Event Log (see below, FIG. 44). In the event of a failure of the lock to release the PU, the MP may observe a failure signal, block 1143. He can override the electromagnetic apparatus with a mechanical release 184B (FIG. 8) that can be performed by the enabler after entering the proper alphanumeric combination to the lock 184A (FIG. 8). The MP tells the enabler the correct combination, after viewing it, block 1144. (It may be provided during the data-commands handshake.)

The PU is separated from the SU upon instruction by the MP (block 807, FIG. 16C), at which point the MP a separation signal is generated, and displayed in block 1145, and the Event Log. After enabler transportation of the unit to the victim, and proper placement on the ground, elements 178 (FIG. 8) cause the generation of a portable unit touchdown signal (block 829, FIG. 18A) which is displayed on the PU Deployment Screen, block 1146.

Figure 29:
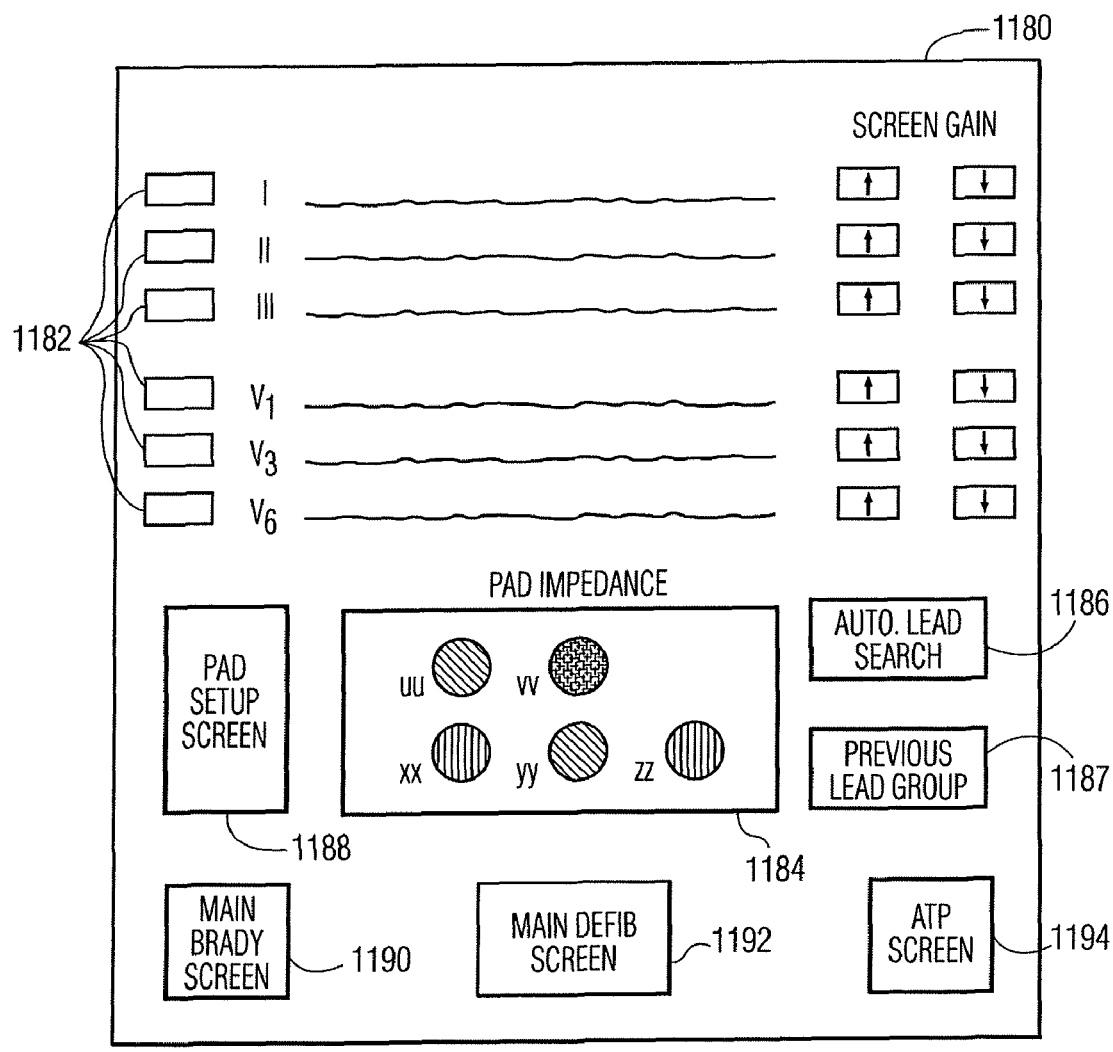
FIG. 29 illustrates a touch-sensitive display screen at the central station for initial assessment of pad contact and of ECG.

Once the PU is on the ground next to the victim, the MP deploys the video boom 112 (FIG. 6B, and block 830 of FIG. 18A) while speaking to the enabler and quickly re-establishing that audio contact is good (block 834 of FIG. 18B). The bottom of the PU Deployment Screen allows the MP to go to either:

a) the Communication and Master Control Screen, FIG. 25, if audio communication needs refinement, by touching 1147;
b) the Video Control and Instruction Screen, FIG. 28, by touching 1148; or
c) the Initial ECG Screen, FIG. 29, by touching 1149.

The start time and elapsed time of the event are displayed in blocks 1138 and 1139 of screen 1135.

6.2.2 The Video Control and Instruction Screen

This screen, 1160, allows the MP to:

a) manipulate the video boom;
b) adjust viewing parameters for what he sees;
c) provide instructional material for the enabler; and
d) determine the format and mode of operation of the PU screens 156.

The controls at the upper right hand portion of screen 1160 allows the MP to manipulate the video boom, and thereby get a better view of the victim and ECG pad application. In a preferred embodiment of the invention, the video boom has one or more angulations along its shaft, which can be controlled (like a medical endoscope) by the MP. The joystick (see FIGS. 3 and 49) facilitates control of the boom vector. The length of the boom is also controllable. Controls for focus, zoom, brightness and contrast are available. Depending on bandwidth availability, the MP may wish to adjust the frame rate for his own or for the enabler's video.

Victim clothing removal is facilitated by having the MP indicate what area specifically must be exposed. Electrode pad application is facilitated by showing either a cartoon representation of the victim (by touching 1163) or by showing the actual victim (by touching 1162) and then superimposing either a cartoon of a properly placed electrode pad, an image of an actual in proper position, or markings on the video screen which indicate proper placement (see block 879, FIG. 18E). The composite image is shown on one of the PU screens, and on screen-in-screen 1161. Markings to indicate proper pad placement may be generated by touching 1164 and then touching the appropriate spot on 1161, or using the mouse or joystick to accomplish this. If the MP wishes to display a superimposition of the actual electrode pad, he selects the choice of electrode pad among the six touch sensitive blocks 1166. (Once the pad backing is removed, the system "knows" which pad has been selected. However, backing removal should occur not occur until after the beginning of the pad placement instructions.) When the MP has selected his pad choice, he tells the enabler which shelf in the tool-kit (FIG. 7A) to get it from, and touches "SHOW" 1167. If the MP changes his selection, he touches "CANCEL 1168" and is then at liberty to make another selection. After successful pad application, the MP touches "INITIAL ECG SCREEN" 1169 which takes him to screen 1180 for ECG setup (see Section 6.2.3).

The lower right hand portion of screen 1160 allows the MP to select the format of each of the PU screens 156. Their content is displayed on 1171A and 1171B.

If the enabler can not properly hear the MP after PU placement at the victim side, and if this condition is not remedied by any of the audio options available, the MP may select to use text messages for his instructions to the enabler. He does so by touching 1174 and then touching either 1172A or 1172B to select the particular PU screen he would like to allocate for such messages. He can facilitate enabler viewing of these messages using the available controls for brightness, contrast and font size. If the MP cannot properly hear the enabler, and cannot remedy the situation, he can ask the enabler to use a touch sensitive yes/no (or multiple choice) format to answer MP questions, block 1177, or ask his own questions (using a virtual, touch sensitive keyboard), block 1178. The MP can place these formats on each PU screen by touching one of 1177 and 1178 and then touching one of 1172A and 1172B. The MP can determine which screen is allocated for pad placement (including the choice of both) using 1175 and 1176, and can show an image of himself (which may be reassuring to the enabler) by selecting 1179. If the MP wishes to display more than two items, he can use a screen-in-screen format by touching 1173.

6.2.3 Initial ECG Screen

Once the electrode pad is in place, the MP optimizes his electrocardiogram recording, if necessary, using the Initial ECG Screen 1180 shown in FIG. 29.

The presence of multiple electrodes on some of the available choices for ECG pad means that the MP will have choices for ECG lead selection that would not be available if only two electrode pads were in use. The ECG is displayed on the upper portion of the screen with touch sensitive gain controls to the right of each displayed lead. The name of the ECG lead whose vector orientation most closely resembles that of the each tracing displayed to its left. If the MP wishes to view other ECG leads, he can replace the three lower tracings with alternate choices by touching 1186. If he wishes to view a previous group of three he selects 1187. A unipolar measurement of the impedance of each pad (as a measure of how well it is contacting the victim's chest) is displayed in screen 1184. Each pad may be:

a) shown in green or red, as a "go-no go" classification;
b) shown in a format with more than two colors and an equal number of possible classifications; and/or
c) shown associated with a number (indicated as "uu", "vv", "xx", "yy" and "zz" in FIG. 29).

Based on what he sees, the MP will want to go from screen 1180 to either:

a) the appropriate pad setup screen (FIGS. 30-32), by touching 1188, if he wishes to select non-standard choices of electrode recording format By this time, the system will know which pad he has selected since the pad backing would have been removed. He therefore need not specify which of the three electrode pad setup screens he needs;
b) the Main Pacing Screen, by touching 1190;
c) the Main Defibrillation Screen by touching 1192; or
d) the Anti-Tachycardia Pacing Screen by touching 1194.

Elements 1182 are for use during pacing adjustment (see below).

6.3 Arrhythmia Management Screens

FIGS. 30-40 show examples of possible arrhythmia management screen configurations. These examples do not constitute unique configurations. Other embodiments are possible, including:

a) embodiments with two or more of the individually shown screens merged into one;
b) embodiments with one of the individually shown screens divided into two or more screens;
c) embodiments in which there are a larger or a smaller number of choices for the value of a particular parameter (e.g. the value of defibrillation energy, FIG. 34) available for the MP to select;
d) embodiments in which there are one or more different choices for the value of a particular parameter (e.g. 75 joules for the value of defibrillation energy, FIG. 34) available for the medical professional to select;
e) embodiments in which one or more of the parameters shown as selectable by the MP, may be either selected by an algorithm outside the control of the MP, or may be fixed (e.g. pulse shape);
f) embodiments in which one or more features of arrhythmia control are not utilized (e.g. anti-tachycardia pacing, FIG. 37);
g) embodiments in which the storage and display of previously used parameter values (e.g. "SHOW PREVIOUS", element 1202A, FIG. 33) is either formatted differently, or not available to the MP; and h) embodiments in which there either are a larger number, or a smaller number of commands leading to therapy delivery (e.g. the three command sequence: "SELECT PREVIOUS", element 1202A; "ACCEPT", element 1206; and "DELIVER", element 1208 [all in FIG. 33]).

6.3.1 Defibrillation Management Screens

Figure 33:
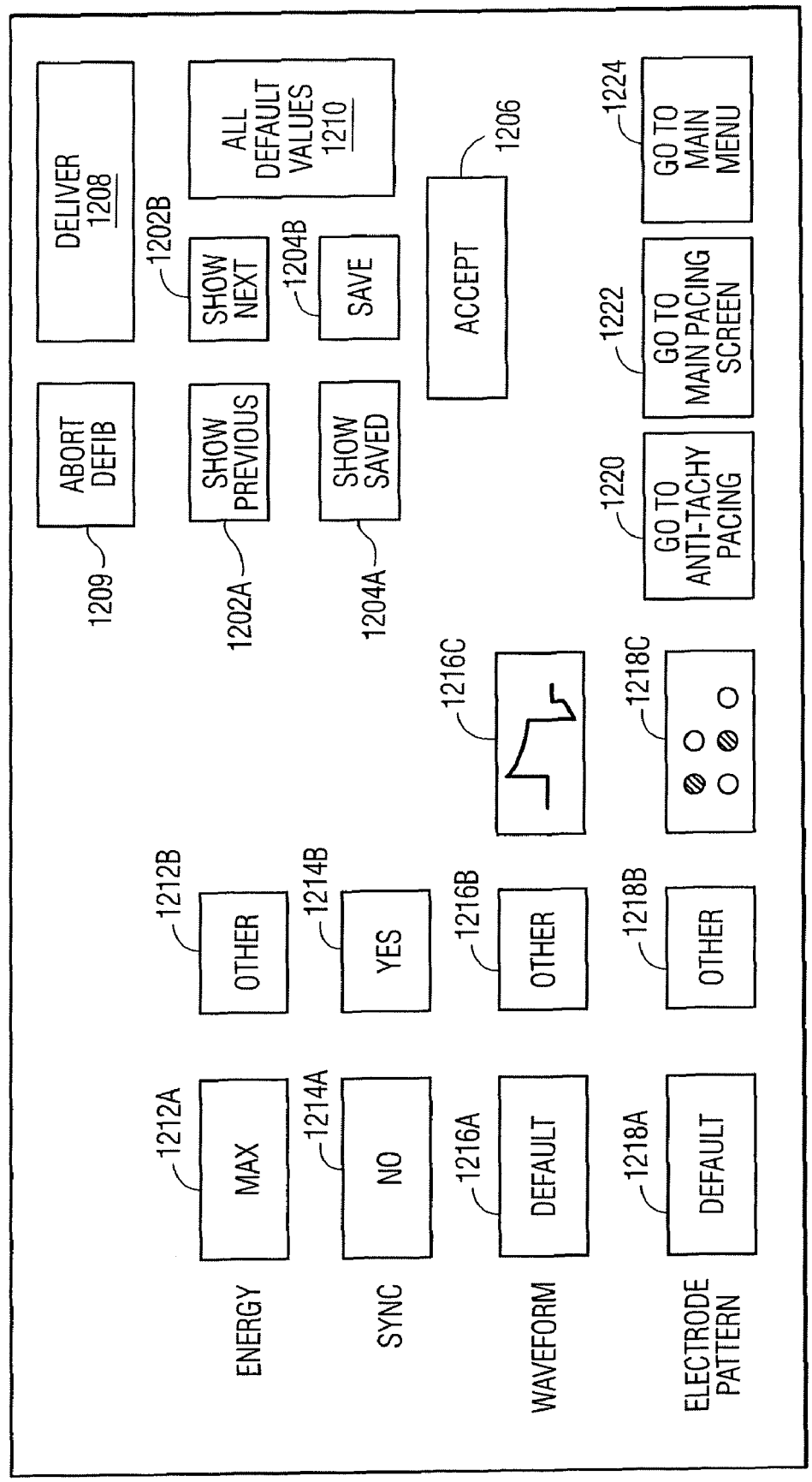
FIG. 33 illustrates a touch-sensitive display screen at the central station for selection of defibrillation electrodes, and control of the defibrillation energy, waveform and synchronization.

FIG. 33 shows the Main Defibrillation Screen 1200. The buttons on it, (touch sensitive, light sensitive, actual depressable buttons, keyboard or voice entries) allow the MP to select defibrillation parameters, and deliver a shock.

Figure 30:
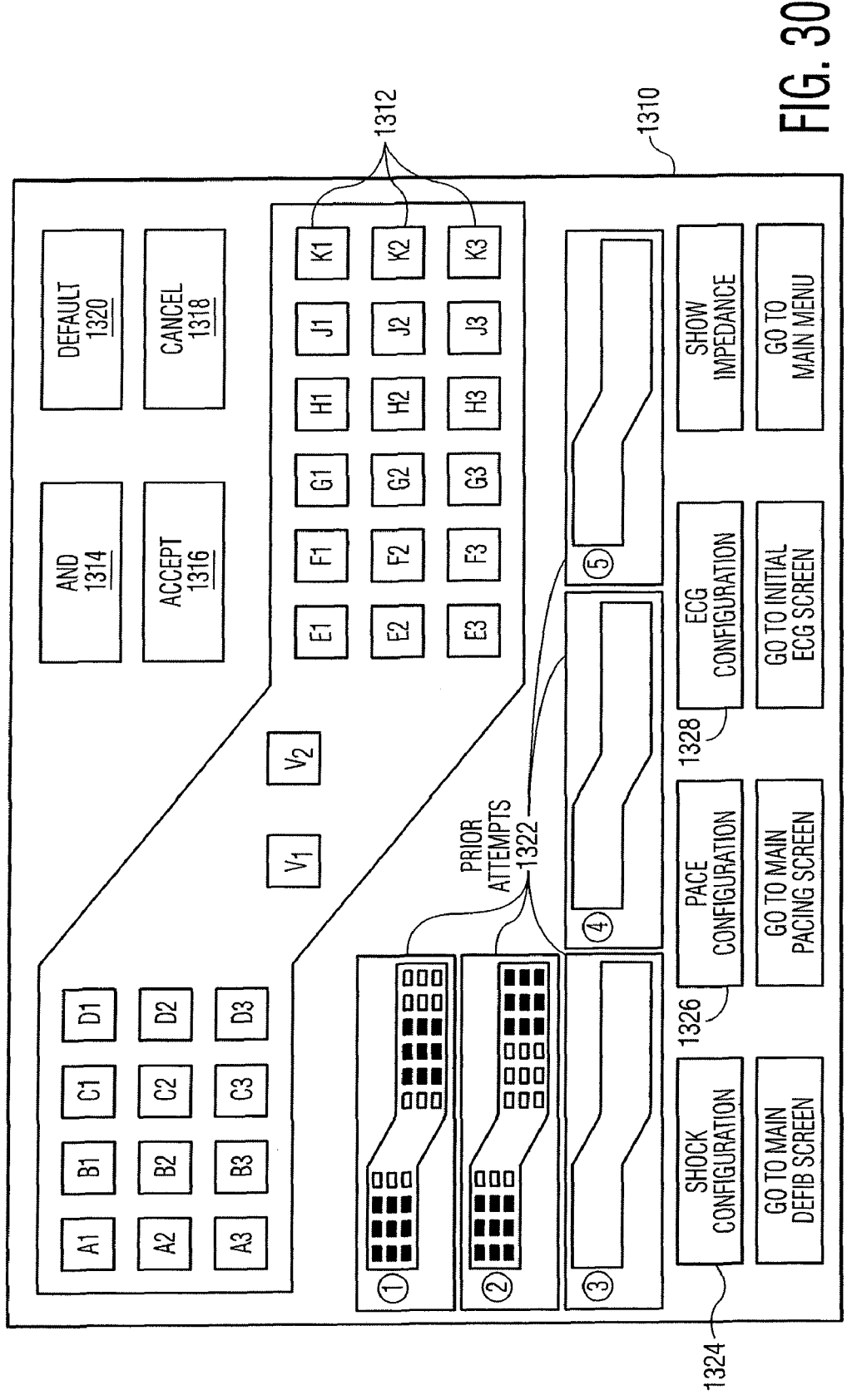
FIG. 30 illustrates a touch-sensitive display screen at the central station for selection of electrodes on the matrix electrode pad.
Figure 32:
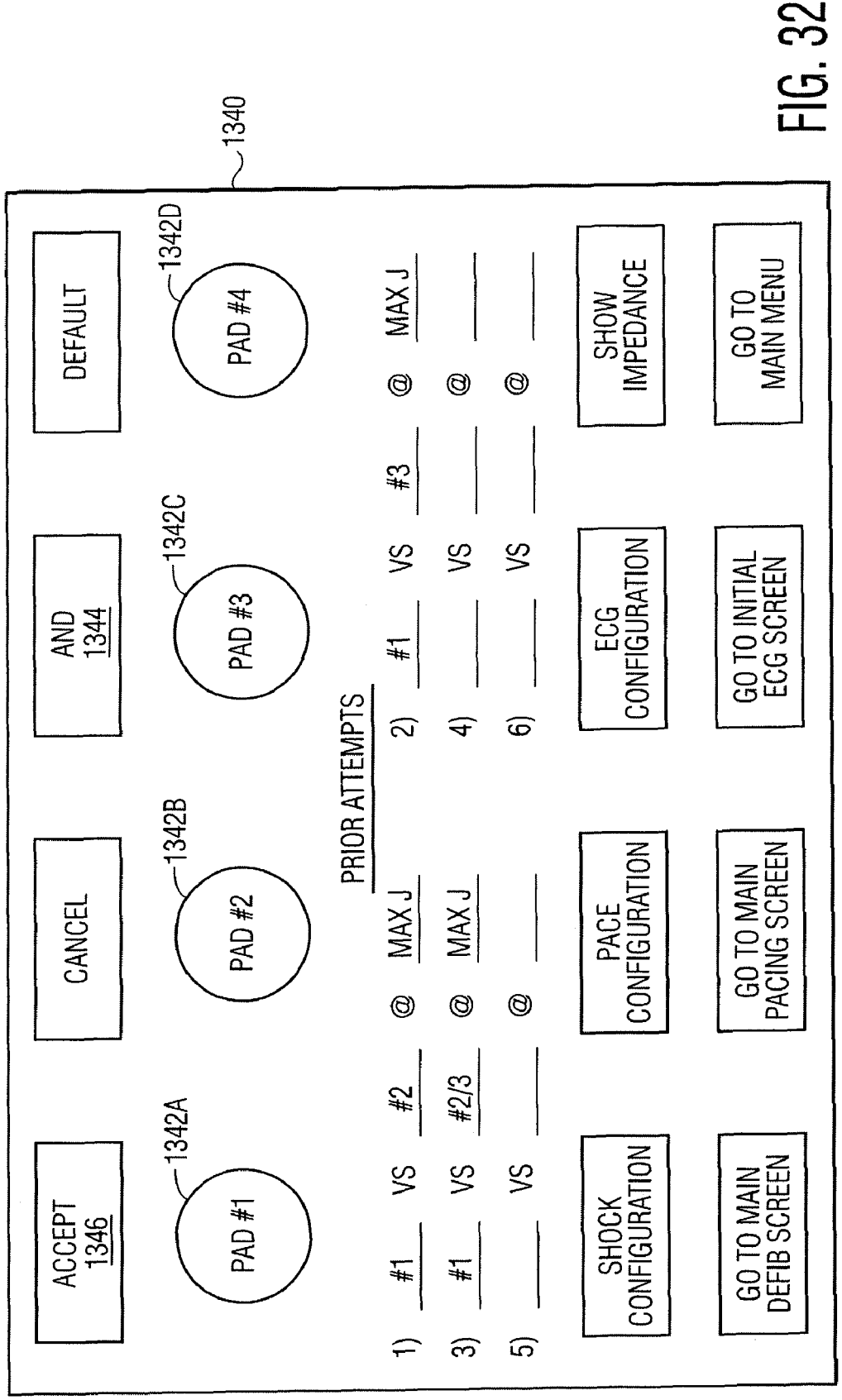
FIG. 32 illustrates a touch-sensitive display screen at the central station for selection of electrodes when multiple single electrode pads are used.

In the embodiment which corresponds to FIGS. 30-36, selection of defibrillation parameters will consist of either using default values (which requires only Main Defibrillation Screen 1200) or will require the accessing of one or more other screens for the selection of:

a) non-default values of defibrillation energy (FIG. 34); and/or, b) non-default values of pulse synchronization (FIG. 35); and/or, c) non-default values of pulse shape (FIG. 36); and/or, d) non-default values of electrode configuration (FIGS. 30-32).

6.3.1.1 Paths to Main Defibrillation Screen

The MP 301 ordinarily first reaches the Main Defibrillation Screen from the Initial ECG Screen (FIG. 29), upon MP's recognition that the victim is in either ventricular fibrillation or shock-requiring ventricular tachycardia. Other routes by which the MP would arrive at the Main Defibrillation Screen are:

a) from any of the aforementioned screens (FIGS. 30-32 and 34-36) used for specifying non-default values of defibrillation parameters;

b) from the Anti-Tachycardia Pacing Parameters Screen (FIG. 37);

c) from the Main Pacing Screen (FIG. 38); and, d) from the Screen Menu (FIG. 43).

6.3.1.2 Method of Operation: Defibrillation Screens
6.3.1.2.1 Default Values: Main Defibrillation Screen If the MP decides to defibrillate using default values, he:

a) selects "ALL DEFAULT VALUES" 1210;

b) touches "ACCEPT" 1206;

c) waits for the confirmation signal from the PU that charging has been completed;

d) confirms the persistence of a shock-requiring rhythm; and, e) touches "DELIVER" 1208.

This causes the PU to deliver an asynchronous shock via the default electrode configuration, with the default parameters of energy and pulse shape. (This was the case for the initial shock during the sample cardiac arrest described in Table 11, Time: 2:20-2:25.)

Typical default values are:

a) Energy=maximal;

b) Synchronization=off;

c) Waveform=biphasic; and, d) Electrodes=α and δ (when using the five electrode pad).

The actual default values may be set in a number of ways:

a) They may be programmed in a way such that, once initially set, no user of the system has access to them;

b) They may be programmed such that MPs do not have access, but such that certain members of the staff do have access; or c) They may be programmed so that MPs have access, for example, via a password.

As indicated in the sample cardiac arrest section, touching "ACCEPT" on the Main Defibrillation Screen results in the transmission of a command from the central station to the portable unit to begin charging its high voltage capacitors in preparation for shock delivery. Touching "DELIVER" results in the transmission of a command to deliver the programmed energy and waveform via the programmed combination of electrodes, in either a synchronized or asynchronous fashion, as programmed. If the tachycardia or fibrillation were to terminate in the few seconds between the MP's touching of "ACCEPT" and the completion of capacitor charging, the MP would touch "ABORT DEFIB" 1209, which would send a command to the PU to discharge its capacitors internally (i.e. not through the victim). The MP would also select "ABORT DEFIB" if the tachycardia or fibrillation changed to a rhythm which might respond to anti-tachycardia pacing (see Section 6.3.2, below).

6.3.1.2.2 Non-Default Values

Instead of selecting "ALL DEFAULT VALUES" for the defibrillation parameters, the MP may select one or more non-default values. A non-default value is selected by touching 1212B (non-default energy), 1214B (for synchronized energy delivery, i.e. the non-default approach), 1216B (non-default waveform) or 1218B (non-default electrode configuration). Each of the non-default buttons 1212B, 1214B, 1216B and 1218B leads to a different defibrillation detail screen (1230, 1240, 1260, 1290, 1310 and 1340) which contains a menu which lists possible non-default settings.

Each of the aforementioned defibrillation detail screens, when selected, may be displayed in a variety of ways:

a) A detail screen may overlay 1200, the Main Defibrillation Screen. Once the MP selects the appropriate value on the defibrillation detail screen, the detail screen disappears, and the main defibrillation screen (no longer covered by the detail screen) is again visible.

b) Selecting a defibrillation detail screen may cause it to appear on a second MP work screen (e.g. central station monitor 332, FIG. 3), with the Main Defibrillation Screen 1200 remaining visible on a first MP work screen (e.g. central station monitor 330, FIG. 3).

c) Selecting a defibrillation detail screen may cause it to split the screen such that one half is the main defibrillation screen, and the other half is the defibrillation detail screen.

d) Selecting a defibrillation detail screen may cause it to become a "screen-in-screen" with the inner screen being the detail and the outer screen being the Main Defibrillation Screen 1200.

Once the MP has selected a non-default value and has then returned to the Main Defibrillation Screen, he may either a) select default values for the other defibrillation parameters, or b) select other non-default values for one or more of the remaining parameters.

To select a default value for one of the defibrillation parameters, the MP touches the appropriate one of buttons 1212A (default energy, the maximum value), 1214A (synchronization off), 1216A (default waveform, biphasic) or 1218A (default electrode pattern). An example of this approach is presented in Section 4.2 which describes an hypothetical cardiac arrest (see Table 11, Time 2:31-2:33: After selecting non-default values for the defibrillating electrodes, the MP selects default values for each of the other three parameters.)

Embodiments of the invention are possible in which non-selection of a parameter results in the selection of the default value.

Default selections that have been chosen by the medical professional are preferably indicated on the Main Defibrillation Screen by either highlighting, backlighting, coloring or otherwise visually emphasizing the word within the button (1212A, 1214A, 1216A or 1218A) that corresponds to the selection.

Non-default selections that have been chosen by the MP are also preferably displayed on the Main Defibrillation Screen. One method of doing this would be as follows:

a) A non-default energy value, if selected, would be displayed as a number within button 1212B, replacing the word "OTHER".

b) Synchronization, if selected, would be indicated by either highlighting, backlighting, coloring or otherwise visually emphasizing the word "YES" within button 1214B.

c) A non-default pulse contour, if selected, would be displayed, along with the numerical parameters which specify it, in the Pulse Contour Miniscreen 1216C. This screen-within-screen would be similar or identical to its counterpart element 1278 on the Pulse Shape Screen (see below, Section 6.3.1.2.2.3).

d) A non-default electrode pattern, if selected, would be displayed in Miniscreen 1218C. The content of this Miniscreen would show the pattern of electrodes selected for energy delivery, in a manner similar or analogous to the display in element 1322 (see below, Section 6.3.1.2.2.4.2). With electrode pads other than the matrix electrode pad, those electrodes selected for energy delivery could be either (i) displayed in Miniscreen 1218C, or (ii) listed within button 1218B, replacing the word "OTHER".

When all of the defibrillation parameters have been selected, the MP:

a) touches "ACCEPT" 1206;

b) waits for the confirmation signal from the PU that charging has been completed;

c) confirms the persistence of a shock-requiring rhythm; and, d) touches "DELIVER" 1208.

This causes the PU to deliver a shock via the electrode configuration, and with the parameters that have been selected. If the MP wished to abort the shock after charging had begun, he would touch "ABORT DEFIB" 1209.

The MP may, during the course of a resuscitation, need to shock a victim more than once. In such a situation, the MP may wish to review the parameter choices selected for one or more previous shocks. Touching "SHOW PREVIOUS" 1202A results in the display of each of:

a) the energy, b) synchronization, c) electrode choice, and d) the waveform for the previous shock. The choices for these previously selected parameters are displayed on the Main Defibrillation Screen in a manner similar or identical to that mentioned above, for the display of current parameter selections, using the display capability of 1212A,B; 1214A,B; 1216A-C and 1218A-C.

If, after touching "SHOW PREVIOUS", the MP wishes to select all of the displayed parameters, he touches "ACCEPT" 906. If, after touching "SHOW PREVIOUS", the MP wishes to select some but not all of the displayed parameters, he over-writes the parameters he wishes to change, and then touches "ACCEPT".

Touching "SHOW PREVIOUS" a second time, results in the display of the parameters used for the next previous shock, i.e. the shock before the immediately preceding shock. Each successive time that "SHOW PREVIOUS" is touched, the parameter values for the next earlier shock are displayed. Any of these sets of displayed values may be selected (with or without modification, as indicated above,) by touching "ACCEPT" 906.

If the MP, using "SHOW PREVIOUS", views two or more sets of previous values, and then wishes to "reverse direction", i.e. to again view the parameter values of the next most recent shock, he touches "SHOW NEXT" 1202B. Touching "SHOW NEXT" a second time, results in the display of the parameters used for the next most recent shock. Each successive time that "SHOW NEXT" is touched, the parameter values for the next shock are displayed. Thus the MP may move either backwards (using "SHOW PREVIOUS") or forwards (using "SHOW NEXT") through the sequence of already delivered shocks and review their parameters. Any of these sets of parameters may be selected (with or without modification) by touching "ACCEPT" 906.

An alternate method of displaying sets of previously utilized parameters is for the MP to save desirable sets to memory. This is accomplished by having the MP touch "SAVE" 1204B. Later on (either during treatment of the same victim or alternatively during the treatment of another victim) the MP may retrieve these values by touching "SHOW SAVED" 1204A. If, after touching "SHOW SAVED", the MP wishes to select all of the displayed parameters, he touches "ACCEPT" 1206. If, after touching "SHOW SAVED", the MP wishes to select some but not all of the displayed parameters, he over-writes the parameters he wishes to change, and then touches "ACCEPT".

When more than one set of values is saved, the sets can be labelled in various ways including:

a) having each saved event time-stamped, or time- and date-stamped;

b) numbering the saved events;

c) naming the saved events with a keyboard entry at the time the event is saved; and, d) combinations of the above.

When more than one event has been saved, touching "SHOW SAVED" 1204A results in the display of the list of saved sets of parameters and the appropriate identifier. The MP can then choose among them either by keyboard entry or by viewing them on a touch sensitive screen, with the MP selecting the desired set by touch.

The method of displaying previously used sets of defibrillation parameters discussed hereinabove is not unique. One alternate method shows previous parameter sets on-screen, without having to request their display. This is discussed below in Section 6.3.1.2.2.4 regarding the electrode setup screens shown in FIGS. 30-32.

6.3.1.2.2.1 Defibrillation Energy Screen

Figure 34:
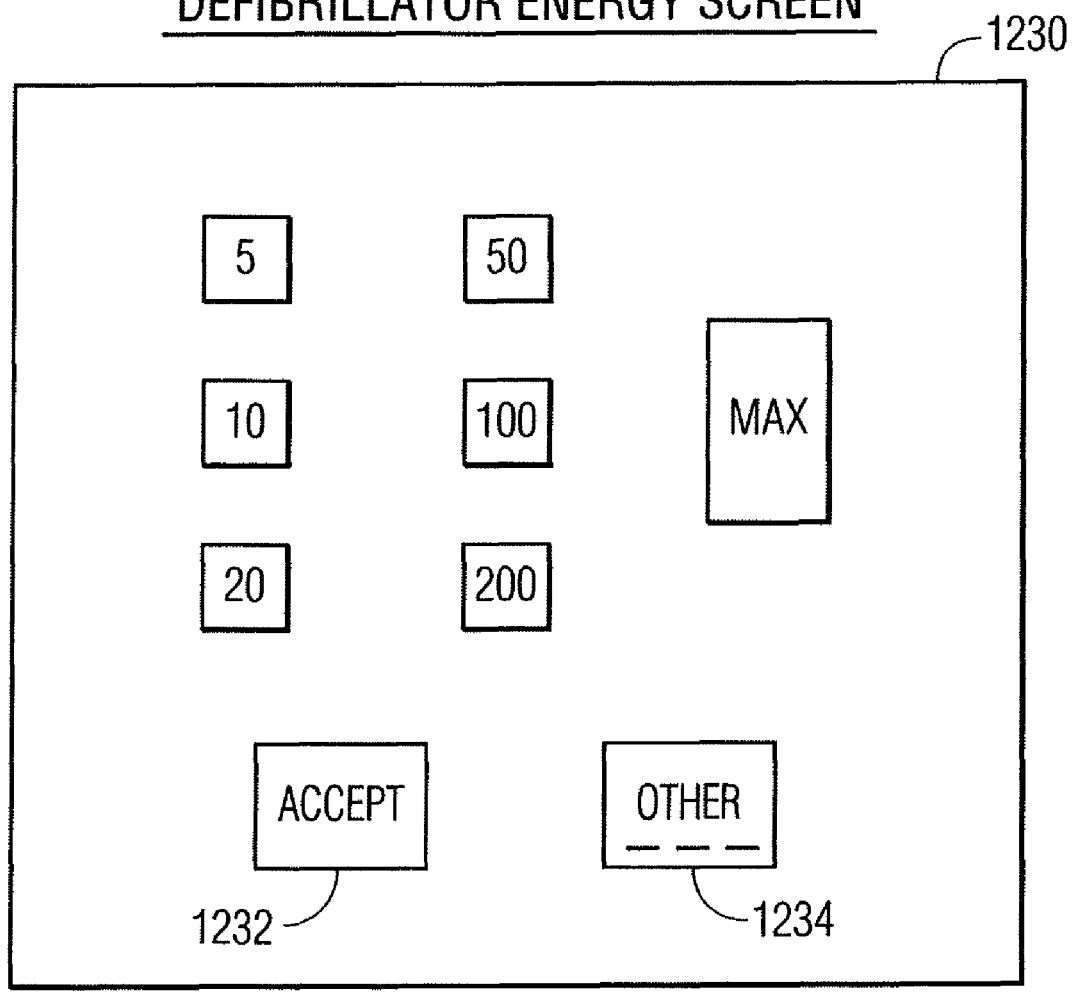
FIG. 34 illustrates a touch-sensitive display screen at the central station for control of the on the defibrillator energy.
Figure 35:
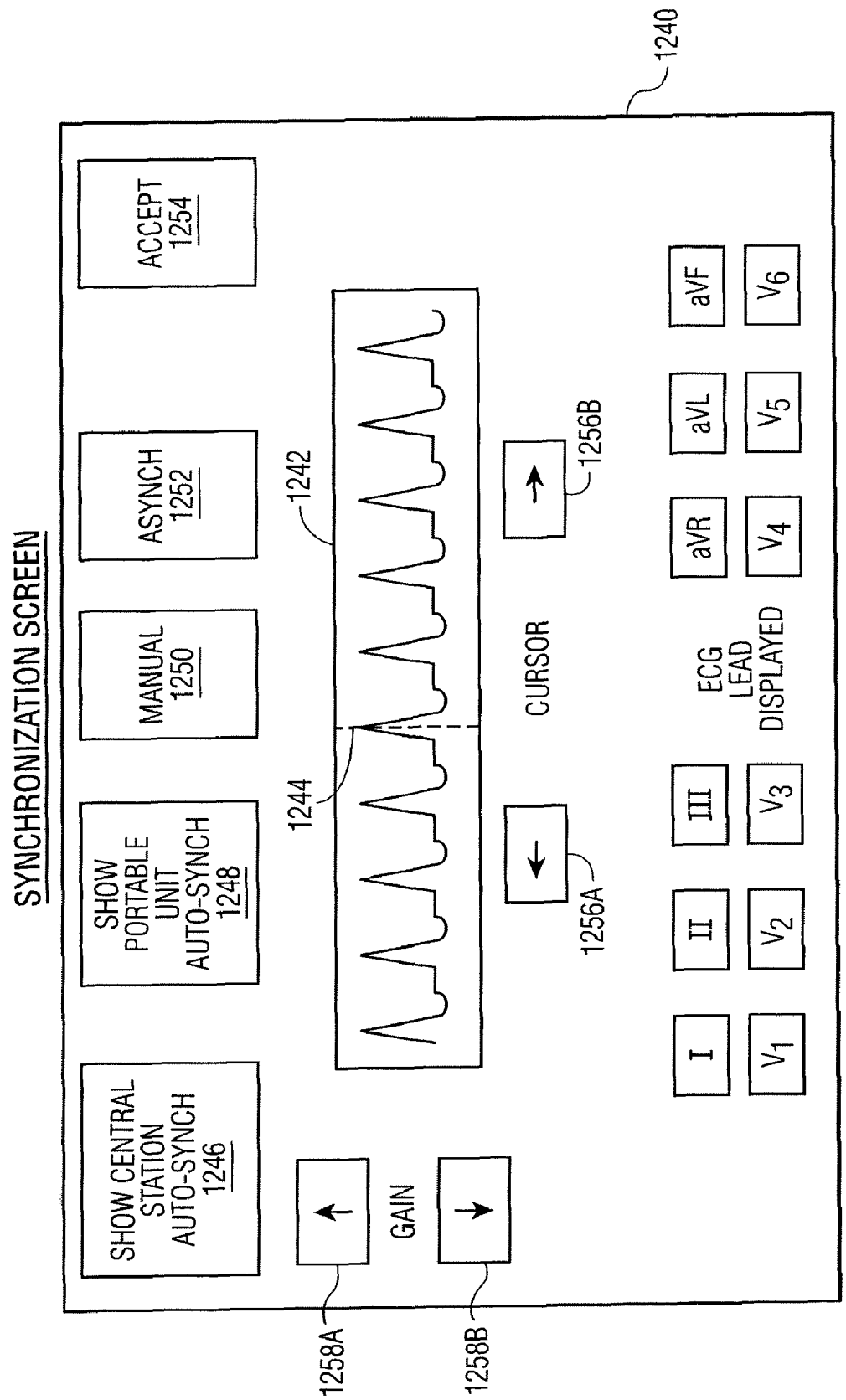
FIG. 35 is illustrates a touch-sensitive display screen at the central station for control of the defibrillator synchronization.

If a less than maximal energy output is desired, the MP touches the "OTHER" button 1212B in the Energy section of the screen which would lead to the display of the Defibrillator Energy Screen 1230 (FIG. 34). This screen 1230 shows seven values of energy ranging from 5 joules to maximal. (Although values at the low end would be impractical for defibrillation, they could be used for the synchronized conversion of ventricular tachycardia or atrial flutter.) A particular value of energy is selected (in the case of a touch sensitive screen, for example) by touching within the box corresponding to that value, followed by touching within the box labelled "ACCEPT". Touching one of the buttons which specifies the energy value results in highlighting, backlighting, coloring or otherwise visually emphasizing the number within the button. Touching "ACCEPT" returns the MP to the Main Defibrillation Screen.

If the MP changes his mind after touching a particular energy value, he may over-write the previous choice by simply selecting another value. On the Defibrillation Energy Screen, this would result in visual emphasis of the new choice, and removal of visual emphasis of the over-written choice.

An alternative embodiment would not have the "ACCEPT" button. In this embodiment, the act of touching one of the buttons which delineate a particular energy value would both select that value and return the MP to the Main Defibrillation Screen.

If the MP desired an energy value that was not among the screen choices, he could touch "OTHER" 1234 and then enter the value via the keyboard; The value would be displayed on the defibrillation energy screen in button 1234, replacing the word "OTHER". The MP would then touch "ACCEPT" 1232 on the Defibrillation Energy Screen (or press "Enter" on the Keyboard).

6.3.1.2.2.2 Synchronization Screen

During ventricular fibrillation, the ECG waveform is aperiodic and the MP will want to use an asynchronous shock. For certain cases of ventricular tachycardia, however, the MP may desire a shock which is synchronized to a particular moment of the "R-wave" of the ECG waveform. With an R-wave synchronized shock, a lower (and sometimes much lower) amount of energy may be used for termination of tachycardia. This would be advantageous in a conscious, a semi-conscious or a very large victim.

An R-wave synchronized shock is also necessary if a shock is being used to treat atrial fibrillation, supraventricular tachycardia or atrioventricular reciprocating tachycardia. Although these latter three tachycardias are not as directly life-threatening as ventricular tachycardia of ventricular fibrillation, at times they do pose a major threat to a victim's safety. Therefore, an MP may encounter a victim who is unconscious or severely compromised as a result of one of these rhythms, and accordingly may deem it appropriate to use a synchronized shock to terminate the tachycardia.

Care must be taken to avoid mistakenly delivering the shock on the "T-wave;" T-wave shocks may actually precipitate ventricular fibrillation. Circuitry for automatically selecting the peak of the R-wave as the desired moment for energy delivery is known in the art. In clinical practice a manually operated defibrillator, when operated in the synchronous mode, displays its assessment of the R-wave peak, so that the operator may confirm that synchronization is proper, prior to energy delivery.

In a preferred embodiment of the invention, when desiring to deliver an R-wave synchronous shock, the MP will assure that the timing of the shock is indeed synchronous with the R-wave of the ECG. This is done by first selecting "YES" 1214B on the Main Defibrillation Screen, which results in the display of the Synchronization Screen 1240, shown in FIG. 35. The victim's ECG is displayed in window 1242 of screen 1240, with a vertical cursor (or other on-screen indicator) 1244 marking the moment of maximal R wave amplitude as determined by the central station-based algorithm. The cursor may mark one or all of the displayed beats. If the MP feels that the cursor does, in fact, mark the point of the R-wave peak, he touches "ACCEPT" 1254 which returns him to the Main Defibrillation Screen, where he can go on to choose any shock parameters which have not yet been specified.

If the MP feels that the cursor has not been properly placed, he has three options:

a) He can observe a determination of the R-wave peak by a portable unit algorithm;

b) He can manually select his own synchronization timing; or, c) He can abandon synchronization and return to asynchronous energy delivery.

The MP can select any of these choices by touching 1248, 1250 or 1252 respectively, on the top portion of screen 1240.

The first of the aforementioned three choices is the use of the PU-determined R-wave peak. The MP can, in a preferred embodiment, display the selection of the R-wave peak by circuitry within the PU. (The PU selection will not necessarily be identical to the R wave peak selected by a central station algorithm, if transmission of the PU ECG signal resulted in distortion of the signal.) The MP displays the PU-selected R wave peak by touching "SHOW PORTABLE UNIT AUTO-SYNCH" 1248. If he agrees with it, he touches "ACCEPT" 1254, and returns to the Main Defibrillation Screen. If he wishes to again view the R-wave peak selection based on the central station signal, he touches 1246 "SHOW CENTRAL STATION AUTO-SYNCH".

The second choice of the aforementioned three choices is manual selection of synchronization timing. By touching the "MANUAL" button 1250, the MP enables buttons 1256A and 1256B which allow him to move the cursor to the right or left on ECG display 1242. Such movement may be accomplished by either:

a) continuously touching one of the buttons, resulting in movement of the cursor at a constant rate;

b) repeatedly touching the button, resulting in movement of the cursor by a fixed amount per touch; or, c) a combination of a) and b).

When the cursor reaches the desired position, the MP touches "ACCEPT" 1254 which returns him to the Main Defibrillation Screen.

Screen 1240 shows additional means of enhancing the peak of R-wave selection process. The degree of amplification of the ECG signal display may be adjusted up or down using gain control buttons 1258A and 1258B. At the bottom of screen 1240, there are 12 buttons which allow for selecting different ECG leads for display. This allows the MP to avoid a lead choice in which the T-wave amplitude is not significantly smaller than the R-wave amplitude. Depending on the electrode pad being used, one or more lead choices may not be available.

If the MP decides to abandon synchronization, either a) because of uncertainty in distinguishing R-waves from T-waves (as is occasionally the case whether the distinction is operator or algorithm-based), or b) because the rhythm may have deteriorated in the moments after the decision was made to attempt a synchronized energy delivery, the MP touches "ASYNCH" 1252, followed by "ACCEPT" 1254, and is returned to the Main Defibrillation Screen.

6.3.1.2.2.3 Pulse Shape Screen

A preferred embodiment of the invention, allows the MP to select the details of the defibrillation pulse contour. If the MP desires to use a defibrillation waveform other than a pre-specified biphasic waveform, he touches "OTHER" 1216B on the Main Defibrillation Screen, which takes him to Pulse Shape Screen 1260, FIG. 36.

This screen allows for the MP three groups of options:

a) the delivery of a monophasic defibrillation pulse;

b) the delivery of a biphasic pulse whose shape is other than the default; and, c) the delivery of a waveform which is more complex than the default biphasic pulse.

The MP can select a monophasic pulse by touching "MONOPHASIC" 1262. He would then either utilize a default value of pulse width by selecting "ACCEPT" 1270, or would specify a particular pulse width value by:

a) touching "PULSE WIDTH" 1268;

b) next, using the keyboard to input a numerical value for the pulse width; and then c) touching "ACCEPT" 1270 on Pulse Shape Screen 1260, which returns him to the Main Defibrillation Screen.

The MP can tailor the shape of the default biphasic pulse by using the "LEADING P.W." button 1272A to specify the width of the first phase, and using the "TRAILING P.W." button 1272B to specify the width of the second phase. Each of buttons 1272A and 1272B is used in a manner analogous to that of button 1268: that is, after touching each one, the MP inputs a pulse width value via the keyboard. After the two values of width have been inputted, touching "ACCEPT" 1270, returns the MP to screen 1200, and allows for the delivery of the specified biphasic pulse, once energy, synchronization and route are specified.

The delivery of a waveform with three or more phases is selected by touching "OTHER" 1266, on screen 1260. The width of the first phase is then specified by touching "I" 1276A, and then entering its value via the keyboard. Similarly the width of the second phase is specified by touching "II" 1276B, and then entering its value via the keyboard. The third phase is specified by touching "III" 1276C and then specifying its width. If a fourth phase is desired, the MP touches "ADDITIONAL" 1276D and using the keyboard to input information about each additional phase.

In a preferred embodiment of the invention, the MP's choice of the number of phases in the defibrillation pulse would be displayed by visually emphasizing the word in the selected button. For example, the word "MONOPHASIC" would be highlighted after button 1262 is touched. Numeric selections would be displayed by inserting the appropriate numeric value into the corresponding button. For example, the number "6.0", if selected for the width of the leading component of a biphasic pulse, would appear inside of button 1272A, beneath the words "LEADING P.W.".

As is the case with other screens, the MP has the option of changing an already specified parameter choice by "over-writing it," i.e. by selecting a new choice. For example, if the MP brought up Pulse Shape Screen 1260 initially intending to select a monophasic pulse, then selected the monophasic pulse by touching "MONOPHASIC" 1262, and then changed his mind, and wanted a biphasic pulse he could either a) touch "DEFAULT" 1274 which would select the default biphasic waveform, or b) touch "BIPHASIC" 1264, after which he would need to input the values of leading and trailing pulse width, as described above, to select a biphasic pulse with a width differing from the default setting. Changing a previously selected choice of phase number results in visual emphasis of the word inside the button corresponding to the new choice and removal of the emphasis on the no longer selected choice. The display of numeric values is also adjusted to reflect a change of choice.

If the MP has already touched "ACCEPT" 1270 and thereby returned to the Main Defibrillation Screen 1200, he still has the option of changing his waveform choice, as long as he has not delivered the shock. He would do so by again touching "OTHER" 1216B on screen 900, which would return him to Pulse Shape Screen 1260, after which he can over-write his previous choice.

The method of specifying pulse shape described herein is not unique. Multiple other approaches are possible including:
  a) allocating more or all information inputting to the keyboard;
  b) using different arrangements of buttons to specify the pulse contour (for example, the function of pulse width specification using buttons 1268, 1272A, 1272B, 1276A, 1276B, 1276C and 1276D could be accomplished using a smaller number of buttons);
  c) specifying "tilt" (a measure of the rate of decline in voltage during the pulse) rather than (or in addition to) pulse width, and/or,
  d) specifying other descriptors of pulse shape including the maximum and/or minimum amplitude of each phase, delays between phases, and the waveform contour details—if other than the classic truncated exponential;
  e) using a "library" of pre-stored pulse shapes.

Pulse Contour Miniscreen 1278 allows the MP to have an image of the pulse that he "constructs," using the options available on the pulse shape screen. The Miniscreen may also display the numerical values for each parameter which specifies the selected shape.

The MP may call up previous choices of parameter values for the Pulse Shape Screen by touching buttons analogous to those on the Main Defibrillation Screen. In particular:
  a) "SHOW PREVIOUS" 1280A on screen 1260 is analogous in function to "SHOW PREVIOUS" 1202A on screen 1200;
  b) "SHOW NEXT" 1280B on screen 1260 is analogous in function to "SHOW NEXT" 1202B on screen 1200;
  c) "SHOW SAVED" 1282A on screen 1260 is analogous in function to "SHOW SAVED" 1204A on screen 1200; and,
  d) "SAVE" 1282B on screen 1260 is analogous in function to "SAVE" 1204B on screen 1200.

"SHOW PREVIOUS", "SHOW NEXT" and "SHOW SAVED" parameters are displayed in the same way that current selections are. The MP may accept a saved set of waveform parameters "as is" or modify some of the waveform parameters by over-writing and then accept, as per the discussion in Section 6.3.1.2.2.

Since the MP may also use the Pulse Shape Screen to specify the shape of a pacing pulse (see below), and since the shape of the pacing pulse may be different from that of the defibrillating pulse, means are provided for indicating which of the two pulse types is being specified. The default pulse assignment (i.e. defibrillation vs. pacing) is based on the immediately prior screen used by the MP: If the prior screen was the Main Defibrillation Screen, then the default arrangement is for screen 1260 to specify the shape of the defibrillation pulse. If the prior screen was the Main Pacing Screen 1370 (see text below and FIG. 38), then the default arrangement is for screen 1260 to specify the shape of the pacing pulse. One of buttons 1284 ("DEFIB PULSE") and 1286 ("PACING PULSE") is highlighted or visually emphasized at all times, indicating which of the two types of pulses is being selected. Should the MP wish to specify the other pulse type, he does so by first touching the non-highlighted of the two buttons, and then selecting the desired specifications for the alternate pulse. (Touching "ACCEPT" next takes the MP a) to the Main Pacing Screen 1370 if he had just specified the pacing pulse shape parameters, or b) to the Main Defibrillation Screen 1200 if he had just specified the defibrillation pulse shape parameters.)

6.3.1.2.2.4 Electrode Setup Screens

The MP may decide to use non-default values of defibrillating electrode choice if:
  a) a prior defibrillation attempt with the default electrode choice was unsuccessful;
  b) the patient is large;
  c) the patient is small;
  d) a high impedance value indicates that the either one or more electrodes is making poor contact with the victim, or there is a damaged pad wire; or,
  e) the MP sees (via the video camera) that the pad was attached to the victim with either an improper position or orientation.

In a preferred embodiment of the invention the tearing of conductive strip 266 (FIG. 5E) at the time of pad application would have already informed the system which type of electrode pad(s) (five electrode vs. matrix pad vs. single electrodes) has been applied to the victim (discussed above in Section 3.2). In this preferred embodiment, if the MP selects non-default electrodes by touching "OTHER" 1218B on the Main Defibrillation Screen 1200, the central station monitors will display the pad setup screen which corresponds to the electrode pad system which has been attached to the victim. Three types of electrode pad systems are discussed hereinbelow:

a) the five-electrode torso-shaped pad system (discussed in Section 3.2);

b) the matrix pad system (discussed in Section 3.3); and, c) the multiple single pad system (discussed in Section 3.4).

6.3.1.2.2.4.1 Five Electrode Pad Setup Screen

In a preferred embodiment of the invention, when a five electrode pad is attached to the victim, if the MP does not want to use the default selection of electrodes (pads α and δ) for defibrillation, he touches "OTHER" 1218B on the Main Defibrillation Screen 1200. The system will then display screen 1290, the Five Electrode Pad Setup Screen, shown in FIG. 31. From this screen the MP can select any combination of electrodes for defibrillation energy application. (The screen can also be used to select the electrodes used for pacing energy application and for ECG recording, when the five-electrode pad is in use and the default selections of pacing and/or ECG electrodes are not desired.)

For example, the MP might want to apply defibrillation energy between the α and δ pads. (This example is also presented in Section 4.2 [Sample Cardiac Arrest], Table 11, Time 2:31, and is discussed in Section 4.3.1.1 [The MP Decision to Change the Defibrillation Vector for the Second Shock].) To do so, working from Screen 1290, he touches:

1) "PAD α" 1292A; then,
2) "AND" 1294; then,
3) "PAD ε" 1292E; then,
4) "ACCEPT" 1296.

Touching "ACCEPT" 1296 returns the MP to the Main Defibrillation Screen 1200.

Touching the "AND" button demarcates the completion of the cathodal electrode selection and is followed by the start of the anodal selection (or vice versa). This approach allows the MP to use more than two electrodes and, in such a situation, to let the system know which electrodes are to be electrically common. For example, if the MP desires to administer a shock in which the δ and ε electrodes are electrically common, and in which energy is applied between the α electrode and the composite δ/ε electrode, working from Screen 1290, he touches:

1) "PAD α" 1292A; then,
2) "AND" 1294; then,
3) "PAD δ" 1292D; then,
4) "PAD ε" 1292E; then,
5) "ACCEPT" 1296.

Because of the need to specify multiple pads while working from this screen, changing a selection by over-writing, as was the method for some other screens, would not result in clear specifications. Therefore, the "CANCEL" button 1298, allows the MP to delete the entire electrode entry and start all over. (In an alternative embodiment, only the last electrode choice would be deleted by touching "CANCEL". Each successive time it is touched would result in the deletion of the next prior electrode choice.) If the MP changes his mind about non-default electrodes, and decides to use the default electrode pair, he can simply touch "DEFAULT" 1300, which selects the α and δ electrodes, and returns the MP to the Main Defibrillation Screen.

Screen 1290 illustrates a method of displaying prior shocks that differs from the "SHOW LAST" and "SHOW SAVED" buttons on the Main Defibrillation and on the Pulse Shape Screen. The "PRIOR ATTEMPTS" section of the Five Electrode Pad Setup Screen 1290 lists, in tabular form, the sequence of electrode and energy specifications for each prior shock. In a preferred embodiment, it would also display the each pad selection as it is chosen; for example, if a fourth shock was being programmed, and the γ and ε electrodes were being selected, then the fourth entry on the screen would show:

a) "4) ____ VS ____ @____ " prior to electrode selection;

b) "4) _γ_ VS ____ @____ " after γ electrode selection; and c) "4) _γ_ VS _ε_ @____ " after ε electrode selection.

Alternate embodiments of the invention could use:

a) this format for other screens including screens 1200 and 1260;

b) the "SHOW LAST" and "SHOW SAVED" formats for screen 1290 (and for the other electrode pad setup screens discussed below—which are shown in FIGS. 30 and 32 with the "PRIOR ATTEMPTS" format of screen 1290);

c) hybrids of the "PRIOR ATTEMPTS" format and the "SHOW LAST"/"SHOW SAVED" format; and, d) different formats which allow the MP to access information about prior attempts.

The electrodes on the five electrode pad, in addition to their defibrillating function, can also be used for ECG recording (see above) and for pacing the heart (see below). Screen 1290 can be use in any of these three situations, when the MP desires non-default electrode choices. The choice of electrodes for one of these three functions (e.g. defibrillation) need not be the same as the choice for another (e.g. pacing).

Figure 38:
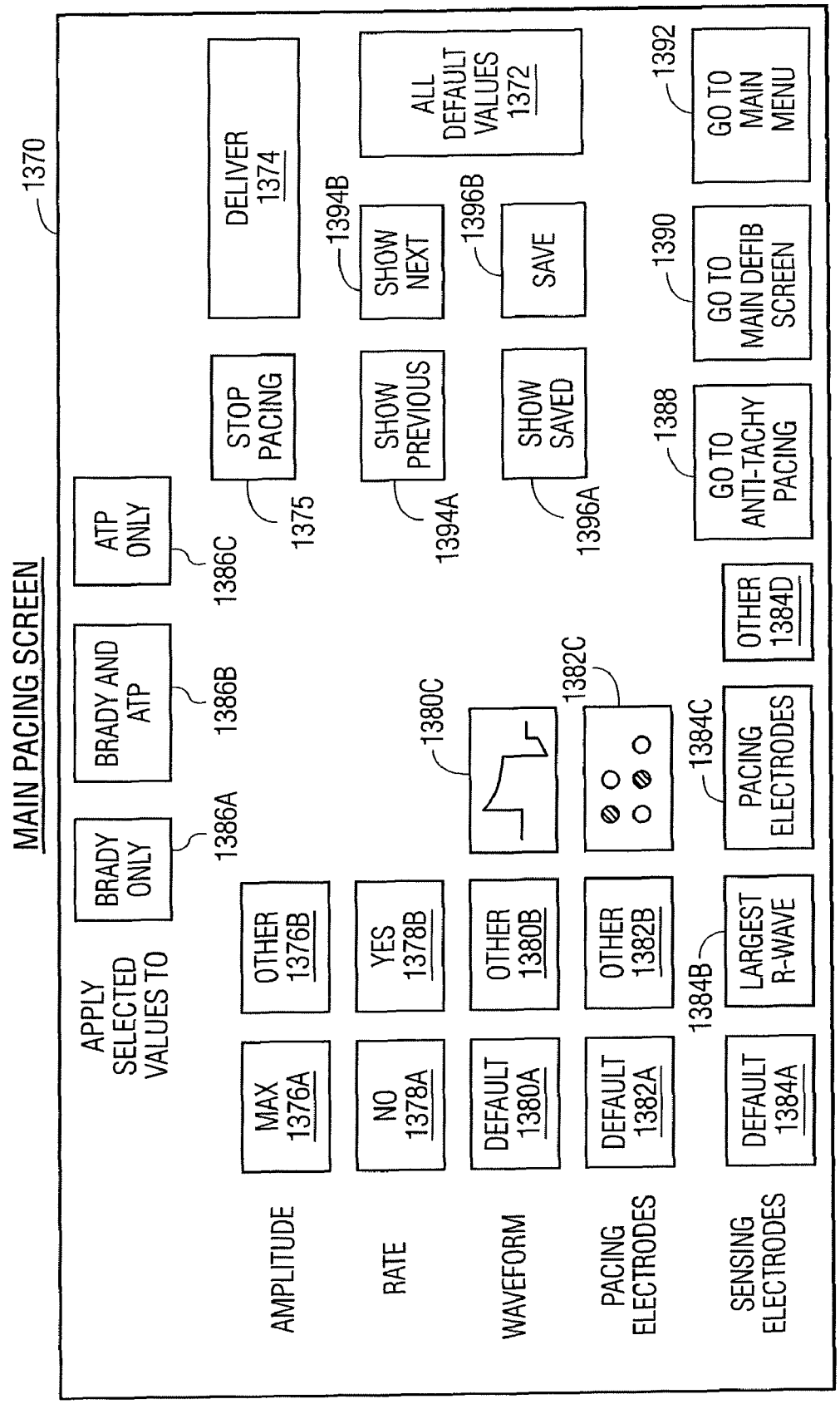
FIG. 38 illustrates a touch-sensitive display screen at the central station for selection of pacing electrodes and for control of the cardiac pacing parameters and waveform.

In a preferred embodiment, the screen which the MP used to select screen 1290 will determine which of the three functions (defibrillation, pacing or ECG recording) is specified by his electrode choices. For example, if the MP is working from the Main Defibrillation Screen 1200 and touches "OTHER" 1218B, the electrodes he then selects on screen 1290 will be the defibrillation electrodes. If the MP arrived at Screen 1290 from the Main Defibrillation Screen, but then wished to select pacing electrodes, he would touch "PACE CONFIGURATION" 1304, and then enter his choice of pacing electrodes in the same manner as was done for entering the defibrillation electrodes. The "SHOCK CONFIGURATION" button 1302 lets the MP select shock electrodes if he arrives at screen 1290 from either the Initial ECG Screen (FIG. 29) or from the Main Pacing Screen (FIG. 38). The "ECG CONFINGURATION" button 1306 lets the MP select ECG electrodes if he arrived at screen 1290 from either the Main Defibrillation Screen or the Main Pacing Screen. In a preferred arrangement of this embodiment, there is an on-screen indication of which of the three functions—defibrillation, pacing or ECG—is being selected. For example, if the MP is selecting the shock electrode configuration, the words "SHOCK CONFIGURATION" of button 1302 would be either highlighted, backlit, blinking, etc.

The Five Electrode Pad Setup Screen 1290 is intended for use with electrode pad 204A (FIG. 5A), in which each electrode may function as an ECG electrode or an electrode for energy delivery. This pad does not contain electrodes intended only for ECG recording. A setup screen which would accommodate electrode pads 204B and 207 (FIGS. 5B and 5C) with five defibrillating electrodes and 7 additional ECG electrodes is not shown. Its appearance would be analogous to that of screen 1290, and the selection of non-default defibrillating electrodes would be identical to the above description for the use of screen 1290.

6.3.1.2.2.4.2 Matrix Electrode Pad Setup Screen

In a preferred embodiment of the invention, when a matrix electrode pad is attached to the victim, if the MP does not want to use the default selection of electrodes for defibrillation, he touches "OTHER" 1218B on the Main Defibrillation Screen 1200. The system will then display screen 1310, the Matrix Electrode Pad Setup Screen, shown in FIG. 30. A typical array of default matrix pad electrodes for the composite right-sided electrode would be a combination of nine electrodes: A1-A3, B1-B3 and C1-C3 rendered electrically common upon the appropriate command to the portable unit. A typical array of default matrix pad electrodes for the composite left-sided electrode would be a combination of nine electrodes: G1-G3, H1-H3 and J1-J3 rendered electrically common upon the appropriate command to the portable unit. From screen 1310 the MP can select any combination of matrix pad electrodes for defibrillation energy application. He selects matrix pad electrodes by touching the buttons 1312 that correspond to the matix pad electrodes that he wants to include. (The screen can also be used to select the matrix pad electrodes used for pacing energy application and for ECG recording, when the matrix electrode pad is in use and the default selection is not desired.)

For example, the MP might want to apply defibrillation energy between two more widely separated groups of electrodes than those specified as the default. To do so, working from screen 1310, he touches:

1) "A1", then "A2", then "A3"; then,
2) "B1", then "B2", then "B3"; then,
3) "C1", then "C2", then "C3"; then,
4) "AND" 1314; then,
5) "H1", then "H2", then "H3"; then;
6) "J1", then "J2", then "J3"; then,
7) "K1", then "K2", then "K3"; then,
8) "ACCEPT" 1316.

After each of the matrix electrode selection buttons is touched, the label within the button (i.e. "A1", "A2", "A3" etc.) is visually highlighted, allowing the MP to easily keep track of his choices.

The buttons "AND" 1314, "ACCEPT" 1316, "CANCEL" 1318 and "DEFAULT" 1320 function in the same manner as the corresponding buttons on the aforementioned Five Electrode Pad Setup Screen 1290.

In a preferred embodiment of the invention, there is a "PRIOR ATTEMPTS" area of screen 1310 which shows the matrix electrode combinations which were used in prior defibrillation attempts. As shown in FIG. 30, those matrix electrodes selected to form composite electrodes at the time of prior defibrillation attempts may be represented by filled in boxes (and those matrix electrodes not used may be represented by non-filled in boxes), in a miniature version of the matrix electrode pad. In a preferred embodiment of the invention, touching within one of the buttons 1322 which contain the miniature matrix pad representations, results in highlighting of all of those matrix electrode buttons 1312 corresponding to the filled in 1322 selections. This enlargement step, reduces the chance of an error. If the MP then wishes to choose the displayed matrix electrode pattern for shock administration, he touches "ACCEPT" 1316.

The energy and other shock-related parameters associated with a particular prior attempt, though not shown in FIG. 30, could be shown if desired.

Since the selection of matrix electrode combinations is potentially more time consuming than the selection of electrodes on non-matrix pads, an alternate embodiment would display, within screen 1310, a menu of other commonly used matrix electrode combinations—even if they had not been selected during the current victim's prior defibrillation attempts. These other commonly used combinations could be displayed instead of, or in addition to, prior attempts involving the current victim.

Other time saving approaches may include (but are not limited to):

a) the ability to select two adjacent matrix electrodes (e.g. A1 and B1) simultaneously by touching the corresponding buttons simultaneously. This could also be accomplished with four adjacent buttons (e.g. A1, A2, B1 and B2) simultaneously;

b) the ability to select a 3 by 3 array of matrix electrodes (e.g. A1, A2, A3, B1, B2, B3, C1, C2 and C3) by touching the center electrode (B2, in the example) twice. Alternatively, another button labeled "ACTIVATE 3 BY 3 MATRIX" could be added to screen 1310, which would be touched after B2 is touched, to activate the aforementioned nine electrodes.

c) the ability to select a 3 by 4 array of matrix electrodes (e.g. each of the A, B, C and D matrix electrodes) by touching the two inner matrix electrodes (B2 and C2) twice; Alternatively, another button labeled "ACTIVATE 3 BY 4 MATRIX" could be added to screen 1310, which would be touched after B2 and C2 are touched, to activate the aforementioned twelve electrodes;

d) the ability to select a rectangular array of matrix electrodes by movement of the computer mouse 314 (FIG. 3)—e.g. by clicking the mouse button and holding it down starting at the upper left corner of the rectangle, and dragging to the lower right corner and then releasing the mouse button;

e) the ability to shift an already selected rectangular array of electrodes in the up, down, right or left directions, by using the four corresponding arrow keys on the keyboard.

In a preferred embodiment of the invention, various precautions are taken to avoid the selection of matrix electrodes that may result in:

a) impossible matrix electrode combinations (e.g. where a particular matrix element is listed as part of both the right-sided and the left composite electrodes);

b) medically unreasonable electrode combinations (e.g. where both the right and the left composite electrodes are too close together [A specific example would be the selection of the nine matrix electrodes in columns E, F and G for the right sided composite electrode and the selection of the nine electrodes in columns H, J and K for the left sided composite electrode.]); or c) situations that would cause a medically undesirable high current density because of small composite electrode area (e.g. if only a single matrix electrode (e.g. A1) was used as a composite electrode).

Methods for preventing or discouraging the use of potentially unwise electrode choices include:

a) locking out impossible and highly unreasonable choices, and displaying a message to the MP, explaining the reason for the lock-out, on the lower portion of the central station monitor 330. (See FIG. 3; The lower portion of 330 displays "MAJOR SYSTEM PROMPTS/MESSAGES TO MP".)

b) for unconventional or possibly unwise choices, displaying a message to the MP on the lower portion of the central station monitor 332. (See FIG. 3; The lower portion of 332 displays "MINOR SYSTEM PROMPTS/MESSAGES TO MP".) The message could ask the MP to touch a "YES" button to confirm his intention to go ahead with the selection;

c) for composite electrode choices which have already failed and are selected again, a minor system prompt on monitor 332 could be displayed.

The "SHOCK CONFIGURATION," "PACE CONFIGURATION" and "ECG CONFIGURATION" buttons 1324, 1326 and 1328 are analogous in function to buttons 1302, 1304 and 1306 on the Five Electrode Pad Setup Screen 1290, and on-screen indication of which of the three electrode functions is being selected is provided.

6.3.1.2.2.4.3 Multiple Single Pad Setup Screen

FIG. 32 shows screen 1340, used by the MP when the portable unit is used with two or more pads which contain single defibrillating electrodes. Buttons 1342A-1342D, corresponding to each of four single electrodes, are analogous to buttons 1292A-1292E on the Five Electrode Pad Setup Screen 1290. This screen could be used with two, three or four defibrillating electrodes. A screen which accomodates more than four electrodes is possible.

During system operation, the MP would select one or more electrodes, then "AND" 1344, then another group of one or more electrodes, and then "ACCEPT" 1346. In a preferred embodiment of the invention, the MP would know the anatomic location of the enabler's placement of each of pads #1, #2 ... by having observed their placement.

The remainder of the Multiple Single Pad Electrode Screen 1340 and its use, is identical to the Five Electrode Pad Setup Screen, except for a slight difference in the spatial arrangement of the buttons.

6.3.1.3 Unconventional Defibrillation Methods

Although not incorporated into the above discussion of pulse shape and electrode selection methodology, it would be possible to apply different waveforms between different electrode pairs. For example, "waveform A" could be applied between electrode pad #1 and electrode pad #2; "Waveform B" could be applied between electrode pad #3 and electrode pad #4 (or between electrode pads #2 and #3). Situations in which three or more waveforms are applied to non-identical pairs of electrodes would also be possible. Each waveform could carry a different energy. This multi-waveform approach would require the presence of a) additional screen selections to accommodate this variation, and b) additional defibrillator circuits within the PU. Such a situation is shown schematically in figure XX.

Situations in which combinations of electrode pads are used are also possible. For example, one of the five electrode pads or the matrix electrode pad, could be used with one or more single electrodes placed on the victim's back, or elsewhere. Alternatively one of the five electrode pads or a conventionally placed matrix electrode pad, could be used along with a matrix electrode pad placed on the victim's back. This multi-pad approach would require the presence of additional screen selections to accommodate this variation. As long as only one waveform is used no additional PU defibrillating circuits would be necessary. Additional defibrillator circuits within the PU would be required only if more than one waveform is used.

6.3.1.4 Paths From Main Defibrillation Screen

Besides paths to screens which allow for the specification of non-default defibrillation settings (FIGS. 30-32 and 34-36), three other exit pathways are available:

a) "GO TO ANTI-TACHY PACING" 1220 is accessed to allow an MP to attempt to terminate certain tachycardias by the technique of overdrive pacing. These tachycardias may occur after a defibrillation attempt (See Section 6.3.2, below).

b) "GO TO MAIN PACING SCREEN" 1222 is accessed to allow an MP to perform bradycardia pacing. Bradycardia may occur after a successful defibrillation (See Section 6.3.3, below).

c) "GO TO MAIN MENU" 1224 allows the MP to then go to any other screen.

6.3.2 Anti-Tachycardia Pacing Screen 6.3.2.1 General Considerations

FIG. 37 shows the Anti-Tachycardia Pacing Parameters Screen 1350. In a preferred embodiment of the invention, the MP can use it to cause the PU to administer bursts of rapid ventricular pacing, in an attempt to terminate an episode of ventricular tachycardia.

In a preferred arrangement of this embodiment, the MP selects either the "ALL DEFAULT VALUES" button 1352, or selects up to five non-default values which specify the anti-tachycardia pacing parameters.

6.3.2.2 Default Values

Typical values of anti-tachycardia pacing default parameters would include:

a) a pacing cycle length which is 82% of the tachycardia RR interval;

b) 8 pacing impulses;

c) an inter-burst decrement (the amount of decrease in paced RR interval between two successive burst pacing attempts) of 10 MSEC;

d) an intra-burst decrement (the amount of decrease in paced RR interval between successive beats within a burst) of 0 MSEC; and, e) a last R to S1 interval (the interval from the last tachycardia R-wave to the first ATP stimulus) of 80%.

Among the aforementioned five parameters, the factors which most clearly increase the aggressiveness of anti-tachycardia pacing are:

a) a smaller % RR;

b) a larger inter-burst decrement; and, c) a larger intra-burst decrement.

To deliver the pacing stimulation to the victim specified by the default parameters, the MP would touch "ALL DEFAULT VALUES" 1352 followed by "DELIVER" 1354.

6.3.2.3 Non-Default Values

If the MP wished to select a non-default value of ATP rate, he would touch one of the nine buttons labelled "72", "74", "76", "78", "80", "84", "86", "88" or "90". If he wished to select a value which did not correspond to the labels on the aforementioned buttons, he could either:

a) select "OTHER" 1358, and then use the keyboard to enter the desired value; or, b) select "90" and then touch the "+2" button 1360A once if he wished to select a value of 92%, twice if he wished to deliver a value of 94%, etc.; or, c) select "72" and then touch the "−2" button 1360B once if he wished to select a value of 70%, twice if he wished to deliver a value of 68% etc.

If the MP wished to specify the default value for ATP pacing rate (but wished to specify non-default values for one or more of the other ATP parameters), he would touch either "82" (if this value had been set as the default value) or "DEFAULT" 1356A.

If the MP wished to select a particular pacing rate (the increment above the tachycardia rate being a measure of aggressiveness), rather than using the aforementioned approach based on the RR interval of the tachycardia, he could:

a) select "OTHER" 1358; then, b) use the keyboard to enter "RATE"; then, c) use the keyboard to enter the numeric value of the pacing rate.

In an alternate embodiment of the invention, the MP could select the pacing rate by formatting the ATP Parameters Screen so that:

a) a sub-menu of pacing rates is displayed instead of the sub-menu of % RR shown in FIG. 37; or, b) both pacing rate and % RR sub-menus are displayed; or, c) either a sub-menu of pacing rates or a sub-menu of % RR is displayed at any one time; and a button is present which lets the MP select one of these two sub-menus.

For each of the four remaining ATP parameters, the MP would then go on to either: a) select a default value using one or more of "DEFAULT" buttons 1356B-1356E; or b) select a particular non-default value. Once each of the five ATP parameters had been selected, the MP would touch "DELIVER" 1354, to cause the PU to stimulate the victim with the specified ATP. If at any point before the delivery of the ATP, the MP wished to change his choice for one or more of the already selected ATP parameters, he could do so by over-writing the already-selected choice.

The ability to display the parameters of prior pacing attempts, or to display a "library" of selectable ATP parameter "packages", though not shown in FIG. 37, is an optional feature.

6.3.2.4 Paths from Anti-Tachycardia Pacing Screen

An unsuccessful anti-tachycardia pacing attempt may result in acceleration of ventricular tachycardia to a faster (and hence, less well tolerated) rate, or conversion of ventricular tachycardia to ventricular fibrillation. In either of these two cases, prompt delivery of a shock is desirable. By touching "GO TO MAIN DEFIB SCREEN" 1362, the Main Defibrillation Screen 1200 is accessed.

Occasionally, following the successful pace termination of VT, a slow heart rate occurs. By touching "GO TO MAIN PACING SCREEN" 1364, the Main Pacing Screen (see below) is accessed, allowing the prompt delivery of pacing at an appropriate rate (typically 50 to 100 beats per minute). The MP may also need to access the Main Pacing Screen if he wishes to change any of the parameters of the anti-tachycardia pacing pulse (amplitude, contour, electrodes) from the default values (see below).

6.3.3 Bradycardia Management Screens

Bradycardia or slow heart rate may be observed a) following the MP termination of any tachycardia or fibrillation (as was the case during the sample cardiac arrest described in Section 4.2, Table 11, Time=2:43), b) as the victim's initial heart rhythm. External electrical stimulation of the heart, external pacing, as is known in the art, can result in an acceleration of the heart rate to the rate of the external stimulation. In a preferred embodiment of the invention, the portable unit is capable of performing such pacing, under the direction of the MP.

The Main Pacing Screen 1370 (FIG. 38) is the MP's primary access to the control of bradycardia pacing. The screen layout is similar to that of the Main Defibrillation Screen 1200, and most of the control buttons have analogous functions on each of these two screens. The selection of bradycardia pacing parameters will consist of either using default values (which requires only the Main Pacing Screen) or will require the accessing of one or more other screens for the selection of:

a) non-default values of pacing pulse amplitude (FIG. 39); and/or, b) non-default values of bradycardia pacing rate (FIG. 40); and/or, c) non-default values of pacing pulse shape (FIG. 36); and/or, d) non-default values of pacing electrode configuration (FIGS. 30-32); and/or e) non-default values of "sensing", that is, the use of ECG information showing spontaneous activity of the heart, to reset the timing of pacing impulses.

6.3.3.1 Paths to Main Pacing Screen

The routes by which the MP arrives at the Main Pacing Screen 1370 are:

a) from the Main Defibrillation Screen (FIG. 33), if bradycardia is observed after the administration of a shock;

b) from the Anti-Tachycardia Pacing Parameters Screen (FIG. 37), if bradycardia is observed after tachycardia termination by ATP;

c) from the Initial ECG Screen (FIG. 29), following the recognition of bradycardia as the initial victim rhythm;

d) from any of the screens that may be used to select non-default values of pacing parameters (FIGS. 30-32, 36, 39 and 40); and, e) from the Screen Menu (FIG. 43).

6.3.3.2 Method of Operation: Bradycardia Pacing Screens 6.3.3.2.1 Default Values If the MP decides to pace using default values, he selects "ALL DEFAULT VALUES" 1372, followed by "DELIVER" 1374 (as was the case for the initial pacing during the sample cardiac arrest described in Table 11, Time: 2:46). Touching "DELIVER" results in the transmission of a command from the central station to the portable unit to deliver pacing with the programmed parameters, via the appropriate electrodes. Touching "STOP PACING" 1375 results in the transmission of a command from the CS to PU to terminate pacing.

A possible set of default values is:

a) Amplitude=maximum b) Rate=60 beats per minute ("BPM");

c) Waveform=monophasic;

d) Pacing electrodes=$\alpha$ and $\delta$ (when using the five electrode pad); and, e) Sensing=off.

The actual default values may be set in a number of ways which were discussed above (see Section 6.3.1.2.1).

6.3.3.2.1.1 Common versus Different Parameters for Bradycardia Pacing and for Anti-Tachycardia Pacing In the default mode of operation for screen 1370, the selected pacing and sensing parameters (except, of course, for rate) are applied for both bradycardia pacing and for antitachycardia pacing. The MP may, however, wish to use different parameters for these two types of pacing. If so, he can set them separately by touching "BRADY ONLY" 1386A or "ATP ONLY" 1386C prior to entering choices intended for only that one type of pacing. If he is entering ATP values, he a) does not enter a value for rate on screen 1370, and b) does touch "GO TO ANTI-TACHY PACING" 1388 after having entered the non-rate parameters.

If the MP, at any time after touching either "BRADY ONLY" 1386A or "ATP" ONLY 1386C wishes to return to the default mode of simultaneously setting both bradycardia and ATP pacing parameters (other than rate), the MP touches "BRADY AND ATP" 1386B and then enters the common parameters.

In a preferred embodiment of the invention, the default setting for the aforementioned common pacing parameters (viz. "BRADY AND ATP") is independent of the default setting for the other pacing parameters (e.g. amplitude, waveform, etc.) For example, if "BRADY ONLY" 1386A had been selected, followed by "ALL DEFAULT VALUES" 1372, the result would be that all bradycardia pacing values would be set to default values (but that ATP pacing parameters, if already set with one or more non-default values, would be unchanged). Also, if the system is operating in the BRADY AND ATP mode, then the selection of a non-default value of amplitude, for example, does not require the MP to touch "BRADY AND ATP" 1386B to reaffirm this.

6.3.3.2.2 Non-Default Values

Instead of selecting "ALL DEFAULT VALUES" 1372 for the pacing parameters, the MP may select one or more non-default values. A non-default value is selected by touching 1376B (non-default amplitude); 1378B (non-default rate); 1380B (non-default waveform); 1382B (non-default pacing electrode configuration); or 1384B, 1384C or 1384D (the three non-default sensing buttons). Each of these non-default buttons (except for the non-default sensing buttons, which are discussed below) leads to a different pacing detail screen (1260, 1290, 1310, 1340, 1400 [Pacing Amplitude Screen] and 1420 [Bradycardia Pacing Rate Screen]) which contains a menu which lists possible non-default settings. The approaches to displaying these pacing detail screens are the same as for displaying the defibrillation detail screens (see Section 6.3.1.2.2).

Once the MP has selected a non-default value and has then returned to the Main Pacing Screen, he may either a) select default values for the other pacing parameters, or b) select other non-default values for one or more of the remaining parameters.

To select a default value for one of the pacing parameters, the MP touches the appropriate one of buttons 1376A (default amplitude), 1378A (default rate), 1380A (default waveform), 1382A (default pacing electrode pattern) or 1384A (default sensing). An example of this approach is presented in Section 4.2 which describes an hypothetical cardiac arrest (see Table 11, Time 2:57-2:59: After selecting a non-default value for the pacing rate, the MP selects default values for each of the other four parameters.)

As was the case with the defibrillation screens, the selection of the default value of a pacing parameter preferably results in visual emphasis or highlighting of the word "DEFAULT" within the button (1376A, 1378A, 1380A, 1382A or 1384A) that corresponds to the default selection.

Non-default values are also preferably displayed on the Main Pacing Screen (FIG. 38) in an approach analogous to the defibrillation display:

a) A non-default value of pacing amplitude, if selected, would be displayed as a number within button 1376B, replacing the word "OTHER".

b) A non-default value of pacing rate, if selected, would be displayed as a number within button 1378B, replacing the word "OTHER".

c) A non-default pulse contour, if selected, would be displayed, along with the numerical parameters which specify it, in the Pulse Contour Miniscreen 1380C. This screen-within-screen would be analogous to its counterpart element 1216C on the Main Defibrillation Screen.

d) A non-default pacing electrode pattern, if selected, would be displayed in Miniscreen 1382C. The content of this Miniscreen would show the pattern of electrodes selected for pacing energy delivery, presented in a manner similar or analogous to the display in element 1322 (FIG. 30). With electrode pads other than the matrix electrode pad, those electrodes selected for pacing energy delivery could be either (i) displayed in Miniscreen 1382C, or (ii) listed within button 1382B, replacing the word "OTHER".

e) There are three non-default sensing choices. The amplitude of the largest R-wave (if one is present) and the lead from which it is recorded would be displayed in button 1384B. The amplitude of the R-wave corresponding to the lead selected for pacing would be displayed in button 1384C. The R-wave amplitude corresponding to a manually selected choice of sensing lead other than the aforementioned would be displayed in button 1384D.

When all of the pacing parameters have been selected, the MP touches "DELIVER" 1374, to deliver pacing via the electrode configuration, and with the parameters that have been selected. This format differs slightly from that of defibrillation, in that the step of touching an "ACCEPT" button (element 1206, FIG. 33), though required for defibrillation, is not required for pacing. Two reasons for requiring this step only during defibrillation are: a) Since capacitor charging within the PU takes a number of seconds, the requirement for touching a second button after charging is complete allows the MP to abort a shock if VT or VF terminates during charging; and b) The additional step serves a fail-safe function, making accidental or inappropriate defibrillation less likely.

As was the case when all of the pacing parameters are the default ones, when the MP touches the "STOP PACING" button 1375, the CS transmits a command to the PU for pacing cessation.

As was this case with the review of previous defibrillation efforts, the MP may want to review previous pacing efforts. The method for such review is analogous to that discussed in Sections 6.3.1.2.2 and 6.3.1.2.2.3 above: "SHOW PREVIOUS" 1394A, "SHOW NEXT" 1394B, "SAVE SAVED" 1396A and "SAVE" 1396B on the Main Pacing Screen all function identically to their counterparts on the Main Defibrillation Screen.

6.3.3.2.2.1 Pacing Amplitude Screen

Figure 39:
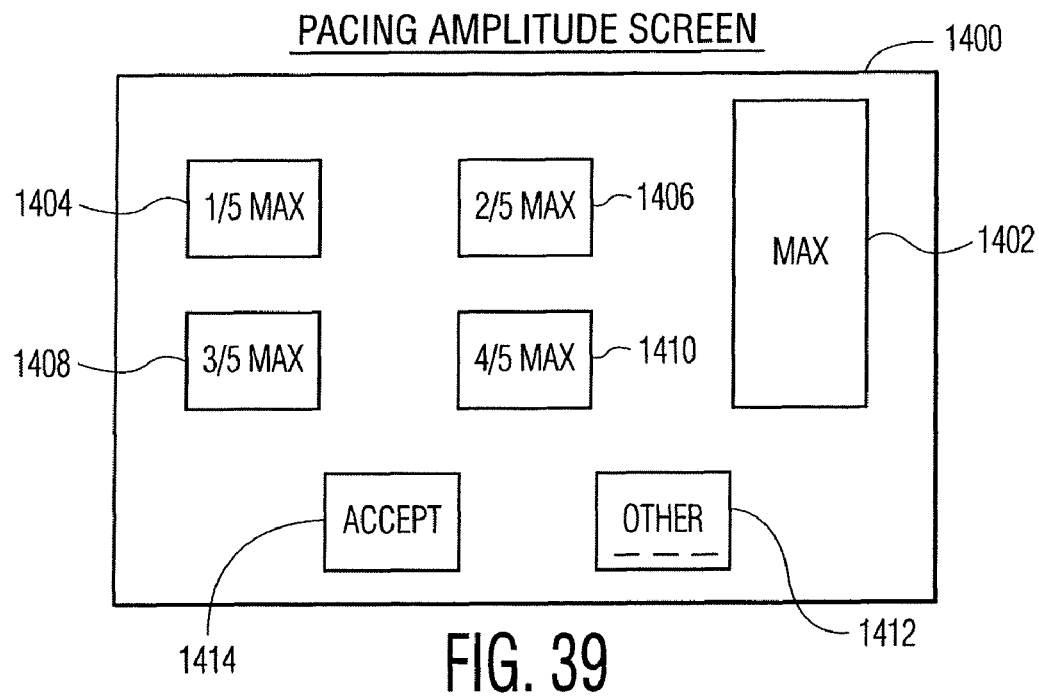
FIG. 39 illustrates a touch-sensitive display screen at the central station for control of the cardiac pacing amplitude.

FIG. 39 shows one possible example of a screen which would allow the medical professional to control the energy of the PU pacing pulse. The screen is arrived at by touching "OTHER" 1376B on the Main Pacing Screen, or from the Screen Menu (FIG. 43). The default value of amplitude is the maximum pacing amplitude of the PU, selected by touching the "MAX" 1402 button. Buttons 1404 ("⅕ MAX"), 1406 ("⅖ MAX"), 1408 ("⅗ MAX") and 1410 ("⅘ MAX") allow for the selection of lesser values of amplitude; These choices might be considerations in a semi-conscious or conscious victim. Another method of specifying the amplitude would be for the MP to touch the button labeled "OTHER", 1412, and then enter the desired value of amplitude via keyboard; The keyboard entry would then replace the word "OTHER" on the screen. The keyboard entry could be: a) a fraction other than the choices in buttons 1404, 1406, 1408 and 1410; or b) a numeric value, followed by the desired units (e.g. "V" for volts or "A" for milliamps). After entering a value for the amplitude, touching "ACCEPT" 1414 returns the MP to the Main Pacing Screen 1370, where the selected value of pacing amplitude appears within button 1376B.

If the MP decides to change his choice before touching "ACCEPT", he may over-write the choice. If he changes his choice after touching "ACCEPT", he would touch "OTHER" 1376B on the Main Pacing Screen, which would return him to the Pacing Amplitude Screen 1400.

Embodiments of the invention are possible in which:

a) there are a greater or a lesser number of buttons which select pacing amplitude, and in which the values that they specify are fractions other than fifths (e.g. ⅓ and ⅔);

b) the buttons which specify the amplitude specify actual output values (i.e. numbers of volts or milliamps), rather than fractions of the maximum output;

c) both the pacing amplitude and pulse width are selected on the same screen;

d) the amplitude is fixed;

e) the amplitude and pulse width may be varied, but not independently; i.e. in which the MP chooses from a menu of pre-specified pairs of values for pacing amplitude and pulse width; and/or, f) the amplitude is not fixed, but is determined by the system in which an "auto-capture" feature determines if "capture" (i.e. cardiac depolarization) has occurred, and utilizes an algorithm to optimize pacing amplitude and/or pacing pulse width.

6.3.3.2.2.2 Bradycardia Pacing Rate Screen

Figure 40:
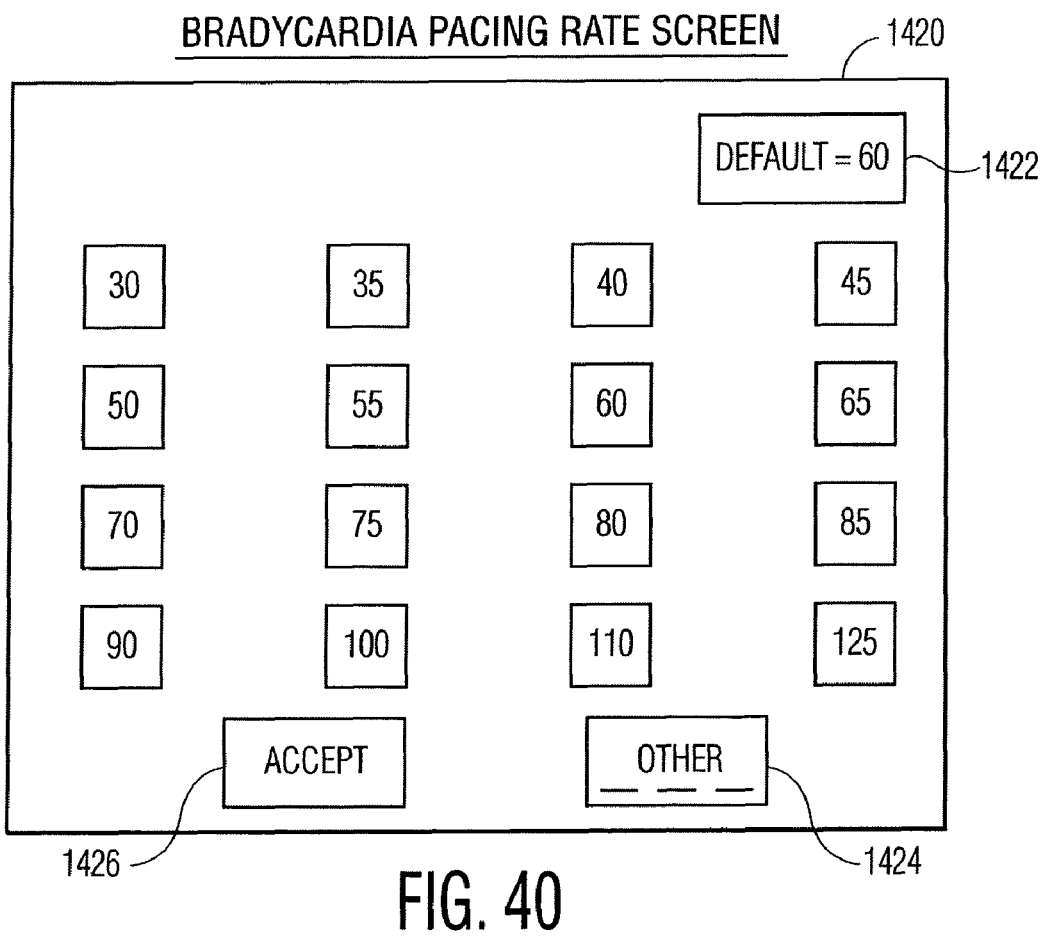
FIG. 40 illustrates a touch-sensitive display screen at the central station for control of the bradycardia pacing rate.

FIG. 40 shows one possible example of a screen which would allow the medical professional to control the rate of PU pacing. The screen is arrived at by touching "OTHER" 1378*b* on the Main Pacing Screen, or from the Screen Menu. The buttons labelled "30" through "125" (indicating the rate in beats per minute [BPM]) allow the MP to select a rate in this range. If after reaching the Bradycardia Pacing Rate Screen, the MP changes his mind and decides to utilize the default value of 60 BPM, he can select it by touching either a) button 1422 labeled "DEFAULT=60", or b) the button labeled "60". Another method of specifying the rate would be for the MP to touch the button labeled "OTHER" 1424 and then enter the rate via the keyboard. The keyboard entry would then replace the word "OTHER" in button 1424. After entering a value for the rate, the MP touches "ACCEPT" 1426 which returns him to the Main Pacing Screen 1370, where the selected value of pacing rate appears within button 1378B. The MP can change his choice of pacing rate using a method analogous to that described for changing pacing amplitude in the previous section.

Embodiments of the invention are possible in which:
a) the rate is specified only by keyboard;
b) the rate is specified only by buttons with pre-selected values, as in FIG. 40;
c) the buttons display values of rate other than those in FIG. 40; and/or,
d) the rate is not programmable.

6.3.3.2.2.3 Pulse Shape Screen/Pacing

In a preferred embodiment of the invention the MP may control the width or shape of the pacing pulse by touching button 1380B on the Main Pacing Screen. This takes him to Pulse Shape Screen 1260. In a preferred arrangement of this embodiment, the words "PACING PULSE" inside of button 1286 would then either blink or be otherwise visually emphasized, making it clear that the screen selections apply to the pacing pulse width and shape, not the defibrillator pulse width and shape.

The default value of pacing waveform is monophasic. The MP specifies one or more parameters using Pulse Shape Screen 1260, in a manner analogous to that described for the defibrillation pulse (see Section 6.3.1.2.2.3). He then touches "ACCEPT" 1270 to return to the Main Pacing Screen, where the pulse width is then indicated in button 1380B, and the pulse contour and any other pulse descriptors selected are shown in Pulse Contour Miniscreen 1380C.

Embodiments of the invention are possible in which:
a) the pulse shape screen for pacing is not identical to the pulse shape screen for defibrillation;
b) the MP cannot control any parameter of pulse contour except the pulse width;
c) the MP cannot control any parameter of pulse contour, including the width;
d) the MP controls of pulse shape and/or width are keyboard based; and/or,
e) the MP control of pulse width is via a single screen form which both pacing amplitude and pulse width are controlled.

6.3.3.2.2.4 Pacing Electrodes

If the MP wishes to select a non-default value of pacing electrode configuration, he can do so by touching button 1382B on the Main Pacing Screen. This takes him to the appropriate one of the three Electrode Pad Setup Screens shown in FIGS. 30-32. On arrival at the setup screen, the "PACE CONFIGURATION" button blinks or is visually highlighted, indicating that the screen is being used to set this function. The MP then makes his electrode choice in a manner analogous to the process for the selection of defibrillation electrodes (described in 6.3.1.2.2.4). He then touches "ACCEPT" to return to the Main Pacing Screen. The selected configuration is indicated within Miniscreen 1382C, and, when feasible (as discussed above), within button 1382B.

6.3.3.2.2.5 Pacemaker Sensing

In a preferred embodiment of the invention, pacing by the PU is asynchronous in the default mode, i.e. the PU pacemaker output is not influenced by a voltage applied to any of the electrode pads. The alternative to asynchronous pacing, the so-called "demand mode," allows the PU-based pacemaker to sense the victim's own cardiac activity, and to reset its pacemaker timing cycle upon sensing such activity, in a manner which is well known in the art.

The value of the asynchronous mode of operation is that it avoids the potential problem of inappropriate inhibition of pacemaker output by non-cardiac signals-signals which may be generated by movement of either the victim or the cable which connects the PU with the victim. The value of the demand mode is that it prevents "competitive pacing": the generation of unwanted pacing stimuli which may cause a deterioration in the victim's cardiac status.

If the MP desires to pace in the demand mode, he has three options, which are discussed hereinbelow.

6.3.3.2.2.5.1 Sensing from the Electrode Arrangement with the Largest R-Wave The first demand mode option is for the MP to touch button 1384B on the Main Pacing Screen, which causes the system to select the electrode pair whose R-wave has the largest amplitude, for sensing. This pair may or may not be the same as the electrode pair used for pacing. Each member of the pair may be a single electrode, or a composite of multiple electrodes rendered electrically common.

6.3.3.2.2.5.2 Sensing from the Electrode Arrangement used for Pacing

The second sensing option, accessed by touching button 1384C, is to use the pacing electrodes for sensing. With both the first and the second option, the MP is aided, in a preferred arrangement by the display of the numeric value of the R-wave amplitude within boxes 1384B and 1384C.

6.3.3.2.2.5.3 Sensing from an Electrode Arrangement Selected by the MP

The third demand pacing approach involves having the MP examine the ECG waveform on a number of ECG lead arrangements, and then select his choice for sensing from among the examined arrangements. In this embodiment of the invention, when the MP touches "OTHER" 1384D, the Initial ECG Screen 1180 (FIG. 29) is displayed. The R-wave amplitude for each of the ECG recordings is advantageously displayed within the buttons 1182 to the left of each tracing. If the MP does not see an ECG lead that he wishes to use among those displayed on the Initial ECG Screen, he then touches "AUTO LEAD SEARCH" 1186 which results in the substitution of the three ECG leads with the largest R-waves for those displayed on the lower ECG rows of the Initial ECG Screen. Touching "AUTO LEAD SEARCH" on that screen (FIG. 29) a second time causes the display of the three electrode arrangements with the next largest R-waves. This process of ECG review may be repeated until either a) the MP identifies a desirable ECG sensing arrangement, or b) the MP decides to pursue one of the aforementioned other sensing formats. If at any time the MP wishes to go back to a previously shown group of three ECG tracings, he touches "PREVIOUS LEAD GROUP" 1187.

If the MP identifies a possibly desirable ECG sensing electrode arrangement, he selects it by touching the button 1182 to the left of the desirable ECG tracing. Each of the two electrodes or the components of each of the two electrode groups that make up the sensing electrode arrangement are optionally displayed in Miniscreen 1184, using a format similar to element 1322 of FIG. 30. Various optional on-screen display formats may tell the MP whether sensing of the selected ECG format would be effective including: a) the overlay of a pair of horizontal lines parallel to the baseline of the selected tracing, which demarcate the sensing threshold; and b) the superimposition of a dot above each sensed event. If the MP desires to increase or decrease the sensitivity he could use either: a) the arrow up and arrow down key to the right of the tracing, or b) the keyboard arrow keys. If the MP wishes to change the selected lead to another, he does so by touching a different one of the 1182 buttons, which over-writes his previous selection. After completing the selection process (whether successful or not) the MP touches button 1190 "MAIN PACING SCREEN" which returns him to screen 1370. The system will utilize the electrode arrangement corresponding to the last button selection among elements 1182 for sensing purposes. If no electrode arrangement was selected, it will prompt the MP (either by highlighting each of buttons 1384A, 1384B and 1384C) or with a text message shown on the Major System Prompts Monitor 330 (FIG. 3). If the MP does not wish to use the electrode arrangement corresponding to the last selection on screen 1180, he selects one of the other sensing options on the Main Pacing Screen 1370.

When the five electrode pads with separate ECG electrodes 204B and 207 (FIGS. 5B and 5C) are utilized, an alternate approach to sensing electrode selection is possible. It entails displaying a screen analogous to screen 1290 (the Five Electrode Pad Setup Screen) but containing in addition, touch sensitive buttons which allow the selection of ECG electrodes. The MP then selects sensing electrodes by touching the corresponding buttons on the screen, as an alternate approach to selecting an ECG lead (for sensing) from screen 1180.

There are a very large number of other possible methods of selecting sensing electrodes. Variations in the sensing electrode selection method involve both algorithmic features (i.e. the sequence of button selections) and display features (the screen formats, keyboard formats and hybrid formats).

A beneficial result of providing all of these options and tools for the MP, is that the MP can make use of this flexibility in exercising his best judgment while resuscitating the victim.

6.3.3.2.3 Termination of Pacing

Termination of pacing was discussed above in Sections 6.3.3.2.1 and 6.3.3.2.2. If the MP terminates pacing and later wishes to resume it, touching "DELIVER" 1374 on the Main Pacing Screen will result in the resumption of pacing with the all of the same parameters as were in effect at the moment of pacing cessation.

6.3.3.3 Paths from Main Pacing Screen

Besides paths to screens which allow for the specification of non-default pacing settings (FIGS. 30-32, 39 and 40), three other exit pathways are available:

a) "GO TO ANTI-TACHY PACING" 1388 takes the MP to the Anti-Tachycardia Pacing Parameters Screen 1350 (FIG. 37).

b) "GO TO MAIN DEFIB SCREEN" 1390 takes the MP to the Main Defibrillation Screen 1200 (FIG. 33). Should VT or VF occur during pacing or pacing setup, this allows the MP to have rapid access to defibrillation.

c) "GO TO MAIN MENU" 1392 takes the MP to the Screen Menu (FIG. 43), which allows the MP to then go to any other screen.

6.4 MP-Directed PU Diagnostic Check and Maintenance Screen

FIG. 41 shows the screen 1490 used by the MP or a technical/maintenance person for checking PU and SU function (see Section 8.1 and FIGS. 55A and 55B).

The MP can obtain a list of problem PUs by touching 1491, and viewing the list in screen-in-screen 1500. In a preferred embodiment of the invention, these units would have detected a fault during their daily self check and called it in to the CS (see Section 8.1). He can view previously downloaded data about a selected unit by touching 1492.

The MP contacts the PU by touching 1493 to select the transmission mode (e.g. either through the SU, or directly; either wireless or wire), and then touching 1494. This results in a handshaking routine shown in FIGS. 12D, 12E, 12F, 13B and 14O, leading to the setting of the master control unit 130 to state 4.

The MP then touches 1495 to download and display the results of daily PU-SU checks, and then clears this memory, if he chooses to, by touching 1496.

Besides the PU and SU communication equipment daily evaluation data available from the download, the MP can further assess this by issuing the central station beacon, touching 1506, to test the PU and SU receivers. He can evaluate audio input and output at the PU by touching 1504, which allows him to either issue an audio tone or voice prompt originating at the PU. If necessary he can then adjust audio characteristics of the PU with options 3B (see above and Table 20) and 6A. He selects from among these choices by touching 1505B or 1505C respectively, each of which leads to a menu of options displayed on screen 1500. The MP can also cause the production of one or more tones or a voice originating at the CS, have it transmitted and enunciated through the PU speaker, and listen to it through the PU microphone. This may lead to other adjustments involving options 3 or options 6. Alternatively, if at that point the MP wishes to make other communication enhancement adjustments involving the CS, he can select from the option 1 menu by touching 1505A, or option 8 menu by touching 1505D.

The MP can assess the high voltage circuitry by touching 1508, followed by 1510, and, if he chooses, 1509. He can display the current video image by touching 1511. If he chooses, he can deploy the video boom by touching 1512 and working from the video control screen. In a preferred embodiment of the invention, he can extend the boom sufficiently to allow the flexible portion of it to bend a full 180 degrees, allowing him to visually inspect the PU. Alternatively, he could observe the PU without such bending if a there was a properly oriented mirror on the wall opposite the PU, i.e. by looking at the PU in the mirror.

If the MP detects a problem that requires remedy, he has the following options:

a) If the problem is remediable by a software manipulation, he can load additional software by first touching 1513 to enable this function;

b) If the PU requires replacement, he can show the nearest PU (either in service currently, or not yet in service) by touching 1514;

c) He can send a text message which will appear on one of the PU screens 156;

d) He can contact the CS administrator by touching 1516, or himself dispatch a maintenance person to the faulty PU; and/or e) He can activate the PU alarm by touching 1517.

6.5 Master Triage Screen

In the event of an overflow in emergency call volume, the MP or a central station administrator or "CSA" can redistribute emergency events to other central stations or to MPs who may be working with a computer outside of a central station. As shown in FIG. 42, the CSA works from screen 1550 to do this.

Unassigned cases appear at the top of the screen in boxes 1552A (which shows an emergency waiting to be handled by an MP) and 1552B (which shows a PU which has called in because of an abnormality picked up during its daily diagnostic check). Additional such cases would appear in box 1552C and in the boxes to its right. These boxes may show identifying information and a few word statement of the problem and its urgency, as assessed by a call screener.

In the lower portion of the screen the status of each working MP is accessed, one per broken line box. Thus MP #1 in CS #1 is controlled in the upper left box with buttons 1559A-C. The CSA can see that the MP is working on a victim by box 1559A. If the CSA wishes to speak to the MP he touches 1559B. If he wishes to view the case, he touches SHOW CASE 1554, followed by 1559A. This results in the display of the victim ECG of this case in screen 1557 and the event log in 1558. The CSA can use these to assess whether this MP could handle a second simultaneous case. If the CSA wishes to assign a second case to the MP, the CSA touches the following sequence of three touch sensitive buttons:

a) the button corresponding to the case to be assigned (whether as yet unassigned, or currently assigned to another MP); then b) the MOVE CASE button 1556; and then c) the button corresponding to an unassigned spot.

For example, if none of the three MPs in CS #1 was available to handle the unassigned case indicated by box 1552A, the CSA could assign it to MP #2 in CS #2 by touching 1552A, then 1556, and then 1560. Alternatively, the MP could assign the case to MP #3 in CS #1 by touching 1552A, then 1556 and then 1561.

6.6 Main Screen Menu

FIG. 43 shows a touch sensitive screen 1600 which allows the MP to go from it to any other screen. The upper portion of this screen 1602A-1602H shows the contents of each of the active CS screens. The lower portion shows a list of all of the touch sensitive and non-touch sensitive screens.

The MP selects a screen for display by touching the box with its description and then touching the destination screen from among 1602A-1602H. Split screen display would be accomplished by touching sequentially touching one screen title box, then touching a second one, and then touching the destination screen from among 1602.

If the MP wishes to select the Main Screen Menu when it is not displayed, he can touch "CONTROL M" on the keyboard or some other designated "hot-key." If he wishes to clear a choice he can touch "CONTROL C" or a different hot key.

In addition to the screens already discussed the MP can view:

a) medical information from databases maintained at the CS, at another CS or elsewhere;

b) medical information about the victim if it is available either from a doctor's office, a hospital record, a pharmacy or another database. Such viewing would involve transmission of medical information in compliance with local and federal statutes, as would all transmissions of information during and after the MP encounter with the victim. In addition, if the victim or a person with the victim has a magnetically or optically readable card which carries his vital medical information, it can be scanned by inserting into 185 (FIG. 8), and displayed on the CS console;

c) legal information relating to the termination of therapy, whether it be federal, state or local statute, and legal information about the documented wishes of the victim, if any, and if such documentation is available, whether it be a "living will" or other advanced health care directive;

d) information about choices that he has made which the system claims to be medically unreasonable (e.g. the selection of defibrillation electrodes which are too close together). The MP is informed by prompts of the CS screens, and can get further information including the reason why the choice is felt to be unwise and alternate recommendations by touching the appropriate boxes on the Main Screen Menu; and e) information about AED performance (by touching "AED STATUS") in the event of a communication interruption requiring a change in master control from state 1 (MP guided therapy) to state 2 (AED guided therapy). Another time that the MP might choose "AED STATUS" is if he is unsure about whether a rhythm is VF or asystole and thinks that signal degradation during communications is hindering his analysis. In such a circumstance he could find out the AED assessment of the rhythm, since such assessment is based on data which may not be distorted; and f) the Event Log.

6.7 Command Confirmation and Event Log

FIG. 44 shows a screen which documents all MP actions and all telemetry relating to PU events.

In the case of MP commands, the presence of each of four confirmation signals (or the absence of one or more) is indicated in the four indicator boxes 1704. These boxes could turn green when as each confirmation signal is received, and red if one is not (as per the flow diagram in FIG. 24), or could give a numeric value, if appropriate. For example, the right-most box after "CHARGE PU CAPACITORS" could indicate either the charge time, the voltage prior to discharge, or both.

In the case of MP telemetry, each event is documented by a single indicator box 1702. This could also be a binary indicator, or could give a numeric value. For example, in the case of the "ECG SIGNALS," a measure of the amplitude could be displayed.

The information in this log becomes part of the victim's permanent medical record. It is preserved and handled using the security measures that are professionally and legally appropriate.

7. Block Diagrams: Units and Major Components of the System

7.1 The Portable Unit

Figure 45:
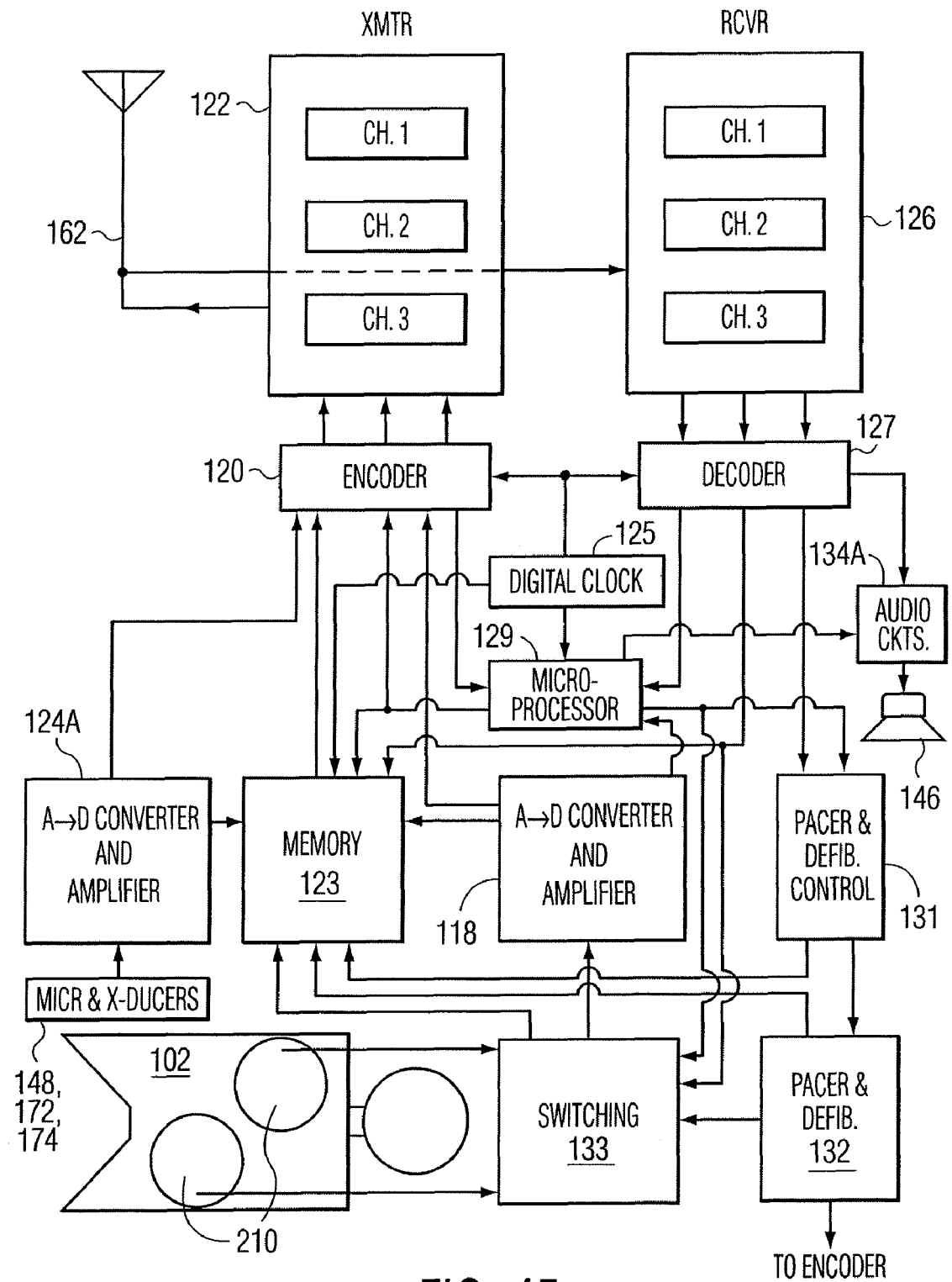
FIG. 45 is a general block diagram of the electronic circuits employed at a remote station of the cardiac monitoring and external defibrillation system according to the present invention.

FIG. 45 shows an embodiment of the portable unit 104. The victim 102 is attached to it via electrode pads 210 which can record his ECG, and administer electric current to perform cardiac pacing or defibrillation. Switching circuits 133 are used to switch the pads between ECG recording on the one hand, and pacing or defibrillation on the other. In one embodiment of the invention, the PU interfaces with an electrode pad 204B (FIG. 5B) in which some electrodes may be used only for ECG recording.

ECG signals are amplified and digitized by analog to digital converter and amplifier 118. The three outputs of 118 are to:

a) the PU memory 123, from which they may be retrieved at a later time during the event for use by the MP, or after the event, by appropriately authorized and identified medical personnel;

b) to encoder 120, at which the signals are processed for transmission via transmitter 122, to antenna 162, from whence they are transmitted to the central station either directly, or via a stationary unit or other repeater unit (see FIG. 59); and c) microprocessor 129.

Commands from the medical professional are received by receiver 126 via antenna 162, and then are decoded by decoder 127. The decoder has multiple outputs (see FIG. 51A, 51B and discussion below) including:

a) the MP's voice signals which are processed by audio circuits 134A and heard by the enabler through speaker 146;

b) commands sent by the MP to circuits 131 which control the output of the pacemaker and defibrillator 132;

c) the PU memory, where each command is securely maintained, time stamped by digital clock 125, as part of the victim's medical record;

d) commands from the MP to microprocessor 129 which determine the state of the master control unit, which determines the overall control of the PU; and e) commands sent by the MP to switching circuits 133 which control electrode pad selection for defibrillation, pacing and ECG recording.

In the event of communication failure which prevents either initial or ongoing communication between the PU and the central station, the backup AED function allows the unit to function at a basic level. The microprocessor in this situation processes and analyzes ECG signals and, based on such analysis and on prior programming provides outputs to the circuits 131 which control the pacemaker and defibrillator 132. A record of these outputs is also stored in memory 123. Redundancy in the transmitter and the receiver makes a communication failure less likely to occur. In the figure, three channels are shown for each of the transmitter and receiver. The ability of the MP or the system to have access to multiple channels and multiple communication modalities makes the communications system robust.

The transmitter and receiver, both shown attached to antenna 162 need not necessarily share the same antenna.

In a preferred embodiment of the invention, each command issued by the MP results in the issuance of multiple confirmation signals, which let the MP know that the command has been properly processed and executed. In FIG. 45, an output of the pacemaker and defibrillator unit 132 which carries such confirmation signals goes to encoder 120 from whence they are transmitted to the MP.

Other information transmitted to the MP includes:

a) the enabler's voice, via microphone 148 (FIG. 6A);

b) blood pressure data from cuff 172; and c) oxygen saturation data from transducer;

each of which goes to analog to digital converter and amplifier 124A from whence it goes to the encoder and then the transmitter.

All data transmissions containing victim information are transmitted in an appropriately encrypted and secure format. If the MP wishes to download events from memory, he may send the appropriate command and do so. He may also upload new information to memory concerning PU function and maintenance.

Figure 46:
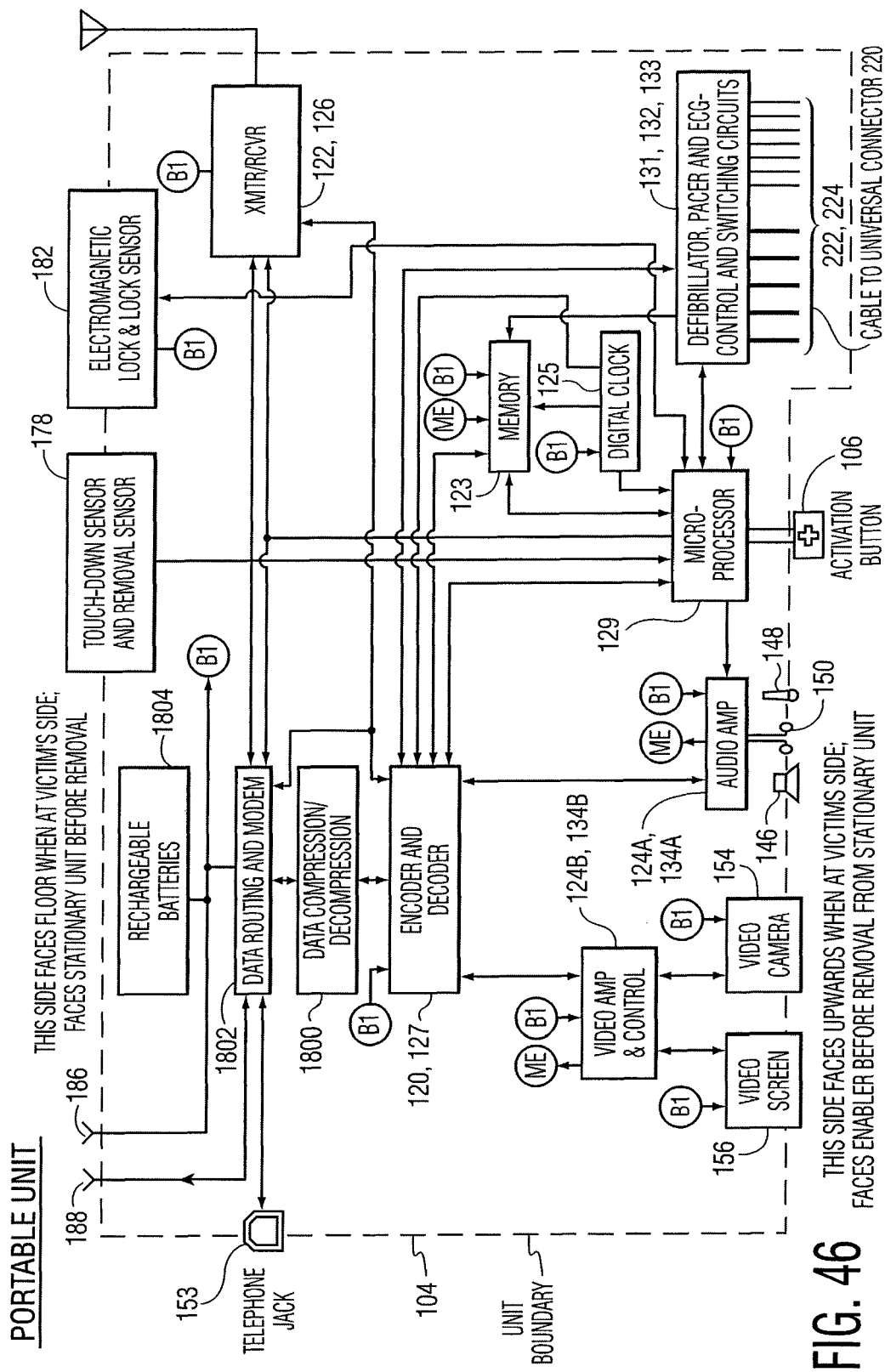
FIG. 46 is a detailed block diagram of the electronic circuits of the portable unit.

FIG. 46 shows another embodiment of the portable unit which illustrates additional features of its operation.

Elements along the boundary of the unit correspond to their placement as shown in FIGS. 6A and 8. The front of the unit (i.e. the side that faces an enabler as he approaches the unit) includes video screens 156, video camera 154, speaker 146, microphone 148 and activation button 106. A telephone handset 150 is shown in the front in this figure; it is located on the side in FIGS. 6A and 6B.

The rear of the unit, i.e. the side which faces away from the enabler initially includes touchdown and removal sensor 178 and the electromagnetic lock and lock sensor 182, both of which supply information to microprocessor 129. The microprocessor also provides control signals for the electromagnetic lock. Connectors 188 and 186 convey information and power between the PU and the stationary unit.

A telephone jack 153 and antenna are shown on the sides of the PU.

The PU contains rechargeable batteries 1804 which are charged from the stationary unit via 186. Power is distributed, circle B1, to each energy requiring component.

The output of video camera 154 is amplified by video amplifier 124B; microphone outputs are amplified by 124A. In a preferred embodiment of the invention the outputs of each, along with ECG signals and signals from digital clock 125, memory 123 and microprocessor 129, after encoding, are subject to data compression at block 1800. Outgoing data is then routed at block 1802 to any of:

a) the telephone system via data connection 188 to the SU;

b) the telephone system via transmitter 122;

c) the telephone system via jack 153;

d) the internet or a non-public data sharing network via either 188, 122 or 153; or e) the central station or a repeater unit (see FIGS. 58 and 59) via radio frequency or microwave transmission.

The management of data routing may be performed by the MP or by equipment in the central station via signals sent to 1802 via the PU receiver 126; or b) by microprocessor 129.

Incoming data is decompressed at by 1800. Decoded information, in addition to the functions discussed above, is also used to control the video boom 112 (FIG. 6B) and camera via amplifier 134B.

During the handshaking process, there may be need to adjust the characteristics of the PU transmitter and receiver, the PU audio circuits, other PU input and output circuits, data routing and the modem. The source of such adjusting signals may be from either end, i.e. the MP/central station or the PU microprocessor.

During the communications handshake, PU transmitter and modem adjustments may occur, and are among the operations referred to as "options 6B" (see FIG. 14 and table 20). PU receiver and modem adjustments may occur, and are among the operations referred to as "options 3A". Adjustments in the routing of data from the PU, referred to as "options 7" may occur as well. These adjustments may be initiated by the PU microprocessor which, in FIG. 46, is shown to control these units. They may also be initiated from the central station end, by either the MP or equipment within the CS; Such control is indicated as output from the decoder 127 to the transmitter/receiver 122, 126 and to data routing and modem 1802.

The characteristics of audio circuits 124A which amplify and process the enabler's voice are controlled by signals transmitted from the central station or by the PU microprocessor. These characteristics (as well as the characteristics of non-audio inputs) may be adjusted by commands from the CS during the data-commands handshake or the audio handshake; Such adjustments have been referred to as "options 6A" (see FIG. 14 and table 20). Circuits 134A which amplify and process the MP's voice (as well as those which control non-audio outputs) may also be adjusted during the aforementioned two handshakes; Such adjustments have been referred to as "options 3B."

The PU interfaces with the victim via circuits 131, 132 and 133 (discussed above) which connect to the electrode pads. In FIG. 46, the connection to an electrode pad with five defibrillating and seven sensing electrodes, one of many possibilities, is shown schematically. Ribbon cables 222 and 224 (see FIG. 7B) connect to universal connectors 220 which link the electrode pads to the PU so that they are replaceable.

All appropriate victim-related, command related, PU telemetry, audio and video information is stored in memory via circle ME.

7.2 The Stationary Unit

The SU 108 has three main functions.

a) It serves as a relay unit, communicating with both the PU and the central station, thereby extending the range and flexibility of communications.

b) It is the source of power for the PU rechargeable batteries.

c) It locks the PU to a wall or other stationary object, preventing theft or inappropriate use.

Logic and control circuits 144B supply information 1918 to switches 144C and 144D. While the PU is attached to the SU, Switch 144D is directly connected to the PU input and output data streams via connectors 190 (on the SU side) and 188 (PU side). As shown in the figure, depending on the position of the switch, it can connect the data stream to either a hard-wired interface with the public telephone system 1814 or to a long range transmitter 138 and receiver 140 which may access the cellular telephone system, or communicate via antenna 164 over radio frequency or microwave channels which are not part of the telephone system. Although the switches depicted have two positions, they could allow the selection from among more than two choices, including broadband options.

Switch 144C controls the input and output to the PU short range transmitter 142 and receiver. Once the PU is detached from the SU, the hard-wired data connection via connectors 190 and 188 is no longer functional. As of the time of PU-SU separation, the PU would therefore be likely to communicate with the central station either:

a) directly, through its own transmitter and receiver, as depicted in FIG. 45; or b) indirectly, in which case the PU transmitter and receiver may be in communication with the SU short range transmitter and receiver. These short range units are linked to the long range transmitter and receiver via switch 144C; or c) indirectly, with the short range transmitter 142 and receiver linked, via switch 144C and telephone interface 1814 to the telephone system.

The information which determines the position of switches 144C and 144D comes from decoder 144A which obtains signals from each of:

a) receiver 140, via block 1818B and block LR 1818A;

b) telephone interface 1814; and c) receiver 136, via block 1816B and block SR 1816A;

d) the portable unit, via block 1820B and block X 1820A.

The MP or equipment within the central station would control routing via a) or b) above, while the PU would control it via c) or d) above.

Power supply 1810, supplied with line current via line cord and plug 196, supplies both the SU rechargeable batteries 1812 and the PU batteries via connectors 192 (SU) and 186 (PU).

Locking projection 194 projects into the PU allowing the two to be locked together, when the PU is not in use.

7.3 The Master Control Unit

The master control unit 130 determines the source of control for the most important functions of the PU, as outlined in Table 1 and described in Section 1.3.1.2. The crux of its function is the setting of who controls pacing and defibrillation.

Figure 48:
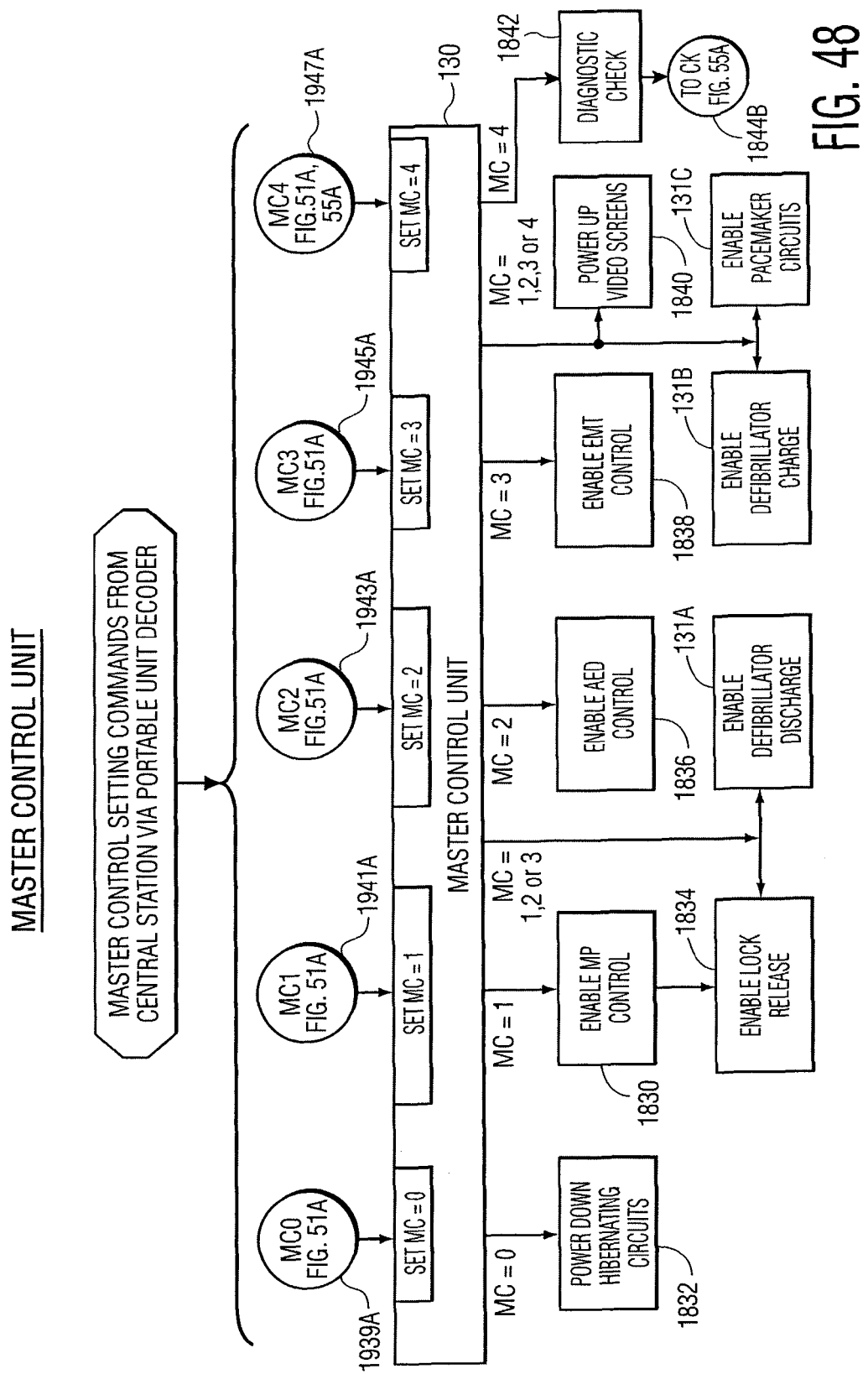
FIG. 48 is a detailed block diagram of the electronic circuits of the master control unit.
Figure 51A:
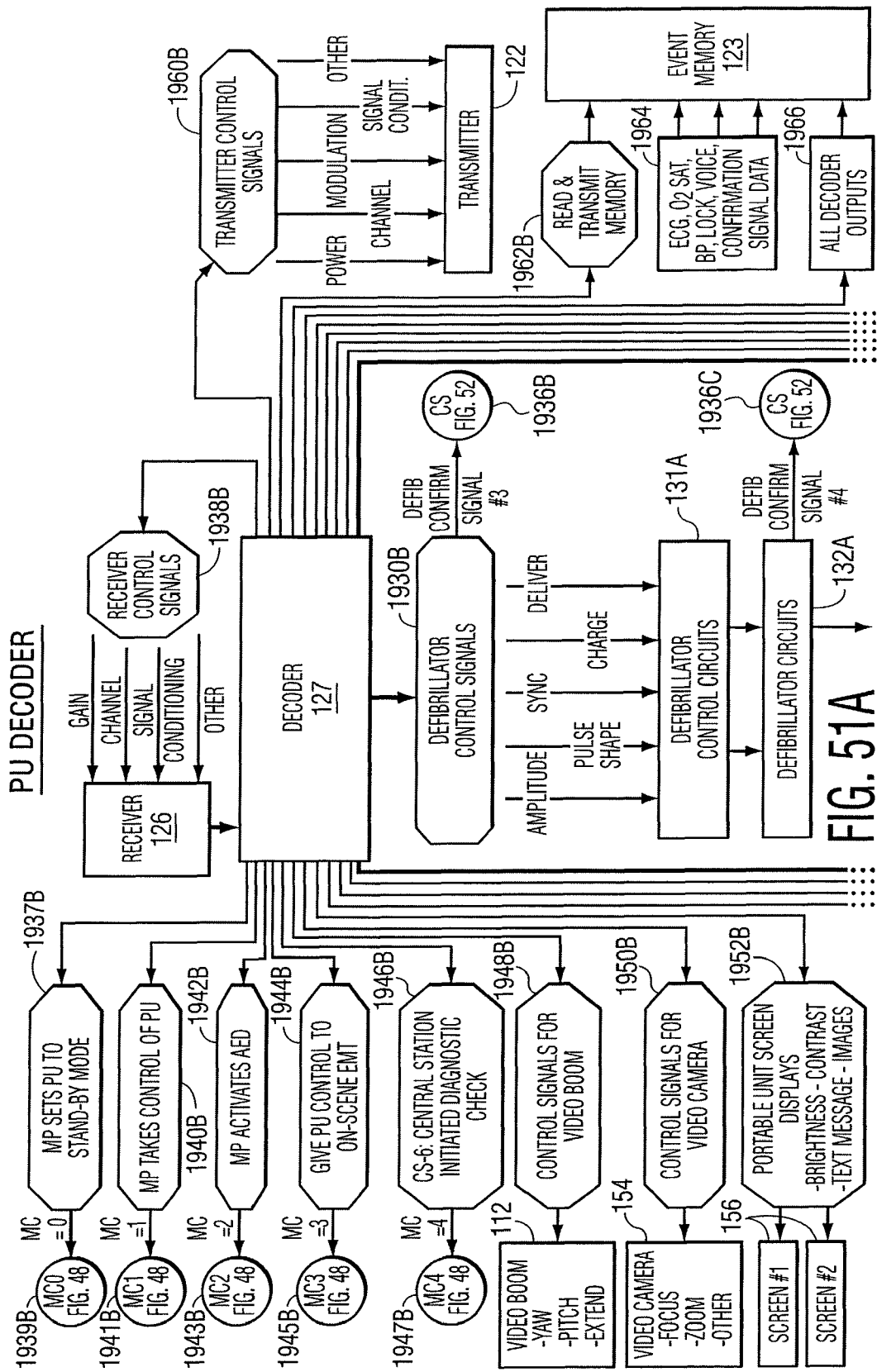
FIG. 51 is a block diagram of the portable unit decoder.
Figure 51B:
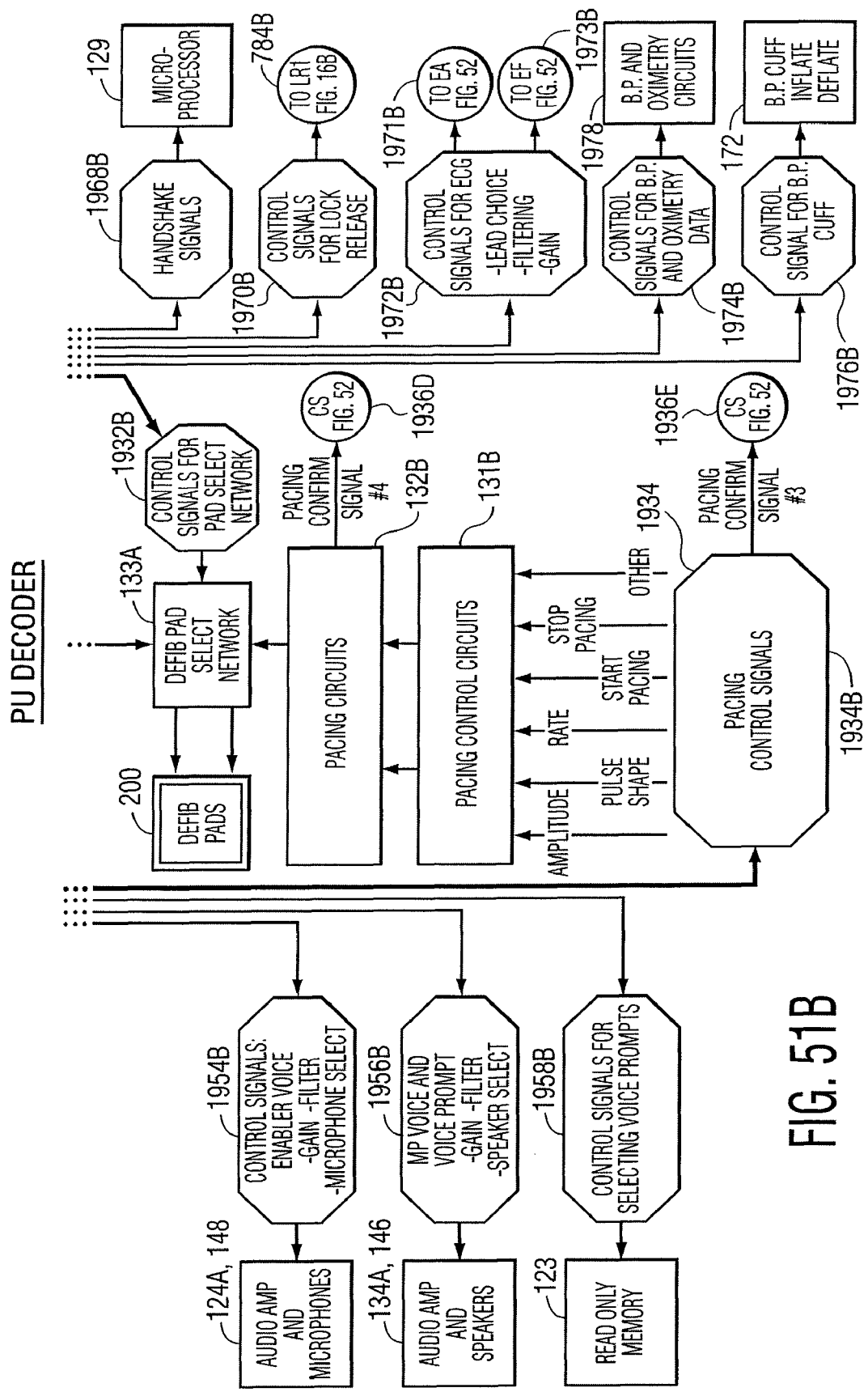
Figure 52:
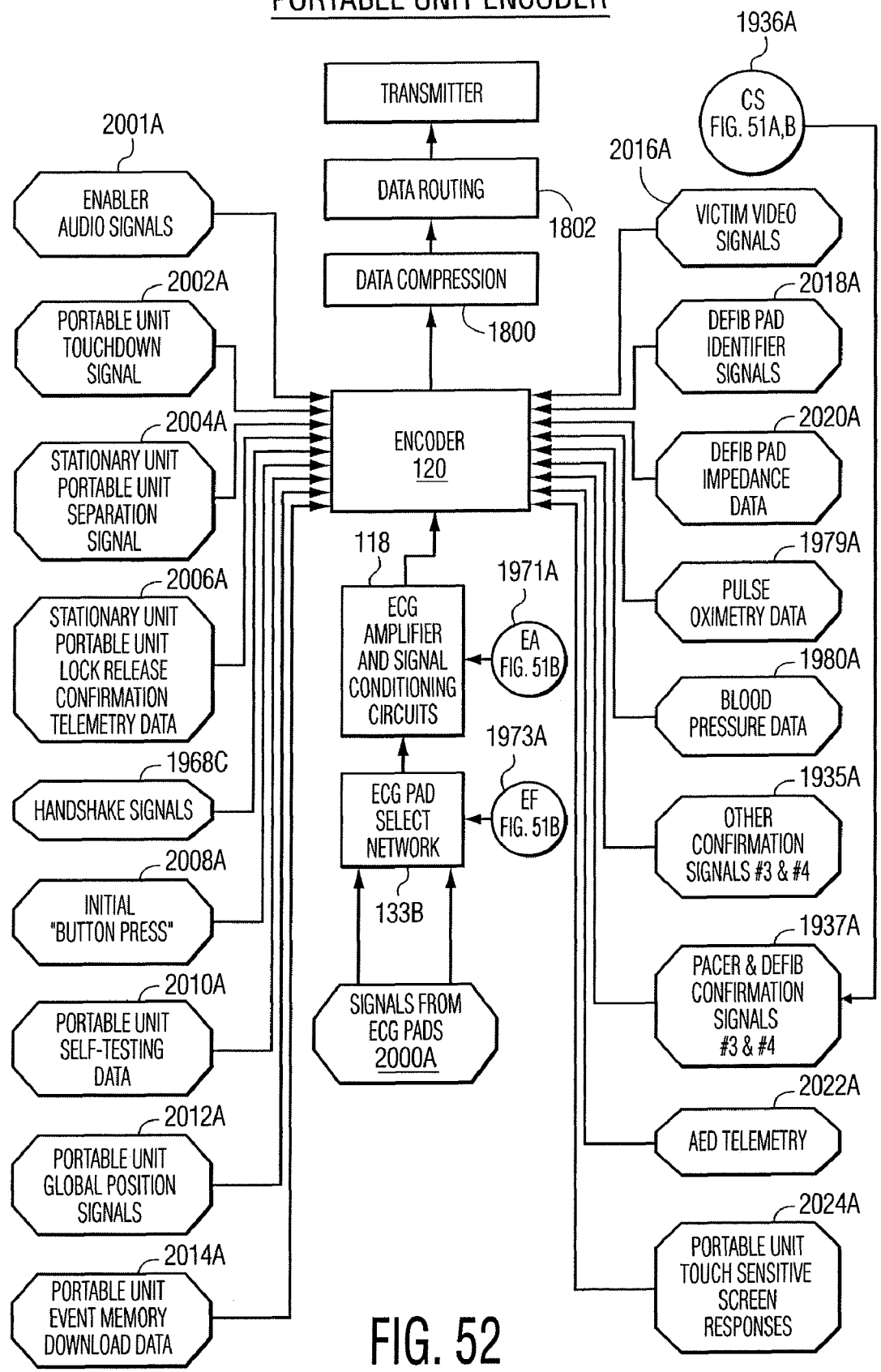
FIG. 52 is a block diagram of the portable unit encoder.

Control signals for the master control unit come from the MP in the central station, to the PU and are decoded by the PU decoder (FIG. 51A and 51B). FIG. 48 shows the five possible control signals from the decoder outputs:

a) SET MC=0, block MC0 1939A;
b) SET MC=1, block MC1 19341A;
c) SET MC=2, block MC2 1943A;
d) SET MC=3, block MC3 1945A; and
e) SET MC=4, block MC4 1947A.

Setting MC=0 results, block 1832, in the powering down of power consuming functions such as video and transmitter circuits.

Setting MC=1, done by the MP after a successful handshaking process with the PU and enabler results in:

a) allowing the MP to control all of the major functions of the PU, block 1830;

b) enabling release of the PU-SU lock, block 1834;

c) enabling defibrillator control circuits that allow charging 131B, discharge 131A and pacing 131C; and d) block 1840, powering up the video screens.

Setting MC=2 differs from the MC=1 setting in that control of pacing and defibrillation are by the on-board AED/P when MC=2. This is the default setting once the PU has been activated by a button press. A signal from the central station, sent after the communications and data-commands handshakes have been properly executed, is required to set MC=1.

Setting MC=3 enables control of the PU by the EMT. Block 1838. Since they would use the device in the same way that a medical professional does, pacing and defibrillation are enabled when MC=3.

Setting MC=4 is the prelude to the PU diagnostic check, block 1842. The signal for this may come form the central station in which case it moves from the PU decoder via block 1947B (FIG. 51A) to block MC4 1947A, to the master control unit 130, to block 1842, to block 1844B, to block CK 1844A starting the PU checking routine. The starting signal may also come from a clock 2100 within the PU (see FIG. 55A) via block 1947C to block MC4 1947A. MC=4 does not enable defibrillator discharge, a safety feature, though it does enable high voltage charging, so that the integrity of the high voltage circuits may be evaluated. MC=4 also does not enable PU-SU lock release.

7.4 The Central Station

FIG. 49 shows a block diagram of the central station. Information about an incoming emergency call may arrive via either the telephone system 1880 or by radio receiver 346. Routing circuits and modem 1850 allow for the handling of multiple simultaneous calls (see FIG. 42). After data decompression 1852, the CS decoder 348 decodes incoming signals and sends them to:

a) memory 1858, b) microprocessor 1854;

c) audio amplifier and processing unit 352A, from whence they go to speaker 320; and d) video amplifier and processing unit 352B, from whence they go to screen 308, showing a video of the victim.

Incoming ECG, blood pressure and oxygen saturation data is sent from the decoder to the microprocessor where it is properly formatted and displayed on screens 302, 304 and 306 (see FIG. 3). Command confirmations are displayed as part of the event log on screen 338 (FIGS. 3 and 44) and signal quality on screen 336 (FIGS. 3 and 25). Other displays include a reproduction of the displays on the PU screens 156, displayed in the CS on screens 322 and 324 (FIGS. 3 and 28), and the real time (from clock 1856) and the elapsed time, displayed on screens 340 and 342.

During the communications handshake, CS transmitter and modem adjustments may occur, and are among the operations referred to as "options 1B" (see FIG. 14 and table 20). CS receiver and additional modem adjustments may occur, and are among the operations referred to as "options 8A". Adjustments in the routing of data from the CS, referred to as "options 2" may occur as well. These adjustments may be initiated by the CS microprocessor which, in FIG. 49, is shown to control these units. Microprocessor output MS 1855 leads to the transmitter via block 1869, transmitted data routing and modem via block 1865, the receiver via block 1873 and received data routing and modem via block 1852.

The characteristics of audio circuits 360A which amplify and process the MP's voice, as well as the characteristics of non-audio inputs, may be adjusted during the data-commands handshake or the audio handshake. Such adjustments have been referred to as "options 1A". Circuits 352A which amplify and process the enabler's voice and circuits which control non-audio outputs may also be adjusted during the aforementioned two handshakes. Such adjustments have been referred to as "options 8B." The CS microprocessor is shown to control these units. Microprocessor output MS 1855 leads to audio amplifier circuits 360A and via blocks 1855 to 1867 to amplifier circuits 352A. The microprocessor also monitors signal quality at audio amplifier 360A, at audio amplifier 352A (block 1853D to block MT 1853A), at main receiver 346 (block 1853B to block MT 1853A) and at transmitter 358 (block 1853D to block MT 1853A).

The MP inputs commands to the microprocessor via any of keyboard 312, mouse 314, joystick 310 (for adjusting PU video boom 112) or any of touch or light sensitive screens 328, 330, 332 and 334. In a preferred embodiment of the invention, screens 330 and 332 display major and minor system prompts and messages to the MP (shown in FIG. 3). These include information about any command which is either incompatible with the system or which may be recognized by the system as potentially unwise, messages which indicate failure to receive a confirmation signal, and messages indicating the detection of a potential or actual faults in a system component.

The commands output the microprocessor and proceed to encoder 356, to data compression 1862, and to transmitted data routing and modem 1864. After this they go either to transmitter 358, with transmitted signals emanating from antenna 1868, or to telephone lines 1880. All encoded signals are time stamped by clock 1856 and stored in memory 1858. The transmitter also intermittently sends out a "central station beacon" signal which is used during the periodic diagnostic checking of the PU and the SU.

Other MP inputs include microphone 316 and video input 362. The latter includes signals from the video camera showing the MP as well as instructional material which the MP may wish to display for the enabler. These inputs are amplified by audio and video amplifiers 360A and 360B, and sent to the encoder from which they follow the same output route as MP commands.

Confirmation signals, discussed above, allow the MP to observe the process of command execution, and to assess a fault in this process. Confirmation signal #1 which confirms proper inputting of a command entails routing of a signal from encoder 356 via block 1853F, via block MT 1853A to microprocessor 1854 with display on screen 338.

A second confirmation signal is generated when the command is further along in its transmission. If it is sent by wireless means, it reenters the system via confirmation receiver 1872, passing through confirmation routing 1874, to confirmation decompression 1876 and then to confirmation decoder 1878. This decoder sends signals to the CS microprocessor 1854 and to the CS memory 1858 (via block 1860B to block MR 1860A). (The other output of decoder 1878 also leads to the CS microprocessor, via the sequence of block 2028B, block CR 2028A (FIG. 54), to block 1854C—the microprocessor portion which results in the formatting and display on CS screen 338).

The third and fourth confirmation signals arrive via main decoder 348 and are discussed below.

A database and data storage system 344 may contain one or more of a) information about the resuscitation system;

b) a medical database which may contain information about general medical issues or about the victim's medical data;

c) a legal database which may contain information about local and federal laws concerning the termination of resuscitation efforts and which may contain specific information about the legal documentation of the wishes of a particular victim regarding resuscitation efforts;

d) information about the location, technical characteristics and repair history for each of the portable and stationary units with which the CS may interact; and e) information about the availability emergency facilities and personnel in the vicinity of any particular PU.

The system is powered by uninterruptible power supply 1866 which will preferentially include many layers of backup. The MP will have access to standard communication modalities including telephone 318.

7.5 The Stationary Unit Decoder

Figure 50:
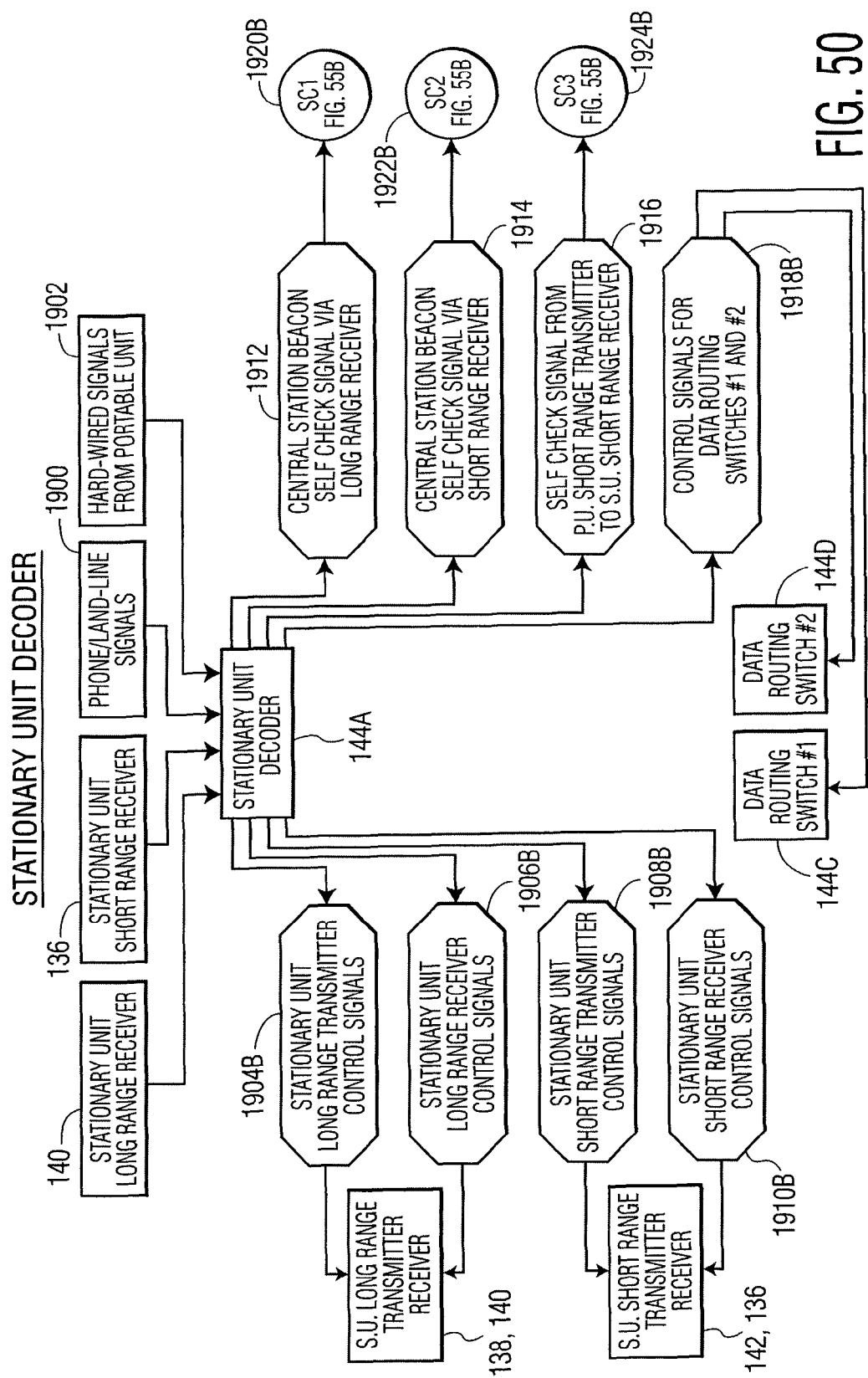
FIG. 50 is a block diagram of the stationary unit decoder.

In order for the SU to perform its functions it requires access to signals from the central station and from the PU. The decoding and routing of these signals is shown in FIG. 50.

The SU decoder 144A receives:

a) signals from the CS via the SU long range receiver 140;

b) signals from the CS (and possibly the portable unit) via phone and land line signals 1900;

c) hard-wired PU signals 1902 via the connectors 188 and 190; and d) PU signals from the SU short range receiver 136.

Figure 47:
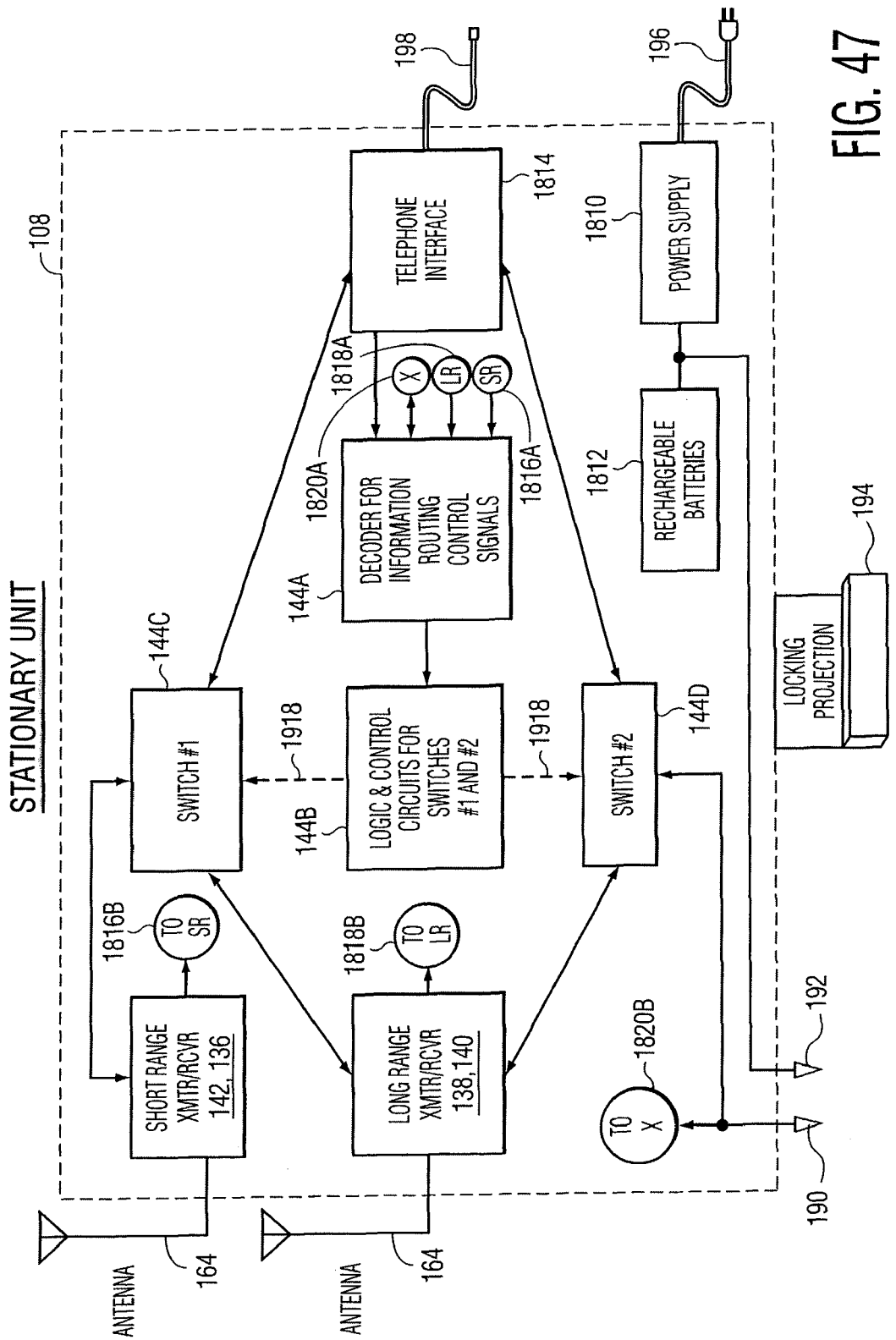
FIG. 47 is a detailed block diagram of the electronic circuits of the stationary unit.

One SU decoder output 1918B controls signal routing within the SU (discussed above in section 6.2). The output is applied to switches 144C and 144D (FIG. 47).

Four of the SU decoder output control features of the SU transmitters and receivers:

a) Output 1904B controls the SU long range transmitter 138;

b) Output 1906B controls the SU long range receiver 140;

c) Output 1908B controls the SU short range transmitter 142;

d) Output 1910B controls the SU short range receiver 136. These components may need to adjusted during any of the handshaking routines.

The SU participates in certain aspects of the diagnostic checking routine (see FIGS. 55A and 55B) and this accounts for the remaining three SU decoder outputs shown in the figure:

a) During the checking routine, the CS beacon signal must be properly received by the SU long range receiver. Receipt of this signal 1912 leads to block 1920B, to block SC1 1920A (FIG. 55B) where it becomes one of the items in a diagnostic check which shows proper SU functioning.

b) During this diagnostic check, this aforementioned or another CS beacon signal must be properly received by the SU short range receiver. Receipt of this signal 1914 leads to block 1922B, to block SC2 1922A (FIG. 55B) where it becomes another items which shows proper SU functioning.

c) Also during the diagnostic check, the PU short range transmitter sends a test signal to the SU short range receiver. The decoded signal 1916 leads to block 1924B, to block SC3 1924A where it registers proper functioning of the involved components.

7.6. The Portable Unit Decoder

FIGS. 51A and 51B show the PU Decoder. It decodes and routes signals coming in to the PU including those which set the master control unit, those which control the defibrillation, pacing and ECG circuits, those which control the PU communications between the PU and the CS.

Signals enter the decoder 127 from the receiver 126. The decoder output includes:

a) PU receiver control signals 1938B which control receiver gain at various points, channel selection, signal conditioning and other receiver parameters;

b) PU transmitter control signals 1960B which control transmitter power, channel, modulation, signal conditioning and other parameters;

c) five signals, 1937B, 1940B, 1942B, 1944B and 1946B which set the master control unit to each of states 0, 1, 2, 3 and 4 respectively. They are sent to the master control unit via blocks 1939B, 1941B, 1943B, 1945B and 1947B respectively;

d) defibrillator control signals 1930B which control each parameter of defibrillation including pulse amplitude, pulse shape, synchronization, the onset of charging and delivery of the shock. These control signals go to defibrillator control circuits 131A, and then to defibrillator circuits 132A whose output pulse is applied to the electrode pads 200 selected by the switching circuits of pad selection network 133A. Decoder signals 1932B control the electrode pad choices of network 133A;

e) pacing control signals 1934B which control each parameter of pacing including pulse amplitude, pulse shape, pacing rate, starting and stopping of pacing, sensing parameters (if any) during pacing and anti-tachycardia pacing features, if this modality is used. These control signals go to pacing control circuits 131B, and then to pacing circuits 132B whose output pulses are applied to the electrode pads 200 selected by the switching circuits of pad selection network 133A. The pacing electrodes may or may be the same as the defibrillation electrodes;

f) control signals 1948B which determine the spatial positioning and orientation of the PU video boom 112;

g) control signals 1950B which control the PU video camera 154;

h) signals 1952B which contain the content for PU screens 156 and which determine viewing parameters such as brightness and contrast;

i) signals 1954B which control the audio amplifier 124A for the enabler voice via microphone 148 (options 6A during the handshaking process);

j) signals 1956B which determine enabler listening parameters such as loudness and filtering (options 3B during the handshaking process); and other signals which carry the MP voice which are applied to the PU audio amplifier 134A and speakers 136;

k) signals 1958B which contain the alphanumeric coding of the PU voice prompts (when used) which are stored in a read only section of the PU memory 123;

l) signals 1962B which cause the data on the current medical event, stored in PU memory 123 (including victim physiologic information, telemetry and voice information, block 1964 and all decoder output records, block 1966) to be read and transmitted to the CS;

m) handshake signals 1968B which are sent to the microprocessor and responded to according to the previously described routine;

n) control signals 1970B for release of the PU-SU lock (FIG. 16B);

o) control signals 1972B for ECG recording which determine which electrode pads are recorded from, block 1973B to block EF 1973A to block 133B, the ECG pad selection network; and which set ECG gain and filtering parameters, block 1971B to block EA 1971A to block 118 ECG amplifier and signal conditioning circuits;

p) control signals 1974B for the blood pressure and pulse oximetry circuits 1978; and q) control signals 1976B which control the inflation of the PU blood pressure device 172.

Confirmation signal #3 originates when a command arrives at the PU decoder. For defibrillation and pacing, these signals go from blocks 1936B and 1936E, respectively to block CS 1936A of the PU encoder (FIG. 52) where they are processed and transmitted to the CS and displayed. These signals indicate that a command has properly traversed the CS processing unit, CS communications output, the CS to PU communications link, PU communications input, PU communications output, the PU to CS link, CS communications input and CS processing output. All other commands which originate in the CS will be associated with a similar confirmation signal (not shown in FIGS. 51A and 51B).

Confirmation signal #4 indicates actual execution of the command. Such fourth confirmation signals for defibrillation and pacing go from blocks 1936C and 1936D respectively, via block 1936A to the PU encoder.

7.7 The Portable Unit Encoder

In order for the MP to make decisions about the management of a cardiac arrest of other urgent situation, he must be provided with victim physiologic data. Such data, along with PU telemetry and communications information is encoded by the PU encoder 120, compressed at block 1800, appropriately routed at block 1802 and transmitted to the central station via direct wire, cable, or wireless route.

Signals which are encoded include:

a) signals 2000A from the ECG pads;

b) enabler audio signals 2001A;

c) the PU touchdown signal 2002A;

d) the SU-PU separation signal 2004A e) SU-PU lock release telemetry data 2006A;

f) handshake signals 1968C;

g) the initial "button press" signal 2008A;

h) PU diagnostic checking data 2010A (see FIG. 55A and 55B);

i) PU global positioning signals 2012A (useful for tracking a unit which is lost or stolen, or one which during operation has been moved substantially from the corresponding SU location);

j) data 2014A from the PU memory concerning the event in progress (may be utilized if communication between PU and CS was interrupted and later restored);

k) victim video signals 2016A;

l) defibrillation pad identifier signals 2018A (indicating removal of the ECG pad cover during application to the victim);

m) defibrillation pad impedance data 2020A, indicating the adequacy of contact between the pad and the victim;

n) pulse oximetry data 1979A;

o) blood pressure data 1980A;

p) confirmation signals 1935A and 1937A (see section 7.6);

q) AED telemetry information 2022A (that may be sent during a partial communication failure, in which PU to CS communication is intact, but CS to PU communication is not); and r) portable unit touch sensitive screen responses (see FIG. 15).

7.8 The Central Station Decoder

Figure 53:
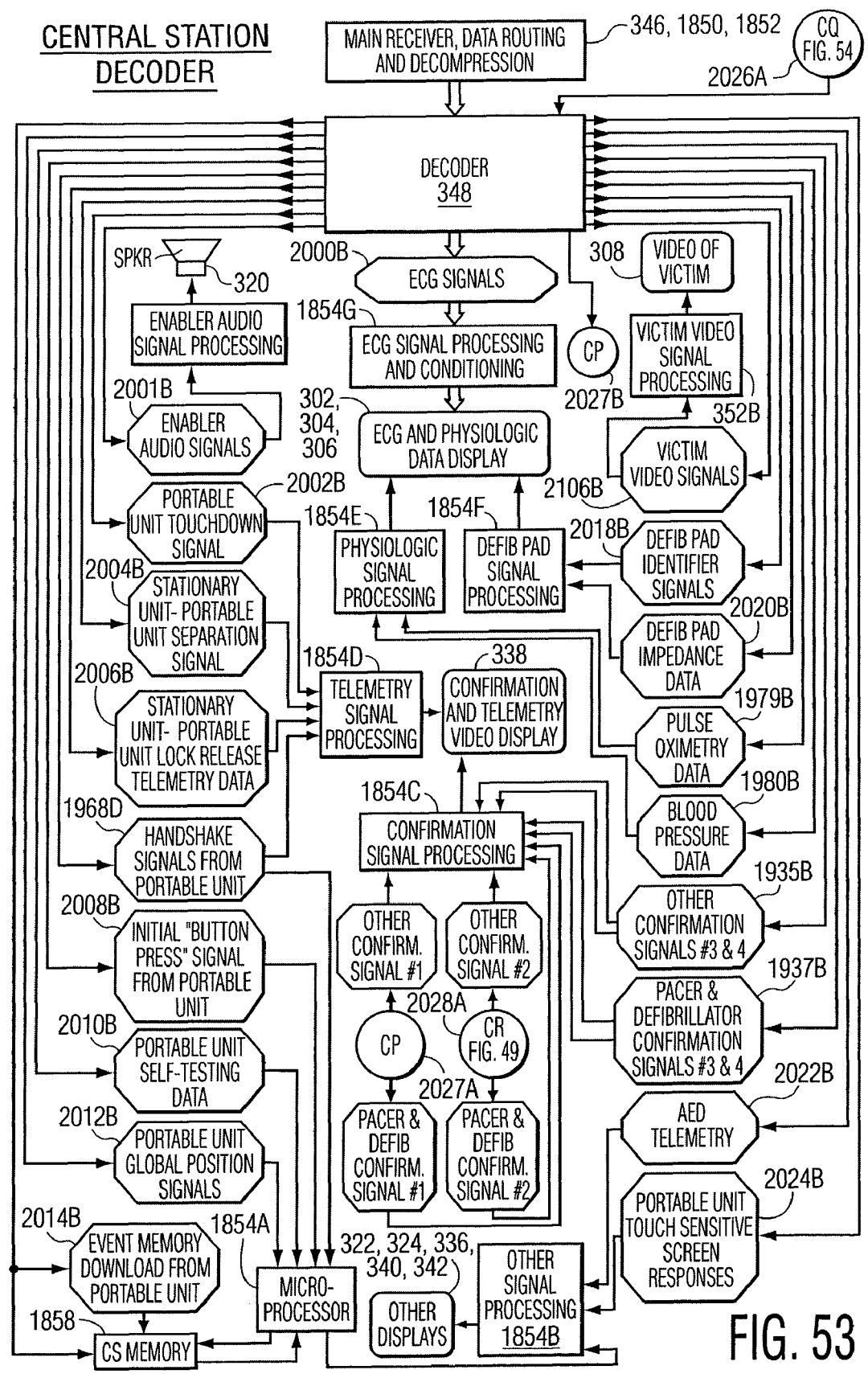
FIG. 53 is a block diagram of the central station decoder.

FIG. 53 shows the central station decoder and routing of signals which emanate from it. Since it decodes signals which have been sent from the portable unit, its outputs generally have corresponding inputs to the PU encoder, shown in FIG. 52. Accordingly, such pairs of elements have been assigned identical numbers, with the source element having an "A" suffix and the received element having a "B" suffix.

Signals reach the central station decoder 348 from the CS main receiver and modem after routing and decompression, elements 346, 1850 and 1852 (FIG. 49).

Signals which are decoded include:

a) ECG signals 2000B. After signal processing and conditioning by microprocessor sub-unit 1854G, they are displayed on ECG screen 302;

b) enabler audio signals 2001B;. After audio signal processing as described previously they result in the output of 320;

c) telemetry signals indicating PU events including the PU touchdown signal 2002B, the SU-PU separation signal 2004B, the SU-PU lock release telemetry data 2006B and handshake signals 1968D. These signals go to microprocessor sub-unit 1854D for processing and formatting of telemetry signals displayed on PU screen 338;

d) signals sent to the microprocessor sub-unit 1854A which are used for logic functions including handshaking signals 1968D, the initial "button press" signal 2008B, PU diagnostic checking data 2010B and PU global positioning signals 2012B;

e) data 2014B from the PU memory concerning the event in progress. This data is sent to the CS memory 1858 which also stores all CS decoder and selected microprocessor outputs;

f) victim video signals 2016B. These are processed by 352B and displayed on screen 308;

g) defibrillation pad identifier signals 2018B and defibrillation pad impedance data 2020B which are processed and formatted by microprocessor sub-unit 1854F and displayed on screens 302;

h) pulse oximetry data 1979B and blood pressure data 1980B which are processed and formatted by microprocessor sub-unit 1854E and displayed on screens 306 and 304 respectively;

i) four confirmation signals for pacing, defibrillation and other commands—confirmation signals #1 (coming from central station encoder [FIG. 54] via block CQ 2026A), confirmation signals #2 (coming from central station confirmation receiver decoder 1878 via block CR 2026A) and confirmation signals #3 and #4, 1935B and 1937B—all of which are processed and formatted by microprocessor sub-unit 1854C and displayed on screen 338;

j) AED telemetry information 2022B and portable unit touch sensitive screen responses 2024B, which along with other information to be displayed related to microprocessor logic functions, are processed and formatted by 1854B and displayed on CS screens 322, 324, 336, 340 and 342.

7.9 The Central Station Encoder

Figure 54:
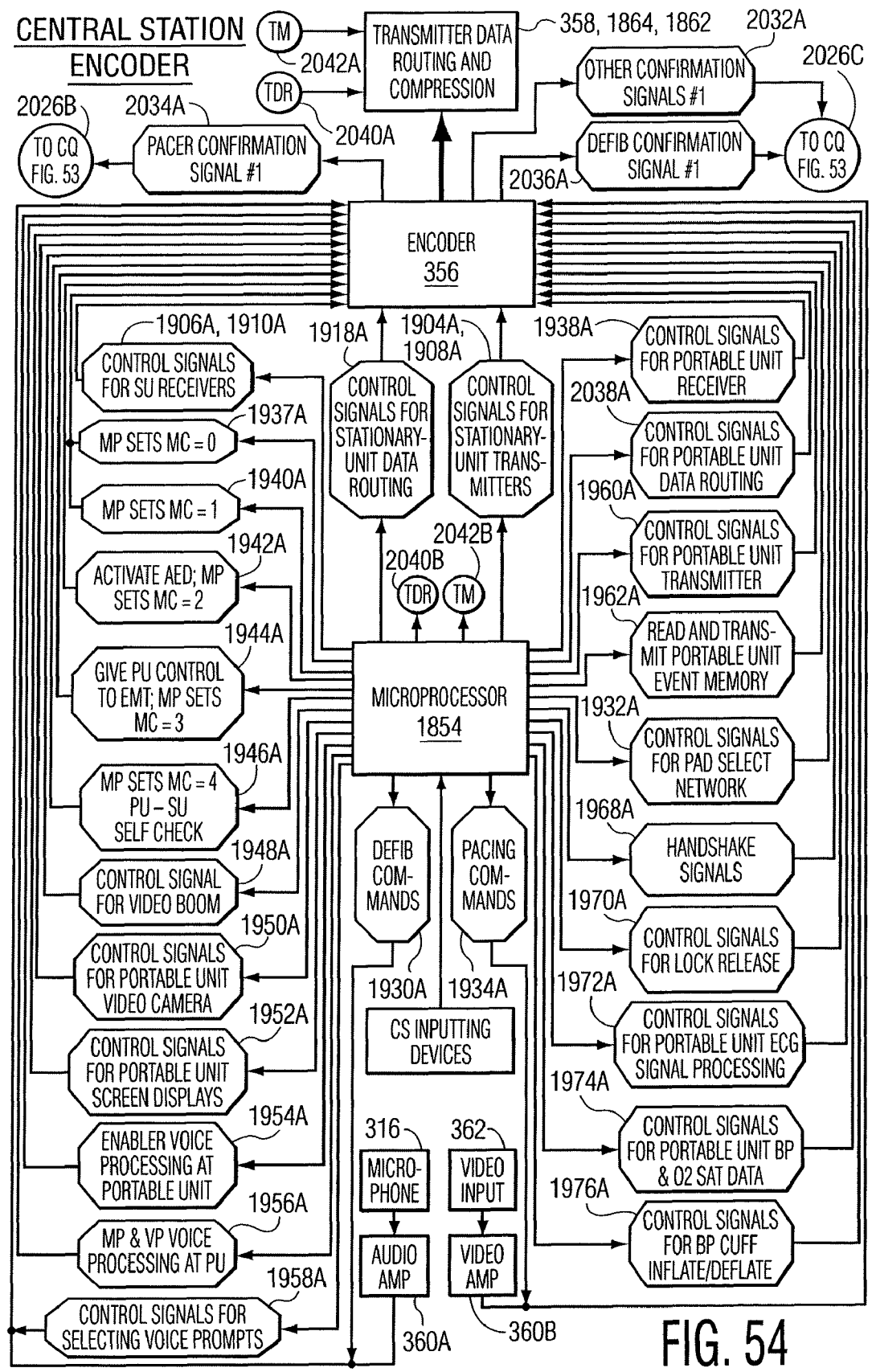
FIG. 54 is a block diagram of the central station encoder.

FIG. 54 shows the central station encoder 356 and associated signals and circuits.

MP commands, entered by CS inputting devices such as the touch sensitive screens 328, 330, 332 and 334, the keyboard 312 and the mouse 314, are registered by microprocessor 1854. All of these commands except those destined for the CS transmitter and data routing circuits are sent to the CS encoder. These commands include:

a) defibrillation and pacing command signals 1930A and 1934A;

b) SU communication control signals including signals 1906A and 1910A for the SU receivers, signals 1904A and 1908A for the SU transmitters and signal 1918A for SU data routing;

c) PU communication control signals including signal 1938A for the PU receiver (options 3A), signal 1956A (options 3B) for MP and voice prompt voice processing at the PU, signal 1954A (options 6A) for enabler voice processing at the PU, signal 1960A for the PU transmitter (options 6B) and signal 2038A for PU data routing (options 7);

d) master control unit state setting commands 1937A, 1940A, 1942A, 1944A and 1946A which command the PU master control unit 130 to enter states 0 through 4 respectively;

e) video control signals 1948A, 1950A and 1952A;

f) control signals for voice prompts 1958A;

g) control signals 1962A to allow the MP access to the PU event memory;

h) control signals 1932A for selecting the defibrillator and pacing pad electrode constituents;

i) handshake signals 1968A;

j) control signals for PU-SU lock release 1970A; and k) control signals for victim physiologic data including signals 1972A to select ECG pads and recording parameters, signals 1974A for blood pressure and oxygen saturation data and signals 1976A for blood pressure cuff inflation and deflation.

Microphone 316 and video input 362, leading to audio and video amplifiers 360A and 360B respectively, input the encoder with signals to be sent to the PU.

The microprocessor outputs which do not go to the encoder are those which control the CS transmitter (options 1B) and CS data routing (options 2). Transmitter control is via block 2040B to block TM 2042A; transmitter data routing is via block 2042B to block TDR 2042A.

Encoder output follows the sequence shown in FIG. 49 with data compression 1862, routing 1864 and transmitter 358.

The encoder produces confirmation signals #1 for pacing 2034A, defibrillation 2036A and other functions 2032A. These confirm proper entry of the command and proceed via block 2026C to signal processing and display.

8. Miscellaneous 8.1 Diagnostic Check

FIGS. 55A and 55B show a flow diagram for a diagnostic check of the PU-SU combination. The check may be initiated, block 2100, by either the clock within the PU (e.g. on a daily basis), or by the central station, block 2102. In the latter case, a signal is sent which initiates the handshaking routine shown in FIGS. 12D, 12E, 12F, 13B and 14O.

As each item is checked, the result of the check is classified as satisfactory or unsatisfactory. For example, if the PU battery check 2104 shows satisfactory battery voltage and minimal deviation from the previous day's value, then block 2106 leads to block 2110B, to block σ 2110A, resulting, block 2148, in in the storage of the information in PU memory. The CS will, in a preferred embodiment of the invention, perform a periodic (e.g. monthly) check, during which the aforementioned information is downloaded. If, however, the results of the battery check were unsatisfactory, block 2106 leads to block 2108B, to block v 2108A. This results in:
  a) storage of the information in PU memory;
  b) immediate notification of the CS; and
  c) optional sounding of a PU alarm or indicator.

Each of the 21 remaining diagnostic evaluations follows a similar format. Normal test results leads to blocks 2110C through 2110Y, then block σ 2110A, and information storage. Abnormal test results leads to blocks 2108C through 2108Y, then block v 2108A, and contacting the CS. The tests include:
  a) blocks 2112 and 2114, checking for SU-PU electrical continuity over assigned pins in data connectors 188 and 190;
  b) block 2116, checking the SU battery;
  c) block 2118, checking all clocks;
  d) block 2120, checking the global positioning system within the PU. If, block 2122, the PU position is substantially the same as the previous day, the result is considered normal;
  e) block 2124, checking the PU touchdown sensor. If, block 2126, it is in the intermediate position, the result is considered normal;
  f) block 2128, checking the SU-PU lock. If, block 2130, it is locked, the result is considered normal;
  g) block 2132, checking the PU activation button. If, block 2134, it is in the open position, the result is considered normal;
  h) block 2136, checking the master control unit state. If, block 2138, the value is 4 (i.e. appropriate for a diagnostic check), the result is normal;
  i) block 2140, charging the high voltage capacitors. If, block 2142, the voltage, charge time, and decay time are all normal, the result is normal;
  j) block 2150, the PU issues an audio tone or voice prompt. It simultaneously records and analyzes the sound, block 2152. If, block 2154, loudness and sound quality are adequate, the result is considered normal. This test allows for the evaluation of both audio input and output at the PU;
  k) block 2156, the PU transmits a test signal to the SU short range receiver. The receiver passes the signal through the SU decoder (FIG. 50) whose output leads to block SC3 1924A via the hard-wire data link between the PU and the SU, and evaluation of the returned signal. A satisfactory quality signal, block 2160, indicates adequate functioning of the PU short range transmitter and the SU short range receiver;
  l) block 2162, the SU short range transmitter, transmits a test signal to the PU receiver and the PU, block 2164 assesses the quality of the received signal. If signal quality is adequate, the result is normal;
  m) in blocks 2168 and 2170, the SU hard-wire telephone hookup is confirmed;
  n) in blocks 2172, 2174, 2176, 2178, 2180 and 2182, each of the receivers in the PU and SU is checked for its ability to detect the CS beacon signal. Information from the SU decoder, via block SC1 1920A and block SC2 1922A is used for the assessment of the two SU receivers;
  o) in blocks 2184, 2186, 2196 and 2198, the oxygen saturation and blood pressure systems are evaluated; and
  p) in blocks 2188, 2190, 2192 and 2194, the defibrillator pads are checked to make sure that their connection to the PU is secure, that their backing is intact and that the resistance between adjacent electrodes is in the expected range.

8.2 Universal Connectors

FIGS. 56A-56F show a series of universal connectors for attaching each type of electrode pad to the PU. There is a single male connector 220, FIG. 56A, which is situated at the PU end of each connection. Its thirty four pins 2300 are sufficient in number to accommodate the matrix electrode pad and two identifier pins (see below). It has two non-conducting locator pins 2302 to facilitate connection of two connectors.

Figure 56A:
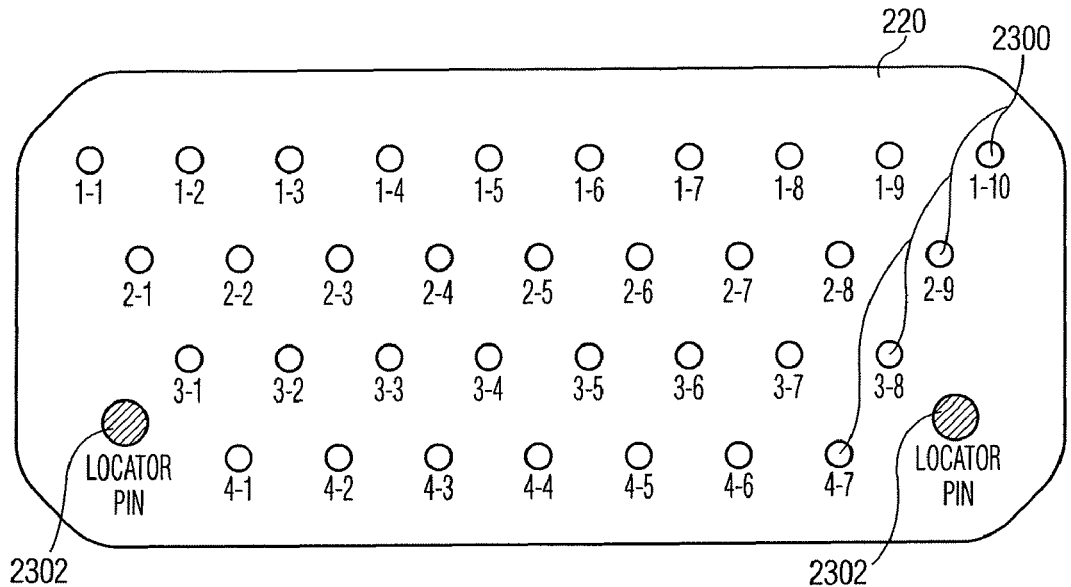
FIGS. 56A, 56B, 56C, 56D, 56E and 56F illustrate possible connector terminal arrangements for connecting a variety of Universal Pads and single electrode pads to the portable unit at a remote station.
Figure 56B:
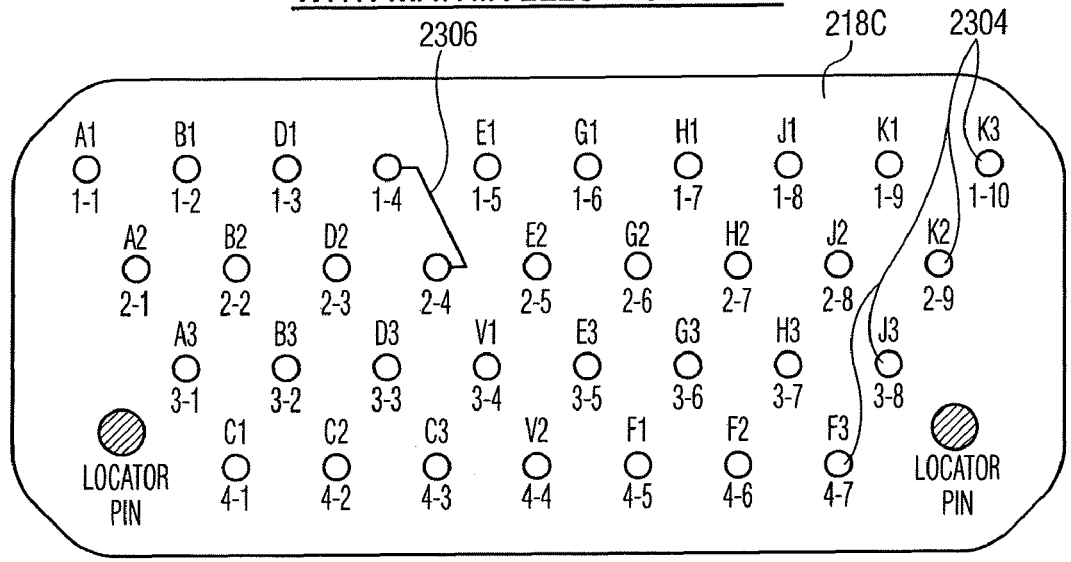

FIG. 56B shows the female universal connector 218C which would attach the matrix electrode pad (FIG. 5F) to the PU. In the figure, receptacles 2304, which accommodate the pins of the male pad, are labeled to show their correspondence to the matrix electrode pad elements. Pins 1-4 and 2-4, are rendered electrically common by a short length of conducting wire 2306 within the connector. Each type of electrode pad has a unique assignment for its two common pins. This allows the PU to determine which type of pad is attached to any of its male connectors (see FIG. 7B).

Thus, if at any time either an enabler, an EMT or a maintenance person attaches the wrong pad to a particular PU connector, the system and the MP will be able to detect this action. In a preferred embodiment of the invention, the MP can also know when the backing of a pad as been removed (see FIG. 5E).

Figure 56C:
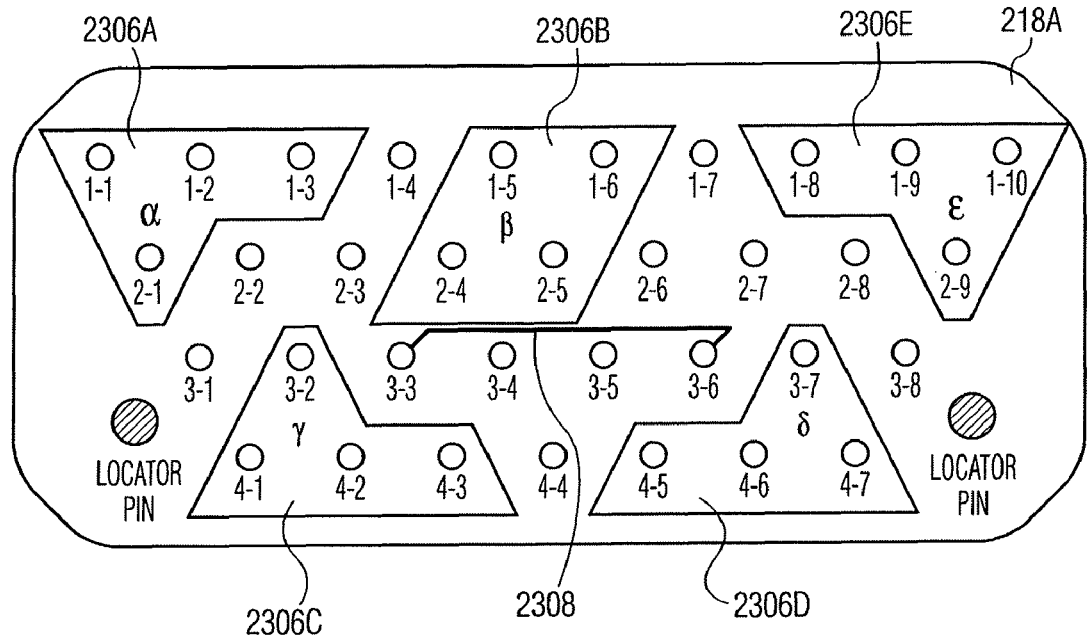

FIG. 56C shows the female universal connector 218A for the five electrode pad without separate ECG electrodes, 204A. Conductive element 2308 will cause the pins which plug into locations 3-3 and 3-6 to be electrically common, the signature for this type of pad. Pins 1-1, 1-2, 1-3 and 2-1 are electrically common with the α electrode 230 of the pad (see FIG. 5A). The assignment of four pins provides a lower resistance conductor for the defibrillating current. (The outline around each group of four pins in the figure is for illustrative purposes and has no functional value.) Elements 2306B show the four conductive receptacles which are electrically common with the pad's β electrode. The pad's remaining three pad electrodes have pin assignments which are indicated by 2306C, 2306D, and 2306E. The pin assignments are selected so that the pins with the greatest electrical potential difference during a shock are as far apart as is practical on the connector.

Figure 56D:
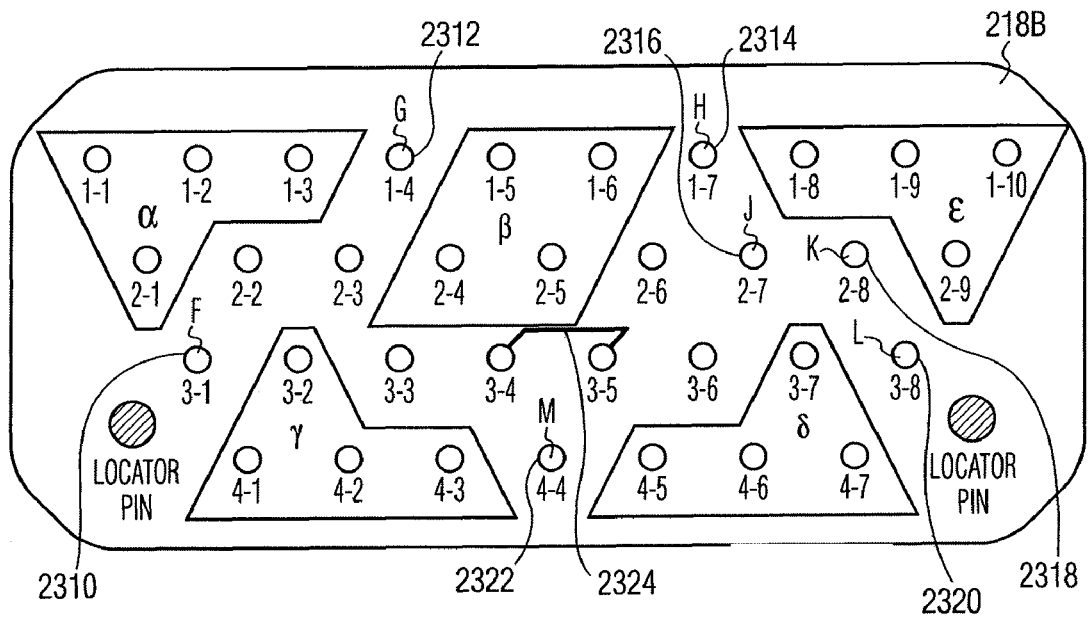

FIG. 56D shows the female universal connector 218B for use with electrode pad 204B, having five large defibrillating electrodes and seven small ECG electrodes. The defibrillating electrode pin assignments are the same as those in FIG. 56C. There are seven additional pins 2310, 2312, 2314, 2316, 2318, 2320 and 2322, which are assigned, one to each of the small ECG electrodes. The seven letters shown in the figure correspond to the identical letters which label the small electrodes in FIG. 5B, and are for illustrative purposes. Conductive element 2324 renders pins 3-4 and 3-5 electrically common, and is the identifier for this type of electrode pad.

Figure 56E:
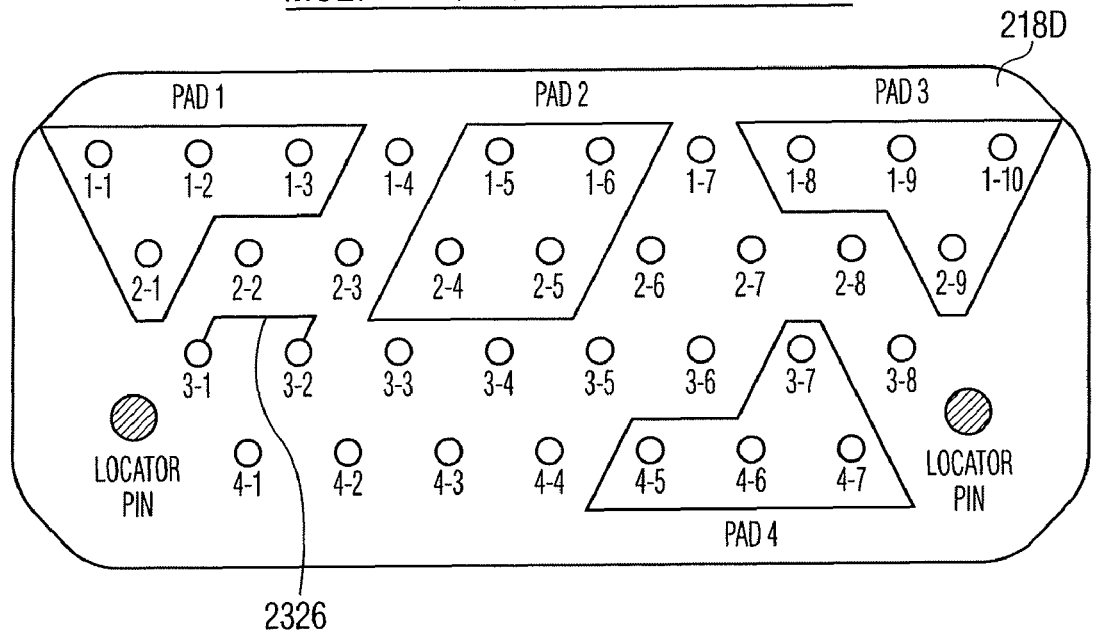

FIG. 56E shows a female universal connector 218D for use with multiple single electrode pads 210. Such an approach is illustrated in FIG. 5G. The pin assignments are the same as those for four of the five electrode pads in FIGS. 56C and 56D. For this pad, the conductive element 2326 lies between locations 3-1 and 3-2.

Figure 56F:
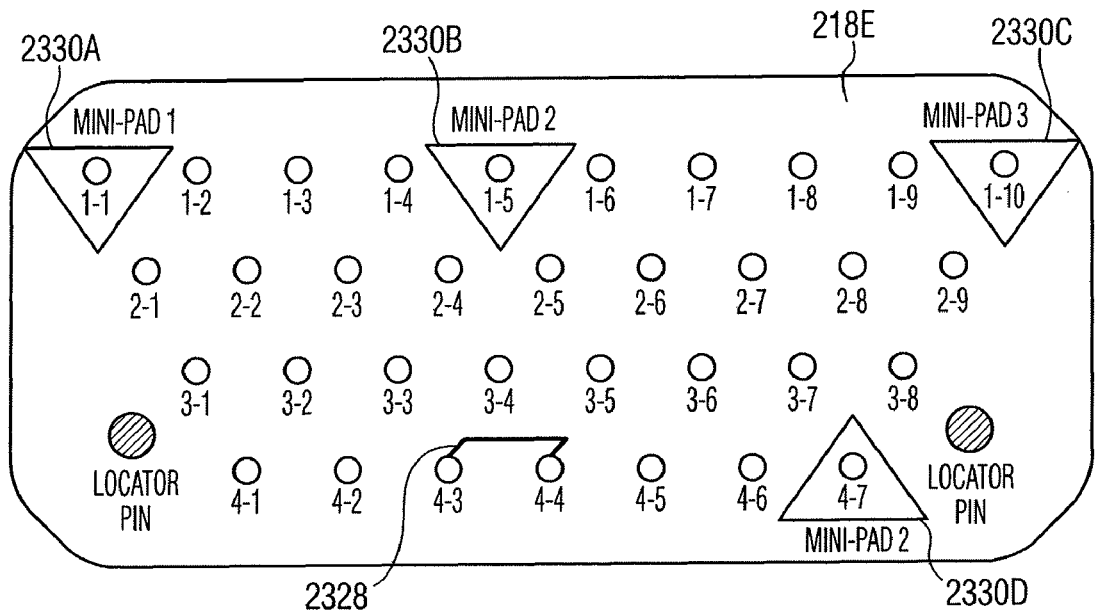

FIG. 56F shows a universal connector 218E intended to be used with mini-pads 211. Since the mini-pads are ECG pads and do not carry large amounts of current, single pin receptacle assignments 2330A-2330D are acceptable. Conductive strip 2328 identifies this type of universal connector.

8.3 Network of Central Stations

Figure 57:
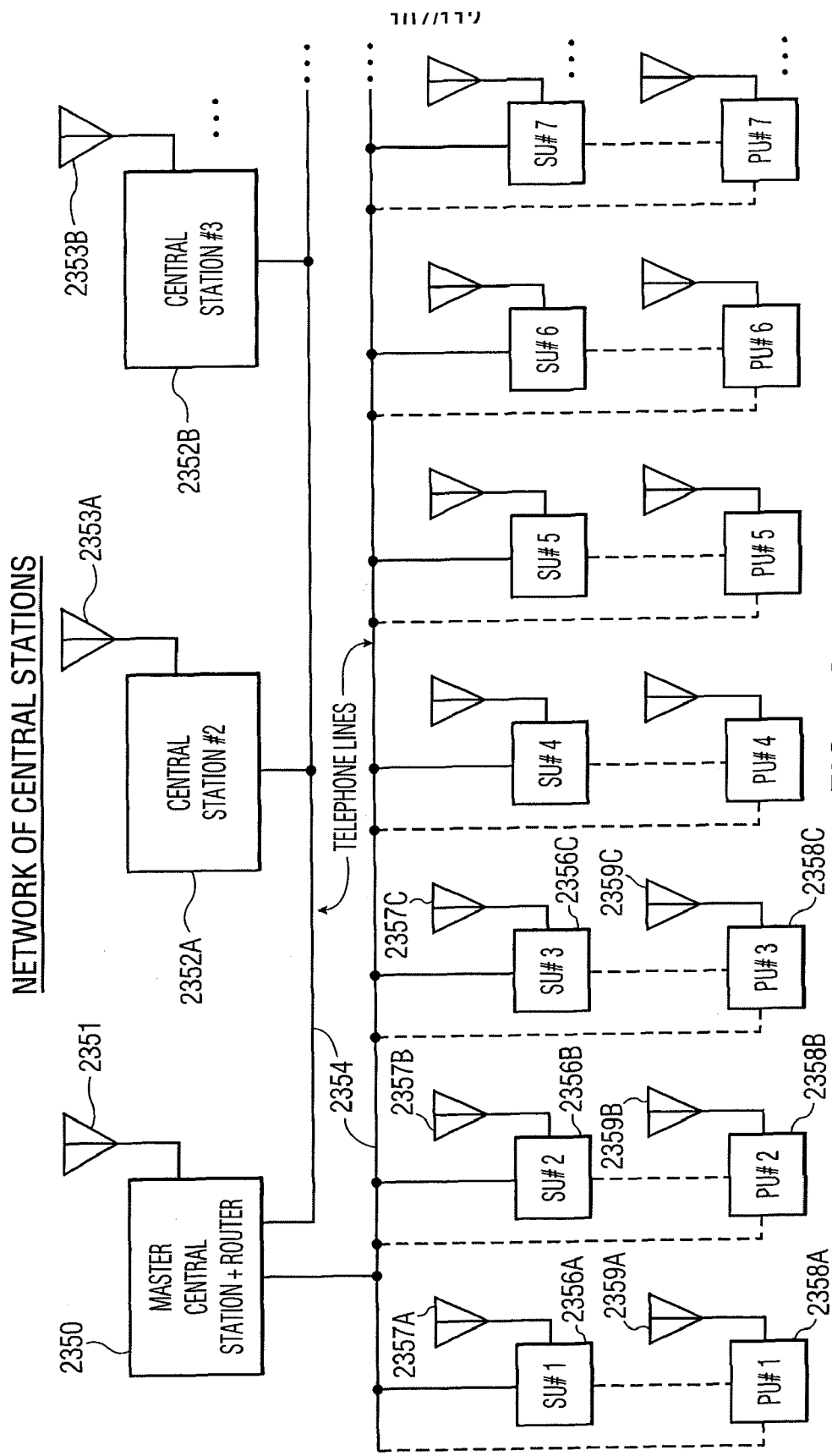
FIG. 57 is a block diagram of a network of central stations.

FIG. 57 shows a network of central stations. The network serves two purposes. First, in the event of a major malfunction in the central station, whether it be equipment related, due to a fire or meteorological event, backup central station functioning would be provided. Second, in the event of an overflow situation —i.e. too many calls for the number of MPs staffing a particular central station—additional MPs from a less busy CS could help to distribute the load.

The figure shows a master central station and router 2350 which communicates with a series of portable units 2358A, 2358B, 2358C . . . through either:

a) wireless links via antenna 2351 and PU antennae 2359A, 2359B, 2359C . . . ;

b) the SUs 2356A, 2356B, 2356C, associated with each of the PUs, which link to the CS via either the telephone lines 2354 or SU antennae 2357A, 2357B, 2357C . . . .

The broken lines extending from each PU indicate that the PU is operating primarily by wireless connection, either to the SU or to the telephone system or other public or private communication network.

Additional central stations 2352A, 2352B . . . are linked to the master CS by either their antennae 2353A, 2353B . . . or by telephone lines 2354

During operation, the MP in the master CS, working from screen 1550 (FIG. 42) can transfer one or more cases to MPs in any of the other CSs (see above). He can transfer unassigned cases, or cases that are in progress. The transfer can be over telephone lines 2354 or by wireless means.

In an alternative embodiment, every central station in the network would be capable of being the master central station. In yet another variant, any or all of central stations 2352A, 2352B . . . could be replaced by a solo MP operating on a personal computer, which is part of a wireless network. The solo MP could work on a regular shift, or could be "activated" only when high volume conditions necessitate his participation.

8.4 Multiple Communication Modalities and Routes

Figure 58:
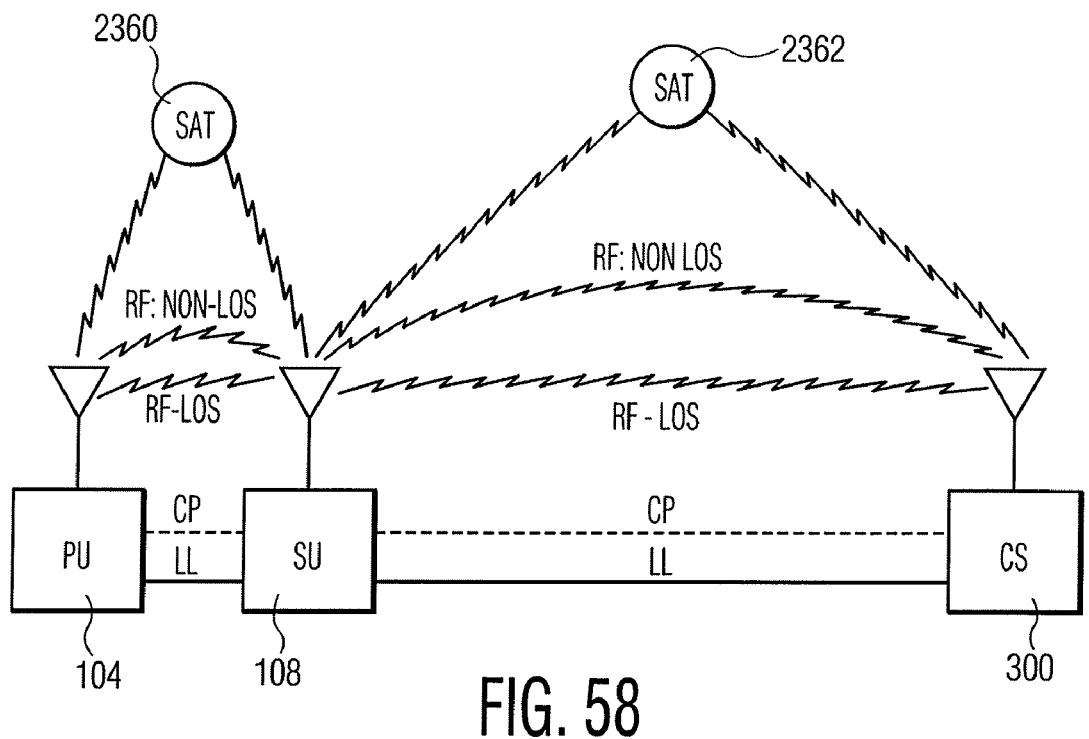
FIG. 58 is a block diagram illustrating the multiplicity of communication options between the portable unit and the stationary unit, and between the stationary unit and the central station.

FIG. 58 depicts the various routes and means by which the PU, the SU and the CS can communicate. Each pair can communicate:

a) using the public or a private telephone system, over land lines, LL;

b) using the public or a private cellular telephone system, depicted by broken lines, CP;

c) by line-of-sight radio frequency communication, RF-LOS;

d) by non-line-of-sight radio frequency communication, RF: non-LOS;

e) using satellite links 2360 and 2362.

The figure shows each of these modalities in place between the members of the PU-SU pair and of the SU-CS pair, but each modality may also apply to the PU-CS pair.

Mixed modalities are possible a) when communication is via the SU and b) within any link. For example, the link from PU to SU may be over the cellular telephone network, while the SU-CS link may be by satellite. In another example, the link between any pair from among the PU, SU and CS may in part be cellular and in part over land lines.

Private broadband cable systems may be used for any of these connections. The internet, accessed via the public telephone system or by cable access, may serve for any of these links.

8.5 Multiple Possible Routes and Relays Between PU and CS

Figure 59:
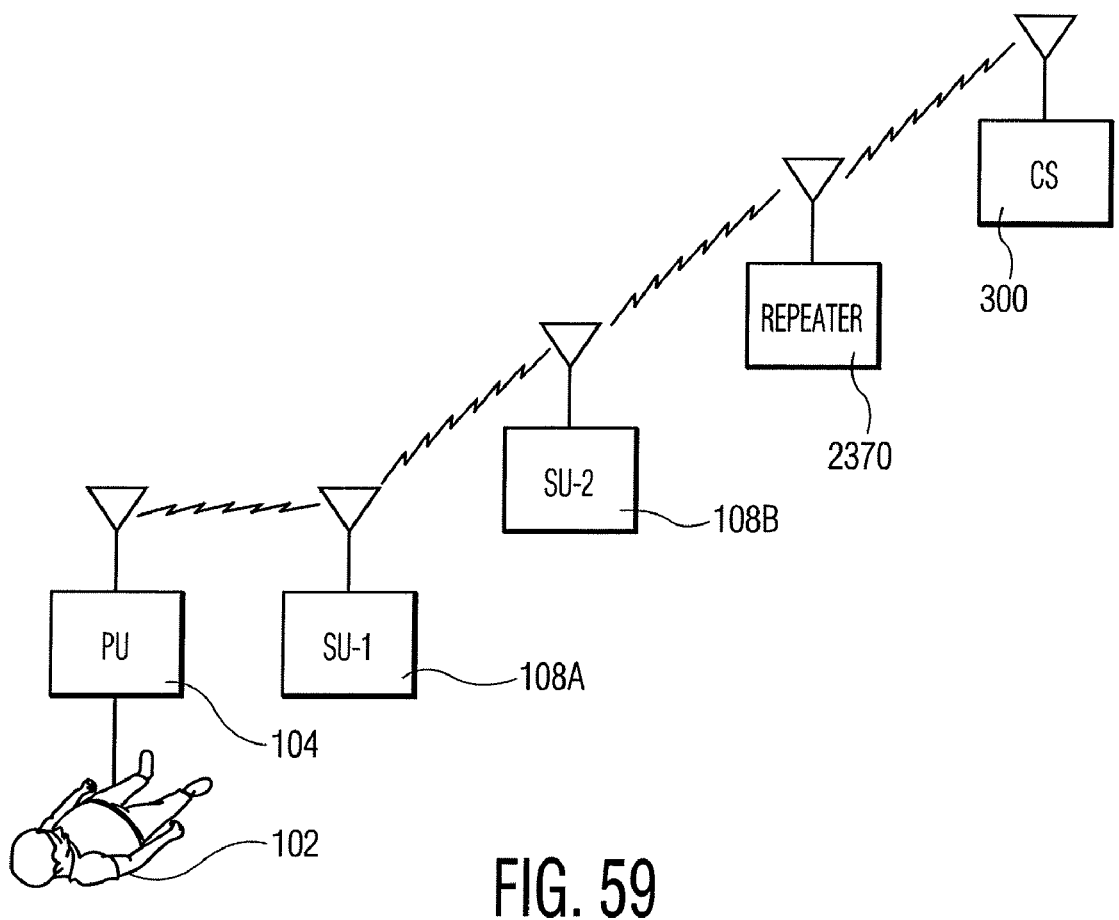
FIG. 59 is a block diagram showing a repeater unit and multiple stationary units deployed among a portable unit and the central station.

The PU 104 may communicate directly with the CS 300, or one or more intervening relay units may link the PU with the CS. Already discussed are the situations in which a) the intermediate relay is the SU alone, or b) the SU and another PU (see Table 13 above). It would also be possible to link the PU 104 with the CS via a) multiple other SUs (e.g. 108A and 108B);

b) repeater units 2370, deployed in strategic locations where the local communication system may not be as robust as desirable;

c) combinations of SUs (e.g. 108A and 108B) and repeater units 2370, as shown in FIG. 59.

The intention of the multiplicity of segments in the PU-CS link would be to produce a more robust communications link than would have been the case if a smaller number of units performed the linkage.

When more than one stationary unit is used to link the PU and the CS, such that one or more "idle" SUs, i.e. SUs not currently carrying victim information from its associated PU, is used:

a) means would be provided for allowing the PU associated with an idle SU to very rapidly come on-line, if an emergency arose in its vicinity. Such a situation would require rapid redirection of the PU-CS link which was using the idle SU;

b) means would be provided for selecting the constituents of a multi-element link between the PU and the CS. Such means could lie within the CS, within each SU or both within the CS and the individual SUs.

8.6 Control of an Implantable Cardioverter-Defibrillator by the MP

Implantable cardioverter-defibrillators, "ICDs," as are known in the art, make their own assessment of a patient's rhythm and treat with preprogrammed parameters. In certain circumstances, the expertise of the MP may allow for better choices of therapy than the choices made by the ICD. Such circumstances include:

a) the situation in which the patient may be getting one or more shocks for a rhythm such as sinus tachycardia, atrial fibrillation or atrial flutter, which the ICD failed to distinguish from ventricular tachycardia or ventricular fibrillation;

b) the situation in which the patient should have gotten a shock but did not, e.g. because VT occurred at a rate which was less than the programmed rate detection rate of the ICD, or because so-called detection enhancements, as are known in the art (e.g. sudden onset), were programmed in such a way that the ICD could not make a proper VT diagnosis; and c) the situation in which a patient will receive or has been receiving shocks for a tachycardia that is well tolerated and could be approached with a gentler termination modality, e.g. anti-tachycardia pacing.

Figure 60:
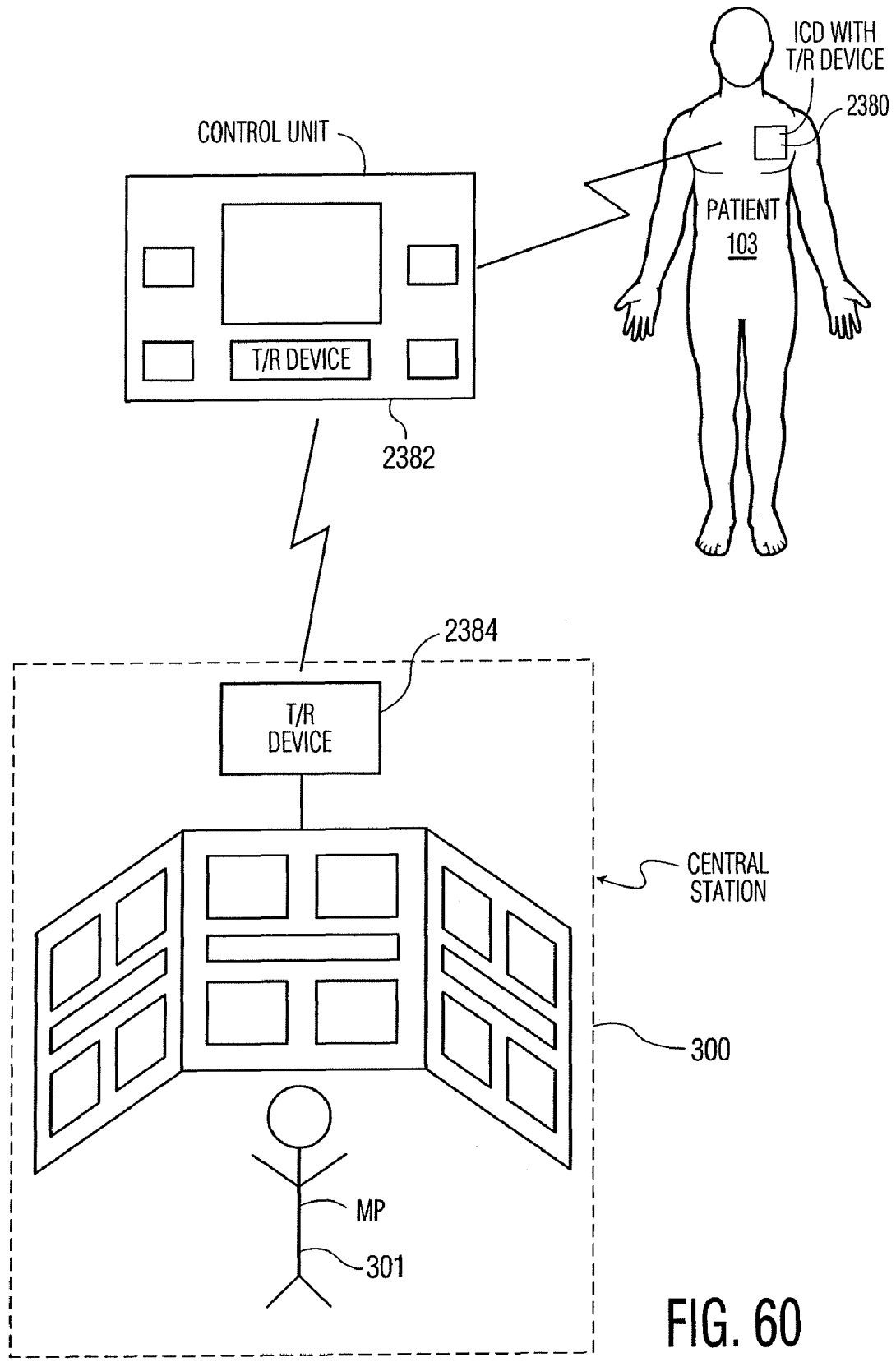
FIG. 60 is a block diagram for communicating with and controlling an implantable cardioverter defibrillator.

FIG. 60 shows a patient 103 with an ICD 2380 which has a transmitting and receiving device. ICD 2380 communicates with transmitting and receiving device 2384 in central station 300 via the transmitting and receive device in a nearby control unit 2382. The nearby control unit allows the transmitter within the ICD to use minimal power, and thereby conserve its batteries. The transmitter within the ICD would be in a stand-by mode until the ICD detected a potentially abnormal heart rhythm. The rhythm would then be transmitted to the MP in the CS via the control unit. The MP could decide whether to let the ICD make its own decision, or he could over-ride the decision. Means could be provided to let the MP preview the ICD decision. The MP could communicate with the patient either by telephone or other means, to determine the appropriateness of therapy which is either more aggressive or less aggressive than is programmed in the ICD. In one embodiment of the invention, the MP could reprogram ICD 2380 to more appropriate settings, based on the event. The MP could notify the patient's physician, who could participate in decision making such as reprogramming. The MP could cause the ICD to deliver therapy for a non-life threatening event at a time when the victim is asleep, such determination being made by the MP after speaking with the victim, or using other communication means.

8.7 Defibrillation Using Two or More Different Shocks in One Victim

Figure 61:
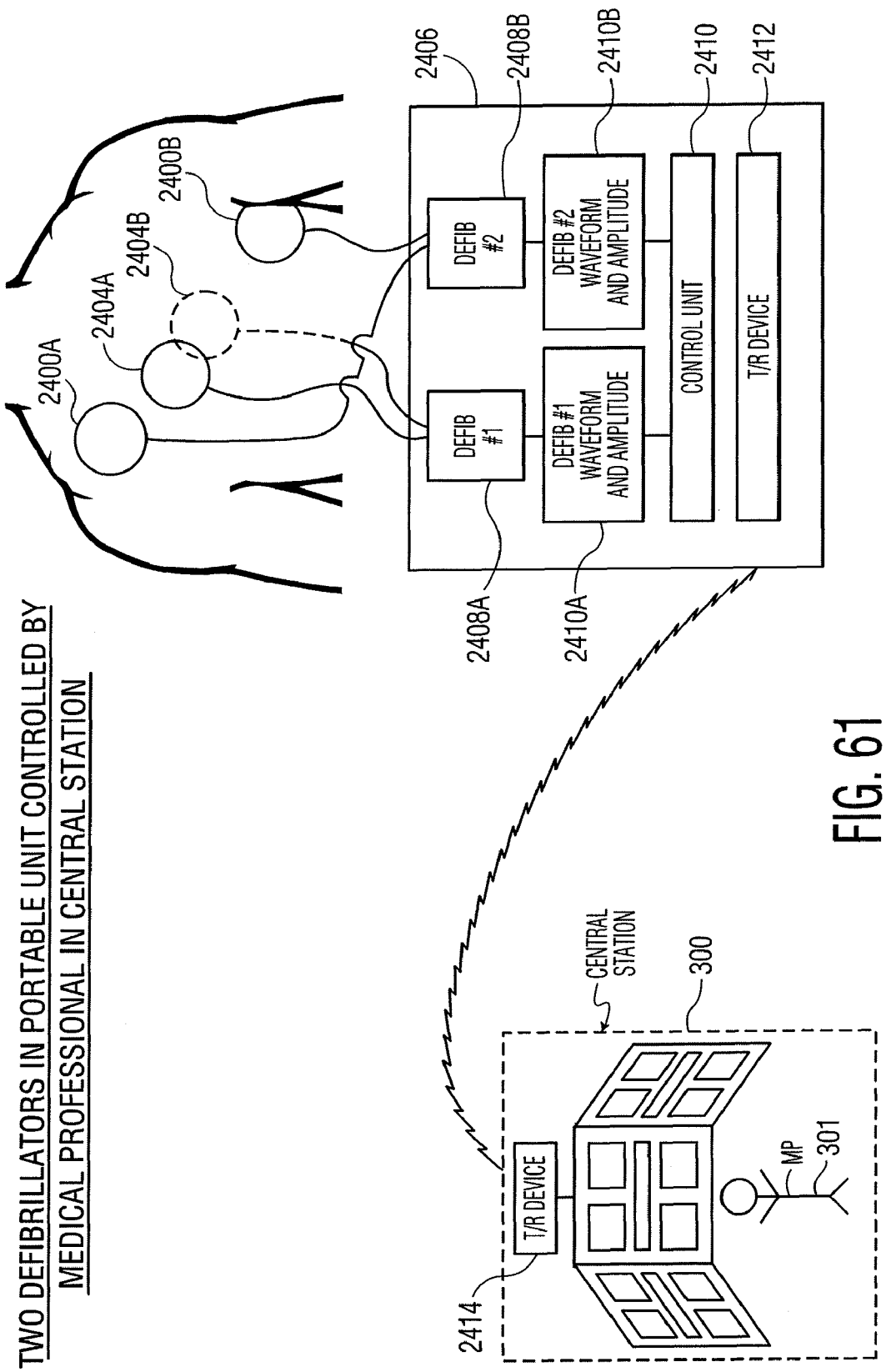
FIG. 61 is a representational diagram showing the use of the system according to the present invention to apply defibrillation pulses by means of two separate defibrillators.

FIG. 61 shows a portable unit 2406 which contains two defibrillation circuits 2408A and 2408B. The output of defibrillation circuit 2408A is applied to the victim via electrode pads 2404A and 2404B. The output of defibrillation circuit 2408B is applied to the victim via electrode pads 2400A and 2400B. The waveform and amplitude of each defibrillator is controlled by circuits 2410A and 2410B, both of which are controlled by control unit 2410. The MP 301 in the CS 300 controls unit 2410 via transmitting and receiving devices 2414 in the CS and 2412 in the PU. The waveform, amplitude and timing parameters selected by the MP for defibrillator 2408A may be the same as or different from those selected for 2408B. The electrodes through which the output of 2408A is applied may be entirely the same as, entirely different from, or have some but not all the same constituents as the electrodes through which the output of 2408B is applied. There may be more than two defibrillators through which energy is applied.

Figure 62:
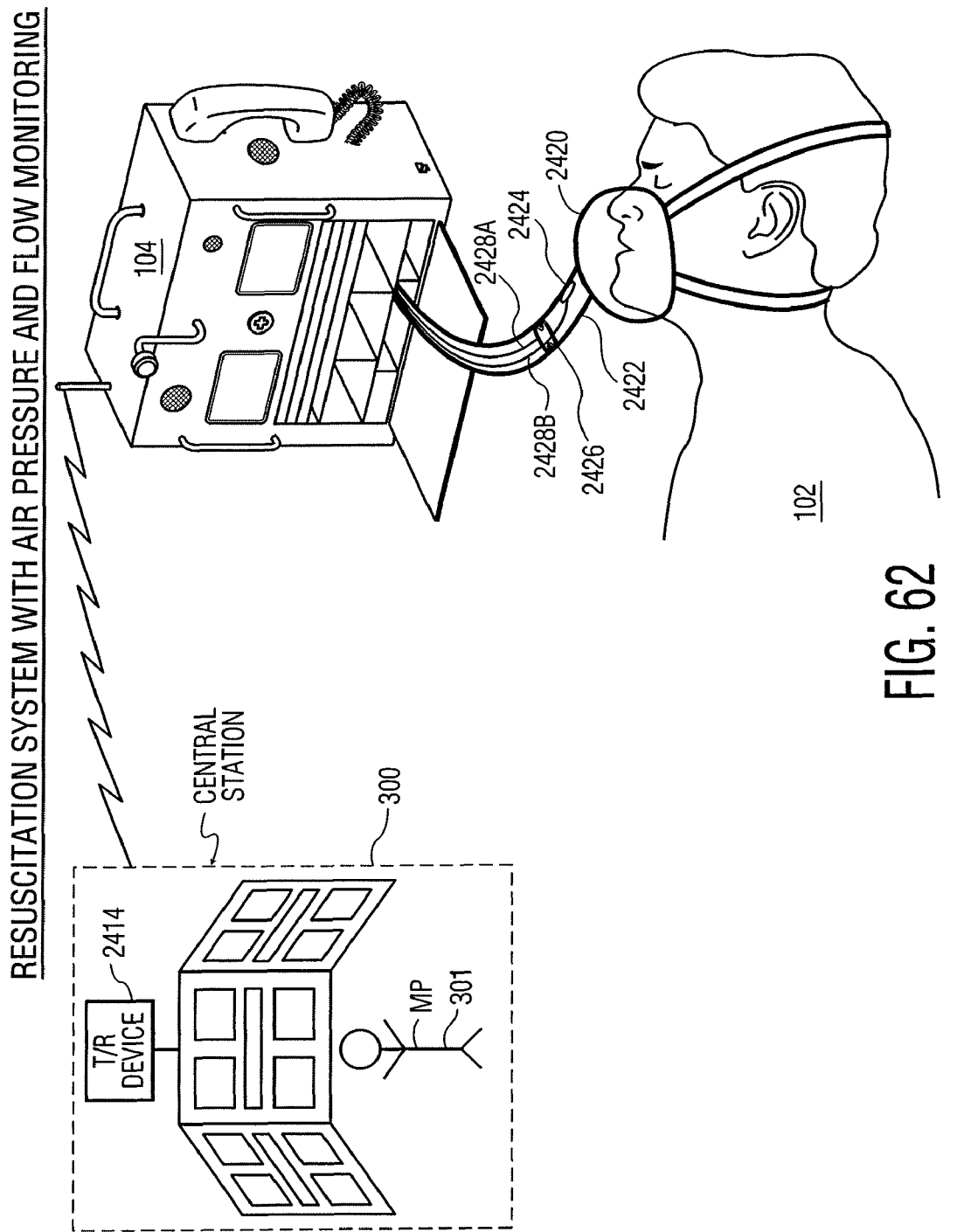
FIG. 62 is a representational diagram showing the use of the system according to the present invention to supply and monitor air to a victim.

8.8 Monitoring Adequacy of Ventilation During Resuscitation Using Pressure and/or Flow Monitoring FIG. 62 shows a means for using the PU 104 to monitor and transmit air pressure and air flow information to the MP in the CS 300 (see Section 4.3.2.2). A tightly fitting mask 2420 is applied to the victim with tubing 2422 that extends to a source of compressed air within the PU. An air flow sensing device 2426 and/or an air pressure sensing device 2424 is contained within the tubing, the mask or the PU. Cables 2428A and 2428B send the information from their respective transducers to the PU microprocessor, after which the information is encoded and sent to the MP in the CS. The information can be used to assess the presence and adequacy of spontaneous respiration. It can be used to assess whether the mask has been applied appropriately so that its outer border is properly applied to the victim and forms a seal. If a hand-pumped ventilation "bag," as is known in the art, is used to ventilate the victim, the flow and pressure information can be used to assess whether the rate and depth of bag compression is appropriate. The mask may be stored in the miscellaneous section 177 of the PU tool-kit (FIG. 7A). The ventilation bag would be stored nearby or brought by the EMT. The gas with which the victim is ventilated need not be pure air; supplemental oxygen may be admixed.

Figure 63:
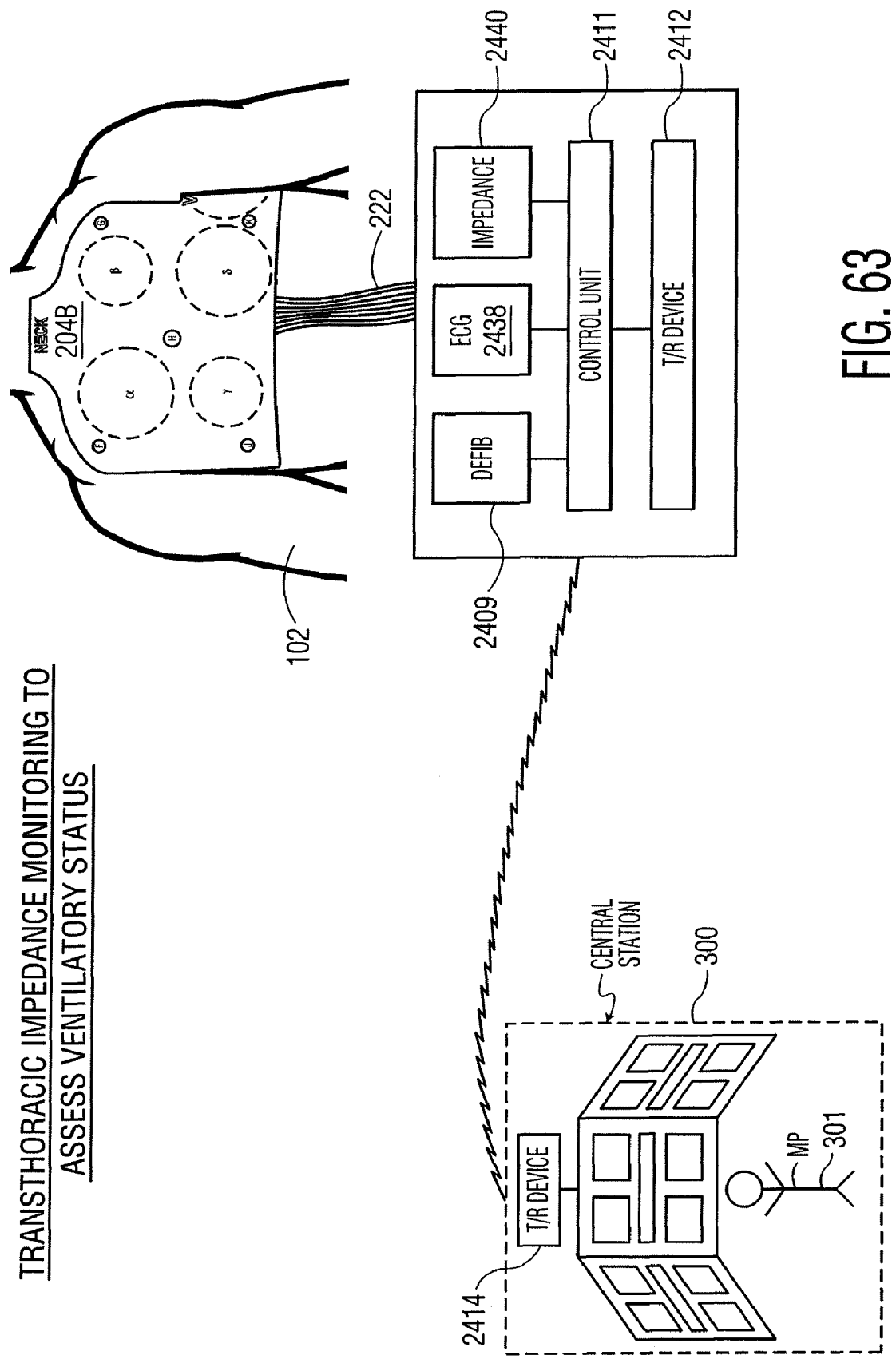
FIG. 63 is a representational diagram showing the use of the system according to the present invention to measure transthoracic impedance.

8.9 Monitoring Adequacy of Ventilation During Resuscitation Using Transthoracic Impedance Since the resistance of air is greater than that of body fluids, the resistance across the chest when the lungs are inflated is greater than when they are deflated. This means may be used to monitor respiratory status. FIG. 63 shows a victim 102 with five electrode pad 204B on his chest. A portable unit is attached to the pad via cable 222. The unit contains a transmitting and receiving apparatus 2412 for communicating with such apparatus 2414 within the CS. This PU contains a control unit which intermittently causes impedance measuring unit 2440 to measure the transthoracic impedance. The data from this unit is sent to the MP. The unit also contains ECG monitoring apparatus 2438 and defibrillating apparatus 2409. The latter is controlled remotely by MP 301.

Appendix 1

Voice Prompt Menu

I) Introductory Statements Menu
   A) You've reached the Central Station. Can you hear this?
   B) Because you couldn't hear me, I've switched to a computer-assisted voice. Can you hear me now?
   C) Please speak louder.
   D) I can hear you, so feel free to speak or answer at any time.
   E) Would you like me to speak louder?
   F) If, at any point, you don't hear me well, or if you would like me to repeat anything, please let me know.
   G) Please pick up the telephone on the right side of this unit. We'll hear each other more clearly when you use it.
   H) A text version of the voice prompts that you are hearing is appearing simultaneously on the left (or right) video screen.
   I) Please look at the video screen on the left (or right) for further written instructions.
   J) I can't hear you, so please answer my questions by selecting a choice on the touch sensitive video screen on the right (or left).
   K) If you touch "KEYBOARD" on the touch sensitive screen, a standard keyboard will appear which will allow you to send me a text message.
   L) Communication with the Central Station is not possible at this moment. Your unit's on-board computer will provide you further instructions. Meanwhile, further attempts will be made to link you directly to the Central Station.

II) Event Description Menu
   A) Please describe the event.
   B) Did the victim lose consciousness?
   C) Did you witness the event?
   D) Are there any witnesses to the event?
   E) How many minutes have passed since the start of the event?
   F) (If victim is conscious:) Is the victim complaining of chest pain?
   G) (If victim is conscious:) Is the victim complaining of shortness of breath?
   H) Can you tell if the victim breathing?
   I) Is there anyone there who knows the victim?
   J) Do we know if the victim takes medication?
   K) Can you or anyone tell me what medications the victim is taking?
   L) Do you know if the victim is diabetic?
   M) Was alcohol involved in this incident?
   N) Was there a physical injury to the victim?
   O) Does the victim have a medical alert bracelet or necklace?
   P) I know this is a difficult situation for you, but please try to calm down.
   Q) Please speak a little more slowly.
   R) Please repeat your last statement.
   S) Please speak louder.

III) Lock Release Menu
   A) You can't remove the portable unit from the wall until I release a lock.
   B) Please do not attempt to remove the portable unit at this time.
   C) Your picture has been taken and transmitted to the Central Station, which will allow us to identify you, if you tamper with this unit.
   D) To remove the portable unit from the wall, grasp the two handles and pull the unit towards your body.
   E) Once the unit has been removed please carry it to the victim's side.
   F) During your trip to the victim's side, I'll attempt to speak with you about other details of the event. If you can't hear me, don't worry or stop; I'll finish the conversation when you get to the victim.
   G) To unlock the unit from its wall mounting, you'll need to use the combination lock on the unit's left side.
   H) Set the front (red) wheel at '6'. Set the second (blue) wheel at '2'. Set the third (white) wheel at '8'. Set the back (green) wheel at '5'.

IV) Trip to Victim Menu
  A) Can you hear me?
  B) Can you hear me now?
  C) Please speak louder.
  D) It's hard to speak while your carrying the unit; We can continue the conversation when you arrive at the victim's side.
  E) Please tell me more about the event.
  F) When we get to the victims side, place the box on the ground as near to the victim as possible. The victim's left side, near the chest, is best. Gently put the unit down so that the side with the screens faces upwards.
  G) Once you've placed the unit on the ground, the tool kit door will open. Inside you'll see various items that you can use to help me find out what's going on and help the victim.
  H) I've called your local 9-1-1. Trained personnel are on the way. In the meantime you and I can get started.
  I) Each moment is precious in this sort of situation, so we'll want to move as quickly as possible.
  J) Have you had any experience with the administration of first aid?
  K) Please describe your experience.
  L) Don't be concerned about that [your inexperience].
  M) I'm an expert in the management of this sort of emergency situation. I'm going to instruct you in some simple steps which require no prior experience. I'll figure out what's going on and make any needed decisions.
V) On Arrival Menu
  A) Can you hear me?
  B) Can you hear me now?
  C) Please speak louder.
  D) Place the box on the ground as near to the victim as possible. The victim's left side, near the chest, is best. Gently put the unit down so that the side with the screens faces upwards.
  E) Is the victim conscious?
  F) When the box rests on the ground, the tool-kit door will release. Open it all the way so that you can easily see its contents.
  G) It may be easier for us to communicate if you use the headset in the tool compartment. Please try this now.
  H) It seems that communicating without the headset worked just as well? Do you agree?
  I) Let's go back to communicating without the headset.
  J) Notice the video camera. It is on a flexible arm which I am now extending. Please grasp this arm and point it in the direction of the victim. You can tell when you have the correct orientation by checking your video screen.
  K) We'll need to attach a special pad to the victim's chest which will allow me to diagnose and treat the patient electrically.
  L) You'll need to remove any clothing covering the victim's chest so we can place an electrical pad directly on his or her skin.
  M) There is a scissors in the tool compartment if you need it.
  N) Please do this as quickly as possible.
  O) Is a telephone jack within twenty five feet of the box?
  P) Please remove the telephone wire from the lower left hand corner of the tool-kit and plug it into the telephone jack.
VI) Attach Pad and Peripherals Menu
  Note: Voice prompts A-O refer to the initial application of pacing/defibrillator pads to the victim's chest.
  A) Look at the top row of the tool-kit. Please peel off the cover marked "5 Electrode Pad—Standard Version," and remove the pad from the tool-kit.
  B) Look at the second row from the top of the tool-kit. Please peel off the cover marked "5 Electrode Pad—With Cutout Section" and remove the pad from the tool-kit.
  C) Look at the third row from the top of the tool-kit. Please peel off the cover marked "32 Electrode Pad" and remove the pad from the tool-kit.
  D) Look at the fourth row from the top of the tool-kit. Please peel off the cover marked "Single Electrode Pads" and remove all of them from the tool-kit.
  E) Look at your video screen to see how we're going to orient the pad on the victim's chest.
  F) Look at your video screen to see how we're going to orient the pads on the victim's chest.
  G) Look at your video screen. I'm going to mark the correct pad position and orientation in red.
  H) Look at your video screen. You'll see a cartoon showing the correct pad placement and orientation
  I) Before applying the pad, we must be sure that the area to which it is applied is bare; Please do so.
  J) Before applying the pad, we must peel the plastic back off of it. Once you do this, you'll expose an adhesive surface.
  K) Try to keep the adhesive back of the pad from coming in contact with anything but the patient.
  L) Apply the pad so that the adhesive surface faces the patient.
  M) Try to apply the pad so that it is properly positioned and oriented upon first contacting the patient.
  N) Try to apply the pad from left to right so that there are no bubbles, or areas where the pad fails to make contact with the victim's skin.
  O) I'd like to be able to look at how you've placed the pad, but you are (or someone is) standing between the video camera and the victim. Please allow me an unobstructed view.
  Note: Voice prompts P-AA are used when the system detects high pad impedance, suggesting inadequate contact between pad and victim's skin.
  P) Please run your hand over all areas of the pad, pressing down firmly to assure that the pad makes good contact.
  Q) Please press down firmly over the area of the pad that I've marked on the video screen.
  R) Please press down firmly over the side of the pad marked "Victim's Left".
  S) Please press down firmly over the side of the pad opposite "Victim's Left".
  T) Please press down firmly over the side of the pad marked "Victim's Right".
  U) Please press down firmly over the top half of the pad.
  V) Please press down firmly over the bottom half of the pad.
  W) Please press down firmly over the center of the pad.
  X) Please apply each individual pad in the position indicated on the screen. They are numbered and color coded to help you.
  Y) Please press down firmly over the red pad (or the pad with a '1' on it).
  Z) Please press down firmly over the white pad (or the pad with a '2' on it).
  AA) Please press down firmly over the blue pad (or the pad with a '3' on it).
  Note: In the case of multiple single pads, similar prompts involving additional pads (e.g. a fourth pad) are possible. This holds true in each of the instances where prompts are listed referring to pads '1,' '2' or '3.'
  Note: Voice prompts AB-BM refer to situations where the enabler is asked to either reposition a pad or pads, or change pad systems. Such requests might occur in the event of one or more unsuccessful defibrillation or pacing attempts. Voice prompts AB-AV ask the enabler to reposition a pad.

AB) Please remove the pad and reposition it as I've shown on the screen.

AC) Please remove the pad and reposition it so that it lies further towards the victim's left.

AD) Please remove the pad and reposition it so that it lies further towards the victim's right.

AE) Please remove the pad and reposition it so that it lies higher up, that is, nearer to the victim's neck.

AF) Please remove the pad and reposition it so that it lies lower down, that is, further from the victim's neck.

AG) Please remove the pad and re-apply it so that it covers the victim evenly, that is, without any bumps or elevations.

AH) Please remove the red pad (or the pad with a '1' on it), and reposition it further towards the victim's left.

AI) Please remove the red pad (or the pad with a '1' on it), and reposition it further towards the victim's right.

AJ) Please remove the red pad (or the pad with a '1' on it) and reposition it further up on the victim, that is, towards his or her neck.

AK) Please remove the red pad (or the pad with a '1' on it) and reposition it further down on the victim, that is, towards his or her feet.

AL) Please remove the red pad (or the pad with a '1' on it) and reposition it as shown on your video screen.

AM) Please remove the white pad (or the pad with a '2' on it) and reposition it further toward the victims left.

AN) Please remove the white pad (or the pad with a '2' on it) and reposition it further toward the victim's right.

AO) Please remove the white pad (or the pad with a '2' on it) and reposition it further up on the victim, that is, towards his or her neck.

AP) Please remove the white pad (or the pad with a '2' on it) and reposition it further down on the victim, that is, towards his or her feet.

AQ) Please remove the white pad (or the pad with a '2' on it) and reposition it as shown on your video screen.

AR) Please remove the blue pad (or the pad with a '3' on it) and reposition it further towards the victim's left.

AS) Please remove the blue pad (or the pad with a '3' on it) and reposition it further towards the victim's right.

AT) Please remove the blue pad (or the pad with a '3' on it) and reposition it further up on the victim, that is, towards his or her neck.

AU) Please remove the blue pad (or the pad with a '3' on it) and reposition it further down on the victim, that is, towards his or her feet.

AV) Please remove the blue pad (or the pad with a '3' on it) and reposition it as shown on your video screen.

Note: Voice prompt AW refers to a situation where one pad system needs to be replaced with a different one. This prompt is likely to be followed by one of prompts VI-A, VI-B, VI-C or VI-D.

AW) We need to switch pads. Please remove the pad that you previously applied to the chest.

Note: Voice prompts AX-BM refer to a situation where a variation on the usual defibrillation pathway is to be attempted. In this case, instructions are given for application of a pad to the victim's back.

AX) We'll need to reposition one of the round pads to the victim's back.

AY) The easiest way to do this is to roll the victim just enough to expose the area we need.

AZ) We'll want to roll the victim towards you.

BA) We'll want to roll the victim away from you.

BB) If there is someone at the scene who can help you with this, please ask them to help.

BC) As we did before, we'll need to apply the pad to bare skin.

BD) There is a scissors in the tool compartment if you need it.

BE) Please remove the red pad (or the pad with a '1' on it), and reposition it on the victim's back, beneath the right shoulder blade.

BF) Please remove the red pad (or the pad with a '1' on it), and reposition it on the victim's back beneath, the left shoulder blade.

BG) Please remove the red pad (or the pad with a '1' on it) and reposition it on the victim's back, as shown on your video screen.

BH) Please remove the white pad (or the pad with a '2' on it) and reposition it on the victim's back, beneath the right shoulder blade.

BI) Please remove the white pad (or the pad with a '2' on it) and reposition it on the victim's back, beneath the left shoulder blade.

BJ) Please remove the white pad (or the pad with a '2' on it) and reposition it on the victim's back, as shown on your video screen.

BK) Please remove the blue pad (or the pad with a '3' on it) and reposition it on the victim's back, beneath the right shoulder blade.

BL) Please remove the blue pad (or the pad with a '3' on it) and reposition it on the victim's back, beneath the left shoulder blade.

BM) Please remove the blue pad (or the pad with a '3' on it) and reposition it on the victim's back, as shown on your video screen.

Note: Voice prompts BN-BV refer to a situation where one of the already connected pad(s) needs to be replaced. This might occur if a pad is damaged or is incorrectly applied.

BN) Look at the fifth row from the top of the tool-kit. Please peel off the cover marked "Spare Pads."

BO) Please remove the pad marked "5 Electrode Pad—Standard Version" from the "Spare Pads" section that you just opened.

BP) Please remove the pad marked "5 Electrode Pad—With Cutout Section" from the "Spare Pads" section that you just opened.

BQ) Please remove the pad marked "32 Electrode Pad" from the "Spare Pads" section that you just opened.

BR) Please remove the cluster of pads marked "Single Electrode Pads" from the section that you just opened.

BS) I'm going to tell you how to attach the Spare Pad that you just removed from the tool-kit. You'll need gently pull the cable of the pad that you've been using out of the tool-kit.

BT) You'll see a connector which connects the pad you've been using to the box. By wiggling its two parts, you can disconnect them.

BU) Now insert the (green) connector of the replacement pad that you just took out of the "Spare Pads" section into the (orange) connector which you just freed up.

BV) Push the two connectors together firmly until you hear a click.

Note: Voice prompts BW-CR refer to the application and adjustment of "mini-pads."

BW) Look at the bottom row of the tool-kit. Peel of the cover marked "Miscellaneous" and remove the package of four multicolored pads.

BX) Open the package. We're going to apply one pad to each arm and leg.

BY) Apply the red pad marked 'RA' to the right arm. Peel the plastic backing off of the pad just before you apply it. The sticky side is the one that must touch the victim's skin.

BZ) Apply the red pad marked 'RA' to the right hand. Peel the plastic backing off of the pad just before you apply it. The sticky side is the one that must touch the victim's skin.

CA) In the same manner, apply the white pad marked 'LA' to the left arm.

CB) In the same manner, apply the white pad marked 'LA' to the left hand.

CC) Now apply one blue pad marked 'LEG' to each leg.

CD) Now apply one blue pad marked 'LEG' to each foot.

CE). Look at your video screen. I'm going to mark the correct mini-pad position in red.

CF) Look at your video screen. You'll see a cartoon showing the correct mini-pad placement.

CG) Please make sure that each mini-pad is applied directly to the victim's bare skin.

CH) Please make sure that the arm or hand mini-pads are applied to the victim's bare skin. You may, however, apply the blue leg mini-pads to a stocking.

CI) Please press down firmly over each of the mini-pads.

CJ) Please press down firmly over the red mini-pad.

CK) Please press down firmly over the white mini-pad.

CL) Please press down firmly over the blue mini-pad on the right leg.

CM) Please press down firmly over the blue mini-pad on the left leg.

CN) Please remove the red, right arm mini-pad and position it as I've shown on the video screen.

CO) Please remove the white, left arm mini-pad and position it as I've shown on the video screen.

CP) Please remove the blue, right leg mini-pad and position it as I've shown on the video screen.

CQ) Please remove the blue, left leg mini-pad and position it as I've shown on the video screen.

CR) My information shows that the victim requires therapy which can only be accomplished with pads which must be applied to the chest.

Note: Voice prompts CB-CE refer to the application of apparatus to the victim for monitoring hemodynamic and respiratory status.

CS) Please take the device from the lower right corner of the tool-kit and place it on one of the victim's fingers.

CT) Please move the finger device to a different one of the victim's fingers

CU) Please look at the video screen for instructions on how to place the finger device.

CV) Please remove the blood pressure device from the right side of the tool-kit and apply it as shown on the video screen.

VII) Shock/Pace Menu

A) The victim has a life threatening heart rhythm problem and I'm going to administer a shock. Please make sure that neither you nor anyone else is now touching the victim.

B) I'm going to administer another shock now. Please make sure that no one is touching the victim.

C) A momentary twitch or jerk of the body when a shock is administered is normal.

D) The victim's heartbeat is too slow. I'm going to try to speed it up by a technique called pacing.

E) You may observe some twitching of the victim's chest muscles while I perform the pacing. This is normal.

F) I'd like you to try to find out if the victim has regained consciousness.

G) Please try speaking loudly to the victim.

VIII) Miscellaneous Menu

A) The victim's heart rhythm is now normal. You did a good job!

B) Trained emergency personnel are on the way and should be arriving soon.

C) Trained emergency personnel are on the way but they will need about five minutes to get here.

D) Trained emergency personnel are on the way but they will need about ten minutes to get here.

E) Trained emergency personnel are on the way but they will need about fifteen minutes to get here.

F) Trained emergency personnel are on the way but they will need about twenty minutes to get here.

G) I have been unable to reach any nearby emergency personnel, but I am continuing to try.

H) Unfortunately, our resuscitation has been unsuccessful up to this point.

I) If we are not successful over the next few minutes, I'm going to ask you to stop your efforts.

J) I'm going to ask you to stop your efforts at this time. We have done all that we can.

K) Please insert all free items except the pad into the tool-kit and close the tool-kit door.

L) We would be most appreciative if you can now return the unit to the place where you got it.

M) Please gently slide the unit back onto the shelf. Keep pushing until you hear the lock engage.

N) Thank you for helping. You did a fine job.

Note: Voice prompts 0-AG refer to CPR administration.

O) The victim's heart rhythm is now normal but he or she would benefit from CPR (cardiopulmonary resuscitation). Have you had any CPR training?

P) Apparatus to assist in ventilating the victim is located in the miscellaneous compartment of the tool-kit.

Q) You may begin CPR now. The pad(s) does not need to be removed from the chest to do this.

R) Is there anyone on the scene who can assist you with CPR?

S) I'm going to show you a very brief video about CPR.

T) Once you get started, I'll provide additional advice.

U) You're doing fine but you need to compress the chest harder.

V) You're doing fine but you don't need to compress the chest that hard.

W) You're doing fine but you need to compress the chest faster.

X) You're doing fine but you don't need to compress the chest that fast.

Y) The point where you compress the chest should be a little closer to the victim's head.

Z) The point where you compress the chest should be a little further from the victim's head.

AA) Please use two hands when compressing the chest.

AB) Use the heel of your hand, that is, the portion nearest to your wrist, to compress the chest.

AC) Ventilating the victim more frequently would help.

AD) You can ventilate the victim less frequently.

AE) The victim is now breathing on his or her own. You can stop ventilating.

AF) The victim's heart is now beating strongly. You can stop CPR.

AG) The victim requires another shock at this time. You'll need to stop CPR for about five seconds. Please make sure that no one is in contact with the victim at this time.

Note: Voice prompts AH through AR are for arriving emergency personnel

AH) Please identify yourself.

AI) The video screen shows a log of the events that have just occurred.

AJ) Please indicate what additional information you would like to have.

AK) If you would like, we can transfer control of this device directly to you. Would you like me to do that?

AL) I'm going to show you a brief instructional video on the use of this device.

AM) I will be available at all times to further instruct you in its proper use.

AN) We can leave the chest pad in place and easily reconnect it to your device.

AO) Gently pull the cable (between pad and tool-kit) so that more of it comes out of the tool-kit. You'll see the green and orange connectors which attach the pad to the box. By wiggling these two connectors, you can disconnect them.

AP) You can then attach the pad to any free connector in your box.

AQ) There are adapters in the "Miscellaneous" section of the tool-kit. They may be used to attach the victim's pad to your defibrillator.

AR) We would appreciate your calling our Central Station at 800 - - - - - - - when you have arrived at your destination so that we may make arrangements to retrieve our portable unit.

IX) Switch to AED Menu

A) This device has not been able to reach the Central Station, where expert medical personnel are available to help you. It will continue to try, and is likely to be successful over the next few minutes.

B) If you are witness to what you believe may be a cardiac arrest, or if you are dealing with an unconscious victim, you may use this device. It will, with minimal assistance from you, allow for the resuscitation of such a victim. It requires no prior training. It will instruct you with voice and test messages. To continue, please press the emergency button again, now.

C) To unlock the unit from its wall mounting, you'll need to use the combination lock on the left side of the unit.

D) Set the front (red) wheel at '6'. Set the second (blue) wheel at '2'. Set the third (white) wheel at '8'. Set the back (green) wheel at '5'.

E) To remove the portable unit from the wall, grasp the two handles and pull the unit towards your body.

F) Once the unit has been removed please carry it to the victim's side.

G) Communication with the Central Station has been interrupted. Control of this device has been transferred to an on-board computer. The computer will instruct you until either communication with the Central Station is re-established, or until the arrival of emergency personnel.

X) Possible AED Voice Prompts

Note: The following is a list of possible voice prompts, mostly from the previous menus, which might be used during a situation in which the Central Station could not be contacted:

From I) Introductory Statements Menu:
H, L
From IV) Trip to Patient Menu:
F, G, H, I
From V) On Arrival Menu:
D, F, G, K, L, M, N
From VI) Attach Pad and Peripherals Menu:
A-F, H-N, P-Z, AA, CB-CE
From VII) Shock/Pace Menu:
A, B, C, D, E
From VIII) Miscellaneous Menu:
A, B, J, L, M, N, P, Q, V, W, Y, Z, AA, AB, AC
From IX) Switch to AED Menu:
A-G In addition, the following voice prompts could be utilized during automatic operation:

A) If the volume is not loud enough for you, please say "louder", or touch the box marked "louder" on the touch sensitive video screen on the right (or left).

B) You may use the telephone handset to hear better.

C) If at any point you would like a prompt repeated, please say "repeat" or touch the box marked "repeat" on the touch sensitive screen.

D) The victim's heart rhythm is now normal, but he or she would benefit from CPR (cardiopulmonary resuscitation). Have you, or anyone on the scene had training in CPR? Please answer by saying the word "yes" or "no", or by touching the answer on the touch sensitive video screen on the right (or left).

Appendix 2

Abbreviations Used $\Delta$ Change
AB Audio Beacon
AED Automatic External Defibrillator
AED/P Automatic External Defibrillator/Pacer
AMP Amplifier
ATP Anti-Tachycardia Pacing
AV Atrioventricular
BP Blood Pressure
BPM Beats Per Minute
BW Bandwidth
COMM Communication
CONF'N Confirmation
CPR Cardiopulmonary Resuscitation
CS Central Station
DEFIB Defibrillator
ECG Electrocardiogram
EMT Emergency Medical Team
EN Enabler
FIG. # Figure Number
FoLanRec Foreign Language Recognition Program
GPS Global Positioning System
Hi Shock High Energy Shock
HS Handshake
HV High Voltage
ICD Implantable Cardioverter-Defibrillator
Interp'r Interpreter
KYBD Keyboard
LE Long Echo=confirmation signal #3
Lo Shock Low Energy Shock
LOS Line of Sight
m:ss Minutes:Seconds
MC Master Counter
MP Medical Professional
NG No Good
NR No Response
$O_2$ SAT Oxygen Saturation
OP Operational
p/$\Delta$ gain apply pressure and/or change gain
PACER Pacemaker
PU Portable Unit
PU-1 First Portable Unit
PU-2 Second Portable Unit
PU/SU Portable Unit/Stationary Unit combination PW Pulse Width
PWD Password
RCVR Receiver
RF Radio frequency
SAT Satellite
SC Screen
SE Short Echo=confirmation signal #2
SM Screen Message
SpeechRec Speech Recognition Program
SPKR Speaker
SU Stationary Unit
SVT Supraventricular Tachycardia
SYNCH Synchronization
TELCO Public Telephone Network
TELEM Telemetry
Text Pr Text Prompts
TSS Touch Sensitive Screen
UC Universal Connector
VF Ventricular Fibrillation
VI Victim
Video Pr Video Prompts
Video CAM Video Camera
VLE Very Long Echo=confirmation signal #4
Voice Pr Voice Prompts
Voice Re Voice Recognition
VSE Very Short Echo=confirmation signal #1
VT Ventricular Tachycardia
XMTR Transmitter
% RR Percentage of interval between heartbeats There has thus been shown and described a novel system for cardiac resuscitation which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. A cardiac monitoring and external defibrillation system which allows an untrained human enabler immediate access to a medical professional who can and will remotely monitor, diagnose and treat a victim of medical emergency at one of a plurality of remote sites, said system comprising, in combination:
(a) a central station comprising:
  (1) a first display device for displaying cardiac information from a victim for evaluation by said medical professional;
  (2) a first input device, responsive to said medical professional, for producing control signals for controlling operation of emergency cardiac monitoring and external defibrillation apparatus at one of said remote sites and the application of a defibrillation pulse to said victim at said one site; and
  (3) a first transmitting/receiving (T/R) device, coupled to said first display device and said first input device, for electronic communication with emergency cardiac monitoring and defibrillation apparatus disposed at each of a plurality of remote sites; and
(b) emergency cardiac monitoring and external defibrillation apparatus disposed at each of a plurality of remote sites, each said apparatus comprising a portable unit including:
  (1) a second transmitting/receiving (T/R) device for electronic communication with said first T/R device of said central station;
  (2) a master control unit, connected to said second T/R device, for controlling the operation of said cardiac monitoring and defibrillation apparatus, said control unit having a plurality of operating states selected from the group consisting of:
    (i) enable remote control by medical professional;
    (ii) enable automatic local control; and
    (iii) enable local control by emergency medical personnel;
  (3) a defibrillator circuit, having a control input coupled to said second T/R device and said master control unit, for generating a defibrillation pulse at a defibrillator circuit output in response to a defibrillation control signal received at said defibrillator circuit control input;
  (4) a logic device for automatic local control of the portable unit, coupled to said second T/R device, to said master control unit and to the control input of said defibrillator circuit, for automatically producing a second defibrillation control signal for controlling the application of said defibrillation pulse to said victim in response to electrocardiogram (ECG) signals received from said victim;
  (5) an electrocardiogram (ECG) circuit, having an ECG circuit output, coupled to said second T/R device and to said logic device, and having an ECG electrode input;
  (6) a plurality of contact electrodes, adapted to be placed by a nearby enabler upon a chest wall of said victim, said plurality of contact electrodes being adapted to be arranged at separate locations on said chest wall for the receipt of ECG signals from said victim and for application of said defibrillation pulse to said victim;
  (7) a connecting cable having a plurality of electric wires for connecting each of said contact electrodes to at least one of (i) said ECG electrode input and (ii) said defibrillator output;
  (8) a second display device, coupled to said ECG circuit output for display of said ECG signals; and
  (9) a second input device, coupled to said control input of said defibrillator circuit, for locally activating defibrillation;
wherein
(1) said ECG signals are transmitted from selected ones of said contact electrodes via said ECG circuit to said central station and displayed on said first display unit for evaluation by said medical professional, (2) said first defibrillation control signal may be transmitted from said central station to said control input of said defibrillator circuit and (3), in response thereto, said defibrillator circuit generates said defibrillation pulse for application to at least one of said contact electrodes for resuscitation of said victim; and wherein said master control unit selects the operating state of said portable unit at the remote site under control of said medical professional at said central station; and
wherein, if enabled by said medical professional, (4) said ECG signals are transmitted from selected ones of said contact electrodes via said ECG circuit and displayed on said second display unit for evaluation by said emergency medical personnel, (5) said first defibrillation control signal may be transmitted from said second input device said control input of said defibrillator circuit, and (6), in response thereto, said defibrillator circuit generates said defibrillation pulse for application to at least one of said contact electrodes for resuscitation of said victim.

2. A cardiac monitoring and external defibrillation system which allows an untrained human enabler immediate access to a medical professional who can and will remotely monitor, diagnose and treat a victim of medical emergency at one of a plurality of remote sites, said system comprising, in combination:
  (a) a central station comprising:
    (1) a display device for displaying cardiac information from a victim for evaluation by said medical professional;
    (2) a first input device, responsive to said medical professional, for producing a first defibrillation control signal for controlling the application of a defibrillation pulse to said victim;
    (3) a second input device, responsive to a medical professional, for producing a defibrillation command signal, for initiating the automatic application of a defibrillation pulse to said victim; and
    (4) a first transmitting/receiving (T/R) device, coupled to said display device and to said first and second input devices, for electronic communication with emergency cardiac monitoring and defibrillation apparatus disposed at each of a plurality of remote sites; and
  (b) emergency cardiac monitoring and external defibrillation apparatus disposed at each of a plurality of remote sites, each said apparatus comprising a portable unit including:
    (1) a second transmitting/receiving (T/R) device for electronic communication with said first T/R device of said central station;
    (2) a logic device for automatic control of the portable unit, coupled to the second T/R device, for automatically producing a second defibrillation control signal for controlling the application of a defibrillation pulse to said victim, upon receipt of a defibrillation command signal from said central station, in response to electrocardiogram (ECG) signals received from said victim;
    (3) a defibrillator circuit, having a control input coupled to said second T/R device and to said logic device, for generating a defibrillation pulse at a defibrillator circuit output in response to a either a first or a second defibrillation control signal received at said defibrillator circuit control input;
    (4) an electrocardiogram (ECG) circuit, having an ECG circuit output, coupled to said second T/R device and to said logic device, and having an ECG electrode input;
    (5) a plurality of contact electrodes, adapted to be placed by a nearby enabler upon a chest wall of said victim, said plurality of contact electrodes being adapted to be arranged at separate locations on said chest wall for the receipt of ECG signals from said victim and for application of said defibrillation pulse to said victim; and
    (6) a connecting cable having a plurality of electric wires for connecting each of said contact electrodes to at least one of (i) said ECG electrode input and (ii) said defibrillator output;
  wherein (1) said ECG signals are transmitted from selected ones of said contact electrodes via said ECG circuit to said central station for evaluation by said medical professional, (2) said logic device includes means for analyzing said ECG signals and produces a signal representing the result of the analysis, said analysis signal being transmitted to said central station via said second and first T/R devices, respectively, for display by said display device for the consideration by said medical professional, whereby said medical professional is able compare the analysis of said logic device with his/her own medical judgment; (3) said first defibrillation control signal may be transmitted from said central station to said control input of said defibrillator circuit and, in response thereto, said defibrillator circuit generates said defibrillation pulse for application to at least one of said contact electrodes for resuscitation of said victim; and (4) said defibrillation command signal may be sent from said central station to said logic device at said remote site and, in response thereto, said defibrillator circuit is responsive to said second defibrillation control signal generated by said logic device to generate said defibrillation pulse for application to said at least one contact electrode for resuscitation of said victim, thereby allowing said medical professional to take advantage of the analysis by said logic device.

3. A cardiac monitoring and external defibrillation and cardiac pacing system which allows an untrained human enabler immediate access to a medical professional who can and will remotely monitor, diagnose and treat a victim of medical emergency at one of a plurality of remote sites, said system comprising, in combination:
  (a) a central station comprising:
    (1) a display device for displaying cardiac information from a victim for evaluation by said medical professional;
    (2) at least one first input device, responsive to said medical professional, for producing a defibrillation control signal for controlling the application of a defibrillation pulse to said victim;
    (3) at least one second input device, responsive to said medical professional, for producing a cardiac pacing control signal for controlling the application of one or more cardiac pacing pulses to said victim; and
    (4) a first transmitting/receiving (T/R) device, coupled to said display device and to said first and said second input devices, for electronic communication with emergency cardiac monitoring, defibrillation and cardiac pacing apparatus disposed at each of a plurality of remote sites; and
  (b) emergency cardiac monitoring and external defibrillation and cardiac pacing apparatus disposed at each of a plurality of remote sites, each said apparatus comprising a portable unit including:
    (1) a second transmitting/receiving (T/R) device for electronic communication with said first T/R device of said central station;
    (2) a defibrillator circuit, having a defibrillation control input coupled to said second T/R device, for producing a defibrillation pulse at a defibrillator circuit output in response to a defibrillation control signal received at said defibrillation control input;
    (3) a cardiac pacing circuit, having a pacing control input coupled to said second T/R device, for producing said one or more cardiac pacing pulses at a pacing circuit output in response to a cardiac pacing control signal received at said pacing control input;
    (4) a logic device, coupled to the second T/R device and to the control input of said defibrillator circuit and to the pacing control input of said cardiac pacing circuit, for automatically producing at least one of a second defibrillation control signal for controlling the application of said defibrillation pulse to said victim, and a second cardiac pacing control signal for controlling the application of said cardiac pacing pulses to said victim, in the absence of proper communication between said first T/R device and said second T/R device, in response to electrocardiogram (ECG) signals received from said victim;

(5) an electrocardiogram (ECG) circuit, having an ECG circuit output, coupled to said second T/R device and to said logic device, and an ECG electrode input;

(6) a plurality of contact electrodes, adapted to be placed by a nearby enabler upon a chest wall of said victim, said plurality of contact electrodes being adapted to be arranged at separate locations on said chest wall for (1) the receipt of ECG signals from said victim; (2) for application of said defibrillation pulse to said victim and (3) for application of said one or more pacing pulses to said victim; and (7) a connecting cable having a plurality of electric wires for connecting each of said contact electrodes to at least one of (i) said ECG electrode input; (ii) said defibrillator output and (iii) said cardiac pacing output;

whereby (1) said ECG signals may be transmitted from selected ones of said contact electrodes via said ECG circuit to said central station for evaluation by said medical professional; (2) said defibrillation control signal and said cardiac pacing control signal may be transmitted from said central station to said defibrillation control input and said pacing control input, respectively; and (3) in response thereto, said defibrillation pulse may be transmitted from said defibrillator output or said cardiac pacing pulses may be transmitted from said cardiac pacing output to selected ones of said contact electrodes for resuscitation of said victim.

4. A cardiac monitoring and external defibrillation system which allows an untrained human enabler immediate access to a medical professional who can and will remotely monitor, diagnose and treat a victim of medical emergency at one of a plurality of remote sites, said system comprising, in combination:

(a) a central station comprising:
  (1) a display device for displaying cardiac information from a victim for evaluation by said medical professional;
  (2) at least one first input device, responsive to said medical professional, for producing a defibrillation control signal for controlling the application of a defibrillation pulse to said victim;
  (3) at least one second input device, responsive to said medical professional, for transmitting instructional information to said enabler; and
  (4) a first transmitting/receiving (T/R) device, coupled to said display device and to said first and said second input devices, for electronic communication with emergency cardiac monitoring and defibrillation apparatus disposed at each of a plurality of remote sites; and (b) emergency cardiac monitoring and external defibrillation apparatus disposed at each of a plurality of remote sites, each said apparatus comprising a portable unit including:
  (1) a second transmitting/receiving (T/R) device for electronic communication with said first T/R device of said central station;
  (2) a defibrillator circuit, having a defibrillation control input coupled to said second T/R device, for producing a defibrillation pulse at a defibrillator circuit output in response to a defibrillation control signal received at said defibrillation control input;
  (3) an instruction receiving device, coupled to said second T/R device, for receiving said instructional information for use by said enabler;
  (4) an electrocardiogram (ECG) circuit, having an ECG circuit output, coupled to said second T/R device, and having an ECG electrode input;
  (5) a plurality of contact electrodes, adapted to be placed by a nearby enabler upon a chest wall of said victim, said plurality of contact electrodes being adapted to be arranged at separate locations on said chest wall for (1) the receipt of ECG signals from said victim; (2) for application of said defibrillation pulse to said victim; and
  (6) a connecting cable having a plurality of electric wires for connecting each of said contact electrodes to at least one of (i) said ECG electrode input; and (ii) said defibrillator;

whereby (1) said ECG signals may be transmitted from selected ones of said contact electrodes via said ECG circuit to said central station for evaluation by said medical professional; (2) said defibrillation control signal may be transmitted from said central station to said defibrillation control input and said pacing control input, respectively; and (3) in response thereto, said defibrillation pulse may be transmitted from said defibrillator output to selected ones of said contact electrodes for resuscitation of said victim.

5. The system defined in claim 4, wherein said second input device includes a microphone and said instruction receiving device includes a speaker, for providing spoken audio instructions to said enabler.

6. The system defined in claim 4, wherein said instruction receiving device includes an instructional display device, for providing video instructions to said enabler.

7. The system defined in claim 6, wherein said instruction receiving device further includes means for storing instructional video information, connected to said instructional display device, for causing said instructional display device to display said video information, whereby said medical professional can activate the display of said video information by means of said second input device.

8. The system defined in claim 7, wherein said instructional video information includes at least one of:
  (i) instructional information concerning the performance of cardiopulmonary resuscitation;
  (ii) instructional information concerning the use of said portable unit; and
  (iii) instructional information concerning the placement of said contact electrodes by said enabler.

9. The system defined in claim 6, wherein said central station further includes means for storing instructional video information, coupled to said second input device and said first T/R device, for causing said instructional display device to display said video information, whereby said medical professional can activate the display of said video information by means of said second input device.

10. The system defined in claim 9, wherein said instructional video information includes at least one of:
  (i) instructional information concerning the performance of cardiopulmonary resuscitation;
  (ii) instructional information concerning the use of said portable unit; and
  (iii) instructional information concerning the placement of said contact electrodes by said enabler.

11. The system defined in claim 6, wherein said central station further includes means for generating instructional video information in substantially real-time, coupled to said second input device, said display device and said first T/R device, for causing said instructional display device to display said video information, said instructional information consisting of at least one of (i) video file information with at least one real-time video annotations by said MP; and (ii) real-time diagrammatic information by said MP.

12. The system defined in claim 11, wherein said emergency cardiac monitoring and external defibrillation apparatus further comprises a video camera, coupled to said second T/R device for the transmission of video images of said victim to said medical professional, and wherein said instructional video information consists of at least one of:

(i) video images of said victim with at least one real-time video annotation by said MP; and (ii) instructional information for said enabler, based on analysis of said victim video image by said MP.

13. A cardiac monitoring and internal defibrillation and pacing system which allows a patient with an implanted cardiac pacing-defibrillator device immediate access to a medical professional who can and will remotely monitor, diagnose and treat a medical emergency, said system comprising, in combination:

(a) a central station comprising:

(1) a display device for displaying cardiac information from a patient for evaluation by said medical professional;

(2) a first input device, responsive to said medical professional, for producing a first defibrillation control signal for controlling the application of a defibrillation pulse to said patient; and (3) a second input device, responsive to said medical professional, for producing a first pacing control signal for controlling the application of a pacing pulse to said patient;

(4) a first transmitting/receiving (T/R) device, coupled to said display device and said first and said second input devices, for electronic communication with emergency cardiac monitoring and defibrillation apparatus disposed at each of a plurality of remote sites; and (b) emergency cardiac monitoring and internal pacing-defibrillation apparatus disposed at each of a plurality of remote sites, each said apparatus comprising a unit implanted in a patient and including:

(1) a second transmitting/receiving (T/R) device for electronic communication with said first T/R device of said central station;

(2) a defibrillator circuit, having a control input coupled to said second T/R device, for generating a defibrillation pulse at a defibrillator circuit output in response to a defibrillation control signal received at said defibrillator circuit control input;

(3) a pacing circuit, having a control input coupled to said second T/R device, for generating at least one pacing pulse at a pacing circuit output in response to a pacing control signal received at said pacing circuit control input;

(4) a logic device for automatic control of the implanted unit, coupled to the second T/R device and to the control inputs of said defibrillator circuit and said pacing circuit, for (i) automatically producing a second defibrillation control signal for controlling the application of said defibrillation pulse to said patient in the absence of proper and timely communication between said first T/R device and said second T/R device, in response to electrogram (EGM) signals received from said patient;

(ii) automatically producing a second pacing control signal for controlling the application of said at least one pacing pulse to said patient in the absence of proper and timely communication between said first T/R device and said second T/R device, in response to electrogram (EGM) signals received from said patient;

(5) an electrogram (EGM) circuit, having an EGM circuit output, coupled to said second T/R device and to said logic device, and having one or more EGM electrode inputs;

(6) a plurality of electrodes, adapted to be coupled at separate locations to internal tissue of said patient, for the receipt of EGM signals from said patient and for application of said defibrillation pulse to said patient; and (7) a means for connecting each of said electrodes to at least one of (i) said EGM electrode inputs and (ii) said defibrillator output;

whereby (1) said EGM signals may be transmitted from selected ones of said electrodes via said EGM circuit to said central station for evaluation by said medical professional, (2) said first defibrillation control signal may be transmitted from said central station to said control input of said defibrillator circuit and in response thereto, said defibrillator circuit may generate said defibrillation pulse for application to at least one of said electrodes for resuscitation of said patient; and wherein, in the absence of proper and timely communication between said first T/R device and said second T/R device, said defibrillator circuit is responsive to said second defibrillation control signal received from said logic device to generate said defibrillation pulse for application to said at least one electrode for resuscitation of said patient, and (3) said first pacing control signal may be transmitted from said central station to said control input of said pacing circuit and in response thereto, said pacing circuit may generate said at least one pacing pulse for application to at least one of said electrodes for resuscitation of said patient; and wherein, in the absence of proper and timely communication between said first T/R device and said second T/R device, said pacing circuit is responsive to said second pacing control signal received from said logic device to generate said at least one pacing pulse for application to said at least one electrode for resuscitation of said patient.

14. The system defined in claim 13, further comprising a control unit, adapted for use at the remote site of each implanted unit, said control unit comprising:

(1) third transmitting/receiving (T/R) device for electronic communication with said first T/R device of said central station; and (2) fourth transmitting/receiving (T/R) device, coupled to said third T/R device, for electronic communication with said second T/R device of said implanted unit;

whereby said implanted unit may communicate with said central station through said control unit.

15. The system defined in claim 14, wherein said first T/R device and said second T/R device include means for direct duplex communication between them, without transmission through said third T/R device and said fourth T/R device, said communication means being selected from the group consisting of:

(i) a wireless transmission link;

(ii) a transmission link with wired and wireless segments; and (iii) a transmission link with the Internet and wireless segments.

* * * * *